US011505545B2

(12) United States Patent

Hübsch et al.

(10) Patent No.: US 11,505,545 B2

(45) Date of Patent: Nov. 22, 2022

(54) ANTHELMINTIC QUINOLINE-3-CARBOXAMIDE DERIVATIVES

(71) Applicant: Bayer Animal Health GMBH, Leverkusen (DE)

(72) Inventors: Walter Hübsch, Wuppertal (DE); Johannes Köbberling, Neuss (DE); Adeline Köhler, Langenfeld (DE); Hans-Georg Schwarz, Dorsten (DE); Daniel Kulke, Leverkusen (DE); Claudia Welz, Düsseldorf (DE); Thomas Ilg, Monheim (DE); Kirsten Börngen, Cologne (DE); Wei Zhuang, Monheim (DE); Nils Griebnow, Dormagen (DE); Claudia Böhm, Hannover (DE); Niels Lindner, Wuppertal (DE); Maike Hink, Vaihingen/Enz (DE); Ulrich Görgens, Ratingen (DE)

(73) Assignee: Bayer Animal Health GmbH, Leverkusen (DE)

( * ) Notice: Subject to any disclaimer, the term of this patent is extended or adjusted under 35 U.S.C. 154(b) by 108 days.

(21) Appl. No.: 17/085,880

(22) Filed: Oct. 30, 2020

(65) Prior Publication Data

US 2021/0115026 A1 Apr. 22, 2021

Related U.S. Application Data

(62) Division of application No. 16/348,797, filed as application No. PCT/EP2017/078319 on Nov. 6, 2017, now Pat. No. 10,889,573.

(30) Foreign Application Priority Data

Nov. 11, 2016 (EP) .................................... 16198550

(51) Int. Cl.

| | |
|---|---|
| ***C07D 405/14*** | (2006.01) |
| ***A61P 33/10*** | (2006.01) |
| ***C07D 405/12*** | (2006.01) |
| ***C07D 413/14*** | (2006.01) |

(52) U.S. Cl.

CPC ............ *C07D 405/14* (2013.01); *A61P 33/10* (2018.01); *C07D 405/12* (2013.01); *C07D 413/14* (2013.01)

(58) Field of Classification Search

CPC ............................... C07D 405/14; A61P 33/10

See application file for complete search history.

(56) References Cited

U.S. PATENT DOCUMENTS

| | | | |
|---|---|---|---|
| 4,343,804 | A | 8/1982 | Munson, Jr. |
| 7,872,036 | B2 | 1/2011 | Toriyabe |
| 8,536,340 | B2 | 9/2013 | Hamamoto |
| 8,697,867 | B2 | 4/2014 | Hamamoto |
| 8,946,234 | B2 | 2/2015 | Maue |
| 8,980,912 | B2 | 3/2015 | Hamamoto |
| 9,580,405 | B2 | 2/2017 | Yang |
| 9,591,857 | B2 | 3/2017 | Buysse |
| 9,717,242 | B2 | 8/2017 | Kagabu |
| 9,750,252 | B2 | 9/2017 | Satoh |
| 9,938,292 | B2 | 4/2018 | Wu |
| 2008/0306048 | A1 | 12/2008 | Kaplan |
| 2013/0210844 | A1 | 8/2013 | Gharat |
| 2014/0213448 | A1 | 7/2014 | Buysse |
| 2014/0275503 | A1 | 9/2014 | Giampietro |
| 2018/0014543 | A1 | 1/2018 | Kai |

FOREIGN PATENT DOCUMENTS

| | | | |
|---|---|---|---|
| CN | 101715774 | A | 6/2010 |
| CN | 101337937 | B | 12/2010 |
| CN | 102391261 | A | 3/2012 |
| CN | 101337940 | B | 5/2012 |
| CN | 103265527 | B | 8/2014 |
| CN | 103109816 | B | 9/2014 |
| CN | 103232431 | B | 11/2014 |
| CN | 103524422 | B | 5/2015 |
| DE | 3639877 | A1 | 5/1988 |
| EP | 2647626 | A1 | 10/2013 |

(Continued)

OTHER PUBLICATIONS

Baumgarten, H.E. et al. (1981). "Napthyridines. IV. Synthesis of Benzo[f]-1,7-naphthyridines (1,2)," J. Heterocyclic Chem. 18: 925-928.

Berge, S. et al. (Jan. 1977). "Pharmaceutical Salts," Journal of Pharmaceutical Sciences; 66(1):1-19.

(Continued)

*Primary Examiner* — Paul V Ward

(74) *Attorney, Agent, or Firm* — McBee Moore & Vanik IP, LLC; Susan McBee

(57) ABSTRACT

The present invention covers new quinoline compounds of general formula (I):

(I)

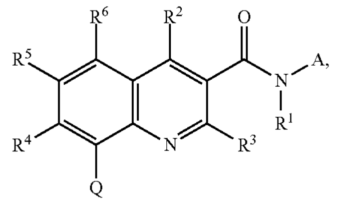

in which A, $R^1$, $R^2$, $R^3$, $R^4$, $R^5$, $R^6$, and Q are as defined herein, methods of preparing said compounds, intermediate compounds useful for preparing said compounds, pharmaceutical compositions and combinations comprising said compounds and the use of said compounds for manufacturing pharmaceutical compositions for the treatment, control and/or prevention of diseases, in particular of helminth infections, as a sole agent or in combination with other active ingredients.

11 Claims, No Drawings

(56) References Cited

FOREIGN PATENT DOCUMENTS

| | | | |
|---|---|---|---|
| JP | 2008214323 | A | 9/2008 |
| JP | 2010018586 | A | 1/2010 |
| WO | WO0204444 | A2 | 1/2002 |
| WO | WO03106457 | A1 | 12/2003 |
| WO | WO2004099160 | A1 | 11/2004 |
| WO | WO2006003494 | A2 | 1/2006 |
| WO | WO2006043635 | A1 | 4/2006 |
| WO | WO2006103120 | A2 | 10/2006 |
| WO | WO2007040280 | A1 | 4/2007 |
| WO | WO2007040282 | A1 | 4/2007 |
| WO | WO2010051926 | A2 | 5/2010 |
| WO | WO2010052161 | A2 | 5/2010 |
| WO | WO2010066780 | A1 | 6/2010 |
| WO | WO2011085575 | A1 | 7/2011 |
| WO | WO2011105506 | A1 | 9/2011 |
| WO | WO2011151146 | A1 | 12/2011 |
| WO | WO2012029672 | A1 | 3/2012 |
| WO | WO2012034403 | A1 | 3/2012 |
| WO | WO2012112363 | A1 | 8/2012 |
| WO | WO2013050317 | A1 | 4/2013 |
| WO | WO2013096151 | A1 | 6/2013 |
| WO | WO2013115391 | A1 | 8/2013 |
| WO | WO2013118071 | A1 | 8/2013 |
| WO | WO2013144213 | A1 | 10/2013 |
| WO | WO2013162715 | A2 | 10/2013 |
| WO | WO2013162716 | A2 | 10/2013 |
| WO | WO2014187846 | A1 | 11/2014 |
| WO | WO2015058021 | A1 | 4/2015 |
| WO | WO2015058028 | A1 | 4/2015 |
| WO | WO2015078800 | A1 | 6/2015 |
| WO | WO2015144001 | A1 | 10/2015 |
| WO | WO2016005276 | A1 | 1/2016 |
| WO | WO2016133011 | A1 | 8/2016 |
| WO | WO2017103851 | A1 | 6/2017 |

OTHER PUBLICATIONS

Blad, C.C. et al. (2012) "Novel 3,6,7-Substituted Pyrazolopyrimidines as Positive Allosteric Modulators for the Hydroxycarboxylic Acid Receptor 2 (GPR109A)," Journal of Medicinal Chemistry, 55: 3563-3567.

Bonnefous, C. et al. (2009). "Discovery of Inducible Nitric Oxide Synthase (iNOS) Inhibitor Development Candidate KD7332, Part 1: Identification of a Novel, Potent, and Selective Series of Quinolinone iNOS Dimerization Inhibitors that are Orally Active in Rodent Pain Models," J. Med. Chem. 52: 3047-3062.

Cross et al. (1976). "International Union of Pure And Applied Chemistry: Organic Chemistry Division Commission on Nomenclature of Organic Chemistry" Pure & Appl. Chem. 45:11-30.

Djerassi, C. et al. (1948). "Brominations with Pyridine Hydrobromide Perbromide," J. Am. Chem. Soc., 70: 417-418.

T.W. Greene and P.G.M. Wuts in "Protective Groups in Organic Synthesis", 3rd edition, Wiley, 1999.

International Search Report dated Jan. 4, 2018 for PCT Application No. PCT/EP2017/078319, filed Nov. 6, 2017, 6 pages.

Kotha, S. et al. (2002). "Recent applications of the Suzuki-Miyaura cross-coupling reaction in organic synthesis," Tetrahedron 58: 9633-9695.

Lennox, A.J.J. et al. (2014). "Selection of boron reagents for Suzuki-Miyaura coupling," Chem. Soc. Rev. 43: 412-443.

Maltais, F. et al. (2009). "In Vitro and In Vivo Isotope Effects with Hepatitis C Protease Inhibitors: Enhanced Plasma Exposure of Deuterated Telaprevir versus Telaprevir in Rats," J. Med. Chem.; 52(24):7993-8001.

Mehlhorn et al. (2016). Encyclopedoa of Parasitology, 4th edition, Springer-Verlag, Berlin Heidelberg.

Mutlib, A. et al. (2000). "The Species-Dependent Metabolism of Efavirenz Produces a Nephrotoxic Glutathione Conjugate in Rats," Toxicology and Applied Pharmacology; 169:102-113.

Müller, S. et al. (2012). "Pyridostatin analogues promote telomere dysfunction and long-term growth inhibition in human cancer cells," Org. Biomol. Chem. 10: 6537-6546.

Ochiana, S.O. et al. (2015). "Repurposing Human PDE4 Inhibitors for Neglected Tropical Diseases. Evaluation of Analogs of the Human PDE4 Inhibitor GSK-256066 as Inhibitors of PDEB1 of Trypanosoma brucei," Chem. Biol. Drug Des. 85: 549-564.

Ohnmacht Jr., C.J. et al. (1971). "Antimalarials. 5. α-Dibutylaminomethyl-and α-(2-Piperidyl)-3-quinolinemethanols," Journal of Medicinal Chemistry 14:17-24.

Perrin, C. et al. (2005). "Stereochemistry of β-Deuterium Isotope Effects on Amine Basicity," J. Am. Chem. Soc.; 127(26):9641-9647.

Perrin, C. et al. (2007). "Secondary Deuterium Isotope Effects on the Acidity of Carboxylic Acids and Phenols," J. Am. Chem. Soc.; 129(14):4490-4497.

Plevova, K. et al. (2015). "Building a library of monofluorinated anilino-methylidenes and spectroscopic studies of their properties," Monatsh Chern 146: 291-302.

Prier, C.K. et al. (2013). "Visible Light Photoredox Catalysis with Transition Metal Complexes: Applications in Organic Synthesis," Chem. Rev. 113: 5322-5363.

Rosman, K. et al. (1998). "Isotopic Compositions of the Elements 1997," Pure & Appl. Chem., 70(1):217-235.

Schneider, F. et al. (2006). "Enhanced Plasma Concentration by Selective Deuteration of Rofecoxib in Rats," Arzneim.-Forsch./Drug Res.; 56(4):295-300.

Schröder, E. et al. (1979). "Non-steroidal anti-inflammatories 4. (1) Substituted aza-naphthylacetic acids with antiphlogistic effect," Eur. J. Med. Chem. 14(6): 499-506.

Sharma, A. et al. (2013). "Nevirapine Bioactivation and Covalent Binding in the Skin," Chem. Res. Toxicol.; 26:410-421.

Shaw, M.H. et al. (2016). "Photoredox Catalysis in Organic Chemistry," J. Org. Chem. 81: 6898-6926.

Tayar, N.E. et al. (1984). "The lipophilicity of deuterium atoms. A comparison of shake-flask and HPLC methods," Int. J. Pharm.; 19(3):271-281.

The Pesticide Manual, 16th Ed., British Crop Protection Council, 2012.

Wendeborn, S. et al. (2000). "A new synthesis of functionalized imidazol-2-ones," Tetahedron Letters 41: 6387-6391.

Wenthur, C. et al. (2013). "Discovery of (R)-(2-Fluoro-4-((-4-methoxyphenyl)ethynyl)phenyl)(3-Hydroxypiperidin-1-yl)methanone (ML337), An mGlu3 Selective and CNS Penetrant Negative Allosteric Modulator (NAM)," J. Med. Chem.; 56:5208-5212.

Wilkinson, J. H. (1950). "Some meso-Amino-acridines and -quinolines derived from 2-Aminodiphenyl," Chemical Society, 1950: 464-468.

Wood, A. "Compendium of Pesticide Common Names," located at http://www.alanwood.net/pesticides/.

Zask, A. et al. (2003). "Synthesis and SAR of Bicyclic Heteroaryl Hydroxamic Acid MMP and TACE Inhibitors," Bioorganic & Medicinal Chemistry Letters 13: 1487-1490.

ANTHELMINTIC QUINOLINE-3-CARBOXAMIDE DERIVATIVES

CROSS REFERENCE TO RELATED APPLICATIONS

This application is a divisional application of U.S. patent application Ser. No. 16/348,797, filed on May 9, 2019, which is a National Stage Application pursuant to 35 U.S.C. § 371 of International Application No. PCT/EP2017/078319, filed on Nov. 6, 2017, which claims the benefit of European Application No. 16198550.2, filed on Nov. 11, 2016.

The present invention covers new quinoline derivatives of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

BACKGROUND

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses. Furthermore, successful prevention of heartworm disease in dogs, which currently solely relies on the utilisation of macrocyclic lactones, is in danger as loss of efficacy for multiple macrocyclic lactones has been described for some regions of the United States of America—especially in those areas where the heartworm challenge for infection is high. Finally, experimental infection studies with *Dirofilaria immitis* larvae from suspected field loss of efficacy cases in the Lower Mississippi Delta provided in vivo confirmation of the existence of macrocyclic lactone resistance.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelmintics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

Certain quinoline carboxamides are described in JP2008-214323A as agents suitable for treatment and/or prevention of skin diseases, like acne vulgaris, dermatitis or the like.

The WO2017103851 discloses quinoline-3-carboxamides as H-PGDS inhibitors, useful for treating atherosclerosis, psoriasis, sinusitis, and duchenne muscular dystrophy.

However, the state of the art does not describe the new quinoline derivatives of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively interact with Slo-1 calcium-gated potassium channels of nematodes. This interaction is characterized by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae.

DESCRIPTION OF THE INVENTION

In accordance with a first aspect, the present invention covers compounds of general formula (I):

(I)

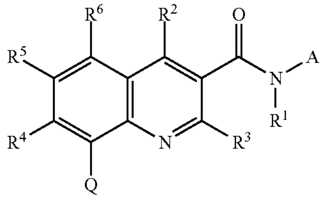

in which:

A is A1 or A2,

A1

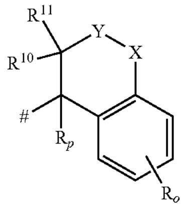

A2

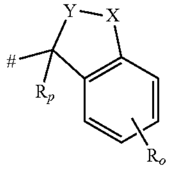

o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SC_2$—$C_1$-$C_4$-alkyl, and —$SC_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SC_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SC_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SC_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SC_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SC_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (═O), or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl, $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$- alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH, and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

As used herein, the position via which a respective substituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms. The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group, or an isomer thereof. Particularly, said group has 1, 2 or 3 carbon atoms ("$C_1$-$C_3$-alkyl"), e.g. a methyl, ethyl, n-propyl or isopropyl group.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH($C_1$-$C_4$-alkyl)" or "—N($C_1$-$C_4$-alkyl)$_2$" means a linear or branched, saturated, monovalent group in which the term "$C_1$-$C_4$-alkyl" is as defined supra, e.g. a methylamino, ethylamino, n-propylamino, isopropylamino, N,N-dimethylamino, N-methyl-N-ethylamino or N,N-diethylamino group.

The term "—S—$C_1$-$C_4$-alkyl", "—S(O)—$C_1$-$C_4$-alkyl" or "—$SO_2$—$C_1$-$C_4$-alkyl" means a linear or branched, saturated group in which the term "$C_1$-$C_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, n-butylsulfonyl, sec-butylsulfonyl, isobutylsulfonyl or tert-butylsulfonyl group.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof.

The term "$C_1$-$C_4$-halogenoalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2- ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The term "benzo-$C_5$-$C_6$-cycloalkyl" means a monovalent, bicyclic hydrocarbon ring wherein a saturated, monovalent, monocyclic hydrocarbon ring which contains 5 or 6 carbon atoms ("$C_5$-$C_6$-cycloalkyl") is annelated to a phenyl ring. Said benzo-$C_5$-$C_6$-cycloalkyl group is for example, a bicyclic hydrocarbon ring, e.g. an indane (i.e. 2,3-dihydro-1H-indene) or tetraline (i.e. 1,2,3,4-tetrahydronaphthalene) group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "heterocycloalkyl" means a monocyclic or bicyclic, saturated or partially saturated heterocycle with 4, 5, 6, 7, 8, 9 or 10 ring atoms in total (a "4- to 10-membered heterocycloalkyl" group), particularly 4, 5 or 6 ring atoms (a "4- to 6-membered heterocycloalkyl" group), which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, oxolanyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl, 1,3-thiazolidinyl or 1,2,4-triazolidinyl, for example; or a 6-membered ring, such as tetrahydropyranyl, tetrahydrothiopyranyl, piperidinyl, morpholinyl, dithianyl, thiomorpholinyl, piperazinyl, oxanyl, 1,3-dioxanyl, 1,4-dioxanyl or 1,2-oxazinanyl, for example; or a 7-membered ring, such as azepanyl, 1,4-diazepanyl or 1,4-oxazepanyl, for example; or a bicyclic 7-membered ring, such as 6-oxa-3-azabicyclo[3.1.1]heptan, for example; or a bicyclic 8-membered ring, such as 5,6-dihydro-4H-furo[2,3-c]pyrrole or 8-oxa-3-azabicyclo[3.2.1]octan, for example; or a bicyclic 9-membered ring, such as octahydro-1H-pyrrolo[3,4-b]pyridine, 1,3-dihydro-isoindol, 2,3-dihydro-indol or 3,9-dioxa-7-azabicyclo[3.3.1]nonan, for example; or a bicyclic 10-membered ring, such as decahydroquinoline or 3,4-dihydroisoquinolin, for example.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, oxaazaspiro[2.5]octyl, azaspiro[4.5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "6- or 10-membered aryl" means a monovalent, monocyclic or bicyclic aromatic ring having 6 or 10 carbon ring atoms, e.g. a phenyl or naphthyl group.

The term "heteroaryl" means a monovalent, monocyclic, bicyclic or tricyclic aromatic ring having 5, 6, 9 or 10 ring atoms (a "5- to 10-membered heteroaryl" group), particularly 5 or 6 ring atoms (a "5- to 6-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, dihydropyridinyl, pyridazinyl, pyrimidinyl, tetrahydropyrimidinyl, pyrazinyl or triazinyl.

The term "heterocyclyl" means a heterocycle selected from the group consisting of heterocycloalkyl and heteroaryl. Particularly, the term "4- to 6-membered heterocyclyl" means a heterocycle selected from the group consisting of 4- to 6-membered heterocycloalkyl and 5- to 6-membered heteroaryl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_4$" encompasses $C_3$, $C_4$, and $C_3$-$C_4$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$—$O_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-05 and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_8$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-lifeof the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains a substitution pattern resulting in α-CH-moiety at the quinoline that has an increased C—H-acidity can exist as a 1,4-dihydroquinoline tautomer, or even a mixture in any amount of the two tautomers, namely:

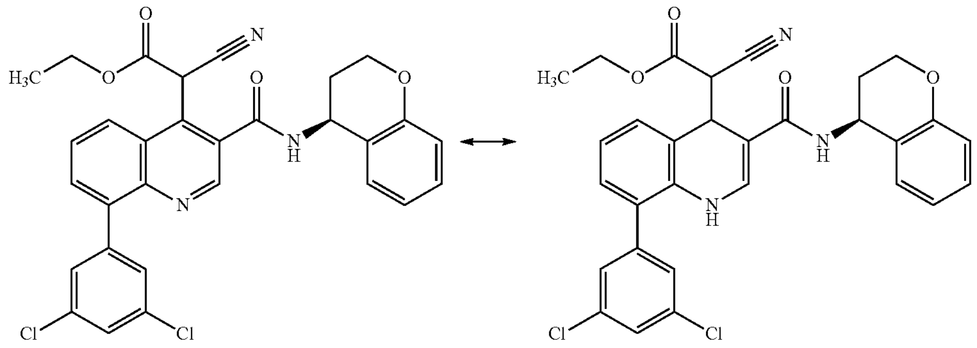 [SMILES: CCOC(=O)C(C#N)c1c(C(=O)N[C@H]2CCOc3ccccc32)cnc2c(-c3cc(Cl)cc(Cl)c3)cccc12 ; CCOC(=O)C(C#N)C1C(C(=O)N[C@H]2CCOc3ccccc32)=CNc2c(-c3cc(Cl)cc(Cl)c3)cccc21]

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quanternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

A is A1 or A2,

A1

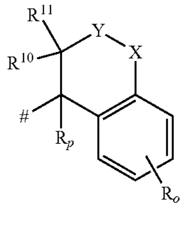

-continued

A2

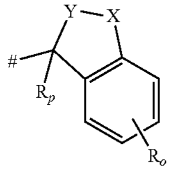

o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_4$-halogenoalkyl having 1 to 5 halogen atoms, $C_1$-$C_4$alkoxy, $C_1$-$C_4$halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$alkenyl, $C_3$-$C_4$alkynyl, $C_1$-$C_4$alkoxy-$C_1$-$C_4$alkyl, $C_3$-$C_6$-cycloalkyl-cyano-$C_1$-$C_4$alkyl, —NH—$C_1$-$C_4$-alkyl, —N($C_1$-$C_4$alkyl)$_2$, $NH_2$—$C_1$-$C_4$alkyl-, $C_4$-alkyl-NH—$C_1$-$C_4$alkyl-, ($C_1$-$C_4$alkyl)$_2$N—$C_1$-$C_4$alkyl-, $C_1$-$C_4$-halogenoalkyl-C(O)— having 1 to 5 halogen atoms, $C_1$-$C_4$alkoxy-C(O)—, benzyloxy-C(O)—, $C_1$-$C_4$alkoxy-$C_1$-$C_4$alkyl-C(O)—, —$SO_2$—$C_1$-$C_4$alkyl, and —$SO_2$—$C_1$-$C_4$halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$halogenoalkyl having 1 to 5 halogen atoms, $C_1$-$C_4$alkoxy, $C_1$-$C_4$halogenoalkoxy having 1 to 5 halogen atoms, —$NH_2$, —NH($C_1$-$C_4$alkyl), —N($C_1$-$C_4$alkyl)$_2$, —$SO_2$—$C_1$-$C_4$alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$alkoxy, $C_1$-$C_4$halogenoalkoxy having 1 to 5 halogen atoms, —$NH_2$, —NH($C_1$-$C_4$alkyl), —N($C_1$-$C_4$alkyl)$_2$, —S(O)—$C_1$-$C_4$-alkyl, —$SO_2$—$C_1$-$C_4$alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$halogenoalkyl having 1 to 5 halogen atoms, $R^2$ is selected from the group consisting of hydrogen, halogen, cyano, —COOH, $C_1$-$C_4$alkoxy-C(O)—, —C(O)—$NH_2$, —C(O)—NH($C_1$-$C_4$-alkyl), —C(O)—N($C_1$-$C_4$alkyl)$_2$,

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SC_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SC_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SC_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SC_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and 4- to 10-membered heterocycloalkyl, $R^3$ is hydrogen, or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (=O), $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$alkoxy-C(O)—, —C(O)—$NH_2$, —C(O)—NH($C_1$-$C_4$alkyl), —C(O)—N($C_1$-$C_4$-alkyl)$_2$, $C_1$-$C_4$alkyl, $C_1$-$C_4$halogenoalkyl having 1 to 5 halogen atoms, $C_1$-$C_4$alkoxy, hydroxy-$C_1$-$C_4$-alkyl, $C_1$-$C_4$halogenoalkoxy having 1 to 5 halogen atoms, $C_3$-$C_6$-cycloalkyl, —$NH_2$, —NH($C_1$-$C_4$alkyl), —N($C_1$-$C_4$alkyl)$_2$, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$alkyl, $C_1$-$C_4$halogenoalkyl having 1 to 5 halogen atoms, $C_1$-$C_4$alkoxy, $C_1$-$C_4$halogenoalkoxy having 1 to 5 halogen atoms, $C_3$-$C_6$-cycloalkyl, —$NH_2$, —NH($C_1$-$C_4$-alkyl), —N($C_1$-$C_4$alkyl)$_2$, —$SO_2$—$C_1$-$C_4$alkyl, —S—$C_1$-$C_4$-halogenoalkyl having 1 to 5 halogen atoms, —S(O)—$C_1$-$C_4$halogenoalkyl having 1 to 5 halogen atoms and —$SO_2$—$C_1$-$C_4$halogenoalkyl having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$alkoxy-C(O)—, —C(O)—$NH_2$, —C(O)—NH($C_1$-$C_4$alkyl), —C(O)—N($C_1$-$C_4$alkyl)$_2$, $C_1$-$C_4$alkyl, $C_1$-$C_4$halogenoalkyl having 1 to 5 halogen atoms, $C_1$-$C_4$alkoxy, hydroxy-$C_1$-$C_4$-alkyl, $C_1$-$C_4$halogenoalkoxy having 1 to 5 halogen atoms, $C_3$-$C_6$-cycloalkyl, —$NH_2$, —NH($C_1$-$C_4$alkyl), —N($C_1$-$C_4$alkyl)$_2$, —$SO_2$—$C_1$-$C_4$alkyl, —S—$C_1$-$C_4$-halogenoalkyl having 1 to 5 halogen atoms, —S(O)—$C_1$-$C_4$halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$alkyl), —N($C_1$-$C_4$alkyl)$_2$;

$C_1$-$C_4$alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$alkoxy-C(O)—, —C(O)—$NH_2$, —C(O)—NH($C_1$-$C_4$alkyl), —C(O)—N($C_1$-$C_4$-alkyl)$_2$, $C_1$-$C_4$alkyl, $C_1$-$C_4$halogenoalkyl having 1 to 5 halogen atoms, $C_1$-$C_4$alkoxy, $C_1$-$C_4$halogenoalkoxy having 1 to 5 halogen atoms, $C_3$-$C_6$-cycloalkyl, —$NH_2$, —NH($C_1$-$C_4$-alkyl), —N($C_1$-$C_4$alkyl)$_2$, —$SO_2$—$C_1$-$C_4$alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$—$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is a substituted phenyl ring of the formula (Q1)

(Q1)

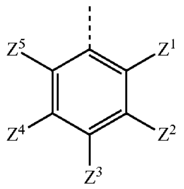

in which:

$Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or Q is a pyridine ring of the formula (Q2)

(Q2)

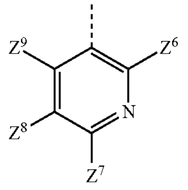

in which:

$Z^6$, $Z^7$, $Z^9$ and $Z^9$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyrimidine ring of the formula (Q3)

(Q3)

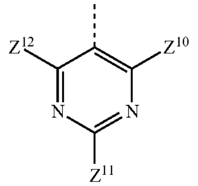

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q4)

(Q4)

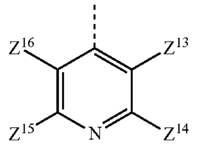

in which:

$Z^{13}$, $Z^{14}$, $Z^{15}$ and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

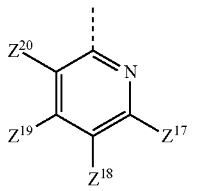

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of the formula (Q6)

(Q6)

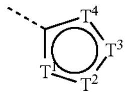

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

(Q7)

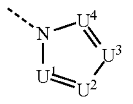

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH, and stereoisomers, tautomers, N-oxides, hydrates, solvates, and salts thereof, and mixtures of same.

In accordance with a third embodiment of the first aspect, the present invention covers compounds of general formula (I), supra, in which:

A is A1 or A2,

A1

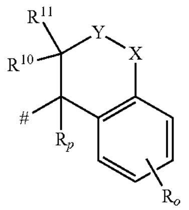

A2

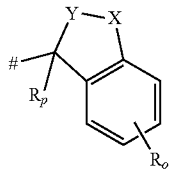

o is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, $R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^9$ together form an oxo group (=O), $R^9$ is $C_1$-$C_4$-alkyl, $R^{10}$ is selected from the group consisting of hydrogen, —OH, $C_1$-$C_4$-alkyl and $C_1$-$C_4$-alkoxy, $R^{11}$ is hydrogen, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of hydrogen;

$C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

Q is a substituted phenyl ring of the formula (Q1)

(Q1)

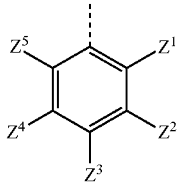

in which:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —$SO_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, or Q is a pyridine ring of the formula (Q2)

(Q2)

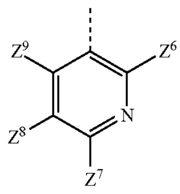

in which:

$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyrimidine ring of the formula (Q3)

(Q3)

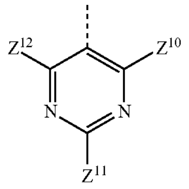

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q4)

(Q4)

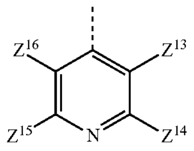

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH ($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

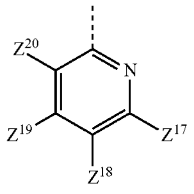

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of the formula (Q6)

(Q6)

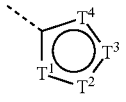

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

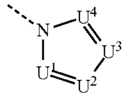

(Q7)

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, wherein when Y is O, S or N—$R^9$, $R^{10}$ is not —OH, and stereoisomers, tautomers, N-oxides, hydrates, solvates, and salts thereof, and mixtures of same.

In accordance with a fourth embodiment of the first aspect, the present invention covers compounds of general formula (I), supra, in which:

A is A1 or A2,

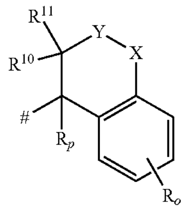

A1

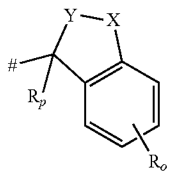

A2 o is 0, 1 or 2,

R is selected from the group consisting of halogen, $C_1$-$C_4$-alkyl and $C_1$-$C_4$-alkoxy, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^1$ is hydrogen or $C_1$-$C_4$-alkyl, $R^2$ is selected from the group consisting of hydrogen, halogen, —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, —OH, cyano, $C_1$-$C_4$-alkoxy-C(O)— and —C(O)—$NH_2$, $C_1$-$C_4$-alkoxy, —$NH_2$, —N($C_1$-$C_4$-alkyl)$_2$, —N($C_1$-$C_4$-alkyl)(C(O)—$C_1$-$C_4$-alkyl); and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH and $C_1$-$C_4$-alkyl, $R^{11}$ is hydrogen, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;

phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and 4- to 10-membered heterocycloalkyl, $R^{15}$ is selected from the group consisting of hydrogen;

$C_1$-$C_4$-alkyl, which is optionally substituted by 1, 2 or 3 substituents independently selected from the group consisting of —OH and —COOH; and a 6-membered heteroaryl, Q is a substituted phenyl ring of the formula (Q1)

(Q1)

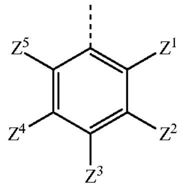

in which:

$Z^1$ and $Z^5$ are independently selected from the group consisting of hydrogen, halogen, $C_1$-$C_4$-alkyl, $C_1$-$C_4$-alkoxy, $C_1$-$C_4$-halogenoalkyl having 1 to 5 halogen atoms $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms, and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, or Q is a pyridine ring of the formula (Q4)

(Q4)

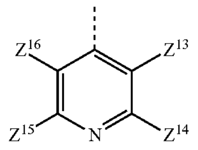

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

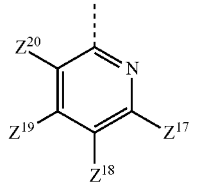

in which:

$Z^{17}$, $Z^{18}$, and $Z^{19}$ are hydrogen, and $Z^{20}$ is halogen, or

Q is a 5-membered aromatic heterocycle of the formula (Q6)

(Q6)

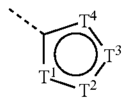

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

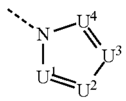

(Q7)

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In accordance with a fifth embodiment of the first aspect, the present invention covers compounds of general formula (I), supra, in which:

A is selected from the group consisting of

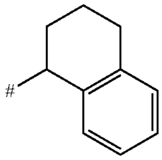
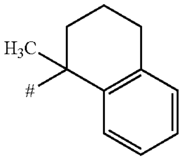
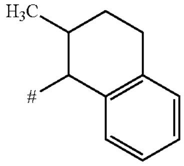
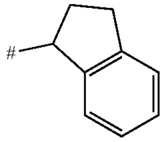
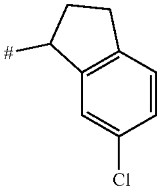
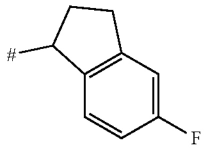
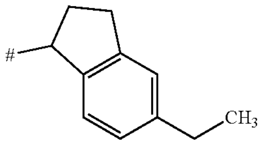
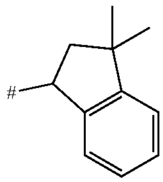
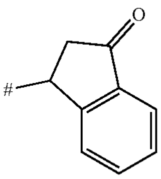
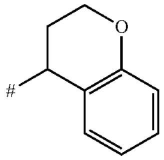
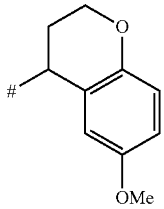
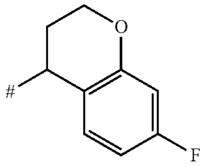

-continued

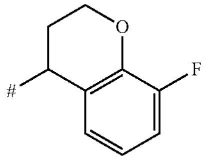
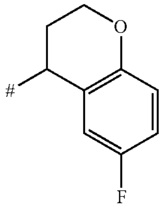
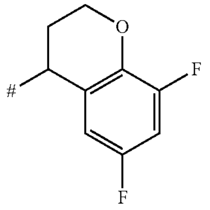
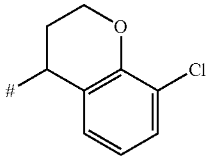
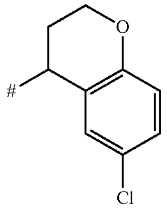
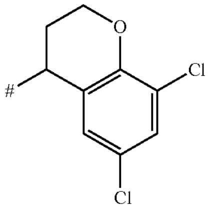
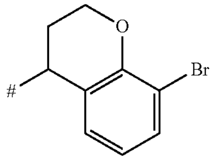
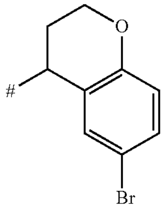
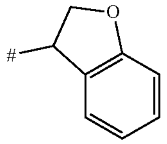
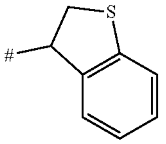
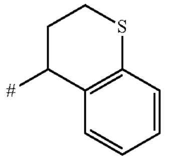
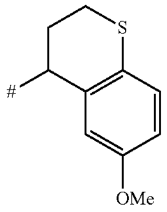
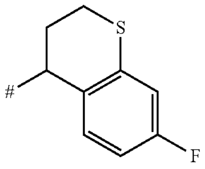
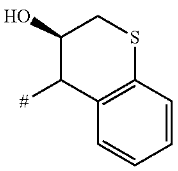
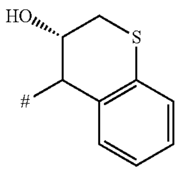
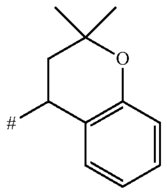
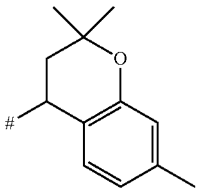

-continued

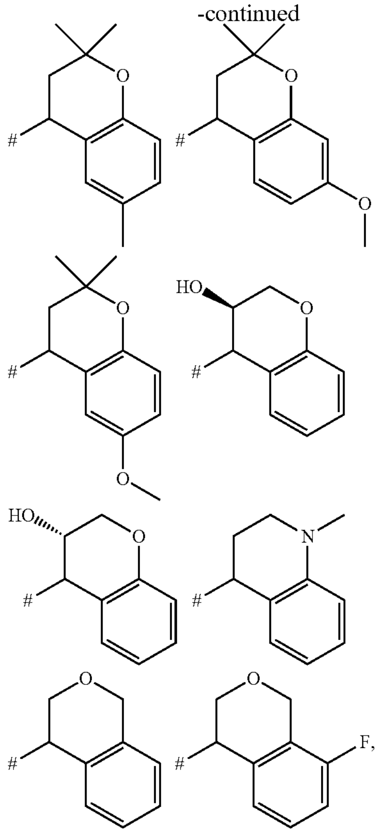

$R^1$ is hydrogen or methyl, $R^2$ is selected from the group consisting of hydrogen, chlorine, iodine, —C(O)—$N(CH_3)_2$,

—$NR^{12}R^{13}$;

—$OR^{14}$;

—$SR^{15}$, —$S(O)R^{15}$, —$SO_2R^{15}$;

methyl, ethyl, propyl, isopropyl, cyclopropyl, cyclobutyl, cyclopentyl, cyclohexyl, ethenyl, propenyl, cyclopentenyl, cyclohexenyl, each of which is optionally substituted by 1 or 2 substituents independently selected from the group consisting of —OH, cyano, ethoxy-C(O)—, —C(O)—$NH_2$, methoxy, $NH_2$, $N(CH_3)_2$, $N(CH_3)(C(O)CH_3)$; and a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,4-triazole, 1,2,3-triazole, 1,2,3,4-tetrazole, pyridine, dihydropyridine, pyrimidine, tetrahydropyrimidine, 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—$NH_2$, methyl, methyl-C(O)—, difluoromethyl, trifluoromethyl, hydroxymethyl-, methoxymethyl-, —$NH_2$, —$NMe_2$, pyrrolidine, $R^3$ is hydrogen or methyl, $R^4$ is selected from the group consisting of hydrogen, fluorine, chlorine, —OH, cyano, methyl, methoxy, trifluoromethyl, trifluoromethoxy and $NH_2$, $R^5$ is selected from the group consisting of hydrogen, fluorine, chlorine, —OH, cyano, methyl, methoxy and trifluoromethyl, $R^6$ is selected from the group consisting of hydrogen, fluorine, chlorine, —OH, cyano, methyl and methoxy, $R^{12}$ and $R^{13}$ are independently selected from the group consisting of hydrogen, —NH(—C(O)-methyl), methoxy;

methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—$NH_2$, —C(O)—$NMe_2$, —NH—C(O)-methyl, methyl, methoxy, cyclopropyl, —$NH_2$, $NMe_2$, S-methyl, S(O)-methyl, $SO_2$-methyl, and $(EtO)_2P(=O)$—;

heterocyclyl-methyl, heterocyclyl-ethyl, wherein the heterocyclyl substituent is selected from the group consisting of oxetane, tetrahydrofurane, tetrahydropyrane pyrrolidine, morpholine, pyrazole, imidazole, 1, 2, 4-oxadiazole, pyridine, each of which is optionally substituted by 1 substituent independently selected from the group consisting of fluorine, chlorine, —OH, oxo and methyl;

phenyl;

2,3-dihydro-1H-indene, and a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, methyl;

$R^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic or a bicyclic heterocycle selected from the group consisting of pyrrolidin and tetrahydropyran, $R^{15}$ is selected from the group consisting of methyl and ethyl, each of which is optionally substituted by 1 substituent independently selected from the group consisting of —OH and —COOH; and pyridine, Q is a substituted phenyl ring of the formula (Q1)

(Q1)

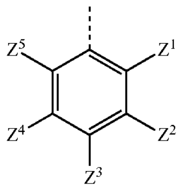

in which:

$Z^1$ and $Z^5$ are independently selected from the group consisting of hydrogen, fluorine, chlorine, methyl, trifluoromethyl and methoxy, $Z^2$ and $Z^4$ are independently selected from the group consisting of hydrogen, fluorine, chlorine, —OH, cyano, methyl, ethyl, tert-butyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy, difluoromethoxy and —$NMe_2$, or Q is a pyridine ring of the formula (Q4)

(Q4)

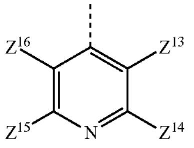

in which:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, $NH_2$, —NHMe —$NMe_2$, —NH—C(O)-Me, morpholinyl, or Q is a pyridine ring of the formula (Q5)

(Q5)

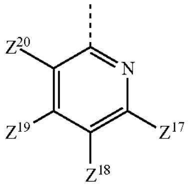

in which:

$Z^{17}$, $Z^{18}$, and $Z^{19}$ are hydrogen, and $Z^{20}$ is fluorine, chlorine, or Q is selected from the group consisting of (Q6-1)

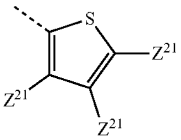

(Q6-2)

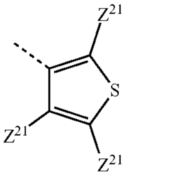

(Q6-3)

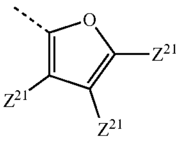

-continued (Q6-4)

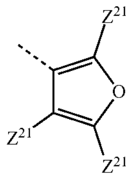

(Q6-5)

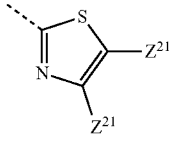

(Q6-6)

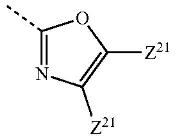

(Q6-7)

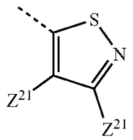

(Q6-8)

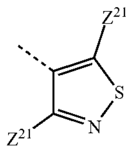

(Q6-9)

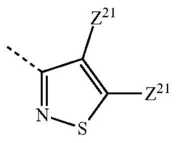

(Q6-10)

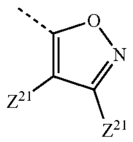

(Q6-11)

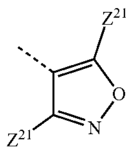

(Q6-12)

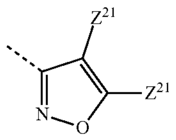

(Q6-13)

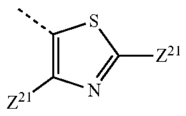

-continued
(Q6-14)
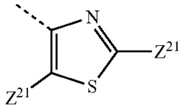
(Q6-15)
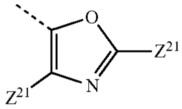
(Q6-16)
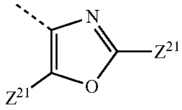
(Q6-17)
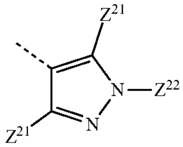
(Q6-18)
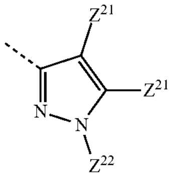
(Q6-19)
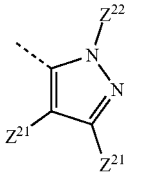
(Q6-20)
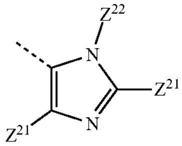
(Q6-21)
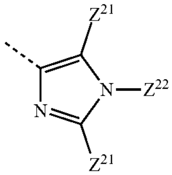
(Q6-22)
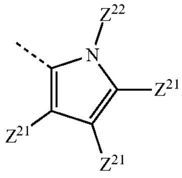
(Q6-23)
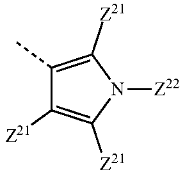
-continued
(Q6-24)
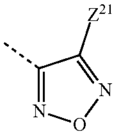
(Q6-25)
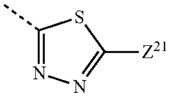
(Q6-26)
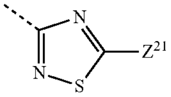
(Q6-27)
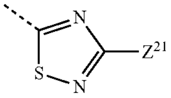
(Q6-28)
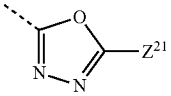
(Q6-29)
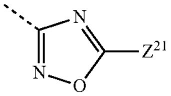
(Q6-30)
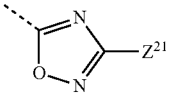
(Q6-31)
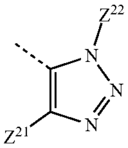
(Q6-32)
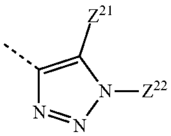
(Q6-33)
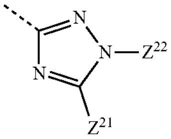
(Q6-34)
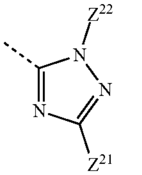
(Q6-35)
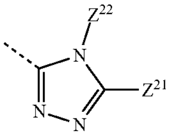

-continued (Q6-36)

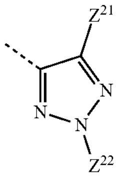

(Q6-37)

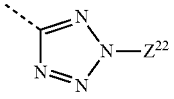

(Q6-38)

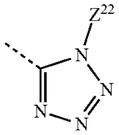

or (Q6-39)

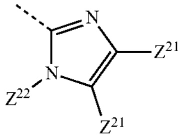

in which:

each $Z^{21}$ is independently selected from the group consisting of hydrogen, fluorine, chlorine, cyano, methyl, trifluoromethyl, methoxy and $Z^{22}$ is hydrogen, methyl, or Q is selected from the group consisting of (Q7-1)

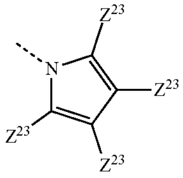

(Q7-2)

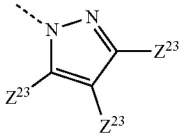

(Q7-3)

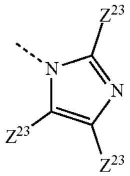

(Q7-4)

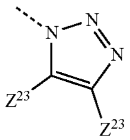

-continued (Q7-5)

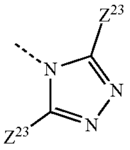

(Q7-6)

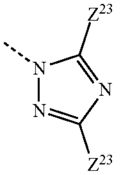

(Q7-7)

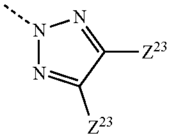

(Q7-8)

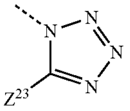

(Q7-9)

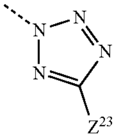

in which:

each $Z^{23}$ is independently selected from the group consisting of hydrogen, fluorine, chlorine, cyano, methyl, trifluoromethyl, methoxy, or Q is selected from the group consisting of

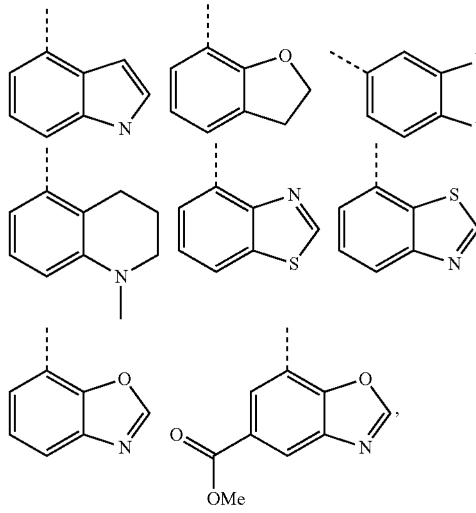

and stereoisomers, tautomers, N-oxides, hydrates, solvates, and salts thereof, and mixtures of same.

In accordance with a sixth embodiment of the first aspect, the present invention covers compounds of general formula (I), supra, in which:

A is selected from the group consisting of

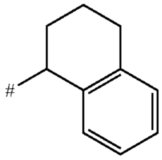
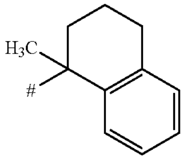
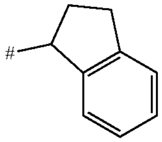
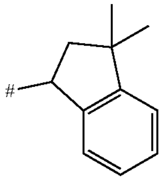
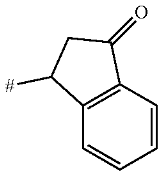
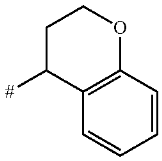
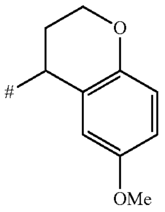
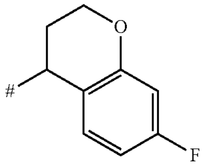
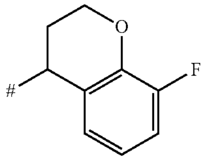
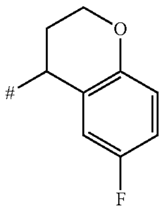
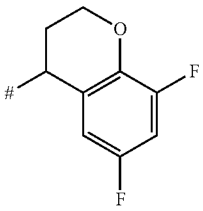
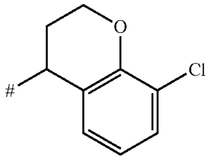
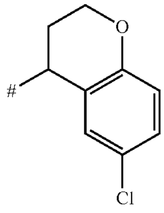
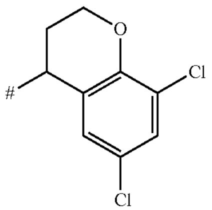
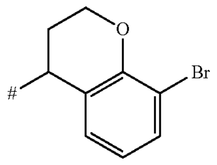
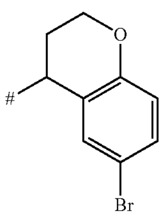
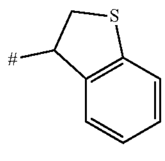
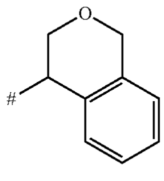

-continued

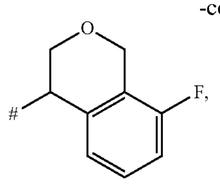

$R^1$ is hydrogen or methyl, $R^2$ is selected from the group consisting of chlorine, iodine, —C(O)—$N(CH_3)_2$,

—$NR^{12}R^{13}$;

—$OR^{14}$;

—$SR^{15}$, —$S(O)R^{15}$, —$SO_2R^{15}$;

methyl, ethyl, propyl, isopropyl, cyclopropyl, cyclobutyl, cyclopentyl, ethenyl, propenyl, each of which is optionally substituted by 1 or 2 substituents independently selected from the group consisting of —OH, cyano, ethoxy-C(O)—, —C(O)—$NH_2$, methoxy, $NH_2$, $N(CH_3)_2$, $N(CH_3)(C(O)CH_3)$; and a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, dihydro-2H-pyrane, 1,2-oxazolidine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,3-triazole, 1,2,3,4-tetrazole, pyridine, dihydropyridine, pyrimidine, tetrahydropyrimidine, each of which is optionally substituted by 1, 2, 3 or 4 substituents independently selected from the group consisting of fluorine, —OH, oxo, —COOH, methoxy-C(O)—, ethoxy-C(O)—, tert-butoxy-C(O)—, —C(O)—$NH_2$, methyl, methyl-C(O)—, difluoromethyl, trifluoromethyl, hydroxymethyl-, methoxymethyl-, —$NH_2$, —$NMe_2$, pyrrolidine, $R^3$ is hydrogen or methyl, $R^4$ is selected from the group consisting of hydrogen, chlorine, fluorine, methyl, methoxy and trifluoromethyl, $R^5$ is selected from the group consisting of hydrogen, chlorine, fluorine, —OH, cyano, methyl, trifluoromethoxy and $NH_2$, $R^6$ is selected from the group consisting of hydrogen, fluorine, chlorine, —OH, cyano, methyl and methoxy, $R^{12}$ and $R^{13}$ are independently selected from the group consisting of hydrogen, —NH(—C(O)-methyl), methoxy;

methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—$NH_2$, —C(O)—$NMe_2$, —NH—C(O)-methyl, methyl, methoxy, cyclopropyl, —$NH_2$, —$NMe_2$, $SO_2$-methyl and $(EtO)_2P(=O)$—;

heterocyclyl-methyl, heterocyclyl-ethyl, wherein the heterocycyl substituent is selected from the group consisting of oxetane, tetrahydrofurane, tetrahydropyrane, pyrrolidine, pyrazole, imidazole, 1, 2, 4-oxadiazole, morpholine, pyridine, each of which is optionally substituted by 1 substituent independently selected from the group consisting of oxo and methyl;

phenyl;

2,3-dihydro-1H-indene, and a monocyclic or a bicyclic heterocycle selected from the group of oxetane, morpholine, tetrahydropyrane, pyridine and pyrazole;

$R^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic or a bicyclic heterocycle selected from the group consisting of pyrrolidin and tetrahydropyran, $R^{15}$ is selected from the group consisting of methyl and ethyl, each of which is optionally substituted by 1 substituent independently selected from the group consisting of —OH and —COOH; and pyridine, Q is a substituted phenyl ring of the formula (Q1)

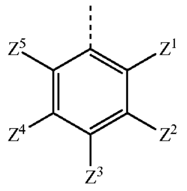

(Q1)

in which:

$Z^1$ and $Z^5$ are independently selected from the group consisting of hydrogen, fluorine, chlorine, methyl, methoxy and trifluoromethyl, $Z^2$ and $Z^4$ are independently selected from the group consisting of hydrogen, fluorine, chlorine, —OH, cyano, methyl, ethyl, tert-butyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy, difluoromethoxy and —$NMe_2$, or Q is a pyridine ring of the formula (Q4)

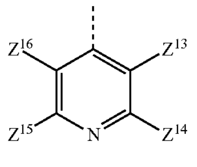

(Q4)

in which:

$Z^{14}$ and $Z^{15}$ are independently selected from the group consisting of hydrogen, fluorine, chlorine, cyano, methyl, methoxy, ethoxy, isopropoxy, hydroxymethyl, $NH_2$, morpholinyl and $Z^{13}$ and $Z^{16}$ are independently selected from the group consisting of hydrogen, fluorine, chlorine, methyl, methoxy, or Q is a pyridine ring of the formula (Q5)

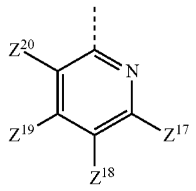

(Q5)

in which:

$Z^{17}$, $Z^{18}$, and $Z^{19}$ are hydrogen, and $Z^{20}$ is fluorine, or

Q is selected from the group consisting of

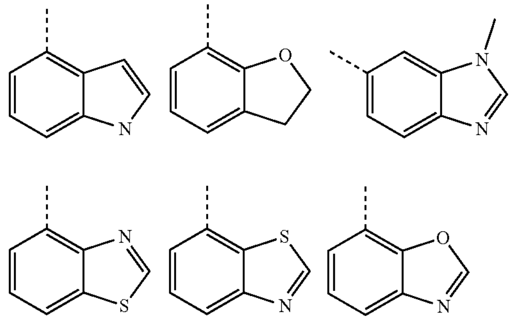

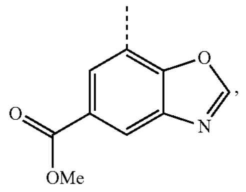

and stereoisomers, tautomers, N-oxides, hydrates, solvates, and salts thereof, and mixtures of same.

In accordance with a seventh embodiment of the first aspect, the present invention covers compounds of general formula (I), supra, in which:

A is selected from the group consisting of

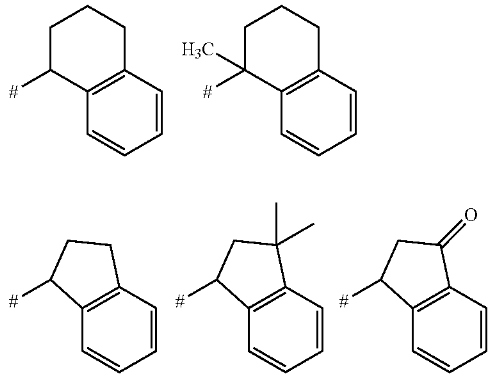

-continued

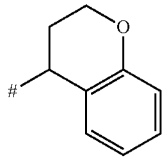
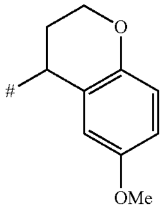

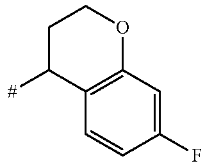
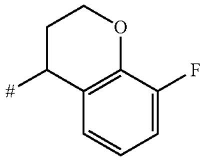

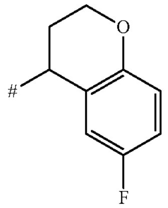
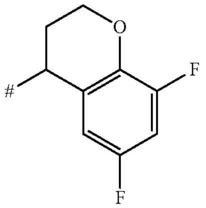

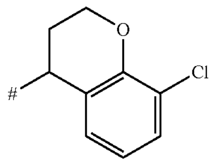
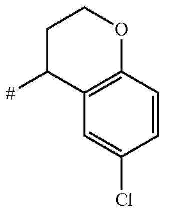

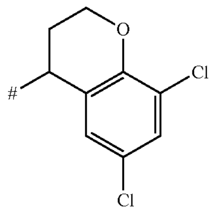
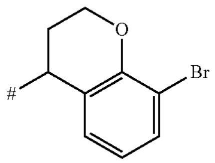

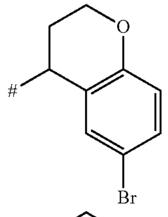
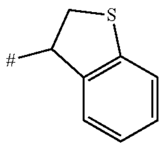

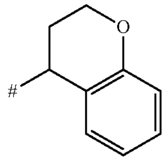
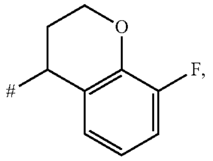

$R^1$ is hydrogen or methyl, $R^2$ is selected from the group consisting of hydrogen, (1S)-2,3-dihydro-1H-inden-1-ylamino, (2,3-difluorobenzyl)oxy, (2-acetamidoethyl)amino, (2-amino-2-oxoethyl) amino, (2-aminoethyl)amino, (2-carboxyethyl)sulfanyl, (2-ethoxy-2-oxoethyl)(methyl)amino, (2-hydroxyethyl) (methyl)amino, (2-hydroxyethyl)amino, hydroxymethyl, methoxymethyl, 2-hydroxyethyl, (2-hydroxyethyl)oxy, (2-hydroxyethyl)sulfanyl, (2-methoxy-2-oxoethyl)amino, (3-methoxy-3-oxopropyl)-methylamino, (2-methoxyethyl)(methyl)amino, (2-methoxyethyl)amino, (2-methoxyethyl)oxy, (2R)-2-(hydroxymethyl)pyrrolidin-1-yl, (2R)-2-(methoxycarbonyl)pyrrolidin-1-yl, (2R)-2-(methoxymethyl)pyrrolidin-1-yl, (2R)-2-(tert-butoxycarbonyl)pyrrolidin-1-yl, (2R)-2-carboxylatopyrrolidin-1-yl, (2R)-2-carboxypyrrolidin-1-yl, (2R,6S)-2,6-dimethylmorpholin-4-yl, 2-(trifluoromethyl)morpholin-4-yl, (2rac)-2-carboxpyrrolidin-1-yl, (2S)-2-(ethoxycarbonyl) pyrrolidin-1-yl, (2S)-2-(hydroxymethyl)pyrrolidin-1-yl, (2S)-2-(methoxycarbonyhpyrrolidin-1-yl, (2S)-2-(methoxymethyl)pyrrolidin-1-yl, (2S)-2-(tert-butoxycarbonyhpyrrolidin-1-yl, (2S)-2-carbamoylpyrrolidin-1-yl, (2S)-2-carboxypyrrolidin-1-yl, (2S)-2-methyl-2,3-dihydro-1H-indol-1-yl, (2S)-2-methylmorpholin-4-yl, (2-tert-butoxy-2-oxoethyl)(methyl)amino, (2-tert-butoxy-2-oxoethyl)amino, 2,2-difluoroethyl(methyl)amino, (3,3,3-trifluoropropyl)amino, (3,3-dimethylbutyl)oxy, (3-amino-3-oxopropyl)(methyl)amino, (3-amino-3-oxopropyl)amino, (3-fluorobenzyl)oxy, (3-methoxy-3-methylbutyl)oxy, (3-methoxybenzyl)oxy, (3R)-3-(hydroxymethyl)pyrrolidin-1-yl, (3R)-3-(methoxycarbonyl) pyrrolidin-1-yl, (3R)-3-aminopyrrolidin-1-yl, (3R)-3-carboxypyrrolidin-1-yl, (3R)-3-hydroxpyrrolidin-1-yl, (3R)-pyrrolidin-3-yloxy, (3rac,4rac)-3-amino-4-fluoropyrrolidin-1-yl, (3S)-3-(dimethylamino)pyrrolidin-1-yl, (3S)-3-(hydroxymethyl)pyrrolidin-1-yl, (3S)-3-(methoxycarbonyhpyrrolidin-1-yl, (3S)-3-hydroxypyrrolidin-1-yl, (carboxylatomethyl)amino, (carboxymethyl) (methyl)amino, (carboxyethyl)amino, (cyclopentylmethyl)oxy, (cyclopropylmethyl)(methyl) amino, (pyridin-2-ylmethyl)amino, (rac)-3-hydroxpyrrolidin-1-yl, [(1R,3S)-3-amino-2,2-dimethylcyclopropyl] amino, [(2R)-1-hydroxybutan-2-yl]amino, [(2S)-1-amino-1-oxopropan-2-yl]amino, [(5-methyl-1,2,4-oxadiazol-3-yl)methyl]amino, [(diethoxyphosphoryl) methyl](methyl)amino, [2-(1H-pyrazol-1-yl)ethyl]amino, 2-(1H-imidazol-1-yl)ethylamino, 2-(1H-imidazol-1-yl) ethyl-methylamino, [2-(cyclopropylamino)ethyl]amino, [2-(dimethylamino)ethyl]amino, [2-(pyrrolidin-1-yl) ethyl]amino, [3-(dimethylamino)-3-oxopropyl]amino, 1,1-dioxidothiomorpholin-4-yl, 1,2-oxazolidin-2-yl, 1,3-dihydro-2H-isoindol-2-yl, 1-cyano-2-ethoxy-2-oxoethyl, 1H-1,2,3-triazol-1-yl, 1H-imidazol-1-yl, 1H-pyrazol-1-yl, 1H-pyrazol-4-yl, 1H-pyrazol-4-ylamino, 2,2-dimethylmorpholin-4-yl, 2,2-dimethylpyrrolidin-1-yl, 2,4-dimethyl-3,5-dioxo-1,2,4-triazolidin-1-yl, 2-acetylhydrazino, 2-amino-2-oxoethyl, 2H-1,2,3-triazol-2-yl, 1H-tetrazol-5-yl, 3-(pyrrolidin-1-yl)azetidin-1-yl, 3,3-difluoroazetidin-1-yl, 3,3-difluoropyrrolidin-1-yl, 3,4-dihydroisoquinolin-2(1H)-yl, 3,9-dioxa-7-azabicyclo[3.3.1]non-7-yl, 3-fluoroazetidin-1-yl, 3-hydroxyazetidin-1-yl, 3-methylazetidin-1-yl, 3-oxopyrazolidin-1-yl, 1-(difluoromethyl)-1H-pyrazol-4-yl, 4-(trifluoromethyl)-1H-pyrazol-1-yl, 1-methyl-piperidin-4-yl, 4-fluoropiperidin-1-yl, 4,4-difluoropiperidin-1-yl, 4-acetylpiperazin-1-yl, 4-oxoimidazolidin-1-yl, 6-oxa-3-azabicyclo[3.1.1]hept-3-yl, 8-oxa-3-azabicyclo[3.2.1]oct-3-yl, amino, anilino, azetidin-1-yl, benzyl(methyl)amino, bis(2-methoxyethyl)amino, chlorine, iodine, cyanomethyl, cyclobutyl(methyl)amino, cyclopentyloxy, cyclopropyl, cyclobutyl, cyclopentyl, cyclopropyl(ethyl)amino, cyclopropyl(methyl)amino, cyclopropylamino, diethylamino, dimethylamino, dimethylaminocarbonyl, aminomethyl, 2-aminoethyl, (dimethylamino)methyl, 2-(dimethylamino)ethyl, [acetyl(methyl)amino]methyl, ethenyl, ethyl, ethyl(2-methoxyethyl)amino, ethylamino, ethyloxy, ethylsulfanyl, ethylsulfinyl, ethylsulfonyl, ethyl(methyl)

amino, isobutyl(methyl)amino, isopropyl(methyl)amino, isopropyl, isopropyloxy, methoxy(methyl)amino, methoxyamino, methyl, methyl(2-methylsulfonylethyl) amino, methyl-oxolan-3-yl]methyl]amino, methyl(oxan-4-ylmethyl)amino, methyl(1-phenylethyl)amino, methyl (2,2,2-trifluoroethyl)amino, oxetan-3-ylmethylamino, methyl(oxetan-3-yl)amino, methyl(phenyl)amino, methyl [2-(2-oxopyrrolidin-1-yl)ethyl]amino, methyl[2-(morpholin-4-yl)ethyl]amino, methylamino, methyloxy, methylsulfanyl, morpholin-4-yl, morpholin-4-ylamino, nitrilomethyl, prop-1-en-2-yl, propyl, propylamino, pyridin-4-yl, pyridin-2-ylsulfanyl, pyridin-4-ylamino, pyrrolidin-1-yl, pyrrolidin-3-yl, oxetan-3-yl, tetrahydrofuran-3-yl, 3,6-dihydro-2H-pyran-4-yl, tetrahydropyran-4-yl, tetrahydro-2H-pyran-4-ylamino, tetrahydro-2H-pyran-4-yloxy, 2-aminopyrimidin-5-yl, 1,3-dimethyl-2,4-dioxo-1,2,3,4-tetrahydropyrimidin-5-yl, 3-fluoro-2-oxo-1,2-dihydropyridin-5-yl, 2-oxo-1,2-dihydropyridin-5-yl, 3-thienyl and thiomorpholin-4-yl, $R^3$ is hydrogen or methyl, $R^4$ is selected from the group consisting of hydrogen, chlorine, fluorine, —OH, cyano, methyl, methoxy, trifluoromethyl, trifluoromethoxy and $NH_2$, $R^5$ is selected from the group consisting of hydrogen, chlorine, fluorine, —OH, cyano, methyl, methoxy and trifluoromethyl, $R^6$ is selected from the group consisting of hydrogen, fluorine, chlorine, —OH, cyano, methyl and methoxy, Q is selected from the group consisting of phenyl, 1,3-benzothiazol-4-yl, 1,3-benzothiazol-7-yl, 1,3-benzoxazol-7-yl, 1H-indol-4-yl, 1-methyl-1H-benzimidazol-6-yl, 2,5-bis(trifluoromethyl)phenyl, 2,3,4-trifluorophenyl, 2,3,5-trichlorophenyl, 2,3,5-trifluorophenyl, 2,3,6-trifluorophenyl, 2,3-dichlorophenyl, 2,3-dichloro-5-cyanophenyl, 2,3-dichloro-5-hydroxyphenyl, 2,3-dihydro-1-benzofuran-7-yl, 2,3-difluorophenyl, 2,4,5-trifluorophenyl, 2,4,6-trifluoro-3-methoxyphenyl, 2,4-difluoro-3-hydroxyphenyl, 2,4-difluoro-3-methoxyphenyl, 2,5-dichlorophenyl, 2-chloro-5-cyanophenyl, 2-chloro-5-methylphenyl, 2,5-difluoro-4-methoxyphenyl, 2,6-difluorophenyl, 2-chloro-6-methylpyridin-4-yl, 3-methylpyridin-4-yl, 2,6-dimethylpyridin-4-yl, 2-chloro-3-fluorophenyl, 2-chloro-4-(dimethylamino) phenyl, 2-chloro-4-fluorophenyl, 2-chloro-5-fluorophenyl, 2-chloro-6-fluorophenyl, 2-chlorophenyl, 2-chloropyridin-4-yl, 3-chloropyridin-4-yl, 2,3-dichloropyridin-4-yl, 2,5-dichloropyridin-4-yl, 2,6-dichloropyridin-4-yl, 3,5-dichloropyridin-4-yl, 2,6-difluoropyridin-4-yl, 3,5-difluoropyridin-4-yl, 2-chloro-3-fluoropyridin-4-yl, 2-cyanopyridin-4-yl, 3-chloro-2-methoxypyridin-4-yl, 5-chloro-2-methoxypyridin-4-yl, 5-fluoro-2-methoxypyridin-4-yl, 5-fluoro-2-isopropyloxypyridin-4-yl, 2,3-dimethoxypyridin-4-yl, 2,6-dimethoxypyridin-4-yl, 2-fluoro-5-methylphenyl, 3-fluoro-5-methylphenyl, 2-fluoro-3-(trifluoromethoxy)phenyl, 2-fluoro-3-(trifluoromethyl)phenyl, 5-fluoro-2-(trifluoromethyl)phenyl, 3-cyano-5-methylphenyl, 2-fluoropyridin-4-yl, 2-ethoxy-5-fluoropyridin-4-yl, 2-(hydroxymethyl)pyridin-4-yl, 2-methylypyridin-4-yl, 2-methoxypyridin-4-yl, 3-methoxypyridin-4-yl, 2-aminopyridin-4-yl, 2-morpholin-4-ylpyridin-4-yl, 3-(dimethylamino)-2,4-difluorophenyl, 3-(dimethylamino)phenyl, 3-(methylamino)phenyl, 3-(trifluoromethyly)phenyl, 3-(trifluoromethoxy)phenyl, 3,4,5-trifluorophenyl, 3,4-dichloro-5-(dimethylamino) phenyl, 3,4-dichlorophenyl, 3,4-difluoro-2-methoxyphenyl, 3,4-difluorophenyl, 3,5-dichloro-4-(dimethylamino) phenyl, 3,5-dichloro-4-fluorophenyl, 3,5-dichlorophenyl, 3,5-difluorophenyl, 4-(difluoromethoxy)-3,5-difluorophenyl, 2,5-dimethylphenyl, 3,5-dimethylphenyl, 3-tert-butyl-5-methylphenyl, 5-tert-butyl-2-chloro-3-methylphenyl, 3-chloro-2-fluoro-5-methylphenyl, 3-chloro-2-fluorophenyl, 3-chloro-2-methylphenyl, 3-chloro-4-(dimethylamino)-5-fluorophenyl, 3-chloro-4-(dimethylamino)phenyl, 3-chloro-4-fluorophenyl, 3-chloro-4-methylphenyl, 3-chloro-5-(dimethylamino) phenyl, 3-chloro-5-(methylsulfanyl)phenyl, 3-chloro-5-(morpholin-4-yl)phenyl, 2-chloro-3-(trifluoromethyl) phenyl, 2-methyl-5-(trifluoromethyl)phenyl, 3-chloro-5-(trifluoromethyl)phenyl, 3-chloro-5-ethylphenyl, 3-chloro-5-fluorophenyl, 3-chloro-5-methoxyphenyl, 3-chloro-5-methylphenyl, 3-chlorophenyl, 3-fluoro-2-methylphenyl, 3-fluoro-4-methoxyphenyl, 3-fluoro-5-methylphenyl, 3-fluoropyridin-2-yl, 3-fluoropyridin-4-yl, 4-chloro-3-(dimethylamino)phenyl, 4-fluoro-3-methoxyphenyl, 5-(methoxycarbonyl)-1,3-benzoxazol-7-yl, 5-chloro-2,4-difluorophenyl, 5-chloro-2-fluoro-3-methylphenyl, 5-chloro-2-fluoro-4-methylphenyl, 5-chloro-2-fluorophenyl, 5-chloro-2-methoxyphenyl, 5-fluoro-2-methylphenyl, 5-fluoro-2-methoxyphenyl, 5-chloro-1H-imidazol-2-yl, 3,5-diethylphenyl, 2-chloro-3,5-diethylphenyl, 3-chloro-2-thienyl, 4-chloro-2-thienyl, 5-chloro-2-thienyl, 2,5-dichloro-3-thienyl, 5-fluoro-2-thienyl, 5-cyano-2-thienyl, 5-cyano-4-methyl-2-thienyl, 5-methyl-2-thienyl, 2,5-dimethyl-3-thienyl, 5-(trifluoromethyl)-2-thienyl and 2-methyl-1,3-thiazol-5-yl, and stereoisomers, tautomers, N-oxides, hydrates, solvates, and salts thereof, and mixtures of same.

In accordance with an eight embodiment of the first aspect, the present invention covers compounds of general formula (I), supra, in which:

A is A3 or A4

A3

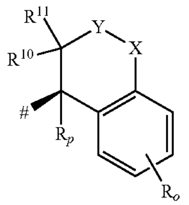

A4

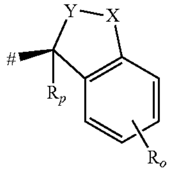

o is 0 or 1,

R is selected from the group consisting of halogen, $C_1$-$C_4$-alkyl and $C_1$-$C_4$-alkoxy, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^1$ is hydrogen or $C_1$-$C_4$-alkyl, $R^2$ is selected from the group consisting of hydrogen, halogen, —C(O)—N($C_1$-$C_4$-alkyl$)_2$;

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, —OH, cyano, $C_1$-$C_4$-alkoxy-C(O)— and —C(O)—$NH_2$$C_1$-$C_4$-alkoxy, —$NH_2$, —N($C_1$-$C_4$-alkyl)$_2$, —N($C_1$-$C_4$-alkyl)(C(O)—$C_1$-$C_4$-alkyl), and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $NH_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH and $C_1$-$C_4$-alkyl, $R^{11}$ is hydrogen, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;

phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and 4- to 10-membered heterocycloalkyl, $R^{15}$ is selected from the group consisting of hydrogen;

$C_1$-$C_4$-alkyl, which is optionally substituted by 1, 2 or 3 substituents independently selected from the group consisting of —OH and —COOH; and a 6-membered heteroaryl, Q is a substituted phenyl ring of the formula (Q1)

(Q1)

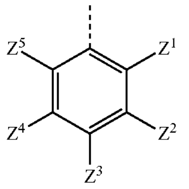

in which:

$Z^1$ and $Z^5$ are independently selected from the group consisting of hydrogen, halogen, $C_1$-$C_4$-alkyl, $C_1$-$C_4$-alkoxy and $C_1$-$C_4$-halogenoalkyl having 1 to 5 halogen atoms, $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, or Q is a pyridine ring of the formula (Q4)

(Q4)

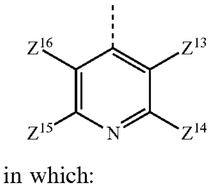

in which:

$Z^{13}$, $Z^{14}$, $Z^{15}$ and $Z^{16}$ are independently selected from the group consisting of hydrogen, halogen, cyano, $C_1$-$C_4$- alkyl, $C_1$-$C_4$-alkoxy, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

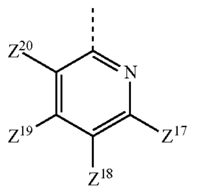

in which:

$Z^{17}$, $Z^{18}$, and $Z^{19}$ are hydrogen, and $Z^{20}$ is halogen, or

Q is a 5-membered aromatic heterocycle of the formula (Q6)

(Q6)

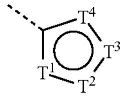

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

(Q7)

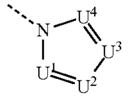

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

Further embodiments of the first aspect of the present invention:

In a further embodiment of the first aspect, the present invention covers compounds of formula (I), supra, in which:

A is A1 or A2,

A1

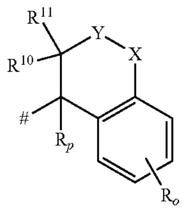

A2

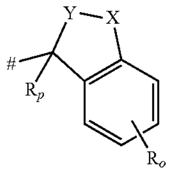

o is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is hydrogen, X, Y are independently selected from the group consisting of $CR^7R^8$, O, S, and N—$R^9$, wherein at least one of X and Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, $R^9$ is $C_1$-$C_4$-alkyl, $R^{10}$ is selected from the group consisting of hydrogen, —OH, $C_1$-$C_4$-alkyl and $C_1$-$C_4$-alkoxy, and $R^{11}$ is hydrogen, wherein when Y is O, S or N—$R^9$, $R^{10}$ is not —OH, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

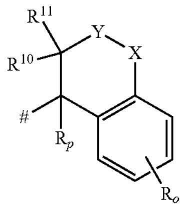

-continued

A2

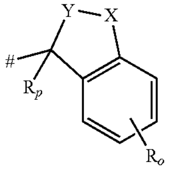

o is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH, $C_1$-$C_4$-alkyl and $C_1$-$C_4$-alkoxy, and $R^{11}$ is hydrogen, wherein when Y is O, S or N—$R^9$, $R^{10}$ is not —OH, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

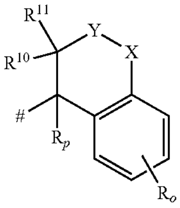

A2

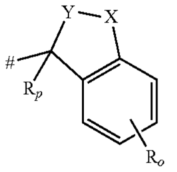

o is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is hydrogen, X, Y are independently selected from the group consisting of $CR^7R^8$, O, and S, wherein at least one of X and Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^{10}$ is selected from the group consisting of hydrogen, —OH, $C_1$-$C_4$-alkyl and $C_1$-$C_4$-alkoxy, and $R^{11}$ is hydrogen, wherein when Y is O, S or N—$R^9$, $R^{10}$ is not —OH, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

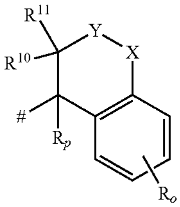

A2

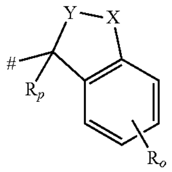

o is 0 or 1,

R is selected from the group consisting of halogen, $C_1$-$C_4$-alkyl and $C_1$-$C_4$-alkoxy, $R_p$ is hydrogen, X is selected from the group consisting of $CR^7R^8$, O, S, and N—$R^9$, Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, $R^9$ is $C_1$-$C_4$-alkyl, $R^{10}$ is selected from the group consisting of hydrogen, —OH and $C_1$-$C_4$-alkyl, and $R^{11}$ is hydrogen, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

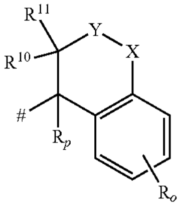

A2

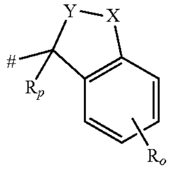

o is 0 or 1,

R is selected from the group consisting of halogen, $C_1$-$C_4$-alkyl and $C_1$-$C_4$-alkoxy, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH and $C_1$-$C_4$-alkyl, and $R^{11}$ is hydrogen, and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

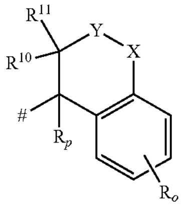

A1

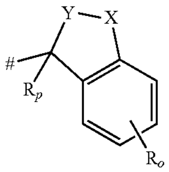

A2 o is 0 or 1,

R is selected from the group consisting of halogen, $C_1$-$C_4$-alkyl and $C_1$-$C_4$-alkoxy, $R_p$ is hydrogen, X is selected from the group consisting of $CR^7R^8$, O and S, Y is $CR^7R^8$ or O, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^{10}$ is selected from the group consisting of hydrogen, —OH and $C_1$-$C_4$-alkyl, and $R^{11}$ is hydrogen, and stereoisomers, tautomers, N-oxides, hydrates, solvates, and salts thereof, and mixtures of same.

In a further embodiment of the first aspect, the present invention covers compounds of formula (I), supra, in which:

A is selected from the group consisting of

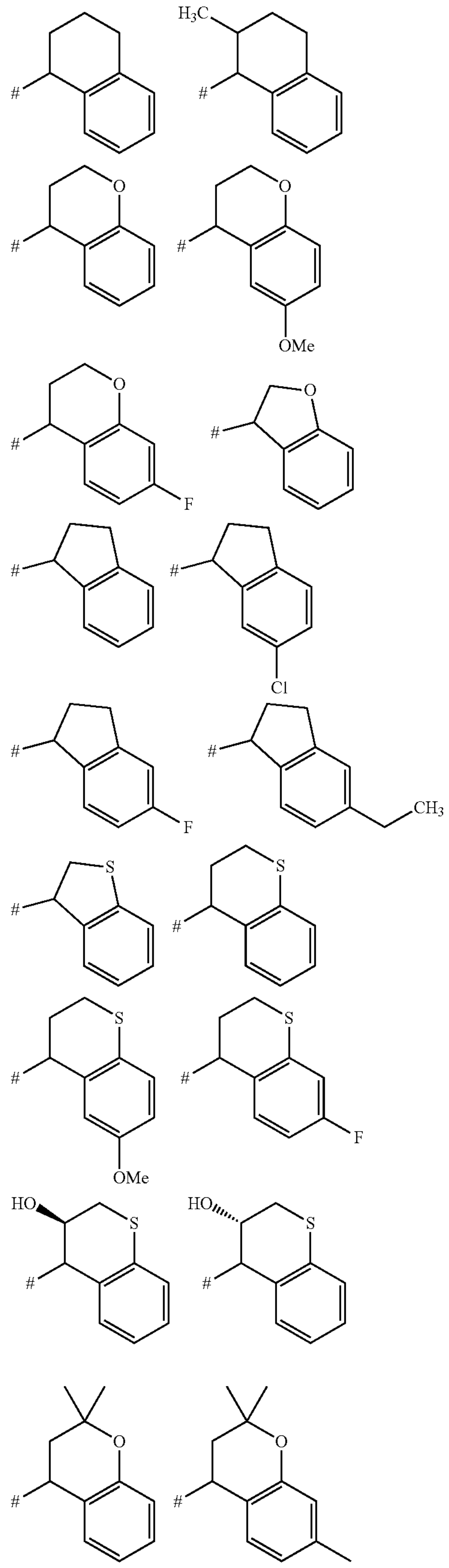

-continued
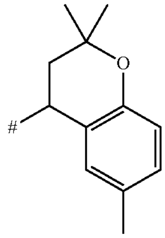
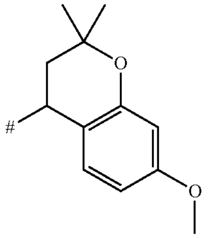
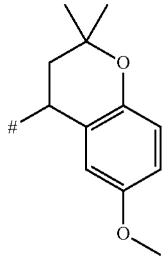
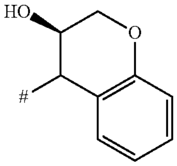
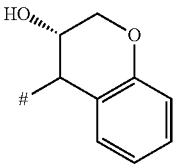
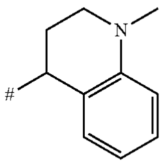
and stereoisomers, tautomers, N-oxides, hydrates, solvates, and salts thereof, and mixtures of same.
In a further embodiment of the first aspect, the present invention covers compounds of formula (I), supra, in which:
A is selected from the group consisting of
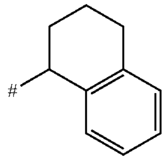
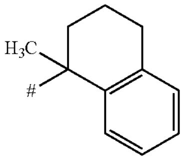
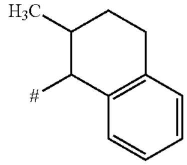
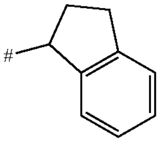
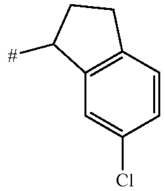
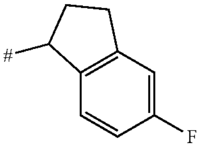
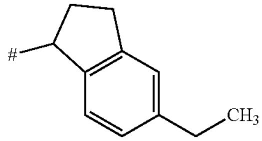
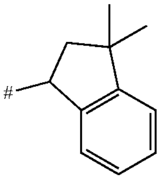
-continued
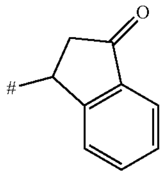
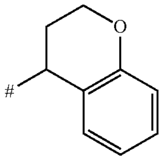
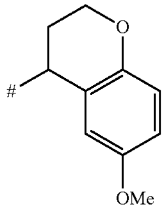
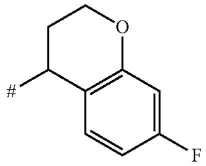
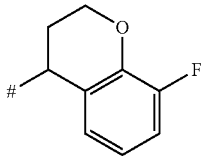
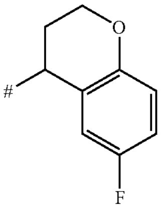
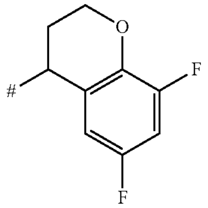
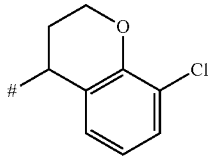
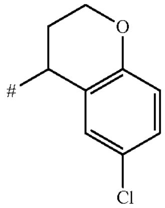
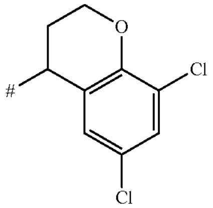
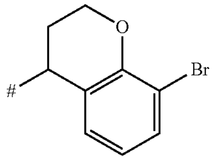
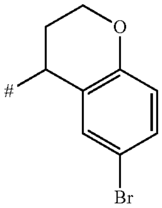
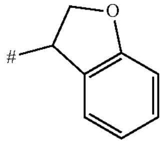
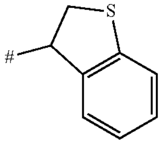
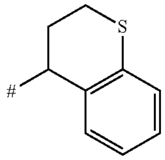
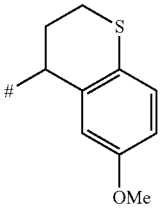
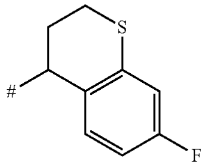
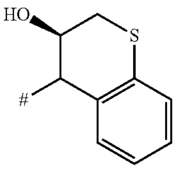

-continued

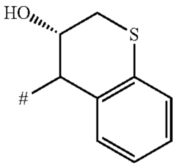
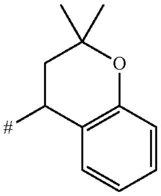
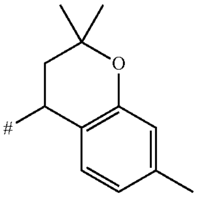
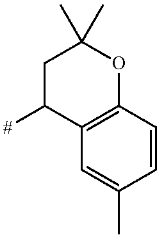
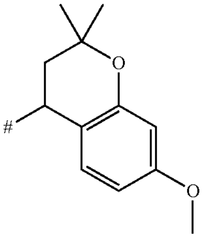
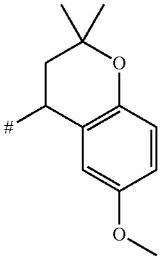
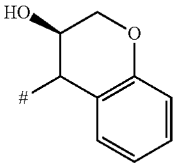
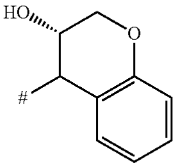
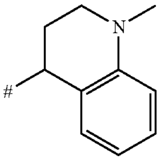
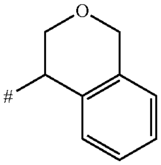
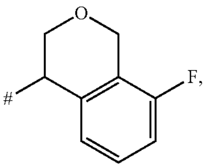

and stereoisomers, tautomers, N-oxides, hydrates, solvates, and salts thereof, and mixtures of same.

In a further embodiment of the first aspect, the present invention covers compounds of formula (I), supra, in which:

A is selected from the group consisting of

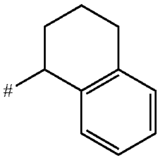
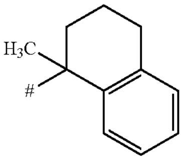

-continued

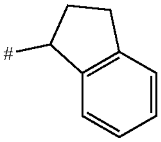
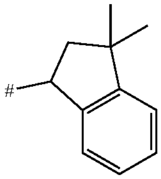
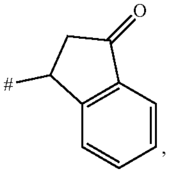
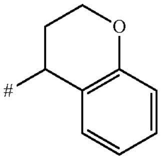
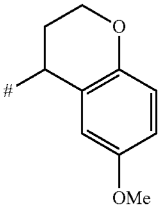
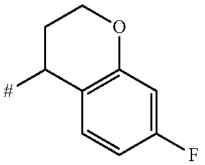
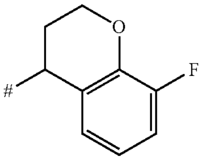
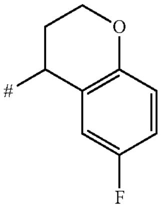
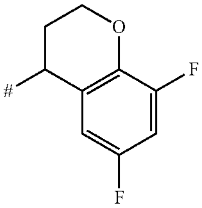
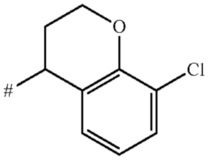
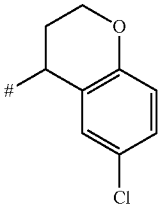
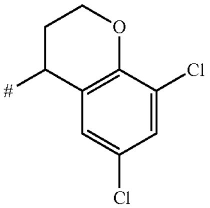
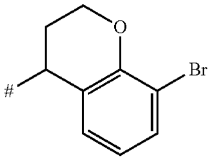
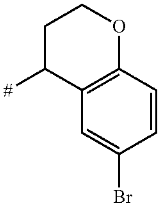
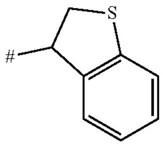
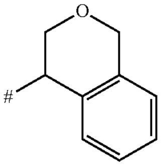
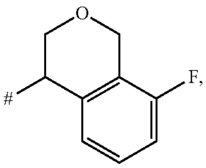

and stereoisomers, tautomers, N-oxides, hydrates, solvates, and salts thereof, and mixtures of same.

In a further embodiment of the first aspect, the present invention covers compounds of formula (I), supra, in which:

$R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$,

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, and 4- to 10-membered heterocycloalkyl, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of hydrogen;

$C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

and stereoisomers, tautomers, N-oxides, hydrates, solvates, and salts thereof, and mixtures of same.

In a further embodiment of the first aspect, the present invention covers compounds of formula (I), supra, in which:

$R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$,

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, and 4- to 10-membered heterocycloalkyl, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of hydrogen;

$C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

and stereoisomers, tautomers, N-oxides, hydrates, solvates, and salts thereof, and mixtures of same.

In a further embodiment of the first aspect, the present invention covers compounds of formula (I), supra, in which:

$R^2$ is selected from the group consisting of hydrogen, halogen,

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, cyano, $C_1$-$C_4$-alkoxy-C(O)— and —C(O)—$NH_2$; and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, alkyl, —S(O)—$C_1$-$C_4$-alkyl, —$SO_2$—$C_1$-$C_4$-alkyl, and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;

phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and 4- to 10-membered heterocycloalkyl, $R^{15}$ is selected from the group consisting of hydrogen;

$C_1$-$C_4$-alkyl, which is optionally substituted by 1, 2 or 3 substituents independently selected from the group consisting of —OH and —COOH; and a 6-membered heteroaryl, and stereoisomers, tautomers, N-oxides, hydrates, solvates, and salts thereof, and mixtures of same.

In a further embodiment of the first aspect, the present invention covers compounds of formula (I), supra, in which:

$R^2$ is selected from the group consisting of hydrogen, halogen, —C(O)—N($C_1$-$C_4$-alkyl)$_2$

—$NR^{12}R^{13}$;

—$OR^{14}$;

—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, —OH, cyano, $C_1$-$C_4$-alkoxy-C(O)— and —C(O)—$NH_2$, $C_1$-$C_4$-alkoxy, —$NH_2$, —N($C_1$-$C_4$-alkyl)$_2$, —N($C_1$-$C_4$-alkyl)(C(O)—$C_1$-$C_4$-alkyl); and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;

phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and 4- to 10-membered heterocycloalkyl, $R^{15}$ is selected from the group consisting of hydrogen;

$C_1$-$C_4$-alkyl, which is optionally substituted by 1, 2 or 3 substituents independently selected from the group consisting of —OH and —COOH; and a 6-membered heteroaryl, and stereoisomers, tautomers, N-oxides, hydrates, solvates, and salts thereof, and mixtures of same.

In a further embodiment of the first aspect, the present invention covers compounds of formula (I), supra, in which:

$R^2$ is selected from the group consisting of hydrogen, chlorine,

—$NR^{12}R^{13}$;

—$OR^{14}$;

—$SR^{15}$, —S(O)$R^{15}$, —$SO_2R^{15}$;

methyl, ethyl, propyl, isopropyl, cyclopropyl, cyclohexyl, propenyl, cyclopentenyl, cyclohexenyl, each of which is optionally substituted by 1 or 2 substituents independently selected from the group consisting of cyano, ethoxy-C(O)—, and —C(O)—$NH_2$; and a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, cyano —OH, oxo, —COOH, methoxy-C(O)—, ethoxy-C(O)—, tert-butoxy-C(O)—, —C(O)—$NH_2$, methyl, methyl-C(O)—, trifluoromethyl, hydroxymethyl-, methoxymethyl-, —$NH_2$, —$NMe_2$, pyrrolidine, $R^{12}$ and $R^{13}$ are independently selected from the group consisting of hydrogen, —NH(—C(O)-methyl), methoxy;

methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—$NH_2$, —C(O)—$NMe_2$, —NH—C(O)-methyl, methyl, methoxy, cyclopropyl, —$NH_2$, $NMe_2$, S-methyl, S(O)-methyl, $SO_2$-methyl, and $(EtO)_2P(=O)$—;

heterocyclyl-methyl, heterocyclyl-ethyl, wherein the heterocyclyl substituent is selected from the group consisting of pyrrolidine, morpholine, pyrazole, 1, 2, 4-oxadiazole, pyridine, each of which is optionally substituted by 1 substituent independently selected from the group consisting of fluorine, chlorine, —OH, oxo and methyl;

phenyl;

2,3-dihydro-1H-indene, and a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, methyl;

$R^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic or a bicyclic heterocycle selected from the group consisting of pyrrolidin and tetrahydropyran, $R^{15}$ is selected from the group consisting of methyl and ethyl, each of which is optionally substituted by 1 substituent independently selected from the group consisting of —OH and —COOH; and pyridine, and stereoisomers, tautomers, N-oxides, hydrates, solvates, and salts thereof, and mixtures of same.

In a further embodiment of the first aspect, the present invention covers compounds of formula (I), supra, in which:

$R^2$ is selected from the group consisting of hydrogen, chlorine, iodine, —C(O)—$N(CH_3)_2$,

—$NR^{12}R^{13}$;

—$OR^{14}$;

—$SR^{15}$, —$S(O)R^{15}$, —$SO_2R^{15}$;

methyl, ethyl, propyl, isopropyl, cyclopropyl, cyclobutyl, cyclopentyl, cyclohexyl, ethenyl, propenyl, cyclopentenyl, cyclohexenyl, each of which is optionally substituted by 1 or 2 substituents independently selected from the group consisting of —OH, cyano, ethoxy-C(O)—, —C(O)—$NH_2$, methoxy, $NH_2$, $N(CH_3)_2$, $N(CH_3)(C(O)CH_3)$; and a monocyclic or a bicyclic heterocycle selected from the group consisting of azetidine, oxetane pyrrolidine, tetrahydrofurane, pyrazolidine, imidazolidine, 1,2,4-triazolidine, piperidine, piperazine, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,4-triazole, 1,2,3-triazole, 1,2,3,4-tetrazole, pyridine, dihydropyridine pyrimidine, tetrahydropyrimidine, 4-oxa-7-azaspiro[2.5]octane, each of which is optionally substituted by 1, 2, 3 or 4 substituents independently selected from the group consisting of fluorine, chlorine, cyano —OH, oxo, —COOH, methoxy-C(O)—, ethoxy-C(O)—, tert-butoxy-C(O)—, —C(O)—$NH_2$, methyl, methyl-C(O)—, difluoromethyl, trifluoromethyl, hydroxymethyl-, methoxymethyl-, —$NH_2$, —$NMe_2$, pyrrolidine, $R^{12}$ and $R^{13}$ are independently selected from the group consisting of hydrogen, —NH(—C(O)-methyl), methoxy;

methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—$NH_2$, —C(O)—$NMe_2$, —NH—C(O)-methyl, methyl, methoxy, cyclopropyl, —$NH_2$, $NMe_2$, S-methyl, S(O)-methyl, $50_2$-methyl, and $(EtO)_2P(=O)$—;

heterocyclyl-methyl, heterocyclyl-ethyl, wherein the heterocyclyl substituent is selected from the group consisting of oxetane, tetrahydrofurane, tetrahydropyrane pyrrolidine, morpholine, pyrazole, imidazole, 1, 2, 4-oxadiazole, pyridine, each of which is optionally substituted by 1 substituent independently selected from the group consisting of fluorine, chlorine, —OH, oxo and methyl;

phenyl;

2,3-dihydro-1H-indene, and a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, methyl;

$R^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic or a bicyclic heterocycle selected from the group consisting of pyrrolidin and tetrahydropyran, $R^{15}$ is selected from the group consisting of methyl and ethyl, each of which is optionally substituted by 1 substituent independently selected from the group consisting of —OH and —COOH; and pyridine, and stereoisomers, tautomers, N-oxides, hydrates, solvates, and salts thereof, and mixtures of same.

In a further embodiment of the first aspect, the present invention covers compounds of formula (I), supra, in which:

$R_p$ is hydrogen or $C_1$-$C_4$-alkyl, and stereoisomers, tautomers, N-oxides, hydrates, solvates, and salts thereof, and mixtures of same.

In a further embodiment of the first aspect, the present invention covers compounds of formula (I), supra, in which:

$R_p$ is hydrogen or methyl, and stereoisomers, tautomers, N-oxides, hydrates, solvates, and salts thereof, and mixtures of same.

In a further embodiment of the first aspect, the present invention covers compounds of formula (I), supra, in which:

$R^3$ is hydrogen or $C_1$-$C_4$-alkyl, and stereoisomers, tautomers, N-oxides, hydrates, solvates, and salts thereof, and mixtures of same.

In a further embodiment of the first aspect, the present invention covers compounds of formula (I), supra, in which: $R^3$ is hydrogen or methyl, and stereoisomers, tautomers, N-oxides, hydrates, solvates, and salts thereof, and mixtures of same.

In a further embodiment of the first aspect, the present invention covers compounds of formula (I), supra, in which:

$R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $NH_2$, and stereoisomers, tautomers, N-oxides, hydrates, solvates, and salts thereof, and mixtures of same.

In a further embodiment of the first aspect, the present invention covers compounds of formula (I), supra, in which:

$R^4$ is selected from the group consisting of hydrogen, chlorine, fluorine, cyano, methyl, methoxy and trifluoromethyl, and stereoisomers, tautomers, N-oxides, hydrates, solvates, and salts thereof, and mixtures of same.

In a further embodiment of the first aspect, the present invention covers compounds of formula (I), supra, in which:

$R^4$ is selected from the group consisting of hydrogen, chlorine, fluorine, —OH, cyano, methyl, methoxy, trifluoromethyl, trifluoromethoxy and $NH_2$, and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, chlorine, fluorine and methyl, and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, chlorine, fluorine, —OH, cyano, methyl, methoxy and trifluoromethyl, and stereoisomers, tautomers, N-oxides, hydrates, solvates, and salts thereof, and mixtures of same.

In a further embodiment of the first aspect, the present invention covers compounds of formula (I), supra, in which:

$R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and stereoisomers, tautomers, N-oxides, hydrates, solvates, and salts thereof, and mixtures of same.

In a further embodiment of the first aspect, the present invention covers compounds of formula (I), supra, in which:

$R^6$ is selected from the group consisting of hydrogen, fluorine, chlorine and methyl, and stereoisomers, tautomers, N-oxides, hydrates, solvates, and salts thereof, and mixtures of same.

In a further embodiment of the first aspect, the present invention covers compounds of formula (I), supra, in which:

$R^6$ is selected from the group consisting of hydrogen, fluorine, chlorine, —OH, cyano, methyl and methoxy, and stereoisomers, tautomers, N-oxides, hydrates, solvates, and salts thereof, and mixtures of same.

In a further embodiment of the first aspect, the present invention covers compounds of formula (I), supra, in which:

Q is a substituted phenyl ring of the formula (Q1)

(Q1)

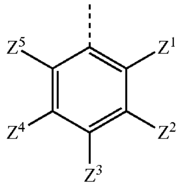

in which:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —$SO_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, or Q is a pyridine ring of the formula (Q2)

(Q2)

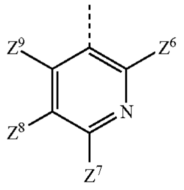

in which:

$Z^6$, $Z^7$, $Z^9$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyrimidine ring of the formula (Q3)

(Q3)

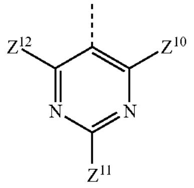

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q4)

(Q4)

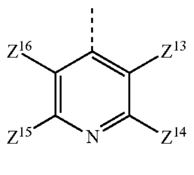

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

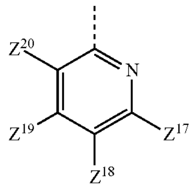

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of the formula (Q6)

(Q6)

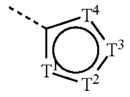

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

(Q7)

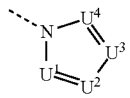

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

Q is a substituted phenyl ring of the formula (Q1)

(Q1)

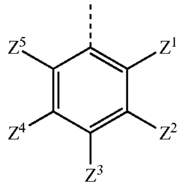

in which:

$Z^1$ and $Z^5$ are independently selected from the group consisting of hydrogen, halogen, $C_1$-$C_4$-alkyl and $C_1$-$C_4$-alkoxy, $Z^2$ and $Z^4$ are independently selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, or Q is a pyridine ring of the formula (Q4)

(Q4)

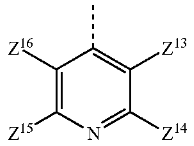

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

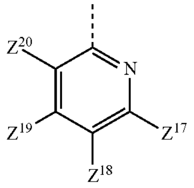

in which:

$Z^{17}$, $Z^{18}$, and $Z^{19}$ are hydrogen, and $Z^{20}$ is halogen, or

Q is a 5-membered aromatic heterocycle of the formula (Q6)

(Q6)

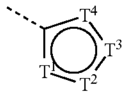

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

(Q7)

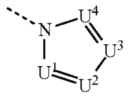

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

Q is a substituted phenyl ring of the formula (Q1)

(Q1)

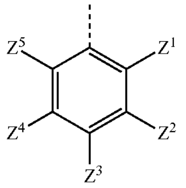

in which:

$Z^1$ and $Z^5$ are independently selected from the group consisting of hydrogen, halogen, $C_1$-$C_4$-alkyl, $C_1$-$C_4$-alkoxy and $C_1$-$C_4$-halogenoalkyl having 1 to 5 halogen atoms $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, or Q is a pyridine ring of the formula (Q4)

(Q4)

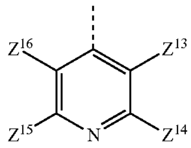

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

(Q5)

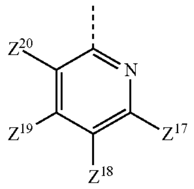

in which:

$Z^{17}$, $Z^{18}$, and $Z^{19}$ are hydrogen, and $Z^{20}$ is halogen, or

Q is a 5-membered aromatic heterocycle of the formula (Q6)

(Q6)

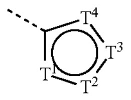

in which:

$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

(Q7)

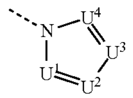

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

Q is a substituted phenyl ring of the formula (Q1)

(Q1)

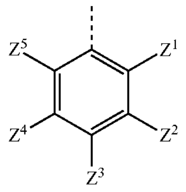

in which:

$Z^1$ and $Z^5$ are independently selected from the group consisting of hydrogen, fluorine, chlorine, methyl and methoxy, $Z^2$ and $Z^4$ are independently selected from the group consisting of hydrogen, fluorine, chlorine, —OH, methyl, ethyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy and —$NMe_2$, or Q is a pyridine ring of the formula (Q4)

(Q4)

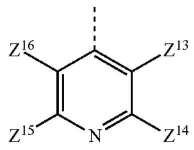

in which:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, $NH_2$, —NHMe —$NMe_2$, —NH—C(O)-Me, morpholinyl, or Q is a pyridine ring of the formula (Q5)

(Q5)

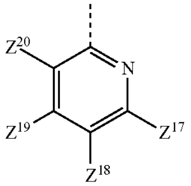

in which:

$Z^{17}$, $Z^{18}$, and $Z^{19}$ are hydrogen, and $Z^{20}$ is fluorine, chlorine, or Q is selected from the group consisting of (Q6-1)

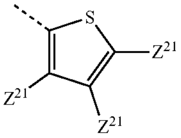

(Q6-2)

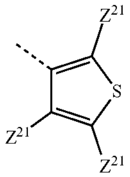

(Q6-3)

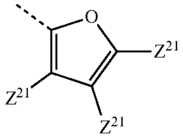

(Q6-4)

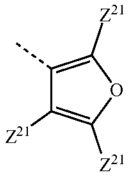

(Q6-5)

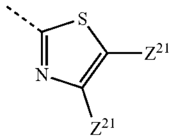

(Q6-6)

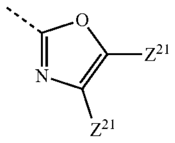

-continued (Q6-7)

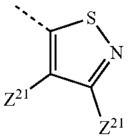

(Q6-8)

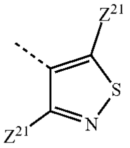

(Q6-9)

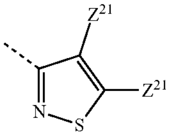

(Q6-10)

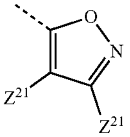

(Q6-11)

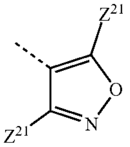

(Q6-12)

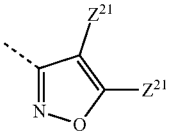

(Q6-13)

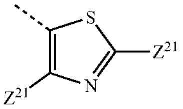

(Q6-14)

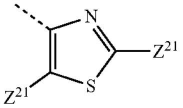

(Q6-15)

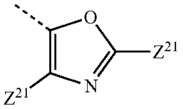

(Q6-16)

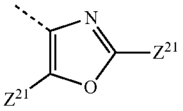

(Q6-17)

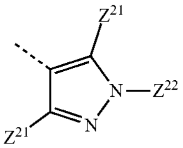

(Q6-18)
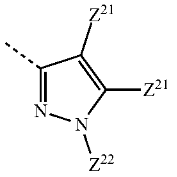
(Q6-19)
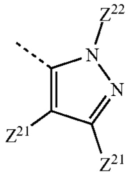
(Q6-20)
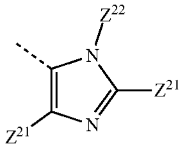
(Q6-21)
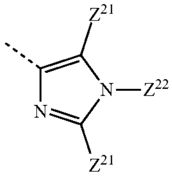
(Q6-22)
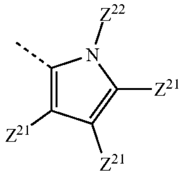
(Q6-23)
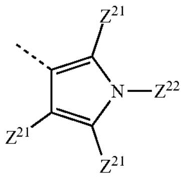
(Q6-24)
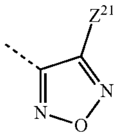
(Q6-25)
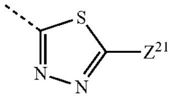
(Q6-26)
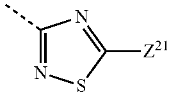
(Q6-27)
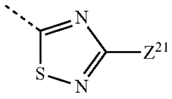
(Q6-28)
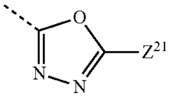
(Q6-29)
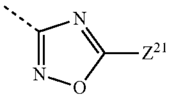
(Q6-30)
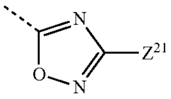
(Q6-31)
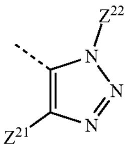
(Q6-32)
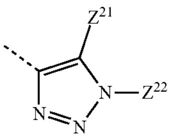
(Q6-33)
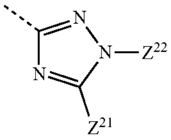
(Q6-34)
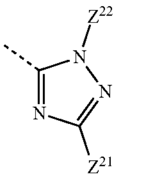
(Q6-35)
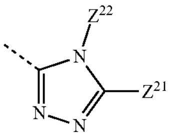
(Q6-36)
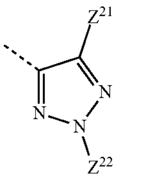
(Q6-37)
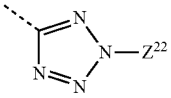
(Q6-38)
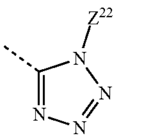

in which:

each $Z^{21}$ is independently selected from the group consisting of hydrogen, fluorine, chlorine, cyano, methyl, trifluoromethyl, methoxy and $Z^{22}$ is hydrogen, methyl, or Q is selected from the group consisting of (Q7-1)

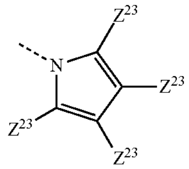

(Q7-2)

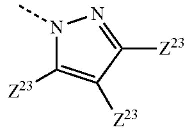

(Q7-3)

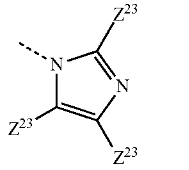

(Q7-4)

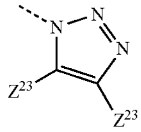

(Q7-5)

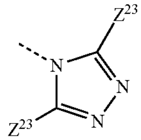

(Q7-6)

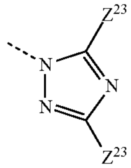

(Q7-7)

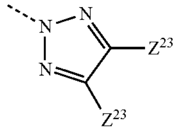

(Q7-8)

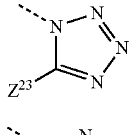

(Q7-9)

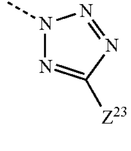

in which:

each $Z^{23}$ is independently selected from the group consisting of hydrogen, fluorine, chlorine, cyano, methyl, trifluoromethyl, methoxy, or Q is selected from the group consisting of

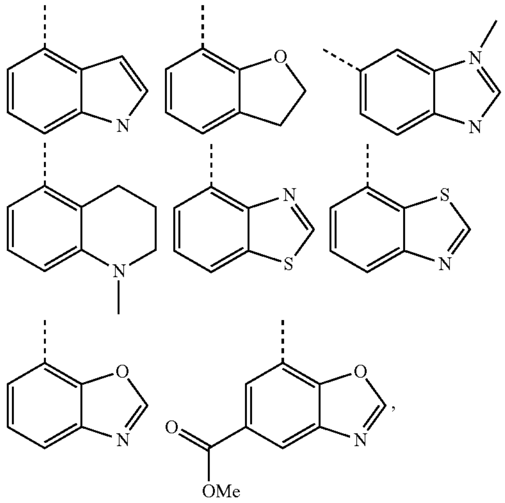

and stereoisomers, tautomers, N-oxides, hydrates, solvates, and salts thereof, and mixtures of same.

In a further embodiment of the first aspect, the present invention covers compounds of formula (I), supra, in which: Q is a substituted phenyl ring of the formula (Q1)

(Q1)

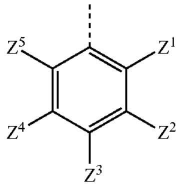

in which:

$Z^1$ and $Z^5$ are independently selected from the group consisting of hydrogen, fluorine, chlorine, methyl, methoxy and trifluoromethyl, $Z^2$ and $Z^4$ are independently selected from the group consisting of hydrogen, fluorine, chlorine, —OH, cyano, methyl, ethyl, tert-butyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy, difluoromethoxy and —$NMe_2$, or Q is a pyridine ring of the formula (Q4)

(Q4)

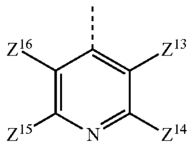

in which:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, $NH_2$, —NHMe —$NMe_2$, —NH—C(O)-Me, morpholinyl, or Q is a pyridine ring of the formula (Q5)
(Q5)
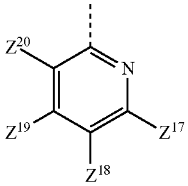
in which:
$Z^{17}$, $Z^{18}$, and $Z^{19}$ are hydrogen, and
$Z^{20}$ is fluorine, chlorine, or
Q is selected from the group consisting of
(Q6-1)
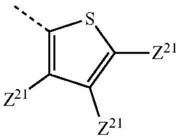
(Q6-2)
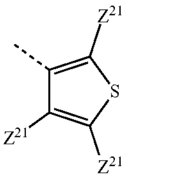
(Q6-3)
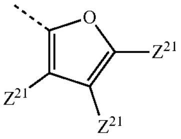
(Q6-4)
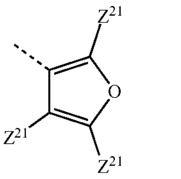
(Q6-5)
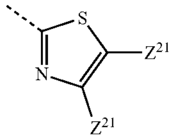
(Q6-6)
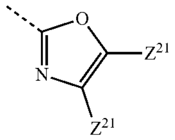
(Q6-7)
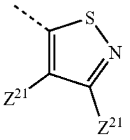
-continued
(Q6-8)
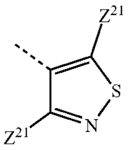
(Q6-9)
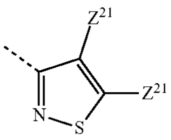
(Q6-10)
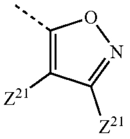
(Q6-11)
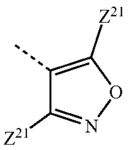
(Q6-12)
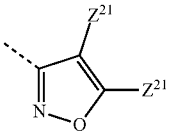
(Q6-13)
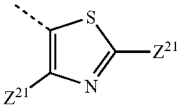
(Q6-14)
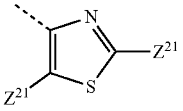
(Q6-15)
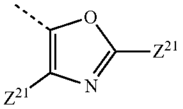
(Q6-16)
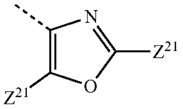
(Q6-17)
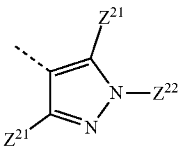
(Q6-18)
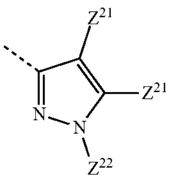

-continued
(Q6-19)
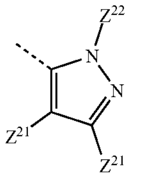
(Q6-20)
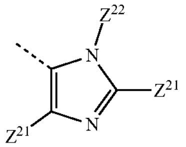
(Q6-21)
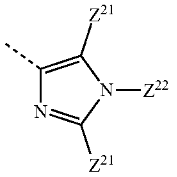
(Q6-22)
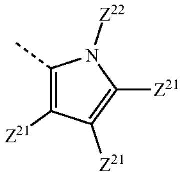
(Q6-23)
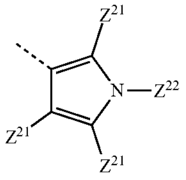
(Q6-24)
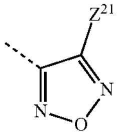
(Q6-25)
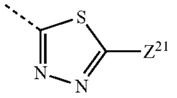
(Q6-26)
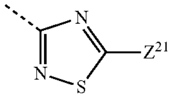
(Q6-27)
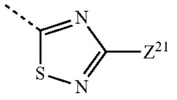
(Q6-28)
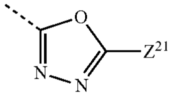
(Q6-29)
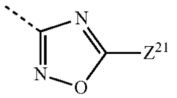
-continued
(Q6-30)
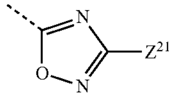
(Q6-31)
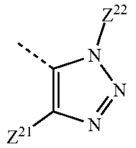
(Q6-32)
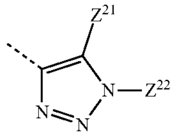
(Q6-33)
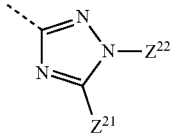
(Q6-34)
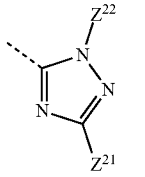
(Q6-35)
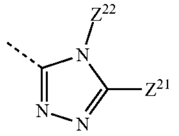
(Q6-36)
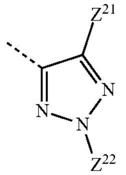
(Q6-37)
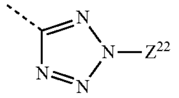
(Q6-38)
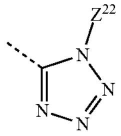
or
(Q6-39)
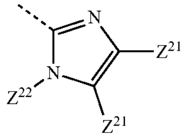
in which:
each $Z^{21}$ is independently selected from the group consisting of hydrogen, fluorine, chlorine, cyano, methyl, trifluoromethyl, methoxy and
$Z^{22}$ is hydrogen, methyl, or Q is selected from the group consisting of (Q7-1)

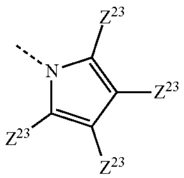

(Q7-2)

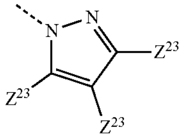

(Q7-3)

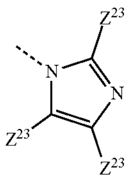

(Q7-4)

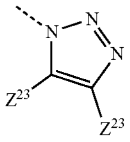

(Q7-5)

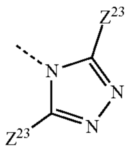

(Q7-6)

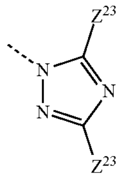

(Q7-7)

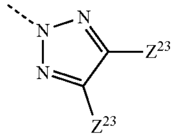

(Q7-8)

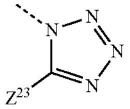

(Q7-9)

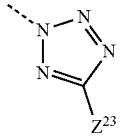

in which:

each $Z^{23}$ is independently selected from the group consisting of hydrogen, fluorine, chlorine, cyano, methyl, trifluoromethyl, methoxy, or Q is selected from the group consisting of

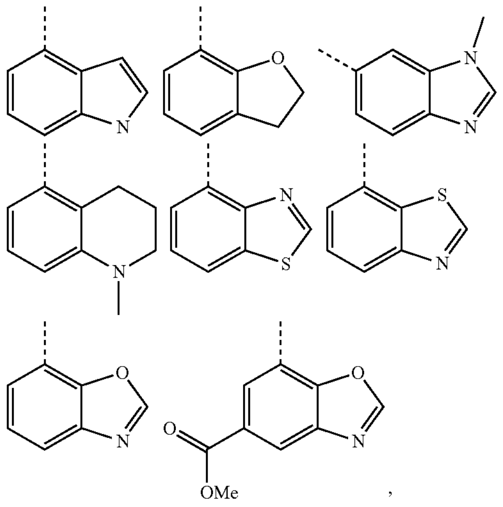

, and stereoisomers, tautomers, N-oxides, hydrates, solvates, and salts thereof, and mixtures of same.

In a further embodiment of the first aspect, the present invention covers compounds of formula (I), supra, in which: Q is a substituted phenyl ring of the formula (Q1)

(Q1)

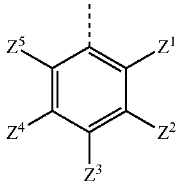

in which:

$Z^1$ and $Z^5$ are independently selected from the group consisting of hydrogen, fluorine, chlorine, methyl, methoxy and trifluoromethyl, $Z^2$ and $Z^4$ are independently selected from the group consisting of hydrogen, fluorine, chlorine, —OH, cyano, methyl, ethyl, tert-butyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy, difluoromethoxy and —$NMe_2$, or Q is a pyridine ring of the formula (Q4)

(Q4)

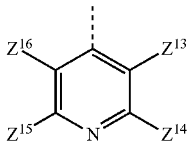

in which:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, $NH_2$, —NHMe —$NMe_2$, —NH—C(O)-Me, morpholinyl, or Q is selected from the group consisting of (Q6-1)

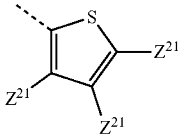

(Q6-2)

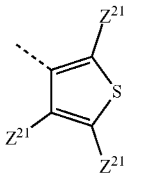

(Q6-13)

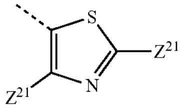

or (Q6-39)

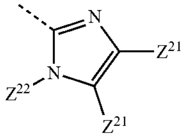

in which:

each $Z^{21}$ is independently selected from the group consisting of hydrogen, fluorine, chlorine, cyano, methyl, trifluoromethyl, methoxy and $Z^{22}$ is hydrogen, methyl, or Q is selected from the group consisting of

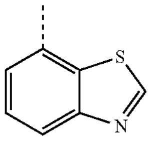

, and stereoisomers, tautomers, N-oxides, hydrates, solvates, and salts thereof, and mixtures of same.

In a further embodiment of the first aspect, the present invention covers compounds of formula (I), supra, in which A is A3 or A4

A3

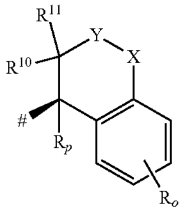

A4

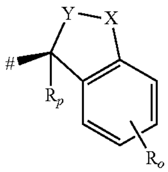

wherein $R_p$ is selected from the group consisting of hydrogen, $C_1$-$C_4$-alkyl; preferably hydrogen, and stereoisomers, tautomers, N-oxides, hydrates, solvates, and salts thereof, and mixtures of same.

In a further aspect of the present invention in any or all of the embodiments according to the first to eighth aspect (including the embodiments under the heading "further embodiments of the first aspect of the present invention") in the definition of X and/or Y "$NR^9$" as defined supra is excluded.

In a further aspect of the present invention in any or all of the embodiments according to the first to eighth aspect (including the embodiments under the heading "further embodiments of the first aspect of the present invention") in the definition of $R^2$ hydrogen is excluded.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers the compounds of general formula (I) which are disclosed in the Example Section of this text, infra.

The compounds according to the invention of general formula (I) can be prepared according to the schemes 1a-e, 2, 3 and 4 as shown in the Experimental Section to the present invention (General Procedures). The schemes and procedures described illustrate synthetic routes to the compounds of general formula (I) of the invention and are not intended to be limiting. It is clear to the person skilled in the art that the order of transformations as exemplified in schemes 1a-e, 2 and 3 can be modified in various ways. The order of transformations exemplified in these schemes is therefore not intended to be limiting. In addition, interconversion of any of the substituents, Q, A, $R^1$, $R^2$, $R^3$, $R^4$, $R^5$ or $R^6$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

In the following, several routes for the preparation of compounds of general formula (I) are described in schemes 1a-e and 2.

In accordance with a second aspect, the present invention covers methods of preparing compounds of general formula (I) as defined supra, said methods comprising the step of allowing an intermediate compound of general formula 1N:

1N

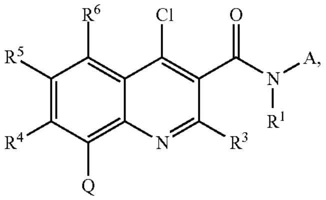

in which A, $R^1$, $R^3$, $R^4$, $R^5$, $R^6$, and Q are as defined for the compound of general formula (I) as defined supra, to react with a compound of general formula 1F:

$R^2H$ 1F, in which $R^2$ is $NR^{12}R^{13}$, $OR^{14}$, or $SR^{15}$, each as defined for the compound of general formula (I) as defined supra, thereby giving a compound of general formula (I):

(I)

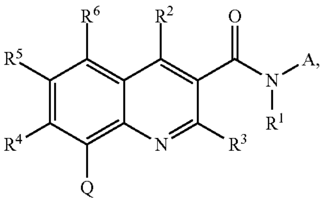

in which A, $R^1$, $R^2$, $R^3$, $R^4$, $R^5$, $R^6$, and Q are as defined supra.

In accordance with an alternative embodiment of the second aspect, the present invention covers methods of preparing compounds of general formula (I) as defined supra, said methods comprising the step of allowing an intermediate compound of general formula 1T:

1T

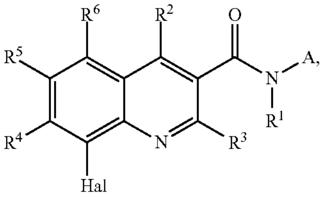

in which A, $R^1$, $R^2$, $R^3$, $R^4$, $R^5$ and $R^6$ are as defined for the compound of general formula (I) as defined supra, and in which Hal is halogen, particularly chlorine, bromine or iodine, to react with a compound of general formula 1H:

$Q\text{-}B(OR)_2$ 1H, in which Q is as defined for the compound of general formula (I) as defined supra, and each R may be individually H or Me or both R are pinacolate, thereby giving a compound of general formula (I):

(I)

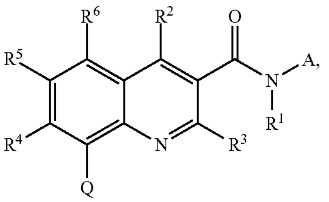

in which A, $R^1$, $R^2$, $R^3$, $R^4$, $R^5$, $R^6$, and Q are as defined supra.

In accordance with an alternative embodiment of the second aspect, the present invention covers methods of preparing compounds of general formula (I) as defined supra, said methods comprising the step of allowing an intermediate compound of general formula 1W:

1W

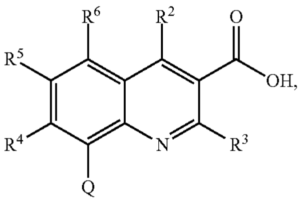

in which Q, $R^2$, $R^3$, $R^4$, $R^5$ and $R^6$ are as defined for the compound of general formula (I) as defined supra, to react with a compound of general formula 1M:

1M

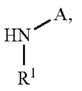

in which $R^1$ and A are as defined for the compound of general formula (I) as defined supra, thereby giving a compound of general formula (I):

(I)

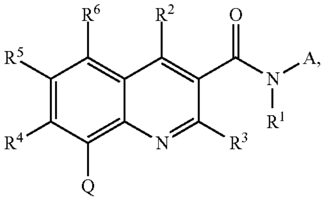

in which A, $R^1$, $R^2$, $R^3$, $R^4$, $R^5$, $R^6$, and Q are as defined supra.

In accordance with an alternative embodiment of the second aspect, the present invention covers methods of preparing compounds of general formula (I) as defined supra, said methods comprising the step of allowing an intermediate compound of general formula 1X:

1X

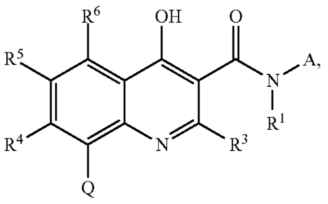

in which Q, A, $R^1$, $R^3$, $R^4$, $R^5$ and $R^6$ are as defined for the compound of general formula (I) as defined supra, to react with a compound of general formula 1Y:

$R^2H$ 1Y, in which $R^2$ is $OR^{14}$ as defined for the compound of general formula (I) as defined supra, thereby giving a compound of general formula (I):

(I)

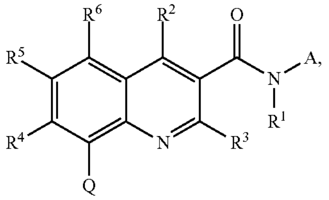

in which A, $R^1$, $R^3$, $R^4$, $R^5$, $R^6$, and Q are as defined supra and $R^2$ is $C^1$-$C^4$-alkoxy which is optionally substituted as defined supra.

In accordance with an alternative embodiment of the second aspect, the present invention covers methods of preparing compounds of general formula (I) as defined supra, said methods comprising the step of allowing an intermediate compound of general formula 1N:

1N

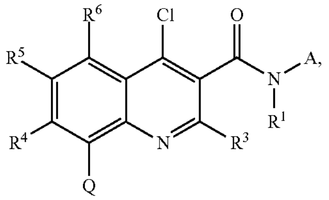

in which Q, A, $R^1$, $R^3$, $R^4$, $R^5$ and $R^6$ are as defined for the compound of general formula (I) as defined supra, to react with a compound of general formula 2A:

$R^2$Met-X 2A, in which $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of general formula (I) as defined supra, Met is magnesium or zinc, and X is chlorine, bromine or iodine, thereby giving a compound of general formula (I):

(I)

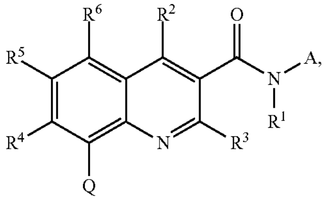

in which A, $R^1$, $R^3$, $R^4$, $R^5$, $R^6$, and Q are as defined supra and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra.

In accordance with a third aspect, the present invention covers methods of preparing compounds of general formula (I) as defined supra, said methods comprising the step of allowing an intermediate compound of general formula 1N:

1N

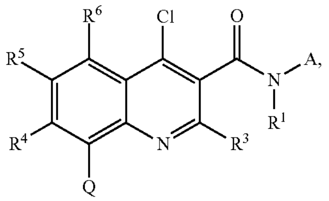

in which A, $R^1$, $R^3$, $R^4$, $R^5$, $R^6$, and Q are as defined for the compound of general formula (I) as defined supra, to react with a compound of general formula 1F:

$R^2$H 1F, in which $R^2$ is $NR^{12}R^{13}$, $OR^{14}$, or $SR^{15}$, each as defined for the compound of general formula (I) as defined supra, thereby giving a compound of general formula (I):

(I)

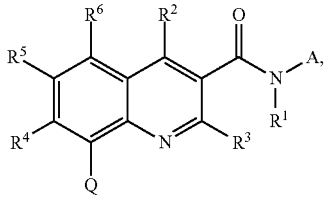

in which A, $R^1$, $R^2$, $R^3$, $R^4$, $R^5$, $R^6$, and Q are as defined supra, then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1T:

1T

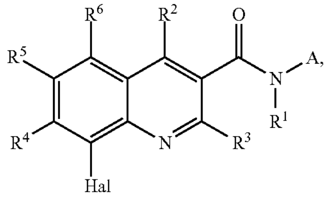

in which A, $R^1$, $R^2$, $R^3$, $R^4$, $R^5$ and $R^6$ are as defined for the compound of general formula (I) as defined supra, and in which Hal is halogen, particularly chlorine, bromine or iodine, to react with a compound of general formula 1H:

Q-B$(OR)_2$ 1H, in which Q is as defined for the compound of general formula (I) as defined supra, and each R may be individually H or Me or both R are pinacolate, thereby giving a compound of general formula (I):

(I)

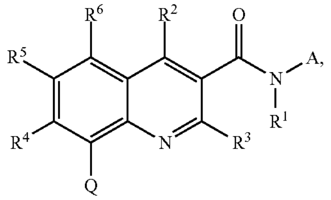

in which A, $R^1$, $R^2$, $R^3$, $R^4$, $R^5$, $R^6$, and Q are as defined supra, then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1W:

1W

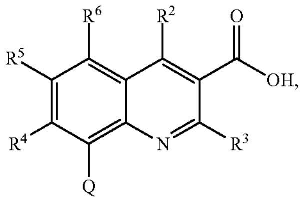

in which Q, $R^2$, $R^3$, $R^4$, $R^5$ and $R^6$ are as defined for the compound of general formula (I) as defined supra, to react with a compound of general formula 1M:

1M

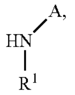

in which $R^1$ and A are as defined for the compound of general formula (I) as defined supra, thereby giving a compound of general formula (I):

(I)

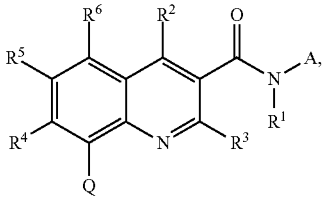

in which A, $R^1$, $R^2$, $R^3$, $R^4$, $R^5$, $R^6$, and Q are as defined supra, then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1X:

1X

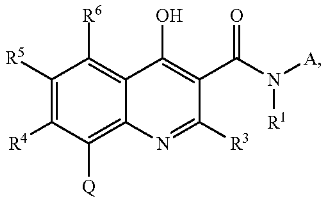

in which Q, A, $R^1$, $R^3$, $R^4$, $R^5$ and $R^6$ are as defined for the compound of general formula (I) as defined supra, to react with a compound of general formula 1Y:

$R^2H$ 1Y, in which $R^2$ is $OR^{14}$ as defined for the compound of general formula (I) as defined supra, thereby giving a compound of general formula (I):

(I)

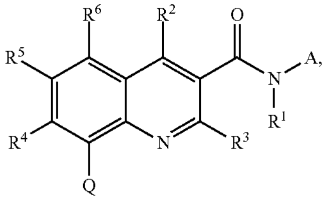

in which A, $R^1$, $R^3$, $R^4$, $R^5$, $R^6$, and Q are as defined supra and $R^2$ is $C_1$-$C_4$-alkoxy which is optionally substituted as defined supra, then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1N:

1N

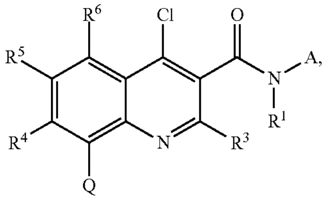

in which Q, A, $R^1$, $R^3$, $R^4$, $R^5$ and $R^6$ are as defined for the compound of general formula (I) as defined supra, in which $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of general formula (I) as defined supra, Met is magnesium or zinc, and X is chlorine, bromine or iodine, thereby giving a compound of general formula (I):

(I)

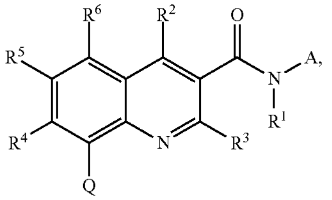

in which A, $R^1$, $R^3$, $R^4$, $R^5$, $R^6$, and Q are as defined supra and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra, then optionally converting said compound into solvates, salts and/or solvates of such salts using the corresponding (i) solvents and/or (ii) bases or acids.

The present invention covers methods of preparing compounds of the present invention of general formula (I), said methods comprising the steps as described in the Experimental Section herein.

In accordance with a fourth aspect, the present invention covers intermediate compounds which are useful for the preparation of the compounds of general formula (I), supra.

Particularly, the inventions covers the intermediate compounds of general formula (II):

(II)

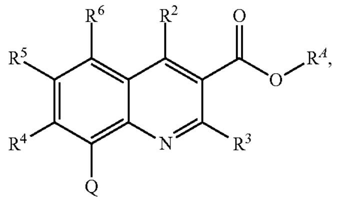

in which $R^2$ is —OH or as defined for the compound of general formula (I) supra, $R^3$, $R^4$, $R^5$, $R^6$, and Q are as defined for the compound of general formula (I) supra, and $R^{4'}$ is H or $C_1$-$C_4$-alkyl, and stereoisomers, tautomers, N-oxides, hydrates, solvates, and salts thereof, and mixtures of same.

Particularly, the inventions covers also the intermediate compounds of general formula (III):

(III)

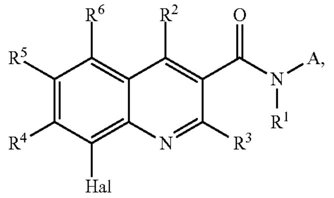

in which $R^2$ is —OH or as defined for the compound of general formula (I) supra, A, $R^1$, $R^3$, $R^4$, $R^5$, and $R^6$ are as defined for the compound of general formula (I) supra, and Hal is halogen, and stereoisomers, tautomers, N-oxides, hydrates, solvates, and salts thereof, and mixtures of same.

In accordance with a fifth aspect, the present invention covers the use of said intermediate compounds for the preparation of a compound of general formula (I) as defined supra.

Particularly, the inventions covers the use of intermediate compounds of general formula (II):

(II)

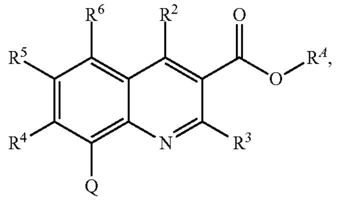

in which $R^2$ is —OH or as defined for the compound of general formula (I) supra, $R^3$, $R^4$, $R^5$, $R^6$, and Q are as defined for the compound of general formula (I) supra, and $R^{4'}$ is H or $C_1$-$C_4$-alkyl, for the preparation of a compound of general formula (I) as defined supra.

Particularly, the inventions covers also the use of intermediate compounds of general formula (III):

(III)

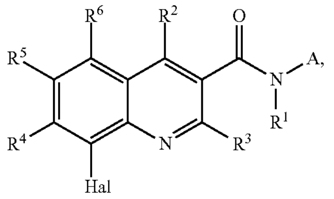

in which $R^2$ is —OH as defined for the compound of general formula (I) supra,

A, $R^1$, $R^3$, $R^4$, $R^5$, and $R^6$ are as defined for the compound of general formula (I) supra, and Hal is halogen, for the preparation of a compound of general formula (I) as defined supra.

The present invention covers the intermediate compounds which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particularly of gastro-intestinal and extra-intestinal helminth infections, more particularly of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp. *Paracapillaria* spp., *Trichinella* spp., *Trichomosoides* spp., *Trichuris* spp.

from the order of the Tylenchida, for example: *Micronema* spp., *Parastrongyloides* spp. *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particularly of gastro-intestinal and extra-intestinal helminth infections, more particularly of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particularly of gastro-intestinal and extra-intestinal helminth infections, more particularly of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using a pharmaceutical composition, in particular a veterinary formulation, comprising an effective amount of a compound of general formula (I), as described supra, or stereoisomers, tautomers, N-oxides, hydrates, solvates, and salts thereof, particularly pharmaceutically acceptable salts thereof, or mixtures of same.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, methaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal).

Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays;

tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixture agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®, lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropyl-cellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropyl-methylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:

one or more first active ingredients, in particular compounds of general formula (I) as defined supra, and one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoroethyl) sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro [indol-3,4'-piperidin]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl) oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio] phenyl]amino]carbonyl]-indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9), N-[4-(aminothioxomethyl)-2-methyl-6-[(methylamino) carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl) methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1] nonane (known from WO 2011/105506 A1, WO 2016/133011 A1) (CAS 1332838-17-1).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim;

macrocyclic lactones, e.g. nemadectin, ivermectin, latidectin, moxidectin, selamectin, eprinomectin, doramectin, emamectin benzoate; milbemycin oxime;

triprene, epofenonane, diofenolan;

Biologicals, hormones or pheromones, for example natural products, e.g. thuringiensin, codlemone or neem components;

dinitrophenols, e.g. dinocap, dinobuton, binapacryl;

benzoylureas, e.g. fluazuron, penfluron;

amidine derivatives, e.g. chlormebuform, cymiazole, demiditraz;

Bee hive varroa acaricides, for example organic acids, e.g. formic acid, oxalic acid.

Non-limiting examples of insecticides and acaricides of particular interest for use in animal health are and include in particular [i.e. Mehlhorn et al Encyclpaedic Reference of Parasitology 4th edition (ISBN 978-3-662-43978-4)]:

Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, selamectin;

Modulators of arthropod octopaminergic receptors: amitraz, BTS27271, cymiazole, demiditraz;

Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;

Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram;

Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril;

from the class of polylether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for “drug holidays”, in which a subject is not dosed with a drug for a certain period of time, to be beneficial to the overall balance between pharmacological effect and tolerability. Furthermore, it is possible to have long-acting treatments, wherein the subject gets treated once for more than four weeks. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Abbreviations

| | |
|---|---|
| aq. | aqueous |
| DMF | dimethylformamide |
| DMSO | dimethylsulfoxide |
| MTBE | methyl-t.-butylether |
| THF | tetrahydrofurane |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical and Chromatography Methods

Analytical and Preparative Liquid Chromatography

Analytical (UP)LC-MS was performed by means of different equipments as described below. The masses (m/z) are reported from the positive mode electrospray ionisation unless the negative mode is indicated (ESI−).

Method L0:

Measurement of log P values was performed according to EEC directive 79/831 Annex V.A8 by HPLC (High Performance Liquid Chromatography) on reversed phase columns with the following methods:

[a] log P value is determined by measurement of LC-UV, in an acidic range, with 0.1% formic acid in water and acetonitrile as eluent (linear gradient from 10% acetonitrile to 95% acetonitrile).

[b] log P value is determined by measurement of LC-UV, in a neutral range, with 0.001 molar ammonium acetate solution in water and acetonitrile as eluent (linear gradient from 10% acetonitrile to 95% acetonitrile).

Calibration was done with straight-chain alkan-2-ones (with 3 to 16 carbon atoms) with known log P values (measurement of log P values using retention times with linear interpolation between successive alkanones). Lambda-max-values were determined using UV-spectra from 200 nm to 400 nm and the peak values of the chromatographic signals.

M+1 (or M+H) means the molecular ion peak, plus or minus 1 a.m.u. (atomic mass unit) respectively, as observed in mass spectroscopy by electrospray ionization (ESI + or −).

Method L1:

Instrument type: Waters ACQUITY SQD UPLC system; column: Waters Acquity UPLC HSS T3 1.8μ 50×1 mm; eluent A: 1 l water+0.25 ml formic acid, eluent B: 1 l acetonitrile+0.25 ml formic acid; gradient: 0.0 min 90% A→1.2 min 5% A→2.0 min 5% A oven: 50° C.; flow: 0.40 ml/min; UV-detection: 208-400 nm.

Method L2:

MS instrument type: Agilent Technologies 6130 Quadrupole LC-MS; HPLC instrument type: Agilent Technologies 1260 Infinity; column: Waters XSelect (C18, 50×2.1 mm, 3.5p); flow: 0.8 mL/min; column temp: 35° C.; eluent A: 0.1% formic acid in acetonitrile; eluent B: 0.1% formic acid in water; lin. gradient: t=0 min 5% A, t=3.5 min 98% A, t=6 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L3:

MS instrument type: Agilent Technologies LC/MSD SL; HPLC instrument type: Agilent Technologies 1100 Series; column: Waters XSelect (C18, 50×2.1 mm, 3.5μ; flow: 0.8 mL/min; column temp: 25° C.; eluent A: 95% acetonitrile+5% 10 mM ammoniumbicarbonate in water;

eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Method L4:

Instrument type: Waters ACQUITY SQD UPLC System; column: Waters Acquity UPLC HSS T3 1.8μ 50×1 mm; eluent A: 1 l water+0.25 ml 99% ige formic acid, Eluent B: 1 l acetonitrile+0.25 ml 99% ige formic acid; gradient: 0.0 min 95% A→6.0 min 5% A→7.5 min 5% A oven: 50° C.; flow: 0.35 ml/min; UV-detection: 210-400 nm.

Method L5:

MS instrument type: Waters SQD; Instrument HPLC: Waters UPLC; column: Zorbax SB-Aq (Agilent), 50 mm×2.1 mm, 1.8 μm; eluent A: water+0.025% formic acid, eluent B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow: 0.600 ml/min; UV-detection: DAD; 210 nm.

Method L6:

MS instrument type: Thermo Scientific FT-MS; HPLC instrument type: Thermo Scientific UltiMate 3000; column: Waters, HSST3, 2.1×75 mm, C18 1.8 μm; eluent A: 1 l water+0.01% formic acid; eluent B: 1 l acetonitril+0.01% formic acid; Gradient: 0.0 min 10% B→2.5 min 95% B→3.5 min 95% B; Ofen: 50° C.; Fluss: 0.90 ml/min; UV-Detektion: 210 nm/optimum integration path 210-300 nm:

Method L7:

MS instrument type: Waters (Micromass) Quattro Micro; HPLC instrument type: Waters UPLC Acquity; column: Waters BEH C18 1.7μ 50×2.1 mm; eluent A: 1 l water+0.01 mol ammoniumformiate, eluent B: 1 l acetonitril; gradient: 0.0 min 95% A→0.1 min 95% A→2.0 min 15% A→2.5 min 15% A→2.51 min 10% A→3.0 min 10% A; oven: 40° C.; flow: 0.5 ml/min; UV-detection: 210 nm.

Method L8:

MS instrument type: Waters SQD2; Instrument HPLC: Waters UPLC; column: Zorbax SB-Aq (Agilent), 50 mm×2.1 mm, 1.8 μm; eluent A: water+0.025% formic acid, eluent B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow: 0.600 ml/min; UV-detection: DAD; 210 nm.

Method L9:

MS instrument type: Agilent Technologies LC/MSD SL; HPLC instrument type: Agilent Technologies 1100 Series; column: Waters XSelect (C18, 50×2.1 mm, 3.5μ; flow: 0.8 mL/min; column temp: 25° C.; eluent A: 95% acetonitrile+5% ammoniumbicarbonate in water; eluent B: 10 mmM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Method L10:

MS instrument type: Agilent Technologies 6130 Quadrupole LC-MS; HPLC instrument type: Agilent Technologies 1260 Infinity; column: Waters XSelect (C18, 30×2.1 mm, 3.5p); flow: 1 mL/min; column temp: 35° C.; eluent A: 0.1% formic acid in acetonitrile; eluent B: 0.1% formic acid in water; lin. gradient: t=0 min 5% A, t=1.6 min 98% A, t=3 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L11:

MS instrument type: Agilent Technologies LC/MSD SL; HPLC instrument type: Agilent Technologies 1100 Series; column: Phenomenex Gemini NX (C18, 50×2.0 mm), 3.0μ; flow: 0.8 mL/min; column temp: 25° C.; eluent A: 95% acetonitrile+5% 10 mM ammoniumbicarbonate in water in acetonitrile pH=9.0; eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Method L12:

MA instrument: Agilent MS Quad 6150; HPLC instrument: Agilent 1290; column: Waters Acquity UPLC HSS T3

1.8 μm 50×2.1 mm; eluent A: 1 l water+0.25 ml 99% formic acid, Eluent B: 1 l acetonitril+0.25 ml 99% formic acid; gradient: 0.0 min 90% A→0.3 min 90% A→1.7 min 5% A→3.0 min 5% A oven: 50° C.; flow: 1.20 ml/min; UV-detection: 205-305 nm.

Method M1:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 1.80 min with a total run time of 2.10 min. The column temperature was at 45° C. with the flow rate of 1.20 mL/min.

Method M2:

The column used was an EVO, 2.6 μm, 3.0×50 mm. A linear gradient was applied, starting at 90% A (A: 0.1% FA in water) and ending at 95% B (B: 0.1% FA in MeCN) over 4.20 min with a total run time of 4.50 min. The column temperature was at 40° C. with the flow rate of 1.00 mL/min.

Method M3:

The column used was a CORTECS C18, 2.7 μm, 2.1×50 mm. A linear gradient was applied, starting at 95% A (A: 0.09% FA in water) and ending at 100% B (B: 0.1% FA in MeCN) over 1.70 min with a total run time of 2.00 min. The column temperature was at 40° C. with the flow rate of 1.00 mL/min.

Method M4:

The column used was a CORTECS C18+, 2.7 μm, 2.1×50 mm. A linear gradient was applied, starting at 90% A (A: 0.1% FA in water) and ending at 100% B (B: 0.1% FA in MeCN) over 1.70 min with a total run time of 2.00 min. The column temperature was at 45° C. with the flow rate of 1.00 mL/min.

Method M5:

The column used was a Kinetex EVO C18, 2.6 μm, 3.0×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Method M6:

The column used was a CORTECS C18, 2.7 μm, 2.1×50 mm. A linear gradient was applied, starting at 95% A (A: 0.09% FA in water) and ending at 100% B (B: 0.1% FA in MeCN) over 2.60 min with a total run time of 3.00 min. The column temperature was at 40° C. with the flow rate of 1.00 mL/min.

Method M7:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.80 min with a total run time of 3.30 min. The column temperature was at 45° C. with the flow rate of 1.20 mL/min.

Method M8:

The column used was a CORTECS C18+, 2.7 μm, 2.1×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Method M9:

The column used was a Kinetex EVO C18, 2.6 μm, 3.0×50 mm. A linear gradient was applied, starting at 90% A (A: 0.1% FA in water) and ending at 95% B (B: 0.1% FA in MeCN) over 4.20 min with a total run time of 4.50 min. The column temperature was at 40° C. with the flow rate of 1.00 mL/min.

Method M10:

The column used was a Kinetex EVO C18, 2.6 μm, 3.0×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Method M11:

The column used was a CORTECS C18+, 2.7 μm, 2.1×50 mm. A linear gradient was applied, starting at 90% A (A: 0.1% FA in water) and ending at 95% B (B: 0.1% FA in MeCN) over 2.70 min with a total run time of 3.00 min. The column temperature was at 40° C. with the flow rate of 1.00 mL/min.

Method M12:

The column used was an Ascentis Express C18, 2.7 μm, 3.0×50 mm. A linear gradient was applied, starting at 90% A (A: 0.09% FA in water) and ending at 100% B (B: 0.1% FA in MeCN) over 1.70 min with a total run time of 2.00 min. The column temperature was at 40° C. with the flow rate of 1.50 mL/min.

Method M13:

The column used was an Ascentis Express C18, 2.7 μm, 2.1×50 mm. A linear gradient was applied, starting at 95% A (A: 0.05% TFA in water) and ending at 100% B (B: 0.05% TFA in MeCN) over 1.70 min with a total run time of 2.00 min. The column temperature was at 40° C. with the flow rate of 1.00 mL/min.

Method M14:

The column used was an Ascentis Express C18, 2.7 μm, 2.1×50 mm. A linear gradient was applied, starting at 95% A (A: 0.05% TFA in water) and ending at 95% B (B: 0.05% TFA in MeCN) over 2.70 min with a total run time of 3.00 min. The column temperature was at 40° C. with the flow rate of 1.00 mL/min.

Method M15:

The column used was an Ascentis Express C18, 2.7 μm, 2.1×50 mm. A linear gradient was applied, starting at 70% A (A: 0.05% TFA in water) and ending at 95% B (B: 0.05% TFA in MeCN) over 2.70 min with a total run time of 3.00 min. The column temperature was at 40° C. with the flow rate of 1.00 mL/min.

Method M16:

The column used was a CORTECS C18, 2.7 μm, 2.1×50 mm. A linear gradient was applied, starting at 95% A (A: 0.09% FA in water) and ending at 100% B (B: 0.1% FA in MeCN) over 1.70 min with a total run time of 2.00 min. The column temperature was at 40° C. with the flow rate of 1.00 mL/min.

Method M17:

The column used was a CORTECS C18+100A, 2.7 μm, 2.1×50 mm. A linear gradient was applied, starting at 90% A (A: 0.1% FA in water) and ending at 100% B (B: 0.1% FA in MeCN) over 1.60 min with a total run time of 2.00 min. The column temperature was at 40° C. with the flow rate of 1.00 mL/min.

Method M18:

The column used was a Kinetex EVO C18, 2.6 μm, 3.0×50 mm. A linear gradient was applied, starting at 90% A (A: 0.09% FA in water) and ending at 100% B (B: 0.1% FA in MeCN) over 1.70 min with a total run time of 2.00 min. The column temperature was at 40° C. with the flow rate of 1.00 mL/min.

Method M19:

The column used was a Kinetex EVO C18 100A, 2.6 μm, 3.0×50 mm. A linear gradient was applied, starting at 90% A (A: 0.1% FA in water) and ending at 100% B (B: 0.1% FA in MeCN) over 1.60 min with a total run time of 2.00 min. The column temperature was at 40° C. with the flow rate of 1.00 mL/min.

Method M20:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 1.70 min with a total run time of 2.00 min. The column temperature was at 40° C. with the flow rate of 1.50 mL/min.

Method M21:

The column used was a Kinetex EVO C18, 2.6 μm, 3.0×50 mm. A linear gradient was applied, starting at 90% A (A: 0.09% FA in water) and ending at 100% B (B: 0.1% FA in MeCN) over 1.70 min with a total run time of 2.00 min. The column temperature was at 40° C. with the flow rate of 1.50 mL/min.

Method M22:

The column used was a Kinetex EVO C18, 2.6 μm, 3.0×50 mm. A linear gradient was applied, starting at 90% A (A: 0.09% FA in water) and ending at 95% B (B: 0.1% FA in MeCN) over 2.70 min with a total run time of 3.00 min. The column temperature was at 40° C. with the flow rate of 1.50 mL/min.

Method M23:

The column used was an Ascentis Express C18, 2.7 μm, 3.0×50 mm. A linear gradient was applied, starting at 90% A (A: 0.09% FA in water) and ending at 95% B (B: 0.1% FA in MeCN) over 2.70 min with a total run time of 3.00 min. The column temperature was at 40° C. with the flow rate of 1.50 mL/min.

Method M24:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 2.70 min with a total run time of 3.00 min. The column temperature was at 40° C. with the flow rate of 1.50 mL/min.

Method M25:

The column used was a Kinetex EVO C18, 2.6 μm, 4.6×50 mm. A linear gradient was applied, starting at 90% A (A: 5mM$NH_4HCO_3$ in water) and ending at 95% B (B: MeCN) over 1.75 min with a total run time of 2.00 min. The column temperature was at 40° C. with the flow rate of 1.80 mL/min.

Method M26:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 4.90 min with a total run time of 5.30 min. The column temperature was at 45° C. with the flow rate of 1.50 mL/min.

Method M27:

The column used was an Poroshell HPH-C18, 2.7 μm, 3.0×50 mm. A linear gradient was applied, starting at 95% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Method M28:

The column used was a CORTECS C18+, 2.7 μm, 2.1×50 mm. A linear gradient was applied, starting at 90% A (A: 0.1% FA in water) and ending at 95% B (B: 0.1% FA in MeCN) over 2.70 min with a total run time of 3.00 min. The column temperature was at 45° C. with the flow rate of 1.00 mL/min.

Method M29:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 4.60 min with a total run time of 5.30 min. The column temperature was at 40° C. with the flow rate of 1.20 mL/min.

Method M30:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.80 min with a total run time of 3.30 min. The column temperature was at 45° C. with the flow rate of 1.20 mL/min.

Method M31:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 4.70 min with a total run time of 5.00 min. The column temperature was at 45° C. with the flow rate of 1.20 mL/min.

Method M32:

The column used was a CORTECS C18+, 2.7 μm, 2.1×50 mm. A linear gradient was applied, starting at 90% A (A: 0.1% FA in water) and ending at 95% B (B: 0.1% FA in MeCN) over 5.20 min with a total run time of 5.70 min. The column temperature was at 45° C. with the flow rate of 1.00 mL/min.

Method M33:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.20 min with a total run time of 2.60 min. The column temperature was at 40° C. with the flow rate of 1.00 mL/min.

Method M34:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 1.70 min with a total run time of 2.00 min. The column temperature was at 40° C. with the flow rate of 1.20 mL/min.

Method M35:

The column used was a CORTECS C18+, 2.7 μm, 2.1×50 mm. A linear gradient was applied, starting at 95% A (A: 0.09% FA in water) and ending at 95% B (B: 0.1% FA in MeCN) over 2.70 min with a total run time of 3.00 min. The column temperature was at 40° C. with the flow rate of 1.00 mL/min.

Method M36:

The column used was a CORTECS C18+100A, 2.7 μm, 2.1×50 mm. A linear gradient was applied, starting at 90% A (A: 0.1% FA in water) and ending at 100% B (B: 0.1% FA in MeCN) over 2.60 min with a total run time of 3.00 min. The column temperature was at 40° C. with the flow rate of 1.00 mL/min.

Method M37:

The column used was a CORTECS C18, 2.7 μm, 2.1×50 mm. A linear gradient was applied, starting at 95% A (A: 0.09% FA in water) and ending at 95% B (B: 0.1% FA in MeCN) over 2.60 min with a total run time of 3.00 min. The column temperature was at 40° C. with the flow rate of 1.00 mL/min.

Method M38:

The column used was a CORTECS C18, 2.7 μm, 2.1×50 mm. A linear gradient was applied, starting at 95% A (A: 0.05% TFA in water) and ending at 100% B (B: 0.05% TFA in MeCN) over 1.80 min with a total run time of 2.00 min. The column temperature was at 45° C. with the flow rate of 1.00 mL/min.

Method M39:

The column used was an Ascentis Express C18, 2.7 μm, 2.1×50 mm. A linear gradient was applied, starting at 70% A (A: 0.05% TFA in water) and ending at 95% B (B: 0.05% TFA in MeCN) over 5.70 min with a total run time of 6.50 min. The column temperature was at 40° C. with the flow rate of 1.00 mL/min.

Method M40:

The column used was an Ascentis Express C18, 2.7 μm, 2.1×50 mm. A linear gradient was applied, starting at 60% A (A: 0.05% TFA in water) and ending at 95% B (B: 0.05% TFA in MeCN) over 2.70 min with a total run time of 3.00 min. The column temperature was at 40° C. with the flow rate of 1.00 mL/min.

Method M41:

The column used was a Kinetex EVO C18, 2.6 μm, 3.0×50 mm. A linear gradient was applied, starting at 90% A (A: 5 mM $NH_4HCO_3$ in water) and ending at 95% B (B: MeCN) over 1.80 min with a total run time of 2.00 min. The column temperature was at 45° C. with the flow rate of 1.50 mL/min.

Method M42:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 1.70 min with a total run time of 2.00 min. The column temperature was at 40° C. with the flow rate of 1.20 mL/min.

Method M43:

The column used was a Kinetex EVO C18 100A, 2.6 μm, 2.1×50 mm. A linear gradient was applied, starting at 90% A (A: 5 mM $NH_4HCO_3$ in water) and ending at 95% B (B: MeCN) over 2.60 min with a total run time of 3.00 min. The column temperature was at 40° C. with the flow rate of 1.00 mL/min.

Method M44:

The column used was a HPH-C18, 2.7 μm, 3.0×50 mm. A linear gradient was applied, starting at 90% A (A: 5 mM $NH_4HCO_3$ in water) and ending at 100% B (B: MeCN) over 2.60 min with a total run time of 3.00 min. The column temperature was at 40° C. with the flow rate of 1.50 mL/min.

Method 45:

The column used was an Ascentis Express C18, 2.7 μm, 2.1×50 mm. A linear gradient was applied, starting at 95% A (A: 0.05% TFA in water) and ending at 95% B (B: 0.05% TFA in MeCN) over 3.10 min with a total run time of 3.60 min. The column temperature was at 40° C. with the flow rate of 1.00 mL/min.

Method M46:

The column used was an Ascentis Express C18, 2.7 μm, 2.1×50 mm. A linear gradient was applied, starting at 95% A (A: 0.05% TFA in water) and ending at 100% B (B: 0.05% TFA in MeCN) over 2.10 min with a total run time of 2.60 min. The column temperature was at 40° C. with the flow rate of 1.00 mL/min.

Method M47:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 4.20 min with a total run time of 4.50 min. The column temperature was at 40° C. with the flow rate of 1.50 mL/min.

Method M48:

The column used was a Shim-pack XR-ODS, 2.2 μm, 3.0×50 mm. A linear gradient was applied, starting at 80% A (A: 0.05% TFA in water) and ending at 95% B (B: 0.05% TFA in MeCN) over 5.00 min with a total run time of 5.60 min. The column temperature was at 45° C. with the flow rate of 1.20 mL/min.

$^1$H-NMR Data $^1$H-NMR data were determined with a Bruker Avance 400 (equipped with a flow cell (60 μl volume), or with a Bruker AVIII 400 equipped with 1.7 mm cryo CPTCI probe head, or with a Bruker AVIII 400 (400.13 MHz) equipped with a 5 mm probe head, or with a Bruker AVII 600 (600.13 MHz) equipped with a 5 mm cryo TCI probe head, or with a Bruker AVIII 600 (601.6 MHz) equipped with a 5 mm cryo CPMNP probe head, or with a Bruker AVIII 500 (500.13 MHz) equipped with a 5 mm broadband head or a 5 mm Prodigy™ probe head, with tetramethylsilane as reference (0.0) and the solvents $CD_3CN$, $CDCl_3$ or $D_6$-DMSO. Alternative $^1$H- and $^{13}$C-NMR instrument types: Bruker DMX300 ($^1$H-NMR: 300 MHz; $^{13}$C NMR: 75 MHz), Bruker Avance III 400 ($^1$H-NMR: 400 MHz; $^{13}$C NMR: 100 MHz) or Bruker 400 Ultrashield ($^1$H-NMR: 400 MHz; $^{13}$C NMR: 100 MHz).

Chemical shifts (δ) are displayed in parts per million [ppm]; the following abbreviations are used: s=singlet, d=doublet, t=triplet, q=quartet, m=multiplet, br.=broad; coupling constants are displayed in Hertz [Hz].

Experimental Section—General Procedures

The synthesis of the compounds of the formula (I) can be performed according to or in analogy to the following schemes (Scheme 1a-e, Scheme 2 and Scheme 3).

Scheme 1a

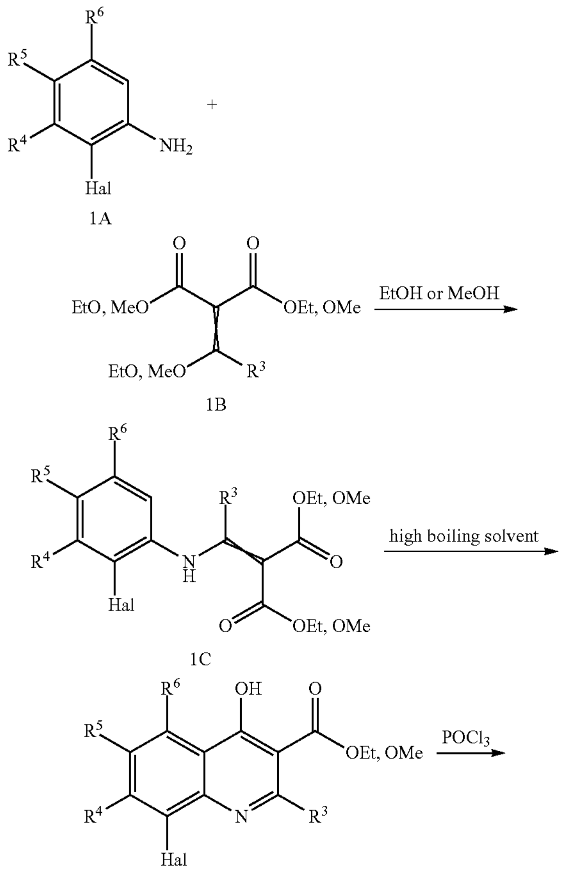

1A

1B

1C

1D

-continued

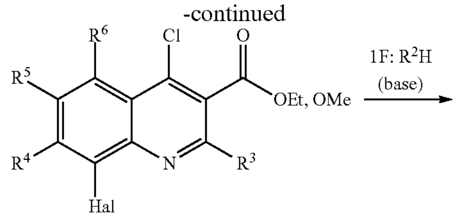

1E

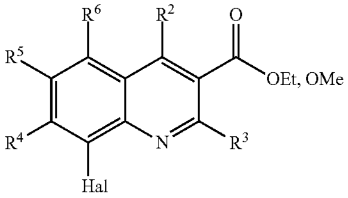

1G

2-Halogen-substituted anilines 1A (Hal=iodine, bromine, chlorine) are commercial available and can be readily converted with (alkoxymethylen)malonates 1B dissolved the corresponding alcohol solvent, preferably under boiling conditions into (anilinomethylene)malonates 1C as described in Monatshefte fuer Chemie, 2015, 146(2), 291-302 or without any solvent as described in WO 2002004444. The ring closure is performed in high boiling solvents, preferably in diphenylether or xylol, to achieve hydroxy quinolines 1D as described in WO 2013118071. The hydroxy quinolines 1D can be easily converted into the corresponding chlorine compounds 1E with a chlorination reagent, preferably refluxing $POCl_3$ as described in WO 2013118071.

Depended on the nature of the nucleophile $R^2H$ 1F, the chloro quinolines 1E reacts with 1F in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain ester intermediates 1G.

Scheme 1b

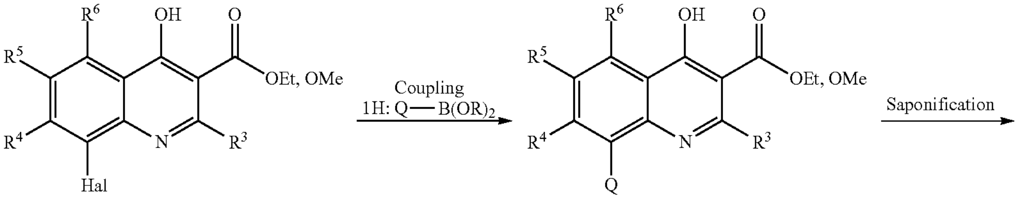

1D 1I

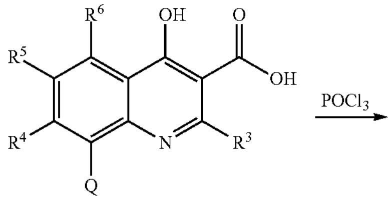

1J

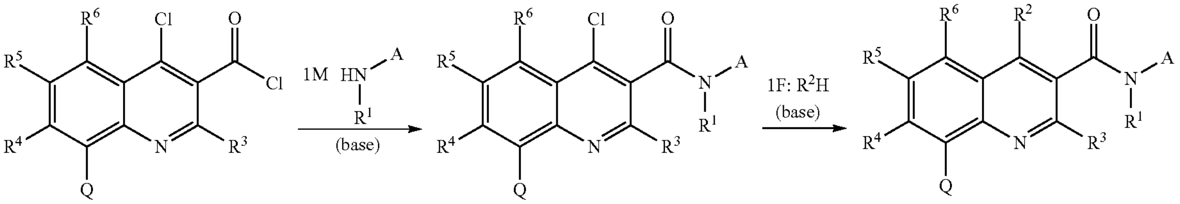

1K 1N (I)

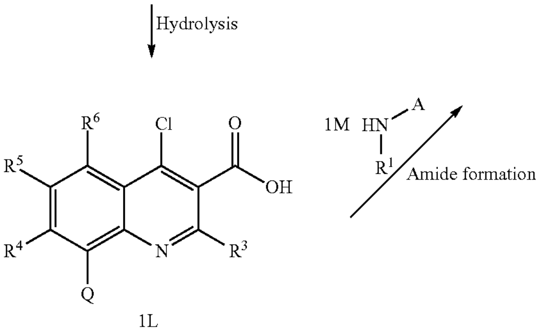

1L

Alternatively, a Suzuki cross coupling reaction of intermediates 1D with boronic acids or boronic esters 1H Q-B $(OR)_2$ (R═H; R=Me or R,R=pinacolate) as described in Chem. Soc. Rev. 2014, 43, 412-443 or in Tetrahedron 2002, 58 (48), 9633-9695 to ester intermediates 11. Subsequently, the ester intermediates 11 can be smoothly saponified e.g. with lithium hydroxide resulting in the corresponding carboxylic acids 1J, which can be easily converted into the corresponding chloro carboxylic chlorides 1K with a chlorination reagent, preferably refluxing $POCl_3$ as described in WO 2013096151. Intermediates 1K react under hydrolytic conditions to yield quinolone carboxylic acids 1L, which are combined with commercial available amines 1M via an amide formation and dehydration reagents, e.g. N-(3-dimethylaminoisopropyl)-N'-ethylcarbodiimide-hydrochloride (EDC) to give amides 1N. Similar syntheses are described in Journal of Medicinal Chemistry 2012, 55, 3563-3567 for example. Intermediates 1K can directly form the amides 1N as the carboxylic acid chlorides 1K are combined with amines 1M under basic conditions, e.g. pyridine, triethylamine or N,N-diisopropyl ethylamine as described in Chemical Biology & Drug Design 2015, 85(5), 549-564. Depended on the nature of the nucleophile $R^2H$ 1F, the chloro quinolines 1N reacts with 1F in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the target compounds of formula (I).

Scheme 1c

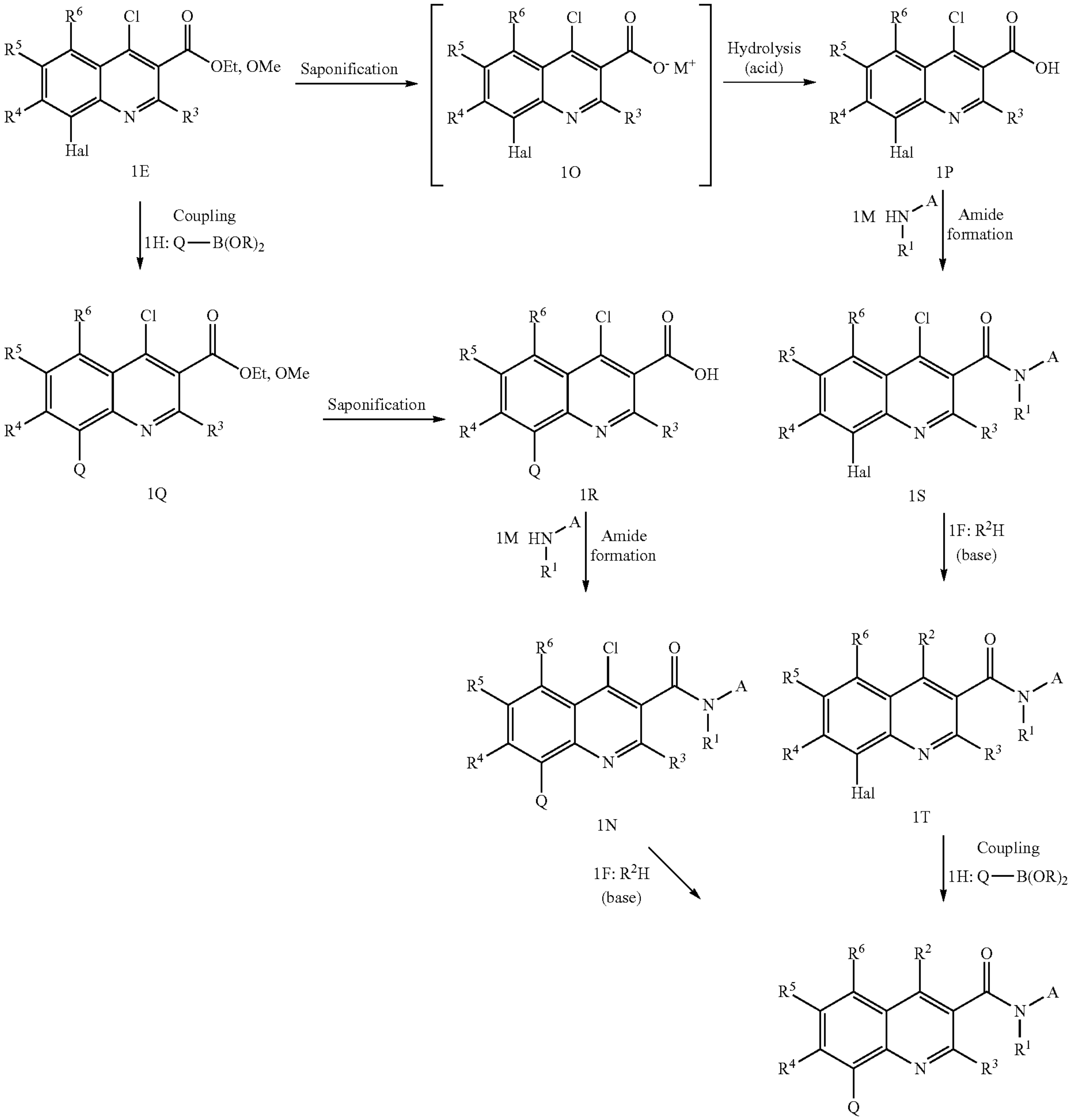

1E, 1O, 1P, 1Q, 1R, 1S, 1N, 1T, (I)

Chloro quinolines 1E can be smoothly saponified e.g. with lithium hydroxide resulting in the corresponding carboxylates 1O, obtained e.g. as lithium salt, or resulting in the carboxylic acids 1P after acid hydrolysis. Subsequently, the intermediate carboxamides 1S are obtained by amide coupling conditions, e.g. via carboxylic acid chlorides formed from 1P which are combined with amines 1M under basic conditions, e.g. pyridine, triethylamine or N,N-diisopropyl ethylamine or via amide formation from the carboxylic acids 1P which are combined with amines 1M and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example. Dependend on the nature of the nucleophile $R^2H$ 1F, the chloro quinolines 1S react with 1F in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the intermediate carboxamides 1T. A Suzuki cross coupling reaction of intermediate carboxamides 1T with boronic acids or boronic esters 1H Q-B(OR)2 (R=H; R=Me or R,R=pinacolate) as described in Chem. Soc. Rev. 2014, 43, 412-443 or in Tetrahedron 2002, 58 (48), 9633-9695 leads to the final products of formula (I).

Alternatively, chloro quinolines 1E react via a Suzuki cross coupling reaction with boronic acids or boronic esters 1H Q-B(OR)2 (R=H; R=Me or R,R=pinacolate) as described in Chem. Soc. Rev. 2014, 43, 412-443 or in Tetrahedron 2002, 58 (48), 9633-9695 to provide quinoline carboxylic esters 1Q, which can be smoothly saponified e.g. with lithium hydroxide resulting in the corresponding quinoline carboxylic acid 1R. Subsequently, the intermediate carboxamides 1N are obtained by amide coupling conditions, e.g. via carboxylic acid chlorides formed from 1R which are combined with amines 1M under basic conditions, e.g. pyridine, triethylamine or N,N-diisopropyl ethylamine or via amide formation from the carboxylic acids 1R which are combined with amines 1M and dehydration reagents, e.g. N-(3-dimethylaminoisopropyl)-N'-ethylcarbodiimide-hydrochloride (EDC). Similar syntheses are described in Journal of Medicinal Chemistry 2012, 55, 3563-3567 for example. Dependend on the nature of the nucleophile $R^2H$ 1F, the chloro quinolines 1N react with 1F in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the the final products of formula (I) as well.

Scheme 1d

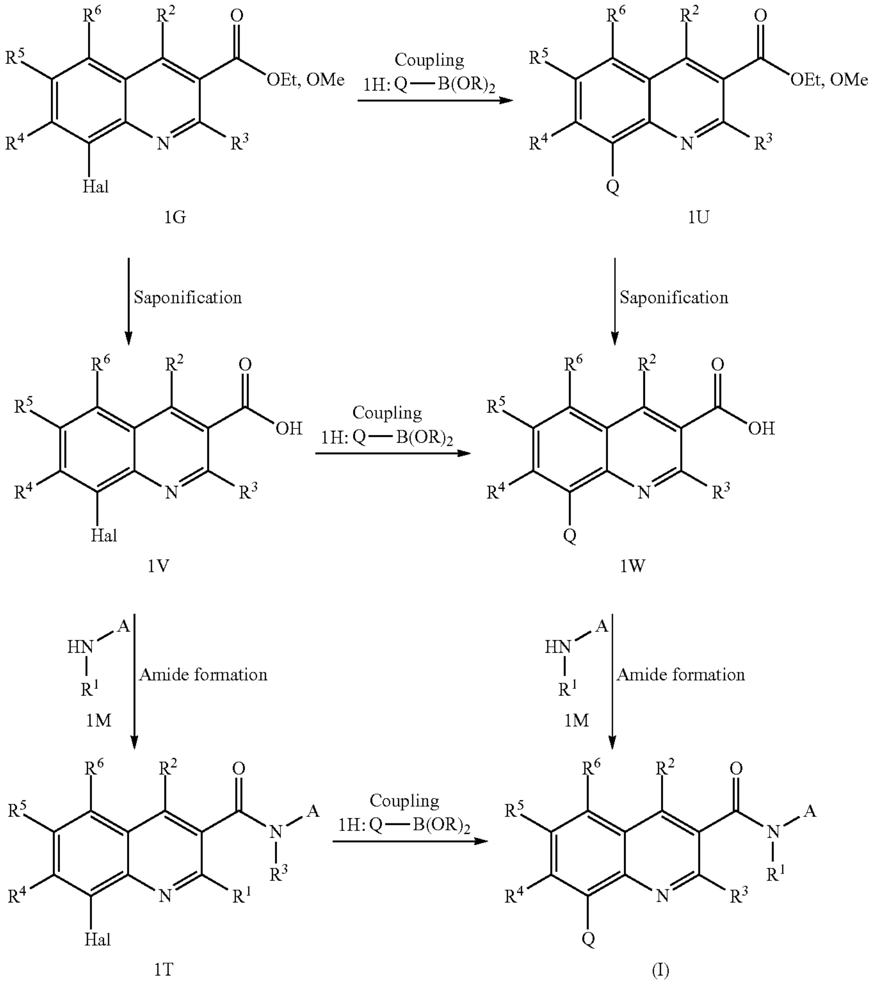

Quinoline carboxylic esters 1G can be converted via a Suzuki cross coupling reaction with boronic acids or boronic esters 1H Q-B(OR)2 (R═H; R=Me or R,R=pinacolate) as described in Chem. Soc. Rev. 2014, 43, 412-443 or in Tetrahedron 2002, 58 (48), 9633-9695 to provide quinoline carboxylic esters 1U, which can be smoothly saponified e.g. with lithium hydroxide resulting in the corresponding quinoline carboxylic acid 1W. Subsequently, the final products of formula (I) are obtained by amide coupling conditions, e.g. via carboxylic acid chlorides formed from 1W which are combined with amines 1M under basic conditions, e.g. pyridine, triethylamine or N,N-diisopropyl ethylamine or via amide formation from the carboxylic acids 1W which are combined with amines 1M and dehydration reagents, e.g. N-(3-dimethylamino-isopropyl)-N'-ethylcarbodiimide-hydrochloride (EDC). Similar syntheses are described in Journal of Medicinal Chemistry 2012, 55, 3563-3567 for example.

Alternatively, quinoline carboxylic esters 1G can be saponified first and then converted via a Suzuki cross coupling reaction with boronic acids or boronic esters 1H Q-B(OR)2 (R═H; R=Me or R,R=pinacolate) into quinoline carboxylic acids 1W or transformed into quinoline carboxamides 1T by means of amide coupling conditions, e.g. via quinoline carboxylic acid chlorides formed from 1V which are combined with amines 1M under basic conditions, e.g. pyridine, triethylamine or N,N-diisopropyl ethylamine or via amide formation from the quinolone carboxylic acids 1V which are combined with amines 1M and dehydration reagents, e.g. N-(3-dimethylaminoisopropyl)-N'-ethylcarbodiimide-hydrochloride (EDC). Finally, quinoline carboxamides 1T can be converted via a Suzuki cross coupling reaction with boronic acids or boronic esters 1H Q-B(OR)2 (R═H; R=Me or R,R=pinacolate) as described in Chem. Soc. Rev. 2014, 43, 412-443 or in Tetrahedron 2002, 58 (48), 9633-9695 into final products of formula (I).

Scheme 1d'

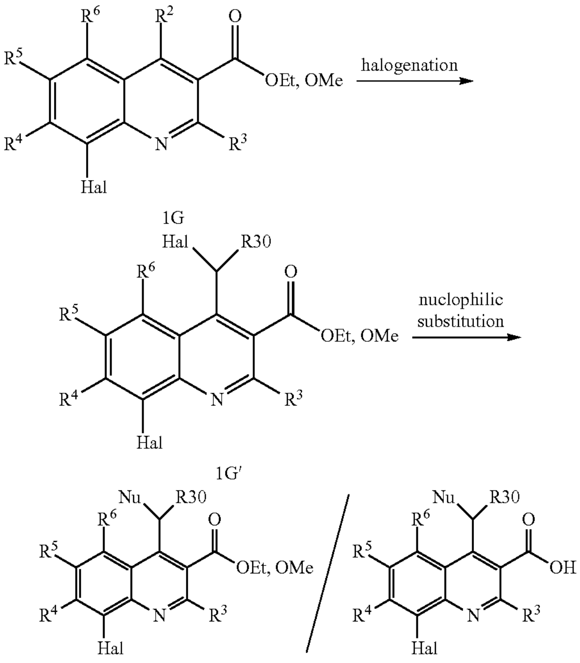

1G

1G'

1G'' / 1V''

A subgroup of 1G, where $R^2$ is an alkyl group, such as methyl ($R_{30}$═H) can be halogenated, e.g. brominated by brominating agents such as bromine, N-bromo-succinimide, pyridinium tribromide or phenyltrimethylammonium tribromide to bromoalkylderivatives 1G' as described e.g. in J. Heterocl. Chem. 1981, vol. 18, 925-928, J. Med. Chem., 2009, vol. 52, 3047-3062 or J. Am. Chem. Soc., 1948, 70, 417-418. Such bromoalkyl compounds 1G' can be substituted by nucleophiles such as amines, alcohols or thiols or their salts, occasionally in presence of base according to standard procedures to furnish substituted alkyl-quinolines 1G". Under the reaction conditions of the nucleophilic substitution the esters 1G" can be further converted to the corresponding acids 1V" or they can be isolated and converted in a separate hydrolysis step to the acids 1V". Then, the final products (I) can be obtained from the acids 1V" by amide formation and coupling of the group Q by the methods described in scheme 1d.

Scheme 1e

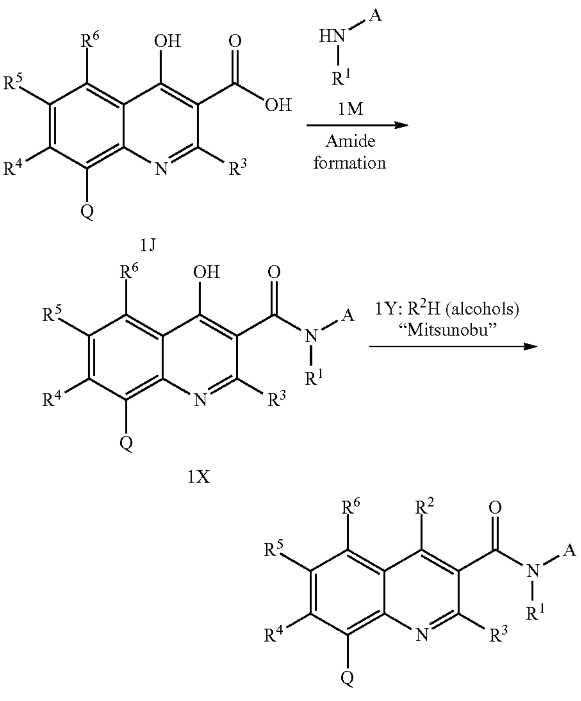

1J

1X (I)

($R^2$ = optionally substituted $C_1$-C4-alkoxy)

Hydroxy quinolones 1X are obtained by amide coupling conditions, e.g. via carboxylic acid chlorides formed from 1J which are combined with amines 1M under basic conditions, e.g. pyridine, triethylamine or N,N-diisopropyl ethylamine or via amide formation from the carboxylic acids 1J which are combined with amines 1M and dehydration reagents, e.g. N-(3-di-methylaminoisopropyl)-N'-ethylcarbodiimide-hydrochloride (EDC). Similar syntheses are described in Journal of Medicinal Chemistry 2012, 55, 3563-3567 for example. The final products of formula (I) are obtained by a Mitsunobu reaction of hydroxy quinolones 1X with alcohols 1Y ($R^2$═$C_1$-$C_4$-alkoxy, optionally substituted) in the presence of dehydrating reagents, e.g. diisopropyl-(E)-diazene-1,2-dicarboxylate and triphenylphosphine as described in Organic & Biomolecular Chemistry 2012, 10(32), 6537-6546.

Scheme 2

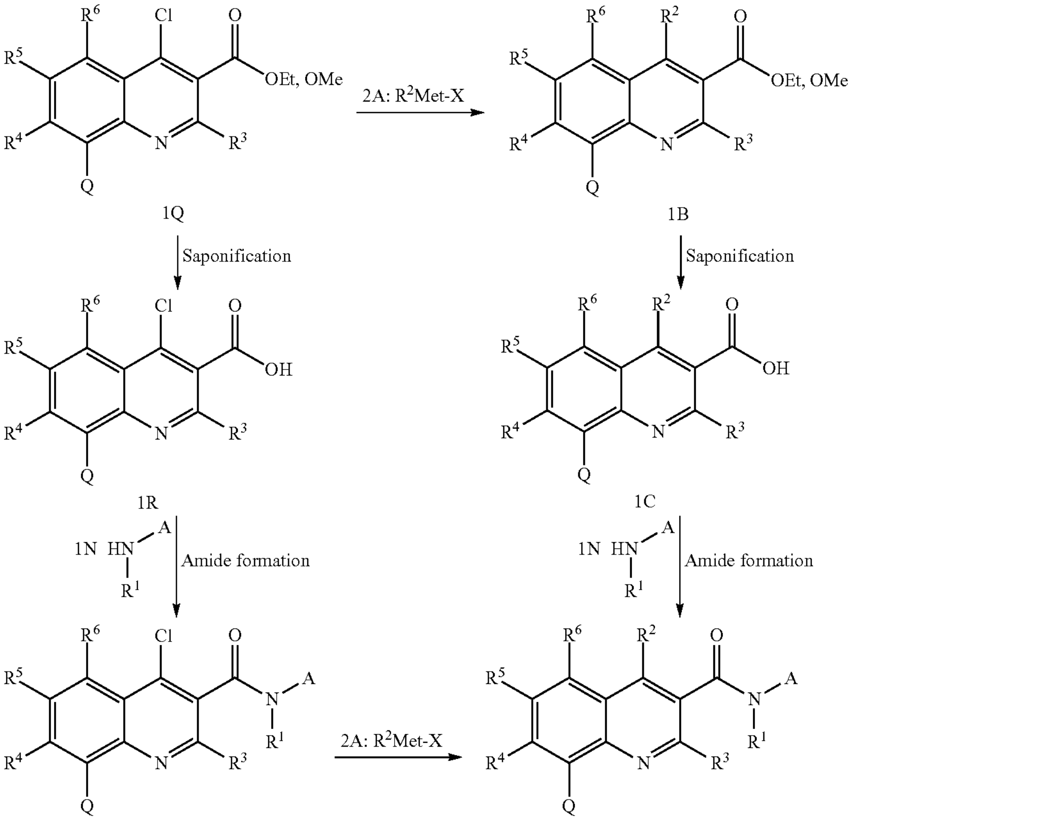

1Q 1B 1R 1C 1N I-a ($R^2$ = $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of with is optionally substituted as defined for the compound of general formula (I) as defined supra)

Quinoline carboxylic ester intermediates 1Q or quinolone carboxamide intermediates 1N can be converted with certain Grignard- or metal organic compounds 2A: $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X═I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of general formula (I) as defined supra, as described in Tetrahedron Letters, 2000, 41(33), 6387-6391 for example, into ester intermediates 2B or final compounds I-a.

Scheme 3

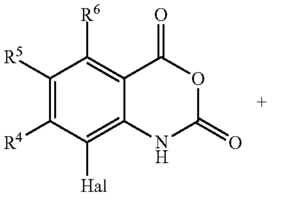

3A

-continued

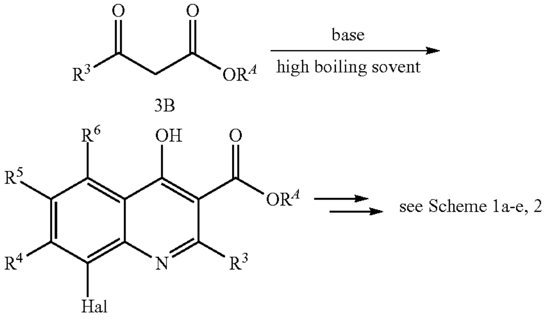

3B

3C ($R^3$ = $C_1$-$C_4$-alkyl)

$R^3$ = C1-C4-alkyl

An alternative route to obtain hydroxyl ester 3C($R^3$═$C_1$-$C_4$-alkyl, $R^A$=methyl, ethyl or t.-butyl) uses commercial available 2H-3,1-oxazine-2,4(1H)-diones 3A (Hal=iodine, bromine, chlorine) in a decarboxylation reaction with ketoesters 3B ($R^3$═$C_1$-$C_4$-alkyl, $R^A$=methyl, ethyl or t.-butyl) in the presence of a base, e.g. sodium hydride in polar high boiling solvents, e.g. N,N-dimethyl acetamide as described in US 20080306048. The following steps can be performed according to Scheme 1a-e or Scheme 2.

Scheme 4

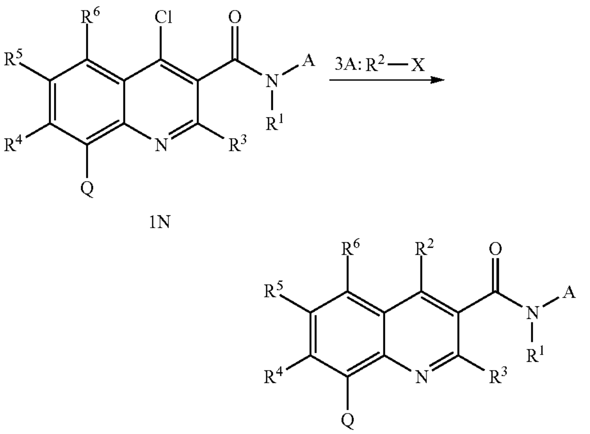

1N

I-a

Quinolone carboxamide intermediates 1N can be converted by photoredox catalysis with certain alkyl, clycloalkyl and hetercyclooalkyl halides or carboxylic acids 3A: $C_1$-$C_4$-alkyl-X, $C_3$-$C_6$-cycloalkyl-X, $C_3$-$C_6$-cycloalkenyl-X, heterocycloalkyl-X (X═Br, COOH) introducing $C_1$-$C_4$-alkyl, $C_3$-$C_6$-cycloalkyl, $C_3$-$C_6$-cycloalkenyl, heterocycloalkyl each of which is optionally substituted as defined for the compound of general formula (I) as defined supra, as described in J. Org. Chem., 2016, 81 (16), pp 6898-6926 or Chem. Rev., 2013, 113 (7), pp 5322-5363.

EXPERIMENTAL SECTION—EXAMPLES

Synthesis of 8-(3,5-dichlorophenyl)-N-[(4S)-3,4-dihydro-2H-chromen-4-yl]-4-($R^2$)quinoline-3-carboxamides (examples 135, 137, 150, 188, 189, 243, 261, 264, 273)

Step 1

8-(3,5-dichlorophenyl)-4-hydroxyquinoline-3-carboxylic acid

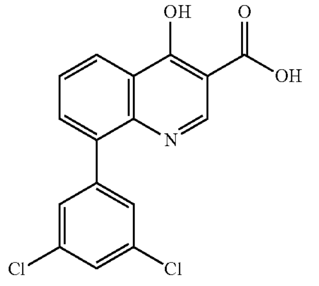 [SMILES: O=C(O)c1cnc2c(-c3cc(Cl)cc(Cl)c3)cccc2c1O]

Under argon atmosphere a flask was charged with ethyl 8-bromo-4-hydroxy-quinoline-3-carboxylate (15.0 g, 50.7 mmol) (Gharat, al., WO 2013/118071), 3,5-dichlorobenzene boronic acid (11.6 g, 60.8 mmol), potassium carbonate (14.0 g, 101 mmol) 1,1'-bis(diphenylphosphino)ferrocene-palladium(II)dichloride dichloromethane complex (1.24 g, 1.52 mmol) and a degassed 5:1 mixture of dioxan and water (190 ml). The suspension was stirred overnight at 70° C. Then an aqueous solution of sodium hydroxide (5 M, 101 ml, 505 mmol) was added and the dark mixture was refluxed for 6 h. Subsequently, hot water (110 ml), methanol (70 ml) and charcoal (2.5 g) were added and refluxing continued for a few minutes. The mixture was filtered hot and the filter cake washed with methanol/water (1:1). 5 M acetic acid (150 ml, 750 mmol) was added slowly under stirring to the hot filtrate to achieve a pH range of 6-7. Further 90 ml of water were added and the solvents were partially removed under reduced pressure. The suspension was cooled under stirring to RT and lateron to 0° C. The precipitate was filtered off, washed with methanol/water (2:1), stirred in MTBE, filtered off again and dried in vacuo.

Yield: 17.5 g (92% purity, 95% of th.)

LC-MS (Method L1): $R_t$=1.02 min; MS (ESIpos): m/z=334 $[M+H]^+$ $^1$H-NMR Peaklist (400 MHz, DMSO-d6) δ[ppm]: −0.008 (1.06), 0.008 (0.98), 1.909 (9.53), 2.524 (1.24), 2.670 (0.41), 3.162 (0.87), 3.175 (0.89), 3.568 (5.51), 7.609 (2.04), 7.628 (3.44), 7.650 (15.61), 7.654 (16.00), 7.769 (2.83), 7.773 (4.62), 7.778 (2.66), 7.788 (3.38), 7.791 (3.46), 7.806 (2.84), 7.809 (2.66), 7.874 (0.44), 7.879 (0.42), 7.948 (0.51), 7.952 (0.48), 8.364 (3.52), 8.368 (3.54), 8.385 (3.50), 8.388 (3.26), 8.603 (10.14), 12.202 (1.00).

Step 2

4-chloro-8-(3,5-dichlorophenyl)quinoline-3-carbonyl chloride

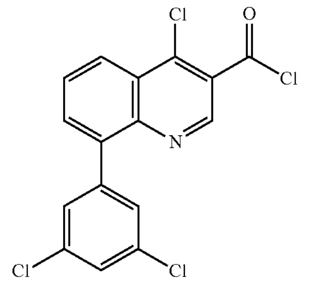 [SMILES: O=C(Cl)c1cnc2c(-c3cc(Cl)cc(Cl)c3)cccc2c1Cl]

To a suspension of 8-(3,5-dichlorophenyl)-4-hydroxyquinoline-3-carboxylic acid (step 1) (8.10 g, 24.2 mmol) in chloroform (48 ml) under stirring were added DMF (4 drops) and oxalylchloride (40 ml, 460 mmol) slowly during 1 h at ambient temperature, causing significant gas evolution. Then, the mixture was slowly heated to reflux and stirred at reflux temperature for 3.5 h. The volatiles were evaporated under reduced pressure and the residue was co-evaporated twice with dry dichloromethane and once with dry THF. The crude product (9.0 g, 100%) was used in the next step.

$^1$H-NMR (400 MHz, CHLOROFORM-d): δ [ppm]=9.42 (s, 1H), 8.53 (dd, 1H), 7.89-7.95 (m, 1H), 7.80-7.87 (m, 1H), 7.53 (d, 2H), 7.46 (t, 1H).

Step 3

4-chloro-8-(3,5-dichlorophenyl)quinoline-3-carboxylic acid

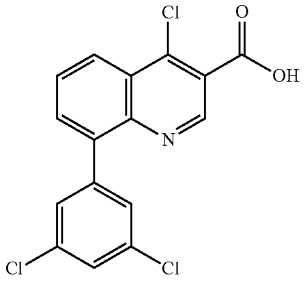 [SMILES: O=C(O)c1cnc2c(-c3cc(Cl)cc(Cl)c3)cccc2c1Cl]

4-chloro-8-(3,5-dichlorophenyl)quinoline-3-carbonyl chloride (step 2) (5.40 g, 14.6 mmol) was suspended in THF (100 ml). Water (25 ml) and sodium hydrogencarbonate (2.0 g, 23.8 mmol) were added until a pH 5 is maintained and the reaction mixture was stirred overnight at ambient temperature. The THF was largely removed under reduced pressure at a bath temperature not exceeding 40° C. Acetonitril (20 ml) was added and the organic solvents were removed again under reduced pressure. This procedure was repeated and the suspension was cooled to 0° C. The precipitate was filtered off, washed with little volumes of acetonitrile/water (2:1) and petrolether and dried in vacuo.

Yield: 5.10 g (93% purity, 92% of th.)

LC-MS (Method L1): $R_f$=1.16 min; MS (ESIpos): m/z=352 $[M+H]^+$ $^1$H-NMR Peaklist (400 MHz, DMSO-d6) δ[ppm]: −0.008 (1.29), 0.008 (1.20), 1.760 (0.44), 2.329 (0.64), 2.367 (0.44), 2.524 (2.38), 2.671 (0.63), 2.711 (0.43), 3.601 (0.50), 7.654 (1.72), 7.660 (4.30), 7.664 (6.77), 7.669 (16.00), 7.673 (7.64), 7.804 (1.91), 7.823 (3.49), 7.843 (3.22), 7.887 (3.53), 7.890 (3.71), 7.904 (2.79), 8.354 (3.04), 8.357 (3.11), 8.375 (2.85), 8.378 (2.73), 8.907 (6.32).

Step 4a 4-chloro-8-(3,5-dichlorophenyl)-N-[(4S)-3,4-dihydro-2H-chromen-4-yl]quinoline-3-carboxamide (Example 4)

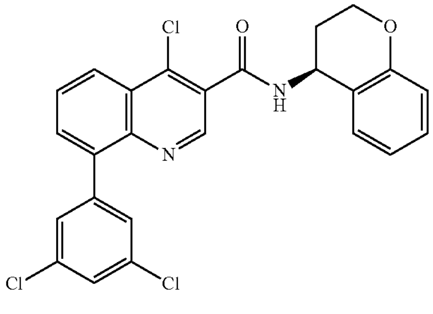 [SMILES: O=C(N[C@H]1CCOc2ccccc21)c1cnc2c(-c3cc(Cl)cc(Cl)c3)cccc2c1Cl]

To a solution of 4-chloro-8-(3,5-dichlorophenyl)quinoline-3-carboxylic acid (step 3) (7.60 g, 21.6 mmol) in THF (110 ml) were added under stirring (4S)-chroman-4-amine hydrochloride (4.4 g, 23.7 mmol), triethylamine (12 ml, 86 mmol) and after 10 min at ambient temperature a solution of 2,4,6-tripropyl-1,3,5,2,4,6-trioxatriphosphinane 2,4,6-trioxide in ethylacetate (19 ml, 50 content, 32 mmol), whereafter the temperature of the mixture was raised to 36° C. After stirring overnight at ambient temperature further (4S)-chroman-4-amine hydrochloride (0.8 g, 4.3 mmol), triethylamine (3 ml, 21.5 mmol) and a solution of 2,4,6-tripropyl-1,3,5,2,4,6-trioxatriphosphinane 2,4,6-trioxide in ethylacetate (3.85 ml, 50% content, 6.5 mmol) were added and stirring continued at ambient temperature for another night. Then water was added and most of the organic solvents evaporated under reduced pressure. The formed precipitate was filtered off and washed with petrolether and was dried in vacuo.

Yield: 10.0 g (94% purity, 90% of th.)

LC-MS (Method L1): $R_f$=1.35 min; MS (ESIpos): m/z=483 $[M+H]^+$ $^1$H-NMR Peaklist (400 MHz, DMSO-d6) δ[ppm]: 1.356 (1.31), 1.743 (2.45), 1.752 (3.18), 1.759 (6.79), 1.768 (3.21), 1.776 (2.57), 1.988 (0.51), 2.059 (0.99), 2.066 (1.07), 2.076 (1.22), 2.084 (1.26), 2.093 (1.57), 2.100 (1.38), 2.209 (1.45), 2.221 (1.33), 2.229 (1.27), 2.242 (0.90), 2.366 (0.47), 3.585 (2.47), 3.601 (5.93), 3.617 (2.49), 4.221 (0.89), 4.241 (2.24), 4.249 (1.82), 4.262 (2.18), 4.270 (2.80), 4.279 (2.21), 4.287 (1.82), 4.296 (1.93), 4.315 (0.75), 5.267 (0.91), 5.282 (2.01), 5.301 (2.05), 5.315 (0.88), 6.791 (3.63), 6.811 (4.03), 6.917 (1.84), 6.936 (3.82), 6.955 (2.20), 7.161 (2.03), 7.179 (3.22), 7.199 (1.53), 7.380 (3.39), 7.399 (3.19), 7.680 (16.00), 7.879 (0.46), 7.893 (2.16), 7.912 (3.99), 7.932 (3.43), 8.009 (4.26), 8.026 (2.94), 8.389 (3.75), 8.410 (3.33), 8.962 (9.97), 9.251 (3.23), 9.272 (3.16).

Step 4b 4-chloro-8-(3,5-dichlorophenyl)-N-[(1S)-2,3-dihydro-1H-inden-1-yl]quinoline-3-carboxamide (Example 3)

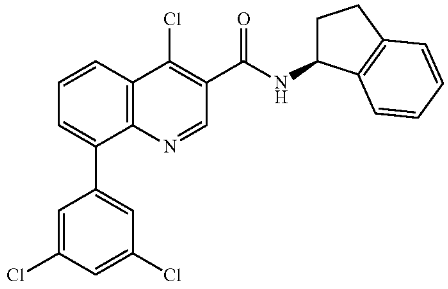 [SMILES: O=C(N[C@H]1CCc2ccccc21)c1cnc2c(-c3cc(Cl)cc(Cl)c3)cccc2c1Cl]

To a stirred mixture of 4-chloro-8-(3,5-dichlorophenyl)quinoline-3-carbonyl chloride (step 2) (480 mg, 1.29 mmol) in DMF (4 ml) was added triethylamine (0.36 ml, 2.6 mmol) and then dropwise a solution of (1S)-indan-1-amine (0.18 ml, 2.6 mmol) in dichloromethane (1.2 ml) at 0° C. The reaction mixture was stirred 1 h at 0° C., then warmed to ambient temperature and the pH adjusted to 5-6 with 1 M acetic acid followed by addition of water and extraction with dichloromethane. The organic phases were separated and evaporated under reduced pressure and the residue was purified by column chromatography on silica (100 g), eluent: cyclohexane/ethyl acetate (9-40%).

Yield: 149 mg (25% of th.)

LC-MS (Method L1): $R_f$=1.37 min; MS (ESIpos): m/z=467 [M+H]$^+$ $^1$H-NMR Peaklist (400 MHz, DMSO-d6) δ[ppm]: 0.008 (1.33), 1.234 (2.20), 1.397 (0.85), 1.924 (1.63), 1.935 (0.83), 1.946 (1.76), 1.956 (1.90), 1.967 (0.79), 1.977 (1.84), 1.998 (0.66), 2.524 (2.18), 2.567 (0.88), 2.575 (0.77), 2.838 (0.77), 2.859 (1.28), 2.878 (2.28), 2.898 (2.50), 2.918 (1.19), 2.951 (1.54), 2.959 (1.64), 2.973 (1.71), 2.980 (1.81), 2.990 (0.99), 2.999 (0.88), 3.012 (0.86), 3.020 (0.74), 3.070 (1.91), 5.542 (1.02), 5.562 (2.83), 5.582 (2.79), 5.602 (0.92), 7.223 (0.96), 7.232 (4.00), 7.240 (4.95), 7.246 (5.24), 7.254 (7.15), 7.263 (2.96), 7.271 (3.67), 7.281 (2.50), 7.293 (1.17), 7.435 (2.55), 7.446 (2.61), 7.456 (2.00), 7.635 (1.10), 7.665 (0.98), 7.678 (13.08), 7.681 (16.00), 7.686 (7.10), 7.689 (3.73), 7.695 (1.37), 7.700 (0.80), 7.895 (2.06), 7.913 (4.25), 7.934 (3.06), 8.004 (4.66), 8.008 (3.27), 8.022 (3.28), 8.026 (2.07), 8.393 (4.14), 8.396 (2.75), 8.414 (3.73), 8.417 (2.39), 8.962 (10.00), 9.118 (3.31), 9.139 (3.23).

Step 5

4-(azetidin-1-yl)-8-(3,5-dichlorophenyl)-N-[(4S)-3,4-dihydro-2H-chromen-4-yl]quinoline-3-carboxamide (Example 135)

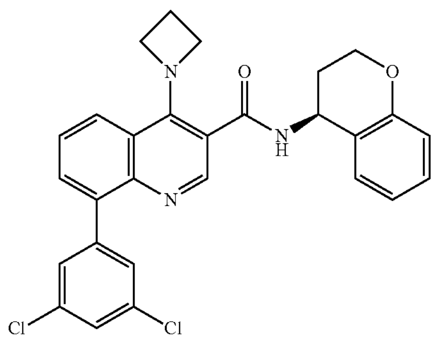 [SMILES: O=C(N[C@H]1CCOc2ccccc21)c1cnc2c(-c3cc(Cl)cc(Cl)c3)cccc2c1N1CCC1]

In a thick-walled microwave vessel triethylamine (84 μl, 0.6 mmol) and azetidine (40 μl, 0.6 mmol) were added to a solution of 4-chloro-8-(3,5-dichlorophenyl)-N-[(4S)-3,4-dihydro-2H-chromen-4-yl]quinoline-3-carboxamide (step 4a) (145 mg, 0.3 mmol) in N-methyl pyrrolidon. The vessel was capped and heated under stirring to 100° C. for 2.5 h. 5 M formic acid (180 μl, 0.9 mmol) and little DMSO were added to the dark mixture and the solution purified by prep. HPLC (C18, gradient: 0.1% aq. formic acid/acetonitrile).

Yield: 93 mg (62% of th.)

LC-MS (Method L1): $R_f$=0.89 min; MS (ESIpos): m/z=504 [M+H]$^+$ $^1$H-NMR Peaklist (400 MHz, DMSO-d6) δ[ppm]: −0.008 (6.30), 0.008 (2.98), 2.004 (1.02), 2.014 (0.94), 2.026 (1.43), 2.041 (1.28), 2.126 (1.31), 2.141 (1.56), 2.373 (2.15), 2.394 (2.92), 2.412 (2.16), 2.433 (1.25), 2.519 (4.80), 2.523 (4.67), 4.243 (3.28), 4.255 (4.75), 4.261 (3.01), 4.270 (2.58), 4.427 (5.50), 4.446 (8.06), 4.466 (4.62), 5.160 (0.92), 5.174 (1.75), 5.194 (1.64), 5.754 (2.42), 6.781 (3.04), 6.785 (3.14), 6.802 (3.39), 6.805 (3.26), 6.887 (1.73), 6.890 (1.66), 6.906 (3.30), 6.909 (2.99), 6.924 (1.93), 6.927 (1.70), 7.142 (1.75), 7.146 (1.77), 7.163 (2.63), 7.180 (1.31), 7.185 (1.20), 7.291 (2.83), 7.311 (2.52), 7.434 (2.40), 7.452 (3.13), 7.455 (2.90), 7.473 (2.61), 7.592 (2.65), 7.597 (4.87), 7.602 (5.82), 7.611 (16.00), 7.616 (8.48), 7.698 (3.62), 7.701 (3.63), 7.716 (3.07), 7.719 (2.82), 8.058 (3.06), 8.061 (3.05), 8.080 (2.76), 8.083 (2.47), 8.430 (11.34), 8.946 (2.94), 8.966 (2.74).

ethyl N-{8-(3,5-dichlorophenyl)-3-[(4S)-3,4-dihydro-2H-chromen-4-ylcarbamoyl]quinolin-4-yl}-N-methylglycinate (Example 137)

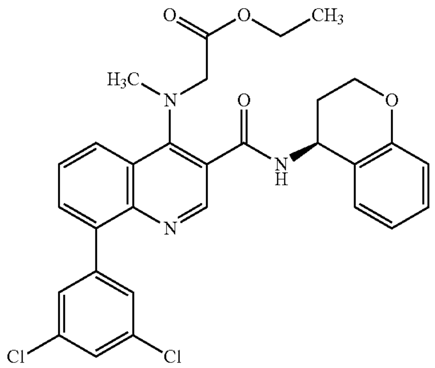 [SMILES: CCOC(=O)CN(C)c1c(C(=O)N[C@H]2CCOc3ccccc32)cnc2c(-c3cc(Cl)cc(Cl)c3)cccc12]

Under argon atmosphere a thick-walled microwave vessel was charged with 1,4-diazabicyclo(2.2.2)octane (56 mg, 0.5 mmol), ethyl-N-methylglycinatehydrochloride (1:1) (154 mg, 1.0 mmol), N,N-diisopropylethylamine (350 μl, 2.0 mmol), N-methyl pyrrolidon (0.8 ml) and 4-chloro-8-(3,5-dichlorophenyl)-N-[(4S)-3,4-dihydro-2H-chromen-4-yl]quinoline-3-carboxamide (step 4a) (242 mg, 0.5 mmol). The vessel was capped and the mixture heated under stirring at 100° C. for 3 h. Further amounts of ethyl-N-methylglycinatehydrochloride (1:1) (77 mg, 0.5 mmol), N,N-diisopropylethylamine (170 μl, 1.0 mmol) were added and heating continued for 2 h. 5 M formic acid (0.7 ml, 3.5 mmol) and DMSO (3 ml) were added and the solution purified by prep. HPLC (C18, gradient: 0.1% aq. formic acid/acetonitrile).

Yield: 150 mg (98% purity, 52% of th.)

LC-MS (Method L1): $R_f$=1.38 min; MS (ESIpos): m/z=564 [M+H]$^+$ $^1$H-NMR Peaklist (400 MHz, DMSO-d6) δ[ppm]: −0.008 (0.78), 0.008 (0.70), 1.199 (4.33), 1.217 (9.13), 1.234 (4.62), 1.356 (0.52), 2.063 (0.43), 2.073 (0.48), 2.084 (0.47), 2.099 (0.71), 2.107 (0.59), 2.114 (0.45), 2.193 (0.49), 2.205 (0.59), 2.216 (0.59), 2.227 (0.52), 2.523 (0.52), 3.049 (12.82), 4.052 (6.68), 4.134 (1.34), 4.152 (4.12), 4.170 (4.04), 4.187 (1.27), 4.255 (1.01), 4.267 (1.21), 4.278 (1.65), 4.282 (1.70), 4.293 (0.97), 5.257 (0.42), 5.271 (0.95), 5.291 (0.95), 5.305 (0.42), 6.792 (1.74), 6.812 (1.94), 6.901 (0.87), 6.919 (1.84), 6.937 (1.07), 7.154 (0.86), 7.157 (0.93), 7.175 (1.47), 7.193 (0.70), 7.196 (0.71), 7.362 (1.56), 7.380 (1.46), 7.645 (16.00), 7.688 (1.26), 7.707 (1.75), 7.728 (1.59), 7.840 (1.89), 7.842 (2.05), 7.857 (1.58), 7.860 (1.56), 8.354 (1.72), 8.357 (1.80), 8.376 (1.63), 8.379 (1.60), 8.757 (6.02), 9.197 (1.69), 9.217 (1.64).

N-{8-(3,5-dichlorophenyl)-3-[(4S)-3,4-dihydro-2H-chromen-4-ylcarbamoyl]quinolin-4-yl}-N-methyl-glycine (Example 150)

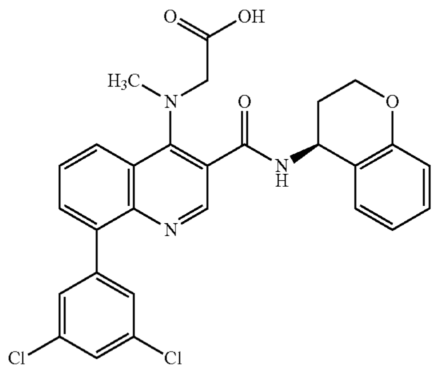 [SMILES: CN(CC(=O)O)c1c(C(=O)N[C@H]2CCOc3ccccc32)cnc2c(-c3cc(Cl)cc(Cl)c3)cccc12]

Ethyl N-{8-(3,5-dichlorophenyl)-3-[(4S)-3,4-dihydro-2H-chromen-4-ylcarbamoyl]quinolin-4-yl}-N-methylglycinate (from example 137) (35 mg, 62 μmol) was stirred in THF (0.3 ml), ethanol (0.3 ml) and 5 M aq. sodium hydroxide (50 μl, 250 μmol) for 1.5 h at ambient temperature. The reaction mixture was acidified to pH 3 by addition of 5 M formic acid and part of the solvents evaporated under reduced pressure. The formed precipitate was filtered off, washed with water and dried in vacuo.

Yield: 27 mg (81% of th.)

LC-MS (Method L1): $R_f$=1.11 min; MS (ESIpos): m/z=536 $[M+H]^+$ $^1$H-NMR Peaklist (400 MHz, DMSO-d6) δ[ppm]: 2.132 (1.28), 2.205 (1.37), 2.328 (0.59), 3.040 (16.00), 3.931 (0.61), 3.975 (4.59), 3.984 (4.71), 4.281 (3.48), 5.309 (1.69), 5.326 (1.68), 6.779 (2.78), 6.799 (3.08), 6.883 (1.42), 6.901 (2.80), 6.920 (1.72), 7.140 (1.56), 7.159 (2.50), 7.175 (1.25), 7.348 (2.66), 7.365 (2.47), 7.643 (14.76), 7.660 (2.25), 7.678 (2.82), 7.699 (1.88), 7.820 (3.02), 7.835 (2.42), 8.139 (1.05), 8.304 (2.56), 8.326 (2.33), 8.755 (6.56).

8-(3,5-dichlorophenyl)-N-[(4S)-3,4-dihydro-2H-chromen-4-yl]-4-(1H-1,2,3-triazol-1-yl)quinoline-3-carboxamide (Example 188)

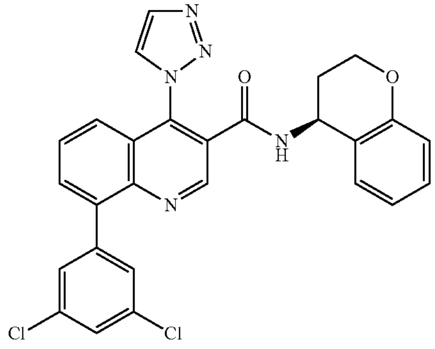 [SMILES: O=C(N[C@H]1CCOc2ccccc21)c1cnc2c(-c3cc(Cl)cc(Cl)c3)cccc2c1-n1ccnn1]

and 8-(3,5-dichlorophenyl)-N-[(4S)-3,4-dihydro-2H-chromen-4-yl]-4-(2H-1,2,3-triazol-2-yl)quinoline-3-carboxamide (Example 189)

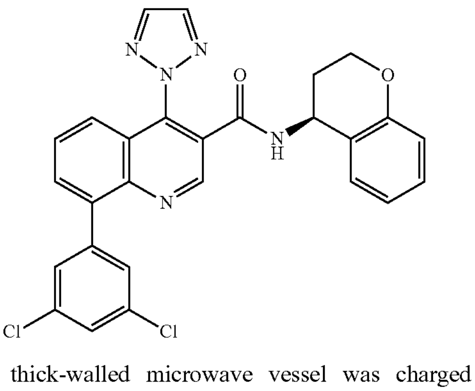

A thick-walled microwave vessel was charged with 4-chloro-8-(3,5-dichlorophenyl)-N-[(4S)-3,4-dihydro-2H-chromen-4-yl]quinoline-3-carboxamide (step 4a) (145 mg, 0.3 mmol), 1,2,3-triazol (62 mg, 0.9 mmol), N-methyl pyrrolidon (0.5 ml), triethylamine (84 μl, 0.6 mmol) and caesium carbonate (98 mg, 0.3 mmol). The vessel was capped and the mixture heated under stirring at 100° C. for 2 h. 5 M formic acid (240 μl, 1.2 mmol) and water (1.5 ml) were added and the precipitate filtered off and discarded. The filtrate was purified by prep. HPLC (C18, gradient: 0.1% aq. formic acid/acetonitrile).

Yield (example 188): 23 mg (15% of th.)

LC-MS (Method L1): $R_f$=1.18 min; MS (ESIneg): m/z=514 $[M-H]^-$ $^1$H-NMR (400 MHz, DMSO-d6): δ [ppm]=9.23 (s, 1H), 9.12 (d, 1H), 8.65 (d, 1H), 8.14 (d, 1H), 8.06 (dd, 1H), 7.80-7.88 (m, 1H), 7.68-7.76 (m, 3H), 7.39-7.46 (m, 1H), 7.10-7.20 (m, 1H), 7.06 (d, 1H), 6.82-6.92 (m, 1H), 6.76 (d, 1H), 4.98-5.09 (m, 1H), 4.18 (td, 1H), 4.00-4.12 (m, 1H), 2.02 (br dd, 1H), 1.73-1.86 (m, 1H).

Yield (example 189): 73 mg (97% purity, 46% of th.)

LC-MS (Method L1): $R_f$=1.27 min; MS (ESIpos): m/z=516 $[M+H]^-$ $^1$H-NMR (400 MHz, DMSO-d6): Shift [ppm]=9.12-9.22 (m, 2H), 8.35 (s, 2H), 8.03 (dd, 1H), 7.87-7.96 (m, 1H), 7.78-7.87 (m, 1H), 7.66-7.76 (m, 2H), 7.25 (d, 1H), 7.10-7.19 (m, 1H), 6.88-6.98 (m, 1H), 6.76 (d, 1H), 4.98-5.14 (m, 1H), 4.07-4.29 (m, 2H), 2.02-2.14 (m, 1H), 1.94 (dtd, 1H).

tert-butyl 1-{8-(3,5-dichlorophenyl)-3-[(4S)-3,4-dihydro-2H-chromen-4-ylcarbamoyl] quinolin-4-yl}-L-prolinate (Example 243)

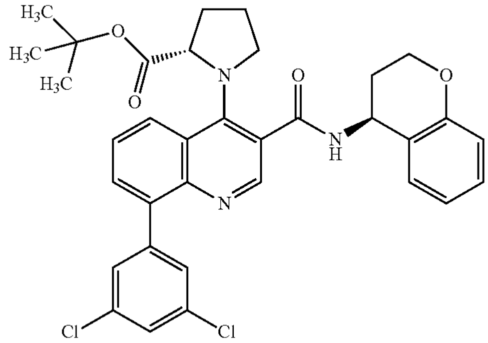 [SMILES: CC(C)(C)OC(=O)[C@@H]1CCCN1c1c(C(=O)N[C@H]2CCOc3ccccc32)cnc2c(-c3cc(Cl)cc(Cl)c3)cccc12]

According to the procedure of example 137 the title compound was synthesized from 4-chloro-8-(3,5-dichlorophenyl)-N-[(4S)-3,4-dihydro-2H-chromen-4-yl]quinoline-3-carboxamide (step 4a) (242 mg, 0.5 mmol) and tert-butyl L-prolinate (171 mg, 1.0 mmol) by heating at 100° C. for 3 h.

Yield: 185 mg (60% of th.)

LC-MS (Method L1): $R_f$=1.39 min; MS (ESIpos): m/z=618 $[M+H]^+$ $^1$H-NMR Peaklist (400 MHz, DMSO-d6) δ[ppm]: 1.198 (16.00), 1.918 (0.63), 1.932 (0.85), 1.945 (0.51), 4.260 (0.44), 6.788 (0.61), 6.808 (0.69), 6.939 (0.64), 7.186 (0.52), 7.394 (0.55), 7.412 (0.51), 7.638 (5.73), 7.655 (0.62), 7.676 (0.53), 7.815 (0.70), 7.832 (0.56), 8.315 (0.60), 8.334 (0.55), 8.684 (2.06), 9.236 (0.58), 9.257 (0.57).

1-{8-(3,5-dichlorophenyl)-3-[(4S)-3,4-dihydro-2H-chromen-4-ylcarbamoyl]quinolin-4-yl}-L-proline (Example 261)

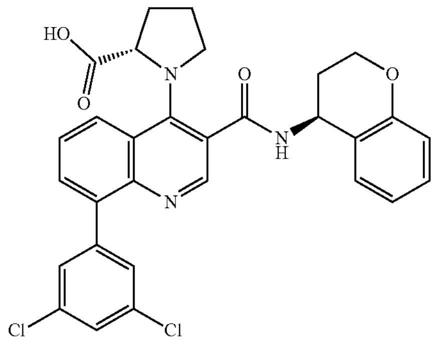 [SMILES: O=C(N[C@H]1CCOc2ccccc21)c1cnc2c(-c3cc(Cl)cc(Cl)c3)cccc2c1N1CCC[C@H]1C(=O)O]

A solution of hydrogen chloride in dioxan (1 ml, 4 M) was added to a solution of tert-butyl 1-{8-(3,5-dichlorophenyl)-3-[(4S)-3,4-dihydro-2H-chromen-4-ylcarbamoyl]quinolin-4-yl}-L-prolinate (from example 243) (155 mg, 0.25 mmol) in DICHLOROMETHANE (0.8 ml) and stirred overnight at ambient temperature. The volatiles were removed under reduced pressure and the residue stirred with dichloromethane and water. The separated water phase was extracted with dichloromethane, the combined organic phases dried and evaporated. The residue was purified by prep. HPLC (C18, gradient: 0.1% aq. formic acid/acetonitrile).

Yield: 52 mg (37% of th.)

LC-MS (Method L1): $R_f$=0.91 min; MS (ESIpos): m/z=562 $[M+H]^+$ $^1$H-NMR Peaklist (500 MHz, DMSO-d6) δ[ppm]: −0.007 (3.09), 0.006 (1.99), 1.907 (2.42), 2.028 (0.58), 2.033 (0.60), 2.044 (0.71), 2.056 (0.83), 2.166 (0.52), 2.175 (0.71), 2.185 (0.75), 2.193 (0.77), 2.204 (0.50), 2.358 (0.89), 2.361 (1.22), 2.365 (0.93), 2.369 (0.58), 2.392 (0.70), 2.407 (0.71), 2.514 (3.50), 2.518 (3.01), 2.522 (2.34), 2.631 (0.87), 2.635 (1.14), 2.639 (0.81), 3.866 (0.46), 3.878 (1.06), 3.895 (0.91), 4.183 (0.43), 4.188 (0.44), 4.205 (1.12), 4.224 (0.89), 4.229 (0.73), 4.243 (0.75), 4.250 (1.08), 4.262 (0.91), 4.277 (0.46), 4.638 (0.83), 4.649 (1.02), 4.654 (1.33), 4.665 (1.06), 5.254 (0.54), 5.264 (1.14), 5.280 (1.10), 5.291 (0.50), 6.786 (2.22), 6.788 (2.18), 6.802 (2.42), 6.804 (2.32), 6.919 (1.16), 6.921 (1.08), 6.933 (2.26), 6.935 (2.11), 6.948 (1.31), 6.950 (1.18), 7.169 (1.12), 7.172 (1.16), 7.186 (1.76), 7.200 (0.93), 7.203 (0.89), 7.388 (1.80), 7.403 (1.70), 7.629 (1.72), 7.634 (4.02), 7.637 (8.89), 7.639 (16.00), 7.642 (4.87), 7.652 (2.18), 7.654 (1.91), 7.669 (1.82), 7.806 (2.51), 7.809 (2.42), 7.821 (2.05), 7.823 (1.86), 8.303 (1.86), 8.320 (1.72), 8.680 (8.25), 12.586 (0.91).

8-(3,5-dichlorophenyl)-N-[(4S)-3,4-dihydro-2H-chromen-4-yl]-4-[(2-hydroxyethyl)sulfanyl]quinoline-3-carboxamide (Example 264)

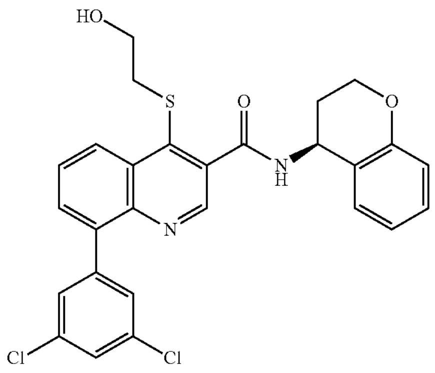 [SMILES: O=C(N[C@H]1CCOc2ccccc21)c1cnc2c(-c3cc(Cl)cc(Cl)c3)cccc2c1SCCO]

A thick-walled vessel was charged with 4-chloro-8-(3,5-dichlorophenyl)-N-[(4S)-3,4-dihydro-2H-chromen-4-yl] quinoline-3-carboxamide (step 4a) (121 mg, 250 μmol), DMSO (0.3 ml), 2-sulfanylethanol (39 mg, 500 μmol) and triethylamine (87 μl, 630 μmol), capped and heated 2h at 100° C. After cooling to ambient temperature 5 M formic acid (300 μl, 1.5 mmol) was added, the mixture dissolved by adding acetonitrile and purified by prep. HPLC (C18, gradient: 0.1% aq. formic acid/acetonitrile).

Yield: 95 mg (72% of th.)

LC-MS (Method L1): $R_f$=1.28 min; MS (ESIpos): m/z=525 $[M+H]^+$ $^1$H-NMR Peaklist (400 MHz, DMSO-d6) δ[ppm]: −0.008 (2.66), 0.008 (2.57), 2.119 (1.04), 2.128 (0.86), 2.366 (0.82), 2.710 (0.82), 3.060 (2.72), 3.077 (6.64), 3.093 (3.50), 3.287 (2.70), 3.438 (1.04), 3.454 (2.48), 3.468 (3.16), 3.481 (2.10), 3.497 (0.89), 4.254 (1.46), 4.263 (1.26), 4.273 (2.24), 4.282 (2.43), 4.297 (1.35), 4.946 (2.06), 4.960 (4.56), 4.974 (1.99), 5.291 (1.28), 5.310 (1.31), 6.781 (2.41), 6.784 (2.61), 6.802 (2.74), 6.805 (2.88), 6.910 (1.33), 6.913 (1.46), 6.928 (2.63), 6.932 (2.57), 6.947 (1.59), 6.950 (1.53), 7.151 (1.31), 7.156 (1.35), 7.173 (2.21), 7.190 (1.24), 7.194 (1.13), 7.448 (2.17), 7.465 (2.06), 7.627 (1.00), 7.632 (1.04), 7.658 (5.73), 7.662 (16.00), 7.666 (6.68), 7.669 (3.41), 7.675 (1.22), 7.838 (1.93), 7.856 (2.97), 7.859 (2.35), 7.877 (2.92), 7.929 (3.21), 7.932 (3.50), 7.946 (2.21), 7.950 (2.06), 8.624 (2.97), 8.627 (2.97), 8.645 (2.70), 8.649 (2.50), 8.881 (10.45), 9.155 (2.48), 9.175 (2.37).

8-(3,5-dichlorophenyl)-N-[(4S)-3,4-dihydro-2H-chromen-4-yl]-4-methoxyquinoline-3-carboxamide (Example 373)

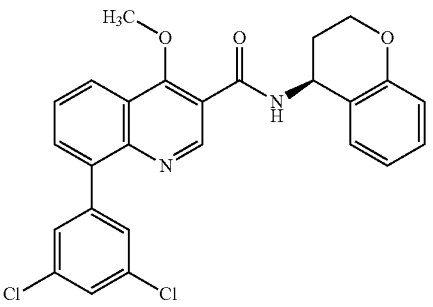 [SMILES: COc1c(C(=O)N[C@H]2CCOc3ccccc32)cnc2c(-c3cc(Cl)cc(Cl)c3)cccc12]

Under argon atmosphere a solution of sodium methylate in methanol (140 µl, 5.4 M, 780 µmol) was added dropwise to a solution of 4-chloro-8-(3,5-dichlorophenyl)-N-[(4S)-3,4-dihydro-2H-chromen-4-yl]quinoline-3-carboxamide (step 4a) (150 mg, 310 µmol) in N-methyl pyrrolidon (1 ml) and the mixture stirred at ambient temperature for 40 min. Acetic acid (250 µl, 5.0 M, 1.2 mmol) was added and the mixture purified by prep. HPLC (C18, gradient: 0.1% aq. formic acid/acetonitrile).

Yield: 94 mg (63% of th.)

LC-MS (Method L1): $R_f$=1.39 min; MS (ESIpos): m/z=479 $[M+H]^+$ $^1$H-NMR Peaklist (400 MHz, DMSO-d6) δ[ppm]: 4.172 (16.00), 4.245 (0.90), 4.254 (1.07), 4.269 (1.49), 4.273 (1.51), 4.283 (0.86), 5.274 (0.83), 5.293 (0.83), 5.754 (12.35), 6.793 (1.40), 6.796 (1.53), 6.814 (1.59), 6.816 (1.66), 6.909 (0.74), 6.912 (0.74), 6.928 (1.55), 6.930 (1.54), 6.946 (0.93), 6.949 (0.91), 7.159 (0.76), 7.163 (0.82), 7.180 (1.29), 7.363 (1.33), 7.380 (1.25), 7.650 (0.88), 7.655 (2.07), 7.659 (2.33), 7.670 (7.40), 7.675 (4.39), 7.702 (1.20), 7.720 (1.66), 7.723 (1.57), 7.741 (1.47), 7.886 (1.69), 7.890 (1.80), 7.904 (1.44), 7.908 (1.42), 8.296 (1.61), 8.299 (1.63), 8.317 (1.54), 8.320 (1.45), 8.811 (5.57), 9.192 (1.36), 9.212 (1.34).

Synthesis of 4-chloro-8-(3,5-dimethylphenyl)-N-[(1S)-1,2,3,4-tetrahydronaphthalen-1-yl]quinoline-3-carboxamide (Example 1)

Step 1 ethyl-4-chloro-8-(3,5-dimethylphenyl)quinoline-3-carboxylate

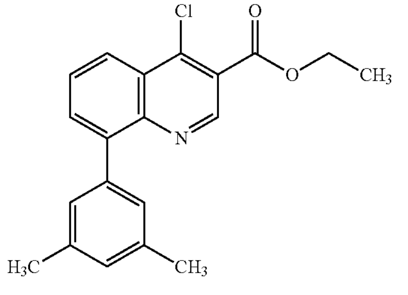 [SMILES: CCOC(=O)c1cnc2c(-c3cc(C)cc(C)c3)cccc2c1Cl]

Under argon atmosphere a flask was charged with ethyl 8-bromo-4-chloroquinoline-3-carboxylate (330 mg, 1.05 mmol) (Zask, al. Bioorganic and Medicinal Chemistry Letters, 2003, 1487-1490; Laxmikant, al. US2013/210844), 3,5-dimethylbenzene boronic acid (189 mg, 1.26 mmol) and a degassed mixture of dioxan (6.6 ml) and water 1.3 ml). Then potassium carbonate (290 mg, 2.10 mmol) and 1,1'-bis(diphenylphosphino)ferrocene-palladium(II)dichloride dichloromethane complex (42.8 mg, 52.5 µmol) were added and the mixture stirred overnight at 50° C. The reaction mixture was filtered through celite and washed with ethyl acetate and water. The organic phase of the filtrate was washed with water and brine, dried over sodium sulfate and evaporated under reduced pressure. The residue was purified by prep. HPLC (C18, gradient: 0.1% aq. formic acid/acetonitrile) and silica gel chromatography (cyclohexane/ethyl acetate—5:1).

Yield: 77.0 mg (21% of th.)

LC-MS (Method L1): $R_f$=1.43 min; MS (ESIpos): m/z=340 $[M+H]^+$

NMR: $^1$H-NMR (400 MHz, DMSO-$d_6$): δ [ppm]=9.13 (s, 1H), 8.42 (dd, 1H), 7.87-7.96 (m, 2H), 7.20 (s, 2H), 7.07 (s, 1H), 4.44 (q, 2H), 2.35 (s, 6H), 1.38 (t, 3H).

Step 2

4-chloro-8-(3,5-dimethylphenyl)quinoline-3-carboxylic acid

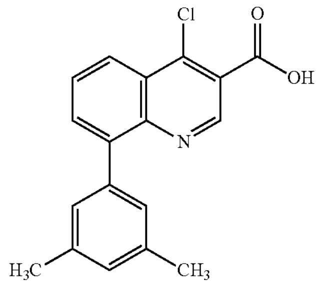 [SMILES: Cc1cc(C)cc(-c2cccc3c(Cl)c(C(=O)O)cnc23)c1]

To ethyl-4-chloro-8-(3,5-dimethylphenyl)quinoline-3-carboxylate (step 1) (84.0 mg, 247 µmol) in 0.5 ml ethanol and 0.5 ml THF was added an aqueous solution of sodium hydroxide (5 M, 150 µl, 740 µmol) and the mixture stirred overnight at ambient temperature. The solvents were removed under reduced pressure, the residue was dissolved in DMSO and 5 M formic acid and purified via prep. HPLC (C18, gradient: 0.1% aq. formic acid/acetonitrile) yielding an off-white solid.

Yield: 75.0 mg (97% of th).

LC-MS (Method L1): $R_f$=1.15 min; MS (ESIpos): m/z=312 $[M+H]^+$ $^1$H-NMR Peaklist (400 MHz, DMSO-d6) δ[ppm]: 2.346 (16.00), 7.062 (1.52), 7.189 (3.52), 7.884 (1.52), 7.895 (1.68), 7.902 (3.49), 8.396 (0.99), 8.403 (0.92), 8.414 (0.88), 8.421 (0.87), 9.116 (2.83).

Step 3

4-chloro-8-(3,5-dimethylphenyl)-N-[(1S)-1,2,3,4-tetrahydronaphthalen-1-yl]quinoline-3-carboxamide (Example 1)

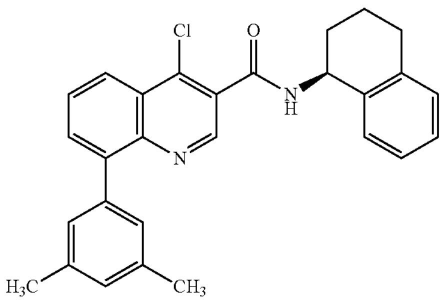 [SMILES: Cc1cc(C)cc(-c2cccc3c(Cl)c(C(=O)N[C@H]4CCCc5ccccc54)cnc23)c1]

4-Chloro-8-(3,5-dimethylphenyl)quinoline-3-carboxylic acid (step 2) (71.0 mg, 228 μmol) in 1.2 ml THF was treated with (1S)-1,2,3,4-tetrahydronaphthalen-1-amine (36.9 mg, 251 μmol) and triethylamine (190 μl, 1.4 mmol) and stirred at 60° C. for 10 min. Then a solution of 2,4,6-tripropyl-1,3,5,2,4,6-trioxatriphosphinane 2,4,6-trioxide in ethylacetate (200 μl, 50% content, 340 μmol) was added, the heating removed and the mixture stirred overnight at ambient temperature. Water and 5 M formic acid (0.6 ml) were added and the solvents removed under reduced pressure. The residue was purified by prep. HPLC (C18, gradient: 0.1% aq. formic acid/acetonitrile).

Yield: 20.0 mg (20% of th)

LC-MS (Method L1): $R_f$=1.42 min; MS (ESIpos): m/z=441 $[M+H]^+$ $^1$H-NMR Peaklist (400 MHz, DMSO-d6) δ[ppm]: −0.008 (4.41), 0.008 (4.06), 2.342 (16.00), 2.759 (1.07), 7.059 (1.60), 7.111 (0.66), 7.128 (1.05), 7.183 (4.61), 7.195 (1.69), 7.202 (0.82), 7.207 (0.96), 7.422 (0.89), 7.438 (0.75), 7.855 (4.02), 7.865 (2.24), 7.869 (2.26), 8.303 (1.26), 8.314 (1.10), 8.317 (1.07), 8.328 (1.10), 8.874 (5.11), 9.102 (0.96), 9.123 (0.96).

Synthesis of 8-(2,3-dichlorophenyl)-N-[(4S)-3,4-dihydro-2H-chromen-4-yl]-4-(morpholin-4-yl)quinoline-3-carboxamide (Example 52)

Step 1

8-bromo-4-chloroquinoline-3-carboxylic acid

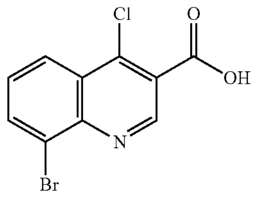 [SMILES: O=C(O)c1cnc2c(Br)cccc2c1Cl]

To a suspension of ethyl-8-bromo-4-chlorquinoline-3-carboxylate (9.44 g, 30.0 mmol) in THF (65 ml) was added an aqueous sodiumhydroxid solution (12 ml, 10 M, 120 mmol) and the mixture stirred vigorously at ambient temperature. After 5 hours, water (12 ml) was added and the mixture stirred overnight at ambient temperature. The supernatant was decanted from the amorphous precipitate which had formed on the wall of the flask and discarded. The precipitate was dried in vacuo, yielding the sodium salt of the title compound.

LC-MS (Method L1): $R_f$=0.70 min; MS (ESIpos): m/z=285 $[M+H]^+$ $^1$H-NMR (400 MHz, DMSO-$d_6$): δ [ppm]=8.98 (s, 1H), 8.29 (dd, 1H), 8.16-8.23 (m, 1H), 7.64 (t, 1H).

The remaining wet solid was dissolved in water (250 ml) at 60° C. and formic acid (57 ml, 5.0 M, 280 mmol) was added under vigorous stirring resulting in a pH value of 3 and formation of a precipitate. The mixture was cooled to ambient temperature, the precipitate filtered off, washed with water and dried in vacuo at 40° C.

Yield: 7.0 g (98% purity, 80% of th.)

LC-MS (Method L1): $R_f$=0.70 min; MS (ESIpos): m/z=285 $[M+H]^+$ $^1$H-NMR (400 MHz, DMSO-$d_6$): δ [ppm]=14.12 (br s, 1H), 9.25 (s, 1H), 8.42 (d, 1H), 8.36 (d, 1H), 7.75 (t, 1H).

Step 2

8-bromo-4-chloro-N-[(4S)-3,4-dihydro-2H-chromen-4-yl]quinoline-3-carboxamide

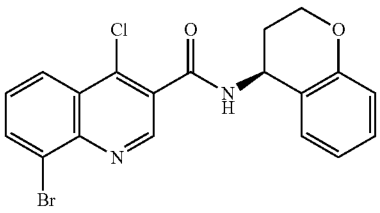 [SMILES: O=C(N[C@H]1CCOc2ccccc21)c1cnc2c(Br)cccc2c1Cl]

8-Bromo-4-chloroquinoline-3-carboxylic acid (step 1) (7.00 g, 24.4 mmol) was dissolved in THF by stirring in an oilbath of 50° C. for 10 min. The heating was removed, (4S)-chroman-4-amine hydrochloride (5.44 g, 29.3 mmol), N,N-diisopropyl-ethyl-amine (17 ml, 98 mmol) and a solution of 2,4,6-tripropyl-1,3,5,2,4,6-trioxatriphosphinane 2,4,6-trioxide in ethyl acetate (23 ml, 50 content, 39 mmol) were added, which caused an increase in temperature to 45° C. Stirring was continued for 30 min and water (300 ml) was added under continuous stirring to support precipitation of a solid. The precipitate was collected, washed with water and dried in vacuo.

Yield: 9.50 g (93% of th.)

LC-MS (Method L1): $R_f$=1.01 min; MS (ESIneg): m/z=417 $[M+H]^-$ $^1$H-NMR Peaklist (400 MHz, DMSO-d6) δ[ppm]: 2.047 (0.74), 2.054 (0.99), 2.063 (1.54), 2.070 (1.66), 2.081 (1.85), 2.088 (1.86), 2.097 (2.49), 2.104 (2.18), 2.113 (1.49), 2.120 (1.08), 2.197 (1.06), 2.206 (1.61), 2.218 (2.41), 2.231 (2.17), 2.239 (2.10), 2.252 (1.56), 2.264 (1.01), 2.273 (0.71), 2.328 (0.42), 2.670 (0.47), 4.205 (1.18), 4.212 (1.43), 4.233 (3.76), 4.240 (2.80), 4.253 (3.08), 4.261 (2.42), 4.277 (2.42), 4.285 (3.12), 4.293 (2.75), 4.302 (3.10), 4.313 (1.33), 4.321 (1.40), 4.329 (1.04), 5.266 (1.51), 5.281 (3.35), 5.300 (3.35), 5.315 (1.47), 6.793 (5.60), 6.814 (6.35), 6.922 (2.99), 6.940 (6.44), 6.959 (3.78), 7.162 (3.04), 7.165 (3.11), 7.183 (5.15), 7.201 (2.48), 7.382 (5.42), 7.401 (5.04), 7.713 (4.62), 7.733 (8.03), 7.754 (5.29), 8.312 (6.79), 8.324 (8.26), 8.327 (8.69), 8.345 (6.64), 9.042 (16.00), 9.264 (4.77), 9.285 (4.67).

Step 3

8-bromo-N-[(4S)-3,4-dihydro-2H-chromen-4-yl]-4-(morpholin-4-yl)quinoline-3-carboxamide

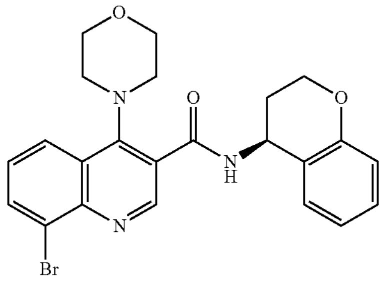 [SMILES: O=C(N[C@H]1CCOc2ccccc21)c1cnc2c(Br)cccc2c1N1CCOCC1]

To a suspension of 8-bromo-4-chloro-N-[(4S)-3,4-dihydro-2H-chromen-4-yl]quinoline-3-carboxamide (step 2) (9.50 g, 22.7 mmol) in THF (70 ml), morpholine (6.0 ml, 68 mmol) and 1,4-diazabicyclo[2.2.2]octane (2.55 g, 22.7 mmol) were added and stirred for 1.5 h at 80° C. bath temperature. Water was added (30 ml) and the THF evaporated under reduced pressure. More water was added and the suspension stirred first at 50° C. then at ambient temperature. The precipitate was filtered off, washed with water and dried in vacuo.

Yield: 10.5 g (98% of th.)

LC-MS (Method L1): $R_f$=0.92 min; MS (ESIneg): m/z=466 $[M-H]^-$ $^1$H-NMR Peaklist (400 MHz, DMSO-d6) δ[ppm]: −0.149 (0.41), −0.008 (4.42), 0.008 (3.18), 2.041 (0.54), 2.048 (0.76), 2.056 (1.13), 2.063 (1.19), 2.076 (1.30), 2.091 (1.80), 2.098 (1.57), 2.106 (1.11), 2.197 (0.74), 2.206 (1.17), 2.218 (1.70), 2.231 (1.59), 2.240 (1.58), 2.253 (1.13), 2.262 (0.74), 2.274 (0.52), 2.327 (0.60), 2.366 (0.49), 2.523 (2.30), 2.669 (0.66), 2.710 (0.48), 3.217 (0.69), 3.228 (1.18), 3.248 (4.71), 3.258 (11.00), 3.269 (11.28), 3.279 (5.00), 3.842 (8.92), 3.853 (14.13), 3.864 (8.07), 4.214 (0.80), 4.221 (1.01), 4.242 (2.68), 4.249 (2.03), 4.263 (2.41), 4.271 (2.08), 4.276 (2.00), 4.286 (2.44), 4.293 (2.07), 4.302 (2.18), 4.314 (0.86), 4.321 (0.96), 4.329 (0.65), 5.245 (1.10), 5.259 (2.45), 5.279 (2.44), 5.292 (1.06), 6.797 (4.29), 6.815 (4.84), 6.927 (2.26), 6.929 (2.16), 6.946 (4.75), 6.964 (2.87), 7.164 (2.33), 7.167 (2.40), 7.185 (3.85), 7.202 (1.91), 7.206 (1.79), 7.385 (4.05), 7.403 (3.77), 7.499 (3.74), 7.518 (5.40), 7.538 (4.06), 8.123 (4.80), 8.125 (5.04), 8.142 (4.71), 8.144 (4.51), 8.197 (4.92), 8.199 (4.64), 8.218 (4.71), 8.753 (16.00), 9.177 (3.99), 9.197 (3.89).

Step 4

8-(2,3-dichlorophenyl)-N-[(4S)-3,4-dihydro-2H-chromen-4-yl]-4-(morpholin-4-yl)quinoline-3-carboxamide (Example 52)

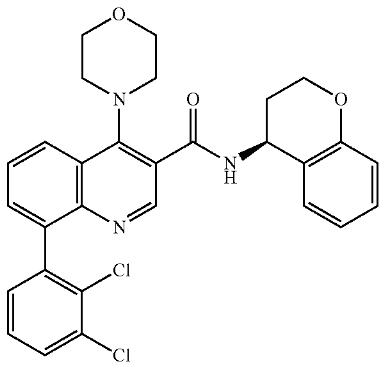 [SMILES: O=C(N[C@H]1CCOc2ccccc21)c1cnc2c(-c3cccc(Cl)c3Cl)cccc2c1N1CCOCC1]

Under argon atmosphere potassium carbonate (1.29 g, 9.31 mmol) was dissolved in a degassed 5:1 mixture of dioxan and water (21 ml) by sonification. 1,1'-bis(diphenylphosphino)ferrocene-palladium(II)dichloride dichloromethane complex (190 mg, 0.23 mmol) and 8-bromo-N-[(4S)-3,4-dihydro-2H-chromen-4-yl]-4-(morpholin-4-yl) quinoline-3-carboxamide (step 3) (2.18 g, 4.65 mmol) were added, followed by 2,3-dichlorobenzene boronic acid (977 mg, 5.12 mmol). The vessel was closed and stirred at 80° C. bath temperature for 2.5 h. Water was added and the mixture extracted with ethyl acetate. The organic phases were dried and evaporated under reduced pressure. The residue was purified by column-chromatography on silica (10 g), eluent: cyclohexane/ethyl acetate (15-35%). The obtained solid was stirred in a mixture of MTBE (30 ml) and methanol (1.5 ml), filtered off an dried in vacuo.

Yield: 2.03 g (82% of th.)

LC-MS (Method L1): $R_f$=1.13 min; MS (ESIpos): m/z=534 $[M+H]^+$ $^1$H-NMR Peaklist (600 MHz, DMSO-d6) δ[ppm]: 2.056 (0.40), 2.199 (0.43), 2.208 (0.44), 2.214 (0.44), 3.269 (0.65), 3.280 (1.04), 3.289 (1.15), 3.300 (1.36), 3.307 (1.17), 3.321 (0.61), 3.335 (16.00), 4.233 (0.78), 4.237 (0.53), 4.247 (0.59), 4.251 (0.49), 4.261 (0.49), 4.267 (0.62), 4.272 (0.54), 4.278 (0.63), 5.239 (0.42), 5.246 (0.54), 5.260 (0.42), 6.781 (1.24), 6.794 (1.32), 6.911 (0.70), 6.915 (0.74), 6.928 (0.40), 7.150 (0.59), 7.162 (0.96), 7.175 (0.49), 7.310 (0.47), 7.312 (0.47), 7.323 (0.59), 7.324 (0.57), 7.336 (0.53), 7.338 (0.53), 7.348 (0.71), 7.350 (0.72), 7.357 (1.04), 7.370 (0.95), 7.420 (0.46), 7.432 (1.04), 7.445 (1.07), 7.457 (0.42), 7.664 (0.76), 7.676 (1.51), 7.690 (2.57), 7.693 (1.60), 7.704 (2.49), 7.716 (0.68), 8.281 (1.15), 8.283 (1.14), 8.295 (1.07), 8.297 (1.02), 8.588 (1.70), 8.595 (1.82), 9.166 (0.54), 9.180 (1.03), 9.195 (0.56).

Synthesis of 8-(3-chlorophenyl)-N-[(4S)-3,4-dihydro-2H-chromen-4-yl]-4-(dimethyl-amino)-7-fluoroquinoline-3-carboxamide (Example 141)

Step 1 ethyl 8-bromo-7-fluoro-4-hydroxyquinoline-3-carboxylate

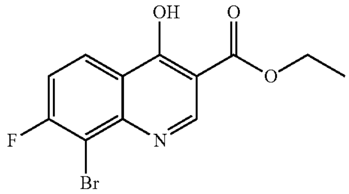 [SMILES: CCOC(=O)c1cnc2c(Br)c(F)ccc2c1O]

A mixture of 2-bromo-3-fluoroaniline (24.89 g, 131 mmol) and diethyl ethoxymethylenemalonate (28.33 g, 131 mmol, 26 mL) was stirred at room temperature for 16 h. Stirring was continued at 250° C. under vacuo (60 mbar) for 6 h. The reaction mixture was allowed to cool to room temperature. The solid residue was stirred in refluxing ethyl acetate (400 mL). The precipitate was filtered off and washed with ethyl acetate. The solid was stirred in a refluxing mixture of ethanol (400 mL) and methanol (40 mL). The hot suspension was filtered off. The solid was washed with ethanol and dried on air.

Yield: 28.60 g (83 mmol, 63% of th.)

LC-MS (Method L2): $R_f$=1.73 min, m/z=314/316 $(M+H)^+$ $^1$H-NMR (400 MHz, DMSO-d6) δ 11.78 (s, 1H), 8.45 (s, 1H), 8.22 (m, 1H), 7.50-7.39 (m, 1H), 4.23 (d, J=7.1 Hz, 2H), 1.28 (t, J=7.1 Hz, 3H).

Step 2 ethyl 8-bromo-4-chloro-7-fluoroquinoline-3-carboxylate

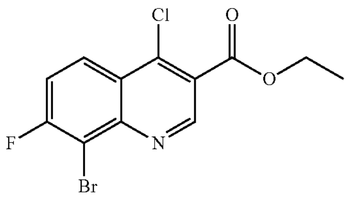

To stirring phosphorus oxychloride (38.4 g, 250 mmol, 23 mL) was added ethyl 8-bromo-7-fluoro-4-hydroxyquinoline-3-carboxylate (step 1) (23.6 g, 75 mmol). The resulting suspension was stirred at 80° C. for 1 h. The mixture was allowed to cool to room temperature and was poured out into vigorously stirred ice-water (100 mL). The resulting mixture was left standing for two days at room temperature. The precipitate was collected by filtration and was washed with water until the filtrate was neutral. Solids were triturated in a mixture of diethyl ether and diisopropyl ether (1:1; 1 L). Solids were filtered off. The filtrate was concentrated in vacuo at 25° C. After co-evaporation of the residue with toluene 21.3 g (64 mmol, 85% of theory) of the title compound were obtained.

Yield: 21.3 g (64 mmol, 85% of th.)

LC-MS (Method L2): $R_f$=2.18 min, m/z=332/334 $(M+H)^+$

Step 3 ethyl 8-bromo-4-(dimethylamino)-7-fluoroquinoline-3-carboxylate

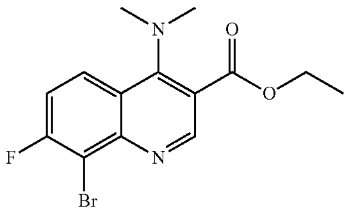 [SMILES: CCOC(=O)c1cnc2c(Br)c(F)ccc2c1N(C)C]

To a solution of ethyl 8-bromo-4-chloro-7-fluoroquinoline-3-carboxylate (step 2) (14.31 g, 43 mmol) in dry tetrahydrofuran (150 mL) were added triethyl amine (8.71 g, 86 mmol, 12 mL) and dimethylamine (2 M in tetrahydrofuran; 48 mmol, 24 mL). The reaction mixture was stirred for 16 h at room temperature. Solids were filtered off and washed with tetrahydrofuran. The filtrate was concentrated in vacuo to afford the title compound.

Yield: 12.66 g (37 mmol, 86% of th.)

LC-MS (Method L2): $R_f$=1.75 min, m/z=341/343 $(M+H)^+$ $^1$H-NMR (400 MHz, DMSO-d6) δ 8.86 (s, 1H), 8.28 (dd, J=9.4, 6.1 Hz, 1H), 7.63 (dd, J=9.4, 8.2 Hz, 1H), 4.39 (q, J=7.1 Hz, 2H), 3.07 (s, 6H), 1.36 (t, J=7.1 Hz, 3H).

Step 4 ethyl 8-bromo-4-(dimethylamino)-7-fluoroquinoline-3-carboxylate hydrochloride

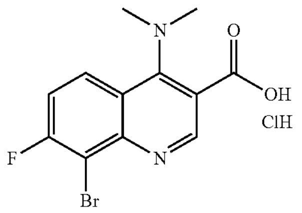 [SMILES: CN(C)c1c(C(=O)O)cnc2c(Br)c(F)ccc12 ; Cl]

To a solution of ethyl 8-bromo-4-(dimethylamino)-7-fluoroquinoline-3-carboxylate (step 3) (14.0 g, 41 mmol) in tetrahydrofuran (100 mL) was added a solution of lithium-hydroxide monohydrate (11.5 g, 274 mmol) in water (100 mL). The mixture was stirred for 16 h at 75° C. and was allowed to cool to room temperature. Layers were separated and the aqueous layer was extracted with tetrahydrofuran (2×150 mL). Combined organic layers were concentrated in vacuo and hydrochloric acid (4 M; 100 mL) was added. The solid was filtered off, washed with water and diethyl ether and was dried on air to afford the title compound.

Yield: 10.6 g (30 mmol, 74% of th.)

LC-MS (Method L2): $R_f$=1.21 min, m/z=313/315 (M+H)+

$^1$H-NMR (400 MHz, DMSO-d6) δ 8.73 (s, 1H), 8.41 (dd, J=9.4, 5.7 Hz, 1H), 7.66 (dd, J=9.4, 8.1 Hz, 1H), 3.35 (s, 6H) [acidic protons were not detected].

Step 5

8-bromo-N-[(4S)-3,4-dihydro-2H-chromen-4-yl]-4-(dimethylamino)-7-fluoroquinoline-3-carboxamide

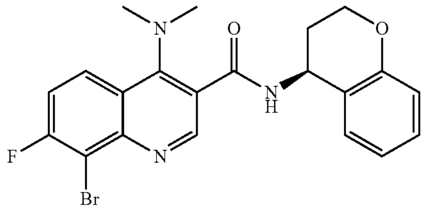 [SMILES: CN(C)c1c(C(=O)N[C@H]2CCOc3ccccc32)cnc2c(Br)c(F)ccc12]

To a solution of 8-bromo-4-(dimethylamino)-7-fluoroquinoline-3-carboxylic acid hydrochloride (step 4) (2.00 g, 5.7 mmol) in N,N-dimethylformamide (50 mL) were added 1-[bis(dimethylamino)-methylene]-1H-1,2,3-triazolo[4,5-b]pyridinium 3-oxid hexafluorophosphate (2.18 g, 5.7 mmol) and N,N-diisopropylethylamine (4.21 g, 32.6 mmol, 5.7 mL). The mixture was stirred at room temperature for 1 h. (4S)-Chroman-4-amine hydrochloride (1.06 g, 5.7 mmol) was added. The reaction mixture was stirred for 16 h at room temperature. The mixture was poured out into water (200 mL). Solids were filtered off, washed with water and were dried in vacuo. After co-evaporation with toluene and ethyl acetate the title compound was obtained.

Yield: 1.90 g (4.3 mmol, 75% of th.)

LC-MS (Method L2): $R_f$=1.78 min, m/z=444/446 $(M+H)^+$ $^1$H-NMR (400 MHz, DMSO-d6) δ 9.12 (d, J=8.1 Hz, 1H), 8.70 (s, 1H), 8.23 (dd, J=9.4, 6.1 Hz, 1H), 7.59 (dd, J=9.3, 8.3 Hz, 1H), 7.37 (d, J=6.8 Hz, 1H), 7.22-7.14 (m, 1H), 6.98-6.90 (m, 1H), 6.81 (dd, J=8.2, 1.0 Hz, 1H), 5.29-5.20 (m, 1H), 4.34-4.19 (m, 2H), 3.06 (s, 6H), 2.27-2.15 (m, 1H), 2.11-2.00 (m, 1H).

Step 6

8-(3-chlorophenyl)-N-[(4S)-3,4-dihydro-2H-chromen-4-yl]-4-(dimethyl-amino)-7-fluoroquinoline-3-carboxamide (Example 141)

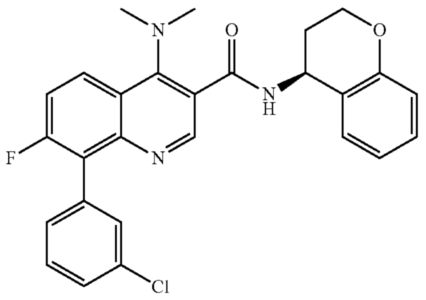 [SMILES: CN(C)c1c(C(=O)N[C@H]2CCOc3ccccc32)cnc2c(-c3cccc(Cl)c3)c(F)ccc12]

In an 8 mL screw capped vial, to a degassed (1 min, nitrogen) mixture of 8-bromo-N-[(4S)-3,4-dihydro-2H-chromen-4-yl]-4-(dimethylamino)-7-fluoroquinoline-3-carboxamide (100 mg, 0.225 mmol), (3-chlorophenyl)boronic acid (42 mg, 0.270 mmol) and sodium carbonate (72 mg, 0.675 mmol) in a mixture of tetrahydrofuran (1.30 mL) and water (0.25 mL) was added 1,1'-bis(diphenylphosphino) ferrocenepalladium(II) dichloride (3 mg, 0.005 mmol). The reaction mixture was stirred for 16 h at 60° C. and was cooled to room temperature. Water (5 mL) was added and the aqueous layer was extracted with dichloromethane (3×3 mL) by phase separator. Solvents were removed in vacuo. Purification by flash column chromatography (heptane, 5%-35% ethyl acetate) afforded the title compound.

Yield: 56 mg (0.118 mmol, 52% of th.)

LC-MS (Method L2): $R_f$=3.03 min, m/z=476 $(M+H)^+$ $^1$H-NMR (400 MHz, DMSO-d6) δ 9.08 (d, J=8.2 Hz, 1H), 8.58 (s, 1H), 8.27 (dd, J=9.4, 6.2 Hz, 1H), 7.60 (t, J=9.3 Hz, 1H), 7.55-7.45 (m, 3H), 7.43-7.31 (m, 2H), 7.20-7.12 (m, 1H), 6.95-6.88 (m, 1H), 6.83-6.76 (m, 1H), 5.28-5.19 (m, 1H), 4.32-4.19 (m, 2H), 3.07 (s, 6H), 2.25-2.14 (m, 1H), 2.09-1.98 (m, 1H).

Synthesis of 8-(2,3-dichlorophenyl)-N-[(4S)-3,4-dihydro-2H-chromen-4-yl]-4-[methyl (oxetan-3-yl) amino]quinoline-3-carboxamide (Example 331)

Step 1 ethyl 8-bromo-4-[methyl(oxetan-3-yl)amino]quinoline-3-carboxylate

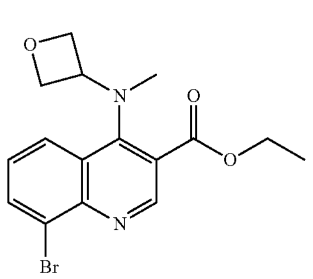 [SMILES: CCOC(=O)c1cnc2c(Br)cccc2c1N(C)C1COC1]

A flask was charged with ethyl 8-bromo-4-chloroquinoline-3-carboxylate (1.26 g, 4 mmol) (Zask, al. Bioorganic and Medicinal Chemistry Letters, 2003, 1487-1490; Laxmikant, al. US2013/210844), 1-methyl-3-oxetanamine (0.42 g, 4 mmol), N,N-diisopropyl-ethylamin (0.62 g, 4.8 mmol) in 40 mL Acetonitril. The reaction mixture was refluxed for 24 hours. Then the solvent was removed under reduced pressure and the remaining material was dissolved in ethyl acetate and washed twice with water. The organic phase was separated, dried over calcium sulfate, filtered and the filtrate was removed under reduced pressure. The resulting residue was purified by reverse phase column chromatography (eluent water/acetonitrile gradient).

Yield: 1.2 g (3.2 mmol, 82% of th.)

$^1$H-NMR (400 MHz, DMSO-d6) δ 8.94 (s, 1H), 8.20 (d, 1H), 8.14 (d, 1H), 7.55 (dd, 1H), 4.72-4.62 (m, 5H, oxetanyl), 4.43-4.38 (q, 2H), 3.10 (s, 3H), 1.37 (t, 3H).

Step 2 ethyl 8-(2,3-dichlorophenyl)-4-[methyl(oxetan-3-yl) amino]quinoline-3-carboxylate

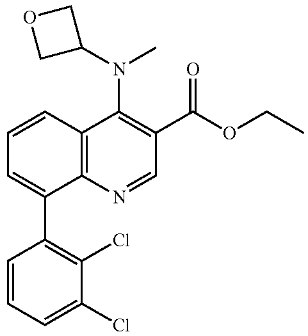 [SMILES: CCOC(=O)c1cnc2c(-c3cccc(Cl)c3Cl)cccc2c1N(C)C1COC1]

In an microwave vial, to a degassed (1 min, argon) mixture of ethyl 8-bromo-4-[methyl(oxetan-3-yl)amino]quinoline-3-carboxylate (step 1) (500 mg, 1.37 mmol), (2,3-dichlorophenyl)boronic acid (261 mg, 1.37 mmol), an aqueous solution of cesium carbonate (2M, 1.37 mL, 2.74 mmol) and dioxane (12.5 mL) was added 1,1'-bis(diphenylphosphino)ferrocenepalladium(II) dichloride (111 mg, 0.14 mmol). The reaction mixture was treated in a Biotage microwave oven for 25 minutes at 100° C. The reaction mixture was filtered via a sodium sulfate/silica gel cartridge and purified by reverse phase column chromatography (eluent water/acetonitrile gradient).

Yield: 600 mg (98% of th.)

$^1$H-NMR (400 MHz, DMSO-d6) δ 8.77 (s, 1H), 8.21 (t, 1H), 7.74 (d, 2H), 7.71 (d, 1H), 7.45 (t, 1H), 7.36 (d, 1H), 4.76-4.65 (m, 5H, oxetanyl), 4.40-4.34 (q, 2H), 3.14 (s, 3H), 1.34 (t, 3H).

Step 3

8-(2,3-dichlorophenyl)-4-[methyl(oxetan-3-yl) amino]quinoline-3-carboxylic acid

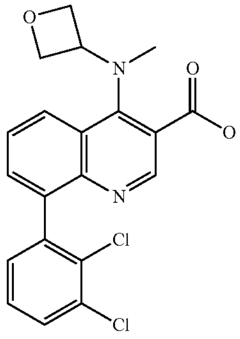

Ethyl 8-(2,3-dichlorophenyl)-4-[methyl(oxetan-3-yl)amino]quinoline-3-carboxylate (step 2) (580 mg, 1.34 mmol) was dissolved in 20 mL dioxane and mixed with LiOH (35.4 mg, 1.48 mmol) in 5 mL water. The reaction mixture was heated for 16 hours at 60° C. The dioxane was removed under reduced pressure, the remaining solution was taken into a mixture of ethyl acetate and water. The aqueous phase was separated and treated with 1N HCl until pH 5. This acidified solution was extracted twice with ethyl acetate, the combined extracts were dried, filtered and the solvent was removed under reduced pressure. The obtained compound was used in the next step without further purification.

Yield: 570 mg (99% of th.)

$^1$H-NMR (400 MHz, DMSO-d6) δ 12.00 (bs, 1H, COOH), 8.73 (s, 1H), 8.24-8.22 (dd, 1H), 7.23-7.68 (m, 3H), 7.44 (t, 1H), 7.37-7.35 (dd, 1H), 4.76-4.65 (m, 5H, oxetanyl), 3.13 (s, 3H).

Step 4

8-(2,3-dichlorophenyl)-N-[(4S)-3,4-dihydro-2H-chromen-4-yl]-4-[methyl(oxetan-3-yl)amino]-quinoline-3-carboxamide (Example 331)

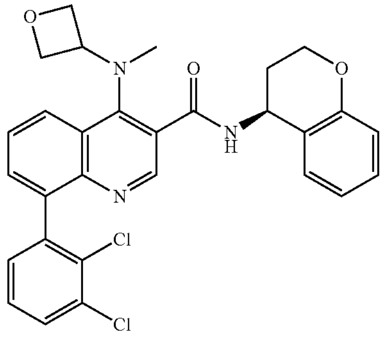 [SMILES: CN(c1c(C(=O)N[C@H]2CCOc3ccccc32)cnc2c(-c3cccc(Cl)c3Cl)cccc12)C1COC1]

A flask was charged with 8-(2,3-dichlorophenyl)-4-[methyl(oxetan-3-yl)amino]quinoline-3-carboxylic acid (step 3) (260 mg, 0.645 mmol), (4S)-chroman-4-amine hydrochloride (131.7 mg, 0.71 mmol), N,N-diisopropyl ethylamine (250 mg, 1.93 mmol), 4-(N,N-dimethylamino) pyridine (39.4 mg, 0.32 mmol), 1-hydroxy-1H-benzotriazole (43.5 mg, 0.32 mmol) and 1-ethyl-3-(3-dimethylaminopropyl)carbodiimide hydrochloride (123.6 mg, 0.645 mmol) in 10 mL dichloromethane. The reaction mixture was stirred at ambient temperature overnight, then mixed with water, the dichloromethane phase was separated, dried via a sodium sulfate/silica gel cartridge and the solvent was removed under reduced pressure. The residue was purified by reverse phase column chromatography (eluent water/acetonitrile gradient) to obtain the title compound.

Yield: 130 mg (0.24 mmol, 37% of th.)

$^1$H-NMR Peaklist (399,9532 MHz, DMSO): δ=9.1403 (1.94); 9.1288 (2); 9.1208 (2.32); 9.1103 (1.85); 8.6012 (10.54); 8.4715 (0.58); 8.3155 (1.57); 8.2143 (2.25); 8.1975 (2.56); 8.1729 (1.06); 7.7323 (2.07); 7.7127 (5.31); 7.6894 (10.46); 7.6737 (1.95); 7.4635 (1.67); 7.4521 (1.74); 7.4433 (2.94); 7.4332 (2.77); 7.4235 (2.08); 7.4143 (1.65); 7.3824 (1.86); 7.3618 (4.63); 7.3428 (4.44); 7.3225 (1.63); 7.1895 (1.81); 7.171 (3.64); 7.1535 (2.27); 6.9433 (2.6); 6.9255 (4.32); 6.9084 (2.02); 6.8059 (4.77); 6.7848 (4.45); 6.5782 (0.9); 5.2488 (1.97); 5.237 (2); 4.725 (1.91); 4.697 (7.04); 4.6722 (5.48); 4.6575 (5.6); 4.5955 (1.22); 4.5844 (1.61); 4.2921 (2.17); 4.2752 (3.94); 4.2675 (3.64); 4.2552 (2.23); 4.2471 (2.41); 4.2281 (0.89); 3.3183 (319.34); 3.2701 (0.87); 3.2496 (0.61); 3.1747 (0.71); 3.081 (16); 3.0759 (15.54); 2.9497 (1.08); 2.6703 (8.96); 2.5893 (0.63); 2.5051 (1239.6); 2.5012 (1583.24); 2.4971 (1204.24); 2.3276 (9.3); 2.2832 (0.88); 2.2475 (1.34); 2.2286 (1.72); 2.2205 (1.78); 2.1313 (0.96); 2.074 (5.92); 2.0168 (0.96); 1.2694 (0.87); 1.169 (4.47); 1.0034 (0.71); 0.9887 (0.75); 0.1463 (2.93); −0.0001 (642.47); −0.0792 (0.67); −0.1497 (3.13); −3.3083 (0.55).

Synthesis of 8-(3,5-dichlorophenyl)-N-[(1S)-2,3-dihydro-1H-inden-1-yl]-4-ethoxyquinoline-3-carboxamide (Example 134)

Step 1

8-(3,5-dichlorophenyl)-N-[(1S)-2,3-dihydro-1H-inden-1-yl]-4-hydroxyquinoline-3-carboxamide

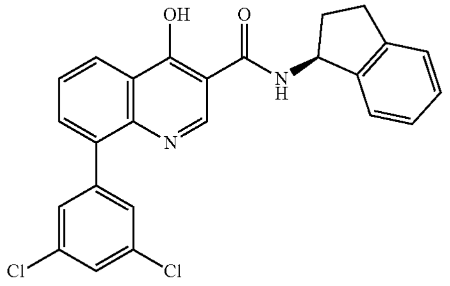 [SMILES: O=C(N[C@H]1CCc2ccccc21)c1cnc2c(-c3cc(Cl)cc(Cl)c3)cccc2c1O]

A solution of 8-(3,5-dichlorophenyl)-4-hydroxyquinoline-3-carboxylic acid (5.50 g, 16.5 mmol) in THF was treated stirred with (1S)-indan-1-amine (2.5 ml, 20 mmol) and trimethylamine (9.2 ml, 66 mmol) for 10 min at ambient temperature. Then a solution of 2,4,6-tripropyl-1,3,5,2,4,6-trioxatriphosphinane 2,4,6-trioxide in ethylacetate (19.6 ml, 50% content, 33 mmol) was added an stirred overnight at ambient temperature. Water (100 ml) was added and the THF evaporated under reduced pressure. More water and ethyl acetate were added and the mixture cleared by filtration. The aqueous phase was extracted with ethyl acetate and the combined organic phases dried and evaporated under reduced pressure. The residue was purified by column chromatography on silica (340 g) with cyclohexane/ethyl acetate (15-40%). Two fractions were isolated:

Yield: 3.0 g (98% purity, 40% of th.) and 0.69 g (94% purity, 9% of th.)

LC-MS (Method L1): $R_f$=1.27 min; MS (ESIneg): m/z=447 $[M+H]^-$ $^1$H-NMR Peaklist (400 MHz, DMSO-d6) δ[ppm]: 1.849 (1.87), 1.868 (2.39), 1.880 (2.59), 1.900 (2.50), 1.921 (1.16), 2.578 (3.74), 2.588 (3.08), 2.841 (1.03), 2.862 (1.82), 2.882 (2.65), 2.902 (3.54), 2.922 (2.00), 2.977 (2.56), 2.990 (2.71), 2.999 (2.71), 3.029 (1.74), 5.474 (1.16), 5.493 (3.52), 5.512 (3.77), 5.531 (1.67), 7.197 (1.27), 7.214 (3.91), 7.233 (6.17), 7.256 (5.56), 7.280 (7.00), 7.298 (9.89), 7.316 (4.52), 7.521 (2.83), 7.540 (5.61), 7.560 (4.06), 7.626 (14.53), 7.631 (16.00), 7.695 (5.87), 7.713 (5.06), 7.804 (5.42), 8.297 (4.58), 8.318 (4.68), 8.611 (4.35), 8.624 (4.69), 10.285 (4.44), 10.304 (4.72), 11.637 (3.53).

Step 2

8-(3,5-dichlorophenyl)-N-[(1S)-2,3-dihydro-1H-inden-1-yl]-4-ethoxyquinoline-3-carboxamide (Example 134)

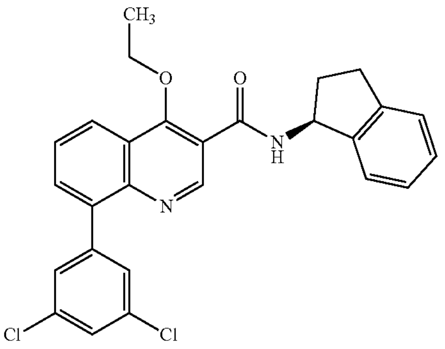 [SMILES: CCOc1c(C(=O)N[C@H]2CCc3ccccc32)cnc2c(-c3cc(Cl)cc(Cl)c3)cccc12]

8-(3,5-dichlorophenyl)-N-[(1S)-2,3-dihydro-1H-inden-1-yl]-4-hydroxyquinoline-3-carboxamide (step 1) (70.0 mg, 156 μmol), ethanol (27 μl, 470 μmol), triphenylphosphine (61.3 mg, 234 μmol) and diisopropyl-(E)-diazene-1,2-dicarboxylate (46 μl, 230 μmol) were stirred in THF (1 ml) at ambient temperature for 6 h. 5 M formic acid (93 μl, 470 μmol) was added, the solvent evaporated and the residue purified by prep. HPLC (C18, gradient: 0.1% aq. formic acid/acetonitrile).

Yield: 40 mg (92% purity, 49% of th.)

LC-MS (Method L7): $R_f$=2.60 min; MS (ESIpos): m/z=477 $[M+H]^+$ $^1$H-NMR (Peaklist) (500 MHz, DMSO-d6) δ[ppm]: −0.007 (4.15), 0.007 (3.67), 1.235 (1.26), 1.395 (7.56), 1.409 (16.00), 1.423 (7.72), 1.950 (1.18), 1.966 (1.28), 1.975 (1.34), 1.991 (1.30), 2.522 (1.98), 2.853 (1.24), 2.869 (1.51), 2.885 (1.92), 2.901 (0.85), 2.981 (1.03), 2.989 (1.09), 2.999 (1.11), 3.006 (1.07), 3.013 (0.81), 3.286 (5.84), 4.352 (1.51), 4.354 (1.53), 4.366 (4.56), 4.368 (4.83), 4.380 (4.46), 4.383 (4.79), 4.394 (1.38), 4.396 (1.51), 5.533 (0.78), 5.549 (2.29), 5.564 (2.27), 5.580 (0.78), 5.754 (0.91), 7.227 (2.02), 7.231 (3.49), 7.238 (4.46), 7.245 (4.52), 7.249 (3.34), 7.260 (1.11), 7.278 (2.99), 7.290 (1.65), 7.294 (1.20), 7.400 (2.19), 7.406 (2.33), 7.417 (2.00), 7.654 (2.35), 7.658 (5.35), 7.661 (4.98), 7.674 (15.77), 7.678 (10.55), 7.714 (2.52), 7.729 (3.39), 7.731 (3.32), 7.745 (2.97), 7.889 (3.47), 7.891 (3.80), 7.903 (3.01), 7.906 (3.03), 8.304 (3.32), 8.307 (3.57), 8.321 (3.16), 8.324 (3.16), 8.842 (11.93), 8.998 (2.83), 9.015 (2.77).

Synthesis of 8-(3,5-dichlorophenyl)-N-[(4S)-3,4-dihydro-2H-chromen-4-yl]-4-ethyl quino-line-3-carboxamide (Example 350)

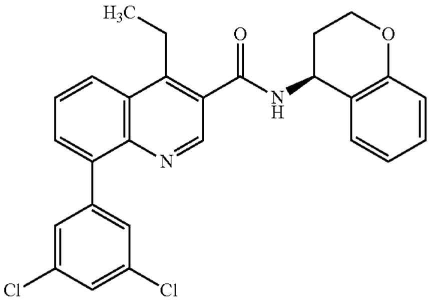

A solution of diethylzinc in heptane (400 μl, 1.0 M, 400 μmol) was added dropwise to a mixture of 4-chloro-8-(3,5-dichlorophenyl)-N-[(4S)-3,4-dihydro-2H-chromen-4-yl] quinoline-3-carboxamide (step 4, example 4) (97 mg, 200 μmol) and 1,1'-bis(diphenylphosphino)ferrocene-palladium (II)dichloride dichloromethane complex (32.7 mg, 40.0 μmol) in dioxan (2 ml) and stirred at 90° C. overnight under an argon atmosphere. 5 M formic acid (160 μl, 5.0 M, 800 μmol) and DMSO (1 ml) were added and the filtered mixture was purified twice by preparative HPLC (C18, gradient: 0.1% aq. formic acid/acetonitrile).

Yield: 52 mg (98% purity, 53% of th.)

LC-MS (Method L1): $R_f$=1.35 min; MS (ESIpos): m/z=477 $[M+H]^+$ $^1$H-NMR Peaklist (400 MHz, DMSO-d6) δ[ppm]: 1.303 (2.43), 1.322 (5.61), 1.341 (2.50), 3.252 (2.09), 3.271 (2.06), 4.250 (1.06), 4.259 (1.62), 4.268 (1.95), 4.275 (1.54), 4.284 (1.06), 5.305 (0.92), 5.325 (0.92), 6.783 (1.53), 6.785 (1.66), 6.803 (1.75), 6.806 (1.83), 6.911 (0.78), 6.914 (0.83), 6.930 (1.72), 6.932 (1.71), 6.948 (1.03), 6.951 (1.00), 7.149 (0.86), 7.153 (0.89), 7.170 (1.43), 7.350 (1.48), 7.370 (1.41), 7.652 (16.00), 7.752 (1.09), 7.770 (1.68), 7.791 (1.47), 7.871 (1.93), 7.874 (2.04), 7.889 (1.44), 7.892 (1.42), 8.319 (1.50), 8.322 (1.58), 8.340 (1.43), 8.343 (1.39), 8.839 (5.77), 9.102 (1.60), 9.123 (1.55).

Isolation of 8-(3-chloro-5-ethylphenyl)-N-[(4S)-3,4-dihydro-2H-chromen-4-yl]-4-ethylquinoline-3-carboxamide (Example 351)

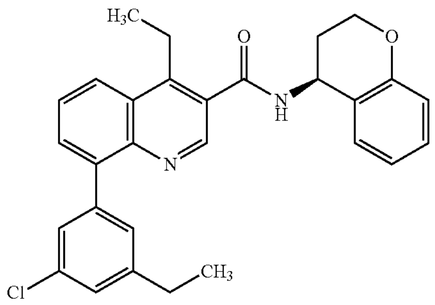 [SMILES: CCc1cc(Cl)cc(-c2cccc3c(CC)c(C(=O)N[C@H]4CCOc5ccccc54)cnc23)c1]

The preparative HPLC separation described in example 350 yielded the title compound as a by-product.

Yield: 12 mg (100% purity, 13% of th.)

LC-MS (Method L1): $R_f$=1.36 min; MS (ESIpos): m/z=471 $[M+H]^+$ $^1$H-NMR (400 MHz, DMSO-$d_6$): δ [ppm]=9.10 (d, 1H), 8.81 (s, 1H), 8.29 (dd, 1H), 7.72-7.83 (m, 2H), 7.46 (t, 1H), 7.31-7.40 (m, 3H), 7.17 (t, 1H), 6.93 (td, 1H), 6.79 (dd, 1H), 5.27-5.35 (m, 1H), 4.22-4.31 (m, 2H), 3.21-3.29 (m, 2H) superimpose by water signal, 2.64-2.73 (m, 2H), 2.16-2.26 (m, 1H), 2.01-2.11 (m, 1H), 1.32 (t, 3H), 1.23 (t, 3H).

Synthesis of 8-(3,5-dichlorophenyl)-N-[(4S)-3,4-dihydro-2H-chromen-4-yl]-4-(prop-1-en-2-yl)quinoline-3-carboxamide (Example 317)

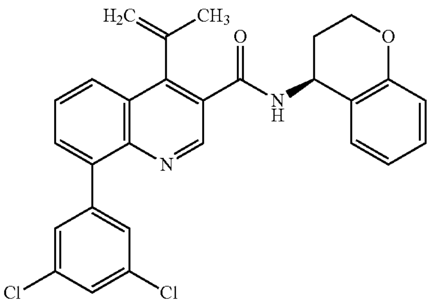 [SMILES: C=C(C)c1c(C(=O)N[C@H]2CCOc3ccccc32)cnc2c(-c3cc(Cl)cc(Cl)c3)cccc12]

Under argon atmosphere and continuous sonication potassium carbonate (571 mg, 4.13 mmol) was dissolved in a thick-walled vessel in a 5:1 degassed mixture of dioxan and water (7.0 ml). 1,1'-bis(diphenylphosphino)ferrocene-palladium(II)dichloride dichloromethane complex (84.4 mg, 103 μmol) and 4-chloro-8-(3,5-dichlorophenyl)-N-[(4S)-3,4-dihydro-2H-chromen-4-yl]quinoline-3-carboxamide (step 4, example 4) (1.00 g, 2.07 mmol) were added, followed by 4,4,5,5-tetramethyl-2-(prop-1-en-2-yl)-1,3,2-dioxaborolane (0.49 ml, 4.1 mmol). The vessel was capped and stirred at 80° C. for 4 h. 5 M formic acid (1.3 ml) and water were added and the mixture extracted with ethyl acetate. The organic phases were dried and evaporated under reduced pressure. The residue was purified by column chromatography on silica (50 g), eluent: cyclohexane/ethyl acetate (7-16%).

Yield: 885 mg (87% of th.)

LC-MS (Method L1): $R_f$=1.39 min; MS (ESIpos): m/z=489 $[M+H]^+$ $^1$H-NMR (400 MHz, DMSO-d6): Shift [ppm]=8.88-9.00 (m, 2H), 8.04 (dd, 1H), 7.90 (dd, 1H), 7.76 (dd, 1H), 7.67 (s, 3H), 7.32 (br d, 1H), 7.11-7.22 (m, 1H), 6.92 (t, 1H), 6.78 (dd, 1H), 5.54 (s, 1H), 5.18-5.30 (m, 1H), 5.03 (br s, 1H), 4.16-4.33 (m, 2H), 2.12-2.26 (m, 4H), 1.95-2.06 (m, 1H).

Synthesis of 8-(3,5-dichlorophenyl)-N-[(4S)-3,4-dihydro-2H-chromen-4-yl]-4-isopropyl-quinoline-3-carboxamide (Example 359)

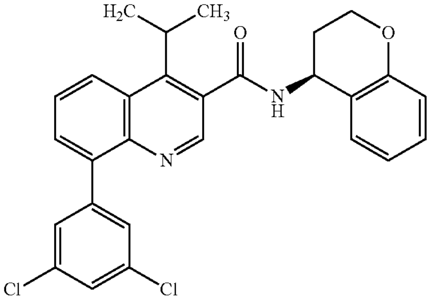 [SMILES: CC(C)c1c(C(=O)N[C@H]2CCOc3ccccc32)cnc2c(-c3cc(Cl)cc(Cl)c3)cccc12]

Under argon atmosphere 8-(3,5-dichlorophenyl)-N-[(4S)-3,4-dihydro-2H-chromen-4-yl]-4-(prop-1-en-2-yl)quinoline-3-carboxamide (from example 317) (150 mg, 306 μmol) was dissolved in ethyl acetate (7 ml) and ethanol (3.5 ml). Pd on charcoal (44 mg, 10%) was added and the mixture hydrogenated under normal pressure at ambient temperature for 1.5 h. The catalyst was filtered off through Celite, washed with an ethyl acetate/ethanol mixture (2:1) and the filtrate evaporated under reduced pressure. The residue was purified two times by prep. HPLC (C18, gradient: 0.1% aq. formic acid/acetonitrile).

Yield: 64 mg (42% of th.)

LC-MS (Method L1): $R_f$=1.41 min; MS (ESIpos): m/z=491 $[M+H]^+$ $^1$H-NMR (400 MHz, DMSO-d6): Shift [ppm]=9.12 (d, 1H), 8.76 (s, 1H), 8.45 (d, 1H), 7.85 (d, 1H), 7.74 (t, 1H), 7.61-7.66 (m, 3H), 7.36 (d, 1H), 7.17 (t, 1H), 6.93 (t, 1H), 6.79 (d, 1H), 5.25-5.31 (m, 1H), 4.21-4.31 (m, 2H), 3.82-3.92 (m, 1H), 2.21 (td, 1H), 2.06 (ddd, 1H), 1.56 (br d, 3H), 1.53 (br d, 3H).

Synthesis of ethyl cyano{8-(3,5-dichlorophenyl)-3-[(4S)-3,4-dihydro-2H-chromen-4-ylcarbamoyl]quinolin-4-yl}acetate (Example 354)

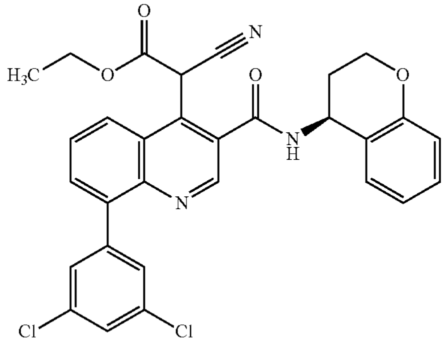 [SMILES: CCOC(=O)C(C#N)c1c(C(=O)N[C@H]2CCOc3ccccc32)cnc2c(-c3cc(Cl)cc(Cl)c3)cccc12]

Under argon atmosphere sodium hydride (165 mg, 60% content, 4.13 mmol) was added at 0° C. to a solution of ethyl-cyanoacetate (0.44 ml, 4.1 mmol) in dry N-methyl pyrrolidon, stirred at ambient temperature for 15 min until the evolution of gas had ceased. Then 4-chloro-8-(3,5-dichlorophenyl)-N-[(4S)-3,4-dihydro-2H-chromen-4-yl]quinoline-3-carboxamide (1.00 g, 2.07 mmol) was added and the mixture stirred at 70° C. for 3 h. After cooling to ambient temperature 5 M formic acid (1.2 ml, 6.2 mmol) and water were added and the mixture extracted two times with ethyl acetate. The combined organic phases were dried and evaporated under reduced pressure. The residue was purified by column chromatography on silica (100 g) with cyclohexane/ethyl acetate (5-50%).

Yield: 650 mg (96% purity, 54% of th.)

LC-MS (Method L6): $R_f$=2.46 min; MS (ESIpos): m/z=560 $[M+H]^+$ $^1$H-NMR Peaklist (400 MHz, DMSO-d6) δ[ppm]: −0.008 (3.55), 0.008 (3.23), 0.146 (0.40), 0.890 (0.44), 1.157 (2.49), 1.175 (7.53), 1.188 (4.41), 1.193 (9.23), 1.205 (8.20), 1.211 (4.25), 1.215 (2.56), 1.223 (4.21), 1.233 (2.01), 1.245 (1.50), 1.250 (2.12), 1.264 (0.77), 1.268 (1.05), 1.988 (9.00), 2.083 (0.45), 2.092 (0.48), 2.104 (0.46), 2.116 (0.65), 2.129 (0.70), 2.163 (1.14), 2.176 (1.60), 2.187 (1.26), 2.327 (0.47), 2.366 (0.41), 2.523 (1.67), 2.669 (0.54), 2.710 (0.46), 3.998 (2.03), 4.002 (0.89), 4.021 (2.14), 4.038 (2.14), 4.056 (0.79), 4.133 (0.51), 4.151 (0.98), 4.168 (0.93), 4.175 (0.83), 4.186 (0.84), 4.193 (1.11), 4.202 (2.21), 4.210 (1.51), 4.219 (4.66), 4.228 (3.20), 4.236 (4.66), 4.246 (3.73), 4.254 (2.15), 4.263 (1.53), 4.272 (0.85), 4.287 (1.21), 4.298 (1.72), 4.309 (1.16), 5.226 (0.78), 5.245 (0.83), 5.266 (0.79), 5.285 (0.73), 6.794 (1.56), 6.804 (5.05), 6.815 (1.91), 6.826 (4.30), 6.837 (0.92), 6.856 (1.42), 6.866 (0.52), 6.875 (0.87), 6.917 (0.71), 6.936 (1.45), 6.955 (0.86), 7.142 (0.96), 7.145 (0.95), 7.163 (1.28), 7.173 (0.83), 7.177 (0.93), 7.194 (1.20), 7.212 (0.58), 7.387 (1.34), 7.408 (1.79), 7.429 (1.14), 7.599 (0.99), 7.603 (1.04), 7.683

(16.00), 7.702 (0.43), 7.875 (1.05), 7.879 (1.00), 7.897 (2.37), 7.914 (1.62), 7.918 (1.55), 8.002 (3.30), 8.019 (2.41), 8.408 (1.18), 8.423 (1.48), 8.443 (1.15), 9.112 (4.72), 9.124 (4.29), 9.517 (1.49), 9.525 (1.44), 9.537 (1.51), 9.544 (1.34).

Synthesis of 4-(cyanomethyl)-8-(3,5-dichlorophenyl)-N-[(4S)-3,4-dihydro-2H-chromen-4-yl]quinoline-3-carboxamide (Example 355)

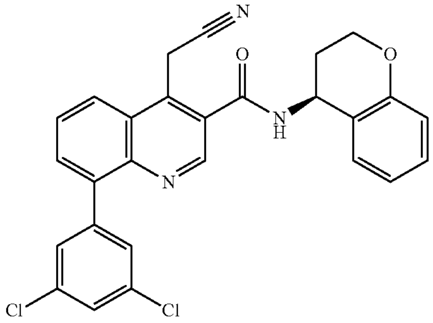 [SMILES: N#CCc1c(C(=O)N[C@H]2CCOc3ccccc32)cnc2c(-c3cc(Cl)cc(Cl)c3)cccc12]

A solution of ethyl cyano{8-(3,5-dichlorophenyl)-3-[(4S)-3,4-dihydro-2H-chromen-4-ylcarbamoyl]quinolin-4-yl}acetate (example 354) (300 mg, 0.54 mmol) in DMSO (2.4 ml) was treated with sodium chloride (63 mg, 1.1 mmol) and water (0.24 ml) and heated under stirring overnight at 90° C. Water (2.5 ml) was added, the precipitate filtered off, washed with water and dried in vacuo.

Yield: 250 mg (99% purity, 95% of th.)

LC-MS (Method L1): $R_f$=1.24 min; MS (ESIpos): m/z=488 $[M+H]^+$ $^1$H-NMR Peaklist (400 MHz, DMSO-d6) δ[ppm]: 2.099 (0.43), 2.136 (0.80), 2.145 (0.69), 2.205 (0.64), 2.224 (0.67), 2.239 (0.54), 4.266 (1.68), 4.277 (2.29), 4.711 (6.99), 5.278 (0.45), 5.294 (1.03), 5.312 (1.04), 5.326 (0.45), 6.798 (2.04), 6.818 (2.30), 6.899 (1.01), 6.917 (2.07), 6.936 (1.19), 7.163 (1.04), 7.182 (1.68), 7.200 (0.79), 7.387 (1.76), 7.405 (1.62), 7.677 (16.00), 7.883 (1.06), 7.903 (1.92), 7.922 (1.56), 7.988 (2.46), 8.006 (1.65), 8.417 (1.93), 8.437 (1.73), 9.029 (5.73), 9.379 (1.69), 9.399 (1.68).

Synthesis of 4-(2-amino-2-oxoethyl)-8-(3,5-dichlorophenyl)-N-[(4S)-3,4-dihydro-2H-chromen-4-yl]quinoline-3-carboxamide (Example 360)

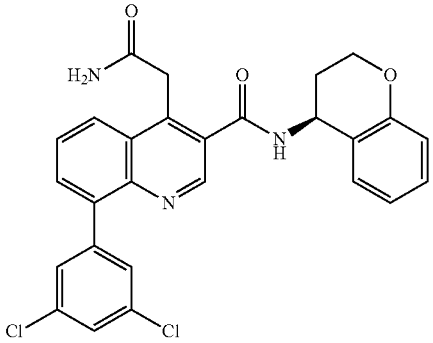 [SMILES: NC(=O)Cc1c(C(=O)N[C@H]2CCOc3ccccc32)cnc2c(-c3cc(Cl)cc(Cl)c3)cccc12]

A suspension of 4-(cyanomethyl)-8-(3,5-dichlorophenyl)-N-[(4S)-3,4-dihydro-2H-chromen-4-yl]quinoline-3-carboxamide (example 355) (150 mg, 307 μmol) in conc. hydrochloric acid (0.77 ml, 37%) and dioxan (0.5 ml) was stirred 3 days at ambient temperature. The solid was filtered off, washed with dioxan and dried in vacuo.

Yield: 90 mg (92% purity, 53% of th.)

LC-MS (Method L1): $R_f$=1.13 min; MS (ESIpos): m/z=506 $[M+H]^+$ $^1$H-NMR Peaklist (400 MHz, DMSO-d6) δ[ppm]: −0.149 (0.40), 0.008 (3.42), 2.068 (0.55), 2.085 (0.61), 2.095 (0.80), 2.208 (0.74), 2.220 (0.70), 2.229 (0.68), 2.242 (0.51), 2.327 (0.61), 2.366 (0.61), 2.670 (0.57), 2.710 (0.54), 2.794 (0.77), 3.568 (2.60), 4.179 (0.56), 4.197 (0.56), 4.216 (3.94), 4.225 (3.86), 4.238 (1.19), 4.264 (1.32), 4.283 (1.00), 5.270 (0.46), 5.285 (1.06), 5.304 (1.07), 5.319 (0.51), 6.779 (1.94), 6.800 (2.15), 6.883 (0.98), 6.899 (2.02), 6.918 (1.20), 7.147 (1.02), 7.164 (1.67), 7.185 (0.81), 7.349 (2.28), 7.369 (1.67), 7.659 (16.00), 7.764 (1.23), 7.782 (1.93), 7.803 (1.67), 7.894 (2.35), 7.910 (1.74), 7.989 (1.55), 8.349 (1.83), 8.368 (1.68), 8.949 (6.32), 9.468 (1.76), 9.488 (1.75).

The filtrate was adjusted to pH 6 by addition of aqueous sodiumbicarbonate (7 ml, 1.5 M) and extracted with ethyl acetate. The combined organic phases were dried, evaporated and the residue purified by prep. HPLC (C18, gradient: 0.1% aq. formic acid/acetonitrile) yielding a second crop (40 mg, 100% purity, 26% of th.)

Synthesis of 4-cyano-8-(3,5-dichlorophenyl)-N-[(4S)-3,4-dihydro-2H-chromen-4-yl]quinoline-3-carboxamide (Example 362)

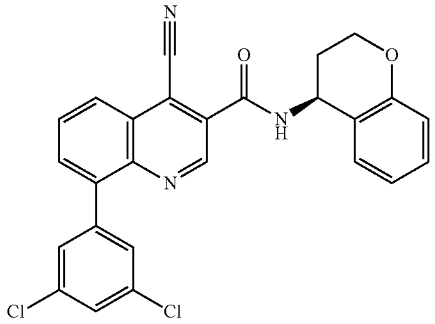 [SMILES: N#Cc1c(C(=O)N[C@H]2CCOc3ccccc32)cnc2c(-c3cc(Cl)cc(Cl)c3)cccc12]

Under argon atmosphere a thick-walled microwave vessel was charged with 4-chloro-8-(3,5-dichlorophenyl)-N-[(4S)-3,4-dihydro-2H-chromen-4-yl]quinoline-3-carboxamide (1.00 g, 2.07 mmol), copper(I)cyanide (185 mg, 2.07 mmol), sodiumcarbonate (219 mg, 2.07 mmol), 1,1'-bis(diphenylphosphino)ferrocene-palladium(II)dichloride dichloromethane complex (169 mg, 0.21 mmol) and N-methyl pyrrolidon (7.2 ml), capped and heated overnight under stirring at 120° C. The reaction mixture was added to a 3:1 mixture of saturated aq. ammoniumchloride/conc. aqueous ammonia (120 ml) and ethyl acetate, stirred for 30 min and filtered through celite. The phases were separated, the organic phase washed three times with a 3:1 mixture of saturated aq. ammoniumchloride/conc. aq. ammonia, then brine and dried. The residue (1.06 g) was purified by column chromatography on silica (100 g) with cyclohexane/ethyl acetate (3-30%).

Yield: 760 mg (93% purity, 72% of th.)

LC-MS (Method L1): $R_f$=1.44 min; MS (ESIpos): m/z=474 $[M+H]^+$ $^1$H-NMR Peaklist (400 MHz, DMSO-d6) δ[ppm]: −0.008 (0.70), 0.008 (0.49), 1.398 (16.00), 1.988 (0.45), 2.519 (0.43), 6.790 (0.48), 6.849 (0.44), 6.851 (0.45), 6.870 (0.51), 6.872 (0.48), 6.966 (0.40), 7.673 (0.41), 7.696 (4.12), 7.933 (0.43), 7.951 (0.60), 7.953 (0.54), 7.972 (0.53), 8.054 (0.67), 8.057 (0.62), 8.071 (0.49), 8.075 (0.41), 9.279 (0.96), 9.311 (0.50).

Synthesis of 8-(2,3-dichlorophenyl)-N-[(4S)-3,4-dihydro-2H-chromen-4-yl]-4-(dimethylamino)-2-methylquinoline-3-carboxamide (Example 481)

Step 1 tert-butyl 8-bromo-4-hydroxy-2-methylquinoline-3-carboxylate

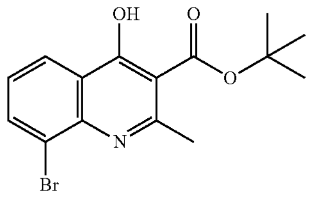 [SMILES: Cc1nc2c(Br)cccc2c(O)c1C(=O)OC(C)(C)C]

A three-necked flask was charged with sodium hydride (910 mg, 22.7 mmol, 60% dispersion in mineral oil) and dry DMF (50 mL). 3-Bromoisatoic anhydride (5 g, 20.6 mmol) was added slowly (0.42 g, 4 mmol), followed by dropwise addition of tert-butyl 3-oxobutanoate (3.6 g, 22.7 mmol) dissolved in 50 mL DMF at room temperature. The reaction mixture was heated to 120° C. for 10 minutes. Then the solvent was removed under reduced pressure and the remaining material was dispersed in water and extracted twice with dichloromethane. The combined organic layers were dried over sodium sulfate, filtered and reduced in vacuo. The resulting residue was purified by silica gel flash chromatography (eluent cyclohexane/ethyl acetate gradient).

Yield: 1.05 g (2.96 mmol, 15% of th.)

$^1$H-NMR (400 MHz, DMSO-d6) δ 10.48 (s, 1H), 8.10-8.08 (d, 1H), 8.02-7.99 (d, 1H), 7.31-7.27 (t, 1H), methyl singulett under DMSO signal, 1.51 (s, 9H).

Step 2

8-bromo-4-chloro-2-methylquinoline-3-carbonyl chloride

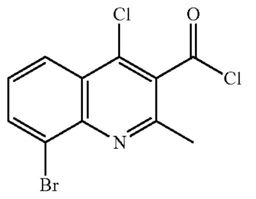 [SMILES: Cc1nc2c(Br)cccc2c(Cl)c1C(=O)Cl]

A three-necked flask was charged with tert-butyl 8-bromo-4-hydroxy-2-methylquinoline-3-carboxylate (1.2 g, 3.54 mmol)) and phosphorus oxychloride (42 g, 274 mmol) and heated to reflux for 16 h. The reaction mixture was reduced in vacuo and used as such in the next step.

Step 3

8-bromo-4-chloro-N-[(4S)-3,4-dihydro-2H-chromen-4-yl]-2-methylquinoline-3-carboxamide

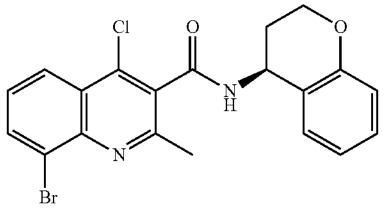 [SMILES: Cc1nc2c(Br)cccc2c(Cl)c1C(=O)N[C@H]1CCOc2ccccc21]

8-Bromo-4-chloro-2-methylquinoline-3-carbonyl chloride (raw product from step 2) (1 g, 3.13 mmol) was dissolved in 60 mL acetonitril and mixed with (4S)-chroman-4-amine hydrochloride (582 mg, 3.13 mmol) and triethylamine (951 mg, 9.4 mmol) at 0° C. The reaction mixture was allowed to warm to room temperature and stirred until complete conversion. The solvent was removed under reduced pressure; the remaining solution was extracted twice with dichloromethane. The combined organic layers were dried over sodium sulfate, filtered and reduced in vacuo. The resulting residue was purified by silica gel flash chromatography (eluent cyclohexane/ethyl acetate gradient).

Yield: 766 mg (1.77 mmol, 55% of th.)

$^1$H-NMR (400 MHz, DMSO-d6) δ 9.29 (d, 1H, NH), 8.26-8.22 (t, 2H), 7.66-7.62 (dd, 1H), 7.38 7.36 (d, 1H), 7.20-7.16 (t, 1H), 6.97-6.93 (t, 1H), 6.82-6.80 (d, 1H), 5.32-5.28 (m, 1H), 4.34-4.29 (m, 1H), 4.23-4.17 (m, 1H), 2.71 (s, 3H), 2.28-2.22 (m, 1H), 2.10-2.03 (m, 1H).

Step 4

8-bromo-N-[(4S)-3,4-dihydro-2H-chromen-4-yl]-4-(dimethylamino)-2-methylquinoline-3-carboxamide

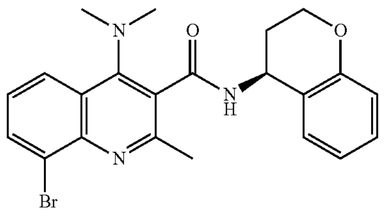 [SMILES: Cc1nc2c(Br)cccc2c(N(C)C)c1C(=O)N[C@H]1CCOc2ccccc21]

8-Bromo-4-chloro-N-[(4S)-3,4-dihydro-2H-chromen-4-yl]-2-methylquinoline-3-carboxamide (step 3) (766 mg, 1.77 mmol) in 30 mL dioxane were distributed to three microwave flasks (20 mL volume). Each of it was charged with 3.7 mL aqueous dimethylamine solution (40%, combined 8.87 mmol). The reaction mixtures were heated in a microwave oven (Anton Paars Monowave 400) to 100° C. for 40 minutes. The reaction mixtures were combined and the solvent was removed under reduced pressure. The resulting residue was purified by silica gel flash chromatography (eluent cyclohexane/ethyl acetate gradient).

Yield: 625 mg (1.42 mmol, 73% of th.)

$^1$H-NMR (400 MHz, DMSO-d6) δ 9.07 (d, 1H, NH), 8.08-8.02 (2d, 2H), 7.41-7.37 (t, 1H), 7.32 7.31 (d, 1H), 7.20-7.16 (t, 1H), 6.96-6.92 (t, 1H), 6.82-6.79 (d, 1H), 5.28-5.26 (m, 1H), 4.35-4.27 (m, 1H), 4.23-4.16 (m, 1H), 3.01 (s, 6H), 2.61 (s, 3H), 2.28-2.19 (m, 1H), 2.10-2.02 (m, 1H).

Step 5

8-(2,3-dichlorophenyl)-N-[(4S)-3,4-dihydro-2H-chromen-4-yl]-4-(dimethylamino)-2-methylquinoline-3-carboxamide (Example 481)

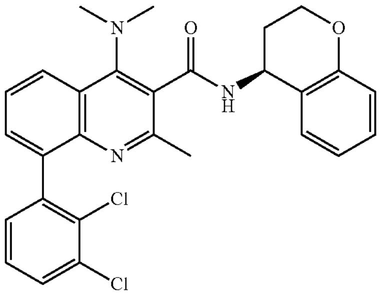 [SMILES: Cc1nc2c(-c3cccc(Cl)c3Cl)cccc2c(N(C)C)c1C(=O)N[C@H]1CCOc2ccccc21]

To a degassed (1 min, argon) mixture of 8-bromo-N-[(4S)-3,4-dihydro-2H-chromen-4-yl]-4-(dimethylamino)-2-methylquinoline-3-carboxamide (step 4) (200 mg, 0.45 mmol), (2,3-dichlorophenyl)boronic acid (130 mg, 0.68 mmol), potassium carbonate (125.5 mg, 0.90 mmol), water (3.5 mL) and dioxane (12 mL) was added 1,1'-bis(diphenylphosphino)ferrocenepalladium(II) dichloride (18.5 mg, 0.02 mmol). The reaction mixture was stirred for 16 h at 85° C., then cooled down to room temperature, diluted with water and extracted twice with dichloromethane. The combined organic layers were dried over sodium sulfate, filtered and reduced in vacuo. The resulting residue was purified by silica gel flash chromatography (eluent cyclohexane/ethyl acetate gradient) to obtain the title compound.

Yield: 159 mg (0.31 mmol, 66% of th.)

$^1$H-NMR (400 MHz, DMSO-d6) δ 9.06 (d, 1H, NH), 8.17-8.15 (d, 1H), 7.68-7.66 (d, 1H), 7.58-7.55 (m, 2H), 7.42-7.42 (m, 1H), 7.32-7.30 (m, 2H), 7.17-7.15 (t, 1H), 6.93-6.91 (t, 1H), 6.80-6.78 (d, 1H), 5.28-5.24 (m, 1H), 4.32-4.27 (m, 1H), 4.23-4.17 (m, 1H), 3.04 (s, 6H), methyl singulett under DMSO signal, 2.24-2.18 (m, 1H), 2.08-2.02 (m, 1H).

Synthesis of 8-(3,5-dichlorophenyl)-N-[(4S)-3,4-dihydro-2H-chromen-4-yl]-4-(tetrahydro-2H-pyran-4-yl)quinoline-3-carboxamide (Example 539)

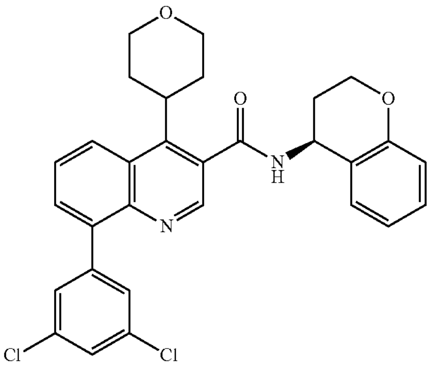 [SMILES: O=C(N[C@H]1CCOc2ccccc21)c1cnc2c(-c3cc(Cl)cc(Cl)c3)cccc2c1C1CCOCC1]

Under argon atmosphere 8-(3,5-dichlorphenyl)-N-[(4S)-3,4-dihydro-2H-chromen-4-yl]-4-(3,6-dihydro-2H-pyran-4-yl)chinolin-3-carboxamide (60.0 mg, 113 μmol) was dissolved in ethyl acetate/ethanol (2:1, 6 ml). The catalyst, 10% palladium on charcoal (20 mg), was added, argon replaced by hydrogen and the mixture stirred under atmospheric pressure of hydrogen for 4.5 h. More 10% palladium on charcoal (20 mg) was added under argon and hydrogenation continued under atmospheric pressure for 6 h. The reaction mixture was filtered over celite, rinsed with ethyl acetate and concentrated in vacuo. The residue (66 mg) was purified by prep. HPLC (C18, gradient: 0.1% aq. formic acid/acetonitrile).

Yield: 11 mg (18% of th.)

LC-MS (Method L1): Rt=1.28 min; MS (ESIpos): m/z=533 $[M+H]^+$ $^1$H-NMR (400 MHz, DMSO-d6) δ[ppm]: 0.008 (2.51), 1.235 (0.43), 1.676 (1.54), 1.713 (2.60), 1.751 (1.67), 2.057 (0.97), 2.072 (1.11), 2.085 (1.87), 2.218 (1.33), 2.231 (1.31), 2.240 (1.26), 2.252 (0.92), 2.327 (0.56), 2.366 (0.60), 2.429 (2.14), 2.460 (2.25), 2.670 (0.69), 2.710 (0.67), 3.464 (1.07), 3.493 (1.97), 3.520 (2.14), 3.546 (2.15), 3.575 (1.18), 3.738 (1.26), 4.010 (3.17), 4.023 (2.81), 4.038 (2.85), 4.219 (0.82), 4.240 (2.21), 4.247 (1.78), 4.260 (2.15), 4.268 (2.70), 4.279 (2.21), 4.295 (1.97), 5.293 (0.94), 5.307 (2.08), 5.327 (2.08), 5.342 (0.90), 5.754 (5.00), 6.785 (3.97), 6.804 (4.38), 6.918 (1.97), 6.937 (4.07), 6.956 (2.40), 7.158 (2.10), 7.176 (3.37), 7.193 (1.61), 7.405 (3.52), 7.423 (3.20), 7.613 (13.15), 7.617 (16.00), 7.648 (4.20), 7.653 (5.68), 7.748 (2.29), 7.766 (3.65), 7.787 (3.20), 7.856 (4.95), 7.874 (3.52), 8.510 (3.43), 8.531 (3.17), 8.777 (12.63), 9.140 (3.54), 9.161 (3.54).

Synthesis of N-[(4S)-3,4-dihydro-2H-chromen-4-yl]-4-(methoxymethyl)-8-(2,3,5-trifluorophenyl)quinoline-3-carboxamide (Example 686)

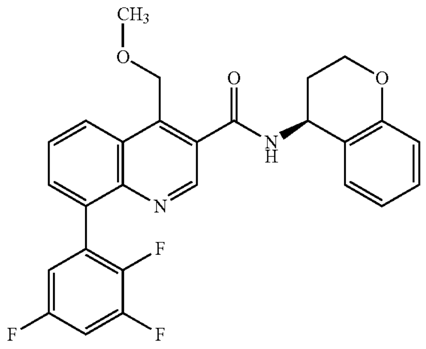 [SMILES: COCc1c(C(=O)N[C@H]2CCOc3ccccc32)cnc2c(-c3cc(F)cc(F)c3F)cccc12]

Step 1 ethyl 8-bromo-4-methylquinoline-3-carboxylate

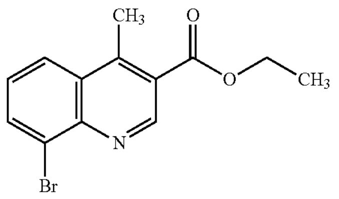 [SMILES: CCOC(=O)c1cnc2c(Br)cccc2c1C]

To a solution of ethyl 8-bromo-4-hydroxy-quinoline-3-carboxylate (3.00 g, 9.54 mmol) (Gharat, al., WO 2013/118071) in THF (45 ml) was added under argon cobalt(II) acetylacetonate (2.45 g, 9.54 mmol). The mixture was warmed in an oil bath of 60° C., dimethylzink (solution in toluene, 1.9 ml, 2.0 M, 3.8 mmol) was added dropwise and stirred at this temperature for 1 h. During a period of 4.5 h more dimethylzink (solution in toluene, 6.2 ml, 2.0 M, 12.4 mmol) was added at this temperature in several portions until almost all starting material was consumed (HPLC monitoring). The mixture was poured into water (250 ml), containing acetic acid (1.8 ml), the organic solvents largely evaporated under diminished pressure and the aqueous phase extracted with ethylacetate. The combined organic phases were dried and evaporated to dryness. The residue (3.1 g) was purified by column chromatography on silica (100 g), eluent: cyclohexane/ethyl acetate (3-10%) yielding the titel compound (1.25 g, 45% of theory)

LC-MS (Method L4): $R_f$=3.06 min; MS (ESIpos): m/z=294 $[M+H]^+$ $^1$H-NMR (400 MHz, DMSO-d6) δ[ppm]: 1.369 (4.76), 1.387 (9.98), 1.405 (4.89), 2.934 (16.00), 4.393 (1.57), 4.411 (4.77), 4.429 (4.71), 4.447 (1.51), 7.615 (1.30), 7.634 (2.23), 7.655 (1.46), 8.253 (1.85), 8.271 (1.76), 8.340 (2.09), 8.361 (1.99), 9.185 (3.32).

Step 2 ethyl 8-bromo-4-(bromomethyl)quinoline-3-carboxylate

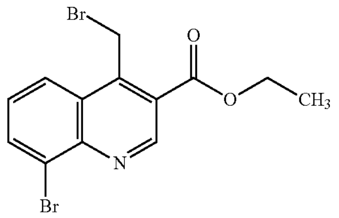 [SMILES: CCOC(=O)c1cnc2c(Br)cccc2c1CBr]

Ethyl-8-bromo-4-methylquinoline-3-carboxylate (1.50 g, 5.10 mmol) was dissolved in THF (23 ml). Phenyltrimethylammonium tribromide (3.07 g, 8.16 mmol) and acetic acid (1.5 ml, 25 mmol) were added and the mixture stirred at ambient temperature.

More phenyltrimethylammonium tribromide (0.96 g, 2.5 mmol) was added and stirred for 3 d at ambient temperature. Another portion of phenyltrimethylammonium tribromide (0.96 g, 2.5 mmol) and acetic acid (0.9 ml, 15.3 mmol) were added and stirring continued overnight. The reaction mixture was diluted with water and dichloromethane. The aqueous phase was extracted with dichloromethane and the combined organic layers were washed with an aqueous sodium hydrogencarbonate solution, dried and concentrated in vacuo at 30° C.

The residue was stirred for 1 h in MTBE (80 ml). The solid was filtered off, washed with MTBE and dried in vacuo. The crude (3.23 g) was purified by column chromatography, eluent cyclohexane/ethyl acetate (3-22%).

Yield: 985 mg (90.5% purity, 47% of th.)

LC-MS (Method L1): $R_f$=1.11 min; MS (ESIpos): m/z=371 $[M+H]^+$ $^1$H-NMR (500 MHz, DMSO-d6) δ[ppm]: 1.401 (7.41), 1.415 (16.00), 1.429 (7.42), 1.435 (0.41), 4.441 (2.26), 4.455 (7.12), 4.470 (6.98), 4.484 (2.13), 5.479 (11.96), 5.758 (1.31), 7.721 (2.28), 7.736 (2.76), 7.738 (2.62), 7.753 (2.43), 8.311 (2.94), 8.314 (3.02), 8.326 (2.85), 8.329 (2.69), 8.446 (2.62), 8.448 (2.54), 8.463 (2.57), 8.465 (2.29), 9.311 (8.57).

Step 3

8-bromo-4-(methoxymethyl)quinoline-3-carboxylic acid

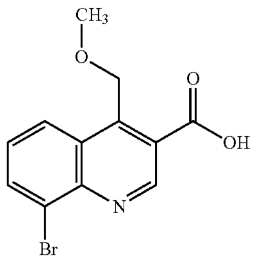 [SMILES: COCc1c(C(=O)O)cnc2c(Br)cccc12]

A suspension of ethyl 8-bromo-4-(bromomethyl)quinoline-3-carboxylate (1.14 g, 3.06 mmol) in methanol (15 ml) was treated dropwise with sodium methoxide (solution in methanol, 5.4 M) at ambient temperature during which dissolution occurred and later a solid precipitated. After 1.5 h THF (5 ml) and water (3 ml) were added and stirring continued over night at ambient temperature. The solution was then diluted with 20 mL of water and the pH was adjusted to 4 by addition of acetic acid (5 M). After concentration in vacuo to remove most of the organic solvents the remaining mixture was distributed between ethyl acetate and water. The aqueous layer was extracted several times with ethyl acetate and the combined organic layers were dried and concentrated in vacuo. This material (363 mg, 91% purity, 37% of theory) was suitable for further use. The aqueous phase war concentrated to a small volume under reduced pressure, diluted with DMSO and purified by prep. HPLC (C18, gradient: 0.1% aq. formic acid/acetonitrile) yielding a second crop (270 mg, 100% purity, 30% of theory).

LC-MS (Method L1): $R_f$=0.69 min; MS (ESIpos): m/z=296 $[M+H]^+$ $^1$H-NMR (500 MHz, DMSO-d6) δ[ppm]: 1.221 (0.47), 3.184 (0.52), 5.199 (16.00), 7.611 (3.54), 7.627 (5.28), 7.643 (3.76), 8.238 (4.81), 8.252 (4.56), 8.351 (4.61), 8.367 (4.38), 9.215 (10.02).

Step 4

8-bromo-N-[(4S)-3,4-dihydro-2H-chromen-4-yl]-4-(methoxymethyl)quinoline-3-carboxamide

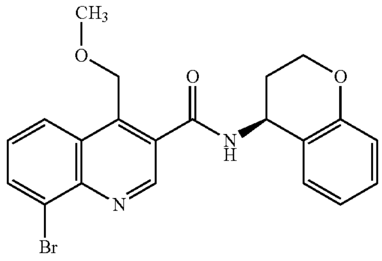 [SMILES: COCc1c(C(=O)N[C@H]2CCOc3ccccc32)cnc2c(Br)cccc12]

A solution of 8-bromo-4-(methoxymethyl)quinoline-3-carboxylic acid (360 mg, 1.22 mmol) in THF (6 ml) was treated with (4S)-chroman-4-amine hydrochloride (1:1) and trimethylamine (680 µl, 4.9 mmol). The mixture was warmed to 45° C., 2,4,6-tripropyl-1,3,5,2,4,6-trioxatriphosphinane 2,4,6-trioxide (solution in ethyl acetate, 23 ml, 50% content, 39 mmol) was added, the heating removed and the mixture stirred at ambient temperature overnight. After dilution with water (pH 8-9) the THF was removed in vacuo. The precipitate was filtered off and dissolved in approx. 10 ml of warm acetone. Warm water was added (10 mL) and the mixture was allowed to cool to RT. The solid was filtered off, washed with acetone/water (1:2) and dried in vacuo.

Yield: 391 mg (95% purity, 72% of th.)

LC-MS (Method L1): $R_f$=0.96 min; MS (ESIpos): m/z=427 $[M+H]^+$ $^1$H-NMR (600 MHz, DMSO-d6) δ[ppm]: 1.235 (0.52), 2.090 (2.20), 2.230 (2.15), 3.287 (16.00), 4.241 (2.66), 4.293 (2.83), 4.998 (8.92), 5.314 (2.68), 6.800 (2.83), 6.811 (3.13), 6.943 (3.04), 7.183 (3.03), 7.397 (3.01), 7.612 (3.03), 8.211 (2.99), 8.221 (3.08), 8.311 (2.87), 8.324 (2.94), 8.998 (4.49), 9.207 (2.80).

Step 5

N-[(4S)-3,4-dihydro-2H-chromen-4-yl]-4-(methoxymethyl)-8-(2,3,5-trifluorophenyl)quinoline-3-carboxamide (Example 686)

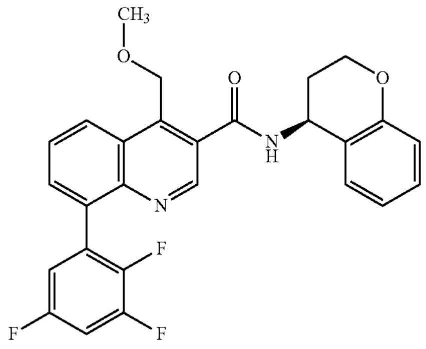 [SMILES: COCc1c(C(=O)N[C@H]2CCOc3ccccc32)cnc2c(-c3cc(F)cc(F)c3F)cccc12]

Under argon a vessel was charged with 8-bromo-N-[(4S)-3,4-dihydro-2H-chromen-4-yl]-4-(methoxymethyl)quinoline-3-carboxamide (90 mg, 211 µmol), 2,3,5-trifluorobenzene boronic acid (55.6 mg, 316 µmol), 1,1'-bis(diphenylphosphino)ferrocene-palladium(II)dichloride dichloromethane complex (8.60 mg, 10.5 µmol), potassium carbonate (58.2 mg, 421 µmol) and with a degassed 5:1 mixture of dioxan and water (0.73 ml). The mixture was stirred overnight at 70° C. It was diluted with ethyl acetate, filtered through a sodium sulfate plug and concentrated in vacuo. The crude was purified by prep. HPLC (C18, gradient: 0.1% aq. formic acid/acetonitrile.

Yield: 31 mg (31% of th.)

LC-MS (Method L1): $R_f$=1.14 min; MS (ESIpos): m/z=479 $[M+H]^+$ $^1$H-NMR (600 MHz, DMSO-d6) δ[ppm]: 0.005 (1.04), 2.043 (0.47), 2.048 (0.60), 2.053 (0.96), 2.058 (1.04), 2.065 (1.12), 2.069 (1.07), 2.077 (1.37), 2.081 (1.20), 2.087 (2.11), 2.092 (0.63), 2.193 (0.58), 2.199 (0.86), 2.202 (0.81), 2.207 (1.32), 2.213 (0.97), 2.216 (1.31), 2.221 (1.32), 2.230 (0.99), 2.236 (0.64), 2.239 (0.62), 2.244 (0.46), 2.793 (0.55), 3.345 (8.00), 4.220 (0.71), 4.225 (0.87), 4.234 (0.90), 4.239 (2.32), 4.244 (1.61), 4.253 (1.77), 4.258 (1.47), 4.268 (1.42), 4.273 (1.80), 4.279 (1.58), 4.285 (1.91), 4.292 (0.78), 4.298 (0.84), 4.303 (0.65), 5.037 (16.00), 5.287 (0.91), 5.297 (1.95), 5.310 (1.96), 5.320 (0.92), 6.790 (3.66), 6.791 (3.76), 6.803 (4.00), 6.804 (3.99), 6.917 (1.85), 6.918 (1.84), 6.929 (3.75), 6.931 (3.68), 6.942 (2.14), 6.943 (2.05), 7.159 (1.78), 7.161 (1.80), 7.173 (3.01), 7.184 (1.56), 7.187 (1.49), 7.259 (1.51), 7.267 (1.49), 7.274 (1.49), 7.376 (3.08), 7.388 (2.95), 7.609 (0.49), 7.614 (0.63), 7.619 (0.75), 7.624 (1.18), 7.628 (1.14), 7.633 (1.23), 7.638 (1.18), 7.642 (1.18), 7.646 (0.74), 7.651 (0.65), 7.657 (0.56), 7.800 (2.66), 7.812 (3.85), 7.814 (3.18), 7.826 (3.61), 7.873 (4.17), 7.875 (4.29), 7.885 (3.06), 7.887 (2.94), 8.416 (3.61), 8.418 (3.65), 8.430 (3.48), 8.432 (3.27), 8.890 (12.74), 9.184 (3.52), 9.197 (3.43).

Synthesis of N-[(4S)-3,4-dihydro-2H-chromen-4-yl]-4-(oxetan-3-yl)-8-(2,3,5-trifluorophenyl)quinoline-3-carboxamide (Example 660)

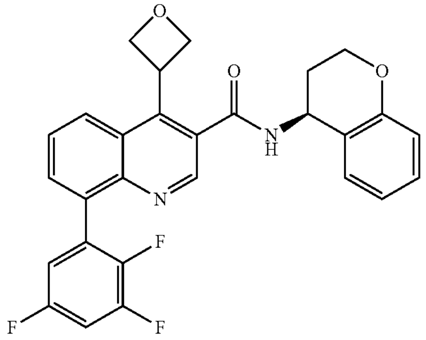 [SMILES: O=C(N[C@H]1CCOc2ccccc21)c1cnc2c(-c3cc(F)cc(F)c3F)cccc2c1C1COC1]

In a 100 mL round bottom flask, a mixture of 4-chloro-N-[(4S)-3,4-dihydro-2H-chromen-4-yl]-8-(2,3,5-trifluorophenyl)quinoline-3-carboxamide (500 mg, 1.066 mmol), anhydrous lithium hydroxide (51 mg, 2.133 mmol), 3-bromooxetane (0.133 mL, 1.600 mmol), [4,4'-bis(1,1-dimethylethyl)-2,2'-bipyridine-N1,N1']bis[3,5-difluoro-2-[5-(trifluoromethyl)-2-pyridinyl-N]phenyl-C] iridium(III) hexafluorophosphate (24 mg, 0.021 mmol) and tris(trimethylsilyl)silane (0.329 mL, 1.066 mmol) in 1,2-dimethoxyethane (20 mL) was degassed by purging with argon. In a 50 mL round bottom flask, a mixture of nickel(II) chloride ethylene glycol dimethyl ether complex (14 mg, 0.064 mmol) and 4,4'-di-tert-butyl-2,2'-bipyridine (17 mg, 0.064 mmol) in 1,2-dimethoxyethane (10 mL) was gently warmed with a heatgun, purged with argon and stirred for five minutes. By syringe half of this nickel-catalyst mixture (5 mL) was added to the reaction mixture. The resulting suspension was purged with argon for five minutes and was subsequently stirred under irradiation with blue LED light for 18 h while cooling with a fan. The reaction mixture was diluted with dichloromethane (30 mL). Water (10 mL) was added and the layers were separated. The aqueous layer was extracted with dichloromethane (2×10 mL). Combined organic layers were dried with sodium sulfate and solvents were removed in vacuo. Purification by flash column chromatography (80 g; heptane, 10%-60% ethyl acetate) and preparative HPLC (Method 11) afforded 0.054 g (0.110 mmol; 10% of theory) of the title compound.

LC-MS (Method 2): $R_f$=3.65 min; m/z=491 $(M+H)^+$ $^1$H-NMR (400 MHz, DMSO-$d_6$) δ 9.26 (d, J=8.1 Hz, 1H), 8.87 (s, 1H), 7.91-7.87 (m, 1H), 7.84-7.73 (m, 2H), 7.70-7.57 (m, 1H), 7.35 (d, J=7.8 Hz, 1H), 7.30-7.23 (m, 1H), 7.19 (t, J=7.8 Hz, 1H), 6.93 (t, J=7.5 Hz, 1H), 6.81 (d, J=8.2 Hz, 1H), 5.31-5.11 (m, 4H), 4.84-4.70 (m, 2H), 4.34-4.21 (m, 2H), 2.25-2.15 (m, 1H), 2.08-2.01 (m, 1H).

TABLE 1

Examples

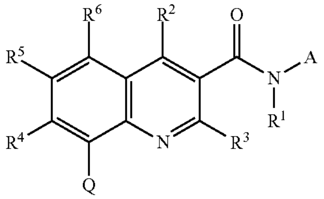

(I)

| Number | R1 | R2 | R3 | R4 | R5 | R6 | Q | A |
|---|---|---|---|---|---|---|---|---|
| 1 | H | chloro | H | H | H | H | 3,5-dimethylphenyl | (1S)-1,2,3,4-tetrahydronaphth-alen-1-yl |
| 2 | H | chloro | H | H | H | H | 3,5-dichlorophenyl | (1S)-1,2,3,4-tetrahydronaphth-alen-1-yl |
| 3 | H | chloro | H | H | H | H | 3,5-dichlorophenyl | (1S)-2,3-dihydro-1H-inden-1-yl |
| 4 | H | chloro | H | H | H | H | 3,5-dichlorophenyl | (4S)-3,4-dihydro-2H-chromen-4-yl |
| 5 | H | chloro | H | H | H | H | 3-chlorophenyl | (4S)-3,4-dihydro-2H-chromen-4-yl |
| 6 | H | chloro | H | H | H | H | 3-chlorophenyl | (1S)-2,3-dihydro-1H-inden-1-yl |
| 7 | H | chloro | H | H | H | H | 2,3-dichlorophenyl | (4S)-3,4-dihydro-2H-chromen-4-yl |
| 8 | H | dimethylamino | H | H | H | H | 3,5-dichlorophenyl | (4S)-3,4-dihydro-2H-chromen-4-yl |
| 9 | H | dimethylamino | H | H | H | H | 3,5-dichlorophenyl | (1S)-2,3-dihydro-1H-inden-1-yl |
| 10 | H | dimethylamino | H | H | H | H | 2-chloro-6-fluorophenyl | (4S)-3,4-dihydro-2H-chromen-4-yl |
| 11 | H | dimethylamino | H | H | methyl | H | 3,5-dichlorophenyl | (1S)-2,3-dihydro-1H-inden-1-yl |
| 12 | H | dimethylamino | H | H | methyl | H | 3,5-dichlorophenyl | (4S)-3,4-dihydro-2H-chromen-4-yl |
| 13 | H | dimethylamino | H | H | H | H | 3,5-dichloro-4-fluorophenyl | (4S)-3,4-dihydro-2H-chromen-4-yl |
| 14 | H | pyrrolidin-1-yl | H | H | H | H | 3,5-dichlorophenyl | (4S)-3,4-dihydro-2H-chromen-4-yl |
| 15 | H | dimethylamino | H | H | H | H | 3,5-dimethylphenyl | (4S)-3,4-dihydro-2H-chromen-4-yl |
| 16 | H | dimethylamino | H | H | H | H | 3,5-dichlorophenyl | (1S)-1,2,3,4-tetrahydronaphth-alen-1-yl |
| 17 | H | morpholin-4-yl | H | H | H | H | 3,5-dichlorophenyl | (4S)-3,4-dihydro-2H-chromen-4-yl |
| 18 | H | dimethylamino | H | methyl | H | H | 3,5-dichlorophenyl | (4S)-3,4-dihydro-2H-chromen-4-yl |
| 19 | H | dimethylamino | H | methyl | H | H | 3,5-dichlorophenyl | (1S)-2,3-dihydro-1H-inden-1-yl |
| 20 | H | morpholin-4-yl | H | H | H | H | 3,5-dichlorophenyl | (1S)-1,2,3,4-tetrahydronaphth-alen-1-yl |
| 21 | H | dimethylamino | H | fluoro | H | H | 3,5-dichlorophenyl | (1S)-2,3-dihydro-1H-inden-1-yl |
| 22 | H | dimethylamino | H | fluoro | H | H | 3,5-dichlorophenyl | (4S)-3,4-dihydro-2H-chromen-4-yl |
| 23 | H | methylamino | H | H | H | H | 3,5-dichloro-4-fluorophenyl | (4S)-3,4-dihydro-2H-chromen-4-yl |
| 24 | H | methylamino | H | H | H | H | 3,5-dichlorophenyl | (4S)-3,4-dihydro-2H-chromen-4-yl |
| 25 | H | morpholin-4-yl | H | H | H | H | 3-chlorophenyl | (4S)-3,4-dihydro-2H-chromen-4-yl |
| 26 | H | 1H-imidazol-1-yl | H | H | H | H | 3,5-dichlorophenyl | (4S)-3,4-dihydro-2H-chromen-4-yl |
| 27 | H | (1S)-2,3-dihydro-1H-inden-1-ylamino | H | H | H | H | 3-chlorophenyl | (1S)-2,3-dihydro-1H-inden-1-yl |
| 28 | H | (1S)-2,3-dihydro-1H-inden-1-ylamino | H | H | H | H | 2,3-dichlorophenyl | (1S)-2,3-dihydro-1H-inden-1-yl |
| 29 | H | dimethylamino | H | H | H | H | 2-chloro-5-fluorophenyl | (4S)-3,4-dihydro-2H-chromen-4-yl |

TABLE 1-continued

Examples

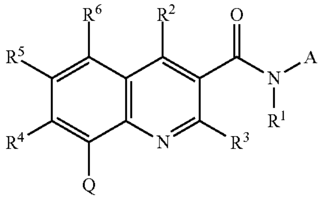

(I)

| Number | R1 | R2 | R3 | R4 | R5 | R6 | Q | A |
|---|---|---|---|---|---|---|---|---|
| 30 | H | dimethylamino | H | H | H | H | 3,4-difluorophenyl | (4S)-3,4-dihydro-2H-chromen-4-yl |
| 31 | H | dimethylamino | H | H | H | H | 4-fluoro-3-methoxyphenyl | (4S)-3,4-dihydro-2H-chromen-4-yl |
| 32 | H | dimethylamino | H | H | H | H | 2,4-difluoro-3-methoxyphenyl | (4S)-3,4-dihydro-2H-chromen-4-yl |
| 33 | H | dimethylamino | H | H | H | H | 3-fluoro-2-methylphenyl | (4S)-3,4-dihydro-2H-chromen-4-yl |
| 34 | H | dimethylamino | H | H | H | H | 2,3-dichlorophenyl | (4S)-3,4-dihydro-2H-chromen-4-yl |
| 35 | H | morpholin-4-yl | H | H | H | H | 3-chlorophenyl | (1S)-2,3-dihydro-1H-inden-1-yl |
| 36 | H | dimethylamino | H | H | H | H | 3-chloro-2-methylphenyl | (4S)-3,4-dihydro-2H-chromen-4-yl |
| 37 | H | dimethylamino | H | H | H | H | 5-chloro-2-fluorophenyl | (4S)-3,4-dihydro-2H-chromen-4-yl |
| 38 | H | dimethylamino | H | H | H | H | 2,4,6-trifluoro-3-methoxyphenyl | (4S)-3,4-dihydro-2H-chromen-4-yl |
| 39 | H | dimethylamino | H | H | H | H | 3-chloro-5-(trifluoromethyl)phenyl | (4S)-3,4-dihydro-2H-chromen-4-yl |
| 40 | H | dimethylamino | H | H | fluoro | H | 3,5-dichlorophenyl | (4S)-3,4-dihydro-2H-chromen-4-yl |
| 41 | H | dimethylamino | H | H | fluoro | H | 3,5-dichloro-4-fluorophenyl | (4S)-3,4-dihydro-2H-chromen-4-yl |
| 42 | H | morpholin-4-yl | H | H | fluoro | H | 3,5-dichlorophenyl | (4S)-3,4-dihydro-2H-chromen-4-yl |
| 43 | H | morpholin-4-yl | H | H | fluoro | H | 3,5-dichloro-4-fluorophenyl | (4S)-3,4-dihydro-2H-chromen-4-yl |
| 44 | H | dimethylamino | H | H | H | H | 3-chloro-5-methylphenyl | (4S)-3,4-dihydro-2H-chromen-4-yl |
| 45 | H | dimethylamino | H | H | H | H | 3-chloro-4-fluorophenyl | (4S)-3,4-dihydro-2H-chromen-4-yl |
| 46 | H | dimethylamino | H | H | H | H | 3-chloro-5-fluorophenyl | (4S)-3,4-dihydro-2H-chromen-4-yl |
| 47 | H | dimethylamino | H | H | H | H | 3,4,5-trifluorophenyl | (4S)-3,4-dihydro-2H-chromen-4-yl |
| 48 | H | dimethylamino | H | H | H | H | 2-fluoro-3-(trifluoromethoxy)yl)phenyl | (4S)-3,4-dihydro-2H-chromen-4-yl |
| 49 | H | dimethylamino | H | H | H | H | 3,5-difluorophenyl | (4S)-3,4-dihydro-2H-chromen-4-yl |
| 50 | H | dimethylamino | H | H | H | H | 2-fluoro-3-(trifluoromethyl)phenyl | (4S)-3,4-dihydro-2H-chromen-4-yl |
| 51 | H | dimethylamino | H | H | H | H | 3-chloro-2-fluorophenyl | (4S)-3,4-dihydro-2H-chromen-4-yl |
| 52 | H | morpholin-4-yl | H | H | H | H | 2,3-dichlorophenyl | (4S)-3,4-dihydro-2H-chromen-4-yl |
| 53 | H | morpholin-4-yl | H | H | H | H | 2,4-difluoro-3-methoxyphenyl | (4S)-3,4-dihydro-2H-chromen-4-yl |
| 54 | H | morpholin-4-yl | H | H | H | H | 3,5-dichloro-4-fluorophenyl | (4S)-3,4-dihydro-2H-chromen-4-yl |
| 55 | H | dimethylamino | H | H | H | H | 3-fluoro-4-methoxyphenyl | (4S)-3,4-dihydro-2H-chromen-4-yl |
| 56 | H | dimethylamino | H | H | H | H | 3-chloro-4-methylphenyl | (4S)-3,4-dihydro-2H-chromen-4-yl |
| 57 | H | dimethylamino | H | H | H | H | 2,4,5-trifluorophenyl | (4S)-3,4-dihydro-2H-chromen-4-yl |
| 58 | H | amino | H | H | H | H | 3,5-dichlorophenyl | (4S)-3,4-dihydro-2H-chromen-4-yl |
| 59 | H | benzyl(methyl)amino | H | H | H | H | 3,5-dichlorophenyl | (4S)-3,4-dihydro-2H-chromen-4-yl |

TABLE 1-continued

Examples

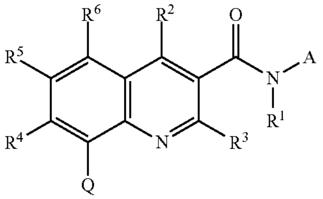

(I)

| Number | R1 | R2 | R3 | R4 | R5 | R6 | Q | A |
|---|---|---|---|---|---|---|---|---|
| 60 | H | dimethylamino | H | H | H | H | 2-chloro-3-fluorophenyl | (4S)-3,4-dihydro-2H-chromen-4-yl |
| 61 | H | dimethylamino | H | H | H | H | 3-fluoro-5-methylphenyl | (4S)-3,4-dihydro-2H-chromen-4-yl |
| 62 | H | dimethylamino | H | H | H | H | 3-fluoropyridin-2-yl | (4S)-3,4-dihydro-2H-chromen-4-yl |
| 63 | H | dimethylamino | H | H | H | H | 2-fluoropyridin-4-yl | (4S)-3,4-dihydro-2H-chromen-4-yl |
| 64 | H | dimethylamino | H | H | H | H | 2-methoxypyridin-4-yl | (4S)-3,4-dihydro-2H-chromen-4-yl |
| 65 | H | dimethylamino | H | H | H | H | 2-chloropyridin-4-yl | (4S)-3,4-dihydro-2H-chromen-4-yl |
| 66 | H | dimethylamino | H | H | H | H | 2,6-dimethylpyridin-4-yl | (4S)-3,4-dihydro-2H-chromen-4-yl |
| 67 | H | diethylamino | H | H | H | H | 3,5-dichlorophenyl | (4S)-3,4-dihydro-2H-chromen-4-yl |
| 68 | H | 4-(trifluoromethyl)-1H-pyrazol-1-yl | H | H | H | H | 3,5-dichlorophenyl | (4S)-3,4-dihydro-2H-chromen-4-yl |
| 69 | H | 1H-pyrazol-4-ylamino | H | H | H | H | 3,5-dichlorophenyl | (1S)-2,3-dihydro-1H-inden-1-yl |
| 70 | H | dimethylamino | H | H | H | H | 3-(dimethylamino)phenyl | (4S)-3,4-dihydro-2H-chromen-4-yl |
| 71 | H | dimethylamino | H | H | H | H | 1-methyl-1H-benzimidazol-6-yl | (4S)-3,4-dihydro-2H-chromen-4-yl |
| 72 | H | 1H-pyrazol-1-yl | H | H | H | H | 3,5-dichlorophenyl | (4S)-3,4-dihydro-2H-chromen-4-yl |
| 73 | H | dimethylamino | H | H | H | H | 1H-indol-4-yl | (4S)-3,4-dihydro-2H-chromen-4-yl |
| 74 | H | (2-hydroxyethyl)amino | H | H | H | H | 3,5-dichlorophenyl | (4S)-3,4-dihydro-2H-chromen-4-yl |
| 75 | H | (2-methoxyethyl)(methyl)amino | H | H | H | H | 3,5-dichlorophenyl | (4S)-3,4-dihydro-2H-chromen-4-yl |
| 76 | H | (2-methoxyethyl)amino | H | H | H | H | 3,5-dichlorophenyl | (4S)-3,4-dihydro-2H-chromen-4-yl |
| 77 | H | 4-oxoimidazolidin-1-yl | H | H | H | H | 3,5-dichlorophenyl | (4S)-3,4-dihydro-2H-chromen-4-yl |
| 78 | H | bis(2-methoxyethyl)amino | H | H | H | H | 3,5-dichlorophenyl | (4S)-3,4-dihydro-2H-chromen-4-yl |
| 79 | H | pyrrolidin-1-yl | H | H | H | H | 3,5-dichlorophenyl | (1S)-2,3-dihydro-1H-inden-1-yl |
| 80 | H | (2S)-2-carboxypyrrolidin-1-yl | H | H | H | H | 3,5-dichlorophenyl | (1S)-2,3-dihydro-1H-inden-1-yl |
| 81 | H | dimethylamino | H | H | H | H | 2,3,4-trifluorophenyl | (4S)-3,4-dihydro-2H-chromen-4-yl |
| 82 | H | morpholin-4-yl | H | H | H | H | 2,3,4-trifluorophenyl | (4S)-3,4-dihydro-2H-chromen-4-yl |
| 83 | H | morpholin-4-yl | H | H | H | H | 2-fluoro-3-(trifluoromethoxy)phenyl | (4S)-3,4-dihydro-2H-chromen-4-yl |
| 84 | H | (3R)-3-aminopyrrolidin-1-yl | H | H | H | H | 3,5-dichlorophenyl | (1S)-2,3-dihydro-1H-inden-1-yl |
| 85 | H | 3,4-dihydroisoquinolin-2(1H)-yl | H | H | H | H | 3,5-dichlorophenyl | (1S)-2,3-dihydro-1H-inden-1-yl |
| 86 | H | anilino | H | H | H | H | 3,5-dichlorophenyl | (1S)-2,3-dihydro-1H-inden-1-yl |
| 87 | H | isobutyl(methyl)amino | H | H | H | H | 3,5-dichlorophenyl | (1S)-2,3-dihydro-1H-inden-1-yl |
| 88 | H | [2-(dimethylamino)ethyl]amino | H | H | H | H | 3,5-dichlorophenyl | (1S)-2,3-dihydro-1H-inden-1-yl |

TABLE 1-continued

Examples

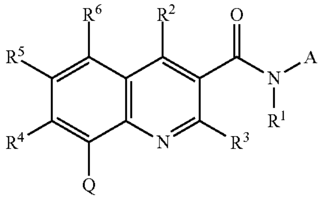

(I)

| Number | R1 | R2 | R3 | R4 | R5 | R6 | Q | A |
|---|---|---|---|---|---|---|---|---|
| 89 | H | (2-methoxyethyl)amino | H | H | H | H | 3,5-dichlorophenyl | (1S)-2,3-dihydro-1H-inden-1-yl |
| 90 | H | ethyl(2-methoxyethyl)amino | H | H | H | H | 3,5-dichlorophenyl | (1S)-2,3-dihydro-1H-inden-1-yl |
| 91 | H | (2S)-2-(methoxymethyl)pyrrolidin-1-yl | H | H | H | H | 3,5-dichlorophenyl | (1S)-2,3-dihydro-1H-inden-1-yl |
| 92 | H | (2R)-2-(methoxymethyl)pyrrolidin-1-yl | H | H | H | H | 3,5-dichlorophenyl | (1S)-2,3-dihydro-1H-inden-1-yl |
| 93 | H | bis(2-methoxyethyl)amino | H | H | H | H | 3,5-dichlorophenyl | (1S)-2,3-dihydro-1H-inden-1-yl |
| 94 | H | (3S)-3-(dimethylamino)pyrrolidin-1-yl | H | H | H | H | 3,5-dichlorophenyl | (1S)-2,3-dihydro-1H-inden-1-yl |
| 95 | H | tetrahydro-2H-pyran-4-ylamino | H | H | H | H | 3,5-dichlorophenyl | (1S)-2,3-dihydro-1H-inden-1-yl |
| 96 | H | [2-(pyrrolidin-1-yl)ethyl]amino | H | H | H | H | 3,5-dichlorophenyl | (1S)-2,3-dihydro-1H-inden-1-yl |
| 97 | H | (3,3,3-trifluoropropyl)amino | H | H | H | H | 3,5-dichlorophenyl | (1S)-2,3-dihydro-1H-inden-1-yl |
| 98 | H | morpholin-4-ylamino | H | H | H | H | 3,5-dichlorophenyl | (1S)-2,3-dihydro-1H-inden-1-yl |
| 99-1 | H | (pyridin-2-ylmethyl)amino) | H | H | H | H | 3,5-dichlorophenyl | (1S)-2,3-dihydro-1H-inden-1-yl |
| 99-2 | H | [(2R)-1-hydroxybutan-2-yl]amino | H | H | H | H | 3,5-dichlorophenyl | (1S)-2,3-dihydro-1H-inden-1-yl |
| 100 | H | (2-hydroxyethyl)amino | H | H | H | H | 3,5-dichlorophenyl | (1S)-2,3-dihydro-1H-inden-1-yl |
| 101 | H | (3R)-3-hydroxypyrrolidin-1-yl | H | H | H | H | 3,5-dichlorophenyl | (1S)-2,3-dihydro-1H-inden-1-yl |
| 102 | H | 3-hydroxyazetidin-1-yl | H | H | H | H | 3,5-dichlorophenyl | (1S)-2,3-dihydro-1H-inden-1-yl |
| 103 | H | 3-(pyrrolidin-1-yl)azetidin-1-yl | H | H | H | H | 3,5-dichlorophenyl | (1S)-2,3-dihydro-1H-inden-1-yl |
| 104 | H | cyclopropyl(ethyl)amino | H | H | H | H | 3,5-dichlorophenyl | (1S)-2,3-dihydro-1H-inden-1-yl |
| 105 | H | cyclobutyl(methyl)amino | H | H | H | H | 3,5-dichlorophenyl | (1S)-2,3-dihydro-1H-inden-1-yl |
| 106 | H | (cyclopropylmethyl)(methyl)amino | H | H | H | H | 3,5-dichlorophenyl | (1S)-2,3-dihydro-1H-inden-1-yl |
| 107 | H | 2,2-dimethylmorpholin-4-yl | H | H | H | H | 3,5-dichlorophenyl | (1S)-2,3-dihydro-1H-inden-1-yl |
| 108 | H | 1,2-oxazolidin-2-yl | H | H | H | H | 3,5-dichlorophenyl | (1S)-2,3-dihydro-1H-inden-1-yl |
| 109 | H | (2S)-2-methyl-2,3-dihydro-1H-indol-1-yl | H | H | H | H | 3,5-dichlorophenyl | (1S)-2,3-dihydro-1H-inden-1-yl |
| 110 | H | methyl(2,2,2-trifluoroethyl)amino | H | H | H | H | 3,5-dichlorophenyl | (1S)-2,3-dihydro-1H-inden-1-yl |
| 111 | H | 1,3-dihydro-2H-isoindol-2-yl | H | H | H | H | 3,5-dichlorophenyl | (1S)-2,3-dihydro-1H-inden-1-yl |
| 112 | H | 3,3-difluoropyrrolidin-1-yl | H | H | H | H | 3,5-dichlorophenyl | (1S)-2,3-dihydro-1H-inden-1-yl |
| 113 | H | (2S)-2-carbamoylpyrrolidin-1-yl | H | H | H | H | 3,5-dichlorophenyl | (1S)-2,3-dihydro-1H-inden-1-yl |
| 114 | H | methyl(1-phenylethyl)amino | H | H | H | H | 3,5-dichlorophenyl | (1S)-2,3-dihydro-1H-inden-1-yl |
| 115 | H | (3-amino-3-oxopropyl)(methyl)amino | H | H | H | H | 3,5-dichlorophenyl | (1S)-2,3-dihydro-1H-inden-1-yl |
| 116 | H | 4-acetylpiperazin-1-yl | H | H | H | H | 3,5-dichlorophenyl | (1S)-2,3-dihydro-1H-inden-1-yl |
| 117 | H | 1,1-dioxidothiomorpholin-4-yl | H | H | H | H | 3,5-dichlorophenyl | (1S)-2,3-dihydro-1H-inden-1-yl |

TABLE 1-continued

Examples

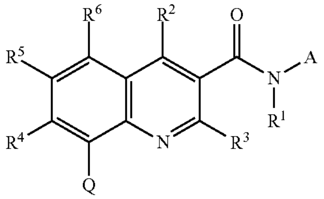

(I)

| Number | R1 | R2 | R3 | R4 | R5 | R6 | Q | A |
|---|---|---|---|---|---|---|---|---|
| 118 | H | benzyl(methyl)amino | H | H | H | H | 3,5-dichlorophenyl | (1S)-2,3-dihydro 1H-inden-1-yl |
| 119 | H | 3-fluoroazetidin-1-yl | H | H | H | H | 3,5-dichlorophenyl | (1S)-2,3-dihydro-1H-inden-1-yl |
| 120 | H | 3-methylazetidin-1-yl | H | H | H | H | 3,5-dichlorophenyl | (1S)-2,3-dihydro-1H-inden-1-yl |
| 121 | H | 3,3-difluoroazetidin-1-yl | H | H | H | H | 3,5-dichlorophenyl | (1S)-2,3-dihydro-1H-inden-1-yl |
| 122 | H | [3-(dimethylamino)-3-oxopropyl]amino | H | H | H | H | 3,5-dichlorophenyl | (1S)-2,3-dihydro-1H-inden-1-yl |
| 123 | H | [(5-methyl-1,2,4-oxadiazol-3-yl)methyl]amino | H | H | H | H | 3,5-dichlorophenyl | (1S)-2,3-dihydro-1H-inden-1-yl |
| 124 | H | (3-amino-3-oxopropyl)amino | H | H | H | H | 3,5-dichlorophenyl | (1S)-2,3-dihydro-1H-inden-1-yl |
| 125 | H | [2-(1H-pyrazol-1-yl)ethyl]amino | H | H | H | H | 3,5-dichlorophenyl | (1S)-2,3-dihydro 1H-inden-1-yl |
| 126 | H | (2-acetamidoethyl)amino | H | H | H | H | 3,5-dichlorophenyl | (1S)-2,3-dihydro-1H-inden-1-yl |
| 127 | H | [(2S)-1-amino-1-oxopropan-2-yl]amino | H | H | H | H | 3,5-dichlorophenyl | (1S)-2,3-dihydro-1H-inden-1-yl |
| 128 | H | (2-methoxy-2-oxoethyl)amino | H | H | H | H | 3,5-dichlorophenyl | (1S)-2,3-dihydro-1H-inden-1-yl |
| 129 | H | (2-amino-2-oxoethyl)amino | H | H | H | H | 3,5-dichlorophenyl | (1S)-2,3-dihydro 1H-inden-1-yl |
| 130 | H | dimethylamino | H | H | H | H | 3-chlorophenyl | (4S)-3,4-dihydro-2H-chromen-4-yl |
| 131 | H | methoxyamino | H | H | H | H | 3,5-dichlorophenyl | (4S)-3,4-dihydro-2H-chromen-4-yl |
| 132 | H | dimethylamino | H | H | H | H | 2,3,5-trichlorophenyl | (4S)-3,4-dihydro-2H-chromen-4-yl |
| 133 | H | morpholin-4-yl | H | H | H | H | 2,3,5-trichlorophenyl | (4S)-3,4-dihydro-2H-chromen-4-yl |
| 134 | H | methylamino | H | H | H | H | 3,5-dichlorophenyl | (4S)-3,4-dihydro-2H-chromen-4-yl |
| 135 | H | azetidin-1-yl | H | H | H | H | 3,5-dichlorophenyl | (4S)-3,4-dihydro-2H-chromen-4-yl |
| 136 | H | pyridin-4-ylamino | H | H | H | H | 3,5-dichlorophenyl | (4S)-3,4-dihydro-2H-chromen-4-yl |
| 137 | H | (2-ethoxy-2-oxoethyl)(methyl)amino | H | H | H | H | 3,5-dichlorophenyl | (4S)-3,4-dihydro-2H-chromen-4-yl |
| 138 | H | (2-hydroxyethyl)(methyl)amino | H | H | H | H | 3,5-dichlorophenyl | (4S)-3,4-dihydro-2H-chromen-4-yl |
| 139 | H | dimethylamino | H | fluoro | H | H | 3,4-dichlorophenyl | (4S)-3,4-dihydro-2H-chromen-4-yl |
| 140 | H | dimethylamino | H | fluoro | H | H | 3,4-difluorophenyl | (4S)-3,4-dihydro-2H-chromen-4-yl |
| 141 | H | dimethylamino | H | fluoro | H | H | 3-chlorophenyl | (4S)-3,4-dihydro-2H-chromen-4-yl |
| 142 | H | morpholin-4-yl | H | fluoro | H | H | 3,5-difluorophenyl | (4S)-3,4-dihydro-2H-chromen-4-yl |
| 143 | H | morpholin-4-yl | H | fluoro | H | H | 3-chloro-5-fluorophenyl | (4S)-3,4-dihydro-2H-chromen-4-yl |
| 144 | H | morpholin-4-yl | H | H | fluoro | H | 3,4-dichlorophenyl | (4S)-3,4-dihydro-2H-chromen-4-yl |
| 145 | H | dimethylamino | H | H | fluoro | H | 3,4-dichlorophenyl | (4S)-3,4-dihydro-2H-chromen-4-yl |
| 146 | H | dimethylamino | H | H | fluoro | H | 2,3-dichlorophenyl | (4S)-3,4-dihydro-2H-chromen-4-yl |
| 147 | H | dimethylamino | H | H | H | H | 3,5-dichlorophenyl | (4S)-6-methoxy-3,4-dihydro-2H-chromen-4-yl |
| 148 | H | dimethylamino | H | H | H | H | 3,5-dichlorophenyl | (1S)-5-methoxy-2,3-dihydro-1H-inden-1-yl |

TABLE 1-continued

Examples (I)

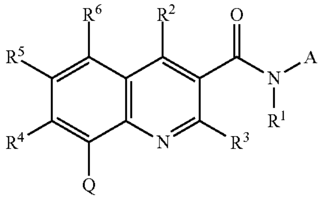

| Number | R1 | R2 | R3 | R4 | R5 | R6 | Q | A |
|---|---|---|---|---|---|---|---|---|
| 149 | H | methyl[2-(morpholin-4-yl)ethyl]amino | H | H | H | H | 3,5-dichlorophenyl | (4S)-3,4-dihydro-2H-chromen-4-yl |
| 150 | H | (carboxymethyl)(methyl) amino | H | H | H | H | 3,5-dichlorophenyl | (4S)-3,4-dihydro-2H-chromen-4-yl |
| 151 | H | dimethylamino | H | H | H | H | 3-(dimethylamino)-2,4-difluorophenyl | (4S)-3,4-dihydro-2H-chromen-4-yl |
| 152 | H | dimethylamino | H | H | H | H | 3,5-dichlorophenyl | (4S)-7-fluoro-3,4-dihydro-2H-chromen-4-yl |
| 153 | H | ethylamino | H | H | H | H | 3,5-dichlorophenyl | (4S)-3,4-dihydro-2H-chromen-4-yl |
| 154 | H | 2-acetylhydrazino | H | H | H | H | 3,5-dichlorophenyl | (4S)-3,4-dihydro-2H-chromen-4-yl |
| 155 | H | morpholin-4-yl | H | fluoro | H | H | 3-chloro-2-fluorophenyl | (4S)-3,4-dihydro-2H-chromen-4-yl |
| 156 | H | morpholin-4-yl | H | fluoro | H | H | 3,4-dichlorophenyl | (4S)-3,4-dihydro-2H-chromen-4-yl |
| 157 | H | morpholin-4-yl | H | fluoro | H | H | 3,4-difluorophenyl | (4S)-3,4-dihydro-2H-chromen-4-yl |
| 158 | H | morpholin-4-yl | H | H | fluoro | H | 3,4-difluorophenyl | (4S)-3,4-dihydro-2H-chromen-4-yl |
| 159 | H | morpholin-4-yl | H | H | fluoro | H | 3-chlorophenyl | (4S)-3,4-dihydro-2H-chromen-4-yl |
| 160 | H | morpholin-4-yl | H | H | fluoro | H | 3-chloro-2-fluorophenyl | (4S)-3,4-dihydro-2H-chromen-4-yl |
| 161 | H | morpholin-4-yl | H | H | fluoro | H | 2-chloro-3-fluorophenyl | (4S)-3,4-dihydro-2H-chromen-4-yl |
| 162 | H | morpholin-4-yl | H | H | fluoro | H | 3,5-difluorophenyl | (4S)-3,4-dihydro-2H-chromen-4-yl |
| 163 | H | morpholin-4-yl | H | H | fluoro | H | 3-chloro-5-fluorophenyl | (4S)-3,4-dihydro-2H-chromen-4-yl |
| 164 | H | morpholin-4-yl | H | H | fluoro | H | 5-chloro-2-fluorophenyl | (4S)-3,4-dihydro-2H-chromen-4-yl |
| 165 | H | morpholin-4-yl | H | H | fluoro | H | 2-chloro-4-fluorophenyl | (4S)-3,4-dihydro-2H-chromen-4-yl |
| 166 | H | morpholin-4-yl | H | H | fluoro | H | 2,3-dichlorophenyl | (4S)-3,4-dihydro-2H-chromen-4-yl |
| 167 | H | morpholin-4-yl | H | fluoro | H | H | 3-chlorophenyl | (4S)-3,4-dihydro-2H-chromen-4-yl |
| 168 | H | dimethylamino | H | fluoro | H | H | 3,5-difluorophenyl | (4S)-3,4-dihydro-2H-chromen-4-yl |
| 169 | H | dimethylamino | H | fluoro | H | H | 3-chloro-5-fluorophenyl | (4S)-3,4-dihydro-2H-chromen-4-yl |
| 170 | H | morpholin-4-yl | H | fluoro | H | H | 5-chloro-2-fluorophenyl | (4S)-3,4-dihydro-2H-chromen-4-yl |
| 171 | H | dimethylamino | H | fluoro | H | H | 3-chloro-2-fluorophenyl | (4S)-3,4-dihydro-2H-chromen-4-yl |
| 172 | H | dimethylamino | H | fluoro | H | H | 2-chloro-4-fluorophenyl | (4S)-3,4-dihydro-2H-chromen-4-yl |
| 173 | H | dimethylamino | H | H | fluoro | H | 3,4-difluorophenyl | (4S)-3,4-dihydro-2H-chromen-4-yl |
| 174 | H | dimethylamino | H | H | fluoro | H | 3-chlorophenyl | (4S)-3,4-dihydro-2H-chromen-4-yl |
| 175 | H | dimethylamino | H | H | fluoro | H | 3-chloro-2-fluorophenyl | (4S)-3,4-dihydro-2H-chromen-4-yl |
| 176 | H | dimethylamino | H | H | fluoro | H | 2-chloro-3-fluorophenyl | (4S)-3,4-dihydro-2H-chromen-4-yl |
| 177 | H | dimethylamino | H | H | fluoro | H | 3,5-difluorophenyl | (4S)-3,4-dihydro-2H-chromen-4-yl |
| 178 | H | dimethylamino | H | H | fluoro | H | 3-chloro-5-fluorophenyl | (4S)-3,4-dihydro-2H-chromen-4-yl |

TABLE 1-continued

Examples (I)

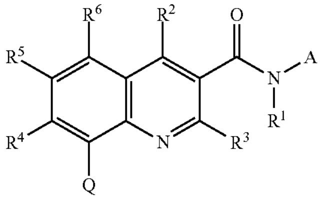

| Number | R1 | R2 | R3 | R4 | R5 | R6 | Q | A |
|---|---|---|---|---|---|---|---|---|
| 179 | H | dimethylamino | H | H | fluoro | H | 5-chloro-2-fluorophenyl | (4S)-3,4-dihydro-2H-chromen-4-yl |
| 180 | H | dimethylamino | H | H | fluoro | H | 2-chloro-4-fluorophenyl | (4S)-3,4-dihydro-2H-chromen-4-yl |
| 181 | H | thiomorpholin-4-yl | H | H | H | H | 3,5-dichlorophenyl | (4S)-3,4-dihydro-2H-chromen-4-yl |
| 182 | H | (2-tert-butoxy-2-oxoethyl)amino | H | H | H | H | 3,5-dichlorophenyl | (4S)-3,4-dihydro-2H-chromen-4-yl |
| 183 | H | (2-tert-butoxy-2-oxoethyl)(methyl)amino | H | H | H | H | 3,5-dichlorophenyl | (4S)-3,4-dihydro-2H-chromen-4-yl |
| 184 | H | propylamino | H | H | H | H | 3,5-dichlorophenyl | (4S)-3,4-dihydro-2H-chromen-4-yl |
| 185 | H | (2-aminoethyl)amino | H | H | H | H | 3,5-dichlorophenyl | (4S)-3,4-dihydro-2H-chromen-4-yl |
| 186 | H | (3R)-3-hydroxypyrrolidin-1-yl | H | H | H | H | 3,5-dichlorophenyl | (4S)-3,4-dihydro-2H-chromen-4-yl |
| 187 | H | (3S)-3-hydroxypyrrolidin-1-yl | H | H | H | H | 3,5-dichlorophenyl | (4S)-3,4-dihydro-2H-chromen-4-yl |
| 188 | H | 1H-1,2,3-triazol-1-yl | H | H | H | H | 3,5-dichlorophenyl | (4S)-3,4-dihydro 2H-chromen-4-yl |
| 189 | H | 2H-1,2,3-triazol-2-yl | H | H | H | H | 3,5-dichlorophenyl | (4S)-3,4-dihydro-2H-chromen-4-yl |
| 190 | H | morpholin-4-yl | H | H | H | H | 3-chloro-4-fluorophenyl | (4S)-3,4-dihydro-2H-chromen-4-yl |
| 191 | H | morpholin-4-yl | H | H | H | H | 5-chloro-2,4-difluorophenyl | (4S)-3,4-dihydro-2H-chromen-4-yl |
| 192 | H | morpholin-4-yl | H | fluoro | H | H | 3,5-dichlorophenyl | (4S)-3,4-dihydro-2H-chromen-4-yl |
| 193 | H | (3rac)-3-hydroxypyrrolidin-1-yl | H | H | H | H | 3,5-dichloro-4-fluorophenyl | (4S)-3,4-dihydro-2H-chromen-4-yl |
| 194 | H | (3rac)-3-hydroxypyrrolidin-1-yl | H | H | H | H | 2,3-dichlorophenyl | (4S)-3,4-dihydro-2H-chromen-4-yl |
| 195 | H | (3rac)-3-hydroxypyrrolidin-1-yl | H | H | H | H | 5-chloro-2,4-difluorophenyl | (4S)-3,4-dihydro-2H-chromen-4-yl |
| 196 | H | (3rac)-3-hydroxypyrrolidin-1-yl | H | H | H | H | 3-chloro-4-fluorophenyl | (4S)-3,4-dihydro-2H-chromen-4-yl |
| 197 | H | dimethylamino | H | H | H | H | 5-chloro-2,4-difluorophenyl | (4S)-3,4-dihydro-2H-chromen-4-yl |
| 198 | methyl | dimethylamino | H | H | H | H | 3,5-dichlorophenyl | (4S)-3,4-dihydro-2H-chromen-4-yl |
| 199 | H | methyl(phenyl)amino | H | H | H | H | 3,5-dichlorophenyl | (4S)-3,4-dihydro-2H-chromen-4-yl |
| 200 | H | morpholin-4-yl | H | fluoro | H | H | 2,3-dichlorophenyl | (4S)-3,4-dihydro-2H-chromen-4-yl |
| 201 | H | 3,3-difluoropyrrolidin-1-yl | H | H | H | H | 3,5-dichlorophenyl | (4S)-3,4-dihydro-2H-chromen-4-yl |
| 202 | H | 3-oxopyrazolidin-1-yl | H | H | H | H | 3,5-dichlorophenyl | (4S)-3,4-dihydro-2H-chromen-4-yl |
| 203 | H | 1,1-dioxidothiomorpholin-4-yl | H | H | H | H | 3,5-dichlorophenyl | (4S)-3,4-dihydro-2H-chromen-4-yl |
| 204 | H | morpholin-4-yl | H | H | H | H | 2,3-dihydro-1-benzofuran-7-yl | (4S)-3,4-dihydro-2H-chromen-4-yl |
| 205 | H | morpholin-4-yl | H | chloro | H | H | 2,3-dichlorophenyl | (4S)-3,4-dihydro-2H-chromen-4-yl |
| 206 | H | morpholin-4-yl | H | chloro | H | H | 3,5-dichlorophenyl | (4S)-3,4-dihydro-2H-chromen-4-yl |
| 207 | H | dimethylamino | H | chloro | H | H | 2,3-dichlorophenyl | (4S)-3,4-dihydro-2H-chromen-4-yl |
| 208 | H | dimethylamino | H | chloro | H | H | 3,5-dichlorophenyl | (4S)-3,4-dihydro-2H-chromen-4-yl |
| 209 | H | morpholin-4-yl | H | H | H | fluoro | 2,3-dichlorophenyl | (4S)-3,4-dihydro-2H-chromen-4-yl |
| 210 | H | morpholin-4-yl | H | H | H | fluoro | 3,5-dichlorophenyl | (4S)-3,4-dihydro-2H-chromen-4-yl |

TABLE 1-continued

Examples

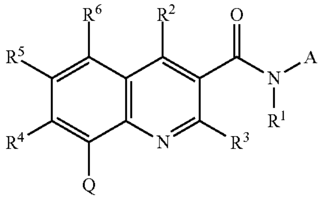

(I)

| Number | R1 | R2 | R3 | R4 | R5 | R6 | Q | A |
|---|---|---|---|---|---|---|---|---|
| 211 | H | morpholin-4-yl | H | H | chloro | H | 3,5-dichlorophenyl | (4S)-3,4-dihydro-2H-chromen-4-yl |
| 212 | H | morpholin-4-yl | H | H | chloro | H | 2,3-dichlorophenyl | (4S)-3,4-dihydro-2H-chromen-4-yl |
| 213 | H | dimethylamino | H | H | chloro | H | 2,3-dichlorophenyl | (4S)-3,4-dihydro-2H-chromen-4-yl |
| 214 | H | morpholin-4-yl | H | H | H | methyl | 2,3-dichlorophenyl | (4S)-3,4-dihydro-2H-chromen-4-yl |
| 215 | H | morpholin-4-yl | H | H | H | methyl | 3,5-dichlorophenyl | (4S)-3,4-dihydro-2H-chromen-4-yl |
| 216 | H | morpholin-4-yl | H | H | H | H | 5-(methoxycarbonyl)-1,3-benzoxazol-7-yl | (4S)-3,4-dihydro-2H-chromen-4-yl |
| 217 | H | dimethylamino | H | H | H | methyl | 3,5-dichlorophenyl | (4S)-3,4-dihydro-2H-chromen-4-yl |
| 218 | H | dimethylamino | H | H | H | methyl | 2,3-dichlorophenyl | (4S)-3,4-dihydro-2H-chromen-4-yl |
| 219 | H | dimethylamino | H | H | H | H | 2,4-difluoro-3-hydroxyphenyl | (4S)-3,4-dihydro-2H-chromen-4-yl |
| 220 | H | morpholin-4-yl | H | H | H | H | 3-fluoro-2-methylphenyl | (4S)-3,4-dihydro-2H-chromen-4-yl |
| 221 | H | morpholin-4-yl | H | H | H | H | 5-chloro-2-fluorophenyl | (4S)-3,4-dihydro-2H-chromen-4-yl |
| 222 | H | morpholin-4-yl | H | H | H | H | 2,3,5-trifluorophenyl | (4S)-3,4-dihydro-2H-chromen-4-yl |
| 223 | H | (3rac)-3-hydroxypyrrolidin-1-yl | H | H | H | H | 5-chloro-2-fluorophenyl | (4S)-3,4-dihydro-2H-chromen-4-yl |
| 224 | H | morpholin-4-yl | H | H | H | H | 1,3-benzothiazol-4-yl | (4S)-3,4-dihydro-2H-chromen-4-yl |
| 225 | H | morpholin-4-yl | H | H | H | H | 3-fluoro-5-methylphenyl | (4S)-3,4-dihydro-2H-chromen-4-yl |
| 226 | H | morpholin-4-yl | H | H | H | H | 3-chloro-2-fluorophenyl | (4S)-3,4-dihydro-2H-chromen-4-yl |
| 227 | H | morpholin-4-yl | H | H | H | H | 2-chloro-5-fluorophenyl | (4S)-3,4-dihydro-2H-chromen-4-yl |
| 228 | H | morpholin-4-yl | H | H | H | H | 3-chloro-5-methoxyphenyl | (4S)-3,4-dihydro-2H-chromen-4-yl |
| 229 | H | methylamino | H | H | H | H | 3-chlorophenyl | (4S)-3,4-dihydro-2H-chromen-4-yl |
| 230 | H | morpholin-4-yl | H | H | H | H | 2,5-difluoro-4-methoxyphenyl | (4S)-3,4-dihydro-2H-chromen-4-yl |
| 231 | H | morpholin-4-yl | H | H | H | H | 5-chloro-2-fluoro-4-methylphenyl | (4S)-3,4-dihydro-2H-chromen-4-yl |
| 232 | H | morpholin-4-yl | H | H | H | H | 3,4-difluoro-2-methoxyphenyl | (4S)-3,4-dihydro-2H-chromen-4-yl |
| 233 | H | morpholin-4-yl | H | trifluoromethyl | H | H | 3,5-dichlorophenyl | (4S)-3,4-dihydro-2H-chromen-4-yl |
| 234 | H | morpholin-4-yl | H | H | H | H | 3,5-difluorophenyl | (4S)-3,4-dihydro-2H-chromen-4-yl |
| 235 | H | morpholin-4-yl | H | H | H | H | 3-chloro-5-(trifluoromethyl)phenyl | (4S)-3,4-dihydro-2H-chromen-4-yl |
| 236 | H | methylamino | H | H | H | H | 3-chloro-2-fluorophenyl | (4S)-3,4-dihydro-2H-chromen-4-yl |
| 237 | H | methylamino | H | H | H | H | 2,3,5-trichlorophenyl | (4S)-3,4-dihydro-2H-chromen-4-yl |
| 238 | H | morpholin-4-yl | H | H | H | H | 2-chloro-3-fluorophenyl | (4S)-3,4-dihydro-2H-chromen-4-yl |
| 239 | H | morpholin-4-yl | H | H | H | H | 5-chloro-2-fluoro-3-methylphenyl | (4S)-3,4-dihydro-2H-chromen-4-yl |

TABLE 1-continued

Examples

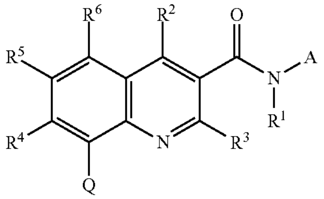

(I)

| Number | R1 | R2 | R3 | R4 | R5 | R6 | Q | A |
|---|---|---|---|---|---|---|---|---|
| 240 | H | morpholin-4-yl | H | H | H | H | 3-chloro-2-fluoro-5-methylphenyl | (4S)-3,4-dihydro-2H-chromen-4-yl |
| 241 | H | (2S)-2-(tert-butoxycarbonyl)pyrrolidin-1-yl | H | H | H | H | 3,5-dichlorophenyl | (1S)-2,3-dihydro-1H-inden-1-yl |
| 242 | H | (2S)-2-(tert-butoxycarbonyl)pyrrolidin-1-yl | H | H | H | H | 3,5-dichlorophenyl | (4S)-3,4-dihydro-2H-chromen-4-yl |
| 243 | H | (2R)-2-(tert-butoxycarbonyl)pyrrolidin-1-yl | H | H | H | H | 3,5-dichlorophenyl | (4S)-3,4-dihydro-2H-chromen-4-yl |
| 244 | H | (3rac)-3-hydroxypyrrolidin-1-yl | H | H | H | H | 3-fluoro-5-methylphenyl | (4S)-3,4-dihydro-2H-chromen-4-yl |
| 245 | H | (3rrac)-3-hydroxypyrrolidin-1-yl | H | H | H | H | 3,4-difluoro-2-methoxyphenyl | (4S)-3,4-dihydro-2H-chromen-4-yl |
| 246 | H | (3rac)-3-hydroxypyrrolidin-1-yl | H | H | H | H | 2,5-difluoro-4-methoxyphenyl | (4S)-3,4-dihydro-2H-chromen-4-yl |
| 247 | H | dimethylamino | H | H | H | H | 2,3,6-trifluorophenyl | (4S)-3,4-dihydro-2H-chromen-4-yl |
| 248 | H | methoxy(methyl)amino | H | H | H | H | 2-chlorophenyl | (4S)-3,4-dihydro-2H-chromen-4-yl |
| 249 | H | methoxy(methyl)amino | H | H | H | H | 2,3-dichlorophenyl | (4S)-3,4-dihydro-2H-chromen-4-yl |
| 250 | H | methoxy(methyl)amino | H | H | H | H | 3,5-dichlorophenyl | (4S)-3,4-dihydro-2H-chromen-4-yl |
| 251 | H | morpholin-4-yl | H | H | H | H | 1,3-benzothiazol-7-yl | (4S)-3,4-dihydro-2H-chromen-4-yl |
| 252 | H | cyclopropyl(methyl)amino | H | H | H | H | 2-chlorophenyl | (4S)-3,4-dihydro-2H-chromen-4-yl |
| 253 | H | cyclopropyl(methyl)amino | H | H | H | H | 2,3-dichlorophenyl | (4S)-3,4-dihydro-2H-chromen-4-yl |
| 254 | H | cyclopropyl(methyl)amino | H | H | H | H | 3,5-dichlorophenyl | (4S)-3,4-dihydro-2H-chromen-4-yl |
| 255 | H | (2S)-2-(methoxycarbonyl)pyrrolidin-1-yl | H | H | H | H | 3,5-dichlorophenyl | (4S)-3,4-dihydro-2H-chromen-4-yl |
| 256 | H | dimethylamino | H | trifluoromethyl | H | H | 3,5-dichlorophenyl | (4S)-3,4-dihydro-2H-chromen-4-yl |
| 257 | H | (3rac)-3-hydroxypyrrolidin-1-yl | H | H | H | H | 3,5-difluorophenyl | (4S)-3,4-dihydro-2H-chromen-4-yl |
| 258 | H | (3rac)-3-hydroxypyrrolidin-1-yl | H | H | H | H | 2-chloro-3-fluorophenyl | (4S)-3,4-dihydro-2H-chromen-4-yl |
| 259 | H | (3rac)-3-hydroxypyrrolidin-1-yl | H | H | H | H | 2-chloro-5-fluorophenyl | (4S)-3,4-dihydro-2H-chromen-4-yl |
| 260 | H | (3rac)-3-hydroxypyrrolidin-1-yl | H | H | H | H | 3-chlorophenyl | (4S)-3,4-dihydro-2H-chromen-4-yl |
| 261 | H | (3rac)-3-hydroxypyrrolidin-1-yl | H | H | H | H | 3-chloro-5-methoxyphenyl | (4S)-3,4-dihydro-2H-chromen-4-yl |
| 262 | H | (3rac)-3-hydroxypyrrolidin-1-yl | H | H | H | H | 3-chloro-2-fluorophenyl | (4S)-3,4-dihydro-2H-chromen-4-yl |
| 263 | H | (2R)-2-(methoxycarbonyl)pyrrolidin-1-yl | H | H | H | H | 3,5-dichlorophenyl | (4S)-3,4-dihydro-2H-chromen-4-yl |
| 264 | H | 2,2-dimethylpyrrolidin-1-yl | H | H | H | H | 3,5-dichlorophenyl | (4S)-3,4-dihydro-2H-chromen-4-yl |
| 265 | H | ethylamino | H | H | H | H | 3,5-dichlorophenyl | (4S)-3,4-dihydro-2H-chromen-4-yl |
| 266 | H | (2S)-2-carboxypyrrolidin-1-yl | H | H | H | H | 3,5-dichlorophenyl | (4S)-3,4-dihydro-2H-chromen-4-yl |
| 267 | H | morpholin-4-yl | H | H | H | H | 5-chloro-2-methoxyphenyl | (4S)-3,4-dihydro-2H-chromen-4-yl |

TABLE 1-continued

Examples (I)

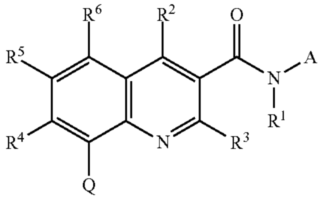

| Number | R1 | R2 | R3 | R4 | R5 | R6 | Q | A |
|---|---|---|---|---|---|---|---|---|
| 268 | H | morpholin-4-yl | H | H | H | H | 5-fluoro-2-methoxyphenyl | (4S)-3,4-dihydro-2H-chromen-4-yl |
| 269 | H | (3rac)-3-hydroxypyrrolidin-1-yl | H | H | H | H | 5-chloro-2-methoxyphenyl | (4S)-3,4-dihydro-2H-chromen-4-yl |
| 270 | H | (3rac)-3-hydroxypyrrolidin-1-yl | H | H | H | H | 5-fluoro-2-methoxyphenyl | (4S)-3,4-dihydro-2H-chromen-4-yl |
| 271 | H | (3rac)-3-hydroxypyrrolidin-1 yl | H | H | H | H | 3-chloro-5-(trifluoromethyl) phenyl | (4S)-3,4-dihydro-2H-chromen-4-yl |
| 272 | H | (3rac)-3-hydroxypyrrolidin-1-yl | H | H | H | H | 5-chloro-2-fluoro-3-methylphenyl | (4S)-3,4-dihydro-2H-chromen-4-yl |
| 273 | H | cyclopropylamino | H | H | H | H | 3,5-dichlorophenyl | (4S)-3,4-dihydro-2H-chromen-4-yl |
| 274 | H | (2R)-2-carboxypyrrolidin-1-yl | H | H | H | H | 3,5-dichlorophenyl | (4S)-3,4-dihydro-2H-chromen-4-yl |
| 275 | H | (3rac)-3-hydroxypyrrolidin-1-yl | H | H | H | H | 3-chloro-2-fluoro-5-methylphenyl | (4S)-3,4-dihydro-2H-chromn-4-yl |
| 276 | H | (carboxylatomethyl)amino | H | H | H | H | 3,5-dichlorophenyl | (4S)-3,4-dihydro-2H-chromen-4-yl |
| 277 | H | dimethylamino | H | H | H | H | 2,6-difluorophenyl | (4S)-3,4-dihydro-2H-chromen-4-yl |
| 278 | H | morpholin-4-yl | H | fluoro | H | H | 2,6-difluorophenyl | (4S)-3,4-dihydro-2H-chromen-4-yl |
| 279 | H | dimethylamino | H | fluoro | H | H | 2,6-difluorophenyl | (4S)-3,4-dihydro-2H-chromen-4-yl |
| 280 | H | morpholin-4-yl | H | H | H | H | 1,3-benzoxazol-7-yl | (4S)-3,4-dihydro-2H-chromen-4-yl |
| 281 | H | (3S)-3-(methoxycarbonyl)pyrrolidin-1-yl | H | H | H | H | 3,5-dichlorophenyl | (4S)-3,4-dihydro-2H-chromen-4-yl |
| 282 | H | (3R)-3-(methoxycarbonyl)pyrrolidin-1-yl | H | H | H | H | 3,5-dichlorophenyl | (4S)-3,4-dihydro-2H-chromen-4-yl |
| 283 | H | (3R)-3-hydroxypyrrolidin-1-yl | H | H | H | H | 3,5-dichlorophenyl | (4S)-3,4-dihydro-2H-chromen-4-yl |
| 284 | H | (3S)-3-hydroxypyrrolidin-1-yl | H | H | H | H | 3,5-dichlorophenyl | (4S)-3,4-dihydro-2H-chromen-4-yl |
| 285 | H | [(diethyoxyphosphoryl)methyl] (methyl)amino | H | H | H | H | 3,5-dichlorophenyl | (4S)-3,4-dihydro-2H-chromen-4-yl |
| 286 | H | [2-(cyclopropylamino)ethyl] amino | H | H | H | H | 3,5-dichlorophenyl | (4S)-3,4-dihydro-2H-chromen-4-yl |
| 287 | H | (2R)-2-(hydroxymethyl)pyrrolidin-1-yl | H | H | H | H | 3,5-dichlorophenyl | (4S)-3,4-dihydro-2H-chromen-4-yl |
| 288 | H | (2S)-2-(hydroxymethyl)pyrrolidin-1-yl | H | H | H | H | 3,5-dichlorophenyl | (4S)-3,4-dihydro-2H-chromen-4-yl |
| 289 | H | [(1R,3)S-3-amino-2,2-dimethylcyclopropyl]amino | H | H | H | H | 3,5-dichlorophenyl | (4S)-3,4-dihydro-2H-chromen-4-yl |
| 290 | H | (2S)-2-methylmorpholin-4-yl | H | H | H | H | 3,5-dichlorophenyl | (4S)-3,4-dihydro-2H-chromen-4-yl |
| 291 | H | (3rac,4rac)-3-amino-4-fluoropyrrolidin-1-yl | H | H | H | H | 3,5-dichlorophenyl | (4S)-3,4-dihydro-2H-chromen-4-yl |
| 292 | H | (2rac)-2-carboxypyrrolidin-1-yl | H | H | H | H | 3,5-dichlorophenyl | (1S)-2,3-dihydro-1H-inden-1-yl |
| 293 | H | dimethylamino | H | H | H | H | 3,4-dichloro-5-(dimethylamino) phenyl | (4S)-3,4-dihydro-2H-chromen-4-yl |
| 294 | H | dimethylamino | H | H | H | H | 3-chloro-5-(dimethylamino) phenyl | (4S)-3,4-dihdyro-2H-chromen-4-yl |

TABLE 1-continued

Examples

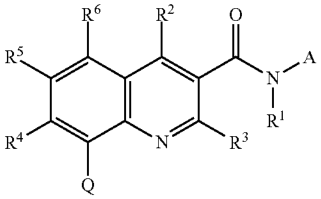

(I)

| Number | R1 | R2 | R3 | R4 | R5 | R6 | Q | A |
|---|---|---|---|---|---|---|---|---|
| 295 | H | (3rac)-3-hydroxypyrrolidin-1-yl | H | H | H | H | 5-chloro-2-fluoro-4-methylphenyl | (4S)-3,4-dihydro-2H-chormen-4-yl |
| 296 | H | dimethylamino | H | H | H | H | phenyl | (4S)-3,4-dihydro-2H-chromen-4-yl |
| 297 | H | (2-hydroxyethyl)amino | H | H | H | H | 3,5-dichlorophenyl | (1S)-2,3-dihydro-1H-inden-1-yl |
| 298 | H | (2-methoxyethyl)amino | H | H | H | H | 3,5-dichlorophenyl | (1S)-2,3-dihydro-1H-inden-1-yl |
| 299 | H | (2R)-2-carboxylatopyrrolidin-1-yl | H | H | H | H | 3,5-dichlorophenyl | (1S)-2,3-dihydro-1H-inden-1-yl |
| 300 | H | 6-oxa-3-azabicyclo[3.1.1]hept-3-yl | H | H | H | H | 3,5-dichlorophenyl | (4S)-3,4-dihydro-2H-chromen-4-yl |
| 301 | H | 3,9-dioxa-7-azabicyclo[3.3.1]non-7-yl | H | H | H | H | 3,5-dichlorophenyl | (4S)-3,4-dihydro-2H-chromen-4-yl |
| 302 | H | 8-oxa-3-azabicyclo[3.2.1]oct-3-yl | H | H | H | H | 3,5-dichlorophenyl | (4S)-3,4-dihydro-2H-chromen-4-yl |
| 303 | H | (2R,6)S-2,6-dimethylmorpholin-4-yl | H | H | H | H | 3,5-difluorophenyl | (4S)-3,4-dihydro-2H-chromen-4-yl |
| 304 | H | (2R,6S)-2,6-dimethylmorpholin-4-yl | H | H | H | H | 2,3-dichlorophenyl | (4S)-3,4-dihydro-2H-chromen-4-yl |
| 305 | H | (2R,6S)-2,6-dimethylmorpholin-4-yl | H | H | H | H | 2,3-dichlorophenyl | (1S)-2,3-dihydro-1H-inden-1-yl |
| 306 | H | (2R,6S)-2,6-dimethylmorpholin-4-yl | H | H | H | H | 3,5-difluorophenyl | (1S)-2,3-dihydro-1H-inden-1-yl |
| 307 | H | dimethylamino | H | H | H | H | 4-chloro-3-(dimethylamino) phenyl | (4S)-3,4-dihydro-2H-chromen-4-yl |
| 308 | H | dimethylamino | H | H | H | H | 3,5-dichloro-4-(dimethylamino) phenyl | (4S)-3,4-dihydro-2H-chromen-4-yl |
| 309 | H | morpholin-4-yl | H | methyloxy | H | H | 2,3-dichlorophenyl | (4S)-3,4-dihydro-2H-chromen-4-yl |
| 310 | H | morpholin-4-yl | H | methyloxy | H | H | 3,5-dichlorophenyl | (4S)-3,4-dihydro-2H-chromen-4-yl |
| 311 | H | dimethylamino | H | H | H | H | 3-chloro-4-(dimethylamino) phenyl | (4S)-3,4-dihydro-2H-chromen-4-yl |
| 312 | H | dimethylamino | H | H | H | H | 3-(methylamino)phe-nyl | (4S)-3,4-dihydro-2H-chrome-4-yl |
| 313 | H | morpholin-4-yl | H | H | H | H | 2,6-difluorophenyl | (4S)-3,4-dihydro-2H-chromen-4-yl |
| 314 | H | morpholin-4-yl | H | trifluoromethyl | H | H | 2,3-dichlorophenyl | (4S)-3,4-dihydro-2H-chromen-4-yl |
| 315 | H | dimethylamino | H | trifluoromethyl | H | H | 2,3-dichlorophenyl | (4S)-3,4-dihydro-2H-chromen-4-yl |
| 316 | H | dimethylamino | H | H | chloro | H | 3,5-dichlorophenyl | (4S)-3,4-dihydro-2H-chromen-4-yl |
| 317 | H | (3rac)-3-hydroxypyrrolidin-1-yl | H | H | H | H | 3,5-dichlorophenyl | (4S)-3,4-dihydro-2H-chromen-4-yl |
| 318 | H | (3S)-3-(hydroxymethyl)pyrrolidin-1-yl | H | H | H | H | 3,5-dichlorophenyl | (4S)-3,4-dihydro-2H-chromen-4-yl |
| 319 | H | morpholin-4-yl | H | H | H | H | 2-chlorophenyl | (4S)-3,4-dihydro-2H-chromen-4-yl |
| 320 | H | (2S)-2-(ethoxycarbonyl)pyrrolidin-1-yl | H | H | H | H | 3,5-dichlorophenyl | (4S)-3,4-dihydro-2H-chromen-4-yl |
| 321 | H | 2,4-dimethyl-3,5-dioxo-1,2,4-triazolidin-1-l | H | H | H | H | 2,3-dichlorophenyl | (4S)-3,4-dihydro-2H-chromen-4-yl |
| 322 | H | morpholin-4-yl | H | H | H | H | 3-(trifluoromethoxy) phenyl | (4S)-3,4-dihydro-2H-chromen-4-yl |

TABLE 1-continued

Examples

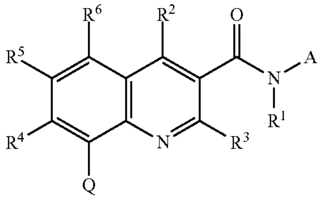

(I)

| Number | R1 | R2 | R3 | R4 | R5 | R6 | Q | A |
|---|---|---|---|---|---|---|---|---|
| 323 | H | dimethylamino | H | H | H | H | 3-chloro-5-(morpholin-4-yl)phenyl | (4S)-3,4-dihydro-2H-chromen-4-yl |
| 324 | H | dimethylamino | H | H | H | H | 2-chloro-4-(dimethylamino) phenyl | (4S)-3,4-dihydro-2H-chromen-4-yl |
| 325 | H | dimethylamino | H | H | H | H | 3-chloro-4-(dimethylamino)-5-fluorophenyl | (4S)-3,4-dihydro-2H-chromen-4-yl |
| 326 | H | dimethylamino | H | methyloxy | H | H | 2,3-dichlorophenyl | (4S)-3,4-dihydro-2H-chromen-4-yl |
| 327 | H | dimethylamino | H | methyloxy | H | H | 3,5-dichlorophenyl | (4S)-3,4-dihydro-2H-chromen-4-yl |
| 328 | H | methyl[2-(2-oxopyrrolidin-1-yl)ethyl]amino | H | H | H | H | 3,5-dichlorophenyl | (4S)-3,4-dihydro-2H-chromen-4-yl |
| 329 | H | (3R)-3-(hydroxymethyl)pyrrolidin-1-yl | H | H | H | H | 3,5-dichlorophenyl | (4S)-3,4-dihydro-2H-chromen-4-yl |
| 330 | H | dimethylamino | H | fluoro | H | H | 2,3-dichlorophenyl | (4S)-3,4-dihydro-2H-chromen-4-yl |
| 331 | H | methyl(oxetan-3-yl)amino | H | H | H | H | 2,3-dichlorophenyl | (4S)-3,4-dihydro-2H-chromen-4-yl |
| 332 | H | (3R)-3-carboxypyrrolidin-1-yl | H | H | H | H | 3,5-dichlorophenyl | (4S)-3,4-dihydro-2H-chromen-4-yl |
| 333 | H | methyloxy | H | H | H | H | 3,5-dichloro-4-fluorophenyl | (4S)-3,4-dihydro-2H-chromen-4-yl |
| 334 | H | ethyloxy | H | H | H | H | 3,5-dichlorophenyl | (1S)-2,3-dihydro-1H-inden-1-yl |
| 335 | H | isopropyloxy | H | H | H | H | 3,5-dichlorophenyl | (4S)-3,4-dihydro-2H-chromen-4-yl |
| 336 | H | isopropyloxy | H | H | H | H | 3,5-dichlorophenyl | (1S)-2,3-dihydro-1H-inden-1-yl |
| 337 | H | cylcopentyloxy | H | H | H | H | 3,5-dichlorophenyl | (1S)-2,3-dihydro-1H-inden-1-yl |
| 338 | H | (2-methoxyethyl)oxy | H | H | H | H | 3,5-dichlorophenyl | (4S)-3,4-dihydro-2H-chromen-4-yl |
| 339 | H | tetrahydro-2H-pyran-4-yloxy | H | H | H | H | 3,5-dichlorophenyl | (4S)-3,4-dihydro-2H-chromen-4-yl |
| 340 | H | (2-hydroxyethyl)oxy | H | H | H | H | 3,5-dichlorophenyl | (4S)-3,4-dihydro-2H-chromen-4-yl |
| 341 | H | ethyloxy | H | H | H | H | 3,5-dichlorophenyl | (4S)-3,4-dihydro-2H-chromen-4-yl |
| 342 | H | (3,3-dimethylbutyl)oxy | H | H | H | H | 3,5-dichlorophenyl | (1S)-2,3-dihydro-1H-inden-1-yl |
| 343 | H | (3-fluorobenzyl)oxy | H | H | H | H | 3,5-dichlorophenyl | (1S)-2,3-dihydro-1H-inden-1-yl |
| 344 | H | (2,3-difluorobenzyl)oixy | H | H | H | H | 3,5-dichlorophenyl | (1S)-2,3-dihydro-1H-inden-1-yl |
| 345 | H | (3-methoxybenzyl)oxy | H | H | H | H | 3,5-dichlorophenyl | (1S)-2,3-dihydro-1H-inden-1-yl |
| 346 | H | (3R)-pyrrolidin-3-yloxy | H | H | H | H | 3,5-dichlorophenyl | (1S)-2,3-dihydro-1H-inden-1-yl |
| 347 | H | (3-methoxy-3-methylbutyl)oxy | H | H | H | H | 3,5-dichlorophenyl | (1S)-2,3-dihydro-1H-inden-1-yl |
| 348 | H | (cyclopentylmethyl)oxy | H | H | H | H | 3,5-dichlorophenyl | (1S)-2,3-dihydro-1H-inden-1-yl |
| 349 | H | isopropyloxy | H | H | H | H | 3,5-dichlorophenyl | (1S)-2,3-dihydro-1H-inden-1-yl |
| 350 | H | ethyl | H | H | H | H | 3,5-dichlorophenyl | (4S)-3,4-dihydro-2H-chromen-4-yl |
| 351 | H | ethyl | H | H | H | H | 3-chloro-5-ethylphenyl | (4S)-3,4-dihydro-2H-chromen-4-yl |
| 352 | H | methyl | H | H | H | H | 3-chloro-5-methylphenyl | (4S)-3,4-dihydro-2H-chromen-4-yl |

TABLE 1-continued

Examples (I)

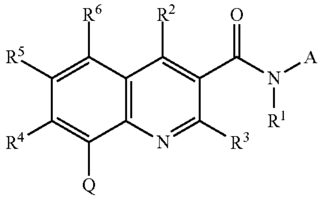

| Number | R1 | R2 | R3 | R4 | R5 | R6 | Q | A |
|---|---|---|---|---|---|---|---|---|
| 353 | H | methyl | H | H | H | H | 3,5-dichlorophenyl | (4S)-3,4-dihydro-2H-chromen-4-yl |
| 354 | H | 1-cyano-2-ethoxy-2-oxoethyl | H | H | H | H | 3,5-dichlorophenyl | (4S)-3,4-dihydro-2H-chromen-4-yl |
| 355 | H | cyanomethyl | H | H | H | H | 3,5-dichlorophenyl | (4S)-3,4-dihydro-2H-chromen-4-yl |
| 356 | H | propyl | H | H | H | H | 3,5-dichlorophenyl | (4S)-3,4-dihydro-2H-chromen-4-yl |
| 357 | H | prop-1-en-2-yl | H | H | H | H | 3,5-dichlorophenyl | (4S)-3,4-dihydro-2H-chromen-4-yl |
| 358 | H | cyclopropyl | H | H | H | H | 3,5-dichlorophenyl | (4S)-3,4-dihydro-2H-chromen-4-yl |
| 359 | H | isopropyl | H | H | H | H | 3,5-dichlorophenyl | (4S)-3,4-dihydro-2H-chromen-4-yl |
| 360 | H | 2-amino-2-oxoethyl | H | H | H | H | 3,5-dichlorophenyl | (4S)-3,4-dihydro-2H-chromen-4-yl |
| 361 | H | nitrilomethyl | H | H | H | H | 3,5-dichlorophenyl | (4S)-3,4-dihydro-2H-chromen-4-yl |
| 362 | H | (2-hydroxyethyl)sulfanyl | H | H | H | H | 3,5-dichlorophenyl | (1S)-2,3-dihydro-1H-inden-1-yl |
| 363 | H | pyridin-2-ylsulfanoyl | H | H | H | H | 3,5-dichlorophenyl | (4S)-3,4-dihydro-2H-chromen-4-yl |
| 364 | H | (2-hydroxyethyl)sulfamoyl | H | H | H | H | 3,5-dichlorophenyl | (4S)-3,4-dihydro-2H-chromen-4-yl |
| 365 | H | methylsulfanoyl | H | H | H | H | 3-chloro-5-(methylsulfanyl)phenyl | (4S)-3,4-dihydro-2H-chromen-4-yl |
| 366 | H | ethylsulfanoyl | H | H | H | H | 2,3-dichlorophenyl | (4S)-3,4-dihydro-2H-chromen-4-yl |
| 367 | H | ethylsulfanoyl | H | H | H | H | 3,5-dichlorophenyl | (4S)-3,4-dihydro-2H-chromen-4-yl |
| 368 | H | ethylsulfinyl | H | H | H | H | 2,3-dichlorophenyl | (4S)-3,4-dihydro-2H-chromen-4-yl |
| 369 | H | ethylsulfonyl | H | H | H | H | 2,3-dichlorophenyl | (4S)-3,4-dihydro-2H-chromen-4-yl |
| 370 | H | ethylsulfinyl | H | H | H | H | 3,5-dichlorophenyl | (4S)-3,4-dihydro-2H-chromen-4-yl |
| 371 | H | ethylsulfonyl | H | H | H | H | 3,5-dichlorophenyl | (4S)-3,4-dihydro-2H-chromen-4-yl |
| 372 | H | (2-carboxyethyl)sulfamoyl | H | H | H | H | 3,5-dichlorophenyl | (4S)-3,4-dihydro-2H-chromen-4-yl |
| 373 | H | methyloxy | H | H | H | H | 3,5-dichlorophenyl | (4S)-3,4-dihydro-2H-chromen-4-yl |
| 374 | H | (2rac)-2-(trifluoromethyl)morpholin-4-yl | H | H | H | H | 3,5-dichlorophenyl | (4S)-3,4-dihydro-2H-chromen-4-yl |
| 375 | H | (2-methoxy-2-oxoethyl)amino | H | H | H | H | 3,5-dichlorophenyl | (4S)-3,4-dihydro-2H-chromen-4-yl |
| 376 | H | H | H | H | H | H | 2,3-dichlorophenyl | (4S)-3,4-dihydro-2H-chromen-4-yl |
| 377 | H | dimethylamino | H | H | H | H | 5-fluoro-2-methoxypyridin-4-yl | (4S)-3,4-dihydro-2H-chromen-4-yl |
| 378 | H | dimethylamino | H | H | H | H | 2-cyanopyridin-4-yl | (4S)-3,4-dihydro-2H-chromen-4-yl |
| 379 | H | dimethylamino | H | H | H | H | 2-aminopyridin-4-yl | (4S)-3,4-dihydro-2H-chromen-4-yl |
| 380 | H | dimethylamino | H | H | H | H | 2-methylpyridin-4-yl | (4S)-3,4-dihydro-2H-chromen-4-yl |
| 381 | H | dimethylamino | H | H | H | H | 3-methylpyridin-4-yl | (4S)-3,4-dihydro-2H-chromen-4-yl |

TABLE 1-continued

Examples

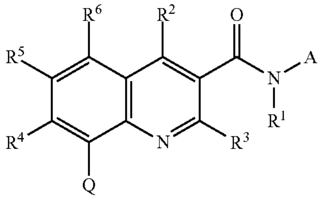

(I)

| Number | R1 | R2 | R3 | R4 | R5 | R6 | Q | A |
|---|---|---|---|---|---|---|---|---|
| 382 | H | dimethylamino | H | H | H | H | 3-chloropyridin-4-yl | (4S)-3,4-dihydro-2H-chromen-4-yl |
| 383 | H | dimethylamino | H | H | H | H | 3-fluoropyridin-4-yl | (4S)-3,4-dihydro-2H-chromen-4-yl |
| 384 | H | methylamino | H | H | H | H | 2,3-dichlorophenyl | (4S)-3,4-dihydro-2H-chromen-4-yl |
| 385 | H | methylamino | H | H | H | H | 2,3,5-trifluorophenyl | (4S)-3,4-dihydro-2H-chromen-4-yl |
| 386 | H | isopropyl | H | H | H | H | 2,3,5-trichlorophenyl | (4S)-3,4-dihydro-2H-chromen-4-yl |
| 387 | H | dimethylamino | H | H | H | H | 5-cyano-4-methyl-2-thienyl | (4S)-3,4-dihydro-2H-chromen-4-yl |
| 388 | H | dimethylamino | H | H | H | H | 2,5-dimethyl-3-thienyl | (4S)-3,4-dihydro-2H-chromen-4-yl |
| 389 | H | dimethylamino | H | H | H | H | 5-cyano-2-thienyl | (4S)-3,4-dihydro-2H-chromen-4-yl |
| 390 | H | dimethyamino | H | H | H | H | 5-chloro-2-thienyl | (4S)-3,4-dihydro-2H-chromen-4-yl |
| 391 | H | dimethylamino | H | H | H | H | 5-methyl-2-thienyl | (4S)-3,4-dihydro-2H-chromen-4-yl |
| 392 | H | 3-fluoroazetidin-1-yl | H | H | H | H | 3,5-dichlorophenyl | (4S)-3,4-dihydro-2H-chromen-4-yl |
| 393 | H | 4-fluoropiperidin-1-yl | H | H | H | H | 3,5-dichlorophenyl | (4S)-3,4-dihydro-2H-chromen-4-yl |
| 394 | H | 3,3-difluoroazetidin-1-yl | H | H | H | H | 3,5-dichlorophenyl | (4S)-3,4-dihydro-2H-chromen-4-yl |
| 395 | H | methylamino | H | fluoro | H | H | 3,5-dichlorophenyl | (4S)-3,4-dihydro-2H-chromen-4-yl |
| 396 | H | pyridin-4-yl | H | H | H | H | 3,5-dichlorophenyl | (4S)-3,4-dihydro-2H-chromen-4-yl |
| 397 | H | 2-oxo-1,2-dihydropyridin-5-yl | H | H | H | H | 3,5-dichlorophenyl | (4S)-3,4-dihydro-2H-chromen-4-yl |
| 398 | H | 4,4-difluoropiperidin-1-yl | H | H | H | H | 3,5-dichlorophenyl | (4S)-3,4-dihydro-2H-chromen-4-yl |
| 399 | H | dimethylamino | H | H | H | H | 2-morpholin-4-ylpyridin-4-yl | (4S)-3,4-dihydro-2H-chromen-4-yl |
| 400 | H | dimethylamino | H | H | H | H | 5-chloro-2-methoxypyridin-4-yl | (4S)-3,4-dihydro-2H-chromen-4-yl |
| 401 | H | dimethylamino | H | H | H | H | 3-methoxypyridin-4-yl | (4S)-3,4-dihydro-2H-chromen-4-yl |
| 402 | H | dimethylamino | H | H | H | H | 2-(hydroxymethyl)pyridin-4-yl | (4S)-3,4-dihydro-2H-chromen-4-yl |
| 403 | H | dimethylamino | H | H | H | H | 3,5-difluoropyridin-4-yl | (4S)-3,4-dihydro-2H-chromen-4-yl |
| 404 | H | cyclobutyl | H | H | H | H | 3,5-dichlorophenyl | (4S)-3,4-dihydro-2H-chromen-4-yl |
| 405 | H | 2-hydroxyethylamino | H | H | H | H | 2,3-dichlorophenyl | (4S)-3,4-dihydro-2H-chromen-4-yl |
| 406 | H | isopropyl | H | H | H | H | 3-chlorophenyl | (4S)-3,4-dihydro-2H-chromen-4-yl |
| 407 | H | isopropyl | H | H | H | H | 3-(trifluoromethoxy)phenyl | (4S)-3,4-dihydro-2H-chromen-4-yl |
| 408 | H | isopropyl | H | H | H | H | 2-fluoro-3-(trifluoromethyl)phenyl | (4S)-3,4-dihydro-2H-chromen-4-yl |
| 409 | H | isopropyl | H | H | H | H | 3-chloro-2-fluorophenyl | (4S)-3,4-dihydro-2H-chromen-4-yl |
| 410 | H | isopropyl | H | H | H | H | 5-chloro-2-fluorophenyl | (4S)-3,4-dihydro-2H-chromen-4-yl |

TABLE 1-continued

Examples

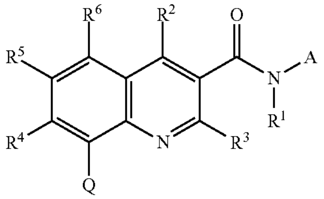

(I)

| Number | R1 | R2 | R3 | R4 | R5 | R6 | Q | A |
|---|---|---|---|---|---|---|---|---|
| 411 | H | isopropyl | H | H | H | H | 3-(trifluoromethyl)phenyl | (4S)-3,4-dihydro-2H-chromen-4-yl |
| 412 | H | 2-aminopyrimidin-5-yl | H | H | H | H | 3,5-dichlorophenyl | (4S)-3,4-dihydro-2H-chromen-4-yl |
| 413 | H | dimethylamino | H | H | H | H | 2,6-difluoropyridin-4-yl | (4S)-3,4-dihydro-2H-chromen-4-yl |
| 414 | H | dimethylamino | H | H | H | H | 2-chloro-3-fluoropyridin-4-yl | (4S)-3,4-dihydro-2H-chromen-4-yl |
| 415 | H | dimethylamino | H | H | H | H | 2,5-dichloropyridin-4-yl | (4S)-3,4-dihydro-2H-chromen-4-yl |
| 416 | H | dimethylamino | H | H | H | H | 5-fluoro-2-isopropyloxy-pyridin-4-yl | (4S)-3,4-dihydro-2H-chromen-4-yl |
| 417 | H | dimethylamino | H | H | H | H | 2-ethoxy-5-fluoropyridin-4-yl | (4S)-3,4-dihydro-2H-chromen-4-yl |
| 418 | H | isopropyl | H | H | H | H | 2-chloro-5-fluorophenyl | (4S)-3,4-dihydro-2H-chromen-4-yl |
| 419 | H | isopropyl | H | H | H | H | 3-chloro-5-fluorophenyl | (4S)-3,4-dihydro-2H-chromen-4-yl |
| 420 | H | isopropyl | H | H | H | H | 2-chloro-3-(trifluoromethyl)phenyl | (4S)-3,4-dihydro-2H-chromen-4-yl |
| 421 | H | isopropyl | H | H | H | H | 2-chloro-3-fluorophenyl | (4S)-3,4-dihydro-2H-chromen-4-yl |
| 422 | H | isopropyl | H | H | H | H | 2,5-dimethyl-3-thienyl | (4S)-3,4-dihydro-2H-chromen-4-yl |
| 423 | H | isopropyl | H | H | H | H | 2,5-dichloro-3-thienyl | (4S)-3,4-dihydro-2H-chromen-4-yl |
| 424 | H | 2-aminoethyl | H | H | H | H | 3,5-dichlorophenyl | (4S)-3,4-dihydro-2H-chromen-4-yl |
| 425 | H | isopropyl | H | fluoro | H | H | 2,5-dimethyl-3-thienyl | (4S)-3,4-dihydro-2H-chromen-4-yl |
| 426 | H | isopropyl | H | fluoro | H | H | 2,5-dichloro-3-thienyl | (4S)-3,4-dihydro-2H-chromen-4-yl |
| 427 | H | methoxy(methyl)amino | H | H | H | H | 2,3,5-trifluorophenyl | (4S)-3,4-dihydro-2H-chromen-4-yl |
| 428 | H | dimethylamino | H | H | cyano | H | 3,5-dichlorophenyl | (4S)-3,4-dihydro-2H-chromen-4-yl |
| 429 | H | dimethylamino | H | H | hydroxy | H | 3,5-dichlorophenyl | (4S)-3,4-dihydro-2H-chromen-4-yl |
| 430 | H | isopropyl | H | H | H | H | 3,5-difluorophenyl | (4S)-3,4-dihydro-2H-chromen-4-yl |
| 431 | H | isopropyl | H | H | H | H | 3-chloro-5-(trifluoromethyl)phenyl | (4S)-3,4-dihydro-2H-chromen-4-yl |
| 432 | H | (dimethylamino)methyl | H | H | H | H | 3,5-dichlorophenyl | (4S)-3,4-dihydro-2H-chromen-4-yl |
| 433 | H | dimethylamino | H | H | H | H | 2,5-bis(trifluorometh-yl)phenyl | (4S)-3,4-dihydro-2H-chromen-4-yl |
| 434 | H | dimethylamino | H | H | H | H | 5-fluoro-2-(trifluoromethyl)phenyl | (4S)-3,4-dihydro-2H-chromen-4-yl |
| 435 | H | dimethylamino | H | H | H | H | 2-chloro-5-cyanophenyl | (4S)-3,4-dihydro-2H-chromen-4-yl |
| 436 | H | dimethylamino | H | H | H | H | 5-fluoro-2-methylphenyl | (4S)-3,4-dihydro-2H-chromen-4-yl |
| 437 | H | dimethylamino | H | H | H | H | 2-fluoro-5-methylphenyl | (4S)-3,4-dihydro-2H-chromen-4-yl |

TABLE 1-continued

Examples

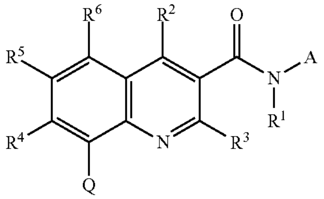

(I)

| Number | R1 | R2 | R3 | R4 | R5 | R6 | Q | A |
|---|---|---|---|---|---|---|---|---|
| 438 | H | isopropyl | H | H | H | H | 3,5-dichloro-4-fluorophenyl | (4S)-3,4-dihydro-2H-chromen-4-yl |
| 439 | H | 3-fluoro-2-oxo-1,2-dihydropyridin-5-yl | H | H | H | H | 3,5-dichlorophenyl | (4S)-3,4-dihydro-2H-chromen-4-yl |
| 440 | H | amino | H | H | H | H | 2,3-dichlorophenyl | (4S)-3,4-dihydro-2H-chromen-4-yl |
| 441 | H | morpholin-4-yl | H | H | H | H | 2,5-dichloro-3-thienyl | (4S)-3,4-dihydro-2H-chromen-4-yl |
| 442 | H | morpholin-4-yl | H | H | H | H | 3-chloro-2-thienyl | (4S)-3,4-dihydro-2H-chromen-4-yl |
| 443 | H | morpholin-4-yl | H | H | H | H | 5-chloro-2-thienyl | (4S)-3,4-dihydro-2H-chromen-4-yl |
| 444 | H | isopropyl | H | H | H | H | 3-chloro-2-fluoro-5-methylphenyl | (4S)-3,4-dihydro-2H-chromen-4-yl |
| 445 | H | 1,2-oxazolidin-2-yl | H | H | H | H | 2,3-dichlorophenyl | (4S)-3,4-dihydro-2H-chromen-4-yl |
| 446 | H | isopropyl | H | H | H | H | 3-chloro-4-fluorophenyl | (4S)-3,4-dihydro-2H-chromen-4-yl |
| 447 | H | isopropyl | H | H | H | H | 2,5-dimethylphenyl | (4S)-3,4-dihydro-2H-chromen-4-yl |
| 448 | H | isopropyl | H | H | H | H | 3-fluoro-5-methylphenyl | (4S)-3,4-dihydro-2H-chromen-4-yl |
| 449 | H | isopropyl | H | H | H | H | 3,4,5-trifluorophenyl | (4S)-3,4-dihydro-2H-chromen-4-yl |
| 450 | H | isopropyl | H | H | H | H | 2,3,5-trifluorophenyl | (4S)-3,4-dihydro-2H-chromen-4-yl |
| 451 | H | isopropyl | H | H | H | H | 2-methyl-5-(trifluoromethyl) phenyl | (4S)-3,4-dihydro-2H-chromen-4-yl |
| 452 | H | methoxy(methyl)amino | H | H | H | H | 2,3,5-trifluorophenyl | (1S)-2,3-dihydro-1H-inden-1-yl |
| 453 | H | isopropyl | H | H | H | H | 2,5-dichlorophenyl | (4S)-3,4-dihydro-2H-chromen-4-yl |
| 454 | H | 1H-pyrazol-4-yl | H | H | H | H | 3,5-dichlorophenyl | (4S)-3,4-dihydro-2H-chromen-4-yl |
| 455 | H | isopropyl | H | fluoro | H | H | 3,5-dichlorophenyl | (4S)-3,4-dihydro-2H-chromen-4-yl |
| 456 | H | dimethylamino | H | H | H | H | 2-methyl-1,3-thiazol-5-yl | (4S)-3,4-dihydro-2H-chromen-4-yl |
| 457 | H | dimethylamino | H | H | H | H | 4-chloro-2-thienyl | (4S)-3,4-dihydro-2H-chromen-4-yl |
| 458 | H | dimethylamino | H | H | H | H | 5-(trifluoromethyl)-2-thienyl | (4S)-3,4-dihydro-2H-chromen-4-yl |
| 459 | H | dimethylamino | H | H | H | H | 5-fluoro-2-thienyl | (4S)-3,4-dihydro-2H-chromen-4-yl |
| 460 | H | dimethylamino | H | H | H | H | 3,5-dichloropyridin-4-yl | (4S)-3,4-dihydro-2H-chromen-4-yl |
| 461 | H | morpholin-4-yl | H | H | H | H | 2,5-bis(trifluorometh-yl)phenyl | (4S)-3,4-dihydro-2H-chromen-4-yl |
| 462 | H | morpholin-4-yl | H | H | H | H | 2,5-dichlorophenyl | (4S)-3,4-dihydro-2H-chromen-4-yl |
| 463 | H | morpholin-4-yl | H | H | H | H | 5-fluoro-2-(trifluoromethyl) phenyl | (4S)-3,4-dihydro-2H-chromen-4-yl |
| 464 | H | morpholin-4-yl | H | H | H | H | 2-chloro-5-cyanophenyl | (4S)-3,4-dihydro-2H-chromen-4-yl |
| 465 | H | morpholin-4-yl | H | H | H | H | 2-chloro-5-methylphenyl | (4S)-3,4-dihydro-2H-chromen-4-yl |
| 466 | H | morpholin-4-yl | H | H | H | H | 5-fluoro-2-methylphenyl | (4S)-3,4-dihydro-2H-chromen-4-yl |

TABLE 1-continued

Examples (I)

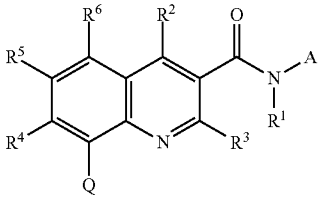

| Number | R1 | R2 | R3 | R4 | R5 | R6 | Q | A |
|---|---|---|---|---|---|---|---|---|
| 467 | H | morpholin-4-yl | H | H | H | H | 2-fluoro-5-methylphenyl | (4S)-3,4-dihydro-2H-chromen-4-yl |
| 468 | H | moprholin-4-yl | H | H | H | H | 2,5-dimethylphenyl | (4S)-3,4-dihydro-2H-chromen-4-yl |
| 469 | H | dimethylamino | H | H | H | H | 2,5-dichlorophenyl | (4S)-3,4-dihydro-2H-chromen-4-yl |
| 470 | H | dimethylamino | H | H | H | H | 2-chloro-5-methylphenyl | (4S)-3,4-dihydro-2H-chromen-4-yl |
| 471 | H | dimethylamino | H | H | H | H | 2,5-dimethylphenyl | (4S)-3,4-dihydro-2H-chromen-4-yl |
| 472 | H | dimethylamino | H | H | H | H | 2,6-dimethoxypyridin-4-yl | (4S)-3,4-dihydro-2H-chromen-4-yl |
| 473 | H | dimethylamino | H | H | H | H | 2-chloro-6-methylpyridin-4-yl | (4S)-3,4-dihydro-2H-chromen-4-yl |
| 474 | H | dimethylamino | H | H | H | H | 2,3-dimethoxypyridin-4-yl | (4S)-3,4-dihydro-2H-chromen-4-yl |
| 475 | H | dimethylamino | H | H | H | H | 3-chloro-2-methoxypyridin-4-yl | (4S)-3,4-dihydro-2H-chromen-4-yl |
| 476 | H | dimethylamino | H | H | H | H | 2,3-dichloropyridin-4-yl | (4S)-3,4-dihydro-2H-chromen-4-yl |
| 477 | H | isopropyl | H | fluoro | H | H | 2,3-dichlorophenyl | (4S)-3,4-dihydro-2H-chromen-4-yl |
| 478 | H | vinyl | H | H | H | H | 3,5-dichlorophenyl | (4S)-3,4-dihydro-2H-chromen-4-yl |
| 479 | H | isopropyl | H | fluoro | H | H | 3-(trifluoromethoxy)phenyl | (4S)-3,4-dihydro-2H-chromen-4-yl |
| 480 | H | morpholin-4-yl | H | H | H | H | 2,5-dimethyl-3-thienyl | (4S)-3,4-dihydro-2H-chromen-4-yl |
| 481 | H | morpholin-4-yl | methyl | H | H | H | 2,3-dichlorophenyl | (4S)-3,4-dihydro-2H-chromen-4-yl |
| 482 | H | 2,2-difluoroethyl(methyl(amino | H | H | H | H | 2,3-dichlorophenyl | (4S)-3,4-dihydro-2H-chromen-4-yl |
| 483 | H | morpholin-4-yl | methyl | H | H | H | 3,5-dichlorophenyl | (4S)-3,4-dihydro-2H-chromen-4-yl |
| 484 | H | oxetan-3-ylmethylamino | H | H | H | H | 2,3-dichloropehnyl | (4S)-3,4-dihydro-2H-chromen-4-yl |
| 485 | H | morpholin-4-yl | H | fluoro | H | H | 3,5-dichlorophenyl | (1S)-2,3-dihydro-1H-inden-1-yl |
| 486 | H | morpholin-4-yl | H | fluoro | H | H | 1,3-benzothiazol-7-yl | (4S)-3,4-dihydro-2H-chromen-4-yl |
| 487 | H | isopropyl | H | fluoro | H | H | 2,3,5-trifluorophenyl | (4S)-3,4-dihydro-2H-chromen-4-yl |
| 488 | H | isopropyl | H | fluoro | H | H | 3-(trifluoromethyl)phenyl | (4S)-3,4-dihydro-2H-chromen-4-yl |
| 489 | H | 3-thienyl | H | H | H | H | 3,5-dichlorophenyl | (4S)-3,4-dihydro-2H-chromen-4-yl |
| 490 | H | morpholin-4-yl | H | fluoro | H | H | 2,5-dimethylphenyl | (4S)-3,4-dihydro-2H-chromen-4-yl |
| 491 | H | morpholin-4-yl | H | fluoro | H | H | 2,3-dichlorophenyl | (1S)-2,3-dihydro-1H-inden-1-yl |
| 492 | H | morpholin-4-yl | H | fluoro | H | H | 2,3-dichlorophenyl | (1S)-1,2,3,4-tetrahydronaphthalen-1-yl |

TABLE 1-continued

Examples (I)

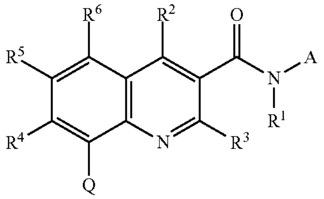

| Number | R1 | R2 | R3 | R4 | R5 | R6 | Q | A |
|---|---|---|---|---|---|---|---|---|
| 493 | H | dimethylamino | H | H | H | H | 3,5-dichlorophenyl | (3rac)-2,3-dihydro-1-benzothiophen-3-yl |
| 494 | H | cyclopentyl | H | H | H | H | 3,5-dichlorophenyl | (4S)-3,4-dihydro-2H-chromen-4-yl |
| 495 | H | moprholin-4-yl | H | H | H | H | 2,3-dichloro-5-hydroxyphenyl | (4S)-3,4-dihydro-2H-chromen-4-yl |
| 496 | H | morpholin-4-yl | H | H | H | methoxy | 2,3-dichlorophenyl | (4S)-3,4-dihydro-2H-chromen-4-yl |
| 497 | H | morpholin-4-yl | H | H | H | methoxy | 5-chloro-2-fluorophenyl | (4S)-3,4-dihydro-2H-chromen-4-yl |
| 498 | H | morpholin-4-yl | H | H | methoxy | H | 3,5-dichlorophenyl | (4S)-3,4-dihydro-2H-chromen-4-yl |
| 499 | H | morpholin-4-yl | H | H | methoxy | H | 2,3-dichlorophenyl | (4S)-3,4-dihydro-2H-chromen-4-yl |
| 500 | H | moprholin-4-yl | H | H | methoxy | H | 5-chloro-2-fluorophenyl | (4S)-3,4-dihydro-2H-chromen-4-yl |
| 501 | H | dimethylamino | H | H | methoxy | H | 3,5-dichlorophenyl | (4S)-3,4-dihydro-2H-chromen-4-yl |
| 502 | H | dimethylamino | H | H | methoxy | H | 2,3-dichlorophenyl | (4S)-3,4-dihydro-2H-chromen-4-yl |
| 503 | H | dimethylamino | H | H | methoxy | H | 5-chloro-2-fluorophenyl | (4S)-3,4-dihydro-2H-chromen-4-yl |
| 504 | H | dimethylamino | H | H | H | methoxy | 3,5-dichlorophenyl | (4S)-3,4-dihydro-2H-chromen-4-yl |
| 505 | H | dimethylamino | H | H | H | methoxy | 2,3-dichlorophenyl | (4S)-3,4-dihydro-2H-chromen-4-yl |
| 506 | H | dimethylamino | H | H | H | methoxy | 5-chloro-2-fluorophenyl | (4S)-3,4-dihydro-2H-chromen-4-yl |
| 507 | H | dimethylamino | H | H | H | chloro | 3,5-dichlorophenyl | (4S)-3,4-dihydro-2H-chromen-4-yl |
| 508 | H | dimethylamino | H | H | H | chloro | 2,3-dichlorophenyl | (4S)-3,4-dihydro-2H-chromen-4-yl |
| 509 | H | dimethylamino | H | H | H | chloro | 5-chloro-2-fluorophenyl | (4S)-3,4-dihydro-2H-chromen-4-yl |
| 510 | H | dimethylamino | H | H | trifluoro-methyl | H | 2,3-dichlorophenyl | (4S)-3,4-dihydro-2H-chromen-4-yl |
| 511 | H | dimethylamino | H | H | trifluoro-methyl | H | 5-chloro-2-fluorophenyl | (4S)-3,4-dihydro-2H-chromen-4-yl |
| 512 | H | morpholin-4-yl | H | H | trifluoro-methyl | H | 3,5-dichlorophenyl | (4S)-3,4-dihydro-2H-chromen-4-yl |
| 513 | H | morpholin-4-yl | H | H | trifluoro-methyl | H | 2,3-dichlorophenyl | (4S)-3,4-dihydro-2H-chromen-4-yl |
| 514 | H | morpholin-4-yl | H | H | trifluoro-methyl | H | 5-chloro-2-fluorophenyl | (4S)-3,4-dihydro-2H-chromen-4-yl |
| 515 | H | methyl(oxan-4-ylmethyl)amino | H | H | H | H | 2,3-dichlorophenyl | (4S)-3,4-dihydro-2H-chromen-4-yl |
| 516 | H | methoxy(methyl)amino | H | fluoro | H | H | 2,3,5-trifluorophenyl | (4S)-3,4-dihydro-2H-chromen-4-yl |
| 517 | H | morpholin-4-yl | H | H | hydroxy | H | 2,3-dichlorophenyl | (4S)-3,4-dihydro-2H-chromen-4-yl |
| 518 | H | oxetan-3-ylmethylamino | H | H | H | H | 3,5-dichlorophenyl | (4S)-3,4-dihydro-2H-chromen-4-yl |
| 519 | H | (3rac)-pyrrolidin-3-yl | H | H | H | H | 3,5-dichlorophenyl | (4S)-3,4-dihydro-2H-chromen-4-yl |
| 520 | H | 1-(difluoromethyl)-1H-pyrazol-4-yl | H | H | H | H | 3,5-dichlorophenyl | (4S)-3,4-dihydro-2H-chromen-4-yl |
| 521 | H | morpholin-4-yl | H | H | hydroxy | H | 2,3-dichloro-5-hydroxyphenyl | (4S)-3,4-dihydro-2H-chromen-4-yl |
| 522 | H | dimethylamino | methyl | H | H | H | 3,5-dichlorophenyl | (4S)-3,4-dihydro-2H-chromen-4-yl |
| 523 | H | dimethylamino | methyl | H | H | H | 2,3-dichlorophenyl | (4S)-3,4-dihydro-2H-chromen-4-yl |

TABLE 1-continued

Examples

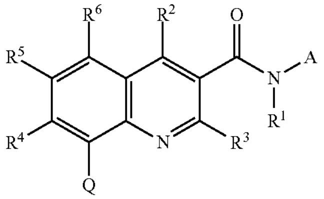

(I)

| Number | R1 | R2 | R3 | R4 | R5 | R6 | Q | A |
|---|---|---|---|---|---|---|---|---|
| 524 | H | dimethylamino | methyl | H | H | H | 2,3,5-trifluorophenyl | (4S)-3,4-dihydro-2H-chromen-4-yl |
| 525 | H | ethyl(methyl)amino | H | H | H | H | 2,3-dichlorophenyl | (4S)-3,4-dihydro-2H-chromen-4-yl |
| 526 | H | isopropyl(methyl)amino | H | H | H | H | 2,3-dichlorophenyl | (4S)-3,4-dihydro-2H-chromen-4-yl |
| 527 | H | ethyl(methyl)amino | H | H | H | H | 3,5-dichlorophenyl | (4S)-3,4-dihydro-2H-chromen-4-yl |
| 528 | H | dimethylamino | H | amino | H | H | 5-chloro-2-fluorophenyl | (4S)-3,4-dihydro-2H-chromen-4-yl |
| 529 | H | dimethylamino | H | amino | H | H | 3,5-dichlorophenyl | (4S)-3,4-dihydro-2H-chromen-4-yl |
| 530 | H | morpholin-4-yl | H | H | H | methoxy | 3,5-dichlorophenyl | (4S)-3,4-dihydro-2H-chromen-4-yl |
| 531 | H | morpholin-4-yl | H | H | H | chloro | 5-chloro-2-fluorophenyl | (4S)-3,4-dihydro-2H-chromen-4-yl |
| 532 | H | morpholin-4-yl | H | H | H | chloro | 2,3-dichlorophenyl | (4S)-3,4-dihydro-2H-chromen-4-yl |
| 533 | H | morpholin-4-yl | H | H | H | chloro | 3,5-dichlorophenyl | (4S)-3,5-dihydro-2H-chromen-4-yl |
| 534 | H | isopropyl(methyl)amino | H | H | H | H | 3,5-dichlorophenyl | (4S)-3,4-dihydro-2H-chromen-4-yl |
| 535 | H | methoxy(methyl)amino | H | chloro | H | H | 2,6-dichloropyridin-4-yl | (4S)-3,4-dihydro-2H-chromen-4-yl |
| 536 | H | morpholin-4-yl | H | amino | H | H | 5-chloro-2-fluorophenyl | (4S)-3,4-dihydro-2H-chromen-4-yl |
| 537 | H | morpholin-4-yl | H | amino | H | H | 2,3-dichlorophenyl | (4S)-3,4-dihydro-2H-chromen-4-yl |
| 538 | H | morpholin-4-yl | H | amino | H | H | 3,5-dichlorophenyl | (4S)-3,4-dihydro-2H-chromen-4-yl |
| 539 | H | oxan-4-yl | H | H | H | H | 3,5-dichlorophenyl | (4S)-3,4-dihydro-2H-chromen-4-yl |
| 540 | H | morpholin-4-yl | H | fluoro | H | H | 3,4,5-trifluorophenyl | (4S)-3,4-dihydro-2H-chromen-4-yl |
| 541 | H | methylamino | H | fluoro | H | H | 2,3-dichlorophenyl | (4S)-3,4-dihydro-2H-chromen-4-yl |
| 542 | H | methylamino | H | fluoro | H | H | 2,3,5-trifluorophenyl | (4S)-3,4-dihydro-2H-chromen-4-yl |
| 543 | H | morpholin-4-yl | H | fluoro | H | H | 2,5-dichloro-3-thienyl | (4S)-3,4-dihydro-2H-chromen-4-yl |
| 544 | H | morpholin-4-yl | H | fluoro | H | H | 2,5-dimethyl-3-thienyl | (4S)-3,4-dihydro-2H-chromen-4-yl |
| 545 | H | methylamino | H | fluoro | H | H | 2,6-dichloropyridin-4-yl | (4S)-3,4-dihydro-2H-chromen-4-yl |
| 546 | H | morpholin-4-yl | H | fluoro | H | H | 4-(difluoromethoxy)-yl)-3,5-difluorophenyl | (4S)-3,4-dihydro-2H-chromen-4-yl |
| 547 | H | methylamino | H | fluoro | H | H | 4-(difluoromethoxy)-3,5-difluorophenyl | (4S)-3,4-dihydro-2H-chromen-4-yl |
| 548 | H | moprholin-4-yl | H | fluoro | H | H | 2,3-difluorophenyl | (4S)-3,4-dihydro-2H-chromen-4-yl |
| 549 | H | morpholin-4-yl | H | fluoro | H | H | 2,3,4-trifluorophenyl | (4S)-3,4-dihydro-2H-chromen-4-yl |
| 550 | H | morpholin-4-yl | H | fluoro | H | H | 2,6-dichloropyridin-4-yl | (4S)-3,4-dihydro-2H-chromen-4-yl |
| 551 | H | dimethylamino | H | amino | H | H | 2,3-dichlorophenyl | (4S)-3,4-dihydro-2H-chromen-4-yl |

TABLE 1-continued

Examples (I)

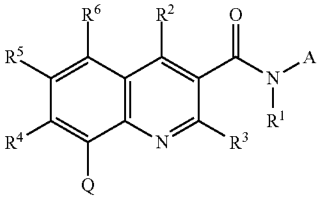

| Number | R1 | R2 | R3 | R4 | R5 | R6 | Q | A |
|---|---|---|---|---|---|---|---|---|
| 552 | H | methyl | H | H | H | H | 2,3-dichlorophenyl | (4S)-3,4-dihydro-2H-chromen-4-yl |
| 553 | H | morpholin-4-yl | H | chloro | H | H | 2,6-dichloropyridin-4-yl | (4S)-3,4-dihydro-2H-chromen-4-yl |
| 554 | H | methyl | H | H | H | H | 2,3,5-trifluorophenyl | (4S)-3,4-dihydro-2H-chroman-4-yl |
| 555 | H | dimethylamino | H | H | H | H | 3,5-dichlorophenyl | (1rac)-1-methyl-3,4-dihydro-2H-naphthalen-1-yl |
| 556 | H | morpholin-4-yl | H | chloro | H | H | 3,5-difluorophenyl | (4S)-3,4-dihydro-2H-chromen-4-yl |
| 557 | H | morpholin-4-yl | H | chloro | H | H | 3-chloro-5-fluorophenyl | (4S)-3,4-dihydro-2H-chromen-4-yl |
| 558 | H | morpholin-4-yl | H | chloro | H | H | 3-(trifluoromethyl) phenyl | (4S)-3,4-dihydro-2H-chromen-4-yl |
| 559 | H | dimethylamino | H | hydroxy | H | H | 5-chloro-2-fluorophenyl | (4S)-3,4-dihydro-2H-chromen-4-yl |
| 560 | H | dimethylamino | H | hydroxy | H | H | 2,3-dichlorophenyl | (4S)-3,4-dihydro-2H-chromen-4-yl |
| 561 | H | dimethylamino | H | hydroxy | H | H | 3,5-dichlorophenyl | (4S)-3,4-dihydro-2H-chromen-4-yl |
| 562 | H | 4-oxoimidazolidin-1-yl | H | H | H | H | 2,3-dichlorophenyl | (4S)-3,4-dihydro-2H-chromen-4-yl |
| 563 | H | 4-oxoimidazolidin-1-yl | H | H | H | H | 2,3,5-trichlorophenyl | (4S)-3,4-dihydro-2H-chromen-4-yl |
| 564 | H | morpholin-4-yl | H | chloro | H | H | 3-chloro-2-fluorophenyl | (4S)-3,4-dihydro-2H-chromen-4-yl |
| 565 | H | morpholin-4-yl | H | chloro | H | H | 5-chloro-2-fluorophenyl | (4S)-3,4-dihydro-2H-chromen-4-yl |
| 566 | H | 2-hydroxyethylamino | H | H | H | H | 2,3,5-trichlorophenyl | (4S)-3,4-dihydro-2H-chromen-4-yl |
| 567 | H | 2-hydroxyethylamnio | H | H | H | H | 2,3,5-trifluorophenyl | (4S)-3,4-dihydro-2H-chromen-4-yl |
| 568 | H | 2-hydroxyethylamino | H | H | H | H | 2,6-dichloropyridin-4-yl | (4S)-3,4-dihydro-2H-chromen-4-yl |
| 569 | H | 4-oxoimidazolidin-1-yl | H | H | H | H | 3-(trifluoromethoxy) phenyl | (4S)-3,4-dihydro-2H-chromen-4-yl |
| 570 | H | ethyl | H | H | H | H | 3-(trifluoromethoxy) yl)phenyl | (4S)-3,4-dihydro-2H-chromen-4-yl |
| 571 | H | methyl | H | H | H | H | 3-(trifluoromethoxy) phenyl | (4S)-3,4-dihydro-2H-chromen-4-yl |
| 572 | H | methyl | H | H | H | H | 2,3,5-trichlorophenyl | (4S)-3,4-dihydro-2H-chromen-4-yl |
| 573 | H | ethyl | H | H | H | H | 2,3,5-trichlorophenyl | (4S)-3,4-dihydro-2H-chromen-4-yl |
| 574 | H | dimethylamino | H | H | H | H | 3,5-diethylphenyl | (4S)-3,4-dihydro-2H-chromen-4-yl |
| 575 | H | ethyl | H | H | H | H | 2,3-dichlorophenyl | (4S)-3,4-dihydro-2H-chromen-4-yl |
| 576 | H | morpholin-4-yl | H | chloro | H | H | 2,3,5-trifluorophenyl | (4S)-3,4-dihydro-2H-chromen-4-yl |
| 577 | H | 2-hydroxyethylamino | H | fluoro | H | H | 2,3-dichlorophenyl | (4S)-3,4-dihydro-2H-chromen-4-yl |
| 578 | H | 2-hydroxyethylamino | H | fluoro | H | H | 3,5-dichlorophenyl | (4S)-3,4-dihydro-2H-chromen-4-yl |
| 579 | H | 2-hydroxyethylamino | H | fluoro | H | H | 2,3,5-trifluorophenyl | (4S)-3,4-dihydro-2H-chromen-4-yl |

TABLE 1-continued

Examples

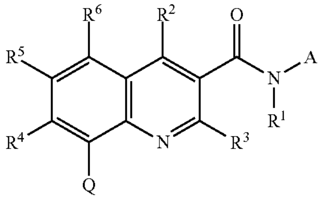

(I)

| Number | R1 | R2 | R3 | R4 | R5 | R6 | Q | A |
|---|---|---|---|---|---|---|---|---|
| 580 | H | dimethylamino | H | H | H | H | 3,5-dichlorophenyl | (4rac)-6-bromochroman-4-yl |
| 581 | H | dimethylamino | H | H | H | H | 3,5-dichlorophenyl | (4rac)-3,4-dihydro-1H-isochromen-4-yl |
| 582 | H | dimethylamino | H | H | H | H | 2-chloro-3,5-diethylphenyl | (4S)-3,4-dihydro-2H-chromen-4-yl |
| 583 | H | morpholin-4-yl | H | H | H | H | 2-chloro-3,5-diethylphenyl | (4S)-3,4-dihydro-2H-chromen-4-yl |
| 584 | H | morpholin-4-yl | H | hydroxy | H | H | 5-chloro-2-fluorophenyl | (4S)-3,4-dihydro-2H-chromen-4-yl |
| 585 | H | dimethylaminocarbonyl | H | H | H | H | 3,5-dichlorophenyl | (4S)-3,4-dihydro-2H-chromen-4-yl |
| 586 | H | dimethylamino | H | H | H | H | 3-tert-butyl-5-methylphenyl | (4S)-3,4-dihydro-2H-chromen-4-yl |
| 587 | H | moprholin-4-yl | H | H | H | H | 3-tert-butyl-5-methylphenyl | (4S)-3,4-dihydro-2H-chromen-4-yl |
| 588 | H | morpholin-4-yl | H | H | H | H | 3,5-diethylphenyl | (4S)-3,4-dihydro-2H-chromen-4-yl |
| 589 | H | 2-hydroxyethyl(methyl)amino | H | H | H | H | 2,3-dichlorophenyl | (4S)-3,4-dihydro-2H-chromen-4-yl |
| 590 | H | 2-hydroxyethyl(methyl)amino | H | H | H | H | 2,3,5-trichlorophenyl | (4S)-3,4-dihydro-2H-chromen-4-yl |
| 591 | H | 2-hydroxyethyl(methyl)amino | H | H | H | H | 2,6-dichloropyridin-4-yl | (4S)-3,4-dihydro-2H-chromen-4-yl |
| 592 | H | hydroxymethyl | H | H | H | H | 3,5-dichlorophenyl | (4S)-3,4-dihydro-2H-chromen-4-yl |
| 593 | H | 2-hydroxyethyl | H | H | H | H | 3,5-dichlorophenyl | (4S)-3,4-dihydro-2H-chromen-4-yl |
| 594 | H | morpholin-4-yl | H | H | H | H | 3-cyano-5-methylphenyl | (4S)-3,4-dihydro-2H-chromen-4-yl |
| 595 | H | methyl-[[-(3rac)-oxolan-3-yl]methyl]amino | H | fluoro | H | H | 2,3-dichlorophenyl | (4S)-3,4-dihydro-2H-chromen-4-yl |
| 596 | H | 2-(1H-pyrazol-1-yl)ethylamino | H | fluoro | H | H | 2,3,5-trifluorophenyl | (4S)-3,4-dihydro-2H-chromen-4-yl |
| 597 | H | 2-hydroxyethylamino | H | fluoro | H | H | 2,6-dichloropyridin-4-yl | (4S)-3,4-dihydro-2H-chromen-4-yl |
| 598 | H | dimethylamino | H | H | H | H | 3-cyano-5-methylphenyl | (4S)-3,4-dihydro-2H-chromen-4-yl |
| 599 | H | 2-(1H-imidazol-1-yl)ethylamino | H | fluoro | H | H | 2,3-dichlorophenyl | (4S)-3,4-dihydro-2H-chromen-4-yl |
| 600 | H | methyl | H | H | H | H | 2-chloro-5-fluorophenyl | (4S)-3,4-dihydro-2H-chromen-4-yl |
| 601 | H | dimethylamino | H | H | H | H | 5-tert-butyl-2-chloro-3-methylphenyl | (4S)-3,4-dihydro-2H-chromen-4-yl |
| 602 | H | 4-oxoimidazolidin-1-yl | H | H | H | H | 2-chloro-5-fluorophenyl | (4S)-3,4-dihydro-2H-chromen-4-yl |
| 603 | H | ethyl | H | H | H | H | 2-chloro-5-fluorophenyl | (4S)-3,4-dihydro-2H-chromen-4-yl |
| 604 | H | 4-oxoimidazolidin-1-yl | H | H | H | H | 5-chloro-2-fluorophenyl | (4S)-3,4-dihydro-2H-chromen-4-yl |
| 605 | H | methyl | H | H | H | H | 5-chloro-2-fluorophenyl | (4S)-3,4-dihydro-2H-chromen-4-yl |
| 606 | H | 2-hydroxyethyl(methyl)amino | H | H | H | H | 2,3,5-trifluorophenyl | (4S)-3,4-dihydro-2H-chromen-4-yl |

TABLE 1-continued

Examples

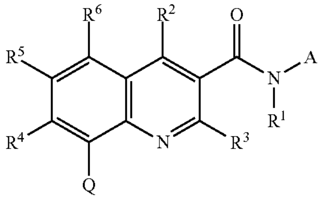

(I)

| Number | R1 | R2 | R3 | R4 | R5 | R6 | Q | A |
|---|---|---|---|---|---|---|---|---|
| 607 | H | morpholin-4-yl | H | H | H | H | 5-tert-butyl-2-chloro-3-methylphenyl | (4S)-3,4-dihydro-2H-chromen-4-yl |
| 608 | H | morpholin-4-yl | H | H | H | H | 2,3-dichloro-5-cyanophenyl | (4S)-3,4-dihydro-2H-chromen-4-yl |
| 609 | H | morpholin-4-yl | H | trifluoro-methoxy | H | H | 5-chloro-2-fluorophenyl | (4S)-3,4-dihydro-2H-chromen-4-yl |
| 610 | H | morpholin-4-yl | H | trifluoro-methoxy | H | H | 2,3-dichlorophenyl | (4S)-3,4-dihydro-2H-chromen-4-yl |
| 611 | H | morpholin-4-yl | H | trifluroo-methoxy | H | H | 3,5-dichlorophenyl | (4S)-3,4-dihydro-2H-chromen-4-yl |
| 612 | H | dimethylamino | H | trifluoro-methoxy | H | H | 5-chloro-2-fluorophenyl | (4S)-3,4-dihydro-2H-chromen-4-yl |
| 613 | H | dimethylamino | H | trifluoro-methoxy | H | H | 2,3-dichlorophenyl | (4S)-3,4-dihydro-2H-chromen-4-yl |
| 614 | H | dimethylamino | H | trifluoro-methoxy | H | H | 3,5-dichlorophenyl | (4S)-3,4-dihydro-2H-chromen-4-yl |
| 615 | H | morpholin-4-yl | H | hydroxy | H | H | 2,3-dichlorophenyl | (4S)-3,4-dihydro-2H-chromen-4-yl |
| 616 | H | morpholin-4-yl | H | hydroxy | H | H | 3,5-dichlorophenyl | (4S)-3,4-dihydro-2H-chromen-4-yl |
| 617 | H | dimethylamino | H | cyano | H | H | 3,5-dichlorophenyl | (4S)-3,4-dihydro-2H-chromen-4-yl |
| 618 | H | dimethylamino | H | H | hydroxy | H | 5-chloro-2-fluorophenyl | (4S)-3,4-dihydro-2H-chromen-4-yl |
| 619 | H | dimethylamino | H | H | hydroxy | H | 2,3-dichlorophenyl | (4S)-3,4-dihydro-2H-chromen-4-yl |
| 620 | H | dimethylamino | H | H | H | H | 3,5-dichlorophenyl | (4rac)-8-fluorochroman-4-yl |
| 621 | H | dimethylamino | H | H | H | H | 3,5-dichlorophenyl | (4rac)-6,8-dichlorochroman-4-yl |
| 622 | H | dimethylamino | H | H | H | H | 3,5-dichlorophenyl | (4rac)-6-chlorochroman-4-yl |
| 623 | H | dimethylamino | H | H | H | H | 3,5-dichlorophenyl | (4rac)-6-fluorochroman-4-yl |
| 624 | H | dimethylamino | H | H | H | H | 2,3-dichloro-5-cyanophenyl | (4S)-3,4-dihydro-2H-chromen-4-yl |
| 625 | H | 2-(1H-imidazol-1-yl)ethylamino | H | H | H | H | 3,5-dichlorophenyl | (4S)-3,4-dihydro-2H-chromen-4-yl |
| 626 | H | morpholin-4-yl | H | H | hydroxy | H | 5-chloro-2-fluorophenyl | (4S)-3,4-dihydro-2H-chromen-4-yl |
| 627 | H | morpholin-4-yl | H | H | hydroxy | H | 3,5-dichlorophenyl | (4S)-3,4-dihydro-2H-chromen-4-yl |
| 628 | H | ethyl | H | H | H | H | 5-chloro-2-fluorophenyl | (4S)-3,4-dihydro-2H-chromen-4-yl |
| 629 | H | methylamino | H | chloro | H | H | 3,5-dichlorophenyl | (4S)-3,4-dihydro-2H-chromen-4-yl |
| 630 | H | morpholin-4-yl | H | chloro | H | H | 3,5-dichlorophenyl | (1rac)-3,3-dimethylindan-1-yl |

TABLE 1-continued

Examples

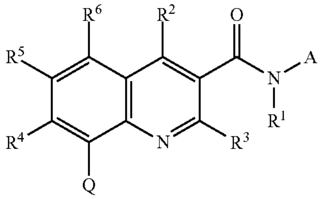

(I)

| Number | R1 | R2 | R3 | R4 | R5 | R6 | Q | A |
|---|---|---|---|---|---|---|---|---|
| 631 | H | [acetyl(methyl)amino]meth-yl | H | H | H | H | 3,5-dichlorophenyl | (4S)-3,4-dihydro-2H-chromen-4-yl |
| 632 | H | dimethylamino | H | H | H | H | 3,5-dichlorophenyl | (4rac)-8-chlorochroman-4-yl |
| 633 | H | dimethylamino | H | H | H | H | 3,5-dichlorophenyl | (4rac)-6,8-difluorochroman-4-yl |
| 634 | H | dimethylamino | H | H | H | H | 3,5-dichlorophenyl | (4rac)-8-bromochroman-4-yl |
| 635 | H | morpholin-4-yl | H | chloro | H | H | 3,5-dichlorophenyl | (1rac)-3-oxoindan-1-yl |
| 636 | H | methylamino | H | chloro | H | H | 2,3,5-trifluorophenyl | (4S)-3,4-dihydro-2H-chromen-4-yl |
| 637 | H | ethylamino | H | fluoro | H | H | 2,3-dichlorophenyl | (4S)-3,4-dihydro-2H-chromen-4-yl |
| 638 | H | ethylamino | H | fluoro | H | H | 3,5-dichlorophenyl | (4S)-3,4-dihydro-2H-chromen-4-yl |
| 639 | H | ethylamino | H | fluoro | H | H | 2,3,5-trifluorophenyl | (4S)-3,4-dihydro-2H-chromen-4-yl |
| 640 | H | ethylamino | H | fluoro | H | H | 2,6-dichloropyridin-4-yl | (4S)-3,4-dihydro-2H-chromen-4-yl |
| 641 | H | 2-acetyloxyethylamino | H | H | H | H | 2,3-dichlorophenyl | (4S)-3,4-dihydro-2H-chromen-4-yl |
| 642 | H | morpholin-4-yl | H | cyano | H | H | 5-chloro-2-fluorophenyl | (4S)-3,4-dihydro-2H-chromen-4-yl |
| 643 | H | 2-(dimethylamino)ethyl | H | H | H | H | 3,5-dichlorophenyl | (4S)-3,4-dihydro-2H-chromen-4-yl |
| 644 | H | 2-(1H-imidazol-1-yl)ethyl-methylamio | H | fluoro | H | H | 3,5-dichlorophenyl | (4S)-3,4-dihydro-2H-chromen-4-yl |
| 645 | H | methyl | H | H | H | H | 2-chloro-5-methylphenyl | (4S)-3,4-dihydro-2H-chromen-4-yl |
| 646 | H | ethyl | H | H | H | H | 2-chloro-5-methylphenyl | (4S)-3,4-dihydro-2H-chromen-4-yl |
| 647 | H | methyl(2-methylsulfonylethyl)ami-no | H | fluoro | H | H | 3,5-dichlorophenyl | (4S)-3,4-dihydro-2H-chromen-4-yl |
| 648 | H | 3-fluoroazetidin-1-yl | H | fluoro | H | H | 3,5-dichlorophenyl | (4S)-3,4-dihydro-2H-chromen-4-yl |
| 649 | H | 2-hydroxyethyl(methyl)a-mino | H | fluoro | H | H | 3,5-dihclorophenyl | (4S)-3,4-dihydro-2H-chromen-4-yl |
| 650 | H | (3-methoxy-3-oxopropyl)-methylamino | H | fluoro | H | H | 3,5-dichlorophenyl | (4S)-3,4-dihydro-2H-chromen-4-yl |
| 651 | H | morpholin-4-yl | H | H | H | cyano | 5-chloro-2-fluorophenyl | (4S)-3,4-dihydro-2H-chromen-4-yl |
| 652 | H | morpholin-4-yl | H | cyano | H | H | 3,5-dichlorophenyl | (4S)-3,4-dihydro-2H-chromen-4-yl |
| 653 | H | 3,6-dihydro-2H-pyran-4-yl | H | H | H | H | 2,3-dichlorophenyl | (4S)-3,4-dihydro-2H-chromen-4-yl |

TABLE 1-continued

Examples

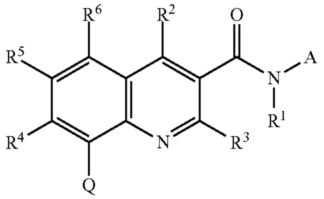

(I)

| Number | R1 | R2 | R3 | R4 | R5 | R6 | Q | A |
|---|---|---|---|---|---|---|---|---|
| 654 | H | 1,3-dimethyl-2,4-dioxo-1,2,3,4-tetrahydropyrimidin-5-yl | H | H | H | H | 3,5-dichlorophenyl | (4S)-3,4-dihydro-2H-chromen-4-yl |
| 655 | H | ethyl | H | H | H | H | 2,3,5-trifluorophenyl | (4S)-3,4-dihydro-2H-chromen-4-yl |
| 656 | H | dimethylamino | H | H | H | H | 5-chloro-1H-imidazol-2-yl | (4S)-3,4-dihydro-2H-chromen-4-yl |
| 657 | H | morpholin-4-yl | H | H | H | cyano | 2,3-dichlorophenyl | (4S)-3,4-dihydro-2H-chromen-4-yl |
| 658 | H | dimethylamino | H | H | H | cyano | 5-chloro-2-fluorophenyl | (4S)-3,4-dihydro-2H-chromen-4-yl |
| 659 | H | dimethylamino | H | H | H | cyano | 2,3-dichlorophenyl | (4S)-3,4-dihydro-2H-chromen-4-yl |
| 660 | H | oxetan-3-yl | H | H | H | H | 2,3,5-trifluorophenyl | (4S)-3,4-dihydro-2H-chromen-4-yl |
| 661 | H | methyl(2-methylsulfonylethyl)amino | H | fluoro | H | H | 2,6-dichloropyridin-4-yl | (4S)-3,4-dihydro-2H-chromen-4-yl |
| 662 | H | iodo | H | H | H | H | 2,3,5-trifluorophenyl | (4S)-3,4-dihydro-2H-chromen-4-yl |
| 663 | H | morpholin-4-yl | H | H | H | cyano | 3,5-dichlorophenyl | (4S)-3,4-dihydro-2H-chromen-4-yl |
| 664 | H | dimethylamino | H | H | H | cyano | 3,5-dichlorophenyl | (4S)-3,4-dihydro-2H-chromen-4-yl |
| 665 | H | dimethylamino | H | H | H | H | 3,5-dichlorophenyl | (4rac)-8-fluoro-3,4-dihydro-1H-isochromen-4-yl |
| 666 | H | 2-hydroxyethyl)methyl)amino | H | fluoro | H | H | 3,5-dichlorophenyl | (1S)-2,3-dihydro-1H-inden-1-yl |
| 667 | H | dimethylamino | H | H | H | H | 3,5-dichlorophenyl | (1rac)-3-oxoindan-1-yl |
| 668 | H | dimethylamino | H | chloro | H | H | 2,6-dichloropyridin-4-yl | (4S)-3,4-dihydro-2H-chromen-4-yl |
| 669 | H | dimethylamino | H | chloro | H | H | 3,5-difluorophenyl | (4S)-3,4-dihydro-2H-chromen-4-yl |
| 670 | H | dimethylamino | H | chloro | H | H | 3-tert-butyl-5-methylphenyl | (4S)-3,4-dihydro-2H-chromen-4-yl |
| 671 | H | dimethylamino | H | chloro | H | H | 3-(trifluoromethyl)phenyl | (4S)-3,4-dihydro-2H-chromen-4-yl |
| 672 | H | dimethylamino | H | chloro | H | H | 3,5-dimethylphenyl | (4S)-3,4-dihydro-2H-chromen-4-yl |
| 673 | H | 2-(1H-pyrazol-1-yl)ethylamino | H | fluoro | H | H | 2,6-dichloropyridin-4-yl | (4S)-3,4-dihydro-2H-chromen-4-yl |
| 674 | H | 2-hydroxyethyl(methyl)amino | H | chloro | H | H | 3,5-dichlorophenyl | (4S)-3,4-dihydro-2H-chromen-4-yl |
| 676 | H | ethyl | H | H | H | H | 2,5-dimethylphenyl | (4S)-3,4-dihydro-2H-chromen-4-yl |
| 677 | H | (3rac)-pyrrolidin-3-yl | H | H | H | H | 2,3,5-trifluorophenyl | (4S)-3,4-dihydro-2H-chromen-4-yl |

TABLE 1-continued

Examples

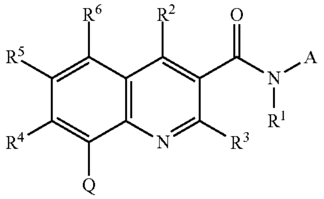

(I)

| Number | R1 | R2 | R3 | R4 | R5 | R6 | Q | A |
|---|---|---|---|---|---|---|---|---|
| 678 | H | (3rac)-tetrahydrofuran-3-yl | H | H | H | H | 2,3,5-trifluorophenyl | (4S)-3,4-dihydro-2H-chromen-4-yl |
| 679 | H | 1-methyl-piperidin-4-yl | H | H | H | H | 2,3,5-trifluorophenyl | (4S)-3,4-dihydro-2H-chromen-4-yl |
| 680 | H | morpholin-4-yl | H | H | H | hydroxy | 2,3-dichlorophenyl | (4S)-3,4-dihydro-2H-chromen-4-yl |
| 681 | H | morpholin-4-yl | H | H | H | hydroxy | 3,5-dichlorophenyl | (4S)-3,4-dihydro-2H-chromen-4-yl |
| 682 | H | dimethylamino | H | H | H | hydroxy | 2,3-dichlorophenyl | (4S)-3,4-dihydro-2H-chromen-4-yl |
| 683 | H | dimethylamino | H | H | H | hydroxy | 3,5-dichlorophenyl | (4S)-3,4-dihydro-2H-chromen-4-yl |
| 684 | H | isopropyl | H | fluoro | H | H | 2,5-dimethylphenyl | (4S)-3,4-dihydro-2H-chromen-4-yl |
| 685 | H | methyl | H | H | H | H | 2,5-dimethylphenyl | (4S)-3,4-dihydro-2H-chromen-4-yl |
| 686 | H | methoxymethyl | H | H | H | H | 2,3,5-trifluorophenyl | (4S)-3,4-dihydro-2H-chromen-4-yl |
| 687 | H | ethyl | H | H | H | H | 3,5-difluorophenyl | (4S)-3,4-dihydro-2H-chromen-4-yl |
| 688 | H | ethyl | H | H | H | H | 2,3,5-trifluorophenyl | (4S)-3,4-dihydro-2H-chromen-4-yl |
| 689 | H | morpholin-4-yl | H | fluoro | H | fluoro | 2,3,5-trifluorophenyl | (4S)-3,4-dihydro-2H-chromen-4-yl |
| 690 | H | dimethylamino | H | fluoro | H | fluoro | 2,3,5-trifluorophenyl | (4S)-3,4-dihydro-2H-chromen-4-yl |
| 691 | H | morpholin-4-yl | H | fluoro | H | fluoro | 3,5-dichlorophenyl | (4S)-3,4-dihydro-2H-chromen-4-yl |
| 692 | H | dimethylamino | H | fluoro | H | fluoro | 3,5-dichlorophenyl | (4S)-3,4-dihydro-2H-chromen-4-yl |
| 693 | H | morpholin-4-yl | H | fluoro | H | fluoro | 2,3-dichlorophenyl | (4S)-3,4-dihydro-2H-chromen-4-yl |
| 694 | H | dimethylamino | H | fluoro | H | fluoro | 2,3-dichlorophenyl | (4S)-3,4-dihydro-2H-chromen-4-yl |
| 695 | H | methyl | H | H | H | H | 3,5-difluorophenyl | (4S)-3,4-dihydro-2H-chromen-4-yl |

TABLE 2

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 1 | | LC-MS (Method L1): Rt = 1.42 min; MS (ESIpos): m/z = 440 [M + H]+ | $^1$H-NMR (400 MHz, DMSO-d6) delta [ppm]: −0.008 (4.41), 0.008 (4.06), 2.342 (16.00), 2.759 (1.07), 7.059 (1.60), 7.111 (0.66), 7.128 (1.05), 7.183 (4.61), 7.195 (1.69), 7.202 (0.82), 7.207 (0.96), 7.422 (0.89), 7.438 (0.75), 7.855 (4.02), 7.865 (2.24), 7.869 (2.26), 8.303 (1.26), 8.314 (1.10), 8.317 (1.07), 8.328 (1.10), 8.874 (5.11), 9.102 (0.96), 9.123 (0.96). |
| 2 | | LC-MS (Method L1): Rt = 1.47 min; MS (ESIpos): m/z = 481 [M + H]+ | $^1$H-NMR (400 MHz, DMSO-d6) delta [ppm]: −0.008 (3.38), 1.805 (1.14), 1.836 (2.05), 1.854 (1.44), 1.862 (1.41), 1.867 (1.25), 1.879 (1.41), 1.887 (1.60), 1.910 (1.44), 1.932 (1.44), 1.946 (1.07), 1.960 (0.93), 2.045 (1.14), 2.069 (1.54), 2.080 (1.05), 2.088 (1.03), 2.746 (1.96), 2.760 (3.98), 2.771 (3.46), 2.787 (1.53), 3.289 (3.24), 5.230 (0.89), 5.248 (1.82), 5.265 (1.70), 5.281 (0.81), 7.111 (2.30), 7.128 (3.40), 7.161 (1.10), 7.166 (1.44), 7.179 (3.34), 7.184 (3.63), 7.190 (3.11), 7.196 (4.53), 7.202 (2.62), 7.208 (2.92), 7.212 (2.70), 7.226 (0.95), 7.422 (3.20), 7.439 (2.63), 7.444 (2.24), 7.675 (7.89), 7.679 (16.00), 7.683 (9.38), 7.687 (5.20), 7.692 (1.77), 7.889 (2.30), 7.907 (3.45), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.909 (4.06), 7.928 (3.18), 7.999 (3.67), 8.002 (4.95), 8.017 (2.68), 8.020 (3.30), 8.383 (3.21), 8.386 (4.14), 8.404 (2.94), 8.407 (3.59), 8.940 (10.21), 9.119 (3.46), 9.141 (3.28). |
| 3 | | LC-MS (Method L1): Rt = 1.37 min; MS (ESIpos): m/z = 467 [M + H]+ | $^1$H-NMR (400 MHz, DMSO-d6) delta [ppm]: 0.008 (1.33), 1.234 (2.20), 1.397 (0.85), 1.924 (1.63), 1.935 (0.83), 1.946 (1.76), 1.956 (1.90), 1.967 (0.79), 1.977 (1.84), 1.998 (0.66), 2.524 (2.18), 2.567 (0.88), 2.575 (0.77), 2.838 (0.77), 2.859 (1.28), 2.878 (2.28), 2.898 (2.50), 2.918 (1.19), 2.951 (1.54), 2.959 (1.64), 2.973 (1.71), 2.980 (1.81), 2.990 (0.99), 2.999 (0.88), 3.012 (0.86), 3.020 (0.74), 3.070 (1.91), 5.542 (1.02), 5.562 (2.83), 5.582 (2.79), 5.602 (0.92), 7.223 (0.96), 7.232 (4.00), 7.240 (4.95), 7.246 (5.24), 7.254 (7.15), 7.263 (2.96), 7.271 (3.67), 7.281 (2.50), 7.293 (1.17), 7.435 (2.55), 7.446 (2.61), 7.456 (2.00), 7.635 (1.10), 7.665 (0.98), 7.678 (13.08), 7.681 (16.00), 7.686 (7.10), 7.689 (3.73), 7.695 (1.37), 7.700 (0.80), 7.895 (2.06), 7.913 (4.25), 7.934 (3.06), 8.004 (4.66), 8.008 (3.27), 8.022 (3.28), 8.026 (2.07), 8.393 (4.14), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.396 (2.75), 8.414 (3.73), 8.417 (2.39), 8.962 (10.00), 9.118 (3.31), 9.139 (3.23). |
| 4 | | LC-MS (Method L1): Rt = 1.33 min; MS (ESIpos): m/z = 483 [M + H]+ | $^1$H-NMR (400 MHz, DMSO-d6) delta [ppm]: 0.008 (2.60), 0.833 (1.52), 0.839 (3.28), 0.855 (3.89), 0.859 (2.26), 0.871 (1.10), 0.876 (0.82), 1.106 (9.55), 1.157 (1.22), 1.175 (2.15), 1.193 (1.15), 1.988 (3.86), 2.058 (0.88), 2.066 (0.96), 2.076 (1.10), 2.086 (2.40), 2.093 (1.49), 2.100 (1.27), 2.109 (0.88), 2.196 (0.93), 2.208 (1.32), 2.221 (1.22), 2.229 (1.16), 2.243 (0.82), 3.076 (2.73), 3.288 (3.01), 4.021 (0.91), 4.038 (0.91), 4.221 (0.77), 4.241 (2.10), 4.249 (1.66), 4.261 (2.02), 4.270 (2.60), 4.279 (2.07), 4.287 (1.71), 4.296 (1.82), 5.266 (0.85), 5.281 (1.90), 5.301 (1.91), 5.315 (0.88), 6.789 (3.17), 6.791 (3.20), 6.809 (3.59), 6.812 (3.55), 6.916 (1.71), 6.918 (1.65), 6.934 (3.51), 6.937 (3.37), 6.953 (2.16), 6.956 (1.99), 7.157 (1.74), 7.162 (1.79), 7.179 (2.96), 7.196 (1.43), 7.200 (1.40), 7.379 (3.11), 7.398 (2.90), 7.676 (7.53), 7.680 (16.00), 7.685 (7.22), 7.688 (4.08), 7.694 (1.49), 7.893 (2.34), 7.911 (3.81), 7.914 (3.22), 7.932 (3.47), 8.006 (4.05), 8.010 (4.08), 8.024 (3.07), 8.027 (2.79), 8.387 (3.53), 8.390 (3.48), 8.408 (3.33), 8.411 (3.06). 8.962 (10.68), 9.251 (3.18), 9.272 (3.11), |
| 5 | | LC-MS (Method L1): Rt = 1.24 min; MS (ESIpos): m/z = 449 [M + H]+ | $^1$H-NMR (400 MHz, DMSO-d6) delta [ppm]: −0.008 (3.48), 0.008 (3.53), 1.157 (0.87), 1.175 (1.69), 1.192 (0.90), 1.988 (2.96), 2.058 (0.97), 2.066 (1.02), 2.075 (1.14), 2.082 (1.14), 2.093 (1.62), 2.100 (1.34), 2.108 (0.97), 2.196 (1.00), 2.209 (1.44), 2.222 (1.34), 2.231 (1.27), 3.289 (3.14), 4.021 (0.70), 4.038 (0.70), 4.221 (0.87), 4.241 (2.39), 4.249 (1.84), 4.261 (2.26), 4.269 (2.89), 4.279 (2.24), 4.287 (1.79), 4.296 (2.04), 5.268 (0.95), 5.282 (2.07), 5.302 (2.07), 5.318 (0.95), 6.788 (3.63), 6.791 (4.03), 6.809 (4.26), 6.811 (4.43), 6.915 (2.02), 6.918 (2.07), 6.934 (4.08), 6.937 (4.13), 6.952 (2.54), 6.956 (2.41), 7.157 (2.04), 7.161 (2.19), 7.178 (3.28), 7.196 (1.67), 7.200 (1.59), 7.378 (3.31), 7.398 (3.16), 7.491 (1.37), 7.496 (1.05), 7.506 (3.83), 7.510 (10.25), 7.515 (4.63), 7.529 (6.47), 7.549 (2.34), 7.572 (3.11), 7.577 (5.20), 7.581 (2.86), 7.589 (1.84), 7.593 (2.59), 7.598 (1.67), 7.675 (2.91), 7.679 (6.05), 7.684 (3.38), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.887 (2.84), 7.905 (4.85), 7.908 (3.73), 7.926 (5.13), 7.958 (5.28), 7.962 (5.82), 7.976 (3.31), 7.979 (2.86), 8.362 (4.30), 8.366 (4.45), 8.383 (4.11), 8.387 (3.83), 8.934 (16.00), 9.244 (3.56), 9.265 (3.46). |
| 6 | | LC-MS (Method L1): Rt = 1.31 min; MS (ESIpos): m/z = 433 [M + H]+ | $^1$H-NMR (400 MHz, DMSO-d6) delta [ppm]: −0.008 (3.23), 0.008 (3.14), 0.853 (0.88), 1.175 (2.40), 1.235 (4.21), 1.925 (1.92), 1.934 (0.91), 1.945 (1.99), 1.956 (2.12), 1.967 (0.92), 1.976 (2.11), 1.998 (0.79), 2.517 (2.33), 2.525 (2.38), 2.568 (0.89), 2.859 (1.26), 2.878 (1.91), 2.899 (2.60), 2.919 (1.22), 2.951 (1.61), 2.959 (1.75), 2.973 (1.77), 2.981 (1.65), 2.990 (0.94), 2.999 (0.87), 3.287 (2.04), 5.544 (1.02), 5.564 (3.03), 5.584 (3.00), 5.604 (0.98), 5.754 (7.31), 6.510 (1.69), 7.232 (5.18), 7.241 (5.18), 7.246 (6.49), 7.255 (9.27), 7.264 (2.87), 7.272 (3.87), 7.281 (2.34), 7.285 (1.99), 7.294 (1.18), 7.434 (2.78), 7.447 (2.68), 7.456 (2.20), 7.488 (0.77), 7.492 (1.58), 7.497 (1.25), 7.507 (4.17), 7.512 (9.71), 7.515 (6.13), 7.517 (5.24), 7.531 (6.56), 7.551 (2.46), 7.574 (3.40), 7.579 (5.63), 7.584 (3.06), 7.592 (1.94), 7.596 (2.78), 7.601 (1.72), 7.676 (3.20), 7.678 (3.96), 7.680 (6.36), 7.685 (3.54), 7.889 (3.03), 7.907 (5.37), 7.910 (3.81), 7.928 (5.57), 7.957 (5.81), 7.961 (6.39), 7.975 (3.50), 7.979 (2.97), 8.368 (4.68), 8.372 (4.77), 8.389 (4.45), 8.393 (4.06), 8.935 (16.00), 9.113 (3.64), 9.134 (3.51). |
| 7 | | LC-MS (Method L1): Rt = 1.24 min; MS (ESIpos): m/z = 483 [M + H]+ | $^1$H-NMR (400 MHz, DMSO-d6) delta [ppm]: 0.008 (3.31), 0.852 (0.82), 1.142 (0.91), 1.157 (1.29), 1.172 (2.28), 1.175 (2.52), 1.192 (1.46), 1.234 (5.59), 1.394 (15.65), 1.398 (16.00), 1.985 (3.80), 1.988 (4.30), 2.039 (2.93), 2.046 (3.13), 2.057 (3.86), 2.064 (3.92), 2.074 (5.03), 2.082 (7.46), 2.086 (6.64), 2.090 (3.57), 2.098 (2.57), 2.185 (3.22), 2.196 (4.56), 2.207 (4.45), 2.218 (4.15), 2.230 (3.16), 2.242 (2.40), 2.251 (1.61), 2.365 (0.76), 2.707 (0.88), 3.288 (5.56), 4.020 (1.05), 4.038 (1.02), 4.204 (2.11), 4.232 (5.79), 4.259 (7.69), 4.268 (7.31), 4.276 (6.03), 4.285 (6.49), 4.296 (2.90), 4.304 (2.52), 4.312 (1.99), 5.251 (2.66), 5.266 (6.52), 5.285 (7.14), 5.300 (3.71), 6.781 (12.26), 6.788 (2.84), 6.801 (13.54), 6.809 (3.01), 6.903 (5.41), 6.922 (11.79), 6.940 (7.05), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 6.953 (1.43), 7.150 (6.38), 7.170 (10.21), 7.189 (4.94), 7.363 (10.65), 7.383 (15.97), 7.403 (10.71), 7.456 (7.17), 7.475 (11.58), 7.495 (5.62), 7.511 (3.80), 7.528 (2.19), 7.548 (0.88), 7.573 (1.93), 7.590 (1.14), 7.677 (2.72), 7.720 (7.52), 7.723 (13.02), 7.727 (7.34), 7.740 (6.82), 7.743 (11.14), 7.747 (6.20), 7.845 (5.00), 7.849 (8.98), 7.852 (5.56), 7.863 (9.83), 7.866 (15.94), 7.870 (9.04), 7.883 (1.11), 7.898 (8.89), 7.902 (9.54), 7.919 (13.05), 7.923 (10.44), 7.937 (5.59), 7.940 (5.21), 7.958 (2.72), 7.976 (1.43), 8.362 (2.05), 8.383 (2.05), 8.397 (12.37), 8.418 (11.26), 8.854 (13.98), 8.860 (14.48), 8.932 (4.65), 9.245 (6.76), 9.254 (6.38), 9.266 (7.08), 9.275 (5.79). |
| 8 | 2.53 | LC-MS (Method L6): Rt = 2.06 min; MS (ESIpos): m/z = 492 [M + H]+ | $^1$H-NMR (400 MHz, DMSO-d6) delta [ppm]: −0.008 (1.11), 0.008 (1.00), 3.066 (16.00), 3.071 (4.46), 3.287 (1.77), 3.926 (1.28), 4.269 (0.87), 6.785 (0.90), 6.788 (0.97), 6.805 (1.03), 6.808 (1.03), 6.925 (0.97), 6.928 (0.93), 6.944 (0.61), 6.947 (0.58), 7.171 (0.77), 7.359 (0.80), 7.378 (0.74), 7.629 (1.51), 7.634 (12.99), 7.647 (1.14), 7.650 (0.96), 7.668 (0.99), 7.790 (1.13), 7.793 (1.20), 7.807 (0.93), 7.811 (0.88), 8.229 (1.01), 8.233 (1.03), 8.251 (0.94), 8.254 (0.89), 8.632 (3.95), 9.084 (0.86), 9.105 (0.84). |
| 9 | | LC-MS (Method L1): Rt = 1.04 min; MS (ESIpos): m/z = 476 [M + H]+ | $^1$H-NMR (400 MHz, DMSO-d6) delta [ppm]: −0.008 (2.94), 0.008 (2.72), 2.323 (0.52), 2.710 (0.57), 3.070 (16.00), 3.286 (4.49), 3.567 (0.42), 5.534 (0.73), 7.220 (1.05), 7.235 (1.05), 7.242 (1.91), 7.267 (0.89), 7.630 (1.27), 7.636 (12.76), 7.648 (1.00), 7.670 (0.93), 7.788 (1.11), 7.792 (1.16), 7.806 (0.97), 8.232 (1.08), 8.253 (0.95), 8.638 (4.07), 8.941 (0.86), 8.962 (0.79). |
| 10 | | LC-MS (Method L6): Rt = 1.69 min; MS (ESIpos): m/z = 476 [M + H]+ | $^1$H-NMR (400 MHz, DMSO-d6) delta [ppm]: −0.008 (1.60), 0.008 (1.51), 2.326 (13.07), 3.055 (16.00), 3.288 (3.31), 6.784 (0.87), 6.787 (0.96), 6.804 (1.02), 6.807 (1.05), 6.922 (0.96), 6.925 (0.93), 6.940 (0.61), 6.943 (0.58), 7.009 (1.28), 7.147 (3.19), 7.584 (0.61), 7.601 (1.16), 7.604 (0.75), 7.622 (1.25), 7.640 (1.28), 7.645 (1.45), 7.658 (0.73), 8.150 (0.99), 8.154 (0.99), 8.170 (0.93), 8.175 (0.84), 8.581 (4.01), 9.069 (0.84), 9.090 (0.81). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 11 | | LC-MS (Method L7): Rt = 2.58 min; MS (ESIpos): m/z = 490 [M + H]+ | $^1$H-NMR (500 MHz, DMSO-d6) delta [ppm]: −0.007 (1.04), 0.007 (1.04), 2.568 (6.31), 3.046 (16.00), 3.286 (1.53), 5.532 (0.72), 5.548 (0.72), 7.220 (1.16), 7.224 (0.84), 7.228 (1.19), 7.233 (1.07), 7.238 (1.68), 7.266 (0.89), 7.403 (0.73), 7.623 (0.69), 7.627 (1.62), 7.631 (1.75), 7.641 (5.09), 7.645 (3.28), 7.664 (1.62), 7.667 (1.70), 8.012 (1.49), 8.014 (1.50), 8.016 (1.25), 8.578 (3.50), 8.934 (0.95), 8.951 (0.93). |
| 12 | | LC-MS (Method L6): Rt = 2.18 min; MS (ESIpos): m/z = 506 [M + H]+ | $^1$H-NMR (400 MHz, DMSO-d6) delta [ppm]: −0.008 (3.00), 0.008 (2.59), 2.566 (6.36), 3.042 (16.00), 3.287 (1.44), 4.270 (0.90), 5.754 (4.48), 6.785 (1.08), 6.806 (1.12), 6.923 (1.03), 6.942 (0.64), 7.168 (0.84), 7.351 (0.82), 7.371 (0.78), 7.621 (0.71), 7.626 (1.60), 7.630 (2.09), 7.639 (6.13), 7.644 (3.08), 7.665 (1.73), 7.670 (1.76), 8.012 (1.45), 8.572 (3.85), 9.076 (0.91), 9.096 (0.91). |
| 13 | | LC-MS (Method L1): Rt = 1.05 min; MS (ESIpos): m/z = 510 [M + H]+ | $^1$H-NMR (400 MHz, DMSO-d6) delta [ppm]: −0.008 (1.31), 0.008 (1.23), 3.065 (16.00), 4.270 (0.87), 6.785 (0.94), 6.788 (1.04), 6.806 (1.05), 6.809 (1.12), 6.926 (0.98), 6.929 (0.96), 6.944 (0.62), 7.171 (0.78), 7.377 (0.73), 7.628 (0.81), 7.646 (1.07), 7.650 (0.98), 7.668 (1.02), 7.802 (4.91), 7.806 (1.58), 7.818 (4.35), 7.824 (1.06), 8.227 (1.02), 8.231 (1.06), 8.249 (0.95), 8.252 (0.89), 8.636 (4.18), 9.087 (0.78), 9.108 (0.78). |
| 14 | | LC-MS (Method L7): Rt = 2.39 min; MS (ESIpos): m/z = 518 [M + H]+ | $^1$H-NMR (400 MHz, CHLOROFORM-d) delta [ppm]: −0.008 (1.09), 0.008 (1.14), 1.562 (5.12), 2.082 (1.48), 2.090 (1.98), 2.098 (3.67), 2.107 (2.27), 2.116 (1.78), 2.588 (16.00), 4.031 (2.54), 4.248 (1.04), 4.259 (1.53), 4.270 (1.04), 6.783 (0.82), 7.213 (0.97), 7.232 (0.93), 7.348 (4.36), 7.353 (5.19), 7.377 (0.81), 7.525 (1.06), 7.530 (1.97), 7.535 (1.20), 7.571 (0.87), 7.590 (1.42), 7.611 (1.29), 7.676 (1.58), 7.679 (1.69), 7.694 (1.17), 7.697 (1.10), 8.088 (1.16), 8.171 (1.22), 8.193 (1.14). |
| 15 | | LC-MS (Method L6): Rt = 1.55 min; MS (ESIpos): m/z = 452 [M + H]+ | $^1$H-NMR (400 MHz, DMSO-d6) delta [ppm]: −0.008 (1.60), 0.008 (1.51), 2.326 (13.07), 3.055 (16.00), 3.288 (3.31), 6.784 (0.87), 6.787 (0.96), 6.804 (1.02), 6.807 (1.05), 6.922 (0.96), 6.925 (0.93), 6.940 (0.61), 6.943 (0.58), 7.009 (1.28), 7.147 (3.19), 7.584 (0.61), 7.601 (1.16), 7.604 (0.75), 7.622 (1.25), 7.640 (1.28), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.645 (1.45), 7.658 (0.73), 8.150 (0.99), 8.154 (0.99), 8.170 (0.93), 8.175 |
| 16 | | LC-MS (Method L6): Rt = 2.26 min; MS (ESIpos): m/z = 490 [M + H]+ | $^1$H-NMR (400 MHz, DMSO-d6) delta [ppm]: 2.756 (0.89), 2.770 (0.83), 3.070 (16.00), 7.124 (0.88), 7.173 (0.86), 7.177 (0.86), 7.190 (1.17), 7.202 (0.75), 7.207 (0.69), 7.389 (0.77), 7.627 (1.23), 7.632 (11.18), 7.645 (1.08), 7.648 (0.95), 7.666 (0.97), 7.783 (1.07), 7.787 (1.17), 7.801 (0.91), 7.805 (0.87), 8.228 (1.01), 8.232 (1.03), 8.250 (0.94), 8.253 (0.90), 8.608 (3.86), 8.972 (0.87), 8.993 (0.85). |
| 17 | | LC-MS (Method L1): Rt = 1.24 min; MS (ESIpos): m/z = 534 [M + H]+ | $^1$H-NMR (400 MHz, DMSO-d6) delta [ppm]: −0.008 (1.02), 0.008 (0.92), 1.169 (0.67), 3.268 (1.80), 3.280 (4.39), 3.287 (5.64), 3.865 (3.30), 3.877 (5.67), 3.889 (3.15), 4.244 (1.15), 4.252 (0.88), 4.265 (1.45), 4.276 (1.35), 4.283 (0.98), 4.292 (0.96), 5.255 (1.02), 5.275 (1.02), 6.786 (1.88), 6.789 (2.08), 6.807 (2.18), 6.810 (2.27), 6.915 (1.06), 6.918 (1.05), 6.934 (2.10), 6.937 (2.04), 6.952 (1.32), 6.955 (1.28), 7.153 (1.06), 7.158 (1.11), 7.175 (1.66), 7.192 (0.85), 7.196 (0.84), 7.380 (1.77), 7.399 (1.67), 7.633 (2.13), 7.636 (4.66), 7.639 (16.00), 7.643 (3.34), 7.682 (1.63), 7.699 (2.18), 7.703 (1.97), 7.721 (2.07), 7.830 (2.42), 7.834 (2.58), 7.848 (2.01), 7.851 (1.90), 8.276 (2.01), 8.280 (2.07), 8.297 (1.93), 8.301 (1.76), 8.699 (8.76), 9.164 (1.90), 9.184 (1.86). |
| 18 | | LC-MS (Method L6): Rt = 1.77 min; MS (ESIpos): m/z = 506 [M + H]+ | $^1$H-NMR (400 MHz, DMSO-d6) delta [ppm]: −0.008 (2.30), 0.008 (2.10), 2.037 (0.83), 2.168 (0.72), 2.180 (0.72), 2.262 (16.00), 3.070 (2.04), 4.217 (0.95), 4.243 (1.45), 4.252 (1.36), 4.259 (1.09), 4.268 (1.06), 5.207 (0.94), 5.226 (0.92), 6.779 (1.82), 6.800 (1.99), 6.881 (1.11), 6.884 (1.13), 6.900 (2.29), 6.903 (2.22), 6.919 (1.39), 6.922 (1.31), 7.140 (0.97), 7.144 (1.05), 7.161 (1.67), 7.179 (0.84), 7.183 (0.82), 7.323 (2.16), 7.343 (1.95), 7.569 (0.80). |
| 19 | | LC-MS (Method L6): Rt = 1.81 min; MS (ESIpos): m/z = 490 [M + H]+ | $^1$H-NMR (400 MHz, DMSO-d6) delta [ppm]: −0.008 (1.93), 0.008 (1.79), 1.879 (0.89), 1.899 (0.96), 1.908 (1.37), 1.930 (1.00), 2.261 (16.00), 2.832 (0.71), 2.851 (0.96), 2.871 (1.31), 2.940 (0.83), 2.949 (0.89), 2.962 (0.93), 2.971 (0.90), 3.081 (2.10), 5.500 (1.37), 5.520 (1.38), 7.201 (1.33), 7.207 (2.03), 7.215 (3.05), 7.223 (2.67), 7.230 (2.32), 7.243 (0.97), 7.248 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.89), 7.258 (2.20), 7.274 (1.48), 7.280 (1.39), 7.361 (1.57), 7.368 (1.60), 7.383 (1.37), 7.546 (0.94), 7.568 (1.01). |
| 20 | | LC-MS (Method L1): Rt = 1.32 min; MS (ESIpos): m/z =532 [M + H]+ | $^1$H-NMR (400 MHz, DMSO-d6) delta [ppm]: 1.149 (1.09), 1.837 (2.38), 2.069 (1.99), 2.757 (4.80), 3.878 (12.72), 5.231 (2.34), 7.125 (3.98), 7.180 (3.90), 7.197 (4.92), 7.213 (3.63), 7.411 (3.59), 7.428 (3.24), 7.636 (16.00), 7.680 (2.42), 7.698 (3.79), 7.718 (2.69), 7.826 (4.25), 7.842 (3.43), 8.280 (3.71), 8.300 (3.40), 8.673 (8.04), 9.047 (3.28), 9.067 (3.16). |
| 21 | | LC-MS (Method L1): Rt = 1.20 min; MS (ESIpos): m/z = 494 [M + H]+ | $^1$H-NMR (400 MHz, DMSO-d6) delta [ppm]: 3.071 (16.00), 5.515 (0.74), 5.535 (0.74), 7.213 (1.11), 7.222 (1.33), 7.230 (1.61), 7.234 (1.34), 7.261 (0.99), 7.381 (0.72), 7.389 (0.77), 7.495 (2.53), 7.500 (2.65), 7.584 (0.68), 7.607 (1.36), 7.630 (0.72), 7.679 (0.71), 7.684 (1.25), 7.689 (0.68), 8.280 (0.72), 8.295 (0.78), 8.304 (0.76), 8.319 (0.70), 8.607 (3.29), 8.927 (0.97), 8.948 (0.95). |
| 22 | | LC-MS (Method L6): Rt = 2.26 min; MS (ESIpos): m/z = 510 [M + H]+ | $^1$H-NMR (400 MHz, DMSO-d6) delta [ppm]: 3.067 (16.00), 4.249 (0.91), 4.258 (0.94), 6.779 (0.92), 6.782 (1.01), 6.800 (1.06), 6.803 (1.10), 6.912 (1.02), 6.915 (1.03), 6.931 (0.61), 7.165 (0.86), 7.339 (0.87), 7.358 (0.82), 7.494 (2.71), 7.499 (2.71), 7.584 (0.72), 7.607 (1.42), 7.630 (0.77), 7.677 (0.88), 7.682 (1.54), 7.687 (0.82), 8.278 (0.75), 8.294 (0.81), 8.302 (0.81), 8.318 (0.73), 8.600 (3.49), 9.066 (0.94), 9.087 (0.93). |
| 23 | | LC-MS (Method L1): Rt = 0:8/ min; MS (ESIpos): m/z = 496 [M + H]+ | $^1$H-NMR (400 MHz, DMSO-d6) delta [ppm]: −0.149 (1.58), −0.008 (15.27), 0.008 (13.12), 0.146 (1.58), 2.154 (1.98), 2.367 (2.04), 2.709 (1.98), 3.054 (12.95), 3.067 (11.82), 3.288 (8.82), 4.260 (5.48), 5.250 (2.09), 6.782 (4.01), 6.803 (4.13), 6.895 (1.92), 6.910 (3.67), 6.928 (2.37), 7.160 (2.83), 7.308 (3.11), 7.325 (2.94), 7.517 (2.49), 7.535 (3.73), 7.556 (3.00), 7.732 (4.18), 7.746 (3.45), 7.784 (14.53), 7.801 (16.00), 8.339 (3.17), 8.360 (3.05), 8.453 (11.82), 8.966 (3.17), 8.987 (3.22). |
| 24 | | LC-MS (Method L1): Rt = 0:86 min; MS (ESIpos): m/z = 478 | $^1$H-NMR (400 MHz, DMSO-d6) delta [ppm]: −0.149 (1.23), −0.008 (10.75), 0.008 (11.29), 0.146 (1.26), 0.850 (1.36), 0.868 (0.82), 2.046 (1.11), 2.061 (1.08), 2.140 (1.17), 2.154 (1.33), 3.055 (9.80), 3.067 (9.17), 3.287 (3.23), 4.246 (2.43), 4.259 (4.02), 4.274 (2.37), 5.230 (1.36), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | [M + H]+ | 5.250 (1.39), 6.778 (2.53), 6.781 (2.78), 6.799 (2.91), 6.802 (3.04), 6.891 (1.39), 6.894 (1.42), 6.909 (2.75), 6.912 (2.81), 6.928 (1.71), 6.931 (1.74), 7.140 (1.36), 7.144 (1.49), 7.161 (2.21), 7.179 (1.14), 7.183 (1.17), 7.305 (2.15), 7.324 (2.09), 7.516 (2.06), 7.534 (2.62), 7.537 (2.50), 7.555 (2.43), 7.595 (1.71), 7.599 (3.98), 7.604 (4.93), 7.615 (16.00), 7.620 (9.01), 7.713 (3.07), 7.716 (3.35), 7.730 (2.69), 7.734 (2.59), 7.792 (1.55), 7.805 (1.49), 8.336 (2.21), 8.340 (2.40), 8.358 (2.25), 8.362 (2.18), 8.446 (9.01), 8.968 (2.50), 8.989 (2.43). |
| 25 | | LC-MS (Method L1): Rt = 1.08 min; MS (ESIpos): m/z = 500 [M + H]+ | $^1$H-NMR (400 MHz, DMSO-d6) delta [ppm]: 3.282 (1.79), 3.293 (1.98), 3.311 (16.00), 6.807 (0.71), 6.932 (0.68), 7.468 (0.89), 7.474 (0.85), 7.493 (0.76), 7.540 (0.71), 7.643 (0.98), 7.780 (0.75), 8.673 (1.65). |
| 26 | | LC-MS (Method L1): Rt = 1.07 | $^1$H-NMR (400 MHz, DMSO-d6) delta [ppm]: −0.008 (4.85), 0.008 (4.19), 1.234 (0.78), 1.710 (0.76), 1.740 (0.93), 1.986 (1.09), 1.999 (1.07), 2.007 (1.05), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | min; MS (ESIpos): m/z = 515 [M + H]+ | 2.021 (0.85), 2.072 (1.71), 2.366 (0.62), 2.709 (0.62), 3.287 (4.75), 3.971 (0.74), 3.977 (0.87), 3.999 (1.86), 4.006 (1.18), 4.021 (1.22), 4.027 (0.93), 4.132 (0.93), 4.139 (1.24), 4.149 (1.14), 4.158 (1.40), 4.168 (0.85), 4.176 (0.89), 4.185 (0.68), 5.041 (0.74), 5.055 (1.65), 5.074 (1.65), 5.088 (0.72), 6.741 (3.06), 6.761 (3.39), 6.837 (1.45), 6.840 (1.45), 6.856 (3.14), 6.874 (1.94), 7.020 (2.31), 7.039 (1.88), 7.122 (1.63), 7.126 (1.53), 7.142 (2.64), 7.160 (1.30), 7.164 (1.22), 7.264 (5.35), 7.499 (5.93), 7.502 (6.65), 7.519 (3.45), 7.523 (3.34), 7.700 (5.90), 7.703 (16.00), 7.802 (2.44), 7.820 (3.22), 7.841 (2.46), 7.917 (3.72), 8.008 (3.14), 8.011 (3.53), 8.027 (2.79), 8.030 (2.85), 8.962 (2.87), 8.982 (2.79), 9.152 (10.38). |
| 27 | | LC-MS (Method L1): Rt = 1.06 min; MS (ESIpos): m/z = 530 | $^1$H-NMR (400 MHz, DMSO-d6): δ [ppm] = 12.73 (br s, 1H), 9.01 (d, 1H), 8.69 (s, 1H), 8.46 (d, 1H), 8.30 (br d, 1H), 8.13 (s, 1H), 7.75 (d, 1H), 7.69 (s, 1H), 7.41-7.62 (m, 4H), 7.07-7.36 (m, 8H), 5.39-5.60 (m, 2H), 2.90-3.07 (m, 2H), 2.73-2.88 (m, 2H), 2.57-2.69 (m, 1H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | 2.53-2.71 (m, 13H), 2.30-2.44 (m, 1H), 2.09 (dq, 1H), 1.93 (dq, 1H). |
| 28 | | LC-MS (Method L1): Rt = 1.09 min; MS (ESIpos): m/z = 564 [M + H]+ | |
| 29 | | LC-MS (Method L1): Rt = 0.88 min; MS (ESIpos): m/z = 476 [M + H]+ | $^1$H-NMR (400 MHz, DMSO-d6) delta [ppm]: 3.072 (16.00), 3.287 (1.21), 5.754 (0.68), 6.774 (0.89), 6.777 (0.93), 6.794 (1.01), 6.797 (0.99), 6.905 (0.97), 6.908 (0.91), 6.923 (0.62), 7.303 (0.79), 7.311 (0.71), 7.324 (0.64), 7.332 (1.23), 7.579 (0.65), 7.633 (3.39), 7.641 (1.60), 7.651 (1.51), 8.240 (1.01), 8.247 (0.94), 8.258 (0.82), 8.265 (0.85), 8.531 (4.23), 9.073 (0.80), 9.093 (0.77). |
| 30 | | LC-MS (Method L1): Rt = 0.88 min; MS (ESIpos): m/z = 460 [M + H]+ | $^1$H-NMR (400 MHz, DMSO-d6) delta [ppm]: −0.008 (0.71), 3.063 (16.00), 4.262 (0.82), 4.270 (0.92), 6.784 (0.87), 6.787 (0.95), 6.805 (1.03), 6.808 (1.04), 6.924 (0.98), 6.927 (0.96), 6.943 (0.63), 6.946 (0.58), 7.171 (0.79), 7.351 (0.81), 7.370 (0.78), 7.496 (0.70), 7.523 (0.72), 7.620 (0.81), 7.637 (1.13), 7.641 (1.00), 7.659 (1.13), 7.751 (1.16), 7.754 (1.21), 7.768 (0.93), 7.772 (0.86), 8.201 (1.03), 8.205 (1.05), 8.222 (0.98), 8.226 (0.90), 8.613 (3.83), 9.077 (0.87), 9.097 (0.85). |
| 31 | | LC-MS (Method L1): Rt = 0.83 min; MS (ESIpos): m/z = 472 [M + H]+ | $^1$H-NMR (400 MHz, DMSO-d6) delta [ppm]: 3.059 (16.00), 3.287 (0.75), 3.855 (10.21), 4.263 (0.81), 4.271 (0.92), 6.785 (0.89), 6.788 (1.00), 6.806 (1.02), 6.808 (1.10), 6.923 (0.99), 6.926 (1.02), 6.942 (0.60), 7.143 (0.67), 7.149 (1.06), 7.154 (1.00), 7.171 (0.85), 7.244 (0.97), 7.265 (0.76), 7.273 (0.99), 7.294 (0.73), 7.344 (0.93), 7.349 (1.64), 7.366 (1.32), 7.370 (1.57), 7.607 (0.73), 7.625 (1.04), 7.628 (0.92), 7.646 (1.00), 7.731 (1.12), 7.735 (1.21), 7.749 (0.87), 7.752 (0.84), 8.176 (0.99), 8.180 (1.04), 8.197 (0.93), 8.201 (0.91), 8.600 (3.83), 9.082 (0.91), 9.103 (0.89). |
| 32 | | LC-MS (Method L1): Rt = 0.87 min; MS | $^1$H-NMR (400 MHz, DMSO-d6) delta [ppm]: −0.008 (1.08), 0.008 (1.10), 3.069 (16.00), 3.944 (7.95), 4.253 (0.96), 4.262 (1.04), 6.777 (1.03), 6.781 (1.18), 6.798 (1.20), 6.801 (1.26), 6.894 (0.57), 6.897 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 490 [M + H]+ | (0.59), 6.912 (1.14), 6.915 (1.14), 6.931 (0.70), 6.934 (0.68), 7.116 (0.62), 7.131 (0.71), 7.134 (0.70), 7.146 (0.75), 7.163 (0.92), 7.186 (0.84), 7.213 (0.89), 7.339 (0.92), 7.358 (0.88), 7.623 (0.67), 7.641 (1.36), 7.643 (0.86), 7.661 (1.47), 7.675 (1.33), 7.679 (1.50), 7.692 (0.67), 8.235 (1.06), 8.239 (1.07), 8.255 (1.01), 8.260 (0.92), 8.549 (4.05), 9.070 (1.00), 9.091 (0.97). |
| 33 | | LC-MS (Method L1): Rt = 0.84 min; MS (ESIpos): m/z = 456 [M + H]+ | $^{1}$H-NMR (400 MHz, DMSO-d6) delta [ppm]: 1.819 (1.63), 1.835 (1.55), 3.072 (16.00), 4.248 (0.89), 4.257 (0.93), 6.777 (0.92), 6.798 (1.00), 6.904 (0.81), 7.160 (1.13), 7.181 (0.99), 7.184 (0.91), 7.328 (0.83), 7.347 (0.76), 7.558 (0.73), 7.562 (0.79), 7.576 (1.27), 7.579 (1.20), 7.618 (1.09), 7.635 (0.76), 7.639 (1.15), 7.656 (0.69), 8.216 (1.00), 8.220 (1.05), 8.237 (0.92), 8.241 (0.89), 8.521 (3.83). |
| 34 | | LC-MS (Method L1); Rt = 0.93 min; MS (ESIpos): m/z = 492 [M + H]+ | $^{1}$H-NMR (400 MHz, DMSO-d6) delta [ppm]: −0.008 (0.91), 0.008 (0.91), 3.074 (16.00), 3.287 (1.06), 4.248 (0.91), 4.255 (1.07), 6.771 (1.09), 6.774 (1.20), 6.792 (1.29), 6.795 (1.32), 6.903 (1.12), 6.922 (0.67), 7.140 (0.60), 7.156 (0.93), 7.324 (1.17), 7.328 (1.10), 7.343 (1.08), 7.347 (1.14), 7.426 (0.79), 7.437 (0.86), 7.628 (1.83), 7.632 (3.18), 7.651 (1.79), 7.669 (0.69), 7.675 (1.55), 7.679 (1.60), 7.695 (1.35), 7.699 (1.26), 8.240 (1.22), 8.246 (1.24), 8.259 (1.08), 8.265 (1.09), 8.520 (2.86). |
| 35 | | LC-MS (Method L1): Rt = 1.12 min; MS (ESIpos): m/z = 484 [M + H]+ | $^{1}$H-NMR (400 MHz, DMSO-d6) delta [ppm]: −0.008 (3.10), 0.008 (2.86), 1.147 (0.97), 1.920 (1.70), 1.930 (0.91), 1.940 (1.83), 1.952 (1.95), 1.961 (0.97), 1.971 (1.89), 1.993 (0.73), 2.366 (2.43), 2.525 (6.69), 2.566 (2.62), 2.710 (2.49), 2.831 (0.79), 2.852 (1.52), 2.871 (2.01), 2.891 (2.68), 2.911 (1.22), 2.963 (1.58), 2.972 (1.70), 2.985 (1.70), 2.994 (1.64), 3.002 (1.03), 3.012 (0.91), 3.024 (0.91), 3.033 (0.79), 3.288 (15.21), 3.297 (13.02), 3.859 (8.40), 3.871 (12.35), 3.882 (7.85), 5.524 (1.03), 5.543 (3.04), 5.563 (3.04), 5.582 (1.03), 7.226 (5.23), 7.234 (5.60), 7.240 (6.14), 7.248 (9.06), 7.258 (2.62), 7.270 (4.02), 7.279 (2.43), 7.292 (1.40), 7.420 (2.92), 7.429 (2.92), 7.442 (2.56), 7.451 (2.31), 7.456 (1.58), 7.466 (3.71), 7.471 (6.39), 7.476 (4.68), 7.479 (4.87), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.497 (6.69), 7.516 (3.10), 7.538 (3.41), 7.542 (5.84), 7.547 (3.29), 7.556 (1.89), 7.560 (3.10), 7.565 (1.64), 7.640 (4.26), 7.644 (6.69), 7.649 (3.89), 7.675 (2.92), 7.693 (4.50), 7.696 (3.83), 7.714 (4.26), 7.777 (5.05), 7.781 (5.23), 7.795 (3.71), 7.799 (3.35), 8.255 (4.14), 8.258 (4.14), 8.276 (3.95), 8.279 (3.65), 8.675 (16.00), 9.020 (4.02), 9.041 (3.89). |
| 36 | | LC-MS (Method L1): Rt = 0.86 min; MS (ESIpos): m/z = 472 [M + H]+ | $^1$H-NMR (400 MHz, DMSO-d6) delta [ppm]: −0.149 (0.70), −0.008 (6.82), 0.008 (6.40), 0.146 (0.83), 1.147 (1.53), 1.926 (4.03), 1.947 (3.76), 2.328 (1.25), 2.366 (2.09), 2.665 (1.11), 2.670 (1.25), 2.710 (2.09), 3.072 (16.00), 3.289 (10.16), 4.248 (1.11), 5.225 (0.56), 6.775 (1.11), 6.796 (1.25), 6.903 (0.83), 7.131 (1.11), 7.159 (1.11), 7.263 (0.83), 7.328 (0.97), 7.346 (0.83), 7.461 (1.25), 7.481 (0.97), 7.564 (0.97), 7.578 (1.39), 7.582 (1.39), 7.619 (1.11), 7.640 (1.25), 7.658 (0.70), 8.216 (1.11), 8.518 (4.31), 9.058 (0.56). |
| 37 | | LC-MS (Method L1): Rt = 0.90 min; MS (ESIpos): m/z = 476 [M + H]+ | $^1$H-NMR (400 MHz, DMSO-d6) delta [ppm]: −0.008 (3.91), 0.008 (3.78), 1.147 (0.96), 2.019 (0.89), 2.028 (1.03), 2.047 (0.96), 2.055 (1.51), 2.062 (1.30), 2.070 (0.89), 2.170 (0.96), 2.182 (1.30), 2.194 (1.30), 2.204 (1.17), 2.327 (0.69), 2.366 (1.44), 2.665 (0.55), 2.669 (0.76), 2.674 (0.55), 2.710 (1.51), 3.081 (16.00), 4.212 (0.69), 4.232 (2.20), 4.240 (1.85), 4.252 (3.50), 4.261 (3.64), 4.268 (2.06), 4.277 (1.99), 4.295 (0.69), 5.218 (0.89), 5.232 (1.92), 5.252 (1.85), 5.266 (0.82), 6.778 (3.50), 6.781 (3.85), 6.799 (4.05), 6.802 (4.26), 6.894 (2.06), 6.897 (2.06), 6.912 (3.98), 6.915 (3.98), 6.931 (2.61), 6.934 (2.40), 7.143 (1.99), 7.147 (2.06), 7.164 (3.09), 7.182 (1.65), 7.186 (1.58), 7.319 (1.65), 7.341 (6.59), 7.364 (4.74), 7.480 (1.51), 7.487 (2.06), 7.495 (1.72), 7.502 (2.27), 7.518 (1.72), 7.528 (1.30), 7.540 (1.30), 7.636 (2.33), 7.654 (3.71), 7.657 (2.95), 7.675 (3.57), 7.730 (3.16), 7.745 (2.06), 8.257 (2.47), 8.277 (2.33), 8.550 (5.15), 9.077 (2.61), 9.097 (2.61). |
| 38 | | LC-MS (Method L6): Rt = 1.80 min; MS | $^1$H-NMR (400 MHz, DMSO-d6) delta [ppm]: −0.149 (1.49), −0.008 (13.57), 0.008 (12.78), 0.146 (1.49), 1.147 (1.73), 2.199 (0.78), 2.327 (1.25), 2.366 (1.88), 2.669 (1.41), 2.710 (1.88), 3.043 (1.65), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 508 [M + H]+ | 3.079 (16.00), 3.287 (12.86), 3.611 (0.63), 3.906 (4.16), 3.922 (4.16), 4.249 (0.78), 5.247 (0.71), 6.777 (1.10), 6.798 (1.18), 6.911 (0.94), 7.160 (0.86), 7.355 (1.18), 7.651 (0.71), 7.669 (1.02), 7.690 (1.18), 7.752 (1.25), 8.280 (1.02), 8.302 (0.94), 8.544 (4.00). |
| 39 | | LC-MS (Method L1): Rt = 0.94 min; MS (ESIpos): m/z = 526 [M + H]+ | $^1$H-NMR (400 MHz, DMSO-d6) delta [ppm]: −0.008 (0.97), 0.008 (0.99), 3.043 (0.70), 3.071 (16.00), 3.289 (2.25), 4.241 (0.92), 4.250 (0.99), 6.769 (1.02), 6.772 (1.12), 6.789 (1.19), 6.792 (1.24), 6.877 (0.58), 6.896 (1.12), 6.914 (0.70), 7.137 (0.61), 7.154 (0.92), 7.318 (0.87), 7.339 (1.14), 7.361 (0.68), 7.374 (0.75), 7.394 (0.75), 7.597 (1.38), 7.604 (2.28), 7.624 (1.55), 7.641 (0.61), 7.776 (0.75), 7.894 (0.85), 7.899 (0.85), 7.904 (0.85), 7.910 (0.73), 8.233 (1.09), 8.239 (1.09), 8.253 (0.97), 8.258 (0.95), 8.473 (2.47), 8.476 (2.79), 9.074 (0.75), 9.094 (0.70). |
| 40 | | LC-MS (Method L1): Rt = 1.28 min; MS (ESIpos): m/z = 510 [M + H]+ | $^1$H-NMR (400 MHz, DMSO-d6) delta [ppm]: −0.008 (1.20), 0.008 (1.12), 3.036 (16.00), 3.287 (1.15), 4.256 (0.82), 4.265 (0.81), 6.785 (0.91), 6.788 (1.01), 6.805 (1.04), 6.808 (1.09), 6.923 (0.98), 6.926 (0.95), 6.942 (0.61), 7.171 (0.77), 7.355 (0.79), 7.374 (0.75), 7.674 (1.45), 7.677 (3.02), 7.681 (6.87), 7.684 (2.17), 7.687 (1.35), 7.794 (0.76), 7.801 (1.01), 7.816 (0.76), 7.823 (0.93), 7.884 (0.86), 7.892 (0.85), 7.910 (0.84), 7.917 (0.75), 8.627 (3.52), 9.120 (0.88), 9.140 (0.86). |
| 41 | | LC-MS (Method L1): Rt = 1.29 min; MS (ESIpos): m/z = 528 [M + H]+ | $^1$H-NMR (400 MHz, DMSO-d6) delta [ppm]: 3.035 (16.00), 3.287 (1.06), 4.256 (0.95), 4.266 (0.97), 6.788 (1.08), 6.808 (1.19), 6.924 (1.08), 7.173 (0.90), 7.355 (0.95), 7.374 (0.86), 7.810 (0.67), 7.817 (0.87), 7.833 (0.70), 7.840 (0.82), 7.861 (3.09), 7.878 (3.15), 7.884 (0.99), 7.891 (0.79), 7.910 (0.83), 7.917 (0.71), 8.631 (3.37), 9.121 (1.00), 9.142 (0.97). |
| 42 | | LC-MS (Method L1): Rt = 1.31 min; MS (ESIpos): m/z = 552 [M + H]+ | $^1$H-NMR (400 MHz, DMSO-d6) delta [ppm]: 2.084 (0.98), 2.091 (0.83), 2.207 (0.87), 2.219 (0.85), 2.229 (0.81), 3.239 (2.45), 3.250 (5.46), 3.261 (5.61), 3.272 (2.65), 3.288 (1.94), 3.860 (4.44), 3.872 (7.25), 3.883 (4.20), 4.238 (1.42), 4.245 (1.11), 4.259 (1.49), 4.266 (1.84), 4.275 (1.47), 4.281 (1.19), 4.290 (1.20), 5.250 (1.36), 5.269 (1.34), 6.787 (2.49), 6.807 (2.79), 6.913 (1.30), 6.916 (0.97), 6.932 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.70), 6.950 (1.60), 7.154 (1.30), 7.175 (2.09), 7.193 (1.03), 7.377 (2.28), 7.395 (2.06), 7.684 (12.45), 7.686 (16.00), 7.839 (1.47), 7.843 (1.61), 7.846 (1.80), 7.861 (1.53), 7.869 (1.65), 7.892 (1.84), 7.899 (1.55), 7.917 (1.79), 7.924 (1.38), 8.694 (6.98), 9.201 (2.39), 9.221 (2.33). |
| 43 | | LC-MS (Method L1): Rt = 1.31 min; MS (ESIpos): m/z = 570 [M + H]+ | $^1$H-NMR (400 MHz, DMSO-d6) delta [ppm]: −0.149 (0.62), −0.008 (6.95), 0.008 (6.61), 0.146 (0.77), 1.146 (1.05), 1.235 (0.81), 2.085 (1.58), 2.208 (1.53), 2.327 (0.77), 2.366 (1.29), 2.670 (0.91), 2.709 (1.39), 3.249 (9.34), 3.260 (9.68), 3.287 (9.96), 3.861 (7.43), 3.872 (12.12), 3.883 (7.23), 4.238 (2.40), 4.266 (3.02), 4.275 (2.49), 4.292 (2.01), 5.250 (2.25), 5.269 (2.25), 6.790 (4.07), 6.808 (4.50), 6.916 (2.01), 6.932 (4.26), 6.954 (2.49), 7.159 (2.20), 7.176 (3.50), 7.197 (1.72), 7.377 (3.69), 7.396 (3.50), 7.856 (2.83), 7.863 (5.37), 7.868 (13.51), 7.884 (16.00), 7.891 (4.55), 7.898 (2.97), 7.916 (3.26), 7.923 (2.54), 8.700 (13.03), 9.202 (3.83), 9.222 (3.78). |
| 44 | | LC-MS (Method | $^1$H-NMR (400 MHz, DMSO-d6) delta [ppm]: −0.008 (2.21), 0.008 (2.14), 2.301 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | L1): Rt = 0.90 min; MS (ESIpos): m/z = 472 [M + H]+ | (2.93), 2.377 (7.46), 3.062 (16.00), 4.263 (0.86), 4.270 (0.99), 6.785 (1.06), 6.788 (1.15), 6.805 (1.22), 6.808 (1.26), 6.905 (0.56), 6.908 (0.59), 6.924 (1.13), 6.927 (1.11), 6.943 (0.70), 6.946 (0.67), 7.153 (0.60), 7.170 (0.91), 7.286 (1.86), 7.333 (1.69), 7.335 (1.73), 7.358 (0.93), 7.374 (0.87), 7.417 (1.07), 7.421 (1.60), 7.610 (0.86), 7.627 (1.27), 7.631 (1.03), 7.648 (1.23), 7.712 (1.31), 7.716 (1.44), 7.730 (0.99), 7.734 (0.91), 8.169 (2.71), 8.193 (1.12), 8.196 (1.15), 8.214 (1.07), 8.218 (1.00), 8.609 (4.09), 9.077 (0.98), 9.098 (0.96). |
| 45 | | LC-MS (Method L1): Rt = 0.89 min; MS (ESIpos): m/z = 476 [M + H]+ | $^1$H-NMR (400 MHz, DMSO-d6) delta [ppm]: −0.008 (2.87), 0.008 (2.38), 3.066 (16.00), 4.242 (0.72), 4.261 (1.05), 4.269 (1.17), 6.785 (1.14), 6.788 (1.20), 6.805 (1.30), 6.808 (1.32), 6.906 (0.63), 6.909 (0.64), 6.924 (1.28), 6.928 (1.24), 6.943 (0.82), 6.946 (0.75), 7.149 (0.62), 7.153 (0.66), 7.171 (1.01), 7.352 (0.99), 7.371 (1.02), 7.477 (0.90), 7.498 (1.55), 7.521 (1.34), 7.580 (0.77), 7.586 (0.81), 7.593 (0.84), 7.598 (0.88), 7.602 (0.64), 7.607 (0.63), 7.614 (0.57), 7.622 (1.17), 7.639 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.40), 7.643 (1.20), 7.661 (1.36), 7.754 (1.52), 7.758 (1.56), 7.772 (1.24), 7.776 (1.13), 7.788 (1.17), 7.794 (1.08), 7.807 (1.15), 7.812 (1.07), 8.205 (1.23), 8.208 (1.27), 8.226 (1.17), 8.230 (1.10), 8.278 (0.69), 8.614 (3.82), 9.077 (1.08), 9.098 (1.06). |
| 46 | | LC-MS (Method L1): Rt = 0.94 min; MS (ESIpos): m/z = 476 [M + H]+ | $^1$H-NMR (400 MHz, DMSO-d6) delta [ppm]: −0.149 (0.83), −0.008 (7.27), 0.008 (6.79), 0.146 (0.83), 2.033 (0.69), 2.041 (0.72), 2.053 (0.69), 2.068 (1.10), 2.076 (0.89), 2.083 (0.66), 2.176 (0.69), 2.189 (0.92), 2.201 (0.92), 2.211 (0.83), 2.236 (0.60), 2.366 (0.98), 2.710 (1.04), 3.074 (16.00), 4.241 (1.55), 4.249 (1.37), 4.261 (2.38), 4.269 (2.62), 4.285 (1.40), 5.226 (0.60), 5.241 (1.40), 5.260 (1.40), 5.275 (0.63), 6.785 (2.53), 6.788 (2.68), 6.806 (2.92), 6.809 (2.95), 6.906 (1.43), 6.909 (1.46), 6.924 (2.86), 6.928 (2.74), 6.943 (1.82), 6.946 (1.67), 7.150 (1.52), 7.154 (1.49), 7.171 (2.23), 7.189 (1.16), 7.193 (1.13), 7.356 (2.32), 7.374 (2.20), 7.429 (1.13), 7.432 (1.46), 7.435 (2.47), 7.438 (2.26), 7.446 (1.31), 7.453 (2.06), 7.457 (2.41), 7.459 (2.77), 7.463 (2.86), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.468 (1.43), 7.473 (1.61), 7.478 (1.13), 7.515 (3.04), 7.519 (4.35), 7.523 (2.26), 7.625 (0.72), 7.631 (2.68), 7.649 (2.86), 7.652 (2.59), 7.670 (2.77), 7.790 (2.95), 7.794 (3.10), 7.809 (2.47), 7.812 (2.32), 8.232 (2.15), 8.235 (2.18), 8.253 (2.06), 8.256 (1.97), 8.418 (1.28), 8.623 (3.81), 9.088 (2.12), 9.108 (2.06). |
| 47 | | LC-MS (Method L1): Rt = 0.92 min; MS (ESIpos): m/z = 478 [M + H]+ | $^1$H-NMR (400 MHz, DMSO-d6) delta [ppm]: −0.149 (0.98), −0.011 (6.35), −0.008 (14.61), 0.008 (8.04), 0.146 (1.09), 1.147 (0.63), 2.033 (1.06), 2.041 (1.06), 2.052 (1.09), 2.068 (1.50), 2.075 (1.28), 2.083 (0.90), 2.176 (1.09), 2.189 (1.39), 2.201 (1.31), 2.211 (1.20), 2.669 (0.60), 3.079 (16.00), 4.220 (0.82), 4.240 (2.37), 4.249 (2.02), 4.260 (3.57), 4.269 (3.60), 4.275 (2.15), 4.285 (1.88), 4.304 (0.65), 5.228 (0.95), 5.240 (1.99), 5.261 (1.91), 5.275 (0.82), 6.787 (3.71), 6.790 (3.68), 6.807 (4.17), 6.810 (3.93), 6.906 (2.15), 6.909 (2.07), 6.924 (4.01), 6.928 (3.68), 6.943 (2.53), 6.947 (2.18), 7.152 (2.07), 7.156 (2.10), 7.173 (3.11), 7.190 (1.58), 7.194 (1.53), 7.352 (3.08), 7.371 (3.03), 7.558 (4.31), 7.575 (4.63), 7.581 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (5.34), 7.599 (4.61), 7.608 (0.93), 7.632 (2.81), 7.650 (3.84), 7.653 (3.35), 7.671 (3.43), 7.791 (4.03), 7.795 (4.09), 7.809 (3.35), 7.813 (2.94), 8.233 (2.78), 8.254 (2.40), 8.444 (1.55), 8.617 (4.03), 9.093 (2.64), 9.113 (2.53). |
| 48 | | LC-MS (Method L1): Rt = 0.98 min; MS (ESIpos): m/z = 526 [M + H]+ | $^1$H-NMR (400 MHz, DMSO-d6) delta [ppm]: −0.149 (1.64), −0.008 (16.00), 0.008 (12.95), 0.146 (1.58), 1.147 (1.58), 2.025 (1.87), 2.033 (2.09), 2.045 (2.32), 2.060 (3.17), 2.068 (2.71), 2.169 (2.04), 2.181 (2.94), 2.195 (2.83), 2.203 (2.83), 2.217 (1.87), 2.327 (1.02), 2.366 (2.15), 2.669 (1.30), 2.709 (2.20), 3.193 (6.61), 4.195 (1.58), 4.216 (4.24), 4.237 (3.56), 4.253 (3.34), 4.262 (4.35), 4.269 (3.79), 4.278 (3.96), 4.289 (1.70), 4.297 (1.92), 5.198 (1.70), 5.212 (3.84), 5.232 (3.84), 6.786 (7.41), 6.789 (7.75), 6.807 (8.54), 6.810 (8.59), 6.888 (4.13), 6.891 (4.18), 6.907 (8.65), 6.910 (8.37), 6.925 (5.37), 6.928 (4.98), 7.149 (4.18), 7.153 (4.35), 7.171 (6.78), 7.188 (3.34), 7.192 (3.39), 7.341 (7.24), 7.360 (6.90), 7.446 (3.39), 7.466 (2.77), 7.516 (4.01), 7.681 (4.47), 7.699 (5.88), 7.720 (4.01), 7.798 (2.94), 8.345 (2.37), 8.479 (3.11), 9.124 (3.00), 9.144 (3.05). |
| 49 | | LC-MS (Method L1): Rt = 0.86 min; MS (ESIpos): m/z = 460 [M + H]+ | $^1$H-NMR (400 MHz, DMSO-d6) delta [ppm]: −0.149 (1.77), −0.008 (16.00), 0.008 (13.79), 0.146 (1.77), 1.147 (1.47), 2.040 (1.77), 2.067 (2.73), 2.073 (2.21), 2.189 (2.43), 2.201 (2.36), 2.211 (2.29), 2.327 (1.40), 2.366 (2.73), 2.669 (1.40), 2.710 (2.65), 3.179 (6.34), 4.207 (1.25), 4.228 (3.47), 4.249 (3.02), 4.259 (3.32), 4.270 (3.61), 4.276 (3.02), 4.286 (3.10), 4.304 (1.33), 5.225 (3.17), 5.245 (3.10), 6.420 (0.59), 6.443 (0.59), 6.792 (6.34), 6.795 (6.64), 6.813 (7.37), 6.816 (7.30), 6.900 (3.39), 6.903 (3.47), 6.918 (6.93), 6.922 (6.78), 6.937 (4.50), 6.940 (4.35), 7.156 (3.54), 7.160 (3.61), 7.178 (5.46), 7.195 (3.24), 7.199 (2.80), 7.217 (0.66), 7.241 (1.11), 7.265 (0.74), 7.319 (9.07), 7.324 (9.73), 7.345 (12.90), 7.366 (6.05), 7.377 (1.84), 7.382 (1.92), 7.398 (1.62), 7.404 (1.33), 7.653 (3.10), 7.671 (4.87), 7.692 (3.76), 7.820 (4.87), 7.836 (3.98), 8.132 (1.25), 8.280 (2.36), 8.538 (1.62), 9.132 (2.51). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 50 | | LC-MS (Method L1): Rt = 0.96 min; MS (ESIpos): m/z = 510 [M + H]+ | $^1$H-NMR (400 MHz, DMSO-d6) delta [ppm]: −0.149 (1.73), −0.008 (16.00), 0.008 (14.73), 0.146 (1.80), 1.147 (1.73), 2.033 (2.47), 2.045 (2.87), 2.060 (3.80), 2.075 (2.47), 2.167 (2.47), 2.180 (3.53), 2.192 (3.47), 2.201 (3.33), 2.214 (2.40), 2.327 (1.33), 2.366 (2.40), 2.669 (1.53), 2.710 (2.40), 3.162 (9.07), 4.196 (1.80), 4.217 (5.20), 4.238 (4.73), 4.250 (4.93), 4.260 (5.33), 4.267 (4.60), 4.275 (4.67), 4.295 (2.07), 5.197 (2.00), 5.213 (4.67), 5.232 (4.67), 5.245 (2.20), 6.784 (9.40), 6.786 (10.33), 6.804 (10.73), 6.807 (11.13), 6.887 (5.20), 6.890 (5.40), 6.906 (10.73), 6.909 (10.67), 6.924 (6.47), 6.928 (6.20), 7.147 (5.13), 7.151 (5.33), 7.168 (8.33), 7.185 (4.13), 7.189 (4.07), 7.347 (8.87), 7.363 (8.33), 7.540 (4.60), 7.680 (3.40), 7.698 (6.33), 7.719 (4.87), 7.790 (8.33), 7.878 (3.47), 8.132 (1.13), 8.342 (3.00), 8.498 (4.40), 9.120 (3.87), 9.138 (3.87). |
| 51 | | LC-MS (Method L1): Rt = 0.89 min; MS (ESIpos): m/z = 476 [M + H]+ | $^1$H-NMR (400 MHz, DMSO-d6) delta [ppm]: −0.149 (1.69), −0.008 (16.00), 0.008 (14.14), 0.146 (1.86), 1.147 (1.52), 2.032 (1.78), 2.060 (2.62), 2.183 (2.37), 2.196 (2.29), 2.205 (2.20), 2.218 (1.61), 2.328 (1.27), 2.332 (1.02), 2.366 (2.88), 2.670 (1.44), 2.710 (3.05), 3.203 (4.99), 4.196 (1.27), 4.217 (3.30), 4.237 (2.88), 4.263 (3.56), 4.271 (3.05), 4.280 (3.13), 5.211 (3.13), 5.231 (3.13), 6.787 (6.26), 6.790 (6.52), 6.808 (7.20), 6.811 (7.11), 6.889 (3.64), 6.892 (3.64), 6.908 (7.53), 6.911 (6.94), 6.927 (4.49), 6.930 (4.23), 7.151 (3.56), 7.155 (3.56), 7.172 (5.59), 7.189 (2.79), 7.193 (2.96), 7.346 (7.28), 7.364 (8.30), 7.436 (3.30), 7.697 (5.67), 7.718 (4.06), 7.778 (2.46), 8.132 (1.69), 8.336 (1.86), 8.478 (2.12), 9.127 (2.37). |
| 52 | | LC-MS (Method L6): Rt = 2.17 min; MS (ESIpos): m/z = 534 [M + H]+ | $^1$H-NMR (400 MHz, DMSO-d6) delta [ppm]: −0.150 (0.80), −0.008 (7.08), 0.008 (6.23), 0.146 (0.85), 1.147 (0.94), 1.234 (1.04), 1.401 (0.66), 2.061 (1.98), 2.184 (1.46), 2.196 (1.94), 2.208 (1.84), 2.218 (1.84), 2.327 (0.66), 2.366 (1.32), 2.669 (0.76), 2.710 (1.37), 3.288 (16.00), 3.336 (2.41), 3.866 (9.35), 3.876 (15.01), 3.888 (8.54), 4.211 (1.09), 4.231 (3.26), 4.239 (2.55), 4.252 (4.48), 4.262 (4.25), 4.270 (2.78), 4.279 (2.83), 4.298 (0.94), 5.241 (2.45), 5.256 (2.41), 5.754 (5.00), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.777 (5.57), 6.794 (5.95), 6.797 (6.14), 6.893 (2.17), 6.912 (4.63), 6.930 (2.69), 7.140 (2.64), 7.161 (4.58), 7.178 (2.08), 7.304 (1.84), 7.307 (1.98), 7.323 (2.88), 7.327 (3.59), 7.333 (2.45), 7.352 (7.69), 7.370 (4.44), 7.413 (2.17), 7.424 (2.55), 7.432 (3.73), 7.444 (4.11), 7.451 (2.08), 7.463 (2.03), 7.655 (2.12), 7.659 (2.93), 7.672 (7.74), 7.677 (7.17), 7.684 (14.35), 7.687 (8.73), 7.704 (12.93), 7.707 (7.46), 7.722 (3.26), 8.277 (5.38), 8.282 (5.47), 8.297 (4.91), 8.302 (4.67), 8.583 (8.50), 8.590 (9.39), 9.143 (2.27), 9.158 (3.16), 9.178 (2.55). |
| 53 | | LC-MS (Method L1): Rt = 1.02 min; MS (ESIpos): m/z = 532 [M + H]+ | $^1$H-NMR (400 MHz, DMSO-d6) delta [ppm]: −0.011 (3.43), −0.008 (7.74), 0.008 (4.34), 0.146 (0.57), 1.157 (2.48), 1.175 (4.93), 1.193 (2.43), 1.988 (8.75), 2.057 (0.67), 2.072 (0.90), 2.080 (0.75), 2.204 (0.82), 2.216 (0.77), 2.225 (0.77), 3.272 (2.97), 3.285 (6.13), 3.297 (8.04), 3.863 (4.09), 3.875 (6.63), 3.887 (3.55), 3.945 (16.00), 4.003 (0.72), 4.021 (2.03), 4.038 (2.03), 4.056 (0.67), 4.236 (1.36), 4.244 (1.09), 4.257 (1.56), 4.270 (1.44), 4.277 (1.09), 4.286 (1.09), 5.250 (1.24), 5.269 (1.16), 6.780 (2.31), 6.783 (2.38), 6.800 (2.55), 6.803 (2.50), 6.902 (1.27), 6.906 (1.27), 6.921 (2.43), 6.924 (2.23), 6.940 (1.54), 6.943 (1.36), 7.100 (0.70), 7.115 (1.01), 7.121 (1.41), 7.128 (0.80), 7.137 (1.63), 7.140 (1.61), 7.146 (1.99), 7.151 (1.98), 7.156 (1.37), 7.166 (2.21), 7.168 (2.40), 7.186 (1.12), 7.190 (1.14), 7.195 (1.44), 7.199 (1.34), 7.216 (1.04), 7.221 (2.01), 7.226 (1.29), 7.243 (0.85), 7.247 (0.80), 7.353 (0.64), 7.356 (0.82), 7.361 (2.01), 7.374 (1.09), 7.377 (1.11), 7.381 (1.86), 7.391 (0.57), 7.465 (0.90), 7.485 (0.60), 7.676 (1.27), 7.694 (3.10), 7.714 (4.29), 7.717 (3.84), 7.722 (3.60), 7.734 (1.24), 7.739 (0.70), 8.095 (0.60), 8.278 (2.26), 8.283 (2.09), 8.298 (2.13), 8.303 (1.81), 8.615 (10.00), 9.154 (2.23), 9.175 (2.11). |
| 54 | | LC-MS (Method L1): Rt = 1.24 min; MS (ESIpos): m/z = 552 | $^1$H-NMR (400 MHz, DMSO-d6) delta [ppm]: −0.149 (1.29), −0.008 (12.61), 0.008 (10.72), 0.146 (1.29), 1.147 (0.91), 1.235 (0.73), 1.988 (0.80), 2.087 (1.68), 2.210 (1.47), 2.231 (1.33), 2.366 (1.33), 2.710 (1.40), 3.267 (4.16), 3.278 (9.96), 3.287 (15.97), 3.864 (7.30), 3.876 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | (12.16), 3.888 (7.06), 4.224 (0.73), 4.244 (2.38), 4.252 (1.92), 4.265 (3.14), 4.276 (3.00), 4.292 (2.06), 5.255 (2.20), 5.275 (2.24), 6.789 (4.37), 6.810 (4.72), 6.916 (1.99), 6.919 (2.06), 6.934 (4.26), 6.953 (2.59), 7.154 (2.24), 7.158 (2.17), 7.175 (3.49), 7.192 (1.71), 7.381 (3.70), 7.399 (3.42), 7.681 (3.00), 7.699 (4.19), 7.702 (3.95), 7.720 (3.84), 7.806 (14.46), 7.822 (14.43), 7.843 (4.61), 7.846 (4.93), 7.861 (3.77), 7.864 (3.67), 8.273 (3.95), 8.277 (4.12), 8.295 (3.81), 8.298 (3.67), 8.704 (16.00), 9.165 (3.98), 9.186 (3.91). |
| 55 | | LC-MS (Method L6): Rt = 1.44 min; MS (ESIpos): m/z = 472 [M + H]+ | $^1$H-NMR (400 MHz, DMSO-d6) delta [ppm]: −0.008 (1.58), 0.008 (1.48), 3.056 (16.00), 3.065 (1.61), 3.289 (1.47), 3.903 (10.43), 3.909 (1.22), 4.271 (0.85), 6.785 (0.92), 6.788 (1.00), 6.805 (1.06), 6.808 (1.08), 6.926 (1.03), 6.929 (0.97), 6.945 (0.63), 7.171 (0.82), 7.220 (0.62), 7.242 (1.22), 7.264 (0.82), 7.354 (0.82), 7.374 (1.35), 7.376 (1.39), 7.382 (0.75), 7.475 (0.94), 7.480 (0.83), 7.507 (0.90), 7.513 (0.86), 7.597 (0.76), 7.615 (1.05), 7.618 (0.89), 7.636 (1.04), 7.717 (1.17), 7.721 (1.25), 7.735 (0.90), 7.739 (0.84), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.156 (1.01), 8.160 (1.04), 8.177 (0.96), 8.181 (0.89), 8.608 (4.20), 9.075 (0.90), 9.096 (0.86). |
| 56 | | LC-MS (Method L6): Rt = 1.79 min; MS (ESIpos): m/z = 472 [M + H]+ | $^1$H-NMR (500 MHz, DMSO-d6) delta [ppm]: 2.403 (6.76), 3.060 (16.00), 3.164 (0.79), 3.174 (0.80), 4.261 (0.74), 6.787 (0.91), 6.789 (0.97), 6.803 (1.01), 6.806 (1.01), 6.925 (0.96), 6.927 (0.92), 6.940 (0.58), 7.170 (0.76), 7.355 (0.76), 7.370 (0.74), 7.431 (1.71), 7.447 (1.38), 7.451 (1.32), 7.614 (0.78), 7.629 (1.13), 7.631 (1.04), 7.636 (1.77), 7.639 (1.64), 7.646 (1.03), 7.721 (1.15), 7.724 (1.19), 7.735 (0.90), 7.738 (0.83), 8.185 (1.00), 8.188 (1.01), 8.202 (0.95), 8.205 (0.87), 8.601 (3.95), 9.077 (0.87), 9.094 (0.83). |
| 57 | | LC-MS (Method L1): Rt = 0.92 min; MS (ESIpos): m/z = 478 [M + H]+ | $^1$H-NMR (500 MHz, DMSO-d6) delta [ppm]: 3.070 (16.00), 6.781 (0.93), 6.783 (1.06), 6.797 (1.06), 6.799 (1.13), 6.915 (0.96), 6.917 (1.03), 6.932 (0.60), 7.165 (0.83), 7.344 (0.86), 7.358 (0.80), 7.637 (0.80), 7.652 (1.06), 7.654 (0.90), 7.669 (1.03), 7.716 (1.03), 7.718 (1.16), 7.730 (0.77), 7.732 (0.77), 8.251 (0.96), 8.254 (1.06), 8.268 (0.93), 8.271 (0.93), 8.559 (3.79), 9.074 (0.90), 9.090 (0.86). |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 58 | 2.11 | | $^{1}$H-NMR (399, 9532 MHz, DMSO) δ = 8.8706 (0.51), 8.8451 (2.08), 8.4185 (0.68), 8.4155 (0.7), 8.3974 (0.66), 8.3942 (0.64), 8.3138 (0.34), 7.7984 (0.62), 7.7955 (0.67), 7.7805 (0.77), 7.7776 (0.75), 7.664 (3.27), 7.6592 (3.77), 7.602 (0.98), 7.5971 (1.58), 7.5922 (0.8), 7.5884 (0.66), 7.5699 (0.62), 7.5674 (0.69), 7.5491 (0.53), 7.2426 (0.53), 7.2249 (0.57), 7.1558 (0.53), 7.1387 (0.34), 6.8988 (0.39), 6.896 (0.43), 6.8801 (0.66), 6.8773 (0.7), 6.8616 (0.34), 6.8587 (0.35), 6.806 (0.78), 6.8035 (0.77), 6.7857 (0.73), 6.7829 (0.66), 5.3292 (0.33), 4.3233 (0.33), 4.2445 (0.35), 3.315 (36.45), 2.6749 (0.48), 2.6702 (0.67), 2.6656 (0.48), 2.5236 (1.77), 2.5187 (2.78), 2.5102 (37.2), 2.5056 (77.48), 2.501 (107.64), 2.4965 (79.14), 2.492 (37.03), 2.3325 (0.44), 2.3279 (0.63), 2.3234 (0.47), 1.9882 (0.43), 1.398 (16), 0.008 (1.74), −0.0001 (52.5), −0.0085 (1.57) |
| 59 | | LC-MS (Method L1): Rt = 1.42 min; MS (ESIpos): m/z = 568 [M + H]+ | $^{1}$H-NMR (400 MHz, DMSO-d6) delta [ppm]: −0.008 (3.35), 0.008 (3.16), 2.093 (0.79), 2.366 (0.71), 2.710 (0.67), 2.925 (16.00), 3.287 (2.93), 4.247 (1.14), 4.254 (1.00), 4.266 (1.71), 4.274 (1.91), 4.289 (1.02), 4.422 (6.70), 5.298 (1.04), 5.319 (1.04), 6.784 (2.02), 6.787 (2.18), 6.804 (2.31), 6.807 (2.37), 6.889 (1.10), 6.893 (1.06), 6.908 (2.16), 6.911 (2.08), 6.927 (1.37), 6.930 (1.31), 7.145 (1.10), 7.150 (1.10), 7.167 (1.66), 7.184 (0.83), 7.188 (0.85), 7.302 (0.69), 7.319 (1.89), 7.333 (0.81), 7.337 (1.46), 7.341 (0.81), 7.389 (2.00), 7.405 (3.56), 7.408 (5.68), 7.421 (2.41), 7.427 (4.85), 7.444 (4.93). 7.461 (2.10), 7.465 (1.46), 7.642 (1.14), 7.646 (2.04), 7.647 (2.98), 7.651 (5.53), 7.656 (14.31), 7.660 (4.91), 7.690 (1.73), 7.708 (2.27), 7.711 (1.98), 7.729 (2.16), 7.835 (2.54), 7.838 (2.66), 7.853 (2.02), 7.857 (1.91). 8.318 (2.18), 8.321 (2.23), 8.339 (2.06), 8.343 (1.85), 8.752 (9.09), 9.153 (2.02), 9.174 (1.98). |
| 60 | | LC-MS (Method L1): Rt = 0.85 min; MS | $^{1}$H-NMR (400 MHz, DMSO-d6) δ [ppm]: 1.988 (0.48), 2.044 (0.43), 2.085 (0.43), 3.066 (2.26), 3.075 (16.00), 3.169 (2.25), 4.230 (0.60), 4.249 (0.92), 4.257 (1.04), 4.271 (0.62), 5.227 (0.50), 5.244 (0.54), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | (ESIpos): m/z = 476 [M + H]+ | 6.775 (1.07), 6.793 (1.18), 6.884 (0.51), 6.903 (1.06), 6.922 (0.68), 7.141 (0.56), 7.158 (0.91), 7.175 (0.50), 7.214 (0.55), 7.331 (0.84), 7.351 (0.82), 7.438 (1.23), 7.449 (1.52), 7.460 (1.03), 7.467 (1.28), 7.625 (0.51), 7.638 (2.53), 7.642 (1.75), 7.657 (1.45), 7.674 (0.45), 8.228 (0.46), 8.248 (0.96), 8.254 (0.96), 8.266 (0.84), 8.273 (0.82), 8.522 (3.66), 9.072 (0.54), 9.091 (0.52). |
| 61 | | LC-MS (Method L6): Rt = 1.62 min; MS (ESIpos): m/z = 456 [M + H]+ | $^1$H-NMR (400 MHz, DMSO-d6) δ [ppm]: −0.008 (4.15), 0.008 (3.77), 2.366 (1.07), 2.386 (6.43), 2.710 (1.00), 3.060 (16.00), 3.287 (5.91), 3.681 (0.59), 4.270 (0.79), 6.787 (0.97), 6.805 (1.00), 6.808 (1.04), 6.923 (0.93), 6.942 (0.66), 7.187 (0.86), 7.221 (1.56), 7.355 (0.76), 7.372 (0.76), 7.608 (0.76), 7.626 (1.07), 7.629 (0.93), 7.647 (1.04), 7.717 (1.14), 7.720 (1.21), 7.734 (0.90), 7.738 (0.79), 8.188 (1.00), 8.192 (1.04), 8.210 (0.93), 8.214 (0.90), 8.606 (3.97), 9.077 (0.83). 9.097 (0.79). |
| 62 | | LC-MS (Method L6): Rt = 1.27 | $^1$H-NMR (500 MHz, DICHLOROMETHANE-d2) δ [ppm]: 3.078 (16.00), 4.203 (0.84), 5.308 (0.97), 5.320 (1.31), 5.341 (0.74), 5.356 (0.72), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | min; MS (ESIpos): m/z = 443 [M + H]+ | 6.815 (1.16), 6.831 (1.27), 6.913 (1.20), 6.927 (0.69), 7.165 (0.71), 7.179 (1.10), 7.297 (0.77), 7.305 (0.99), 7.315 (1.75), 7.331 (1.10), 7.446 (0.67), 7.463 (1.09), 7.554 (0.91), 7.569 (1.18), 7.571 (1.18), 7.586 (0.87), 7.726 (1.17), 7.728 (1.20), 7.740 (1.02), 7.741 (1.01), 8.152 (1.65), 8.166 (1.87), 8.673 (2.52). |
| 63 | | LC-MS (Method L6): Rt = 1.57 min; MS (ESIpos): m/z = 443 [M + H]+ | $^1$H-NMR (500 MHz, DMSO-d6) δ [ppm]: 2.362 (0.64), 2.635 (0.64), 3.075 (16.00), 6.787 (0.94), 6.790 (1.04), 6.804 (1.04), 6.806 (1.09), 6.925 (0.94), 6.927 (0.99), 6.942 (0.59), 7.171 (0.79), 7.355 (0.84), 7.369 (0.79), 7.422 (1.78), 7.603 (0.74), 7.612 (0.79), 7.670 (0.79), 7.684 (0.99), 7.687 (0.99), 7.702 (0.89), 7.857 (1.04), 7.859 (1.19), 7.871 (0.99), 7.873 (1.04), 8.279 (0.99), 8.282 (1.09), 8.296 (0.99), 8.301 (1.88), 8.311 (1.39), 8.626 (3.76), 9.094 (0.84), 9.110 (0.84). |
| 64 | | LC-MS (Method L6): Rt = 1.48 min; MS (ESIpos): | $^1$H-NMR (400 MHz, DMSO-d6) δ [ppm]: −0.008 (1.17), 3.065 (16.00), 3.909 (9.18), 4.260 (0.93), 4.268 (0.99), 5.752 (2.29), 6.786 (1.02), 6.803 (1.15), 6.806 (1.15), 6.923 (1.06), 6.941 (0.64), 7.014 (1.90), 7.016 (2.04), 7.169 (0.88), 7.194 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | m/z = 455 [M + H]+ | (1.22), 7.197 (1.12), 7.207 (1.15), 7.210 (1.10), 7.349 (0.91), 7.368 (0.83), 7.632 (0.74), 7.650 (1.07), 7.653 (0.90), 7.671 (0.98), 7.768 (1.17), 7.772 (1.15), 7.785 (0.90), 7.789 (0.83), 8.205 (1.69), 8.218 (1.63), 8.232 (1.04), 8.236 (1.05), 8.254 (0.98), 8.257 (0.90), 8.602 (3.69), 9.076 (0.93), 9.097 (0.90). |
| 65 | | LC-MS (Method L6): Rt = 1.69 min; MS (ESIpos): m/z = 459 [M + H]+ | $^1$H-NMR (500 MHz, DMSO-d6) δ [ppm]: 2.362 (0.80), 2.635 (0.74), 3.074 (16.00), 4.264 (0.74), 6.790 (1.04), 6.804 (1.04), 6.806 (1.16), 6.926 (0.98), 6.928 (1.04), 6.941 (0.55), 7.173 (0.80), 7.358 (0.86), 7.372 (0.80), 7.654 (1.04), 7.657 (1.16), 7.667 (1.66), 7.680 (0.98), 7.683 (0.98), 7.697 (0.92), 7.752 (1.90), 7.753 (1.96), 7.849 (1.04), 7.852 (1.16), 7.864 (0.98), 7.866 (0.98), 8.277 (0.98), 8.280 (1.10), 8.294 (0.92), 8.297 (0.98), 8.479 (1.53), 8.489 (1.53), 8.630 (3.74), 9.093 (0.92), 9.109 (0.92). |
| 66 | | LC-MS (Method L6): Rt = 1.08 min; MS (ESIpos): m/z = 453 [M + H]+ | $^1$H-NMR (500 MHz, DMSO-d6) δ [ppm]: −0.007 (3.16), 0.007 (2.43), 2.085 (0.91), 2.479 (16.00), 3.063 (15.53), 3.290 (1.71), 4.259 (0.73), 5.753 (4.07), 6.787 (0.96), 6.789 (1.08), 6.805 (1.15), 6.923 (1.01), 6.925 (1.05), 6.938 (0.58), 6.940 (0.59), 7.170 (0.86), 7.229 (4.94), 7.355 (0.90), 7.369 (0.82), 7.626 (0.70), 7.640 (1.04), 7.643 (0.94), 7.657 (0.96), 7.718 (1.11), 7.721 (1.23), 7.732 (0.83), 7.735 (0.84), 8.141 (0.84), 8.219 (0.97), 8.222 (1.05), 8.236 (0.90), 8.239 (0.91), 8.601 (3.53), 9.079 (0.94), 9.095 (0.92). |
| 67 | | LC-MS (Method L1): Rt = 1.42 min; MS (ESIpos): m/z = 520 [M + H]+ | $^1$H-NMR (400 MHz, DMSO-d6) δ [ppm]: −0.008 (1.73), 0.008 (1.62), 1.083 (7.08), 1.101 (16.00), 1.119 (7.35), 2.523 (1.15), 3.360 (2.01), 3.378 (5.98), 3.395 (5.74), 3.413 (1.81), 4.238 (1.03), 4.246 (0.84), 4.259 (1.48), 4.269 (1.39), 4.277 (0.92), 4.286 (0.88), 5.239 (0.96), 5.259 (0.94), 6.786 (1.61), 6.789 (1.77), 6.807 (1.84), 6.809 (1.93), 6.913 (0.87), 6.916 (0.88), 6.931 (1.76), 6.934 (1.80), 6.950 (1.09), 6.953 (1.08), 7.152 (0.90), 7.156 (0.98), 7.174 (1.49), 7.191 (0.74), 7.195 (0.72), 7.362 (1.54), 7.378 (1.43), 7.628 (0.85), 7.634 (2.10), 7.638 (4.21), 7.644 (9.24), 7.649 (4.32), 7.657 (2.01), 7.660 (1.75), 7.678 (1.75), 7.797 (1.98), 7.800 (2.12), 7.815 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 68 | | LC-MS (Method L1): Rt = 1.36 min; MS (ESIpos): m/z = 583 [M + H]+ | $^1$H-NMR (500 MHz, DMSO-d6) δ [ppm]: 1.845 (0.84), 2.040 (0.83), 2.050 (0.89), 2.057 (0.88), 2.068 (0.71), 4.052 (0.72), 4.064 (0.80), 4.069 (1.50), 4.075 (0.94), 4.087 (0.97). 4.092 (0.74), 4.167 (0.77), 4.172 (0.97), 4.180 (0.89), 4.187 (1.11), 5.072 (1.29), 5.088 (1.26), 5.753 (0.58), 6.752 (2.43), 6.754 (2.55), 6.768 (2.63), 6.771 (2.67), 6.844 (1.23), 6.846 (1.20), 6.859 (2.46), 6.861 (2.43), 6.874 (1.49), 6.876 (1.41), 7.069 (2.20), 7.082 (1.84), 7.134 (1.29), 7.138 (1.18), 7.151 (2.04), 7.165 (1.14), 7.168 (0.92), 7.593 (2.44), 7.595 (2.47), 7.610 (2.69), 7.612 (2.56), 7.680 (0.95), 7.709 (1.44), 7.711 (2.27), 7.713 (4.04), 7.716 (8.15), 7.718 (16.00), 7.721 (5.44), 7.831 (2.20), 7.845 (2.64), 7.848 (2.23), 7.863 (2.06), 8.037 (2.79), 8.039 (2.83), 8.051 (2.40), 8.054 (2.29), 8.418 (6.05), 8.870 (4.59), 8.961 (0.63), 9.079 (2.41), 9.095 (2.29), 9.192 (9.46). |
| 69 | | LC-MS (Method L1): Rt = 0.86 min; MS (ESIpos): m/z = 514 [M + H]+ | $^1$H-NMR (400 MHz, DMSO-d6) delta [ppm]: −0.008 (4.56), 0.008 (2.59), 1.234 (0.95), 1.880 (1.58), 1.890 (0.87), 1.901 (1.75), 1.912 (1.84), 1.923 (0.87), 1.933 (1.74), 2.350 (0.80), 2.361 (1.45), 2.369 (1.79), 2.381 (1.55), 2.392 (1.49), 2.401 (1.25), 2.775 (0.78), 2.797 (1.46), 2.816 (1.81), 2.837 (2.31), 2.858 (1.06), 2.937 (1.44), 2.945 (1.55), 2.959 (1.61), 2.966 (1.48), 2.976 (1.06), 2.985 (0.97), 2.998 (0.95), 3.005 (0.79), 5.345 (0.97), 5.365 (2.65), 5.384 (2.58), 5.405 (0.85), 5.754 (15.35), 7.164 (0.99), 7.182 (3.03), 7.195 (4.52), 7.200 (5.02), 7.215 (3.94), 7.230 (2.07), 7.247 (4.63), 7.264 (2.46), 7.277 (3.90), 7.293 (2.68), 7.402 (2.41), 7.420 (3.40), 7.441 (2.65), 7.539 (4.31), 7.610 (2.91), 7.615 (5.39), 7.620 (4.00), 7.646 (16.00), 7.651 (11.73), 7.738 (4.35), 7.756 (3.85), 8.133 (12.50), 8.155 (3.28), 8.795 (9.42), 8.838 (3.65), 8.858 (3.47), 9.979 (4.48), 12.732 (2.72). |
| 70 | | LC-MS (Method L6): Rt = 1.42 min; MS (ESIneg): m/z = 465 [M − H]− | $^1$H-NMR (500 MHz, DMSO-d6) δ [ppm]: 2.912 (16.00), 3.056 (8.85), 3.304 (1.27), 5.751 (0.73), 6.786 (0.85), 6.788 (0.88), 6.802 (0.93), 6.805 (0.92), 6.832 (0.77), 6.848 (0.83), 6.883 (0.92), 6.887 (1.01), 6.888 (1.00), 6.921 (0.87), 6.923 (0.83), 7.219 (0.72), 7.235 (1.00), 7.251 (0.60), 7.591 (0.61), 7.605 (0.91), 7.608 (0.71), 7.622 (0.84), 7.675 (0.96), 7.678 (0.97), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.689 (0.69), 8.132 (0.85), 8.150 (0.79), 8.153 (0.78), 8.168 (0.74), 8.567 (2.33), 9.079 (0.74). |
| 71 | | LC-MS (Method L6): Rt = 0.97 min; MS (ESIneg): m/z = 476 [M − H]− | $^1$H-NMR (500 MHz, CHLOROFORM-d) δ [ppm]: 3.144 (16.00), 3.851 (8.34), 4.212 (0.71), 6.859 (1.08), 6.861 (1.16), 6.875 (1.18), 6.877 (1.26), 6.908 (0.59), 6.910 (0.57), 6.923 (1.17), 6.925 (1.11), 6.938 (0.69), 6.940 (0.64), 7.204 (0.94), 7.302 (0.98), 7.318 (0.92), 7.590 (0.88), 7.604 (1.17), 7.607 (1.08). 7.621 (1.12), 7.653 (1.78), 7.757 (1.31), 7.760 (1.38), 7.772 (1.15), 7.774 (1.07), 7.886 (0.77), 8.127 (1.09), 8.130 (1.10), 8.144 (1.04), 8.147 (0.99), 9.040 (1.35). |
| 72 | | LC-MS (Method L1): Rt = 1.34 min; MS (ESIpos): m/z = 515 [M + H]+ | $^1$H-NMR (400 MHz, DMSO-d6) δ [ppm]: 0.934 (0.65), 0.951 (1.40), 0.969 (0.72), 1.815 (0.91), 1.825 (1.04), 1.842 (1.24), 1.859 (0.77), 2.014 (1.18), 2.027 (1.17), 2.035 (1.12), 2.049 (0.88), 2.694 (1.05), 4.031 (0.92), 4.052 (1.96), 4.059 (1.36), 4.073 (1.35), 4.080 (1.05), 4.158 (1.43), 4.168 (1.30), 4.176 (1.62), 4.186 (0.92), 4.196 (0.91), 5.044 (0.78), 5.058 (1.79), 5.077 (1.81), 5.092 (0.82), 6.686 (3.38), 6.691 (5.17), 6.696 (3.37), 6.736 (3.20), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.754 (3.60), 6.845 (1.55), 6.864 (3.34), 6.883 (2.11), 7.082 (3.20), 7.102 (2.64), 7.117 (1.82), 7.122 (1.57), 7.138 (2.83), 7.156 (1.43), 7.665 (2.79), 7.668 (2.76), 7.686 (3.87), 7.689 (3.76), 7.710 (16.00), 7.714 (7.25), 7.776 (2.70), 7.794 (3.62), 7.815 (2.25), 7.938 (5.43), 7.942 (5.37), 7.987 (3.52), 7.990 (3.35), 8.005 (3.05), 8.008 (2.74), 8.147 (5.19), 8.153 (5.21), 8.914 (3.01), 8.935 (2.93), 9.116 (10.01). |
| 73 | | LC-MS (Method L1): Rt = 0.71 min; MS (ESIpos): m/z = 463 [M + H]+ | $^1$H-NMR (400 MHz, DMSO-d6) δ [ppm]: −0.008 (2.06), 0.008 (1.57), 2.133 (0.74), 2.366 (0.70), 2.524 (2.87), 2.710 (0.70), 3.079 (16.00), 4.252 (0.87), 4.260 (0.94), 5.753 (3.02), 5.955 (1.19), 6.777 (1.02), 6.794 (1.11), 6.881 (0.59), 6.900 (1.22), 6.902 (1.13), 6.918 (0.70), 7.029 (0.98), 7.031 (1.06), 7.047 (1.44), 7.135 (1.44), 7.156 (2.13), 7.174 (1.26), 7.248 (1.09), 7.254 (1.43), 7.262 (1.04), 7.308 (1.02), 7.322 (0.96), 7.342 (0.81), 7.404 (1.37), 7.424 (1.15), 7.629 (0.83), 7.647 (1.07), 7.650 (0.89), 7.668 (1.04), 7.733 (1.26), 7.737 (1.35), 7.751 (0.94), 7.754 (0.87), 8.192 (1.00), 8.196 (1.04), 8.214 (0.98), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.217 (0.87), 8.469 (3.80), 9.059 (0.93), 9.080 (0.89), 11.099 (0.85). |
| 74 | | LC-MS (Method L6): Rt = 1.42 min; MS (ESIpos): m/z = 508 [M + H]+ | $^1$H-NMR (400 MHz, DMSO-d6) δ [ppm]: 3.169 (16.00), 3.645 (1.14), 3.658 (1.38), 6.782 (0.83), 6.799 (0.91), 6.803 (0.87), 6.899 (0.86), 7.602 (1.31), 7.607 (1.19), 7.622 (4.81), 7.627 (2.96), 8.133 (2.91), 8.546 (2.19). |
| 75 | | LC-MS (Method L6): Rt = 2.54 min; MS (ESIpos): m/z = 536 [M + H]+ | $^1$H-NMR (400 MHz, DMSO-d6) δ [ppm]: −0.008 (0.97), 0.008 (0.95), 2.085 (1.49), 3.061 (10.00), 3.173 (16.00), 3.455 (2.24), 3.469 (1.54), 3.554 (0.89), 3.567 (1.31), 3.585 (1.41), 6.788 (1.20), 6.791 (1.37), 6.809 (1.39), 6.812 (1.48), 6.926 (1.31), 6.929 (1.31), 6.944 (0.78), 6.947 (0.77), 7.174 (1.05), 7.357 (1.04), 7.372 (1.00), 7.637 (2.10), 7.641 (10.04), 7.645 (3.82), 7.663 (1.38). 7.667 (1.27), 7.685 (1.30), 7.805 (1.45), 7.809 (1.59), 7.823 (1.19), 7.827 (1.19), 8.299 (1.28), 8.303 (1.36), 8.320 (1.23), 8.324 (1.19), 8.712 (5.32), 9.065 (1.22), 9.086 (1.19). |
| 76 | | LC-MS (Method L1): Rt = 0.92 min; MS (ESIpos): m/z = 522 [M + H]+ | $^1$H-NMR (400 MHz, DMSO-d6) δ [ppm]: −0.008 (2.51), 0.008 (2.41), 2.063 (1.06), 2.073 (1.60), 2.143 (0.95), 2.157 (1.15), 2.327 (0.87), 2.523 (2.45), 2.670 (0.84), 3.334 (4.14), 3.356 (4.85), 3.567 (2.37), 3.581 (5.84), 3.593 (3.89), 3.684 (3.13), 3.697 (2.74), 4.269 (3.13), 4.278 (2.53), 4.286 (1.74), 5.247 (1.52), 5.266 (1.51), 6.783 (2.84), 6.786 (3.12), 6.804 (3.25), 6.807 (3.39), 6.884 (1.49), 6.887 (1.55), 6.903 (3.11), 6.906 (3.03), 6.921 (1.86), 6.924 (1.77), 7.143 (1.48), 7.148 (1.63), 7.165 (2.50), 7.182 (1.18), 7.186 (1.20), 7.294 (2.53), 7.314 (2.37), 7.531 (1.18), 7.551 (1.97), 7.569 (1.32), 7.609 (3.49), 7.614 (3.76), 7.624 (16.00), 7.628 (9.17), 7.750 (2.78), 7.766 (2.37), 8.381 (1.85), 8.402 (1.76), 8.558 (5.29), 9.023 (1.39), 9.042 (1.36). |
| 77 | | LC-MS (Method L1): Rt = 0.88 min; MS (ESIpos): m/z = 533 [M + H]+ | $^1$H-NMR (400 MHz, DMSO-d6) δ [ppm]: 2.063 (0.91), 3.712 (0.91), 4.023 (3.89), 4.028 (3.96), 4.242 (1.32), 4.251 (1.33), 4.261 (1.86), 4.270 (2.06), 4.282 (1.19), 4.674 (1.12), 4.887 (1.03), 4.916 (1.04), 4.929 (2.17), 4.947 (2.17), 4.961 (1.00), 5.241 (1.16), 5.261 (1.09), 5.754 (5.20), 6.794 (2.03), 6.814 (2.13), 6.905 (0.96), 6.907 (1.01), 6.923 (1.92), 6.926 (1.96), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 6.942 (1.13), 6.945 (1.13), 7.156 (1.19), 7.160 (1.25), 7.177 (1.78), 7.195 (0.88), 7.199 (0.81), 7.327 (1.71), 7.346 (1.58), 7.626 (1.09), 7.630 (1.31), 7.640 (16.00), 7.647 (1.70), 7.659 (2.46), 7.664 (2.09), 7.681 (1.56), 7.839 (1.82), 7.842 (2.20), 7.857 (1.59), 7.860 (1.81), 8.138 (2.43), 8.305 (1.86), 8.309 (2.07), 8.327 (1.68), 8.330 (1.74), 8.711 (2.71), 8.734 (6.72), 8.846 (0.69), 9.226 (1.85), 9.246 (1.78). |
| 78 | | LC-MS (Method L1): Rt = 1.41 min; MS (ESIpos): m/z = 580 [M + H]+ | $^1$H-NMR (400 MHz, DMSO-d6) δ [ppm]: 1.356 (0.92), 3.007 (16.00), 3.407 (0.85), 3.421 (1.08), 3.473 (1.23), 3.486 (0.97), 3.552 (1.13), 3.559 (1.40), 3.565 (1.84), 3.573 (1.77), 5.754 (2.61), 6.794 (0.83), 6.813 (0.96), 6.927 (0.88), 7.329 (0.75), 7.638 (0.93), 7.643 (1.08), 7.652 (3.47), 7.657 (2.11), 7.666 (0.89), 7.687 (0.67), 7.810 (0.96), 7.827 (0.77). 8.237 (0.79), 8.240 (0.79), 8.258 (0.74), 8.764 (3.04), 8.881 (0.82), 8.901 (0.79). |
| 79 | | LC-MS (Method L6): Rt = 1.67 min; MS | $^1$H-NMR (400 MHz, DMSO-d6) δ [ppm]: −0.008 (2.20), 0.008 (2.00), 1.091 (1.05), 1.157 (1.00), 1.175 (2.17), 1.193 (1.28), 1.234 (2.13), 1.391 (1.14), 1.908 (3.71), 1.916 (4.42), 1.924 (10.00), 1.932 (4.39), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 502 [M + H]+ | 1.941 (3.75), 1.956 (1.50), 1.988 (1.88), 2.462 (0.91), 2.472 (1.20), 2.689 (7.43), 2.825 (0.94), 2.845 (1.20), 2.865 (1.56), 2.965 (0.92), 2.977 (0.96), 3.288 (1.30), 3.650 (3.10), 3.666 (7.98), 3.682 (2.94), 5.489 (1.79). 5.509 (1.80). 7.211 (2.58), 7.215 (2.00), 7.221 (3.24), 7.228 (2.98), 7231 (3.71), 7.233 (3.97), 7.245 (1.09), 7.259 (2.43), 7.271 (1.46), 7.356 (1.78), 7.365 (1.99), 7.377 (1.40), 7.477 (1.97), 7.495 (2.48), 7.498 (2.33), 7.516 (2.30), 7.604 (1.42), 7.610 (3.39), 7.614 (5.27), 7.620 (16.00), 7.624 (6.54), 7.709 (2.80), 7.713 (3.02), 7.727 (2.49), 7.731 (2.42), 8.263 (2.41), 8.266 (2.49), 8.284 (2.32), 8288 (2.22), 8.452 (9.01), 8.878 (2.24), 8.899 (2.20). |
| 80 | | LC-MS (Method L1): Rt = 0.91 min; MS (ESIpos): m/z = 546 [M + H]+ | $^1$H-NMR (400 MHz, DMSO-d6) δ [ppm]: −0.149 (0.90), −0.008 (7.64), 0.008 (7.69), 0.146 (0.95), 1.175 (0.44), 1.236 (2.24), 1.879 (1.70), 1.916 (1.03), 1.936 (0.98), 1.950 (0.87), 1.968 (0.77), 1.988 (0.87), 2.327 (1.36), 2.366 (1.49), 2.523 (5.17), 2.670 (1.57), 2.710 (1.16), 2.815 (0.49), 2.835 (0.85), 2.855 (1.11), 2.874 (1.26), 2.893 (0.67), 2.959 (0.72), 2.972 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.87), 2.981 (0.80), 2.993 (0.90), 3.021 (0.54), 3.798 (0.87), 3.816 (0.93), 4.640 (1.05), 4.654 (1.23), 4.662 (1.13), 5.511 (0.54), 5.530 (1.39), 5.549 (1.36), 5.567 (0.54), 7.231 (2.24), 7.240 (2.39), 7248 (3.68), 7.253 (2.98), 7.271 (2.68), 7.285 (1.05), 7.446 (1.44), 7.453 (1.57), 7.467 (1.34), 7.629 (1.65), 7.640 (16.00), 7.667 (1.67), 7.801 (2.32), 7.816 (1.85), 8.282 (1.65), 8.301 (1.57), 8.695 (6.92), 12.590 (0.62). |
| 81 | | LC-MS (Method L1): Rt = 0.92 min; MS (ESIpos): m/z = 478 [M + H]+ | $^1$H-NMR (400 MHz, DMSO-d6) δ [ppm]: −0.008 (1.26), 0.008 (1.50). 3.074 (16.00), 4.253 (0.86), 4.262 (0.91), 5.754 (4.63), 6.778 (0.85), 6.781 (0.95), 6.799 (0.99), 6.801 (1.02), 6.913 (0.95), 6.917 (0.94), 6.932 (0.59), 7.164 (0.79), 7.343 (0.82), 7.648 (0.69), 7.665 (1.10), 7.669 (0.79), 7.687 (1.14), 7.721 (1.10), 7.725 (1.20), 7.739 (0.70), 7.743 (0.63), 8.265 (0.99), 8.269 (1.00), 8.286 (0.94), 8.290 (0.86). 8.566 (3.67), 9.075 (0.84). 9.096 (0.82). |
| 82 | | LC-MS (Method L6): | $^1$H-NMR (400 MHz, DMSO-d6) δ [ppm]: 3.288 (1.60), 3.300 (2.14), 3.311 (16.00), 3.865 (1.20), 3.877 (2.00). 3.888 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | Rt = 2.08 min; MS (ESIpos): m/z = 520 [M + H]+ | (1.13), 6.780 (0.66), 6.783 (0.71), 6.800 (0.74), 6.803 (0.77), 6.922 (0.70), 6.925 (0.69), 7.385 (0.70), 7.720 (0.80), 7.741 (0.83), 7.764 (0.84), 7.768 (0.91), 8.304 (0.65), 8.308 (0.66), 8.325 (0.62), 8.635 (2.82), 9.161 (0.64). |
| 83 | | LC-MS (Method L6): Rt = 2.26 min; MS (ESIpos): m/z = 568 [M + H]+ | $^1$H-NMR (400 MHz, DMSO-d6) δ [ppm]: −0.008 (3.64), 0.008 (3.64), 1.988 (0.96), 2.038 (0.93), 2.045 (0.98), 2.057 (1.02), 2.073 (1.49). 2.080 (1.22). 2.189 (0.93), 2.203 (1.36), 2.215 (1.27), 2.224 (1.27), 3.259 (1.29), 3.277 (3.60), 3.290 (8.31), 3.334 (2.18). 3.610 (5.58), 3.867 (6.16), 3.880 (11.07), 3.892 (6.04), 4234 (2.20), 4.241 (1.69), 4.254 (2.29), 4.261 (2.71), 4.269 (2.31), 4.275 (1.84), 4.285 (1.84). 5.232 (0.89), 5.247 (2.02), 5.267 (2.02), 5281 (0.89), 6.685 (0.98), 6.706 (1.07), 6.779 (3.53), 6.782 (3.93), 6.800 (4.02), 6.803 (4.29), 6.901 (1.93), 6.904 (1.98), 6.919 (3.93), 6.922 (3.96), 6.938 (2.44), 6.941 (2.38), 7.146 (1.98), 7.150 (2.13), 7.167 (3.18), 7.185 (1.62), 7.189 (1.60), 7.363 (3.33), 7.380 (3.22), 7.384 (3.18), 7.389 (2.04), 7.409 (4.31), 7.426 (3.07), 7.429 (3.18), 7.466 (2.24), 7.471 (2.76), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.482 (2.33), 7.486 (3.64), 7.490 (1.80), 7.502 (1.51), 7.506 (1.38), 7.602 (1.44), 7.620 (2.38), 7.640 (1.22), 7.704 (2.67), 7.722 (4.38), 7.725 (3.36), 7.742 (4.40), 7.779 (4.49), 7.783 (5.00), 7.797 (2.96), 7.800 (2.76), 8.308 (3.76), 8.312 (3.84), 8.329 (3.56), 8.333 (3.38), 8.612 (16.00), 9.161 (3.69), 9.182 (3.62). |
| 84 | | LC-MS (Method L5): Rt = 0.69 min; MS (ESIpos): m/z = 517 [M + H]+ | |
| 85 | | LC-MS (Method L5): Rt = 1.38 min; MS (ESIpos): m/z = 564 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 86 | | LC-MS (Method L5): Rt = 1.20 min; MS (ESIpos): m/z = 524 [M + H]+ | |
| 87 | | LC-MS (Method L5): Rt = 1.25 min; MS (ESIpos): m/z = 519 [M + H]+ | |
| 88 | 1.3 | LC-MS (Method L5): Rt = 0.71 min; MS (ESIpos): m/z = 519 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 89 | 2.2 | LC-MS (Method L5): Rt = 0.95 min; MS (ESIpos): m/z = 506 [M + H]+ | |
| 90 | 4.9 | LC-MS (Method L5): Rt = 1.33 min; MS (ESIpos): m/z = 534 [M + H]+ | |
| 91 | 2.9 | LC-MS (Method L5): Rt = 1.12 min; MS (ESIpos): m/z = 546 [M + H]+ | |
| 92 | 2.9 | LC-MS (Method L5): Rt = 1.12 min; MS (ESIpos): m/z = 546 [M + H]+ | |
| 93 | | LC-MS (Method L5): Rt = 1.33 min; MS (ESIpos): m/z = 564 [M + H]+ | |
| 94 | | LC-MS (Method L5): Rt = 0.72 min; MS (ESIpos): m/z = 545 [M + H]+ | |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 95 | | LC-MS (Method L5): Rt = 0.96 min; MS (ESIpos): m/z = 532 [M + H]+ | |
| 96 | 1.4 | LC-MS (Method L5): Rt = 0.74 min; MS (ESIpos): m/z = 545 [M + H]+ | |
| 97 | | LC-MS (Method L5): Rt = 1.01 min; MS (ESIpos): m/z = 544 [M + H]+ | |
| 98 | | LC-MS (Method L5): Rt = 0.90 min; MS (ESIpos): m/z = 533 [M + H]+ | |
| 99-1 | 2.2 | LC-MS (Method L5): Rt = 0.97 min; MS (ESIpos): m/z = 539 [M + H]+ | |
| 99-2 | 2.1 | LC-MS (Method L5): Rt = 0.93 min; MS (ESIpos): m/z = 520 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 100 | 1.9 | LC-MS (Method L5): Rt = 0.87 min; MS (ESIpos): m/z = 492 [M + H]+ | |
| 101 | 1.8 | LC-MS (Method L5): Rt = 0.85 min; MS (ESIpos): m/z = 518 [M + H]+ | |
| 102 | | LC-MS (Method L5): Rt = 0.85 min; MS (ESIpos): m/z = 504 [M + H]+ | |
| 103 | | LC-MS (Method L5): Rt = 0.71 min; MS (ESIpos): m/z = 557 [M + H]+ | |
| 104 | | LC-MS (Method L5): Rt = 1.26 min; MS (ESIpos): m/z = 516 [M + H]+ | |
| 105 | | LC-MS (Method L5): Rt = 1.27 min; MS (ESIpos): m/z = 516 [M + H]+ | |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 106 | 3.7 | LC-MS (Method L5): Rt = 1.24 min; MS (ESIpos): m/z = 516 [M + H]+ | |
| 107 | | LC-MS (Method L5): Rt = 1.31 min; MS (ESIpos): m/z = 546 [M + H]+ | |
| 108 | | LC-MS (Method L5): Rt = 1.03 min; MS (ESIpos): m/z = 504 [M + H]+ | |
| 109 | | LC-MS (Method L5): Rt = 1.42 min; MS (ESIpos): m/z = 564 [M + H]+ | |
| 110 | | LC-MS (Method L5): Rt = 1.38 min; MS (ESIpos): m/z = 544 [M + H]+ | |
| 111 | | LC-MS (Method L5): Rt = 1.00 min; MS (ESIpos): m/z = 550 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 112 | 2.6 | LC-MS (Method L1): Rt = 1.10 min; MS (ESIpos): m/z = 538 [M + H]+ | $^1$H-NMR 400 MHz, DMSO-d6) δ [ppm]: −0.008 (3.14), 0.008 (2.96), 0.146 (0.46), 1.917 (0.92), 1.937 (0.96), 1.949 (1.08), 1.968 (0.98), 2.328 (0.72), 2.568 (1.52), 2.587 (2.01), 2.605 (1.54), 2.624 (0.91), 2.640 (0.62), 2.670 (0.64), 2.849 (0.85), 2.868 (1.12), 2.887 (1.37), 2.908 (0.64), 2.974 (0.91), 2.988 (0.95), 3.707 (1.26), 3.726 (2.13), 3.736 (2.13), 3.753 (1.19), 3.841 (2.10), 3.873 (4.31), 3.905 (2.01), 5.508 (0.54), 5.528 (1.68), 5.549 (1.67), 7.224 (2.73), 7.233 (3.15), 7.241 (3.80), 7.271 (2.34), 7.414 (1.68), 7.429 (1.43), 7.640 (16.00), 7.665 (1.81), 7.684 (2.39), 7.705 (2.19), 7.835 (2.72), 7.850 (2.23), 8.239 (2.35), 8.258 (2.17), 8.695 (9.00), 9.086 (2.09), 9.106 (2.05). |
| 113 | | LC-MS (Method L5): Rt = 1.04 min; MS (ESIpos): m/z = 545 [M + H]+ | |
| 114 | | LC-MS (Method L5): Rt = 1.40 min; MS (ESIpos): m/z = 566 [M + H]+ | |
| 115 | | LC-MS (Method L5): Rt = 1.05 min; MS (ESIpos): m/z = 533 [M + H]+ | |
| 116 | 3.4 | LC-MS (Method L5): Rt = 1.25 min; MS (ESIpos): m/z = 559 [M + H]+ | |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 117 | | LC-MS (Method L5): Rt = 1.25 min; MS (ESIpos): m/z = 565 [M + H]+ | |
| 118 | | LC-MS (Method L5): Rt = 1.33 min; MS (ESIpos): m/z = 552 [M + H]+ | |
| 119 | | LC-MS (Method L5): Rt = 0.92 min; MS (ESIpos): m/z = 506 [M + H]+ | |
| 120 | | LC-MS (Method L5): Rt = 0.94 min; MS (ESIpos): m/z = 502 [M + H]+ | |
| 121 | | LC-MS (Method L5): Rt = 1.00 min; MS (ESIpos): m/z = 524 [M + H]+ | |
| 122 | 2 | LC-MS (Method L5): Rt = 0.90 min; MS (ESIpos): m/z = 547 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 123 | | LC-MS (Method L5): Rt = 0.98 min; MS (ESIpos): m/z = 544 [M + H]+ | |
| 124 | | LC-MS (Method L8): Rt = 0.82 min; MS (ESIpos): m/z = 518 [M − H]− | $^1$H-NMR (500 MHz, DMSO-d6) δ [ppm]: 0.007 (0.42), 1.234 (0.43), 1.937 (0.49), 1.954 (1.37), 1.962 (0.72), 1.971 (1.46), 1.979 (1.53), 1.988 (0.69), 1.996 (1.47), 2.013 (0.54), 2.446 (0.68), 2.453 (0.82), 2.462 (1.42), 2.469 (1.84), 2.478 (2.17), 2.518 (7.50), 2.809 (0.67), 2.826 (1.25), 2.842 (1.48), 2.858 (1.88), 2.874 (0.85), 2.960 (1.13), 2.967 (1.21), 2.978 (1.24), 2.984 (1.18), 2.992 (0.89), 2.998 (0.84), 3.009 (0.81), 3.016 (0.70), 3.316 (1.98), 3.664 (0.52), 3.675 (1.21), 3.689 (2.49), 3.701 (2.76), 3.715 (2.35), 3.729 (1.06), 3.740 (0.44), 5.503 (0.84), 5.519 (2.36), 5.535 (2.35), 5.551 (0.79), 6.929 (2.26), 7.192 (0.72), 7.206 (4.09), 7.213 (4.86), 7.220 (5.20), 7.224 (3.60), 7.235 (1.11), 7.255 (3.09), 7.266 (1.77), 7.271 (1.27), 7.362 (2.40), 7.368 (2.53), 7.379 (2.23), 7.400 (2.23), 7.534 (2.37), 7.548 (3.14), 7.550 (2.96), 7.565 (2.60), 7.599 (3.07), 7.603 (6.46), 7.607 (4.90), 7.627 (16.00), 7.631 (11.94), 7.739 (3.66), 7.741 (3.78), 7.754 (3.17), 7.755 (3.13), 7.917 (1.31), 7.928 (2.35), 7.938 (1.20), 8.157 (3.18), 8.334 (3.01), 8.350 (2.81), 8.562 (10.41), 8.850 (3.16), 8.866 (3.04). |
| 125 | 2.1 | LC-MS (Method L5): Rt = 0.95 min; MS (ESIpos): m/z = 542 [M + H]+ | |
| 126 | | LC-MS (Method L5): Rt = 0.87 min; MS (ESIpos): m/z = 533 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 127 | 1.9 | LC-MS (Method L5): Rt = 0.90 min; MS (ESIpos): m/z = 519 [M + H]+ | |
| 128 | 2.1 | LC-MS (Method L5): Rt = 0.97 min; MS (ESIpos): m/z = 520 [M + H]+ | |
| 129 | 1.8 | LC-MS (Method L5): Rt = 0.85 min; MS (ESIpos): m/z = 505 [M + H]+ | |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 130 | | LC-MS (Method L1): Rt = 0.85 min; MS (ESIpos): m/z = 458 [M + H]+ | $^1$H-NMR (400 MHz, DMSO-d6) δ [ppm]: 3.066 (16.00), 4.262 (0.81), 4.270 (0.92), 5.754 (1.15), 6.784 (0.98), 6.787 (1.02), 6.805 (1.10), 6.807 (1.10), 6.923 (0.99), 6.926 (0.97), 7.169 (0.81), 7.353 (0.82), 7.373 (0.79), 7.455 (0.88), 7.460 (1.48), 7.464 (1.00), 7.469 (1.06), 7.487 (1.54), 7.506 (0.70), 7.532 (0.80), 7.536 (1.38), 7.540 (0.75), 7.554 (0.76), 7.623 (0.73), 7.643 (2.49), 7.648 (1.12), 7.662 (1.03), 7.739 (1.15), 7.743 (1.22), 7.757 (0.88), 7.761 (0.82), 8.204 (1.00), 8.208 (1.02), 8.225 (0.96), 8.229 (0.88), 8.611 (3.90), 9.078 (0.87), 9.098 (0.85). |
| 131 | | LC-MS (Method L1): Rt = 1.40 min; MS (ESIpos): m/z = 494 [M + H]+ | $^1$H-NMR (400 MHz, DMSO-d6) δ [ppm]: −0.008 (2.45), 0.008 (2.01), 2.031 (0.91), 2.038 (0.84), 2.086 (1.12), 2.199 (0.70), 3.673 (16.00), 3.742 (5.31), 4.174 (1.20), 4.181 (0.78), 4.195 (0.87), 4.203 (0.99), 4.287 (0.82), 4.296 (0.76), 4.304 (0.93), 5.125 (1.08), 5.142 (1.08), 6.796 (1.69), 6.816 (1.95), 6.878 (0.99), 6.881 (0.91), 6.897 (1.97), 6.916 (1.18), 6.957 (0.91), 6.972 (0.89), 7.152 (1.31), 7.157 (1.12), 7.166 (1.84), 7.171 (2.18), 7.185 (2.45), 7.196 (1.01), 7.206 (1.77), 7.283 (0.80), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.287 (0.91), 7.294 (1.69), 7.314 (1.54), 7.387 (2.01), 7.391 (1.99), 7.406 (1.77), 7.409 (1.59), 7.445 (2.22), 7.449 (2.24), 7.501 (6.85), 7.506 (6.87), 7.717 (0.85), 7.736 (1.54), 7.741 (2.47), 7.746 (1.27), 7.935 (2.81), 7.951 (2.83), 8.166 (0.63), 8.903 (1.69), 8.921 (1.69), 9.904 (1.94), 9.922 (2.56), 9.934 (1.42). |
| 132 | | LC-MS (Method L6): Rt = 2.15 min; MS (ESIpos): m/z = 526 [M + H]+ | $^{1}$H-NMR (400 MHz, DMSO-d6) δ [ppm]: −0.008 (1.84), 0.008 (1.78). 3.075 (16.00), 4.248 (0.91), 4.256 (1.05), 6.774 (1.08), 6.777 (1.18), 6.794 (1.23), 6.797 (1.29), 6.889 (0.56), 6.905 (1.13), 6.908 (1.14), 6.924 (0.71), 6.926 (0.68), 7.142 (0.63), 7.160 (0.95), 7.335 (0.74), 7.468 (0.66), 7.474 (0.64), 7.633 (0.61), 7.650 (1.67), 7.669 (2.82), 7.900 (2.22), 7.906 (2.18), 8.257 (1.14), 8.263 (1.06), 8.276 (1.03), 8.282 (1.00), 8.537 (3.81). |
| 133 | | LC-MS (Method L6): Rt = 2.40 min; MS (ESIpos): m/z = 568 [M + H]+ | $^{1}$H-NMR (400 MHz, DMSO-d6) δ [ppm]: −0.149 (0.91), −0.008 (7.68), 0.008 (7.18), 0.146 (0.91), 2.027 (1.24), 2.035 (1.27), 2.046 (1.34), 2.062 (1.88), 2.070 (1.58), 2.078 (1.17), 2.085 (0.81), 2.184 (1.24), 2.196 (1.71), 2.209 (1.71), 2.218 (1.64), 2.230 (1.07), 2.366 (0.70), 2.710 (0.64), 3.247 (1.24), 3.289 (8.35), 3.334 (1.81), 3.866 (8.18), 3.876 (13.05), 3.888 (7.51), 3.906 (0.97), 4.204 (0.74), 4.212 (0.97), 4.224 (0.91), 4.232 (2.85), 4.240 (2.28), 4.252 (3.66), 4.264 (3.52), 4.271 (2.52), 4.280 (2.52), 4.299 (0.94), 5.241 (2.11), 5.255 (2.08), 5.753 (4.53), 6.776 (4.49), 6.779 (5.00), 6.796 (5.20), 6.799 (5.50), 6.896 (2.21), 6.915 (4.70), 6.933 (2.78), 7.142 (2.55), 7.147 (2.72), 7.164 (4.13), 7.181 (2.11), 7.186 (2.01), 7.357 (4.19), 7.374 (3.96), 7.444 (2.25), 7.450 (2.42), 7.476 (2.68), 7.482 (2.58), 7.686 (1.38), 7.703 (7.55), 7.711 (6.74), 7.720 (16.00), 7.728 (1.71), 7.909 (7.31), 7.915 (7.11), 8.282 (0.91), 8.291 (4.49), 8.300 (3.82), 8.307 (3.66), 8.316 (3.89), 8.325 (0.74), 8.606 (7.01), 8.610 (7.75), 9.160 (2.82), 9.181 (2.72). |
| 134 | 1.9 | LC-MS (Method L1): Rt = 0.84 min; MS (ESIpos): m/z = 578 | $^{1}$H-NMR (400 MHz, DMSO-d6) δ [ppm] = 8.99 (d, 1H), 8.45 (s, 1H), 8.36 (d, 1H), 8.13 (s, 1H), 7.83 (br s, 1H), 7.73 (d, 1H), 7.60-7.63 (m, 3H), 7.54 (t, 1H), 7.32 (d, 1H), 7.16 (t, 1H), 6.91 (t, 1H), 6.79 (d, 1H), 5.21-5.27 (m, 1H), 4.22-4.30 (m, 2H), 3.07 (d, 3H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | 2.52-2.55 (m, 4H), 2.12-2.20 (m, 1H), 2.00-2.08 (m, 1H). |
| 135 | 1.9 | LC-MS (Method L1): Rt = 0.89 min; MS (ESIpos): m/z = 504 [M + H]+ | $^1$H-NMR (400 MHz, DMSO-d6) δ [ppm]: −0.008 (6.30), 0.008 (2.98), 2.004 (1.02), 2.014 (0.94), 2.026 (1.43), 2.041 (1.28), 2.126 (1.31), 2.141 (1.56), 2.373 (2.15), 2.394 (2.92), 2.412 (2.16), 2.433 (1.25), 2.519 (4.80), 2.523 (4.67), 4.243 (3.28), 4.255 (4.75), 4.261 (3.01), 4.270 (2.58), 4.427 (5.50), 4.446 (8.06), 4.466 (4.62), 5.160 (0.92), 5.174 (1.75), 5.194 (1.64), 5.754 (2.42), 6.781 (3.04), 6.785 (3.14), 6.802 (3.39), 6.805 (3.26), 6.887 (1.73), 6.890 (1.66), 6.906 (3.30), 6.909 (2.99), 6.924 (1.93), 6.927 (1.70), 7.142 (1.75), 7.146 (1.77), 7.163 (2.63), 7.180 (1.31), 7.185 (1.20), 7.291 (2.83), 7.311 (2.52), 7.434 (2.40), 7.452 (3.13), 7.455 (2.90), 7.473 (2.61), 7.592 (2.65), 7.597 (4.87), 7.602 (5.82), 7.611 (16.00), 7.616 (8.48), 7.698 (3.62), 7.701 (3.63), 7.716 (3.07), 7.719 (2.82), 8.058 (3.06), 8.061 (3.05), 8.080 (2.76), 8.083 (2.47), 8.430 (11.34), 8.946 (2.94), 8.966 (2.74). |
| 136 | 2.1 | LC-MS (Method L1): Rt = 0.93 min; MS (ESIpos): m/z = 541 [M + H]+ | $^1$H-NMR (400 MHz, CHLOROFORM-d) δ [ppm]: −0.008 (1.56), 0.008 (1.98), 0.069 (0.62), 1.256 (1.23), 1.582 (16.00), 2.171 (1.20), 2.177 (0.59), 5.299 (1.83), 6.997 (0.57), 7.429 (0.69), 7.519 (1.23). |
| 137 | 4.8 | LC-MS (Method L1): Rt = 1.42 min; MS (ESIpos): m/z = 564 [M + H]+ | $^1$H-NMR (400 MHz, DMSO-d6) δ [ppm]: −0.008 (2.04), 0.008 (1.38), 1.199 (3.32), 1.216 (7.07), 1.234 (3.34), 2.086 (1.65), 3.048 (8.16), 4.052 (4.09), 4.134 (0.95), 4.152 (2.94), 4.169 (2.79), 4.187 (0.86), 4.283 (1.07), 6.790 (1.19), 6.793 (1.25), 6.810 (1.31), 6.813 (1.32), 6.917 (1.20), 6.920 (1.17), 7.175 (0.96), 7.378 (0.94), 7.645 (16.00), 7.689 (0.97), 7.707 (1.22), 7.710 (1.08), 7.728 (1.19), 7.840 (1.33), 7.843 (1.41), 7.858 (1.10), 7.861 (1.03), 8.354 (1.21), 8.358 (1.23), 8.375 (1.10), 8.379 (1.01), 8.756 (4.67), 9.196 (1.08), 9.217 (1.02). |
| 138 | 2.7 | LC-MS (Method L1): Rt = 1.12 min; MS (ESIpos): | $^1$H-NMR (400 MHz, DMSO-d6) δ [ppm]: 2.087 (0.95), 2.095 (0.79), 2.206 (0.84), 2.218 (0.81), 2.228 (0.77), 3.056 (16.00), 3.516 (1.41), 3.529 (3.23), 3.541 (2.52), 3.601 (1.41), 3.614 (2.77), 3.628 (2.42), 3.641 (0.85), 4.245 (1.32), 4.253 (1.18), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | m/z = 522 [M + H]+ | 4.265 (2.15), 4.274 (2.23), 4.290 (1.20), 5.100 (1.14), 5.115 (2.39), 5.130 (1.09), 5.279 (1.29), 5.298 (1.29), 5.752 (1.32), 5.754 (1.27), 6.792 (2.55), 6.813 (2.83), 6.910 (1.24), 6.928 (2.57), 6.947 (1.49), 7.159 (1.29), 7.176 (2.06), 7.197 (0.97), 7.357 (2.18), 7.376 (1.99), 7.625 (2.25), 7.628 (2.63), 7.631 (3.12), 7.634 (5.58), 7.638 (12.01), 7.640 (9.99), 7.643 (5.84), 7.646 (4.00), 7.665 (1.93), 7.801 (2.81), 7.819 (2.22), 8.275 (2.37), 8.296 (2.15), 8.673 (7.74), 9.303 (2.25), 9.323 (2.20). |
| 139 | | LC-MS (Method L2): Rt = 3.33 min; m/z = 510/512 [M + H]+ | $^{1}$H-NMR (400 MHz, DMSO-d6) δ 9.08 (d, J = 8.2 Hz, 1H). 8.58 (s, 1H), 8.29, (dd, J = 9.4, 6.2 Hz, 1H), 7.77-7.68 (m, 2H), 7.61 (t, J = 9.3 Hz, 1H), 7.47-7.41 (m, 1H), 7.37-7.31 (m, 1H), 7.20-7.13 (m, 1H), 6.95-6.88 (m, 1H), 6.82-6.77 (m, 1H). 5.27-5.19 (m, 1H), 4.30-4.19 (m, 2H), 3.07 (s, 6H), 2.27-2.12 (m, 1H), 2.07-1.99 (m, 1H). |
| 140 | | LC-MS (Method L2): Rt = 2.98 min; m/z = 478 [M + H]+ | $^{1}$H-NMR (400 MHz, DMSO-d6) δ 9.07 (d, J = 8.2 Hz, 1H). 8.58 (s, 1H), 8.27, (dd, J = 9.4, 6.2 Hz, 1H), 7.64-7.48 (m, 3H), 7.34 (d, J = 6.9 Hz, 1H), 7.31-7.23 (m, 1H), 7.20-7.13 (m, 1H), 6.95-6.88 (m, 1H), 6.82-6.76 (m, 1H), 5.28-5.20 (m, 1H), 4.32-4.19 (m, 2H), 3.06 (s, 6H), 2.22-2.14 (m, 1H), 2.09-1.99 (m, 1H). |
| 141 | | LC-MS (Method L2): Rt = 3.03 min; m/z = 476 [M + H]+ | $^{1}$H-NMR (400 MHz, DMSO-d6) δ 9.08 (d, J = 8.2 Hz, 1H). 8.58 (s, 1H), 8.27, (dd, J = 9.4, 6.2 Hz, 1H), 7.60 (t, J = 9.3 Hz, 1H), 7.55-7.45 (m, 3H), 7.43-7.31 (m, 2H), 7.20-7.12 (m, 1H), 6.95-6.88 (m, 1H), 6.83-6.76 (m, 1H), 5.28-5.19 (m, 1H), 4.32-4.19 (m, 2H), 3.07 (s, 6H), 2.25-2.14 (m, 1H), 2.09-1.98 (m, 1H). |
| 142 | | LC-MS (Method L2): Rt = 3.68 min; m/z = 520 [M + H]+ | $^{1}$H-NMR (400 MHz, DMSO-d6) δ 9.17 (d, J = 8.2 Hz, 1H). 8.67 (s, 1H), 8.34, (dd, J = 9.4, 6.2 Hz, 1H), 7.66 (t, J = 9.3 Hz, 1H), 7.40-7.28 (m, 2H), 7.22-7.13 (m, 3H), 6.96-6.89 (m, 1H), 6.82-6.76 (m, 1H), 5.29-5.21 (m, 1H), 4.33-4.19 (m, 2H), 3.88 (q, J = 5.8, 4.5 Hz, 4H), 3.28 (q, J = 4.5 Hz, 4H), 2.27-2.16 (m, 1H), 2.10-2.00 (m, 1H). |
| 143 | | LC-MS (Method L2): Rt = 3.86 min; | $^{1}$H-NMR (400 MHz, DMSO-d6) δ 9.17 (d, J = 8.1 Hz, 1H), 8.68 (s, 1H), 8.34, (dd, J = 9.4, 6.2 Hz, 1H), 7.66 (t, J = 9.3 Hz, 1H), 7.55-7.49 (m, 1H), 7.40-7.29 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | m/z = 536 [M + H]+ | (m, 3H), 7.21-7.13 (m, 1H), 6.96-6.89 (m, 1H), 6.82-6.76 (m, 1H), 5.29-5.21 (m, 1H), 4.33-4.19 (m, 2H), 3.87 (t, J = 4.5 Hz, 4H), 3.28 (q, J = 4.6 Hz, 4H), 2.26-2.18 (m, 1H), 2.11-2.02 (m, 1H). |
| 144 | | LC-MS (Method L2): Rt = 4.14 min; m/z = 552/554 [M + H]+ | $^1$H-NMR (400 MHz, Chloroform-d) δ 8.85 (s, 1H), 7.83 (dd, J = 9.8, 2.9 Hz, 1H), 7.72 (d, J = 2.0 Hz, 1H), 7.55 (d, J = 8.3 Hz, 1H), 7.50 (dd, J = 8.6, 2.9 Hz, 1H), 7.45 (dd, J = 8.3, 2.0 Hz, 1H), 7.29 (d, J = 7.7 Hz, 1H), 7.26-7.17 (m, 1H), 6.94 (td, J = 7.5, 1.1 Hz, 1H), 6.87 (dd, J = 8.3, 1.0 Hz, 1H), 6.82 (d, J = 7.3 Hz, 1H), 5.38 (d, J = 7.3 Hz, 1H), 4.36 (dq, J = 9.2, 3.4, 2.9 Hz, 1H), 4.20 (ddd, J = 11.6, 9.6, 2.7 Hz, 1H), 3.97-3.84 (m, 4H), 3.44-3.33 (m, 4H), 2.47-2.35 (m, 1H), 2.29-2.19 (m, 1H). |
| 145 | | LC-MS (Method L2): Rt = 3.82 min; m/z = 510/512 [M + H]+ | $^1$H-NMR (400 MHz, Chloroform-d) δ 8.89 (s, 1H), 7.76 (dd, J = 9.9, 2.9 Hz, 1H), 7.72 (d, J = 2.0 Hz, 1H), 7.54 (d, J = 8.3 Hz, 1H), 7.49-7.43 (m, 2H), 7.29 (d, J = 7.7 Hz, 1H), 7.24-7.18 (m, 1H), 7.08 (d, J = 7.5 Hz, 1H), 6.93 (td, J = 7.5, 1.1 Hz, 1H), 6.88-6.84 (m, 1H), 5.40-5.33 (m, 1H). 4.38-4.31 (m, 1H), 4.23-4.16 (m, 1H), 3.10 (s, 6H), 2.44-2.34 (m, 1H), 2.25-2.16 (m, 1H). |
| 146 | | LC-MS (Method L2): Rt = 3.55 min; m/z = 510/512 [M + H]+ | $^1$H-NMR (400 MHz, Chloroform-d) δ 8.85 (d, J = 2.7 Hz, 1H), 7.81 (dd, J = 10.0, 2.8 Hz, 1H), 7.54 (dd, J = 7.9, 1.6 Hz, 1H), 7.40 (dd, J = 8.3, 2.8 Hz, 1H), 7.34-7.15 (m, 4H), 7.07-6.97 (m, 1H), 6.91 (td, J = 7.5, 1.1 Hz, 1H), 6.85 (dd, 1H), 5.40-5.29 (m, 1H), 4.37-4.30 (m, 1H), 4.22-4.14 (m, 1H), 3.12 (s, 6H), 2.43-2.32 (m, 1H), 2.23-2.14 (m, 1H). |
| 147 | 2.76 | | $^1$H-NMR (399, 9532 MHz, DMSO): δ = 9.121 (0.91); 9.1007 (0.93); 8.634 (3.89); 8.3134 (0.72); 8.2547 (0.98); 8.2517 (1.05); 8.2336 (1.09); 8.2306 (1.1); 7.805 (1.01); 7.7903 (1.21); 7.7874 (1.21); 7.6694 (1.03); 7.6485 (1.18); 7.6304 (12.69); 6.8945 (1.38); 6.8875 (1.57); 6.7982 (0.58); 6.7911 (0.47); 6.7761 (1.29); 6.7688 (1.22); 6.7441 (2.53); 6.7219 (1.02); 5.2287 (0.58); 5.2095 (0.58); 4.2178 (0.58); 4.2045 (1.04); 4.1982 (0.85); 4.1864 (0.55); 4.1782 (0.56); 3.6948 (11.21); 3.3162 (70.62); 3.2923 (0.36); 3.0725 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (16); 2.6745 (0.55); 2.6703 (0.76); 2.6659 (0.57); 2.5055 (89.32); 2.5011 (123.65); 2.4967 (94.57); 2.3324 (0.52); 2.328 (0.71); 2.3236 (0.52); 2.1952 (0.33); 2.185 (0.35); 2.1736 (0.35); 2.0579 (0.35); 2.0505 (0.41); 1.3981 (6.55); 0.1458 (0.5); 0.008 (4.19); −0.0001 (108.21); −0.0083 (4.43); −0.1497 (0.5) |
| 148 | 2.84 | | $^1$H-NMR (399, 9532 MHz, DMSO): δ = 8.8981 (0.68), 8.8777 (0.7), 8.6125 (3.39), 8.3132 (0.55), 8.2499 (0.74), 8.2465 (0.82), 8.2286 (0.85), 8.2252 (0.85), 7.805 (0.71), 7.8016 (0.8), 7.7871 (0.96), 7.7838 (0.98), 7.6657 (0.85), 7.6476 (0.82), 7.6444 (0.97), 7.6324 (11.7), 7.3105 (0.9), 7.2897 (1), 6.8463 (0.92), 6.8409 (1.09), 6.7994 (0.64), 6.7934 (0.54), 6.7787 (0.58), 6.7727 (0.53), 5.4719 (0.54), 5.4526 (0.54), 3.7345 (9.41), 3.3174 (129.06), 3.0587 (12.87), 3.0247 (0.38), 2.8426 (0.45), 2.8226 (0.35), 2.6747 (0.57), 2.6702 (0.79), 2.6658 (0.58), 2.5368 (0.56), 2.5237 (2.21), 2.5101 (44.34), 2.5056 (94.37), 2.5011 (132.67), 2.4965 (99.85), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.4921 (48.15), 2.3324 (0.55), 2.3281 (0.77), 2.3234 (0.56), 1.398 (16), 0.1459 (0.57), 0.008 (4.36), −0.0002 (135.3), −0.0084 (4.88), −0.1496 (0.56) |
| 148 | 2.2 | LC-MS (Method L1): Rt = 0.94 min; MS (ESIneg): m/z = 589 [M − H]− | $^1$H-NMR (400 MHz, CHLOROFORM-d) δ [ppm]: 2.171 (1.43), 2.631 (16.00), 3.229 (12.71), 3.305 (1.03), 3.313 (1.03), 4.269 (0.86), 6.828 (1.34), 6.830 (1.40), 6.848 (1.53), 6.851 (1.54), 6.950 (1.41), 6.953 (1.37), 6.969 (0.85), 6.972 (0.79), 7.198 (1.15), 7.327 (1.22), 7.346 (1.12), 7.390 (1.53), 7.395 (2.99), 7.400 (1.71), 7.512 (6.31), 7.517 (5.89), 7.551 (0.97), 7.569 (1.53), 7.572 (1.24), 7.590 (1.44), 7.661 (1.63), 7.665 (1.74), 7.679 (1.23), 7.683 (1.12), 8.058 (1.46), 8.062 (1.45), 8.079 (1.31), 8.083 (1.23), 8.983 (5.10). |
| 150 | 3.1 | LC-MS (Method L1): Rt = 1.11 min; MS (ESIpos): m/z = 536 [M + H]+ | $^1$H-NMR (400 MHz, DMSO-d6) δ [ppm]: 2.132 (1.28), 2.205 (1.37), 2.328 (0.59), 3.040 (16.00), 3.931 (0.61), 3.975 (4.59), 3.984 (4.71), 4.281 (3.48), 5.309 (1.69), 5.326 (1.68), 6.779 (2.78), 6.799 (3.08), 6.883 (1.42), 6.901 (2.80), 6.920 (1.72), 7.140 (1.56), 7.159 (2.50), 7.175 (1.25), 7.348 (2.66), 7.365 (2.47), 7.643 (14.76), 7.660 (2.25), 7.678 (2.82), 7.699 (1.88), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.820 (3.02), 7.835 (2.42), 8.139 (1.05), 8.304 (2.56), 8.326 (2.33), 8.755 (6.56). |
| 151 | | LC-MS (Method L6): Rt = 1.55 min; MS (ESIpos): m/z = 503 [M + H]+ | $^1$H-NMR (400 MHz, DMSO-d6) δ [ppm]: −0.008 (0.73), 0.008 (0.73), 2.827 (5.86), 2.831 (9.97), 2.836 (5.88), 3.063 (16.00), 4.234 (0.56), 4.253 (0.85), 4.262 (0.92), 6.778 (0.94), 6.781 (1.01), 6.799 (1.07), 6.801 (1.08), 6.894 (0.49), 6.897 (0.49), 6.912 (1.00), 6.915 (0.97), 6.931 (0.61), 6.934 (0.57), 7.026 (0.55), 7.043 (0.90), 7.055 (1.02), 7.060 (0.67), 7.082 (0.74), 7.142 (0.50), 7.146 (0.54), 7.164 (0.80), 7.339 (0.78), 7.359 (0.78), 7.606 (0.49), 7.623 (1.27), 7.643 (1.95), 7.650 (1.53), 7.663 (0.52), 8.214 (0.96), 8.220 (0.91), 8.234 (0.91), 8.240 (0.83), 8.542 (4.00), 9.073 (0.89), 9.093 (0.86). |
| 152 | 3 | | $^1$H-NMR (399, 9532 MHz, DMSO): δ = 9.0892 (0.94); 9.0691 (0.96); 8.6414 (4.26); 8.2521 (0.97); 8.2488 (1.02); 8.2308 (1.12); 8.2275 (1.08); 7.8117 (0.96); 7.8084 (1.01); 7.7939 (1.28); 7.7906 (1.21); 7.6681 (1.04); 7.65 (1.06); 7.6469 (1.19); 7.633 (11.43); 7.4321 (0.64); 7.4139 (0.79); 7.411 (0.8); 7.3933 (0.66); 6.7953 (0.48); 6.7887 (0.52); 6.774 (0.91); 6.7673 (0.95); 6.7527 (0.46); 6.746 (0.48); 6.6796 (0.98); 6.673 (0.85); 6.6532 (1.02); 6.6466 (0.82); 5.7538 (9.65); 5.2288 (0.51); 5.2099 (0.52); 4.315 (0.48); 4.3057 (0.46); 4.2996 (0.54); 4.2881 (0.57); 4.2791 (0.52); 4.2653 (0.45); 4.2581 (0.58); 3.3173 (12.38); 3.0582 (16); 2.5238 (0.61); 2.5104 (12.16); 2.5059 (24.77); 2.5014 (33.92); 2.4969 (25.2); 2.4926 (12.16); 2.1993 (0.33); 2.1898 (0.34); 2.177 (0.37); 2.078 (0.34); 2.0714 (0.39); 0.008 (1.15); −0.0002 (30.44); −0.0084 (1.11) |
| 153 | 2.1 | LC-MS (Method L1): Rt = 0.92 min; MS (ESIpos): m/z = 492 [M + H]+ | $^1$H-NMR (600 MHz, DMSO-d6) δ [ppm]: 1.241 (8.09), 1.253 (15.76), 1.265 (7.87), 2.024 (1.23), 2.030 (1.43), 2.037 (1.48), 2.046 (1.79), 2.053 (1.70), 2.146 (1.59), 2.157 (1.87), 2.166 (1.55), 3.508 (1.58), 3.519 (4.30), 3.530 (5.43), 3.540 (4.15), 3.552 (1.33), 4.266 (5.31), 4.273 (4.37), 4.292 (0.68), 5.238 (1.23), 5.248 (2.59), 5.260 (2.52), 5.270 (1.13), 6.788 (4.52), 6.802 (4.77), 6.899 (2.30), 6.912 (4.55), 6.924 (2.56), 7.152 (2.32), 7.165 (3.89), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.177 (1.93), 7.302 (4.05), 7.315 (3.75), 7.522 (2.63), 7.535 (4.17), 7.548 (2.83), 7.606 (6.74), 7.620 (16.00), 7.662 (0.48), 7.731 (4.94), 7.743 (4.36), 7.808 (2.02), 7.816 (3.34), 8.412 (4.22), 8.426 (4.01), 8.509 (10.45), 9.013 (4.02), 9.027 (3.89). |
| 154 | | LC-MS (Method L1): Rt = 0.97 min; MS (ESIpos): m/z = 521 [M + H]+ | $^1$H-NMR (400 MHz, DMSO-d6) δ [ppm]: −0.149 (0.40), −0.008 (3.14), 0.008 (2.78), 0.833 (0.80), 0.851 (1.18), 1.028 (0.44), 1.103 (0.60), 1.118 (0.70), 1.235 (1.90), 1.874 (16.00), 1.914 (1.00), 2.063 (0.78), 2.108 (1.12), 2.163 (0.90), 2.366 (0.68), 2.518 (4.57), 2.523 (3.14), 2.709 (0.54), 3.508 (0.82), 4.232 (0.58), 4.249 (1.20), 4.258 (1.14), 4.275 (1.58), 4.293 (0.98), 4.302 (1.16), 5.233 (0.52), 5.249 (1.04), 5.266 (1.08), 6.776 (2.22), 6.794 (2.46), 6.877 (1.16), 6.893 (2.38), 6.911 (1.44), 7.135 (1.28), 7.155 (2.02), 7.174 (1.06), 7.340 (1.82), 7.359 (1.74), 7.574 (1.36), 7.592 (1.96), 7.617 (4.01), 7.622 (5.21), 7.628 (11.15), 7.633 (5.41), 7.726 (0.58), 7.789 (2.38), 7.805 (2.08), 8.516 (1.20), 8.538 (1.18), 8.604 (3.14), 9.016 (1.62), 9.036 (1.58), 9.575 (0.84), 10.034 (0.98). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 155 | | LC-MS (Method L2): Rt = 3.77 min; MS (ESIpos): m/z = 536 [M + H]+ | $^1$H-NMR (400 MHz, DMSO-d6) δ 9.17 (dd, J = 8.1, 4.5 Hz, 1H), 8.64 (d, J = 2.4 Hz, 1H), 8.37 (dd, J = 9.4, 6.3 Hz, 1H), 7.74-7.64 (m, 2H), 7.47-7.32 (m, 3H), 7.20-7.12 (m, 1H), 6.95-6.88 (m, 1H), 6.82-6.76 (m, 1H), 5.29-5.20 (m, 1H), 4.32-4.18 (m, 2H), 3.93-3.83 (m, 4H), 3.31-3.22 (m, 4H), 2.27-2.16 (m, 1H), 2.10-2.01 (m, 1H). |
| 156 | | LC-MS (Method L2): Rt = 3.96 min; m/z = 552/554 [M + H]+ | $^1$H-NMR (400 MHz, DMSO-d6) δ 9.17 (d, J = 8.1 Hz, 1H), 8.66 (s, 1H), 8.33 (dd, J = 9.4, 6.2 Hz, 1H), 7.79-7.62 (m, 3H), 7.47-7.42 (m, 1H), 7.40-7.34 (m, 1H), 7.21-7.13 (m, 1H), 6.96-6.89 (m, 1H), 6.83-6.76 (m, 1H), 5.29-5.21 (m, 1H), 4.33-4 19 (m, 2H), 3.91-3.83 (m, 4H), 3.30-3.23 (m, 4H), 2.25-2.19 (m, 1H), 2.10-2.02 (m, 1H). |
| 157 | | LC-MS (Method L2): Rt = 3.61 min; m/z = 520 [M + H]+ | $^1$H-NMR (400 MHz, DMSO-d6) δ 9.16 (d, J = 8.1 Hz, 1H), 8.66 (s, 1H), 8.36-8.28 (m, 1H), 7.65 (t, J = 9.3 Hz, 1H), 7.54 (q, J = 8.7 Hz, 2H), 7.41-7.25 (m, 2H), 7.21-7.13 (m, 1H), 6.92 (t, J = 7.1 Hz, 1H), 6.79 (d, J = 8.1 Hz, 1H), 525 (q, J = 5.7 Hz, 1H), 4.33-4.19 (m, 2H), 3.93-3.82 (m, 4H), 3.31-3.21 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (m, 4H), 2.21 (dt, J = 8.6, 4.4 Hz, 1H), 2.11-2.00 (m, 1H). |
| 158 | | LC-MS (Method L2): Rt = 3.85 min; m/z = 520 [M + H]+ | $^1$H-NMR (400 MHz, Chloroform-d) δ 8.86 (s, 1H), 7.82 (dd, J = 9.8, 2.9 Hz, 1H), 7.52-7.44 (m, 2H), 7.36-7.19 (m, 4H), 6.93 (td, J = 7.5, 1.1 Hz, 1H), 6.89-6.80 (m, 2H), 5.43-5.34 (m, 1H), 4.41-4.32 (m, 1H), 4.24-4.15 (m, 1H), 3.96-3.84 (m, 4H), 3.44-3.33 (m, 4H), 2.46-2.36 (m, 1H), 2.28-2.19 (m, 1H). |
| 159 | | LC-MS (Method L2): Rt = 3.95 min; m/z = 518 [M + H]+ | $^1$H-NMR (400 MHz, Chloroform-d) δ 8.85 (s, 1H), 7.81 (dd, J = 9.8, 2.9 Hz, 1H), 7.62-7.59 (m, 1H), 7.52-7.38 (m, 4H), 7.28 (d, J = 7.7 Hz, 1H), 7.24-7.18 (m, 1H), 6.96-6.83 (m, 3H), 5.43-5.30 (m, 1H), 4.40-4.31 (m, 1H), 4.25-4.15 (m, 1H), 3.96-3.83 (m, 4H), 3.44-3.31 (m, 4H), 2.45-2.34 (m, 1H), 2.28-2.17 (m, 1H). |
| 160 | | LC-MS (Method L2): Rt = 3.91 min; m/z = 536 [M + H]+ | $^1$H-NMR (400 MHz, Chloroform-d) δ 8.83 (s, 1H), 7.87 (dd, J = 9.8, 2.9 Hz, 1H), 7.53-7.46 (m, 2H), 7.34-7.26 (m, 2H), 7.24-7.17 (m, 2H), 6.92 (td, J = 7.5, 1.2 Hz, 1H), 6.89-6.80 (m, 2H), 5.40-5.33 (m, 1H), 4.39-4.31 (m, 1H), 4.23-4.12 (m, 1H), 3.96-3.84 (m, 4H), 3.44-3.33 (m, 4H), 2.44-2.34 (m, 1H), 2.26-2.18 (m, 1H). |
| 161 | | LC-MS (Method L2): Rt = 3.83 min; m/z = 536 [M + H]+ | $^1$H-NMR (400 MHz, Chlofoform-d) δ 8.82 (s, 1H), 7.89 (dd, J = 9.8, 2.9 Hz, 1H), 7.45 (dd, J = 8.3, 2.9 Hz, 1H), 7.37-7.18 (m, 4H), 7.14 (d, J = 7.5 Hz, 1H), 6.92 (td, J = 7.5, 1.2 Hz, 1H), 6.86 (dd, J = 8.3, 1.0 Hz, 1H), 6.79 (s, 1H), 5.41-5.34 (m, 1H), 4.39-4.31 (m, 1H), 4.22-4.14 (m, 1H), 3.97-3.87 (m, 4H), 3.47-3.34 (m, 4H), 2.45-2.35 (m, 1H), 2.26-2.18 (m, 1H). |
| 162 | | LC-MS (Method L2): Rt = 3.89 min; m/z = 520 [M + H]+ | $^1$H-NMR (400 MHz, Chloroform-d) δ 8.86 (s, 1H), 7.84 (dd, J = 9.1, 2.9 Hz, 1H), 7.51 (dd, J = 8.6, 2.9 Hz, 1H), 7.29 (d, J = 7.7 Hz, 1H), 7.24-7.12 (m, 3H), 6.97-6.78 (m, 4H), 5.42-5.34 (m, 1H), 4.40-4.32 (m, 1H), 4.24-4.15 (m, 1H), 3.96-3.85 (m, 4H), 3.44-3.33 (m, 4H), 2.46-2.36 (m, 1H), 2.29-2.19 (m, 1H). |
| 163 | | LC-MS (Method L2): Rt = 4.05 min; m/z = 536 | $^1$H-NMR (400 MHz, Chloroform-d) δ 8.85 (s, 1H), 7.84 (dd, J = 9.7, 2.8 Hz, 1H), 7.50 (dd, J = 8.5, 2.8 Hz, 1H), 7.39 (s, 1H), 7.32-7.13 (m, 4H), 6.94 (t, J = 7.1 Hz, 1H), 6.90-6.80 (m, 2H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | 5.42-5.34 (m, 1H), 4.41-4.32 (m, 1H), 4.24-4.15 (m, 1H), 3.96-3.84 (m, 4H), 3.44-3.32 (m, 4H), 2.46-2.35 (m, 1H), 2.29-2.19 (m, 1H). |
| 164 | | LC-MS (Method L2): Rt = 3.94 min; m/z = 536 [M + H]+ | $^1$H-NMR (400 MHz, Chloroform-d) δ 8.83 (s, 1H), 7.86 (dd, J = 9.8, 2.9 Hz, 1H), 7.51 (dd, J = 8.3, 2.7 Hz, 1H), 7.44-7.36 (m, 2H), 7.28 (d, J = 7.8 Hz, 1H), 7.23-7.18 (m, 1H), 7.14 (t, J = 8.9 Hz, 1H), 6.92 (td, J = 7.5, 1.1 Hz, 1H), 6.89-6.81 (m, 2H), 5.41-5.32 (m, 1H), 4.39-4.30 (m, 1H), 4.23-4.14 (m, 1H), 3.95-3.84 (m, 4H), 3.44-3.33 (m, 4H), 2.45-2.33 (m, 1H), 2.27-2.16 (m, 1H). |
| 165 | | LC-MS (Method L2): Rt = 3.82 min; m/z = 536 [M + H]+ | $^1$H-NMR (400 MHz, Chloroform-d) δ 8.83 (s, 1H), 7.87 (dd, J = 9.9, 2.8 Hz, 1H), 7.44 (dd, J = 8.3, 2.8 Hz, 1H), 7.34-7.26 (m, 3H), 7.24-7.18 (m, 1H), 7.10 (td, J = 8.2, 2.5 Hz, 1H), 6.92 (t, J = 7.5 Hz, 1H), 6.86 (d, J = 7.7 Hz, 1H), 6.80 (d, J = 5.9 Hz, 1H), 5.43-5.30 (m, 1H), 4.39-4.31 (m, 1H), 4.22-4.14 (m, 1H), 3.96-3.86 (m, 4H), 3.46-3.34 (m, J = 3.8 Hz, 4H), 2.45-2.35 (m, 1H), 2.27-2.17 (m, 1H). |
| 166 | | LC-MS (Method L2): Rt = 3.95 min; m/z = 552/554 [M + H]+ | $^1$H-NMR (400 MHz, Chloroform-d) δ 8.80 (s, 1H), 7.87 (dd, J = 9.8, 2.9 Hz, 1H), 7.55 (dd, J = 8.0, 1.6 Hz, 1H), 7.43 (dd, J = 8.2, 2.8 Hz, 1H), 7.33-7.17 (m, 4H), 6.94-6.77 (m, 3H), 5.41-5.30 (m, 1H), 4.37-4.31 (m, 1H), 4.21-4.14 (m, 1H), 3.95-3.85 (m, 4H), 3.45-3.33 (m, 4H), 2.44-2.34 (m, 1H), 2.25-2.16 (m, 1H). |
| 167 | | LC-MS (Method L2): Rt = 3.68 min; m/z = 518 [M + H]+ | $^1$H-NMR (400 MHz, DMSO-d6) δ 9.17 (d, J = 8.2 Hz, 1H), 8.66 (s, 1H), 8.32, (dd, J = 9.4.6.2 Hz, 1H), 7.65 (t, J = 9.3 Hz, 1H), 7.56-7.47 (m, 3H), 7.43-7.34 (m, 2H), 7.21-7.14 (m, 1H), 6.97-6.89 (m, 1H), 6.80 (d, J = 8.2, 0.9 Hz, 1H), 5.30-5.22 (m, 1H), 4.33-4.19 (m, 2H), 3.88 (t, J = 4.6 Hz, 4H), 3.32-3.22 (m, 4H), 2.28-2.17 (m, 1H), 2.11-1.98 (m, 1H). |
| 168 | | LC-MS (Method L2): Rt = 3.07 min; m/z = 478 [M + H]+ | $^1$H-NMR (400 MHz, DMSO-d6) δ 9.08 (d, J = 8.2 Hz, 1H), 8.59 (s, 1H), 8.33-8.25 (m, 1H), 7.60 (t, J = 9.3 Hz, 1H), 7.38-7.27 (m, 2H), 7.22-7.12 (m, 3H), 6.95-6.88 (m, 1H), 6.82-6.76 (m, 1H), 5.27-5.19 (m, 1H), 4.32-4.19 (m, 2H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.07 (s, 6H), 2.25-2.14 (m, 1H), 2.09-1.98 (m, 1H). |
| 169 | | LC-MS (Method L2): Rt = 3.26 min; m/z = 494 [M + H]+ | $^1$H-NMR (400 MHz, DMSO-d6) δ 9.08 (d, J = 8.2 Hz, 1H), 8.60 (s, 1H), 8.33-8.26 (m, 1H), 7.61 (t, J = 9.3 Hz, 1H), 7.54-7.49 (m, 1H), 7.39-7.28 (m, 3H), 7.20-7.13 (m, 1H), 6.95-6.88 (m, 1H), 6.82-6.76 (m, 1H), 5.27-5.19 (m, 1H), 4.32-4.19 (m, 2H), 3.07 (s, 6H), 2.25-2.14 (m, 1H), 2.09-1.99 (m, 1H). |
| 170 | | LC-MS (Method L2): Rt = 3.82 min; m/z = 536 [M + H]+ | $^1$H-NMR (400 MHz, DMSO-d6) δ 9.17 (dd, J = 8.1, 3.6 Hz, 1H), 8.66 (d, J = 1.2 Hz, 1H), 8.37 (dd, J = 9.4, 6.3 Hz, 1H), 7.68 (t, J = 9.1 Hz, 1H), 7.63-7.49 (m, 2H), 7.46-7.34 (m, 2H), 7.17 (t, J = 7.7 Hz, 1H), 6.92 (t, J = 7.2 Hz, 1H), 6.80 (d, J = 82 Hz, 1H), 5.30-5.21 (m, 1H), 4.33-4.19 (m, 2H), 3.88 (t, J = 4.3 Hz, 4H), 3.32-3.23 (m, 4H), 2.21 (d, J = 3.1 Hz, 1H), 2.06 (d, J = 6.4 Hz, 1H). |
| 171 | | LC-MS (Method L2): Rt = 3.23 min; m/z = 494 | $^1$H-NMR (400 MHz, DMSO-d6) δ 9.08 (dd, J = 8.1, 4.3 Hz, 1H), 8.56 (d, J = 1.2, Hz, 1H), 8.34 (dd, J = 9.4, 6.3 Hz, 1H), 7.74-7.59 (m, 2H), 7.46-7.31 (m, 3H), 7.16 (t, J = 7.1 Hz, 1H), 6.91 (t, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | J = 7.5 Hz, 1H), 6.79 (d, J = 8.1 Hz, 1H), 5.28-5.18 (m, 1H), 4.32-4.18 (m, 2H), 3.08 (s, 6H), 2.19 (dd, J = 9.0, 4.8 Hz, 1H), 2.09-2.00 (m, 1H). |
| 172 | | LC-MS (Method L2): Rt = 3.05 min; m/z = 494 [M + H]+ | $^1$H-NMR (400 MHz, DMSO-d6) δ 9.07 (d, J = 7.4 Hz, 1H), 8.53 (d, J = 1.2 Hz, 1H), 8.31 (dd, J = 9.5, 6.3 Hz, 1H), 7.64-7.56 (m, 2H), 7.47-7.38 (m, 1H), 7.38-7.29 (m, 2H), 7.19-7.12 (m, 1H), 6.94-6.86 (m, 1H), 6.81-6.75 (m, 1H), 5.22 (q, J = 6.8, 6.3 Hz, 1H), 4.31-4.18 (m, 2H), 3.07 (s, 6H), 2.24-2.13 (m, 1H), 2.07-1.98 (m, 1H). |
| 173 | | LC-MS (Method L2): Rt = 3.40 min; m/z = 478 [M + H]+ | $^1$H-NMR (400 MHz, Chloroform-d) δ 8.91 (s, 1H), 7.75 (dd, J = 9.9, 2.9 Hz, 1H), 7.52-7.44 (m, 2H), 7.36-7.18 (m, 4H), 7.11 (d, J = 7.4 Hz, 1H), 6.93 (td, J = 7.5, 1.1 Hz, 1H), 6.87 (dd, J = 8.3, 1.0 Hz, 1H), 5.40-5.33 (m, 1H), 4.39-4.31 (m, 1H), 4.23-4.15 (m, 1H), 3.10 (s, 6H), 2.44-2.35 (m, 1H), 2.25-2.17 (m, 1H). |
| 174 | | LC-MS (Method L2): Rt = 3.46 min; | $^1$H-NMR (400 MHz, Chloroform-d) δ 8.93 (s, 1H), 7.75 (dd, J = 9.9, 2.9 Hz, 1H), 7.62-7.59 (m, 1H), 7.52-7.46 (m, 2H), 7.44-7.39 (m, 2H), 7.30 (d, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | m/z = 476 [M + H]+ | J = 7.7 Hz, 1H), 7.24-7.18 (m, 1H), 7.12 (d, J = 7.5 Hz, 1H), 6.93 (td, J = 7.5, 1.2 Hz, 1H), 6.87 (dd, J = 8.3, 1.0 Hz, 1H), 5.41-5.34 (m, 1H), 4.39-4.31 (m, 1H), 4.23-4.16 (m, 1H), 3.10 (s, 6H), 2.44-2.35 (m, 1H), 2.25-2.17 (m, 1H). |
| 175 | | LC-MS (Method L2): Rt = 3.59 min; m/z = 494 [M + H]+ | $^1$H-NMR (400 MHz, Chloroform-d) δ 8.88 (s, 1H), 7.81 (dd, J = 10.0, 2.9 Hz, 1H), 7.51-7.45 (m, 2H), 7.34-7.27 (m, 2H), 7.23-7.17 (m, 2H), 7.04 (d, J = 7.6 Hz, 1H), 6.92 (td, J = 7.5, 1.2 Hz, 1H), 6.86 (dd, J = 8.2, 1.1 Hz, 1H), 5.40-5.33 (m, 1H), 4.38-4.31 (m, 1H), 4.22-4.15 (m, 1H), 3.11 (s, 6H), 2.43-2.34 (m, 1H), 2.24-2.16 (m, 1H). |
| 176 | | LC-MS (Method L2): Rt = 3.40 min; m/z = 494 [M + H]+ | $^1$H-NMR (400 MHz, Chloroform-d) δ 8.86 (s, 1H), 7.82 (dd, J = 10.0, 2.9 Hz, 1H), 7.42 (dd, J = 8.3, 2.9 Hz, 1H), 7.37-7.30 (m, 1H), 7.29-7.12 (m, 4H), 7.02 (s, 1H), 6.91 (td, J = 7.5, 1.1 Hz, 1H), 6.85 (dd, J = 8.3, 1.0 Hz, 1H), 5.40-5.32 (m, 1H), 4.37-4.30 (m, 1H), 44.2-2.14 (m, 1H), 3.12 (s, 6H), 2.42-2.33 (m, 1H), 2.23-2.15 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 177 | | LC-MS (Method L2): Rt = 3.51 min; m/z = 478 [M + H]+ | $^1$H-NMR (400 MHz, Chloroform-d) δ 8.91 (s, 1H), 7.78 (dd, J = 9.9, 2.9 Hz, 1H), 7.48 (dd, J = 8.6, 2.9 Hz, 1H), 7.30 (d, J = 7.7 Hz, 1H), 7.24-7.13 (m, 3H), 7.04 (d, J = 7.4 Hz, 1H), 6.94 (td, J = 7.5, 1.2 Hz, 1H), 6.91-6.84 (m, 2H), 5.41-5.34 (m, 1H), 4.39-4.32 (m, 1H), 4.24-4.16 (m, 1H), 3.11 (s, 6H), 2.44-2.35 (m, 1H), 2.25-2.17 (m, 1H). |
| 178 | | LC-MS (Method L2): Rt = 3.73 min; m/z = 494 [M + H]+ | $^1$H-NMR (400 MHz, Chloroform-d) δ 8.90 (s, 1H), 7.77 (dd, J = 9.9, 2.9 Hz, 1H), 7.47 (dd, J = 8.6, 2.9 Hz, 1H), 7.40 (s, 1H), 7.32-7.24 (m, 2H), 7.24-7.18 (m, 1H), 7.15 (dt, J = 8.4, 2.1 Hz, 1H), 7.05 (d, J = 7.5 Hz, 1H), 6.93 (td, J = 7.5, 1.1 Hz, 1H), 6.86 (dd, J = 8.3, 0.9 Hz, 1H), 5.40-5.33 (m, 1H), 4.38-4.31 (m, 1H), 4.23-4.16 (m, 1H), 3.10 (s, 6H), 2.44-2.34 (m, 1H), 2.25-2.16 (m, 1H). |
| 179 | | LC-MS (Method L2): Rt = 3.63 min; m/z = 494 | $^1$H-NMR (400 MHz, Chlofoform-d) δ 8.88 (s, 1H), 7.80 (dd, J = 10.0, 2.9 Hz, 1H), 7.48 (dd, J = 8.3, 2.8 Hz, 1H), 7.44-7.35 (m, 2H), 7.28 (d, J = 7.8 Hz, 1H), 7.23-7.17 (m, 1H), 7.13 (t, J = 8.9 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | Hz, 1H), 7.04 (d, J = 7.4 Hz, 1H), 6.92 (td, J = 7.5, 1.1 Hz, 1H), 6.86 (dd, J = 8.3, 1.0 Hz, 1H), 5.39-5.33 (m, 1H), 4.38-4.30 (m, 1H), 4.22-4.14 (m, 1H), 3.11 (s, 6H), 2.43-2.34 (m, 1H), 2.24-2.16 (m, 1H). |
| 180 | | LC-MS (Method L2): Rt = 3.34 min; m/z = 494 [M + H]+ | $^1$H-NMR (400 MHz, Chloroform-d) δ 8.87 (s, 1H), 7.81 (dd, J = 10.0, 2.9 Hz, 1H), 7.41 (dd, J = 8.3, 2.9 Hz, 1H), 7.34-7.26 (m, 3H), 7.23-7.18 (m, 1H), 7.12-7.00 (m, 2H), 6.92 (td, J = 7.5, 1.2 Hz, 1H), 6.86 (dd, J = 8.3, 1.1 Hz, 1H), 5.40-5.33 (m, 1H), 4.38-4.30 (m, 1H), 4.22-4.14 (m, 1H), 3.12 (s, 6H), 2.43-2.34 (m, 1H), 2.24-2.15 (m, 1H). |
| 181 | | LC-MS (Method L1): Rt = 1.37 min; MS (ESIpos): m/z = 550 [M + H]+ | $^1$H-NMR (400 MHz, DMSO-d6) δ [ppm]: −0.008 (2.14), 0.008 (1.84), 1.356 (0.66), 2.056 (0.64), 2.064 (0.68), 2.075 (0.73), 2.091 (1.03), 2.099 (0.87), 2.106 (0.63), 2.192 (0.43), 2.201 (0.68), 2.213 (0.94), 2.225 (0.91), 2.235 (0.85), 2.247 (0.57), 2.255 (0.46), 2.523 (1.40), 2.899 (3.69), 3.449 (0.46), 3.461 (0.72), 3.480 (2.72), 3.492 (5.13), 3.504 (4.92), 3.515 (2.44), 3.535 (0.65), 4.230 (0.50), 4.251 (1.50), 4.259 (1.25), 4.272 (2.17), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 4.281 (2.06), 4.298 (1.28), 4.317 (0.47), 5.241 (0.65), 5.255 (1.41), 5.274 (1.39), 5.288 (0.61), 6.792 (2.63), 6.810 (2.75), 6.812 (2.85), 6.918 (1.30), 6.921 (1.35), 6.937 (2.66), 6.939 (2.66), 6.955 (1.62), 6.958 (1.57), 7.156 (1.35), 7.160 (1.44), 7.177 (2.18), 7.194 (1.07), 7.198 (1.05), 7.389 (2.31), 7.407 (2.12), 7.632 (5.83), 7.636 (16.00), 7.638 (8.92), 7.689 (1.90), 7.707 (2.69), 7.710 (2.47), 7.728 (2.42), 7.832 (3.00), 7.835 (3.26), 7.850 (2.42), 7.853 (2.35), 8.260 (2.52), 8.263 (2.63), 8.281 (2.36), 8.284 (2.26), 8.718 (9.84), 9.157 (2.51), 9.177 (2.41). |
| 182 | 3.3 | LC-MS (Method L1): Rt = 1.08 min; MS (ESIpos): m/z = 578 [M + H]+ | $^1$H-NMR (400 MHz, DMSO-d6) δ [ppm]: −0.008 (0.74), 0.008 (0.62), 1.407 (16.00), 2.086 (0.51), 2.523 (0.47), 4.258 (0.40), 4.268 (1.03), 4.283 (0.99), 4.289 (0.91), 4.297 (0.51), 4.305 (0.58), 6.787 (0.59), 6.806 (0.68), 6.893 (0.65), 7.167 (0.52), 7.328 (0.53), 7.347 (0.50), 7.578 (0.54), 7.599 (0.48), 7.611 (0.71), 7.615 (0.79), 7.626 (2.75), 7.631 (1.63), 7.769 (0.69), 7.787 (0.59), 8.210 (0.42), 8.334 (0.53), 8.355 (0.50), 8.579 (1.74), 9.051 (0.51), 9.072 (0.50). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 183 | 6 | LC-MS (Method L1): Rt = 1.49 min; MS (ESIpos): m/z = 592 [M + H]+ | $^1$H-NMR (400 MHz, DMSO-d6) δ [ppm]: 1.431 (16.00), 3.042 (4.04), 3.948 (2.03), 4.284 (0.56), 6.792 (0.61), 6.811 (0.68), 6.911 (0.63), 7.173 (0.49), 7.354 (0.52), 7.373 (0.48), 7.644 (7.05), 7.683 (0.45), 7.701 (0.62), 7.722 (0.55), 7.837 (0.68), 7.840 (0.68), 7.855 (0.56), 7.858 (0.51), 8.350 (0.60), 8.353 (0.58), 8.371 (0.56), 8.374 (0.52), 8.763 (2.16), 9.234 (0.57), 9.254 (0.55). |
| 184 | 3 | LC-MS (Method L1): Rt = 0.95 min; MS (ESIpos): m/z = 506 [M + H]+ | $^1$H-NMR (400 MHz, DMSO-d6) δ [ppm]: 0.008 (1.32), 0.912 (7.39), 0.931 (16.00), 0.949 (7.79), 1.634 (0.73), 1.652 (2.85), 1.670 (5.25), 1.688 (5.08), 1.706 (2.51), 1.725 (0.52), 2.008 (0.45), 2.024 (0.86), 2.033 (1.06), 2.042 (1.11), 2.058 (1.52), 2.068 (1.52), 2.086 (3.21), 2.126 (0.70), 2.138 (1.27), 2.155 (1.51), 2.167 (1.10), 2.178 (0.76), 2.328 (0.44), 2.523 (2.24), 2.670 (0.48), 3.451 (1.52), 3.468 (3.30), 3.476 (3.00), 3.482 (2.99), 3.489 (3.03), 3.506 (1.25), 4.235 (0.77), 4.253 (2.65), 4.268 (4.11), 4.278 (3.48), 4.286 (2.21), 4.306 (0.49), 5.236 (1.01), 5.251 (2.08), 5.269 (1.99), 5.284 (0.85), 5.754 (0.58), 6.782 (3.55), 6.803 (3.93), 6.880 (1.99), 6.899 (3.97), 6.917 (2.28), 7.141 (1.96), 7.145 (1.96), 7.162 (3.10), 7.180 (1.49), 7.287 (3.39), 7.305 (3.06), 7.516 (2.25), 7.535 (3.39), 7.555 (2.58), 7.600 (3.94), 7.605 (3.48), 7.621 (14.17, 7.626 (9.44), 7.732 (4.27), 7.750 (3.54), 7.951 (2.25), 8.412 (3.35), 8.433 (3.11), 8.535 (9.75), 8.986 (3.00), 9.006 (2.85). |
| 185 | 2 | LC-MS (Method L1): Rt = 0.72 min; MS (ESIneg): m/z = 505 [M − H]− | $^1$H-NMR (400 MHz, DMSO-d6) δ [ppm]: 1.108 (4.30), 1.783 (2.07), 1.917 (2.11), 1.930 (1.65), 2.075 (1.64), 2.086 (5.94), 2.156 (1.41), 2.171 (1.60), 2.185 (1.08), 2.328 (0.70), 2.366 (0.42), 2.670 (0.85), 2.709 (0.44), 2.752 (4.01), 2.770 (0.64), 2.789 (0.58), 2.994 (3.16), 3.009 (6.19), 3.024 (3.45), 3.168 (0.68), 3.417 (1.38), 3.527 (1.42), 3.731 (1.06), 4.266 (4.94), 5.247, (2.07), 5.260 (1.94), 5.754 (8.83), 6.786 (3.64), 6.806 (4.14), 6.897 (1.83), 6.916 (3.84), 6.934 (2.23), 7.150 (1.96), 7.167 (3.21), 7.186 (1.56), 7.323 (3.41), 7.341 (3.12), 7.540 (2.24), 7.559 (3.64), 7.579 (2.41), 7.611 (7.22), 7.617 (16.00), 7.746 (4.79), 7.763 (4.88), 8.346 (1.16), 8.400 (0.60), 8.421 (3.41), 8.442 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.22), 8.513 (7.91), 8.538 (1.10), 9.052 9 (1.55), 9.069 (1.55). |
| 186 | | LC-MS (Method L1): Rt = 0.80 min; MS (ESIpos): m/z = 534 [M + H]+ | $^1$H-NMR (400 MHz, DMSO-d6) δ [ppm]: −0.149 (0.48), 0.008 (3.60), 0.146 (0.48), 1.140 (6.02), 1.235 (0.55), 1.889 (1.18), 2.031 (2.12), 2.051 (2.52), 2.063 (2.18), 2.073 (1.69), 2.116 (2.61), 2.156 (1.44), 2.170 (1.66), 2.186 (0.98), 2.206 (0.83), 2.327 (1.00), 2.366 (0.43), 2.669 (1.05), 2.710 (0.52), 3.475 (2.09), 3.503 (2.40), 3.737 (1.58), 3.759 (1.14), 3.813 (0.91), 3.835 (1.75), 3.865 (2.04), 3.877 (2.60), 3.892 (1.74), 3.903 (1.61), 4.254 (3.26), 4.266 (5.15), 4.280 (3.06), 4.366 (2.18), 4.538 (0.55), 5.032 (2.78), 5.207 (0.85), 5.221 (1.83), 5.241 (1.89), 5.255 (0.85), 6.781 (3.54), 6.801 (4.00), 6.891 (1.71), 6.910 (3.70), 6.929 (2.12), 7.145 (1.81), 7.162 (2.90), 7.183 (1.41), 7.305 (3.14), 7.324 (2.84), 7.464 (2.18), 7.482 (3.14), 7.503 (2.58), 7.606 (4.72), 7.610 (4.81), 7.621 (16.00), 7.625 (9.59), 7.706 (3.90), 7.724 (3.35), 8.133 (13.65,) 8.279 (3.24), 8.299 (3.04), 8.434 (10.50), 9.044 (3.03), 9.065 (2.98), 12.729 (0.68). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 187 | | LC-MS (Method L1): Rt = 0.80 min; MS (ESIpos): m/z = 534 [M + H]+ | $^1$H-NMR (400 MHz, DMSO-d6) δ [ppm]: −0.149 (0.83), −0.008 (7.47), 0.008 (6.76), 0.146 (0.89), 1.235 (0.41), 1.260 (2.01), 1.335 (2.31), 1.901 (1.24), 2.005 (1.48), 2.017 (2.25), 2.028 (2.37), 2.040 (2.49), 2.049 (2.61), 2.085 (0.53), 2.149 (1.42), 2.167 (1.24), 2.185 (1.19), 2.200 (0.89), 2.327 (1.36), 2.366 (0.83), 2.523 (4.80), 2.670 (1.60), 2.710 (1.07), 3.501 (1.84), 3.527 (2.07), 3.732 (1.54), 3.780 (1.01), 3.800 (1.78), 3.821 (1.54), 3.852 (1.72), 3.862 (1.78), 3.879 (1.54), 3.889 (1.42), 4.258 (5.39), 4.270 (3.32), 4.374 (2.31), 5.029 (3.67), 5.037 (3.61), 5.197 (0.89), 5.212 (2.01), 5.231 (2.07), 5.246 (0.95), 5.753 (8.18), 6.782 (3.61), 6.803 (4.09), 6.895 (1.84), 6.913 (3.97), 6.932 (2.31), 7.147 (1.96), 7.165 (3.20), 7.182 (1.60), 7.310 (3.38), 7.328 (3.08), 7.463 (1.72), 7.483 (2.79), 7.503 (2.13), 7.609 (3.08), 7.621 (16.00), 7.625 (9.84), 7.709 (3.67), 7.725 (3.20), 8.132 (2.01), 8.276 (3.08), 8.297 (2.90), 8.428 (6.76), 9.044 (2.37), 9.065 (2.37), 12.724 (0.71). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 188 | 4.5 | LC-MS (Method L1): Rt = 1.18 min; MS (ESIneg): m/z = 514 [M − H]− | $^1$H-NMR (400 MHz, DMSO-d6) δ [ppm]: −0.008 (2.51), 0.008 (2.40), 1.778 (0.76), 1.789 (0.83), 1.806 (1.00), 1.999 (0.94), 2.012 (0.94), 2.020 (0.92), 2.034 (0.71), 2.327 (0.91), 2.670 (1.00), 4.034 (0.75), 4.055 (1.64), 4.076 (1.16), 4.161 (1.16), 4.171 (1.05), 4.179 (1.30), 4.198 (0.76), 5.017 (0.70), 5.031 (1.46), 5.050 (1.46), 5.065 (0.67), 5.754 (0.43), 6.746 (2.94), 6.766 (3.26), 6.848 (1.33), 6.868 (2.92), 6.885 (1.86), 7.049 (2.67), 7.066 (2.16), 7.127 (1.46), 7.148 (2.40), 7.165 (1.19), 7.419 (2.81), 7.438 (3.05), 7.721 (4.19), 7.724 (6.58), 7.730 (16.00), 7.734 (7.25), 7.816 (2.30), 7.835 (3.08), 7.856 (2.38), 8.049 (3.13), 8.052 (3.29), 8.067 (2.75), 8.136 (6.83), 8.138 (6.75), 8.649 (6.74), 8.652 (6.63), 9.105 (2.64), 9.125 (2.56), 9.233 (10.60). |
| 189 | 5 | LC-MS (Method L1): Rt = 1.27 min; MS (ESIpos): m/z = 534 [M + H]+ | 1H-NMR (400 MHz, DMSO-d6) δ [ppm] = 9.12-9.22 (m, 2H), 8.35 (s, 2H), 8.03 (dd, 1H), 7.88-7.96 (m, 1H), 7.79-7.88 (m, 1H), 7.67-7.76 (m, 2H), 7.25 (d, 1H), 7.11-7.20 (m, 1H), 6.88-6.97 (m, 1H), 6.76 (d, 1H), 5.01-5.13 (m, 1H), 4.07-4.28 (m, 2H), 2.02-2.15 (m, 1H), 1.94 (dtd, 1H). |
| 190 | | LC-MS (Method L1): Rt = 1.11 min; MS (ESIpos): m/z = 518 [M + H]+ | $^1$H-NMR (400 MHz, DMSO-d6) δ [ppm]: −0.149 (1.34), 0.008 (11.80), 0.146 (1.34), 1.234 (0.47), 2.050 (1.17), 2.058 (1.31), 2.072 (1.34), 2.085 (1.95), 2.210 (1.70), 2.222 (1.64), 2.231 (1.56), 2.245 (1.09), 2.327 (1.39), 2.366 (0.75), 2.523 (4.79), 2.669 (1.47), 2.710 (0.78), 3.060 (0.45), 3.162 (0.56), 3.174 (0.58), 3.249 (1.59), 3.269 (5.20), 3.280 (11.55), 3.291 (13.72), 3.864 (8.68), 3.875 (14.11), 3.886 (8.04), 4.223 (0.95), 4.244 (2.73), 4.252 (2.17), 4.265 (3.56), 4.293 (2.25), 4.312 (0.81), 5.245 (1.11), 5.259 (2.50), 5.277 (2.50), 5.292 (1.09), 5.754 (0.53), 6.788 (4.59), 6.809 (5.04), 6.917 (2.25), 6.933 (4.79), 6.952 (2.87), 7.157 (2.56), 7.175 (4.03), 7.192 (1.98), 7.377 (4.26), 7.395 (4.01), 7.484 (3.14), 7.506 (6.04), 7.528 (4.70), 7.586 (2.67), 7.591 (2.98), 7.598 (2.95), 7.603 (3.09), 7.612 (2.11), 7.619 (1.89), 7.625 (1.92), 7.673 (3.28), 7.691 (4.84), 7.712 (4.31), 7.796 (8.77), 7.815 (7.35), 8.253 (4.51), 8.256 (4.54), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.274 (4.20), 8.419 (0.42), 8.679 (16.00), 9.157 (4.45), 9.177 (4.29). |
| 191 | | LC-MS (Method L1): Rt = 1.14 min; MS (ESIpos): m/z = 536 [M + H]+ | $^1$H-NMR (400 MHz, DMSO-d6) δ [ppm]: 3.284 (1.86), 3.296 (2.09), 3.310 (16.00), 3.864 (1.44), 3.875 (2.23), 3.886 (1.28), 4.236 (0.43), 4.260 (0.54), 5.248 (0.41), 6.782 (0.73), 6.802 (0.80), 6.924 (0.74), 6.941 (0.43), 7.168 (0.63), 7.364 (0.68), 7.383 (0.61), 7.593 (0.46), 7.617 (0.89), 7.641 (0.45), 7.675 (0.47), 7.688 (0.55), 7.695 (0.75), 7.706 (0.80), 7.714 (0.54), 7.726 (0.64), 7.774 (0.85), 7.790 (0.54), 8.295 (0.68), 8.313 (0.62), 8.626 (2.30), 9.156 (0.68), 9.176 (0.65). |
| 192 | | LC-MS (Method L1): Rt = 1.25 min; MS (ESIpos): m/z = 552 [M + H]+ | $^1$H-NMR (400 MHz DMSO-d6) δ [ppm]: −0.008 (0.73), 0.008 (0.67), 1.038 (0.70), 1.056 (1.42), 1.073 (0.73), 1.356 (16.00), 2.069 (0.41), 2.183 (2.23), 2.198 (0.40), 2.523 (0.65), 3.162 (5.24), 3.175 (5.43), 3.261 (1.01), 3.272 (2.30), 3.284 (2.43), 3.295 (1.34), 3.862 (1.80), 3.873 (3.10), 3.884 (1.73), 4.062 (0.46), 4.075 (1.30), 4.088 (1.26), 4.101 (0.43), 4.231 (0.62), 4.238 (0.48), 4.252 (0.64), 4.259 (0.79), 4.267 (0.64), 4.274 (0.50), 4.283 (0.53), 4.335 (0.42), 5.238 (0.57), 5.257 (0.58), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.631 (0.75), 6.784 (1.09), 6.802 (1.21), 6.870 (1.34), 6.902 (0.56), 6.905 (0.54), 6.921 (1.16), 6.939 (0.71), 6.942 (0.64), 7.148 (0.56), 7.152 (0.59), 7.169 (0.92), 7.187 (0.45), 7.190 (0.45), 7.362 (0.95), 7.381 (0.90), 7.502 (2.90), 7.506 (3.06), 7.636 (0.78), 7.659 (1.54), 7.682 (0.86), 7.688 (1.02), 7.693 (1.74), 7.698 (0.87), 8.319 (0.77), 8.334 (0.82), 8.342 (0.81), 8.358 (0.73), 8.680 (4.09), 9.152 (1.05), 9.172 (1.01). |
| 193 | | LC-MS (Method L6): Rt = 1.46 min; MS (ESIpos): m/z = 552 [M + H]+ | $^1$H-NMR (400 MHz, DMSO-d6) δ [ppm]: −0.149 (0.61 −0.008 (8.00), 0.008 (5.20), 0.146 (0.61), 1.903 (1.83), 2.018 (3.13), 2.029 (3.53), 2.040 (3.33), 2.050 (3.82), 2.156 (2.07), 2.170 (2.36), 2.185 (1.71), 2.327 (2.03), 2.366 (1.50), 2.518 (10.92), 2.523 (9.71), 2.669 (2.07), 2.710 (1.58), 3.472 (1.54), 3.499 (2.56), 3.523 (1.34), 3.736 (2.19), 3.833 (1.71), 3.863 (2.48), 3.876 (2.52), 3.892 (1.83), 4.257 (5.69), 4.266 (6.05), 4.370 (3.09), 5.029 (4.51), 5.220 (2.48), 5.754 (1.38), 6.783 (4.95), 6.802 (5.28), 6.894 (2.88), 6.913 (5.20), 6.931 (3.01), 7.146 (2.80), 7.164 (4.35), 7.184 (1.99), 7.307 (4.39), 7.326 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (3.78), 7.461 (2.19), 7.480 (3.49), 7.500 (2.36), 7.721 (4.75), 7.739 (4.06), 7.789 (16.00), 7.805 (15.51), 8.275 (3.57), 8.297 (3.25), 8.439 (5.32), 9.042 (3.25), 9.063 (3.09). |
| 194 | | LC-MS (Method L6): Rt = 1.37 min; MS (ESIpos): m/z = 534 [M + H]+ | $^1$H-NMR (400 MHz, DMSO-d6) δ [ppm]: −0.150 (0.76), 1243 (1.14), 1.862 (2.65), 1.904 (3.87), 2.034 (6.99), 2.142 (4.04), 2.157 (4.55), 2.327 (2.86), 2.365 (1.05), 2.668 (3.16), 2.689 (9.05), 2.709 (1.60), 2.889 (0.97), 3.508 (3.16), 3.741 (3.75), 3.873 (5.09), 4.249 (14.53), 4.384 (6.23), 5.049 (4.97), 5.203 (5.26), 5.754 (16.00), 6.770 (9.35), 6.791 (10.32), 6.876 (5.64), 6.895 (11.49), (6.912), (6.48), 7.135 (5.73), 7.153 (8.80), 7.172 (4.63), 7.286 (10.78), 7.305 (12.25), 7.422 (4.88), 7.494 (4.88), 7.537 (6.19), 7.663 (5.05), 8.133 (2.95), 8.331 (10.27), 9.031 (3.83). |
| 195 | | LC-MS (Method L1): Rt = 0.75 min; MS (ESIpos): m/z = 536 [M + H]+ | $^1$H-NMR (400 MHz, DMSO-d6) δ [ppm]: −0.149 (1.44), −0.008 (12.33), 0.008 (10.95), 0.146 (1.32), 1.258 (0.72), 1.902 (4.39), 2.034 (9.32), 2.148 (5.11), 2.164 (5.71), 2.180 (4.39), 2.197 (3.67), 2.327 (4.99), 2.366 (2.71), 2.523 (12.27), 2.670 (4.75), 2.689 (1.26), 2.709 (1.98), 2.812 (0.78), 3.509 (4.03), 3.745 (4.09), 3.874 (7.82), 4.257 (16.00), 4.376 (6.92), 5.037 (7.10), 5.221 (6.32), 5.754 (14.80), 6.777 (11.31), 6.797 (12.27), 6.882 (7.64), 6.901 (15.28), 6.919 (8.84), 7.142 (6.86), 7.159 (10.83), 7.178 (5.23), 7.292 (12.75), 7.311 (11.49), 7.493 (5.29), 7.585 (5.23), 7.664 (9.26), 8.132 (2.05), 8.320 (6.26), 8.361 (10.23), 9.030 (4.45). |
| 196 | | LC-MS (Method L1): Rt = 0.74 min; MS (ESIpos): m/z = 518 [M + H]+ | $^1$H-NMR (400 MHz, DMSO-d6) δ [ppm] −0.149 (0.87), 1.913 (2.01), 2.048 (3.88), 2.170 (2.51), 2.327 (1.94), 2.523 (5.82), 2.669 (1.97), 3.516 (1.51), 3.868 (2.41), 4.265 (7.06), 4.377 (3.51), 5.044 (3.01), 5.223 (2.74), 5.754 (16.00), 6.784 (6.46), 6.803 (6.93), 6.892 (3.08), 6.910 (6.43), 6.928 (3.88), 7.147 (3.25), 7.164 (5.12), 7.183 (2.68), 7.301 (4.92), 7.320 (4.62), 7.492 (5.12), 7.567 (3.68), 7.579 (3.75), 7.684 (3.48), 7.701 (3.18), 7.779 (5.82), 7.784 (5.72), 7.798 (5.82), 7.803 (5.62), 8.131 (2.91), 8.260 (2.74), 8.409 (3.45), 9.059 (1.97). |
| 197 | | LC-MS (Method L1): Rt = | $^1$H-NMR (400 MHz, DMSO-d6) δ [ppm]: 0.008 (0.53), 2.055 (0.47), 2.182 (0.43), 2.194 (0.43), 2.523 (1.20), 3.072 (16.00), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | 0.93 min; MS (ESIpos): m/z = 494 [M + H]+ | 4.234 (0.76), 4.241 (0.67), 4.253 (1.11), 4.261 (1.14), 4.276 (0.61), 5.233 (0.66), 5.253 (0.62), 5.754 (0.79), 6.781 (1.22), 6.799 (1.31), 6.895 (0.67), 6.914 (1.23), 6.933 (0.72), 7.147 (0.66), 7.164 (0.99), 7.182 (0.48), 7.342 (1.07), 7.361 (0.96), 7.586 (0.87), 7.609 (1.65), 7.634 (1.59), 7.652 (1.37), 7.668 (1.04), 7.673 (1.40), 7.687 (1.16), 7.707 (0.85), 7.733 (1.36), 7.747 (0.90), 8.252 (1.19), 8.256 (1.15), 8.273 (1.10), 8.558 (4.01), 9.072 (1.07), 9.092 (0.99). |
| 198 | | LC-MS (Method L1): Rt = 1.17 min; MS (ESIpos): m/z = 506 [M + H]+ | $^1$H-NMR (400 MHz, DMSO-d6) δ [ppm]: −0.008 (2.98), 0.008 (2.20), 1.031 (16.00), 1.046 (15.86), 2.114 (0.42), 2.123 (0.49), 2.130 (0.48), 2.180 (0.43), 2.207 (0.73), 2.231 (0.54), 2.290 (0.86), 2.524 (0.71), 2.599 (7.81), 2.716 (2.57), 2.767 (1.36), 2.782 (4.28), 3.063 (13.77), 3.096 (5.64), 3.118 (5.22), 3.128 (2.34), 3.758 (0.72), 3.774 (0.93), 3.789 (0.67), 4.223 (0.45), 4.234 (0.63), 4.240 (0.73), 4.263 (1.22), 4.268 (1.11), 4.291 (0.83), 4.347 (0.83), 4.356 (1.15), 4.374 (0.55), 4.384 (0.64), 6.029 (0.51), 6.045 (0.60), 6.054 (0.62), 6.070 (0.47), 6.750 (0.57), 6.770 (0.61), 6.816 (1.14), 6.836 (1.59), 6.854 (0.46), 6.942 (0.62), 6.952 (0.92), 6.970 (1.59), 6.989 (0.90), 7.088 (0.43), 7.162 (1.02), 7.181 (1.47), 7.200 (0.67), 7.303 (1.07), 7.322 (0.94), 7.359 (0.50), 7.378 (0.44), 7.584 (1.50), 7.588 (2.38), 7.600 (0.65), 7.604 (0.60), 7.623 (0.60), 7.641 (2.51), 7.645 (2.60), 7.653 (1.17), 7.674 (6.23), 7.678 (4.23), 7.684 (1.61), 7.760 (0.60), 7.763 (0.61), 7.778 (0.49), 7.781 (0.49), 7.810 (1.91), 7.828 (1.43), 8.233 (1.73), 8.252 (1.81), 8.270 (0.45), 8.621 (1.03), 8.626 (0.75), 8.649 (1.42), 8.685 (3.00). |
| 199 | | LC-MS (Method L1): Rt = 1.47 min; MS (ESIpos): m/z = 554 [M + H]+ | $^1$H-NMR (400 MHz, DMSO-d6) δ [ppm]: 1.524 (0.76), 1.830 (0.77), 1.842 (0.85), 2.669 (0.44), 3.368 (16.00), 3.946 (0.56), 3.970 (1.28), 3.993 (1.00), 4.034 (1.18), 4.049 (1.17), 4.939 (1.39), 4.958 (1.38), 5.753 (0.43), 6.593 (3.28), 6.613 (3.44), 6.720 (2.29), 6.740 (2.71), 6.751 (1.49), 6.769 (2.88), 6.792 (2.81), 6.811 (1.48), 6.997 (1.58), 7.015 (1.39), 7.099 (1.40), 7.123 (3.83), 7.142 (4.69), 7.163 (2.24), 7.676 (2.67), 7.680 (2.28), 7.686 (2.02), 7.707 (3.17), 7.716 (8.16), 7.721 (7.33), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.909 (2.73), 7.925 (2.29), 7.963 (2.59), 7.984 (2.17), 8.892 (2.25), 8.912 (2.12), 8.993 (6.13). |
| 200 | | LC-MS (Method L1): Rt = 1.14 min; MS (ESIpos): m/z = 552 [M + H]+ | $^1$H-NMR (400 MHz, DMSO-d6) δ [ppm]: −0.149 (0.45), −0.008 (4.14), 0.008 (3.74), 0.146 (0.49), 1.157 (4.28), 1.175 (8.62), 1.192 (4.37), 1.237 (1.13), 1.398 (6.32), 1.988 (16.00), 2.019 (1.27), 2.040 (1.53), 2.054 (1.76), 2.073 (1.64), 2.191 (1.72), 2.204 (1.64), 2.213 (1.69), 2.227 (1.15), 2.327 (1.34), 2.366 (0.92), 2.522 (4.51), 2.669 (1.41), 2.710 (0.92), 3.247 (1.22), 3.265 (2.51), 3.295 (9.16), 3.874 (12.08), 4.002 (1.25), 4.020 (3.83), 4.038 (3.76), 4.056 (1.29), 4.200 (0.85), 4.224 (2.40), 4.249 (3.43), 4.258 (2.82), 4.275 (2.47), 5.230 (2.35), 5.245 (2.44), 5.754 (7.50), 6.774 (5.36), 6.795 (5.92), 6.887 (2.61), 6.905 (5.47), 6.924 (3.27), 7.142 (2.89), 7.159 (4.46), 7.177 (2.21), 7.181 (2.21), 7.344 (6.79), 7.360 (6.16), 7.363 (7.33), 7.370 (3.55), 7.374 (2.84), 7.389 (3.59), 7.393 (3.43), 7.452 (2.96), 7.466 (3.38), 7.472 (4.89), 7.485 (5.24), 7.491 (2.68), 7.505 (2.61), 7.646 (3.76), 7.669 (6.51), 7.691 (3.88), 7.734 (6.13), 7.737 (6.30), 7.754 (5.36), 7.757 (5.12), 8.341 (3.74), 8.356 (3.99), 8.364 (3.95), 8.380 (3.64), 8.604 (9.75), 8.612 (10.24), 9.143 (2.98), 9.149 (3.15), 9.163 (2.98), 9.170 (2.96). |
| 201 | | LC-MS (Method L1): Rt = 1.08 min; MS (ESIpos): m/z = 554 [M + H]+ | $^1$H-NMR (400 MHz, DMSO-d6) δ [ppm]: −0.008 (2.72), 0.008 (2.48), 2.030 (0.56), 2.039 (0.58), 2.051 (0.60), 2.066 (0.88), 2.073 (0.77), 2.086 (3.11), 2.181 (0.62), 2.193 (0.79), 2.205 (0.79), 2.215 (0.72), 2.227 (0.47), 2.327 (0.60), 2.332 (0.43), 2.523 (1.88), 2.559 (1.25), 2.578 (1.51), 2.596 (1.97), 2.614 (1.49), 2.634 (0.95), 2.651 (0.54), 2.665 (0.50), 2.669 (0.65), 2.674 (0.47), 3.710 (1.27), 3.720 (1.53), 3.728 (2.20), 3.737 (2.18), 3.744 (1.48), 3.755 (1.21), 3.845 (1.98), 3.877 (3.98), 3.909 (1.91), 4.223 (0.41), 4.244 (1.29), 4.252 (1.09), 4.264 (1.96), 4.272 (2.19), 4.287 (1.15), 4.306 (0.42), 5.237 (0.54), 5.251 (1.20), 5.271 (1.20), 5.285 (0.52), 5.754 (4.52), 6.792 (2.31), 6.810 (2.55), 6.812 (2.55), 6.904 (1.13), 6.907 (1.12), 6.923 (2.38), 6.942 (1.43), 6.944 (1.35), 7.156 (1.18), 7.160 (1.25), 7.177 (1.91), 7.195 (0.96), 7.199 (0.91), 7.355 (1.97), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.373 (1.85), 7.638 (16.00), 7.657 (0.42), 7.664 (1.80), 7.682 (2.37), 7.685 (2.13), 7.703 (2.16), 7.834 (2.60), 7.837 (2.71), 7.852 (2.23), 7.855 (2.07), 8.237 (2.33), 8.240 (2.34), 8.258 (2.24), 8.261 (2.06), 8.688 (8.85), 9.217 (2.14), 9.237 (2.09). |
| 202 | | LC-MS (Method L1): Rt = 1.04 min; MS (ESIpos): m/z = 533 [M + H]+ | $^1$H-NMR (400 MHz, DMSO-d6) δ [ppm]: −0.149 (0.84), −0.008 (8.37), 0.008 (8.34), 0.146 (0.90), 0.994 (0.52), 1.236 (1.34), 1.336 (0.57), 1.782 (1.25), 1.916 (1.25), 2.327 (1.74), 2.366 (1.09), 2.670 (1.88), 2.710 (1.09), 2.765 (2.18), 2.781 (4.28), 2.797 (2.15), 3.963 (0.87), 3.984 (2.07), 4.006 (1.34), 4.111 (1.55), 4.873 (1.80), 4.888 (3.60), 4.905 (2.43), 4.921 (1.58), 4.936 (1.88), 4.953 (1.31), 6.688 (3.46), 6.709 (3.87), 6.716 (1.80), 6.735 (3.46), 6.754 (2.51), 6.856 (3.41), 6.875 (2.53), 7.058 (1.66), 7.079 (2.70), 7.097 (1.53), 7.614 (11.50), 7.618 (16.00), 7.636 (4.99), 7.641 (5.42), 7.657 (1.20), 7.680 (1.61), 7.743 (1.77), 7.761 (4.12), 7.781 (3.76), 7.798 (4.58), 7.812 (2.21), 8.383 (2.67), 8.403 (2.70), 8.563 (2.67), 8.580 (2.43), 8.662 (0.57), 9.033 (11.99), 11.367 (0.60). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 203 | | LC-MS (Method L4): Rt = 3.85 min; MS (ESIpos): m/z = 582 [M + H]+ | $^1$H-NMR (400 MHz, DMSO-d6) δ [ppm]: 0.008 (2.46), 2.064 (0.79), 2.071 (0.81), 2.084 (0.92), 2.099 (1.21), 2.206 (0.83), 2.218 (1.14), 2.230 (1.08), 2.240 (1.07), 2.252 (0.73), 2.327 (0.63), 2.522 (1.85), 2.669 (0.67), 3.484 (3.25), 3.654 (5.30), 3.666 (4.89), 4.223 (0.66), 4.244 (1.80), 4.251 (1.36), 4.265 (1.77), 4.272 (2.23), 4.282 (1.77), 4.297 (1.50), 4.316 (0.61), 5.240 (0.78), 5.254 (1.76), 5.273 (1.72), 5.287 (0.74), 5.754 (1.31), 6.794 (3.28), 6.814 (3.60), 6.920 (1.57), 6.937 (3.30), 6.955 (1.94), 7.160 (1.66), 7.163 (1.71), 7.181 (2.72), 7.198 (1.33), 7.392 (2.85), 7.409 (2.68), 7.635 (8.69), 7.639 (16.00), 7.647 (5.36), 7.652 (4.23), 7.707 (2.28), 7.725 (3.22), 7.746 (2.80), 7.872 (3.73), 7.887 (2.92), 8.399 (3.12), 8.417 (2.89), 8.770 (11.57), 9.239 (3.04), 9.260 (2.96). |
| 204 | | LC-MS (Method L1): Rt = 0.83 min; MS (ESIpos): m/z = 508 | $^1$H-NMR (400 MHz, DMSO-d6) δ [ppm]: −0.150 (1.38), −0.008 (13.30), 0.008 (13.66), 0.146 (1.50), 1.235 (1.56), 2.049 (1.20), 2.076 (1.68), 2.206 (1.50), 2.217 (1.62), 2.226 (1.44), 2.322 (2.70), 2.327 (3.60), 2.331 (2.70), 2.366 (2.52), 2.522 (13.90), 2.664 (3.00), 2.669 (3.84), 2.674 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | (2.88), 2.709 (2.46), 3.218 (3.96), 3.241 (9.11), 3.262 (8.45), 3.273 (10.25), 3.285 (11.63), 3.858 (7.85), 3.870 (13.30), 3.881 (7.43), 4.223 (0.72), 4.243 (2.64), 4.251 (2.10), 4.264 (3.90), 4.273 (3.96), 4.289 (2.16), 4.381 (4.85), 4.403 (9.65), 4.425 (4.67), 5.240 (1.02), 5.255 (2.40), 5.275 (2.34), 5.288 (0.96), 5.753 (2.76), 6.784 (4.43), 6.802 (4.91), 6.871 (3.66), 6.890 (7.49), 6.909 (5.87), 6.923 (4.73), 6.942 (2.82), 7.109 (4.55), 7.127 (3.90), 7.151 (2.46), 7.168 (3.78), 7.186 (1.92), 7.237 (4.19), 7.256 (3.78), 7.363 (4.01), 7.382 (3.72), 7.618 (2.64), 7.636 (5.21), 7.657 (5.27), 7.674 (5.69), 7.678 (6.05), 7.692 (3.06), 7.696 (2.52), 8.202 (4.25), 8.206 (4.07), 8.223 (3.90), 8.227 (3.54), 8.583 (16.00), 9.155 (4.25), 9.176 (4.13). |
| 205 | | LC-MS (Method L2): Rt = 3.94 min; m/z = 568/570 [M + H]+ | $^1$H-NMR (400 MHz, Chloroform-d) δ 8.83 (s, 1H), 8.20 (d, J = 9.1 Hz, 1H), 7.67-7.63 (m, 1H), 7.56 (dd, J = 8.0, 1.5 Hz, 1H), 7.34 (td, J = 7.8, 2.5 Hz, 1H), 7.25 (d, J = 7.7 Hz, 1H), 7.23-7.12 (m, 2H), 6.94-6.80 (m, 3H), 5.39-5.31 (m, 1H), 4.38-4 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 206 | | LC-MS (Method L2): Rt = 4.15 min; m/z = 568/570 [M + H]+ | $^1$H-NMR (400 MHz, Chloroform-d) δ 8.85 (s, 1H), 8.17 (d, J = 9.1 Hz, 1H), 7.64 (d, J = 9.1 Hz, 1H), 7.43 (t, J = 1.9 Hz, 1H), 7.30-7.17 (m, 4H), 6.92 (td, J = 7.5, 1.2 Hz, 1H), 6.86 (dd, J = 8.3, 1.0 Hz, 1H), 6.80 (d, J = 7.4 Hz, 1H), 5.40-5.33 (m, 1H) |
| 207 | | LC-MS (Method L2): Rt = 3.41 min; m/z = 526/528 [M + H]+ | $^1$H-NMR (400 MHz, Chloroform-d) δ 8.84 (d, J = 1.7 Hz, 1H), 8.14 (dd, J = 9.1, 1.4 Hz, 1H), 7.62 (d, J = 9.2 Hz, 1H), 7.55 (dd, J = 8.1, 1.5 Hz, 1H), 7.34 (td, J = 7.8, 2.2 Hz, 1H), 7.26 (d, 1H), 7.23-7.14 (m, 2H), 6.94-6.83 (m, 3H), 5.38-5.31 (m, 1H |
| 208 | | LC-MS (Method L2): Rt = 3.61 min; m/z = 526/528 [M + H]+ | $^1$H-NMR (400 MHz, Chloroform-d) δ 8.83 (s, 1H), 8.09 (d, J = 9.1 Hz, 1H), 7.59 (d, J = 9.1 Hz, 1H), 7.42 (s, 1H), 7.32-7.15 (m, 4H), 6.97-6.82 (m, 3H), 5.33 (q, J = 5.2 Hz, 1H), 4.38-4.28 (m, 1H), 4.22-4.13 (m, 1H), 3.12 (s, 6H), 2.42-2.32 (m, 1H |
| 209 | | LC-MS (Method L2): Rt = 3.85 min; m/z = | $^1$H-NMR (400 MHz, Chloroform-d) δ 8.78 (d, J = 1.7 Hz, 1H), 7.57-7.50 (m, 2H), 7.32-7.17 (m, 5H), 6.94-6.77 (m, 3H), 5.40-5.33 (m, 1H), 4.38-4.30 (m, 1H), 4.22-4.14 (m, 1H), 3.91- |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | 552/554 [M + H]+ | 3.80 (m, 4H), 3.44-3.31 (m, 4H), 2.44-2.33 (m, 1H), 2.25- |
| 210 | | LC-MS (Method L2): Rt = 4.13 min; m/z = 552/554 [M + H]+ | $^1$H-NMR (400 MHz, Chloroform-d) δ 8.81 (s, 1H), 7.61 (dd, J = 8.1, 5.3 Hz, 1H), 7.47-7.36 (m, 3H), 7.32-7.18 (m, 3H), 6.93 (td, J = 7.5, 1.1 Hz, 1H), 6.86 (dd, J = 8.3, 1.0 Hz, 1H), 6.81 (d, J = 7.5 Hz, 1H), 5.41-5.33 (m, 1H), 4.40-4.32 (m, 1H), 4. |
| 211 | | LC-MS (Method L2): Rt = 4.39 min; m/z = 568/570 [M + H]+ | $^1$H-NMR (400 MHz, DMSO-d6) δ 9.24 (d, J = 8.0 Hz, 1H), 8.73 (s, 1H), 8.20, (d, J = 2.1 Hz, 1H), 7.92 (d, J = 2.1 Hz, 1H), 7.68 (s, 3H), 7.39 (d, J = 7.6 Hz, 1H), 7.18 (t, J = 7.4 Hz, 1H), 6.93 (t, J = 7.2 Hz, 1H), 6.80 (d, J = 8.1 Hz, 1H), 5.25 (d, J = 7.1 |
| 212 | | LC-MS (Method L2): Rt = 4.12 min; m/z = 568/570 [M + H]+ | $^1$H-NMR (400 MHz, DMSO-d6) δ 9.22 (dd, J = 8.0, 5.3 Hz, 1H), 8.62 (d, J = 3.1 Hz, 1H), 8.22 (d, J = 2.4 Hz, 1H), 7.77 (d, J = 2.3 Hz, 1H), 7.73 (dd, J = 8.0, 1.6 Hz, 1H), 7.46 (td, J = 7.8, 4.5 Hz, 1H), 7.41-7.33 (m, 2H), 7.16 (t, J = 7.0 Hz, 1H), 6.91 ( |
| 213 | | LC-MS (Method L2): Rt = | $^1$H-NMR (400 MHz, DMSO-d6) δ 9.13 (dd, J = 8.1, 5.1 Hz, 1H), 8.54 (d, J = 1.5 Hz, 1H), 8.22 (d, J = 2.4 Hz, 1H), 7.74- |
| | | 3.75 min; m/z = 526/528 [M + H]+ | 7.69 (m, 2H), 7.45 (td, J = 7.8, 4.4 Hz, 1H), 7.41-7.31 (m, 2H), 7.20-7.12 (m, 1H), 6.90 (t, J = 7.5 Hz, 1H), 6.78 (dd, J = 8.2, 1.0 |
| 214 | | LC-MS (Method L2): Rt = 3.27 min; m/z = 548 [M + H]+ | $^1$H-NMR (400 MHz, DMSO-d6) δ 9.21 (dd, J = 8.1, 5.5 Hz, 1H), 8.54 (d, J = 3.0 Hz, 1H), 7.67 (dd, J = 8.0, 1.6 Hz, 1H), 7.52 (d, J = 7.3 Hz, 1H), 7.49-7.34 (m, 3H), 7.33-7.26 (m, 1H), 7.16 (t, J = 7.7 Hz, 1H), 6.91 (t, δ = 7.4 Hz, 1H), 6.79 (d, J = 8.1 |
| 215 | | LC-MS (Method L2): Rt = 3.56 min; m/z = 548 [M + H]+ | $^1$H-NMR (400 MHz, DMSO-d6) δ 9.21 (d, J = 8.2 Hz, 1H), 8.62 (s, 1H), 7.68, (d, J = 7.4 Hz, 1H), 7.63-7.55 (m, 3H), 7.49-7.37 (m, 2H), 7.21-7.14 (m, 1H), 6.97-6.90 (m, 1H), 6.83-6.77 (m, 1H), 5.31-5.23 (m, 1H), 4.33- 4.20 (m, 2H), 3.87-3.78 (m |
| 216 | | LC-MS (Method L1): Rt = 0.94 min; MS (ESIpos): m/z = 565 [M + H]+ | $^1$H-NMR (400 MHz, DMSO-d6) δ [ppm]: 2.326 (0.43), 3.568 (16.00), 3.897 (2.36), 3.910 (6.78), 3.954 (0.55), 4.259 (0.56), 5.263 (0.41), 6.778 (0.76), 6.798 (0.79), 6.909 (0.76), 6.928 (0.43), 7.141 (0.43), 7.162 (0.66), 7.359 (0.68), 7.379 (0.61), 7.754 (0.48), 7.771 (0.70), 7.792 (0.53), 7.952 (0.81), 7.970 (0.69), 8.151 (1.35), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.356 (0.70), 8.378 (0.67), 8.396 (1.42), 8.590 (2.23), 8.803 (2.18), 9.184 (0.66), 9.205 (0.63). |
| 217 | | LC-MS (Method L2): Rt = 3.04 min; m/z = 506 [M + H]+ | $^1$H-NMR (400 MHz, DMSO-d6) δ 9.12 (d, J = 8.2 Hz, 1H), 8.59 (s, 1H), 7.67 (d, J = 7.4 Hz, 1H), 7.62-7.56 (m, 3H), 7.45-7.35 (m, 2H), 7.21-7.14 (m, 1H), 6.97-6.89 (m, 1H), 6.80 (dd, J = 8.2, 1.0 Hz, 1H), 5.30-5.21 (m, 1H), 4.33-4.20 (m, 2H), 2. |
| 218 | | LC-MS (Method L2): Rt = 3.03 min; m/z = 506 [M + H]+ | $^1$H-NMR (400 MHz, DMSO-d6) δ 9.11 (dd, J = 7.9, 5.8 Hz, 1H), 8.49 (d, J = 1.8 Hz, 1H), 7.66 (dd, J = 8.0, 1.6 Hz, 1H), 7.50 (d, J = 7.3 Hz, 1H), 7.45-7.38 (m, 2H), 7.35 (d, J = 6.8 Hz, 1H), 7.33-7.26 (m, 1H), 7.16 (t, J = 7.7 Hz, 1H), 6.91 (t, J = 7. |
| 219 | | LC-MS (Method L6): Rt = 1.28 min; MS (ESIpos): m/z = 476 [M + H]+ | $^1$H-NMR (600 MHz, DICHLOROMETHANE-d2) δ [ppm]: 2.505 (11.27), 3.076 (9.00), 3.332 (16.00), 4.248 (0.52), 4.262 (0.80), 5.254 (0.50), 6.784 (0.99), 6.797 (1.22), 6.915 (0.81), 6.927 (0.45), 7.055 (0.40), 7.071 (0.64), 7.148 (0.45), 7.161 (0.75), 7.343 (0.79), 7.356 (0.75), 7.625 (0.76), 7.643 (1.22), 8.223 (0.76), 8237 (0.72), 8.548 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.64), 9.091 (0.69), 9.104 (0.67), 10.063 (0.80). |
| 220 | | LC-MS (Method L6): Rt = 1.86 min; MS (ESIpos): m/z = 498 [M + H]+ | $^1$H-NMR (400 MHz, DMSO-d6) δ [ppm]: −0.008 (3.32), 0.008 (3.21), 1.236 (0.84), 1.817 (10.47), 1.834 (9.96), 2.029 (1.50), 2.037 (1.62), 2.048 (1.70), 2.064 (2.32), 2.071 (2.04), 2.198 (1.99), 2.210 (1.96), 2.219 (1.89), 2.231 (1.34), 2.327 (0.87), 2.366 (0.64), 2.669 (0.92), 2.710 (0.59), 3.607 (1.18), 3.634 (0.65), 3.880 (16.00), 4.208 (0.97), 4.230 (2.88), 4.257 (4.12), 4.266 (3.48), 4.273 (2.88), 4.282 (2.93), 4.294 (1.13), 4.300 (1.21), 5.224 (1.35), 5.239 (3.07), 5.258 (3.05), 5.273 (1.35), 6.779 (5.76), 6.799 (6.47), 6.894 (2.26), 6.913 (4.68), 6.932 (2.70), 6.998 (2.00), 7.017 (4.09), 7.036 (2.35), 7.146 (3.37), 7.165 (5.23), 7.182 (3.02), 7.199 (4.41), 7.222 (3.20), 7.274 (2.47), 7.352 (5.14), 7.371 (4.90), 7.465 (0.67), 7.486 (0.43), 7.610 (3.69), 7.627 (5.66), 7.676 (4.79), 7.696 (5.53), 7.714 (3.21), 8.095 (0.41), 8.114 (0.45), 8.262 (5.39), 8.283 (5.12), 8.578 (14.71), 9.146 (2.67). |
| 221 | | LC-MS (Method | $^1$H-NMR (400 MHz, DMSO-d6) δ [ppm]: 2.072 (1.74), 2.203 (1.62), 2.327 (1.90), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | L6): Rt = 2.11 min; MS (ESIpos): m/z = 518 [M + H]+ | 2.366 (1.16), 2.669 (2.05), 2.710 (1.47), 3.286 (11.07), 3.877 (14.20), 4.237 (2.72), 4.262 (3.40), 5.249 (2.54), 5.268 (2.69), 6.781 (4.77), 6.802 (5.41), 6.903 (2.42), 6.921 (5.14), 6.940 (2.97), 7.149 (2.63), 7.168 (3.98), 7.185 (2.05), 7.320 (3.24), 7.343 (6.52), 7.365 (7.89), 7.381 (3.79), 7.480 (3.06), 7.487 (4.62), 7.496 (3.43), 7.502 (4.47), 7.510 (2.88), 7.520 (3.15), 7.532 (2.66), 7.543 (2.57), 7.686 (2.75), 7.704 (4.93), 7.725 (4.83), 7.767 (5.66), 7.782 (3.55), 8.292 (4.37), 8.310 (4.10), 8.624 (16.00), 9.156 (4.28), 9.176 (4.41). |
| 222 | | LC-MS (Method L6): Rt = 2.07 min; MS (ESIpos): m/z = 520 [M + H]+ | $^1$H-NMR (400 MHz, DMSO-d6) δ [ppm]: 0.008 (1.64), 2.023 (0.54), 2.038 (1.00), 2.046 (1.02), 2.058 (1.08), 2.073 (1.49), 2.081 (1.28), 2.088 (0.94), 2.184 (0.70), 2.193 (1.09), 2.205 (1.44), 2.217 (1.35), 2.227 (1.31), 2.240 (0.90), 2.248 (0.69), 2.327 (0.51), 2.366 (0.43), 2.669 (0.49), 3.259 (1.78), 3.278 (5.13), 3.289 (11.26), 3.301 (15.43), 3.312 (16.00), 3.867 (7.04), 3.878 (11.75), 3.889 (6.69), 4.209 (0.69), 4.216 (0.81), 4.237 (2.18), 4.245 (1.75), 4.264 (2.74), 4.271 (2.61), 4.287 (2.00), 4.306 (0.79), 5.236 (0.95), 5.250 (2.07), 5.269 (2.07), 5.283 (0.94), 6.783 (3.72), 6.803 (4.15), 6.814 (0.48), 6.906 (1.85), 6.924 (3.92), 6.942 (2.32), 7.148 (1.95), 7.152 (2.07), 7.169 (3.35), 7.190 (2.50), 7.200 (1.81), 7.208 (1.77), 7.222 (1.73), 7.369 (3.48), 7.387 (3.23), 7.562 (0.70), 7.570 (0.83), 7.578 (0.92), 7.585 (1.40), 7.598 (1.38), 7.606 (1.34), 7.611 (1.38), 7.619 (0.86), 7.626 (0.75), 7.634 (0.68), 7.707 (2.41), 7.725 (3.96), 7.746 (3.74), 7.799 (4.59), 7.814 (2.97), 8.285 (0.81), 8.314 (3.61), 8.317 (3.68), 8.335 (3.42), 8.338 (3.29), 8.650 (12.72), 8.724 (0.73), 9.169 (3.62), 9.189 (3.54). |
| 223 | | LC-MS (Method L1): Rt = 0.70 min; MS (ESIpos): m/z = 518 [M + H]+ | $^1$H-NMR (400 MHz, DMSO-d6) δ [ppm]: 1.175 (0.49), 1.863 (1.82), 1.911 (2.02), 2.036 (3.68), 2.085 (1.72), 2.163 (2.23), 2.198 (1.58), 2.327 (1.01), 2.669 (1.08), 2.709 (0.62), 3.163 (3.07), 3.174 (3.15), 3.529 (1.52), 3.655 (0.88), 3.763 (1.37), 3.882 (2.44), 4.089 (0.62), 4.170 (3.56), 4.256 (6.88), 4.379 (3.32), 5.049 (3.25), 5.211 (2.58), 5.753 (9.32), 6.777 (6.14), 6.796 (6.47), 6.881 (3.02), 6.900 (6.29), 6.918 (4.00), 7.140 (3.30), 7.158 (5.04), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.175 (2.77), 7.293 (5.66), 7.311 (5.73), 7.328 (2.80), 7.349 (2.01), 7.502 (5.11), 7.651 (2.66), 8.133 (16.00), 8.321 (3.22), 8.355 (6.29), 8.737 (1.30), 9.047 (1.75), 12.596 (0.49). |
| 224 | | LC-MS (Method L1): Rt = 0.79 min; MS (ESIpos): m/z = 523 [M + H]+ | $^1$H-NMR (400 MHz, DMSO-d6) δ [ppm]: −0.149 (0.93), 0.146 (0.80), 2.056 (2.10), 2.203 (2.12), 2.327 (1.92), 2.366 (1.27), 2.670 (2.02), 2.709 (1.14), 3.893 (16.00), 4.229 (3.13), 4.249 (4.61), 4.256 (4.76), 4.495 (1.40), 5.241 (2.87), 5.258 (2.80), 6.770 (4.84), 6.790 (5.39), 6.878 (2.36), 6.896 (5.10), 6.914 (3.06), 7.134 (2.59), 7.152 (4.45), 7.171 (2.20), 7.333 (4.66), 7.352 (4.38), 7.507 (4.66), 7.525 (7.95), 7.550 (6.37), 7.569 (7.48), 7.588 (3.21), 7.691 (2.72), 7.709 (5.02), 7.730 (4.14), 7.788 (5.95), 7.804 (4.06), 8.195 (5.05), 8.214 (4.89), 8.287 (4.58), 8.308 (4.38), 8.483 (13.31), 9.143 (4.43), 9.164 (4.50), 9.188 (10.17). |
| 225 | | LC-MS (Method L6): Rt = 2.04 min; MS (ESIpos): m/z = 498 [M + H]+ | $^1$H-NMR (400 MHz, DMSO-d6) δ [ppm]: 2.049 (0.55), 2.058 (0.60), 2.069 (0.65), 2.084 (0.92), 2.092 (0.81), 2.200 (0.60), 2.210 (0.84), 2.222 (0.83), 2.231 (0.80), 2.244 (0.52), 2.387 (16.00), 2.670 (0.42), 3.246 (0.74), 3.266 (2.20), 3.278 (5.05), 3.290 (5.63), 3.652 (0.65), 3.863 (4.10), 3.874 (7.04), 3.885 (4.04), 4.225 (0.44), 4.246 (1.32), 4.253 (1.09), 4.267 (1.92), 4.276 (1.85), 4.293 (1.21), 4.312 (0.44), 5.246 (0.55), 5.260 (1.28), 5.279 (1.30), 5.293 (0.57), 5.754 (0.74), 6.788 (2.36), 6.809 (2.64), 6.915 (1.17), 6.933 (2.52), 6.952 (1.46), 7.048 (1.44), 7.072 (1.45), 7.156 (1.29), 7.175 (2.10), 7.191 (2.25), 7.222 (4.45), 7.376 (2.26), 7.395 (2.06), 7.659 (1.34), 7.678 (2.39), 7.698 (2.06), 7.758 (2.87), 7.776 (1.90), 8.243 (2.30), 8.264 (2.08), 8.668 (7.28), 9.157 (2.21), 9.178 (2.16). |
| 226 | | LC-MS (Method L6): Rt = 2.10 min; MS (ESIpos): m/z = 518 [M + H]+ | $^1$H-NMR (400 MHz, DMSO-d6) δ [ppm]: 3.279 (0.79), 3.291 (1.79), 3.312 (16.00), 3.868 (1.47), 3.879 (2.45), 3.889 (1.39), 4.237 (0.46), 4.258 (0.61), 4.286 (0.43), 5.249 (0.45), 5.268 (0.45), 5.754 (0.77), 6.781 (0.85), 6.801 (0.94), 6.904 (0.42), 6.922 (0.86), 6.941 (0.50), 7.149 (0.43), 7.167 (0.75), 7.304 (0.41), 7.324 (1.03), 7.344 (0.75), 7.366 (0.78), 7.385 (1.17), 7.400 (0.72), 7.644 (0.68), 7.695 (0.42), 7.713 (0.86), 7.734 (0.84), 7.754 (1.05), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.769 (0.52), 8.300 (0.71), 8.318 (0.70), 8.629 (2.54), 9.157 (0.74), 9.177 (0.72). |
| 227 | | LC-MS (Method L6): Rt = 2.02 min; MS (ESIpos): m/z = 518 [M + H]+ | $^1$H-NMR (400 MHz, DMSO-d6) δ [ppm]: 2.030 (1.38), 2.038 (1.48), 2.053 (1.64), 2.064 (2.14), 2.072 (1.92), 2.187 (1.53), 2.199 (1.97), 2.210 (1.94), 2.220 (1.83), 2.233 (1.30), 2.669 (0.41), 3.254 (2.20), 3.287 (11.31), 3.876 (16.00), 4.213 (1.15), 4.234 (3.07), 4.241 (2.68), 4.255 (4.56), 4.264 (4.46), 4281 (2.83), 4.300 (1.09), 5.229 (1.31), 5.244 (2.94), 5.262 (2.90), 5.277 (1.27), 5.753 (3.72), 6.777 (4.98), 6.798 (5.63), 6.896 (2.63), 6.914 (5.47), 6.933 (3.20), 7.144 (2.90), 7.163 (4.73), 7.182 (2.38), 7.244 (2.61), 7.265 (2.55), 7.289 (2.22), 7.297 (1.96), 7.311 (3.96), 7.318 (3.43), 7.332 (2.42), 7.340 (2.20), 7.355 (5.09), 7.374 (4.69), 7.573 (3.19), 7.586 (3.35), 7.595 (3.06), 7.608 (2.68), 7.666 (2.45), 7.683 (11.68), 7.703 (5.74), 7.721 (2.06), 8.279 (4.22), 8.283 (4.22), 8.299 (3.93), 8.303 (3.83), 8.598 (13.90), 9.158 (4.80), 9.178 (4.64). |
| 228 | | LC-MS (Method L6): Rt = 2.11 min; MS (ESIpos): m/z = 530 [M + H]+ | $^1$H-NMR (400 MHz, DMSO-d6) δ [ppm]: 2.050 (0.48), 2.057 (0.51), 2.071 (0.57), 2.085 (0.76), 2.092 (0.66), 2.199 (0.53), 2.210 (0.69), 2.221 (0.68), 2.231 (0.64), 2.244 (0.44), 3.245 (0.65), 3.265 (1.89), 3.276 (4.16), 3.288 (4.44), 3.822 (16.00), 3.844 (0.52), 3.864 (3.56), 3.874 (5.85), 3.884 (3.40), 4.246 (1.08), 4.253 (0.91), 4.267 (1.58), 4.276 (1.53), 4.293 (0.98), 5.244 (0.47), 5.258 (1.07), 5.277 (1.07), 5.291 (0.47), 5.754 (1.95), 6.788 (1.90), 6.809 (2.13), 6.916 (0.97), 6.935 (2.06), 6.954 (1.21), 7.062 (2.64), 7.094 (2.80), 7.156 (1.06), 7.175 (1.70), 7.197 (3.47), 7.378 (1.82), 7.397 (1.68), 7.662 (1.05), 7.682 (1.95), 7.701 (1.50), 7.782 (2.37), 7.799 (1.71), 8.251 (1.97), 8.272 (1.79), 8.677 (5.49), 9.160 (1.84), 9.180 (1.81). |
| 229 | | LC-MS (Method L1): Rt = 0.76 min; MS (ESIpos): m/z = 443 [M + H]+ | $^1$H-NMR (400 MHz, DMSO-d6) δ [ppm]: −0.149 (0.69), −0.008 (5.65), 0.008 (5.56), 0.146 (0.66), 1.997 (0.61), 2.012 (1.19), 2.023 (1.58), 2.031 (1.41), 2.044 (2.52), 2.059 (2.38), 2.072 (0.97), 2.127 (0.89), 2.141 (2.46), 2.155 (2.88), 2.169 (1.49), 2.191 (1.36), 2.203 (0.61), 2.327 (1.22), 2.366 (1.05), 2.523 (3.99), 2.669 (1.30), 2.709 (1.13), 3.057 (15.92), 3.069 (16.00), 4.247 (5.37), 4.259 (8.78), 4.273 (5.09), 5.218 (1.36), 5.233 (3.02), 5.253 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.02), 5.267 (1.38), 6.780 (5.48), 6.800 (6.06), 6.889 (2.85), 6.891 (2.82), 6.908 (6.03), 6.926 (3.63), 7.139 (2.88), 7.143 (3.02), 7.160 (4.73), 7.178 (2.35), 7.182 (2.30), 7.304 (5.04), 7.322 (4.71), 7.414 (1.99), 7.434 (5.79), 7.446 (4.98), 7.464 (7.53), 7.484 (3.74), 7.508 (4.98), 7.511 (9.38), 7.515 (6.42), 7.530 (7.11), 7.553 (3.24), 7.632 (8.14), 7.636 (4.76), 7.667 (5.87), 7.684 (4.76), 7.756 (1.49), 8.133 (6.12), 8.233 (1.00), 8.312 (4.40), 8.333 (4.21), 8.424 (15.67), 8.963 (3.43), 8.983 (3.35), 12.706 (0.72). |
| 230 | | LC-MS (Method L6): Rt = 1.93 min; MS (ESIpos): m/z = 532 [M + H]+ | $^1$H-NMR (400 MHz, DMSO-d6) δ [ppm]: 2.039 (0.49), 2.074 (0.74), 2.206 (0.68), 2.217 (0.65), 2.228 (0.62), 3.247 (0.58), 3.279 (4.26), 3.291 (4.54), 3.861 (3.48), 3.872 (5.83), 3.883 (3.38), 3.919 (16.00), 4.240 (1.05), 4.247 (0.85), 4.261 (1.44), 4.288 (0.95), 5.239 (0.43), 5.254 (1.04), 5.273 (1.05), 5.287 (0.48), 5.754 (5.28), 6.783 (2.11), 6.803 (2.33), 6.907 (0.98), 6.926 (2.11), 6.945 (1.22), 7.152 (1.05), 7.172 (2.27), 7.192 (1.76), 7.202 (1.25), 7.220 (1.17), 7.288 (1.26), 7.305 (1.27), 7.318 (1.25), 7.334 (1.22), 7.367 (1.77), 7.386 (1.63), 7.661 (0.93), 7.680 (2.04), 7.700 (1.95), 7.722 (2.44), 7.738 (1.14), 8.258 (1.70), 8.276 (1.55), 8.620 (6.28), 9.153 (1.82), 9.173 (1.77). |
| 231 | | LC-MS (Method L6): Rt = 2.25 min; MS (ESIpos): m/z = 532 [M + H]+ | $^1$H-NMR (400 MHz, DMSO-d6) δ [ppm]: 2.072 (0.90), 2.204 (0.83), 2.327 (0.69), 2.366 (0.42), 2.408 (16.00) 2.670 (0.67), 3.282 (5.02), 3.294 (5.70), 3.862 (3.95), 3.873 (6.80), 3.885 (3.85), 4.237 (1.27), 4.259 (1.58), 4.285 (1.15), 5.249 (1.24), 5.268 (1.26), 6.783 (2.54), 6.803 (2.69), 6.906 (1.22), 6.924 (2.41), 6.941 (1.48), 7.147 (1.32), 7.169 (1.98), 7.186 (1.00), 7.326 (2.64), 7.352 (2.75), 7.365 (2.13), 7.381 (1.93), 7.448 (3.44), 7.465 (3.40), 7.674 (1.50), 7.692 (2.59), 7.713 (2.56), 7.743 (2.91), 7.757 (1.61), 8.273 (2.14), 8.277 (2.20), 8.294 (2.00), 8.612 (8.94), 9.154 (2.17), 9.175 (2.13). |
| 232 | | LC-MS (Method L6): Rt = 1.90 min; MS (ESIpos): m/z = 532 | $^1$H-NMR (400 MHz, DMSO-d6) δ [ppm]: 2.033 (0.68), 2.041 (0.74), 2.052 (0.79), 2.068 (1.07), 2.075 (0.94), 2.189 (0.70), 2.201 (0.97), 2.213 (0.96), 2.222 (0.91), 2.235 (0.63), 2.327 (0.60), 2.366 (0.45), 2.669 (0.68), 2.709 (0.48), 3.254 (0.88), 3.273 (2.55), 3.286 (5.77), 3.588 (15.32), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | 3.591 (16.00), 3.864 (4.82), 3.875 (8.30), 3.886 (4.64), 4.213 (0.57), 4.234 (1.64), 4.241 (1.30), 4.261 (2.03), 4.269 (1.72), 4.276 (1.38), 4.285 (1.39), 4.304 (0.57), 5.232 (0.65), 5.246 (1.48), 5.265 (1.51), 5.279 (0.66), 6.782 (2.77), 6.802 (3.06), 6.901 (1.38), 6.919 (2.88), 6.936 (1.69), 7.032 (0.93), 7.037 (0.97), 7.048 (1.14), 7.053 (2.04), 7.059 (1.39), 7.069 (1.33), 7.075 (1.25), 7.145 (1.39), 7.149 (1.51), 7.167 (2.40), 7.184 (2.10), 7.204 (1.50), 7.227 (1.53), 7.249 (0.88), 7.354 (2.50), 7.372 (2.32), 7.637 (0.62), 7.643 (1.31), 7.655 (4.76), 7.659 (6.97), 7.678 (3.56), 7.695 (1.24), 8.249 (2.35), 8.255 (2.38), 8.269 (2.16), 8.274 (2.15), 8.597 (9.66), 9.143 (2.61), 9.163 (2.55). |
| 233 | | LC-MS (Method L2): Rt = 4.22 min; m/z = 602 (Cl2 pattern) [M + H]+ | $^1$H-NMR (400 MHz, DMSO-d6) δ 9.20 (d, J = 8.1 Hz, 1H), 8.71 (s, 1H), 8.46 (d, J = 8.9 Hz, 1H), 7.98 (d, J = 9.1 Hz, 1H), 7.70 (t, J = 1.9 Hz, 1H), 7.40-7.30 (m, 3H), 7.20-7.13 (m, 1H), 6.95-6.88 (m, 1H), 6.82-6.76 (m, 1H), 5.28-5.20 (m, 1H), 4.32 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 234 | | LC-MS (Method L1): Rt = 1.10 min; MS (ESIpos): m/z = 502 [M + H]+ | $^1$H-NMR (400 MHz, DMSO-d6) δ [ppm]: −0.149 (0.59), −0.008 (5.31), 0.008 (4.81), 0.146 (0.56), 2.049 (1.06), 2.057 (1.15), 2.069 (1.17), 2.084 (1.68), 2.091 (1.48), 2.198 (1.12), 2.211 (1.57), 2.223 (1.45), 2.233 (1.45), 2.246 (0.95), 2.327 (1.17), 2.366 (1.12), 2.523 (3.97), 2.669 (1.34), 2.710 (1.17), 3.249 (1.26), 3.268 (4.20), 3.280 (9.93), 3.291 (10.83), 3.651 (1.90), 3.865 (7.83), 3.876 (13.26), 3.887 (7.52), 4.225 (0.87), 4.245 (2.52), 4.253 (1.99), 4.267 (3.33), 4.293 (2.21), 4.312 (0.81), 5.245 (1.03), 5.259 (2.35), 5.279 (2.38), 5.293 (1.06), 6.789 (4.36), 6.809 (4.90), 6.917 (2.18), 6.933 (4.64), 6.951 (2.80), 7.154 (2.49), 7.157 (2.57), 7.175 (4.00), 7.193 (1.99), 7.247 (1.76), 7.253 (1.29), 7.265 (1.59), 7.271 (3.41), 7.277 (2.49), 7.294 (1.87), 7.300 (1.45), 7.319 (4.84), 7.324 (5.48), 7.340 (6.01), 7.356 (1.23), 7.377 (4.17), 7.396 (3.86), 7.681 (3.13), 7.700 (4.62), 7.720 (4.20), 7.827 (4.95), 7.831 (5.20), 7.845 (4.06), 7.848 (3.92), 8.273 (4.31), 8.276 (4.39), 8.295 (4.11), 8.693 (16.00), 9.165 (4.20), 9.185 (4.11). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 235 | | LC-MS (Method L1): Rt = 1.29 min; MS (ESIpos): m/z = 568 [M + H]+ | $^1$H-NMR (400 MHz, DMSO-d6) δ [ppm]: 2.091 (2.67), 2.220 (2.73), 2.327 (2.60), 2.367 (5.33), 2.668 (4.62), 2.710 (5.79), 3.882 (16.00), 4.244 (3.32), 4.266 (4.62), 5.255 (3.12), 6.789 (4.36), 6.809 (4.81), 6.915 (2.34), 6.934 (4.75), 6.952 (2.73), 7.155 (2.80), 7.174 (4.29), 7.195 (2.15), 7.381 (4.62), 7.399 (4.16), 7.706 (2.47), 7.724 (4.62), 7.743 (2.99), 7.886 (7.28), 7.903 (12.75), 7.985 (7.15), 8.302 (4.75), 8.323 (4.36), 8.693 (9.95), 9.174 (4.29), 9.194 (4.10). |
| 236 | | LC-MS (Method L6): Rt = 1.38 min; MS (ESIpos): m/z = 462 [M + H]+ | $^1$H-NMR (400 MHz, DMSO-d6) δ [ppm]: −0.008 (2.92), 0.008 (2.76), 1.236 (1.50), 1.259 (1.23), 1.299 (0.85), 1.983 (0.59), 1.996 (1.10), 2.008 (1.36), 2.016 (1.23), 2.030 (2.09), 2.044 (1.95), 2.057 (0.80), 2.118 (0.75), 2.132 (2.09), 2.146 (2.34), 2.161 (1.32), 2.181 (1.28), 2.195 (0.53), 2.300 (1.82), 2.327 (0.64), 2.366 (0.61), 2.523 (2.31), 2.669 (0.73), 2.709 (0.69), 3.057 (12.33), 3.070 (12.39), (12.39), 3.341 (0.78), 3.370 (0.41), 3.382 (0.48), 3.874 (0.57), 4.237 (4.47), 4.249 (7.39), 4.264 (4.32), 4.482 (1.02), 4.497 (1.07), 4.858 (10.93), 5.146 (0.64), 5.206 (1.12), 5.221 (2.49), 5.240 (2.47), 5.255 (1.12), 5.359 (0.43), 6.772 (4.55), 6.793 (4.96), 6.878 (2.39), 6.880 (2.39), 6.896 (4.95), 6.899 (4.90), 6.915 (2.97), 6.917 (2.87), 7.132 (2.42), 7.135 (2.57), 7.153 (4.02), 7.170 (2.01), 7.174 (1.96), 7.232 (0.48), 7.250 (0.41), 7.274 (1.85), 7.293 (8.65), 7.312 (7.85), 7.327 (1.21), 7.333 (1.21), 7.345 (3.29), 7.355 (13.29), 7.365 (4.96), 7.376 (1.77), 7.527 (1.53), 7.545 (2.97), 7.566 (2.27), 7.591 (1.64), 7.608 (2.84), 7.629 (4.71), 7.647 (2.65), 7.765 (1.79), 8.133 (0.54), 8.367 (16.00), 8.391 (3.06), 8.958 (2.52), 8.979 (2.52), 10.023 (0.51), 11.746 (5.38). |
| 237 | | LC-MS (Method L6): Rt = 1.57 min; MS (ESIpos): m/z = 512 [M + H]+ | $^1$H-NMR (400 MHz, DMSO-d6) δ [ppm]: −0.150 (0.77), 0.146 (0.83), 0.853 (0.66), 1.235 (5.81), 1.259 (3.13), 1.298 (2.19), 1.985 (1.63), 1.998 (1.98), 2.019 (2.99), 2.035 (2.68), 2.126 (2.85), 2.140 (3.27), 2.159 (2.19), 2.175 (1.95), 2.327 (1.98), 2.366 (1.29), 2.669 (2.37), 2.710 (1.57), 3.051 (15.79), 3.061 (16.00), 3.370 (1.57), 3.382 (1.70), 3.395 (1.15), 3.413 (0.73), 3.508 (0.97), 3.520 (1.18), 3.534 (0.94), 3.561 (1.11), 3.574 (1.22), 4.233 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (6.02), 4.245 (10.37), 4.259 (6.33), 4.482 (2.37), 4.496 (2.33), 4.858 (9.39), 5.131 (0.66), 5.146 (1.29), 5.160 (0.63), 5.198 (1.74), 5.213 (3.69), 5.233 (3.76), 5.247 (1.77), 5.359 (1.22), 6.768 (7.10), 6.788 (7.93), 6.874 (3.27), 6.893 (7.03), 6.911 (4.24), 7.132 (3.58), 7.150 (5.95), 7.171 (2.85), 7.219 (0.56), 7.286 (6.26), 7.307 (11.55), 7.320 (3.51), 7.355 (11.93), 7.365 (3.90), 7.393 (4.45), 7.398 (4.56), 7.418 (4.73), 7.424 (4.42), 7.460 (0.94), 7.518 (4.42), 7.536 (7.55), 7.556 (7.23), 7.585 (8.59), 7.601 (5.11), 7.614 (3.20), 7.634 (2.19), 7.706 (1.01), 7.724 (1.50), 7.774 (2.57), 7.871 (11.10), 7.877 (10.96), 7.910 (2.57), 7.927 (2.23), 7.954 (0.59), 8.022 (0.70), 8.139 (1.18), 8.340 (15.06), 8.374 (5.91), 8.394 (5.57), 8.427 (0.73), 8.946 (4.28), 8.967 (4.28), 10.022 (3.72), 11.746 (4.21). |
| 238 | | LC-MS (Method L1): Rt = 1.05 min; MS (ESIpos): m/z = 518 [M + H]+ | $^1$H-NMR (400 MHz, DMSO-d6) δ [ppm]: −0.008 (0.56), 0.008 (0.52), 2.523 (0.53), 3.277 (0.80), 3.290 (1.68), 3.310 (16.00), 3.333 (0.41), 3.867 (1.46), 3.877 (2.48), 3.889 (1.37), 4.232 (0.50), 4.253 (0.68), 4.264 (0.64), 4.271 (0.44), 4.280 (0.43), 5.241 (0.43), 5.260 (0.43), 6.777 (0.84), 6.798 (0.93), 6.912 (0.84), 6.930 (0.49), 7.141 (0.44), 7.145 (0.46), 7.162 (0.73), 7.354 (0.77), 7.371 (0.72), 7.447 (0.89), 7.456 (1.29), 7.468 (0.84), 7.475 (0.99), 7.668 (0.48), 7.680 (1.31), 7.685 (1.24), 7.690 (1.31), 7.709 (1.11), 7.727 (0.46), 8.286 (0.80), 8.291 (0.82), 8.306 (0.74), 8.311 (0.72), 8.589 (2.41), 9.154 (0.41). |
| 239 | | LC-MS (Method L1): Rt = 1.18 min; MS (ESIpos): m/z = 532 [M + H]+ | $^1$H-NMR (400 MHz, DMSO-d6) δ [ppm]: 2.278 (3.88), 3.284 (1.78), 3.297 (2.06), 3.310 (16.00), 3.875 (2.72), 4.236 (0.51), 4.258 (0.65), 4.285 (0.46), 5.248 (0.49), 5.267 (0.50), 6.782 (0.98), 6.801 (1.08), 6.902 (0.49), 6.921 (0.99), 6.939 (0.59), 7.150 (0.51), 7.168 (0.80), 7.186 (0.41), 7.264 (0.62), 7.271 (0.72), 7.279 (0.66), 7.286 (0.65), 7.367 (0.86), 7.385 (0.82), 7.442 (0.63), 7.452 (0.65), 7.673 (0.52), 7.691 (1.06), 7.711 (1.07), 7.732 (1.23), 7.746 (0.57), 8.279 (0.87), 8.299 (0.80), 8.624 (3.45), 9.154 (0.86), 9.175 (0.85). |
| 240 | | LC-MS (Method L1): Rt = 1.19 min; | $^1$H-NMR (400 MHz, DMSO-d6) δ [ppm]: −0.008 (0.50), 0.008 (0.44), 2.345 (4.63), 3.275 (0.72), 3.287 (1.65), 3.299 (1.87), 3.310 (16.00), 3.865 (1.37), 3.876 (2.36), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | MS (ESIpos): m/z = 532 [M + H]+ | 3.888 (1.31), 4.237 (0.45), 4.259 (0.60), 4.269 (0.56), 5.249 (0.43), 5.268 (0.43), 6.782 (0.83), 6.803 (0.90), 6.924 (0.83), 6.941 (0.49), 7.147 (0.41), 7.150 (0.43), 7.167 (0.71), 7.184 (0.80), 7.192 (0.61), 7.198 (0.56), 7.367 (0.70), 7.385 (0.66), 7.447 (0.53), 7.451 (0.52), 7.463 (0.55), 7.682 (0.43), 7.700 (0.93), 7.720 (1.01), 7.731 (1.02), 7.735 (1.15), 7.748 (0.49), 8.284 (0.71), 8.288 (0.72), 8.305 (0.69), 8.309 (0.65), 8.626 (3.04), 9.154 (0.75), 9.175 (0.74). |
| 241 | | LC-MS (Method L1): Rt = 1.38 min; MS (ESIpos): m/z = 602 [M + H]+ | $^1$H-NMR (400 MHz, DMSO-d6) δ [ppm]: 1.219 (16.00), 1.414 (0.57), 1.908 (0.65), 1.924 (0.64), 1.941 (0.52), 1.959 (0.45), 2.501 (12.69), 2.889 (0.42), 3.164 (0.96), 3.174 (0.90), 5.530 (0.45), 5.549 (0.44), 7.233 (0.64), 7.241 (0.67), 7.250 (1.06), 7.271 (0.78), 7.448 (0.44), 7.456 (0.48), 7.469 (0.40), 7.639 (5.38), 7.652 (0.69), 7.672 (0.56), 7.809 (0.75), 7.826 (0.60), 8.314 (0.64), 8.335 (0.58), 8.687 (2.17), 9.077 (0.63), 9.097 (0.60). |
| 242 | | LC-MS (Method L6): Rt = 1.39 min; MS (ESIpos): m/z = 618 [M + H]+ | $^1$H-NMR (400 MHz, DMSO-d6) δ [ppm]: 1.198 (16.00), 1.918 (0.63), 1.932 (0.85), 1.945 (0.51), 4.260 (0.44), 6.788 (0.61), 6.808 (0.69), 6.939 (0.64), 7.186 (0.52), 7.394 (0.55), 7.412 (0.51), 7.638 (5.73), 7.656 (0.62), 7.676 (0.53), 7.815 (0.70), 7.832 (0.56), 8.315 (0.60), 8.334 (0.55), 8.684 (2.06), 9.236 (0.58), 9.257 (0.57). |
| 243 | | LC-MS (Method L6): Rt = 2.63 min; MS (ESIpos): m/z = 618 [M + H]+ | $^1$H-NMR (400 MHz, DMSO-d6) δ [ppm]: −0.008 (0.59), 0.008 (0.57), 1.194 (16.00), 1.209 (0.55), 2.041 (0.61), 2.056 (0.60), 2.067 (0.49), 2.086 (0.43), 4.279 (0.48), 4.293 (0.85), 4.305 (0.52), 6.785 (0.57), 6.804 (0.64), 6.881 (0.61), 7.163 (0.49), 7.292 (0.52), 7.310 (0.49), 7.643 (3.60), 7.659 (0.61), 7.680 (0.50), 7.819 (0.64), 7.834 (0.53), 8.352 (0.56), 8.371 (0.52), 8.689 (2.03), 9.172 (0.56), 9.192 (0.54). |
| 244 | | LC-MS (Method L6): Rt = 1.27 min; MS (ESIpos): m/z = 498 [M + H]+ | $^1$H-NMR (400 MHz, DMSO-d6) δ [ppm]: −0.008 (2.63), 0.008 (2.13), 1.862 (1.03), 1.885 (0.89), 1.898 (0.91), 2.002 (0.76), 2.023 (1.37), 2.034 (1.59), 2.054 (1.51), 2.156 (0.85), 2.170 (1.04), 2.185 (0.86), 2.201 (0.61), 2.311 (0.43), 2.327 (0.46), 2.376 (16.00), 2.392 (2.37), 2.669 (0.43), 3.033 (0.41), 3.192 (0.48), 3.205 (0.71), 3.213 (0.64), 3.228 (0.83), 3.305 (2.36), 3.461 (0.98), 3.489 (1.75), 3.516 (0.92), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.691 (0.53), 3.707 (1.16), 3.728 (0.79), 3.788 (0.70), 3.805 (0.71), 3.821 (0.86), 3.831 (1.06), 3.844 (1.78), 3.857 (1.54), 3.871 (1.20), 3.883 (0.74), 4.163 (3.03), 4.258 (2.73), 4.266 (3.03), 4.279 (1.47), 4.374 (1.56), 5.215 (0.85), 5.227 (1.09), 5.247 (0.91), 5.260 (0.41), 6.780 (2.43), 6.799 (2.76), 6.891 (1.22), 6.910 (2.68), 6.928 (1.78), 7.014 (1.49), 7.038 (1.51), 7.144 (1.33), 7.162 (2.39), 7.179 (2.31), 7.205 (5.13), 7.253 (0.67), 7.305 (2.22), 7.324 (2.00), 7.450 (1.52), 7.469 (2.29), 7.489 (1.84), 7.638 (2.80), 7.653 (2.35), 8.144 (10.55), 8.227 (2.36), 8.248 (2.20), 8.418 (4.54), 8.423 (4.98), 8.786 (1.00), 9.041 (1.92), 9.061 (1.88). |
| 245 | | LC-MS (Method L6): Rt = 1.24 min; MS (ESIpos): m/z = 532 [M + H]+ | $^1$H-NMR (400 MHz, DMSO-d6) δ [ppm]: −0.149 (0.77), −0.008 (6.72), 0.008 (6.90), 0.146 (0.79), 1.055 (0.79), 1.862 (1.68), 1.885 (1.70), 1.895 (1.97), 2.006 (1.70), 2.027 (2.95), 2.040 (3.20), 2.060 (1.95), 2.072 (1.32), 2.085 (1.63), 2.145 (1.45), 2.159 (1.57), 2.175 (1.52), 2.327 (1.52), 2.365 (1.04), 2.669 (1.41), 2.709 (0.77), 2.976 (0.89), 3.005 (1.41), 3.073 (1.32), 3.083 (1.34), 3.113 (0.93), 3.164 (2.00), 3.177 (2.34), 3.187 (2.36), 3.200 (2.22), 3.304 (2.68), 3.466 (1.97), 3.496 (2.86), 3.524 (1.75), 3.695 (1.16), 3.719 (1.95), 3.737 (1.34), 3.788 (0.68), 3.810 (1.16), 3.828 (1.48), 3.848 (2.50), 3.864 (2.18), 3.874 (3.20), 3.889 (1.95), 3.900 (1.23), 3.937 (0.43), 4.163 (11.73), 4.255 (5.47), 4.374 (2.88), 5.226 (1.84), 5.266 (0.59), 6.772 (4.31), 6.791 (5.17), 6.809 (1.38), 6.879 (2.04), 6.899 (4.70), 6.916 (3.56), 6.935 (0.70), 7.016 (1.41), 7.032 (2.79), 7.048 (1.86), 7.084 (0.86), 7.105 (0.68), 7.137 (2.31), 7.156 (4.45), 7.177 (3.63), 7.204 (2.20), 7.225 (1.41), 7.242 (0.68), 7.287 (3.50), 7.306 (3.22), 7.342 (0.93), 7.359 (0.98), 7.448 (2.31), 7.466 (3.93), 7.487 (3.79), 7.526 (5.13), 7.541 (3.06), 7.688 (1.57), 7.696 (1.68), 7.705 (3.70), 8.204 (16.00), 8.276 (4.47), 8.297 (3.47), 8.360 (10.80), 8.716 (4.06), 9.014 (1.95), 9.027 (2.34), 9.035 (2.07), 9.047 (1.97), 9.155 (0.86), 9.176 (0.79). |
| 246 | | LC-MS (Method L6): Rt = 1.21 min; | $^1$H-NMR (400 MHz, DMSO-d6) δ [ppm]: −0.008 (1.15), 0.008 (1.23), 1.862 (0.77), 1.876 (0.55), 1.888 (0.61), 1.900 (0.68), 1.908 (0.60), 1.997 (0.55), 2.020 (0.91), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | MS (ESIpos): m/z = 532 [M + H]+ | 2.030 (1.23), 2.039 (0.98), 2.049 (0.99), 2.061 (0.58), 2.150 (0.56), 2.165 (0.68), 2.180 (0.59), 2.195 (0.42), 2.523 (0.68), 3.169 (1.12), 3207 (0.44), 3.230 (0.51), 3.305 (0.99), 3.471 (0.58), 3.498 (1.19), 3.525 (0.73), 3.655 (0.44), 3.699 (0.41), 3.723 (0.82), 3.736 (0.56), 3.743 (0.59), 3.803 (0.57), 3.820 (0.55), 3.828 (0.57), 3.835 (0.56), 3.846 (1.52), 3.858 (1.38), 3.873 (0.89), 3.885 (1.01), 3.896 (0.64), 3.911 (16.00), 3.924 (2.42), 4.160 (2.23), 4.247 (1.69), 4.253 (2.01), 4.259 (1.98), 4.374 (1.08), 5.210 (0.63), 5.219 (0.73), 5.231 (0.77), 5.240 (0.56), 6.776 (1.78), 6.794 (1.90), 6.796 (1.93), 6.886 (0.87), 6.904 (1.89), 6.923 (1.25), 7.140 (1.08), 7.148 (1.24), 7.158 (1.75), 7.166 (1.29), 7.175 (1.95), 7.194 (1.17), 7.263 (1.08), 7.280 (1.12), 7.294 (2.16), 7.311 (1.67), 7.451 (1.14), 7.469 (1.65), 7.490 (1.47), 7.599 (1.95), 7.615 (1.51), 8.140 (6.92), 8.264 (1.70), 8.276 (0.41), 8.286 (1.58), 8.370 (4.09), 8.372 (3.69), 8.738 (0.72), 9.025 (1.07), 9.032 (0.96), 9.046 (1.07), 9.053 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 247 | | LC-MS (Method L6): Rt = 1.82 min; MS (ESIpos): m/z = 478 [M + H]+ | $^1$H-NMR (400 MHz, DMSO-d6) δ [ppm]: −0.008 (1.77), 0.008 (1.62), 1.754 (1.10), 3.086 (16.00), 4.249 (0.89), 4.257 (0.88), 5.230 (0.54), 6.777 (1.07), 6.797 (1.20), 6.890 (0.49), 6.908 (1.04), 6.926 (0.63), 7.143 (0.51), 7.160 (0.85), 7.178 (0.42), 7.339 (0.86), 7.357 (0.83), 7.586 (0.46), 7.600 (0.44), 7.669 (0.76), 7.686 (1.09), 7.708 (1.03), 7.788 (1.10), 7.803 (0.82), 8.233 (0.62), 8.303 (1.02), 8.321 (1.02), 8.550 (2.65), 9.066 (0.59), 9.088 (0.56). |
| 248 | 3.41 | | $^1$H-NMR (399, 9532 MHz, DMSO): δ = 8.8586 (3.81); 8.8384 (3.7); 8.7959 (0.89); 8.6133 (16); 8.3145 (0.54); 8.2003 (5.17); 8.1796 (6.09); 8.1605 (0.57); 8.1408 (0.42); 8.1194 (0.37); 7.7297 (2.81); 7.7117 (6.49); 7.6916 (5.56); 7.674 (8.15); 7.6572 (3.78); 7.5658 (3.63); 7.5485 (5.05); 7.5233 (0.53); 7.4659 (2.08); 7.4474 (5.9); 7.4352 (6.58); 7.4201 (10.6); 7.401 (7.64); 7.3696 (4.28); 7.1855 (0.44); 7.1677 (2.86); 7.1479 (5.7); 7.1292 (3.51); 6.9273 (3.58); 6.9086 (6.16); 6.8902 (3.03); 6.7978 (0.51); 6.7802 (7.27); 6.76 (6.4); 5.3045 (0.38); 5.2303 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.66); 5.215 (3.56); 5.1967 (3.61); 5.1821 (1.57); 4.2872 (1.16); 4.2678 (3.46); 4.2545 (6.45); 4.2294 (3.77); 4.209 (1.09); 4.0558 (0.79); 4.0381 (2.17); 4.0204 (2.21); 4.0027 (0.72); 3.7036 (0.64); 3.4987 (41.77); 3.4769 (2.9); 3.3203 (34.08); 3.2937 (39.4); 32522 (2.31); 2.6698 (1.63); 2.5008 (284.9); 2.3275 (1.72); 2.162 (2.06); 2.1511 (2.35); 2.1408 (2.37); 2.0491 (2.34); 2.0417 (2.67); 2.0242 (2.02); 2.0072 (1.6); 1.9885 (9.27); 1.2351 (0.38); 1.1928 (2.3); 1.175 (4.51); 1.1572 (2.22); −0.0001 (28.96); −0.0051 (8.21) |
| 249 | 3.99 | | $^1$H-NMR (399, 9532 MHz, DMSO): δ = 8.8722 (2.6); 8.8534 (4.17); 8.8356 (2.45); 8.6283 (16); 8.3151 (0.4); 8.2158 (4.05); 8.1962 (4.44); 7.7428 (2.44); 7.7248 (7.39); 7.7193 (7); 7.7157 (6.57); 7.7049 (13.43); 7.6994 (14.58); 7.6871 (2.66); 7.4723 (2.01); 7.4623 (2.04); 7.453 (4.25); 7.4429 (3.96); 7.4331 (2.87); 7.4227 (5.23); 7.3996 (4.11); 7.3619 (3.39); 7.3461 (5.37); 7.3279 (2.31); 7.1671 (2.41); 7.1484 (5.12); 7.1288 (3.22); 6.9268 (2.74); 6.9082 (4.77); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.8896 (2.27); 6.7797 (6.81); 6.7595 (6.15); 5.2265 (1.31); 5.2117 (3.11); 5.1938 (3.02); 5.1779 (1.3); 4.2866 (1.01); 4.2674 (3.19); 4.2527 (5.74); 4.245 (5.26); 4.2269 (3.27); 4.2067 (0.94); 4.0557 (0.4); 4.0377 (1.21); 4.0198 (1.19); 4.0022 (0.41); 3.4991 (33.03); 3.3194 (26.59); 3.2941 (42.87); 2.6699 (1.31); 2.6325 (1.42); 2.5047 (173.21); 2.5007 (220.51); 2.4968 (169.05); 2.3277 (1.28); 2.1552 (1.78); 2.1467 (1.98); 2.1354 (1.9); 2.0536 (1.58); 2.0461 (2.06); 2.0382 (2.41); 2.0293 (1.73); 2.0221 (1.72); 2.0124 (1.48); 2.0033 (1.41); 1.9882 (5.54); 1.3973 (0.39); 1.1925 (1.29); 1.1746 (2.48); 1.1569 (1.25); −0.0002 (29.01) |
| 250 | 4.87 | | $^1$H-NMR (399, 9532 MHz, DMSO): δ = 8.8638 (2.16); 8.8431 (2.2); 8.7403 (8.57); 8.3148 (0.35); 8.2096 (2.24); 8.2067 (2.37); 8.1883 (2.63); 8.1855 (2.59); 7.8776 (2.13); 7.8749 (2.29); 7.8598 (2.88); 7.8571 (2.85); 7.7436 (2.21); 7.7227 (2.59); 7.7045 (1.68); 7.6508 (16); 7.4465 (2.08); 7.4284 (2.26); 7.181 (0.97); 7.1773 (1.02); 7.16 (2.16); 7.1425 (1.33); 7.1389 (1.31); 6.9459 (1.54); 6.9275 (2.62); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.9086 (1.24); 6.7901 (2.91); 6.7708 (2.62); 5.246 (0.57); 5.2307 (1.34); 5.2111 (1.31); 5.1962 (0.59); 4.2989 (0.4); 4.2923 (0.34); 4.2803 (1.25); 4.2648 (2.35); 4.2564 (2.18); 4.2462 (1.28); 4.238 (1.35); 4.2183 (0.41); 3.4928 (21.15); 3.3195 (28.27); 3.2832 (18.37); 2.6707 (0.76); 2.5055 (99.44); 2.5013 (134.25); 2.4971 (103.62); 2.3283 (0.8); 2.1902 (0.48); 2.1778 (0.73); 2.169 (0.84); 2.1575 (0.88); 2.1451 (0.68); 2.0765 (0.62); 2.0678 (0.83); 2.0606 (0.98); 2.0512 (0.71); 2.0439 (0.7); 2.034 (0.6); 2.0254 (0.58); 1.3977 (0.96); −0.0002 (18.38) |
| 251 | | LC-MS (Method L4): Rt = 2.76 min; MS (ESIpos): m/z = 523 [M + H]+ | $^1$H-NMR (500 MHz, DMSO-d6) δ [ppm]: 0.832 (0.78), 0.872 (0.63), 1.225 (1.56), 1.239 (2.99), 1.254 (2.68), 1.285 (0.49), 2.012 (5.28), 2.125 (0.61), 2.136 (1.21), 2.143 (1.50), 2.153 (1.46), 2.162 (2.19), 2.172 (2.02), 2.181 (0.79), 2.253 (0.83), 2.265 (1.86), 2.277 (2.20), 2.290 (1.59), 2.306 (1.15), 2.317 (0.53), 3.149 (1.15), 3.179 (10.27), 3.371 (1.35), 3.379 (2.47), 3.394 (3.63), 3.403 (5.57), 3.412 (3.40), 3.423 (3.54), 3.431 (5.99), 3.440 (3.84), 3.456 (2.58), 3.465 (1.35), 3.947 (9.47), 3.955 (15.45), 3.964 (8.40), 4.057 (0.45), 4.071 (1.28), 4.086 (1.30), 4.100 (0.49), 4.278 (4.64), 4.288 (6.97), 4.294 (4.07), 4.299 (4.02), 5.328 (1.19), 5.339 (2.69), 5.354 (2.69), 5.365 (1.19), 5.443 (0.90), 5.448 (1.32), 6.779 (4.78), 6.796 (5.27), 6.863 (2.26), 6.878 (4.67), 6.893 (2.69), 7.124 (2.45), 7.139 (3.94), 7.154 (2.07), 7.309 (4.10), 7.324 (3.86), 7.506 (4.42), 7.520 (5.68), 7.613 (3.66), 7.628 (5.26), 7.644 (3.03), 7.658 (2.51), 7.672 (4.37), 7.689 (3.02), 7.811 (6.72), 7.814 (7.13), 7.818 (4.61), 7.821 (6.00), 7.825 (7.74), 7.828 (6.36), 7.831 (5.94), 8.107 (5.62), 8.123 (5.32), 8.315 (4.53), 8.332 (4.30), 8.604 (16.00), 9.065 (6.90), 9.103 (2.34), 9.118 (2.15). |
| 252 | 2.23 | | $^1$H-NMR (399, 9532 MHz, DMSO): δ = 9.0791 (1.76); 9.0587 (1.8); 8.5559 (7.36); 8.1993 (1.5); 8.1925 (1.41); 8.1814 (1.62); 8.1744 (1.67); 7.6235 (0.75); 7.6058 (2.84); 7.5938 (3.05); 7.5875 (6.22); 7.5767 (0.85); 7.5518 (1.11); 7.5301 (1.53); 7.4508 (0.54); 7.4455 (0.73); 7.4326 (1.69); 7.4272 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.02); 7.4216 (1.16); 7.4156 (2.28); 7.4084 (1.97); 7.4032 (1.72); 7.3998 (1.7); 7.385 (0.7); 7.3589 (1.41); 7.3368 (1.88); 7.3173 (1.39); 7.1739 (0.83); 7.1704 (0.86); 7.1527 (1.79); 7.1353 (1.12); 7.1318 (1.06); 6.9096 (1.27); 6.8915 (2.21); 6.8728 (1.02); 6.7927 (2.53); 6.7726 (2.28); 5.7542 (1.11); 5.2613 (0.49); 5.2466 (1.08); 5.2274 (1.08); 5.213 (0.48); 4.2679 (1.84); 4.2559 (3.15); 4.2415 (1.82); 3.3206 (48.83); 3.1342 (16); 3.0049 (0.62); 2.9974 (0.88); 2.9893 (1.13); 2.981 (0.87); 2.9732 (0.63); 2.9642 (0.34); 2.675 (0.38); 2.6705 (0.51); 2.6658 (0.38); 2.5232 (1.39); 2.5055 (63.06); 2.5011 (86.29); 2.4969 (64.79); 2.3323 (0.36); 2.3281 (0.5); 2.1894 (0.6); 2.1757 (0.69); 2.1696 (0.51); 2.156 (0.74); 2.1399 (0.74); 2.0304 (0.61); 2.0184 (0.69); 1.9969 (0.54); 1.9883 (0.86); 1.3979 (1.47); 0.6101 (1.75); 0.4165 (0.89); 0.0078 (0.39); −0.0001 (10.71); −0.0076 (0.41) |
| 253 | 2.8 | | $^1$H-NMR (399, 9532 MHz, DMSO): δ = 9.0796 (1.17); 9.0621 (1.2); 8.5624 (8.02); 8.2214 (0.93); 8.2105 (1.57); 8.1983 (1.03); 7.6978 (2.04); 7.694 (2.19); 7.6778 (2.53); 7.674 (2.5); 7.6177 (5.4); 7.6041 (4.04); 7.4523 (0.69); 7.4433 (0.72); 7.4327 (1.48); 7.4239 (1.42); 7.4131 (0.92); 7.4041 (0.85); 7.3455 (1.88); 7.329 (3.1); 7.3099 (1.5); 7.174 (0.81); 7.1702 (0.85); 7.1526 (1.69); 7.1353 (1.08); 7.1317 (1.05); 6.9092 (1.19); 6.8909 (2.03); 6.8721 (0.94); 6.793 (2.33); 6.791 (2.35); 6.7726 (2.13); 6.7706 (2.07); 5.2566 (0.41); 5.242 (0.94); 5.2229 (0.94); 5.2089 (0.4); 4.2665 (1.65); 4.2545 (2.8); 4.2402 (1.64); 3.3211 (41.34); 3.1368 (16); 3.0138 (0.45); 3.0047 (0.7); 2.9975 (0.96); 2.9893 (0.98); 2.9811 (0.72); 2.9735 (0.43); 2.6703 (0.39); 2.5235 (1.05); 2.51 (22.39); 2.5056 (47.11); 2.501 (65.73); 2.4966 (49.19); 2.4922 (23.62); 2.3279 (0.38); 2.1883 (0.57); 2.1742 (0.65); 2.1681 (0.49); 2.1546 (0.71); 2.1385 (0.72); 2.0349 (0.45); 2.0228 (0.65); 2.0115 (0.58); 2.0017 (0.49); 1.9882 (1.44); 1.9759 (0.32); 1.3975 (1.3); 1.175 (0.52); 0.6137 (1.77); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 0.5976 (1.39); 0.4649 (0.32); 0.4414 (0.56); 0.4091 (1.27); 0.3695 (0.52); 0.0081 (0.44); −0.0002 (13.08); −0.0084 (0.42) |
| 254 | 3.81 | | $^1$H-NMR (399, 9532 MHz, DMSO): δ = 9.0974 (1.83); 9.0773 (1.86); 8.6752 (7.71); 8.3134 (0.64); 8.2118 (1.85); 8.2091 (1.97); 8.1907 (2.14); 8.1877 (2.13); 7.7947 (1.87); 7.7919 (1.98); 7.777 (2.41); 7.7741 (2.31); 7.6416 (5.47); 7.6376 (12.68); 7.632 (5.99); 7.6281 (3.45); 7.6155 (1.99); 7.6126 (2.16); 7.5945 (1.52); 7.3629 (1.74); 7.3442 (1.88); 7.1889 (0.84); 7.1854 (0.87); 7.1674 (1.81); 7.1502 (1.1); 7.147 (1.07); 6.9334 (1.31); 6.9152 (2.18); 6.8988 (1.01); 6.8964 (1.02); 6.8069 (2.45); 6.7867 (2.52); 5.2728 (0.51); 5.2582 (1.13); 5.2387 (1.12); 5.2248 (0.5); 4.281 (1.89); 4.2694 (3.1); 4.2546 (1.8); 3.3184 (46.33); 3.1217 (16); 3.0207 (0.68); 3.0129 (0.98); 3.0047 (1.28); 2.9963 (0.95); 2.9888 (0.68); 2.9802 (0.33); 2.6749 (0.85); 2.6706 (1.14); 2.6661 (0.85); 2.5101 (68.82); 2.5059 (137.4); 2.5014 (187.25); 2.4971 (140.59); 2.3327 (0.8); 2.3283 (1.08); 2.3241 (0.79); 2.2024 (0.56); 2.1881 (0.67); 2.1696 (0.74); 2.1535 (0.7); 2.0686 (0.34); 2.0557 (0.71); 2.0447 (0.85); 2.0308 (0.51); 2.0226 (0.61); 2.0084 (0.53); 1.398 (3.21); 0.6121 (2.33); 0.5962 (2.26); 0.4148 (1.1); 0.4089 (1.1); 0.3834 (1.16); 0.0079 (1.22); −0.0002 (28.51); −0.0084 (1.03) |
| 255 | | LC-MS (Method L1): Rt = 1.21 min; MS (ESIpos): m/z = 576 [M + H]+ | $^1$H-NMR (400 MHz, DMSO-d6) δ [ppm]: −0.149 (0.40), −0.008 (3.66), 0.008 (2.37), 1.938 (0.67), 2.015 (1.79), 2.073 (1.20), 2.179 (0.64), 2.328 (0.62), 2.366 (0.70), 2.385 (0.71), 2.669 (0.51), 3.356 (0.75), 3.498 (16.00), 3.893 (0.87), 3.915 (0.80), 4.216 (0.97), 4.238 (0.76), 4.267 (0.81), 4.625 (0.99), 4.640 (1.04), 4.659 (0.92), 5.267 (0.86), 6.791 (1.73), 6.810 (1.94), 6.925 (0.82), 6.941 (1.72), 6.959 (1.12), 7.168 (0.89), 7.185 (1.41), 7.202 (0.70), 7.394 (1.48), 7.411 (1.37), 7.645 (11.29), 7.673 (1.76), 7.694 (1.53), 7.820 (1.92), 7.838 (1.61), 8.342 (1.64), 8.361 (1.56), 8.671 (6.40), 9.188 (1.55), 9.208 (1.60). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 256 | | LC-MS (Method L2): Rt = 3.91 min; m/z = 560 [M + H]+ | $^1$H-NMR (400 MHz, DMSO-d6) δ 9.12 (d, J = 8.1 Hz, 1H), 8.62 (s, 1H), 8.43 (d, J = 8.7 Hz, 1H), 7.93 (d, J = 9.1 Hz, 1H), 7.69 (t, J = 1.9 Hz, 1H), 7.37-7.29 (m, 3H), 7.20-7.13 (m, 1H), 6.94-6.87 (m, 1H), 6.79 (dd, J = 8.2.1.0 Hz, 1H), 5.26-5.19 (m |
| 257 | | LC-MS (Method L1): Rt = 0.71 min; MS (ESIpos): m/z = 502 [M + H]+ | $^1$H-NMR (400 MHz, DMSO-d6) δ [ppm]: −0.149 (0.43), 0.146 (0.47), 1.754 (0.43), 1.862 (3.00), 1.901 (2.89), 1.909 (2.71), 2.031 (4.75), 2.040 (4.61), 2.049 (5.14), 2.157 (2.74), 2.171 (3.27), 2.186 (2.55), 2.203 (1.78), 2.327 (0.93), 2.366 (0.74), 2.670 (0.93), 2.709 (0.69), 3.038 (0.45), 3.165 (1.51), 3210 (0.53), 3.232 (0.51), 3.476 (2.42), 3.502 (4.70), 3.528 (2.55), 3.654 (0.43), 3.708 (1.60), 3.732 (3.42), 3.752 (2.34), 3.780 (1.22), 3.802 (2.18), 3.820 (2.17), 3.829 (2.57), 3.851 (3.64), 3.861 (4.91), 3.875 (4.51), 3.888 (3.51), 3.900 (2.05), 4.169 (4.22), 4258 (8.38), 4.267 (9.23), 4.280 (4.38), 4.372 (4.77), 5.035 (5.52), 5.201 (1.06), 5.214 (2.86), 5.227 (3.55), 5.235 (3.58), 5.247 (2.92), 5.261 (1.17), 6.782 (7.98), 6.801 (8.91), 6.893 (3.82), 6.912 (8.02), 6.930 (4.96), 7.145 (4.32), 7.163 (6.95), 7.182 (3.56), 7.211 (2.94), 7.216 (2.31), 7.234 (5.55), 7.240 (4.20), 7 258 (3.02), 7.263 (2.33), 7.307 (16.00), 7.324 (15.84), 7.361 (1.03), 7.377 (1.64), 7.399 (0.96), 7.467 (4.96), 7.486 (7.17), 7.507 (5.81), 7.704 (8.95), 7.722 (7.93), 7.742 (0.47), 7.887 (0.48), 7.901 (0.42), 8.134 (12.65), 8.269 (7.33), 8.291 (7.25), 8.313 (0.63), 8.394 (1.77), 8.432 (13.03), 8.436 (13.82), 8.810 (1.36), 9.046 (5.84), 9.067 (5.58), 12.645 (0.58). |
| 258 | | LC-MS (Method L6): Rt = 1.25 min; MS (ESIneg): m/z = 523 [M − H]− | $^1$H-NMR (400 MHz, DMSO-d6) δ [ppm]: −0.149 (0.99), 0.146 (1.21), 1.055 (1.10), 1.243 (0.89), 1.862 (1.56), 1.907 (1.99), 2.038 (4.22), 2.085 (2.63), 2.159 (2.66), 2.327 (2.09), 2.366 (1.38), 2.669 (2.27), 2.710 (1.45), 3.509 (1.42), 3.743 (1.67), 3.873 (4.19), 4.251 (8.12), 4.394 (3.19), 5.059 (2.13), 5.200 (3.33), 5.754 (16.00), 6.776 (5.14), 6.796 (5.68), 6.875 (3.87), 6.893 (7.49), 6.912 (4.43), 7.138 (3.69), 7.157 (5.46), 7.177 (3.37), 7.289 (6.17), 7.307 (5.53), 7.448 (3.87), 8.132 (3.30), 8.325 (3.87), 9.046 (1.53), 12.220 (0.64). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 259 | | LC-MS (Method L6): Rt = 1.24 min; MS (ESIpos): m/z = 518 [M + H]+ | $^1$H-NMR (400 MHz, DMSO-d6) δ [ppm]: −0.149 (1.71), −0.008 (15.12), 0.008 (13.06), 0.146 (1.65), 1.038 (1.12), 1.055 (2.24), 1.073 (1.12), 1.236 (0.71), 1.862 (3.06), 1.908 (2.82), 2.039 (5.47), 2.085 (3.00), 2.146 (3.35), 2.160 (3.59), 2.180 (2.88), 2.195 (2.53), 2.327 (2.82), 2.332 (2.06), 2.366 (2.29), 2.523 (8.71), 2.669 (2.59), 2.690 (0.53), 2.709 (2.24), 3.509 (2.00), 3.744 (2.29), 3.874 (5.88), 4.238 (8.06), 4.253 (10.94), 4.388 (4.47), 5.054 (3.29), 5.205 (4.24), 5218 (4.18), 5.754 (16.00), 6.774 (7.12), 6.795 (7.59), 6.878 (5.12), 6.896 (10.53), 6.915 (6.06), 7.139 (4.65), 7.157 (7.24), 7.177 (3.76), 7.235 (2.47), 7.290 (10.82), 7.309 (9.65), 7.501 (2.94), 7.561 (4.94), 8.132 (6.47), 8.337 (6.94), 9.043 (2.35), 12.703 (0.71). |
| 260 | | LC-MS (Method L1): Rt = 0.72 min; MS (ESIpos): m/z = 500 [M + H]+ | $^1$H-NMR (400 MHz, DMSO-d6) δ [ppm] 1.898 (1.49), 1.907 (1.43), 2.003 (1.23), 2.023 (2.16), 2.034 (2.52), 2.054 (2.37), 2.156 (1.33), 2.170 (1.58), 2.186 (1.26), 2.202 (0.87), 3.169 (4.19), 3.191 (0.45), 3.203 (0.50), 3.213 (0.51), 3.226 (0.59), 3.305 (1.15), 3.472 (1.52), 3.498 (2.71), 3.524 (1.46), 3.696 (0.91), 3.720 (1.91), 3.741 (1.28), 3.776 (0.63), 3.798 (1.12), 3.817 (1.15), 3.826 (1.36), 3.841 (1.73), 3.853 (2.81), 3.867 (2.34), 3.881 (1.91), 3.893 (1.16), 4.168 (2.20), 4.258 (4.22), 4.266 (4.57), 4.376 (2.54), 5.217 (1.39), 5.228 (1.80), 5.248 (1.46), 5.753 (16.00), 6.780 (4.05), 6.800 (4.44), 6.892 (1.82), 6.910 (3.93), 6.929 (2.45), 7.143 (2.06), 7.162 (3.40), 7.181 (1.72), 7.306 (3.35), 7.325 (3.06), 7.417 (1.77), 7.436 (4.71), 7.450 (3.62), 7.469 (5.99), 7.487 (4.73), 7.503 (3.14), 7.521 (4.74), 7.540 (2.68), 7.635 (6.07), 7.659 (4.38), 7.677 (3.91), 8.153 (14.28), 8.247 (3.60), 8.268 (3.45), 8.421 (6.72), 8.425 (7.54), 8.792 (0.74), 9.041 (2.88), 9.062 (2.77). |
| 261 | | LC-MS (Method L1): Rt = 0.75 min; MS (ESIpos): m/z = 530 [M + H]+ | $^1$H-NMR (400 MHz, DMSO-d6) δ [ppm]: −0.008 (1.36), 0.008 (1.23), 1.897 (0.69), 2.031 (1.04), 2.050 (1.12), 2.156 (0.59), 2.170 (0.71), 2.185 (0.60), 3.169 (0.99), 3.191 (0.41), 3.203 (0.54), 3212 (0.50), 3.226 (0.59), 3.305 (1.07), 3.464 (0.73), 3.490 (1.25), 3.518 (0.67), 3.712 (0.82), 3.734 (0.57), 3.790 (0.55), 3.814 (16.00), 3.829 (3.10), 3.847 (1.23), 3.861 (1.14), 3.874 (1.02), 3.887 (0.52), 4.163 (2.59), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 4.258 (1.91), 4.266 (2.12), 4.374 (1.12), 5.234 (0.76), 5.245 (0.63), 5.754 (0.64), 6.781 (1.81), 6.799 (2.04), 6.893 (0.86), 6.912 (1.84), 6.930 (1.24), 7.025 (1.53), 7.030 (2.93), 7.035 (1.95), 7.075 (2.47), 7.079 (2.80), 7.127 (0.40), 7.145 (0.92), 7.162 (1.62), 7.183 (2.94), 7.186 (3.43), 7.231 (0.46), 7.307 (1.49), 7.326 (1.37), 7.451 (1.09), 7.469 (1.61), 7.490 (1.32), 7.659 (1.99), 7.675 (1.69), 8.151 (5.55), 8.239 (1.63), 8.260 (1.58), 8.422 (3.41), 8.427 (3.75), 8.793 (0.92), 9.041 (1.50), 9.062 (1.45). |
| 262 | | LC-MS (Method L6): Rt = 1.28 min; MS (ESIpos): m/z = 518 [M + H]+ | $^1$H-NMR (400 MHz, DMSO-d6) δ [ppm]: −0.149 (0.82), −0.008 (6.72), 0.008 (6.87), 0.146 (0.82), 0.889 (0.41), 1.236 (0.68), 1.862 (2.00), 1.904 (2.50), 2.036 (4.81), 2.057 (3.23), 2.073 (2.58), 2.148 (2.61), 2.162 (3.02), 2.178 (2.26), 2.196 (1.91), 2.327 (1.88), 2.366 (1.20), 2.523 (5.70), 2.669 (1.82), 2.709 (1.09), 3.524 (2.23), 3.755 (2.17), 3.818 (2.88), 3.885 (3.41), 4.175 (1.41), 4.243 (6.72), 4.256 (8.63), 4.379 (4.34), 5.041 (4.81), 5.211 (3.38), 5.224 (3.41), 5.754 (2.38), 6.775 (7.63), 6.794 (8.22), 6.883 (3.88), 6.899 (8.07), 6.918 (4.81), 7.139 (4.20), 7.156 (6.55), 7.174 (3.29), 7.295 (8.04), 7.312 (8.40), 7.326 (3.90), 7.367 (3.20), 7.383 (4.29), 7.400 (2.00), 7.487 (2.08), 7.506 (3.58), 7.525 (2.50), 7.634 (5.31), 8.133 (16.00), 8.325 (4.08), 8.360 (8.78), 9.040 (2.67), 9.057 (2.67), 12.699 (1.38). |
| 263 | | LC-MS (Method L6): Rt = 2.33 min; MS (ESIpos): m/z = 576 [M + H]+ | $^1$H-NMR (400 MHz, DMSO-d6) δ [ppm]: −0.008 (1.65), 0.008 (1.52), 1.234 (0.49), 2.012 (0.66), 2.029 (0.92), 2.045 (0.89), 2.059 (1.10), 2.075 (1.44), 2.091 (1.89), 2.105 (1.51), 2.122 (0.75), 2.141 (0.59), 2.187 (0.65), 2.204 (0.65), 2.223 (0.59), 2.237 (0.50), 2.470 (0.58), 2.523 (1.48), 3.358 (0.47), 3.375 (0.74), 3.392 (0.84), 3.410 (0.50), 3.489 (16.00) 3.885 (0.41), 3.901 (0.97), 3.922 (0.95), 3.939 (0.41), 4.277 (1.55), 4.291 (2.65), 4.303 (1.60), 4.716 (1.07), 4.729 (1.23), 4.737 (1.20), 4.750 (1.01), 5.254 (0.41), 5.268 (0.92), 5.288 (0.94), 5.301 (0.42), 5.754 (8.22), 6.784 (1.67), 6.804 (1.85), 6.888 (0.85), 6.891 (0.84), 6.906 (1.80), 6.925 (1.08), 7.143 (0.86), 7.147 (0.92), 7.164 (1.44), 7.182 (0.72), 7.186 (0.72), 7.292 (1.53), 7.311 (1.42), 7.639 (1.85), 7.643 (3.39), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.648 (8.87), 7.652 (4.00), 7.673 (1.82), 7.676 (1.64), 7.694 (1.64), 7.821 (2.01), 7.824 (2.06), 7.839 (1.67), 7.842 (1.59), 8.351 (1.69), 8.354 (1.71), 8.372 (1.62), 8.375 (1.52), 8.678 (6.32), 9.190 (1.68), 9.210 (1.63). |
| 264 | | LC-MS (Method L6): Rt = 1.53 min; MS (ESIpos): m/z = 546 [M + H]+ | $^{1}$H-NMR (400 MHz, DMSO-d6) δ [ppm]: 0.146 (0.40), 1.139 (16.00), 1.158 (15.94), 1.234 (0.94), 1.963 (2 29), 1.974 (2.70), 2.061 (3.26), 2.078 (3.19), 2.097 (1.79), 2.163 (1.02), 2.327 (0.81), 2.670 (0.80), 2.710 (0.44), 3.615 (2.37), 4.233 (1.49), 4.254 (2.33), 4.262 (2.43), 5.217 (1.48), 5.236 (1.45), 5.754 (5.93), 6.777 (2.79), 6.798 (3.23), 6.902 (1.43), 6.921 (2.91), 6.940 (1.74), 7.146 (1.44), 7.166 (2.27), 7.184 (1.15), 7.347 (2.34), 7.365 (2.28), 7.641 (4.23), 7.646 (4.54), 7.657 (14.09), 7.661 (8.47), 7.678 (2.81), 7.698 (2.23), 7.819 (3.12), 7.837 (2.42), 8.297 (2.64), 8.318 (2.50), 8.803 (9.16), 8.970 (2.59), 8.991 (2.51). |
| 265 | | LC-MS (Method L1): Rt = 0.89 min; MS (ESIpos): m/z = 492 [M + H]+ | $^{1}$H-NMR (400 MHz, DMSO-d6) δ [ppm]: = 9.00 (d, 1H), 8.51 (s, 1H), 8.41 (d, 1H), 8.14 (s, 1H), 7.82 (t, 1H), 7.70-7.76 (m, 1H), 7.58-7.64 (m, 3H), 7.53 (dd, 1H), 7.30 (d, 1H), 7.13-7.20 (m, 1H), 6.86-6.96 (m, 1H), 6.79 (d, 1H), 5.19-5.30 (m, 1H), 4.21-4.33 (m, 2H), 3.48-3.59 (m, 2H), 1.96-2.22 (m, 2H), 1.25 (t, 3H). |
| 266 | | LC-MS (Method L1): Rt = 0.91 min; MS (ESIpos): m/z = 562 [M + H]+ | $^{1}$H-NMR (500 MHz, DMSO-d6) δ [ppm]: −0.007 (3.09), 0.006 (1.99), 1.907 (2.42), 2.028 (0.58), 2.033 (0.60), 2.044 (0.71), 2.056 (0.83), 2.166 (0.52), 2.175 (0.71), 2.185 (0.75), 2.193 (0.77), 2.204 (0.50), 2.358 (0.89), 2.361 (1.22), 2.365 (0.93), 2.369 (0.58), 2.392 (0.70), 2.407 (0.71), 2.514 (3.50), 2.518 (3.01), 2.522 (2.34), 2.631 (0.87), 2.635 (1.14), 2.639 (0.81), 3.866 (0.46), 3.878 (1.06), 3.895 (0.91), 4.183 (0.43), 4.188 (0.44), 4.205 (1.12), 4.224 (0.89), 4.229 (0.73), 4.243 (0.75), 4.250 (1.08), 4.262 (0.91), 4.277 (0.46), 4.638 (0.83), 4.649 (1.02), 4.654 (1.33), 4.665 (1.06), 5.254 (0.54), 5.264 (1.14), 5.280 (1.10), 5.291 (0.50), 6.786 (2.22), 6.788 (2.18), 6.802 (2.42), 6.804 (2.32), 6.919 (1.16), 6.921 (1.08), 6.933 (2.26), 6.935 (2.11), 6.948 (1.31), 6.950 (1.18), 7.169 (1.12), 7.172 (1.16), 7.186 (1.76), 7.200 (0.93), 7.203 (0.89), 7.388 (1.80), 7.403 (1.70), 7.629 (1.72), 7.634 (4.02), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.637 (8.89), 7.639 (16.00), 7.642 (4.87), 7.652 (2.18), 7.654 (1.91), 7.669 (1.82), 7.806 (2.51), 7.809 (2.42), 7.821 (2.05), 7.823 (1.86), 8.303 (1.86), 8.320 (1.72), 8.680 (8.25), 12.586 (0.91). |
| 267 | | LC-MS (Method L6): Rt = 1.85 min; MS (ESIpos): m/z = 530 [M + H]+ | $^{1}$H-NMR (400 MHz, DMSO-d6) δ [ppm]: 2.068 (1.35), 2.198 (1.21), 2.210 (1.21), 2.220 (1.14), 3.278 (5.85), 3.289 (6.25), 3.311 (12.56), 3.604 (16.00), 4.215 (0.92), 4.237 (1.78), 4.265 (2.72), 5.246 (1.68), 5.263 (1.68), 5.753 (4.55), 6.780 (2.37), 6.800 (2.65), 6.899 (1.40), 6.917 (2.61), 6.935 (1.60), 7.114 (2.89), 7.136 (3.72), 7.164 (2.76), 7.181 (4.24), 7.186 (4.32), 7.355 (2.53), 7.374 (2.43), 7.410 (2.28), 7.415 (2.25), 7.432 (2.02), 7.437 (1.87), 7.527 (0.74), 7.547 (0.73), 7.582 (0.60), 7.629 (6.11), 7.647 (3.02), 7.665 (1.10), 8.224 (2.04), 8.238 (1.98), 8.571 (5.47), 9.139 (2.37), 9.159 (2.29). |
| 268 | | LC-MS (Method L6): Rt = 1.68 min; MS (ESIpos): m/z = 514 [M + H]+ | $^{1}$H-NMR (400 MHz, DMSO-d6) δ [ppm]: 0.008 (1.66), 2.032 (1.12), 2.040 (1.20), 2.051 (1.31), 2.057 (1.32), 2.067 (1.86), 2.072 (1.94), 2.082 (1.19), 2.090 (0.84), 2.178 (0.94), 2.187 (1.30), 2.199 (1.63), 2.211 (1.54), 2.221 (1.49), 2.233 (0.98), 2.242 (0.78), 2.254 (0.49), 2.669 (0.48), 3.233 (0.95), 3.245 (1.65), 3.264 (4.14), 3.277 (8.27), 3.290 (9.38), 3.303 (8.05), 3.310 (8.12), 3.608 (4.08), 3.694 (1.02), 3.841 (0.90), 3.860 (7.34), 3.871 (12.70), 3.882 (7.04), 3.901 (0.86), 4.165 (0.48), 4.175 (0.48), 4.183 (0.53), 4.208 (0.81), 4.216 (1.03), 4.236 (2.56), 4.244 (2.08), 4.257 (3.61), 4.267 (3.55), 4.274 (2.38), 4.283 (2.35), 4.296 (0.92), 4.302 (0.93), 5.186 (0.41), 5.232 (1.10), 5.246 (2.38), 5.265 (2.35), 5.280 (1.03), 5.753 (0.98), 6.749 (0.48), 6.780 (4.50), 6.800 (5.03), 6.834 (0.58), 6.854 (0.72), 6.871 (0.52), 6.897 (2.22), 6.916 (4.62), 6.934 (2.69), 6.999 (3.38), 7.007 (3.89), 7.021 (3.65), 7.029 (3.73), 7.042 (0.46), 7.075 (2.55), 7.087 (2.73), 7.098 (4.07), 7.110 (4.00), 7.143 (2.39), 7.147 (2.50), 7.164 (4.00), 7.176 (2.61), 7.184 (4.22), 7.197 (3.38), 7.205 (3.28), 7219 (1.66), 7.228 (1.63), 7.245 (0.65), 7.265 (0.49), 7.355 (3.98), 7.373 (3.68), 7.519 (0.46), 7.540 (0.43), 7.584 (0.65), 7.599 (0.48), 7.609 (0.82), 7.615 (2.02), 7.629 (9.79), 7.648 (5.53), 7.666 (1.75), 8.217 (3.69), 8.223 (3.68), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 8.236 (3.32), 8.242 (3.35), 8.280 (0.46), 8.532 (1.30), 8.572 (16.00), 9.118 (0.49), 9.140 (4.50), 9.160 (4.10). |
| 269 | | LC-MS (Method L1): Rt = 0.75 min; MS (ESIpos): m/z = 530 [M + H]+ | $^1$H-NMR (400 MHz, DMSO-d6) δ [ppm]: −0.149 (0.88), −0.008 (8.18), 0.008 (7.45), 0.146 (0.90), 1.862 (1.33), 1.901 (1.64), 2.006 (1.70), 2.026 (2.93), 2.039 (3.18), 2.058 (1.87), 2.071 (1.25), 2.144 (1.40), 2.158 (1.62), 2.174 (1.40), 2.192 (1.09), 2.327 (1.27), 2.366 (0.88), 2.669 (1.35), 2.709 (0.82), 2.988 (0.49), 3.018 (0.82), 3.080 (0.76), 3.090 (0.82), 3.120 (0.64), 3.168 (3.38), 3.189 (1.64), 3.199 (1.70), 3.212 (1.83), 3.304 (6.01), 3.458 (2.03), 3.487 (2.61), 3.517 (1.76), 3.654 (0.60), 3.683 (1.07), 3.692 (1.19), 3.715 (2.54), 3.728 (1.58), 3.736 (1.37), 3.767 (0.66), 3.789 (1.35), 3.807 (1.58), 3.831 (1.83), 3.847 (3.20), 3.861 (2.56), 3.874 (3.40), 3.888 (1.23), 4.152 (7.55), 4.252 (5.35), 4.377 (2.97), 5.035 (0.45), 5.209 (1.89), 5.225 (1.93), 5.264 (0.43), 6.772 (4.37), 6.790 (5.03), 6.809 (0.90), 6.878 (2.19), 6.897 (4.78), 6.916 (3.30), 6.935 (0.49), 7.094 (6.19), 7.116 (7.26), 7.135 (2.60), 7.153 (4.41), 7.161 (6.99), 7.168 (8.02), 7.214 (1.25), 7.221 (1.29), 7.289 (3.71), 7.307 (3.41), 7.341 (0.72), 7.361 (0.64), 7.384 (4.27), 7.390 (4.02), 7.406 (3.71), 7.412 (3.61), 7.421 (3.04), 7.440 (4.06), 7.450 (1.05), 7.460 (3.61), 7.501 (5.07), 7.504 (5.29), 7.518 (3.34), 7.659 (1.00), 7.677 (1.58), 8.177 (16.00), 8.233 (4.10), 8.254 (3.80), 8.331 (8.27), 8.335 (8.60), 8.688 (2.58), 9.014 (2.13), 9.024 (2.44), 9.035 (2.24), 9.045 (2.24), 9.145 (0.62), 9.165 (0.59). |
| 270 | | LC-MS (Method L6): Rt = 1.17 min; MS (ESIpos): m/z = 514 [M + H]+ | $^1$H-NMR (400 MHz, DMSO-d6) δ [ppm]: −0.008 (2.06), 0.008 (2.02), 1.862 (0.52), 1.902 (0.65), 1.991 (0.45), 2.008 (0.70), 2.029 (1.17), 2.041 (1.33), 2.052 (0.81), 2.062 (0.77), 2.074 (0.49), 2.085 (0.95), 2.145 (0.64), 2.159 (0.70), 2.175 (0.54), 2.194 (0.46), 3.468 (0.59), 3.498 (0.87), 3.528 (0.48), 3.592 (16.00), 3.702 (0.50), 3.722 (0.73), 3.738 (0.54), 3.795 (0.43), 3.813 (0.59), 3.833 (0.70), 3.855 (1.29), 3.868 (0.86), 3.881 (0.82), 3.893 (0.49), 4.151 (0.44), 4.241 (1.65), 4.254 (2.29), 4.378 (1.10), 5.041 (0.99), 5.210 (0.85), 5.224 (0.81), 5.753 (5.11), 6.773 (1.87), 6.793 (2.06), 6.877 (0.94), 6.896 (1.98), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.914 (1.21), 6.988 (0.94), 6.995 (1.10), 7.010 (0.97), 7.018 (1.04), 7.061 (0.93), 7.072 (1.01), 7.084 (1.51), 7.095 (1.44), 7.136 (1.03), 7.156 (2.10), 7.165 (0.92), 7.177 (1.39), 7.186 (1.11), 7.200 (0.54), 7.208 (0.52), 7.289 (1.68), 7.307 (1.53), 7.430 (0.89), 7.448 (1.57), 7.469 (1.45), 7.511 (1.95), 7.528 (1.16), 8.134 (5.18), 8.235 (1.56), 8.256 (1.45), 8.331 (2.76), 8.335 (3.59), 9.027 (0.68), 9.036 (0.99), 9.047 (0.75), 9.057 (0.91). |
| 271 | | LC-MS (Method L1): Rt = 0.78 min; MS (ESIpos): m/z = 568 [M + H]+ | $^1$H-NMR (400 MHz, DMSO-d6) δ [ppm]: −0.150 (0.71), −0.008 (7.12), 0.008 (7.07), 0.146 (0.81), 1.157 (4.10), 1.175 (8.25), 1.192 (4.07), 1.234 (4.37), 1.258 (1.96), 1.298 (1.33), 1.759 (1.96), 1.913 (1.69), 1.988 (16.00), 2.051 (3.21), 2.153 (1.72), 2.168 (1.96), 2.328 (1.18), 2.366 (0.83), 2.669 (1.15), 3.482 (1.52), 3.509 (3.31), 3.537 (1.72), 3.601 (1.72), 3.749 (2.23), 3.858 (2.43), 3.871 (2.40), 3.884 (2.97), 3.898 (2.04), 4.003 (1.13), 4.021 (3.58), 4.038 (3.51), 4.056 (1.20), 4.179 (2.43), 4.265 (5.40), 4.372 (2.70), 5.035 (4.93), 5.231 (2.18), 5.753 (0.91), 6.782 (5.20), 6.802 (5.72), 6.891 (2.33), 6.910 (5.06), 6.928 (3.21), 7.141 (2.50), 7.162 (4.22), 7.184 (2.11), 7.304 (4.32), 7.322 (4.02), 7.480 (3.31), 7.499 (4.47), 7.519 (3.68), 7.757 (5.37), 7.774 (4.66), 7.854 (7.12), 7.898 (7.95), 7.970 (7.83), 8.137 (1.03), 8.299 (3.12), 8.322 (3.07), 8.420 (9.50), 8.427 (9.79), 8.804 (0.96), 9.056 (3.41), 9.075 (3.53). |
| 272 | | LC-MS (Method L1): Rt = 0.74 min; MS (ESIpos): m/z = 532 [M + H]+ | $^1$H-NMR (400 MHz, DMSO-d6) δ [ppm]: −0.150 (0.66), −0.008 (6.04), 0.008 (5.39), 0.146 (0.68), 1.902 (1.46), 1.911 (1.34), 2.001 (1.38), 2.011 (1.72), 2.032 (2.75), 2.042 (2.15), 2.148 (1.40), 2.161 (1.58), 2.177 (1.24), 2.195 (0.96), 2.270 (16.00), 2.327 (0.88), 2.332 (0.72), 2.366 (0.84), 2.522 (2.61), 2.669 (0.86), 2.709 (0.78), 3.209 (0.40), 3.232 (0.44), 3.479 (1.26), 3.507 (2.19), 3.537 (1.20), 3.738 (1.70), 3.758 (1.16), 3.790 (0.56), 3.813 (1.00), 3.830 (1.10), 3.848 (1.30), 3.857 (1.48), 3.870 (2.75), 3.883 (2.11), 3.896 (1.78), 3.909 (1.08), 4.169 (2.17), 4.244 (3.65), 4.256 (4.49), 4.374 (2.29), 5.034 (3.53), 5.212 (1.76), 5.225 (1.74), 5.233 (1.40), 5.753 (11.87), 6.774 (3.91), 6.793 (4.33), 6.881 (2.01), 6.900 (4.21), 6.918 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.63), 7.135 (2.07), 7.138 (2.15), 7.156 (3.47), 7.174 (1.84), 7.177 (1.76), 7.240 (1.90), 7.247 (2.25), 7.254 (2.13), 7.261 (2.07), 7.295 (3.59), 7.314 (3.31), 7.405 (2.07), 7.411 (2.15), 7.420 (2.31), 7.426 (2.01), 7.458 (2.45), 7.477 (3.53), 7.498 (3.05), 7.604 (4.17), 7.621 (3.31), 8.133 (5.33), 8.299 (3.03), 8.321 (2.85), 8.361 (7.30), 8.365 (8.02), 8.733 (0.70), 9.030 (2.93), 9.051 (2.79). |
| 273 | | LC-MS (Method L6): Rt = 1.74 min; MS (ESIpos): m/z = 504 [M + H]+ | $^1$H-NMR (400 MHz, DMSO-d6) δ [ppm]: −0.008 (2.37), 0.008 (2.35), 0.551 (0.53), 0.566 (0.84), 0.576 (1.24), 0.588 (1.45), 0.599 (1.08), 0.611 (1.48), 0.622 (1.39), 0.632 (0.86), 0.646 (0.65), 0.774 (0.62), 0.784 (0.88), 0.791 (1.19), 0.801 (1.30), 0.811 (1.67), 0.817 (1.59), 0.828 (1.34), 0.846 (0.86), 0.855 (0.50), 1.157 (4.26), 1.175 (8.61), 1.193 (4.39), 1.988 (16.00), 2.033 (0.49), 2.041 (0.65), 2.051 (0.77), 2.059 (0.84), 2.067 (1.09), 2.075 (1.07), 2.086 (1.16), 2.108 (0.49), 2.129 (0.92), 2.141 (0.96), 2.150 (0.81), 2.163 (0.50), 2.176 (0.40), 2.523 (1.27), 3.074 (1.32), 3.081 (1.31), 4.003 (1.26), 4.021 (3.80), 4.038 (3.76), 4.056 (1.22), 4.229 (0.56), 4.237 (0.42), 4.248 (1.37), 4.257 (1.41), 4.268 (1.85), 4.276 (1.87), 4.288 (1.35), 4.296 (1.55), 4.316 (0.56), 5.210 (0.65), 5.225 (1.45), 5.244 (1.46), 5.259 (0.63), 6.783 (2.84), 6.804 (3.11), 6.881 (1.36), 6.884 (1.39), 6.900 (2.84), 6.902 (2.84), 6.918 (1.71), 6.921 (1.66), 7.139 (1.38), 7.143 (1.48), 7.160 (2.30), 7.178 (1.14), 7.182 (1.14), 7.290 (2.42), 7.309 (2.25), 7.495 (2.03), 7.513 (2.65), 7.515 (2.51), 7.534 (2.35), 7.593 (1.59), 7.598 (3.85), 7.602 (4.25), 7.614 (14.30), 7.618 (8.44), 7.726 (3.30), 7.742 (2.69), 7.744 (2.68), 8.497 (2.63), 8.581 (9.25), 8.625 (2.55), 8.644 (2.39), 8.925 (2.56), 8.945 (2.48). |
| 274 | | LC-MS (Method L1): Rt = 0.87 min; MS (ESIpos): m/z = 562 [M + H]+ | $^1$H-NMR (400 MHz, DMSO-d6) δ [ppm]: −0.149 (0.88), 0.146 (0.84), 2.052 (4.40), 2.066 (4.83), 2.214 (1.52), 2.327 (1.69), 2.367 (1.09), 2.669 (1.57), 2.709 (0.86), 3.395 (1.87), 3.910 (1.80), 3.929 (1.91), 4.172 (0.60), 4.289 (4.76), 4.731 (1.76), 4.745 (2.27), 4.764 (1.74), 5.301 (1.84), 5.318 (1.95), 6.770 (3.24), 6.790 (3.65), 6.854 (1.59), 6.872 (3.37), 6.890 (2.08), 7.129 (1.78), 7.146 (2.92), 7.165 (1.59), 7.303 (3.15), 7.322 (2.98), 7.643 (16.00), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.674 (2.68), 7.808 (3.99), 7.825 (3.00), 8.323 (3.22), 8.343 (2.92), 8.686 (8.56), 9.294 (0.92), 12.581 (0.51). |
| 275 | | LC-MS (Method L6): Rt = 1.37 min; MS (ESIpos): m/z = 532 [M + H]+ | $^1$H-NMR (400 MHz, DMSO-d6) δ [ppm]: 1.899 (0.93), 2.033 (1.88), 2.162 (1.12), 2.178 (0.96), 2.337 (16.00), 2.669 (0.47), 3.305 (4.05), 3.485 (0.97), 3.512 (1.74), 3.538 (0.94), 3.742 (1.19), 3.817 (0.74), 3.849 (0.94), 3.873 (2.10), 3.885 (1.33), 3.899 (1.41), 3.911 (0.81), 4.257 (3.03), 4.375 (1.62), 5.036 (0.83), 5.212 (1.24), 6.773 (2.99), 6.793 (3.25), 6.884 (1.29), 6.902 (2.92), 6.920 (1.71), 7.138 (1.51), 7.157 (4.16), 7.174 (3.09), 7.296 (2.55), 7.314 (2.22), 7.418 (2.01), 7.431 (2.00), 7.467 (1.65), 7.484 (2.51), 7.506 (2.14), 7.606 (3.17), 7.623 (2.58), 8.136 (11.05), 8.306 (2.13), 8.327 (1.99), 8.361 (5.15), 8.365 (5.57), 9.029 (2.00), 9.051 (1.92). |
| 276 | | LC-MS (Method L6): Rt = 0.80 min; MS (ESIpos): m/z = 522 [M + H]+ | $^1$H-NMR (400 MHz, DMSO-d6): δ [ppm] = 8.98 (d, 1H), 8.47 (s, 1H), 8.22 (br d, 1H), 8.03 (br s, 1H), 7.74 (d, 1H), 7.52-7.66 (m, 4H), 7.33 (d, 1H), 7.15 (t, 1H), 6.90 (t, 1H), 6.78 (d, 1H), 5.18-5.33 (m, 1H), 4.19-4.33 (m, 2H), 3.80 (br s, 2H), 1.99-2.23 (m, 2H). |
| 277 | | LC-MS (Method L2): Rt = 2.86 min; m/z = 460 [M + H]+. | $^1$H-NMR (400 MHz, DMSO-d6) δ 9.08 (d, J = 8.2 Hz, 1H), 8.53 (s, 1H), 8.28 (m, 1H), 7.78-7.62 (m, 2H), 7.51 (m, 1H), 7.35 (d, J = 7.1 Hz, 1H), 7.25-7.11 (m, 3H), 6.91 (m, 1H), 6.83-6.75 (m, 1H), 5.24 (q, J = 5.8 Hz, 1H), 4.25 (dt, J = 7.8, 4.8 Hz, 2H) |
| 278 | | LC-MS (Method L2): Rt = 3.64 min; m/z = 520 [M + H]+ | $^1$H-NMR (400 MHz, DMSO-d6) δ 9.17 (d, J = 8.1 Hz, 1H), 8.64 (s, 1H), 8.40 (dd, J = 9.4, 6.3 Hz, 1H), 7.70 (t, J = 9.1 Hz, 1H), 7.65-7.55 (m, 1H), 7.36 (d, J = 6.8 Hz, 1H), 7.30-7.21 (m, 2H), 7.20-7.13 (m, 1H), 6.95-6.87 (m, 1H), 6.79 (dd, J = 8.2, |
| 279 | | LC-MS (Method L3): Rt = 3.83 min; m/z = 478 [M + H]+ | $^1$H-NMR (400 MHz, DMSO-d6) δ 9.08 (d, J = 8.2 Hz, 1H), 8.55 (s, 1H), 8.37 (dd, J = 9.4, 6.3 Hz, 1H), 7.68-7.54 (m, 2H), 7.34 (d, J = 6.8 Hz, 1H), 7.30-7.20 (m, 2H), 7.20-7.12 (m, 1H), 6.94-6.87 (m, 1H), 6.79 (dd, J = 8.2, 1.1 Hz, 1H), 5.27-5.19 ( |
| 280 | | LC-MS (Method L1): Rt = | $^1$H-NMR (400 MHz, DMSO-d6): δ [ppm] = 9.19 (d, 1H), 8.62 (s, 1H), 8.57 (s, 1H), 8.34 (dd, 1H), 7.81-7.90 (m, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | 0.89 min; MS (ESIpos): m/z = 507 [M + H]+ | 2H), 7.75 (dd, 1H), 7.47-7.56 (m, 2H), 7.36 (d, 1H), 7.12-7.21 (m, 1H), 6.87-6.97 (m, 1H), 6.79 (d, 1H), 5.20-5.32 (m, 1H), 4.18-4.33 (m, 2H), 3.89 (t, 4H), 2.16-2.28 (m, 1H), 2.00-2.11 (m, 1H). |
| 281 | | LC-MS (Method L6): Rt = 1.59 min; MS (ESIpos): m/z = 576 [M + H]+ | $^1$H-NMR (400 MHz, DMSO-d6) δ [ppm]: −0.008 (1.22), 0.008 (1.27), 2.023 (0.43), 2.058 (0.74), 2.065 (0.63), 2.129 (0.65), 2.148 (0.95), 2.159 (1.39), 2.178 (1.50), 2.197 (0.65), 2.259 (0.60), 2.271 (0.78), 2.289 (0.71), 2.322 (0.52), 2.327 (0.59), 2.523 (1.62), 2.670 (0.57), 3.336 (1.52), 3.354 (0.97), 3.632 (0.46), 3.644 (0.81), 3.656 (0.92), 3.663 (0.86), 3.688 (16.00), 3.711 (1.43), 3.729 (0.81), 3.736 (1.08), 3.764 (1.60), 3.783 (1.39), 3.798 (1.66), 3.815 (1.41), 3.823 (0.84), 3.840 (0.60), 4.236 (1.01), 4.248 (1.31), 4.259 (1.81), 4.273 (1.00), 5.212 (0.93), 5.232 (0.97), 5.245 (0.41), 5.754 (0.44), 6.784 (1.82), 6.804 (1.98), 6.899 (0.92), 6.915 (1.93), 6.934 (1.14), 7.149 (0.92), 7.153 (0.95), 7.170 (1.52), 7.187 (0.76), 7.334 (1.55), 7.352 (1.44), 7.548 (1.35), 7.566 (1.81), 7.569 (1.62), 7.587 (1.49), 7.625 (12.56), 7.756 (2.12), 7.771 (1.68), 7.774 (1.70), 8.265 (1.73), 8.287 (1.54), 8.530 (5.88), 9.104 (1.73), 9.124 (1.66). |
| 282 | | LC-MS (Method L6): Rt = 1.57 min; MS (ESIpos): m/z = 576 [M + H]+ | $^1$H-NMR (400 MHz, DMSO-d6) δ [ppm]: −0.008 (0.90), 0.008 (1.01), 1.356 (0.76), 2.020 (0.41), 2.030 (0.40), 2.056 (0.64), 2.064 (0.53), 2.115 (0.57), 2.134 (0.66), 2.146 (0.97), 2.164 (1.20), 2.184 (0.89), 2.196 (0.51), 2.261 (0.56), 2.273 (0.71), 2.280 (0.50), 2.292 (0.68), 2.323 (0.44), 2.327 (0.41), 2.523 (1.03), 3.333 (1.42), 3.352 (0.88), 3.653 (0.41), 3.665 (0.84), 3.684 (16.00), 3.702 (0.75), 3.721 (1.33), 3.739 (0.72), 3.745 (0.78), 3.776 (2.18), 3.779 (2.21), 3.797 (2.25), 4.241 (0.94), 4.250 (1.38), 4.261 (1.78), 5.218 (0.84), 5.238 (0.83), 5.754 (1.01), 6.784 (1.63), 6.804 (1.77), 6.895 (0.78), 6.897 (0.81), 6.915 (1.64), 6.932 (0.96), 6.934 (0.96), 7.147 (0.79), 7.151 (0.87), 7.168 (1.32), 7.186 (0.66), 7.190 (0.67), 7.328 (1.35), 7.345 (1.25), 7.544 (1.16), 7.562 (1.51), 7.566 (1.48), 7.584 (1.38), 7.624 (12.39), 7.752 (1.74), 7.755 (1.89), 7.770 (1.51), 7.772 (1.51), 8.250 (1.50), 8.253 (1.57), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.271 (1.41), 8.274 (1.38), 8.524 (5.96), 9.102 (1.54), 9.123 (1.50). |
| 283 | | LC-MS (Method L6): Rt = 0.81 min; MS (ESIpos): m/z = 534 [M + H]+ | $^1$H-NMR (400 MHz, DMSO-d6): δ [ppm] = 9.05 (d, 1H), 8.44 (s, 1H), 8.29 (d, 1H), 7.71 (d, 1H), 7.57-7.64 (m, 3H), 7.44-7.52 (m, 1H), 7.32 (d, 1H), 7.11-7.20 (m, 1H), 6.87-6.95 (m, 1H), 6.79 (d, 1H), 5.18-5.28 (m, 1H), 5.03 (d, 1H), 4.36 (br s, 1H), 4.27 (br t, 2H), 3.79-3.93 (m, 2H), 3.68-3.79 (m, 1H), 3.49 (br d, 1H), 2.12-2.24 (m, 1H), 1.97-2.10 (m, 2H), 1.89 (br d, 1H). |
| 284 | | LC-MS (Method L6): Rt = 0.82 min; MS (ESIpos): m/z = 534 [M + H]+ | $^1$H-NMR (400 MHz, DMSO-d6) δ [ppm] = 9.05 (d, 1H), 8.43 (s, 1H), 8.29 (d, 1H), 7.72 (d, 1H), 7.57-7.65 (m, 3H), 7.45-7.51 (m, 1H), 7.32 (d, 1H), 7.17 (t, 1H), 6.92 (t, 1H), 6.79 (d, 1H), 5.22 (br d, 1H), 5.03 (d, 1H), 4.37 (br s, 1H), 4.20-4.31 (m, 2H), 3.68-3.91 (m, 3H), 3.51 (br d, 1H), 2.18 (br dd, 1H), 2.03 (br dd, 2H), 1.91 (br s, 1H). |
| 285 | 4.62 | | $^1$H-NMR (399, 9532 MHz, DMSO): δ = 9.2548 (2.04); 9.2345 (2.1); 8.7855 (7.26); 8.3664 (2.02); 8.3479 (2.11); 8.3453 (2.18); 7.8787 (1.74); 7.8758 (1.94); 7.861 (2.47); 7.8581 (2.48); 7.7622 (1.94); 7.7414 (2.32); 7.7231 (1.43); 7.6547 (16); 7.377 (1.84); 7.3585 (1.98); 7.2033 (0.85); 7.1998 (0.91); 7.1823 (1.91); 7.1646 (1.15); 7.1615 (1.18); 6.9343 (1.34); 6.9157 (2.31); 6.8969 (1.1); 6.8176 (2.6); 6.7972 (2.33); 5.7568 (1.47); 5.3034 (0.53); 5.2897 (1.2); 5.2703 (1.21); 5.2561 (0.53); 4.2926 (1.27); 4.2792 (2.34); 4.2671 (1.8); 4.2581 (1.3); 4.2376 (0.33); 4.0706 (0.7); 4.0524 (2.63); 4.0345 (4.44); 4.0171 (4.89); 3.9996 (4.19); 3.9816 (2.38); 3.9627 (0.67); 3.6304 (3.62); 3.6065 (3.63); 3.3187 (31.43); 3.1462 (13.89); 2.6701 (0.58); 2.6659 (0.46); 2.5055 (77.14); 2.5012 (101.26); 2.4969 (75.96); 2.3321 (0.47); 2.3281 (0.61); 2.3241 (0.48); 2.2488 (0.44); 2.2418 (0.43); 2.2281 (0.71); 2.2163 (0.79); 2.2064 (0.75); 2.1941 (0.66); 2.1845 (0.36); 2.0978 (0.77); 2.0895 (0.89); 2.078 (0.63); 2.0643 (0.6); 2.0543 (0.57); 1.9886 (5.88); 1.3664 (0.32); 1.2071 (5.79); 1.1896 (12.06); 1.1762 (7.45); 1.1746 (7.59); 1.1724 (7.64); 1.1593 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (11.84); 1.1417 (5.55); 0.0079 (0.56); −0.0002 (11.57) |
| 286 | | LC-MS (Method L1): Rt = 0.71 min; MS (ESIpos): m/z = 547 [M + H]+ | $^1$H-NMR (600 MHz, DMSO-d6) δ [ppm]: 0.226 (1.29), 0.233 (4.30), 0.237 (4.63), 0.239 (4.52), 0.243 (4.88), 0.249 (1.40), 0.340 (1.52), 0.346 (4.07), 0.350 (4.50), 0.357 (4.85), 0.360 (3.44), 0.368 (1.04), 1.356 (1.85), 2.038 (0.54), 2.043 (0.74), 2.048 (0.90), 2.055 (1.09), 2.058 (1.29), 2.064 (1.93), 2.069 (2.31), 2.075 (2.90), 2.080 (1.94), 2.085 (1.35), 2.091 (0.59), 2.138 (0.52), 2.147 (0.75), 2.153 (0.91), 2.160 (1.03), 2.166 (0.97), 2.175 (0.71), 2.183 (0.72), 2.430 (0.61), 2.875 (2.56), 2.886 (5.07), 2.896 (2.59), 3.568 (1.55), 3.578 (3.52), 3.587 (3.45), 3.597 (1.35), 4.235 (0.44), 4.240 (0.64), 4.246 (0.51), 4.253 (1.67), 4.259 (1.50), 4.267 (2.05), 4.272 (2.07), 4.280 (1.42), 4.285 (1.84), 4.291 (0.49), 4.299 (0.60), 4.304 (0.43), 5.243 (0.77), 5.253 (1.54), 5266 (1.49), 5.276 (0.69), 6.785 (2.94), 6.787 (3.06), 6.799 (3.15), 6.801 (3.19), 6.884 (1.60), 6.886 (1.58), 6.897 (3.02), 6.899 (2.96), 6.909 (1.78), 6.911 (1.69), 7.149 (1.45), 7.151 (1.48), 7.163 (2.43), 7.174 (1.26), 7.177 (1.19), 7.299 (2.47), 7.312 (2.33), 7.525 (2.41), 7.537 (2.93), 7.539 (2.68), 7.552 (2.48), 7.603 (2.71), 7.606 (5.93), 7.609 (4.64), 7.625 (16.00), 7.628 (11.38), 7.728 (0.51), 7.731 (0.49), 7.740 (3.43), 7.741 (3.45), 7.751 (2.98), 7.753 (2.90), 7.908 (1.67), 8.353 (2.70), 8.354 (2.72), 8.367 (2.61), 8.369 (2.48), 8.549 (9.74), 8.991 (2.87), 9.004 (2.73). |
| 287 | | LC-MS (Method L1): Rt = 0.98 min; MS (ESIpos): m/z = 548 [M + H]+ | $^1$H-NMR (400 MHz, DMSO-d6) δ [ppm]: −0.149 (0.52), 0.146 (0.53), 1.883 (0.77), 1.896 (0.94), 1.912 (1.02), 1.927 (1.11), 1.943 (1.13), 1.961 (0.80), 1.971 (1.04), 1.990 (1.32), 2.009 (0.93), 2.061 (1.59), 2.074 (1.40), 2.084 (1.11), 2.098 (1.33), 2.109 (1.05), 2.191 (2.00), 2.202 (1.93), 2.226 (1.16), 2.240 (0.86), 2.327 (0.57), 2.366 (0.54), 2.669 (0.58), 2.710 (0.53), 3.225 (0.66), 3.239 (1.63), 3.252 (3.85), 3.266 (3.91), 3.279 (2.86), 3.800 (0.70), 3.818 (1.59), 3.838 (1.38), 3.857 (0.53), 4279 (3.25), 4.293 (5.39), 4.304 (3.56), 4.768 (1.59), 4.782 (3.24), 4.795 (1.56), 5.260 (0.71), 5.274 (1.51), 5.293 (1.51), 5.308 (0.71), 6.778 (2.68), 6.798 (3.02), 6.875 (1.45), 6.893 p.03), 6.912 (1.75), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

δ1 (intensity1); δ2 (intensity2); . . . ; δi (intensityi); . . . ; δn (intensityn) or δ1 (intensity1), δ2 (intensity2), . . . ; δi (intensityi), . . . . δn (intensityn)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D6 and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.138 (1.46), 7.156 (2.35), 7.176 (1.18), 7.292 (2.47), 7.310 (2.24), 7.600 (1.83), 7.621 (2.91), 7.638 (16.00), 7.787 (3.16), 7.804 (2.53), 8.227 (2.56), 8.249 (2.35), 8.638 (8.70), 9.180 (2.48), 9.201 (2.46). |
| 288 | | LC-MS (Method L1): Rt = 0.99 min; MS (ESIpos): m/z = 548 [M + H]+ | $^1$H-NMR (400 MHz, DMSO-d6) δ [ppm]: −0.149 (0.41), −0.008 (3.63), 0.008 (3.20), 0.146 (0.42), 0.853 (0.41), 1.235 (1.98), 1.571 (1.78), 1.770 (0.57), 1.783 (0.70), 1.800 (0.80), 1.813 (0.68), 1.832 (0.43), 1.896 (0.87), 1.916 (1.53), 1.934 (1.55), 1.951 (0.86), 1.997 (0.58), 2.004 (0.58), 2.018 (0.64), 2.032 (0.84), 2.105 (0.65), 2.117 (0.95), 2.135 (0.76), 2.149 (0.82), 2.172 (0.84), 2.185 (0.78), 2.193 (0.74), 2.206 (0.55), 2.327 (0.80), 2.366 (0.49), 2.523 (2.44), 2.665 (0.62), 2.669 (0.80), 2.709 (0.47), 3.168 (2.40), 3.202 (3.42), 3.235 (0.84), 3.730 (0.53), 3.748 (1.27), 3.769 (1.21), 3.787 (0.48), 4.172 (0.78), 4.196 (1.49), 4.202 (1.69), 4.217 (1.98), 4.233 (1.24), 4.246 (1.34), 4.252 (1.02), 4.262 (1.06), 4.273 (0.58), 4.281 (0.53), 4.775 (0.76), 5.232 (0.50), 5.246 (1.11), 5.266 (1.12), 5.280 (0.50), 6.792 (2.30), 6.813 (2.51), 6.929 (1.14), 6.946 (2.23), 6.964 (1.27), 7.169 (1.12), 7.173 (1.19), 7.190 (1.80), 7.208 (0.87), 7.409 (1.87), 7.427 (1.76), 7.603 (1.59), 7.622 (2.28), 7.625 (2.41), 7.637 (16.00), 7.651 (0.76), 7.789 (2.46), 7.804 (1.99), 8.208 (1.97), 8.227 (1.82), 8.554 (0.70), 8.654 (8.22), 9.267 (1.92), 9.288 (1.85). |
| 289 | | LC-MS (Method L4): Rt = 2.19 min; MS (ESIneg): m/z = 545 [M − H]− | $^1$H-NMR (400 MHz, DMSO-d6) δ [ppm]: −0.149 (0.41), 0.853 (0.82), 0.936 14.10), (0.967 (12.05), 0.979 (4.08), 1.010 (0.93), 1.091 (4.11), 1.112 (3.92), 1.128 (1.36), 1.141 (1.26), 1.209 (11.78), 1226 (11.85), 1257 (0.62), 1.863 (0.62), 2.038 (2.45), 2.070 (3.11), 2.086 (2.26), 2.124 (1.91), 2.137 (1.96), 2.328 (0.85), 2.366 (0.73), 2.524 (1.17), 2.670 (0.58), 2.711 (3.09), 3.066 (0.92), 3.075 (0.86), 4.217 (1.18), 4.236 (2.48), 4.254 (2.47), 4.264 (2.19), 4.277 (2.14), 4.296 (2.20), 4.323 (1.05), 5.256 (1.20), 5.271 (2.47), 5.288 (2.36), 5.754 (6.01), 6.779 (4.19), 6.800 (4.70), 6.850 (1.07), 6.869 (3.08), 6.886 (3.51), 6.904 (1.82), 6.921 (0.41), 7.137 (2.50), 7.155 (4.01), 7.173 (2.04), 7.246 (2.37), 7.268 (3.62), 7.289 (1.98), 7.527 (2.12), 7.546 (3.59), 7.566 (2.59), 7.595 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (5.35), 7.599 (4.71), 7.629 (16.00), 7.633 (13.65), 7.755 (4.31), 7.772 (3.86), 8.153 (1.08), 8.195 (5.33), 8.334 (0.71), 8.562 (0.74), 8.585 (0.69), 8.632 (2.97), 8.640 (2.11), 8.653 (2.92), 8.664 (5.42), 8.676 (5.87), 8.916 (1.70), 8.935 (3.21), 8.955 (1.84), 8.981 (0.70), 9.001 (0.72), 9.015 (0.69), 9.035 (0.60), 9.091 (0.68), 9.148 (0.75). |
| 290 | | LC-MS (Method L6): Rt = 2.50 min; MS (ESIpos): m/z = 548 [M + H]+ | $^1$H-NMR (400 MHz, DMSO-d6) δ [ppm]: −0.149 (1.02), −0.008 (8.92), 0.008 (8.60), 0.146 (1.00), 1.135 (7.45), 1.150 (7.45), 2.092 (0.86), 2.210 (0.77), 2.222 (0.70), 2.232 (0.75), 2.327 (1.38), 2.366 (0.75), 2.522 (3.76), 2.669 (1.31), 2.709 (0.68), 3.011 (0.88), 3.040 (1.40), 3.065 (1.22), 3.171 (0.86), 3.203 (2.49), 3.237 (1.13), 3.271 (0.95), 3.882 (0.86), 3.904 (1.86), 3.928 (2.90), 4.252 (1.18), 4.260 (1.02), 4.272 (1.81), 4.281 (1.77), 4.297 (0.97), 5.264 (1.11), 5.285 (1.13), 5.754 (6.81), 6.791 (2.20), 6.811 (2.42), 6.898 (1.09), 6.916 (2.17), 6.932 (1.24), 7.158 (1.11), 7.175 (1.77), 7.193 (0.88), 7.373 (1.83), 7.390 (1.67), 7.639 (16.00), 7.682 (1.45), 7.700 (2.08), 7.720 (1.88), 7.832 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (2.51), 7.847 (1.92), 8.269 (2.08), 8.287 (1.92), 8.703 (7.92), 9.162 (1.99), 9.182 (1.90). |
| 291 | | LC-MS (Method L1): Rt = 0.74 min; MS (ESIneg): m/z = 549 [M − H]− | $^1$H-NMR (600 MHz, DMSO-d6) δ [ppm]: 0.005 (0.51), 1.849 (0.72), 1.904 (0.43), 1.909 (0.44), 2.009 (0.42), 2.029 (0.63), 2.039 (0.75), 2.044 (0.67), 2.050 (0.81), 2.054 (0.88), 2.060 (0.72), 2.086 (1.13), 2.161 (0.42), 2.169 (0.75), 2.177 (0.71), 2.184 (0.86), 2.191 (0.78), 2.205 (0.57), 2.517 (0.75), 2.520 (0.73), 2.523 (0.59), 3.517 (0.55), 3.523 (0.43), 3.529 (0.50), 3.553 (0.60), 3.563 (1.79), 3.570 (1.96), 3.578 (0.98), 3.712 (0.61), 3.733 (0.80), 3.751 (0.73), 3.758 (0.72), 3.773 (0.86), 3.777 (1.00), 3.791 (1.38), 3.794 (1.30), 3.803 (1.20), 3.806 (1.23), 4.147 (0.64), 4.191 (0.42), 4.213 (0.68), 4.217 (0.52), 4.233 (0.62), 4.240 (1.21), 4.245 (0.85), 4.253 (2.20), 4.259 (2.32), 4.263 (2.48), 4.271 (1.51), 4.979 (0.68), 4.998 (0.65), 5.070 (0.63), 5.090 (0.60), 5.216 (0.57), 5.226 (1.21), 5.238 (1.18), 5.247 (0.54), 5.761 (0.76), 6.787 (2.54), 6.801 (2.68), 6.909 (1.25), 6.922 (2.41), 6.934 (1.36), 7.154 (1.22), 7.167 (1.95), 7.180 (1.02), |

TABLE 2-continued

| LC-MS and NMR data |
|---|
| NMR peak forms are stated as they appear in the spectra, possible higher order effects have not been considered. |
| NMR peak lists |
| $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. Further details of NMR-data description with peak lists you find in the publication "Citation of NMR Peaklist Data within Patent Applications" of the Research Disclosure Database Number 564025. |

| Example No | logP (Method L0) [a] | LC-MS (Method L2-L5) | NMR or NMR Peaklist |
|---|---|---|---|
| | | | 7.326 (1.05), 7.339 (1.97), 7.351 (1.01), 7.504 (1.06), 7.507 (1.14), 7.519 (2.23), 7.531 (1.20), 7.533 (1.22), 7.621 (16.00), 7.737 (2.63), 7.739 (2.75), 7.749 (2.42), 7.751 (2.42), 8.247 (1.17), 8.261 (2.15), 8.276 (1.14), 8.463 (4.46), 8.474 (4.71), 9.093 (1.35), 9.100 (1.40), 9.107 (1.41), 9.114 (1.26). |
| 292 | | LC-MS (Method L1): Rt = 0.92 min; MS (ESIneg): m/z = 546 [M − H]− | $^1$H-NMR (600 MHz, DMSO-d6) δ [ppm] 0.005 (0.57), 1.860 (0.51), 1.871 (0.77), 1.882 (0.62), 1.890 (0.44), 1.909 (0.41), 1.923 (0.56), 1.930 (0.52), 1.934 (0.54), 1.940 (0.70), 1.946 (0.52), 1.954 (0.72), 1.961 (0.49), 1.974 (0.44), 2.035 (0.45), 2.040 (0.47), 2.049 (0.93), 2.060 (0.97), 2.069 (0.59), 2.080 (0.42), 2.086 (1.00), 2.383 (0.46), 2.386 (0.48), 2.389 (0.45), 2.475 (0.54), 2.482 (0.97), 2.517 (1.22), 2.520 (1.25), 2.523 (0.98), 2.846 (0.43), 2.859 (0.55), 2.871 (0.67), 2.888 (0.55), 2.973 (0.59), 2.988 (0.60), 3.000 (0.43), 3.307 (0.67), 3.386 (0.42), 3.399 (0.44), 3.808 (0.49), 3.822 (0.49), 3.904 (0.48), 3.918 (0.47), 4.649 (0.59), 4.659 (0.66), 4.663 (0.57), 4.672 (0.44), 4.757 (0.59), 4.766 (0.67), 4.771 (0.55), 4.779 (0.49), 5.535 (0.60), 5.547 (0.59), 5.578 (0.65), 5.591 (0.64), 5.761 (4.08), 7.186 (0.77), 7.198 (0.64), 7.207 (0.58), 7.219 (1.00), 7.233 (0.76), 7237 (0.74), 7.239 (0.73), 7.244 (1.42), 7.248 (0.86), 7.251 (0.95), 7.254 (1.18), 7.258 (1.17), 7275 (0.96), 7.286 (0.49), 7.362 (0.89), 7.374 (0.74), 7.450 (0.61), 7.453 (0.66), 7.464 (0.59), 7.623 (0.42), 7.636 (0.92), 7.639 (2.00), 7.644 (16.00), 7.646 (12.97), 7.651 (1.35), 7.654 (1.10), 7.657 (1.10), 7.659 (0.98), 7.665 (0.95), 7.671 (0.88), 7.806 (1.15), 7.809 (1.53), 7.812 (1.33), 7.818 (1.12), 7.821 (1.26), 7.824 (0.95), 8.291 (0.84), 8.293 (0.83), 8.305 (0.81), 8.308 (0.78), 8.314 (0.95), 8.316 (0.95), 8.328 (0.80), 8.330 (0.76), 8.697 (6.20). |
| 293 | | LC-MS (Method L3): Rt = 4.24 min; m/z = 484/486 [M + 1]+ | $^1$H-NMR (400 MHz, DMSO-d6) δ 9.11 (d, J = 8.2 Hz, 1H), 8.61 (s, 1H), 8.22 (dd, J = 8.5, 1.4 Hz, 1H), 7.79 (dd, J = 7.1, 1.4 Hz, 1H), 7.64 (dd, J = 8.5, 7.1 Hz, 1H), 7.46 (d, J = 1.9 Hz, 1H), 7.36 (d, J = 6.8 Hz, 1H), 7.29 (d, J = 2.0 Hz, 1H), 7.21-7.14 (m, 1H), 6.97-6.88 (m, 1H), 6.80 (dd, J = 82, 1.1 Hz, 1H), 5.30-520 (m, 1H), 4.34-4.18 (m, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 2H), 3.06 (s, 6H), 2.79 (s, 6H), 2.27-2.14 (m, 1H), 2.13-1.97 (m, 1H). |
| 294 | | LC-MS (Method L3): Rt = 3.20 min; m/z = 501/503 [M + 1]+ | $^1$H-NMR (400 MHz, DMSO-d6) δ 9.10 (d, J = 8.2 Hz, 1H), 8.60 (s, 1H), 8.19 (dd, J = 8.5, 1.5 Hz, 1H), 7.72 (dd, J = 7.1, 1.5 Hz, 1H), 7.61 (dd, J = 8.4, 7.1 Hz, 1H), 7.36 (d, J = 6.7 Hz, 1H), 7.22-7.12 (m, 1H), 6.97-6.88 (m, 1H), 6.86-6.76 (m, 3H), 6. |
| 295 | | LC-MS (Method L1): Rt = 0.74 min; MS (ESIpos): m/z = 532 [M + H]+ | $^1$H-NMR (400 MHz, DMSO-d6) δ [ppm]: 1.900 (1.01), 1.909 (0.98), 2.019 (1.52), 2.030 (1.94), 2.148 (0.92), 2.162 (1.06), 2.178 (0.86), 2.194 (0.65), 2.399 (16.00), 3.169 (5.63), 3.232 (0.41), 3.305 (3.16), 3.314 (2.97), 3.479 (0.92), 3.506 (1.78), 3.533 (0.99), 3.711 (0.62), 3.734 (1.27), 3.755 (0.85), 3.789 (0.43), 3.811 (0.79), 3.829 (0.80), 3.845 (0.92), 3.856 (1.20), 3.866 (2.03), 3.879 (1.33), 3.894 (1.36), 3.905 (0.71), 4.165 (0.98), 4.256 (3.16), 4.374 (1.70), 5.034 (0.67), 5.214 (1.23), 5.226 (1.24), 6.773 (2.58), 6.793 (2.90), 6.882 (1.30), 6.901 (2.73), 6.919 (1.67), 7.135 (1.40), 7.156 (2.32), 7.174 (1.20), 7.296 (4.04), 7.311 (2.43), 7.323 (2.78), 7.424 (2.66), 7.441 (2.63), 7.460 (1.52), 7.478 (2.53), 7.499 (1.95), 7.614 (2.84), 7.632 (2.37), 8.137 (4.85), 8.291 (2.22), 8.313 (2.08), 8.357 (5.32), 9.028 (1.63), 9.032 (1.65), 9.048 (1.65). |
| 296 | | LC-MS (Method L6): Rt = 1.34 min; MS (ESIpos): m/z = 424 [M + H]+ | $^1$H-NMR (400 MHz, DMSO-d6) δ [ppm]: −0.008 (1.98), 0.008 (2.08), 3.063 (16.00), 4.243 (0.55), 4.262 (0.79), 4.270 (0.88), 4.283 (0.48), 5.248 (0.49), 5.268 (0.51), 6.785 (1.01), 6.805 (1.09), 6.905 (0.49), 6.923 (0.99), 6.939 (0.58), 7.150 (0.51), 7.167 (0.80), 7.348 (0.87), 7.366 (0.87), 7.378 (1.07), 7.396 (0.89), 7.428 (1.31), 7.447 (2.17), 7.465 (0.96), 7.574 (2.11), 7.591 (1.75), 7.595 (1.21), 7.614 (0.67), 7.632 (1.09), 7.652 (1.07), 7.697 (1.20), 7.701 (1.29), 7.715 (0.80), 7.719 (0.73), 8.174 (1.00), 8.177 (1.02), 8.195 (0.93), 8.199 (0.88), 8.583 (3.79), 9.068 (0.83), 9.088 (0.78). |
| 297 | | LC-MS (Method L1): Rt = 0.84 min; MS (ESIpos): m/z = 492 | $^1$H-NMR (600 MHz, DMSO-d6) δ [ppm]: 0.005 (0.54), 1.175 (0.51), 1.233 (0.88), 1.945 (0.48), 1.959 (1.35), 1.966 (0.68), 1.973 (1.44), 1.980 (1.50), 1.987 (0.67), 1.990 (0.61), 1.994 (1.45), 2.008 (0.53), 2.086 (2.18), 2.451 (0.53), 2.457 (0.63), 2.464 (1.16), 2.470 (1.43), 2.477 (1.47), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | [M + H]+ | 2.485 (1.96), 2.517 (0.87), 2.520 (0.88), 2.524 (0.72), 2.822 (0.63), 2.835 (1.18), 2.849 (1.35), 2.862 (1.68), 2.875 (0.78), 2.969 (1.03), 2.975 (1.07), 2.984 (1.12), 2.989 (1.08), 2.995 (0.85), 3.001 (0.81), 3.010 (0.76), 3.016 (0.67), 3.588 (0.86), 3.598 (2.43), 3.602 (2.62), 3.608 (3.14), 3.617 (1.76), 3.632 (0.42), 3.652 (3.34), 3.661 (4.14), 3.669 (1.71), 4.909 (0.68), 5.519 (0.77), 5.533 (2.21), 5.546 (2.18), 5.559 (0.73), 7.191 (0.82), 7.203 (2.41), 7.213 (3.76), 7.216 (3.96), 7.225 (2.72), 7.227 (2.72), 7.237 (1.21), 7.262 (3.11), 7.273 (1.90), 7.357 (2.79), 7.369 (2.30), 7.526 (2.39), 7.538 (2.98), 7.540 (2.73), 7.552 (2.48), 7.608 (2.68), 7.611 (5.84), 7.614 (4.57), 7.628 (15.29), 7.632 (11.06), 7.741 (3.49), 7.713 (3.42), 7.753 (3.14), 7.755 (2.91), 8.061 (1.26), 8.137 (16.00), 8.392 (2.82), 8.394 (2.80), 8.407 (2.71), 8.573 (9.90), 8.877 (2.88), 8.891 (2.74). |
| 298 | | LC-MS (Method L1): Rt = 0.94 min; MS | $^1$H-NMR (600 MHz, DMSO-d6) δ [ppm]: 0.005 (0.41), 1.942 (0.52), 1.957 (1.44), 1.963 (0.74), 1.970 (1.55), 1.977 (1.60), 1.984 (0.73), 1.991 (1.56), 2.005 (0.56), 2.450 (0.57), 2.456 (0.67), 2.463 (1.22), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 506 [M + H]+ | 2.469 (1.51), 2.476 (1.48), 2.484 (1.77), 2.517 (0.76), 2.520 (0.73), 2.523 (0.57), 2.826 (0.69), 2.839 (1.33), 2.852 (1.51), 2.866 (1.87), 2.879 (0.87), 2.972 (1.15), 2.978 (1.19), 2.987 (1.24), 2.993 (1.19), 2.999 (0.94), 3.004 (0.89), 3.013 (0.85), 3.019 (0.75), 3.338 (3.68), 3.398 (0.51), 3.558 (0.53), 3.568 (2.60), 3.576 (6.35), 3.585 (4.12), 3.684 (1.95), 3.692 (4.19), 3.701 (3.62), 3.710 (1.33), 5.515 (0.84), 5.528 (2.43), 5.541 (2.41), 5.555 (0.80), 7.195 (0.86), 7.207 (2.64), 7.216 (3.91), 7.219 (4.26), 7.228 (2.98), 7.230 (2.98), 7.240 (1.27), 7.265 (3.39), 7.276 (2.07), 7.355 (2.95), 7.366 (2.41), 7.533 (1.96), 7.545 (2.81), 7.559 (2.13), 7.613 (4.94), 7.617 (4.00), 7.629 (15.00), 7.632 (10.79), 7.748 (3.54), 7.760 (3.14), 8.100 (1.02), 8.136 (6.62), 8.382 (2.78), 8.396 (2.64), 8.586 (8.69), 8.913 (2.35), 8.927 (2.27). |
| 299 | | LC-MS (Method L6): Rt = 1.72 min; MS | $^1$H-NMR (400 MHz, DMSO-d6) δ [ppm] = 11.89 (d, 1H), 8.62 (s, 1H), 8.16 (d, 1H), 7.70 (d, 1H), 7.58-7.66 (m, 3H), 7.50-7.58 (m, 1H), 7.10-7.30 (m, 4H), 5.51-5.65 (m, 1H), 4.70 (br |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 546 [M + H]+ | d, 1H), 3.95 (br d, 1H), 3.17 (br s, 1H), 2.76-2.99 (m, 2H), 2.30-2.43 (m, 3H), 1.88-2.08 (m, 4H). |
| 300 | 2.6 | LC-MS (Method L1): Rt = 1.14 min; MS (ESIpos): m/z = 546 [M + H]+ | $^1$H-NMR (500 MHz, DMSO-d6) δ [ppm]: 2.060 (0.42), 2.066 (0.45), 2.075 (0.47), 2.088 (0.65), 2.094 (0.56), 2.183 (0.44), 2.193 (0.60), 2.203 (0.58), 2.210 (0.55), 2.443 (1.65), 2.460 (1.72), 3.126 (0.42), 3.139 (0.95), 3.155 (0.91), 3.168 (0.40), 3.453 (1.32), 3.468 (1.45), 3.473 (1.52), 3.487 (1.39), 3.880 (1.72), 3.887 (1.73), 3.902 (1.54), 3.909 (1.48), 4.231 (0.98), 4.237 (0.78), 4.247 (1.45), 4.254 (1.38), 4.268 (0.84), 4.653 (1.89), 4.662 (1.90), 5.254 (0.43), 5.266 (0.90), 5.281 (0.89), 6.781 (1.78), 6.797 (1.91), 6.891 (0.89), 6.906 (1.77), 6.921 (0.96), 7.149 (0.84), 7.152 (0.86), 7.166 (1.42), 7.180 (0.70), 7.389 (1.48), 7.403 (1.38), 7.651 (16.00), 7.694 (1.17), 7.708 (1.63), 7.725 (1.38), 7.846 (1.88), 7.859 (1.51), 8.297 (1.59), 8.313 (1.46), 8.833 (5.84), 9.232 (1.60), 9.248 (1.53). |
| 301 | 3.3 | LC-MS (Method L1): Rt = 1.21 min; MS (ESIpos): m/z = 576 [M + H]+ | $^1$H-NMR (500 MHz, DMSO-d6) δ [ppm]: 0.006 (0.68), 2.065 (0.46), 2.072 (0.53), 2.084 (0.50), 2.093 (0.68), 2.099 (0.58), 2.106 (0.41), 2.204 (0.47), 2.213 (0.62), 2.222 (0.62), 2.230 (0.60), 2.518 (0.74), 3.356 (1.31), 3.379 (1.39), 3.420 (1.28), 3.443 (1.40), 3.759 (0.97), 3.785 (1.89), 3.799 (2.05), 3.813 (2.09), 3.819 (1.80), 4.030 (0.93), 4.054 (2.69), 4.066 (2.67), 4.084 (2.39), 4.108 (0.98), 4.252 (1.06), 4.258 (0.86), 4.268 (1.59), 4.275 (1.59), 4.288 (0.92), 5.257 (0.45), 5.269 (0.98), 5.284 (0.95), 5.295 (0.42), 6.789 (1.89), 6.805 (2.04), 6.916 (0.91), 6.931 (1.88), 6.946 (1.06), 7.155 (0.89), 7.158 (0.91), 7.172 (1.53), 7.186 (0.73), 7.396 (1.60), 7.410 (1.49), 7.641 (16.00), 7.674 (1.24), 7.688 (1.77), 7.705 (1.45), 7.813 (1.96), 7.815 (1.98), 7.827 (1.59), 8.614 (1.68), 8.631 (1.59), 8.696 (5.91), 9.169 (1.74), 9.186 (1.68). |
| 302 | | LC-MS (Method L1): Rt = 1.32 min; MS (ESIpos): m/z = 560 [M + H]+ | $^1$H-NMR (500 MHz, DMSO-d6) δ [ppm]: 0.006 (1.48), 1.977 (2.45), 1.985 (3.20), 2.061 (0.94), 2.067 (1.00), 2.073 (1.28), 2.089 (1.37), 2.094 (1.18), 2.101 (0.84), 2.107 (0.62), 2.196 (0.68), 2.205 (1.01), 2.212 (1.42), 2.222 (1.44), 2.230 (1.70), 2.240 (1.49), 2.252 (3.88), 2.271 (3.21), 2.292 (0.43), 2.361 (0.50), 2.518 (1.55), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.522 (1.14), 2.635 (0.56), 2.976 (2.42), 2.998 (2.58), 3.014 (2.43), 3.037 (2.48), 3.530 (3.55), 3.548 (2.59), 3.554 (3.28), 4.225 (0.63), 4.230 (0.76), 4.247 (2.09), 4.253 (1.54), 4.264 (1.81), 4.271 (1.84), 4.281 (1.90), 4.287 (1.63), 4294 (1.74), 4.303 (0.69), 4.309 (0.76), 4.316 (0.55), 4.414 (3.03), 5.247 (0.90), 5.259 (1.92), 5.274 (1.85), 5.285 (0.82), 6.790 (3.65), 6.806 (3.88), 6.922 (1.77), 6.936 (3.59), 6.951 (2.00), 7.158 (1.76), 7.160 (1.81), 7.174 (2.97), 7.188 (1.47), 7.191 (1.38), 7.393 (3.10), 7.408 (2.87), 7.625 (10.72), 7.629 (16.00), 7.639 (5.39, 7.643 (5.55), 7.646 (2.39), 7.726 (0.54), 7.729 (0.50), 7.740 (2.23), 7.755 (3.44), 7.771 (2.93), 7.838 (3.90), 7.840 (4.07), 7.852 (2.90), 8.405 (3.15), 8.420 (2.90), 8.693 (11.68), 9.142 (3.37), 9.159 (3.24). |
| 303 | 3.94 | | $^1$H-NMR (399, 9532 MHz, DMSO): δ = 9.1897 (3.07); 9.1697 (3.08); 8.6999 (11.32); 8.267 (3.04); 8.2457 (3.34); 8.0999 (0.52); 8.0853 (0.45); 7.842 (3.13); 7.8244 (4.12); 7.72 (2.82); 7.6994 (3.57); 7.681 (2.24); 7.4668 (0.34); 7.4303 (0.34); 7.3979 (2.99); 7.3791 (3.33); 7.3415 (5.08); 7.3244 (4.63); 7.3196 (4.47); 7.3043 (1.56); 7.299 (1.58); 7.2806 (2.03); 7.2747 (2.74); 7.2519 (1.45); 7.1994 (1.49); 7.1795 (3.11); 7.1614 (1.93); 6.936 (2.19); 6.9174 (3.63); 6.8989 (1.79); 6.8126 (4.03); 6.7941 (3.62); 6.5851 (0.63); 6.5692 (0.59); 5.2851 (0.87); 5.2712 (1.94); 5.2526 (2.07); 5.238 (0.95); 4.3128 (0.7); 4.296 (1.79); 4.2741 (2.81); 4.253 (1.76); 4.2464 (2.03); 4.2239 (0.71); 3.9767 (2.68); 3.968 (2.61); 3.3189 (223.97); 3.2442 (2.16); 3.2141 (4.55); 3.1853 (2.46); 2.959 (1.92); 2.9418 (6.23); 2.9307 (3.17); 2.9237 (3.11); 2.9044 (1.79); 2.8953 (1.74); 2.6699 (3.71); 2.5052 (502.23); 2.5009 (661.81); 2.4966 (520.68); 2.3275 (3.85); 2.266 (0.88); 2.2232 (1.38); 2.2135 (1.48); 2.2008 (1.46); 2.1924 (1.27); 2.0867 (1.57); 2.0741 (1.82); 1.2862 (0.38); 1.2687 (0.48); 1.1687 (2.99); 1.1489 (14.24); 1.1439 (16); 1.1337 (15.75); 1.1285 (15.3); 0.9796 (0.37); 0.1461 (0.77); −0.0001 (185.99); −0.1498 (0.83) |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 304 | 4.03 | | $^1$H-NMR (399, 9532 MHz, DMSO): δ = 9.1774 (0.67); 9.1576 (0.76); 8.5944 (2.4); 8.2724 (1.07); 8.2562 (1.18); 7.9525 (2.49); 7.7608 (0.4); 7.7376 (0.43); 7.7214 (0.76); 7.705 (2.49); 7.689 (1.82); 7.6851 (2.8); 7.6687 (1.86); 7.6537 (0.93); 7.5047 (0.32); 7.4854 (0.91); 7.4653 (1.16); 7.4546 (0.67); 7.4446 (1.44); 7.4361 (1.53); 7.4247 (0.93); 7.4155 (0.83); 7.3794 (1.2); 7.3566 (1.16); 7.3429 (0.88); 7.3272 (1.2); 7.3088 (0.58); 7.1857 (0.62); 7.1676 (1.13); 7.1481 (0.72); 6.9174 (0.63); 6.8992 (0.95); 6.8804 (0.48); 6.8023 (1.65); 6.7815 (1.43); 5.2499 (0.69); 5.2313 (0.63); 4.2592 (0.98); 4.2328 (0.72); 3.9863 (0.92); 3.3191 (221.03); 3.2639 (0.83); 3.2244 (0.64); 3.1788 (0.44); 2.9416 (2.82); 2.9215 (1.53); 2.8905 (16); 2.7311 (14.48); 2.6702 (3.3); 2.5232 (7.65); 2.5054 (445.22); 2.5012 (567.66); 2.497 (406.38); 2.3321 (2.56); 2.3276 (3.26); 2.2056 (0.52); 2.1956 (0.59); 2.1834 (0.61); 2.0737 (0.9); 1.1689 (1.1); 1.1501 (5.7); 1.135 (5.9); 0.1463 (0.73); 0.0077 (6.72). −0.0003 (158.9); −0.1492 (0.77) |
| 305 | 4.13 | | $^1$H-NMR (399, 9532 MHz, DMSO): δ = 9.0348 (1.54); 9.027 (1.53); 9.0145 (1.71); 8.5999 (5.17); 8.5952 (4.9); 8.3156 (0.56); 8.2763 (2.51); 8.2726 (2.47); 8.2556 (2.81); 8.2518 (2.69); 7.761 (0.83); 7.7408 (1.05); 7.7366 (1.17); 7.7204 (1.9); 7.7118 (3.55); 7.7079 (3.89); 7.7027 (4.15); 7.6918 (4.33); 7.6878 (4.41); 7.6822 (4.39); 7.6687 (4.22); 7.6652 (4.79); 7.651 (2.14); 7.505 (0.9); 7.4854 (1.99); 7.4656 (2.95); 7.4594 (1.58); 7.4449 (3.55); 7.4401 (3.42); 7.4255 (3.77); 7.4152 (3.13); 7.3825 (1.69); 7.3796 (1.25); 7.3635 (1.11); 7.3418 (1.95); 7.3288 (2.47); 7.3136 (1.38); 7.2798 (1.9); 7.2633 (3.48); 7.2506 (1.55); 7.2324 (3.2); 7.2181 (3.48); 7.2031 (2.13); 7.1855 (0.81); 7.1649 (0.41); 7.1441 (0.33); 6.5786 (0.32); 5.5633 (0.47); 5.5512 (0.67); 5.5336 (1.2); 5.5215 (1.33); 5.5153 (1.19); 3.9808 (2.15); 3.6332 (0.34); 3.3942 (0.37); 3.3649 (0.63); 3.3197 (538.15); 3.2493 (2.06); |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.221 (1.81); 3.1926 (1); 3.1655 (0.46); 3.0162 (0.77); 2.9635 (3.49); 2.9414 (4.71); 2.9076 (2.72); 2.8901 (1.88); 2.8843 (2.04); 2.8632 (1.51); 2.8439 (1.23); 2.8236 (0.74); 2.761 (0.33); 2.7302 (1.28); 2.7155 (0.39); 2.6747 (4.3); 2.67 (5.87); 2.6656 (4.46); 2.6168 (0.41); 2.5905 (0.52); 2.5232 (16.08); 2.5054 (777.81); 2.501 (1009.77); 2.4966 (729.53); 2.4266 (0.57); 2.3322 (4.4); 2.3277 (5.87); 2.3234 (4.4); 2.2742 (0.35); 2.2675 (0.52); 2.2222 (0.32); 2.1718 (0.36); 2.105 (1.65); 2.0945 (1.09); 2.0739 (3); 1.9705 (0.53); 1.9506 (1.22); 1.9296 (1.19); 1.919 (1.2); 1.8967 (1.12); 1.8764 (0.43); 1.2914 (0.37); 1.2694 (0.4); 1.1687 (2.59); 1.1444 (16); 1.1291 (15.53); 1.0966 (0.51); 0.9654 (0.39); 0.1461 (1.27); 0.0078 (11.48); −0.0002 (299.28); −0.0082 (14.69); −0.1498 (1.31) |
| 306 | 4.03 | | $^{1}$H-NMR (399, 9532 MHz, DMSO): δ = 9.0457 (2.18); 9.0244 (2.21); 8.7059 (8.46); 8.3157 (0.33); 8.2677 (2.18); 8.2494 (2.31); 8.0868 (0.34); 7.8391 (2.16); 7.8242 (2.96); 7.7196 (2.12); 7.6988 (2.55); 7.6804 (1.63); 7.4555 (1.75); 7.4412 (2.02); 7.3429 (3.69); 7.3267 (3.62); 7.3056 (1.37); 7.2952 (1.61); 7.2766 (4); 726 (2.09); 7.2539 (1.54); 7.2464 (3.22); 7.2405 (3.62); 7.2316 (3.27); 7.2236 (2.72); 7.2048 (0.59); 7.1689 (0.57); 7.1519 (0.6); 7.1375 (0.42); 6.5782 (0.53); 5.5813 (0.59); 5.5623 (1.71); 5.5425 (1.78); 5.5244 (0.59); 3.9738 (1.83); 3.3197 (331.29); 3.2386 (1.55); 3.2294 (1.7); 3.2119 (1.9); 3.2003 (1.93); 3.0346 (0.53); 3.0265 (0.64); 3.0133 (0.66); 2.9954 (1.02); 2.9859 (1.13); 2.9726 (3.04); 2.9417 (5.18); 2.917 (2.47); 2.897 (1.7); 2.8769 (1.23); 2.8572 (0.9); 2.8366 (0.65); 2.7309 (0.37); 2.6701 (3.8); 2.5751 (0.52); 2.5672 (0.55); 2.5566 (1); 2.5452 (1.54); 2.5053 (506.49); 2.501 (657.35); 2.4967 (480.65); 2.355 (0.43); 2.3278 (3.92); 2.2456 (0.33); 2.2001 (0.4); 2.1674 (0.46); 2.0952 (0.44); 2.074 (1.44); 1.9927 (0.53); 1.9724 (1.13); 1.9617 (0.71); 1.9517 (1.18); 1.9397 (1.1); 1.9195 (1.05); 1.8986 (0.43); 1.2999 (0.38); 1.2692 (0.54); 1.1689 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.6); 1.145 (16); 1.1296 (15.96); 1.1004 (0.93); 0.9694 (0.35); 0.1465 (0.88); 0.0077 (7.81); −0.0003 (197.85); −0.1495 (0.91) |
| 307 | | LC-MS (Method L3): Rt = 4.12 min; m/z = 501/503 [M + 1]+ | $^1$H-NMR (400 MHz, DMSO-d6) δ 9.10 (d, J = 8.2 Hz, 1H), 8.58 (s, 1H), 8.19 (dd, J = 8.5, 1.4 Hz, 1H), 7.74 (dd, J = 7.1, 1.4 Hz, 1H), 7.63 (dd, J = 8.5, 7.1 Hz, 1H), 7.44 (d, J = 82 Hz, 1H), 7.40-7.31 (m, 2H), 7.24-7.13 (m, 2H), 6.97-6.88 (m, 1H), 6. |
| 308 | | LC-MS (Method L3): Rt = 4.61 min; m/z = 535/537 [M + 1]+ | $^1$H-NMR (400 MHz, DMSO-d6) δ 9.10 (d, J = 8.2 Hz, 1H), 8.63 (s, 1H), 8.21 (dd, J = 8.5, 1.3 Hz, 1H), 7.78 (dd, J = 7.1, 1.3 Hz, 1H), 7.63 (s, 3H), 7.37 (d, J = 7.6 Hz, 1H), 722-7.13 (m, 1H), 6.97-6.90 (m, 1H), 6.80 (dd, J = 8.2, 0.9 Hz, 1H), 5.30-5. |
| 309 | | LC-MS (Method L2): Rt = 3.08 min; m/z = 564 [M + H]+ | $^1$H-NMR (400 MHz, DMSO-d6) δ 9.10 (d, J = 7.9 Hz, 1H), 8.49 (s, 1H), 8.31, (d, J = 9.4 Hz, 1H), 7.67-7.60 (m, 2H), 7.44-7.31 (m, 2H), 7.25-7.11 (m, 2H), 6.90 (t, J = 7.4 Hz, 1H), 6.78 (d, J = 8.2 1H), 5.23 (q, J = 6.0 Hz, 1H), 4.31-4.18 (m, 2H), |
| 310 | | LC-MS (Method L2): Rt = 3.26 min; m/z = 564/566 (Cl2 pattern) [M + H]+ | $^1$H-NMR (400 MHz, DMSO-d6) δ 9.20 (d, J = 8.1 Hz, 1H), 8.71 (s, 1H), 8.46, (d, J = 8.9 Hz, 1H), 7.98 (d, J = 9.1 Hz, 1H), 7.70 (t, J = 1.9 Hz, 1H), 7.40-7.30 (m, 3H), 7.20-7.13 (m, 1H), 6.95-6.88 (m, 1H), 6.82-6.76 (m, 1H), 5.28-5.20 (m, 1H), 4.32 |
| 311 | | LC-MS (Method L3): Rt = 4.51 min; m/z = 501/503 [M + 1]+ | $^1$H-NMR (400 MHz, DMSO-d6) δ 9.10 (d, J = 8.2 Hz, 1H), 8.61 (s, 1H), 8.17 (dd, J = 8.5, 1.4 Hz, 1H), 7.72 (dd, J = 7.1, 1.4 Hz, 1H), 7.67-7.58 (m, 2H), 7.51 (dd, J = 8.3, 2.1 Hz, 1H), 7.37 (d, J = 6.8 Hz, 1H), 7.23 (d, J = 8.4 Hz, 1H), 7.21-7.12 (m, 1H |
| 312 | | LC-MS (Method L3): Rt = 4.72 min; m/z = 453 [M + 1]+ | $^1$H-NMR (400 MHz, DMSO-d6) δ 9.09 (d, J = 8.2 Hz, 1H), 8.57 (s, 1H), 8.15 (dd, J = 8.3, 1.6 Hz, 1H), 7.67-7.56 (m, 2H), 7.36 (d, J = 7.5 Hz, 1H), 7.21-7.10 (m, 2H), 6.96-6.89 (m, 1H), 6.83-6.77 (m, 1H), 6.75-6.68 (m, 2H), 6.58-6.52 (m, 1H), 5.6 |
| 313 | | LC-MS (Method L2): Rt = | $^1$H-NMR (400 MHz, DMSO-d6) δ 9.16 (d, J = 8.2 Hz, 1H), 8.60 (s, 1H), 8.32 (m, 1H), 7.81-7.68 (m, 2H), 7.58-7.47 |

TABLE 2-continued

| LC-MS and NMR data |
|---|
| NMR peak forms are stated as they appear in the spectra, possible higher order effects have not been considered. |
| NMR peak lists |
| $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily. The $^{1}$H-NMR peak lists are similar to classical $^{1}$H-NMR prints and contains therefore usually all peaks, which are listed at classical NMR-interpretation. Additionally they can show like classical $^{1}$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation. Further details of NMR-data description with peak lists you find in the publication "Citation of NMR Peaklist Data within Patent Applications" of the Research Disclosure Database Number 564025. |

| Example No | logP (Method L0) [a] | LC-MS (Method L2-L5) | NMR or NMR Peaklist |
|---|---|---|---|
| | | 3.43 min; m/z = 502 [M + H]+. | (m, 1H), 7.37 (d, J = 7.1 Hz, 1H), 7.25-7.12 (m, 3H), 6.92 (m, 1H), 6.82-6.76 (m, 1H), 5.26 (q, J = 5.7 Hz, 1H), 4.26 (m, 2H), 3.88 (t, |
| 314 | | LC-MS (Method L2): Rt = 4.05 min; m/z = 602 [M + H]+ | $^{1}$H-NMR (400 MHz, DMSO-d6) δ 9.23 (dd, J = 8.1, 4.6 Hz, 1H), 8.69 (d, J = 4.0 Hz, 1H), 8.49 (d, J = 9.0 Hz, 1H), 8.01 (d, J = 9.0 Hz, 1H), 7.74 (dd, J = 8.1, 1.4 Hz, 1H), 7.56-7.41 (m, 1H), 7.40-7.23 (m, 2H), 7.17 (t, J = 7.7 Hz, 1H), 6.99-6.86 (m, 1 |
| 315 | | LC-MS (Method L2): Rt = 3.80 min; m/z = 560 [M + H]+ | $^{1}$H-NMR (400 MHz, DMSO-d6) δ 9.14 (dd, J = 8.1, 4.3 Hz, 1H), 8.60 (d, J = 2.5 Hz, 1H), 8.45 (d, J = 8.5 Hz, 1H), 7.95 (d, J = 9.1 Hz, 1H), 7.72 (dd, J = 8.1, 1.5 Hz, 1H), 7.48-7.40 (m, 1H), 7.37-7.27 (m, 2H), 7.15 (t, J = 7.7 Hz, 1H), 6.93-6.87 (m, 1 |
| 316 | | LC-MS (Method L3): Rt = 4.65 min; m/z = 526/528 [M + H]+ | $^{1}$H-NMR (400 MHz, DMSO-d6) δ 9.15 (d, J = 8.1 Hz, 1H), 8.65 (s, 1H), 8.20 (d, J = 2.4 Hz, 1H), 7.87 (d, J = 2.4 Hz, 1H), 7.67 (s, 3H), 7.36 (d, J = 6.7 Hz, 1H), 7.21-7.14 (m, 1H), 6.92 (td, J = 7.5, 1.2 Hz, 1H), 6.80 (dd, J = 8.2, 1.1 Hz, 1H), 5.28-5.2 |

TABLE 2-continued

LC-MS and NMR data
NMR peak forms are stated as they appear in the spectra, possible higher order effects have not been considered.
NMR peak lists
$^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.
The peak list of an example has therefore the form:
$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily. The $^{1}$H-NMR peak lists are similar to classical $^{1}$H-NMR prints and contains therefore usually all peaks, which are listed at classical NMR-interpretation. Additionally they can show like classical $^{1}$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation. Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 317 | | LC-MS (Method L6): Rt = 1.40 min; MS (ESIpos): m/z = 534 [M + H]+ | $^{1}$H-NMR (400 MHz, DMSO-d6) δ [ppm]: −0.149 (1.21), −0.008 (16.00), 0.008 (10.22), 0.146 (1.17), 1.679 (1.28), 1.768 (1.70), 2.062 (1.06), 2.328 (2.24), 2.367 (1.03), 2.524 (9.61), 2.671 (2.06), 2.711 (1.03), 3.648 (2.70), 3.664 (3.87), 3.681 (2.16), 3.818 (1.95), 3.833 (2.52), 3.851 (2.87), 4.252 (2.94), 4.451 (2.50), 5.176 (1.63), 5.755 (3.23), 6.818 (1.81), 6.837 (1.70), 6.894 (1.31), 7.193 (1.60), 7.294 (1.38), 7.620 (3.48), 7.628 (4.43), 7.672 (1.77), 7.692 (1.42), 7.833 (2.98), 7.865 (1.63), 7.970 (6.14), 8.217 (1.67), 8.234 (1.67), 8.477 (2.98), 8.881 (10.47), 9.374 (0.85). |
| 318 | | LC-MS (Method L1): Rt = 0.81 min; MS (ESIpos): m/z = 548 [M + H]+ | $^{1}$H-NMR (400 MHz, DMSO-d6) δ [ppm]: −0.149 (0.83), −0.008 (6.59), 0.146 (0.79), 1.156 (0.87), 1.175 (1.80), 1.192 (0.87), 1.235 (0.41), 1.660 (1.14), 1.679 (1.24), 1.690 (1.49), 1.710 (1.37), 1.903 (1.53), 1.988 (3.52), 1.999 (1.41), 2.012 (2.20), 2.028 (2.14), 2.048 (1.84), 2.058 (1.57), 2.165 (1.18), 2.181 (1.02), 2.197 (0.75), 2.327 (1.16), 2.366 (0.85), 2.393 (1.28), 2.411 (1.60), 2.428 (1.39), 2.669 (1.26), 2.709 (0.81), 3.162 (2.53), 3.175 |

TABLE 2-continued

LC-MS and NMR data

NMR peak forms are stated as they appear in the spectra, possible higher order effects have not been considered.

NMR peak lists $^1H$-NMR data of selected examples are written in form of $^1H$-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1H$ spectra, we use tetramethylsilane and/or the chemical shift of the solvent used, especially in the case of spectra measured in DMSO. Therefore in NMR peak lists, tetramethylsilane peak can occur but not necessarily.

The $^1H$-NMR peak lists are similar to classical $^1H$-NMR prints and contains therefore usually all peaks, which are listed at classical NMR-interpretation.

Additionally they can show like classical $^1H$-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1H$-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1H$-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (2.69), 3.381 (0.77), 3.408 (1.45), 3.421 (1.62), 3.440 (1.20), 3.467 (1.26), 3.483 (3.03), 3.494 (2.47), 3.510 (2.92), 3.528 (1.91), 3.676 (1.47), 3.697 (2.53), 3.716 (2.92), 3.724 (2.72), 3.742 (3.19), 3.768 (1.62), 4.020 (0.71), 4.038 (0.79), 4.073 (0.66), 4.087 (0.68), 4.172 (0.56), 4.254 (4.73), 4.264 (2.90), 4.717 (2.13), 4.729 (4.29), 4.742 (2.05), 5.193 (0.81), 5.207 (1.74), 5.226 (1.76), 5.240 (0.87), 5.754 (0.50), 6.777 (3.46), 6.797 (3.81), 6.896 (1.66), 6.913 (3.44), 6.931 (1.97), 7.144 (1.84), 7.161 (2.90), 7.180 (1.41), 7.319 (2.94), 7.338 (2.71), 7.477 (2.16), 7.496 (2.96), 7.517 (2.65), 7.606 (4.71), 7.610 (5.82), 7.619 (16.00), 7.623 (9.06), 7.711 (3.79), 7.727 (3.19), 7.873 (0.50), 8.267 (3.11), 8.288 (2.92), 8.442 (11.23), 9.024 (3.13), 9.044 (3.03). |
| 319 | | LC-MS (Method L6): Rt = 1.94 min; MS (ESIpos): m/z = 500 | $^1H$-NMR (400 MHz, DMSO-d6) δ [ppm]: 2.062 (2.28), 2.197 (2.14), 2.209 (2.13), 2.218 (2.01), 2.327 (0.67), 2.670 (0.64), 3.876 (16.00), 4.213 (1.25), 4.234 (3.18), 4.254 (4.91), 4.262 (4.94), 5.244 (2.95), 5.261 (2.87), 6.776 (4.46), 6.796 (4.81), 6.893 (2.44), 6.911 (4.65), 6.930 (2.84), |

TABLE 2-continued

LC-MS and NMR data

NMR peak forms are stated as they appear in the spectra, possible higher order effects have not been considered.

NMR peak lists $^1H$-NMR data of selected examples are written in form of $^1H$-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1H$ spectra, we use tetramethylsilane and/or the chemical shift of the solvent used, especially in the case of spectra measured in DMSO. Therefore in NMR peak lists, tetramethylsilane peak can occur but not necessarily.

The $^1H$-NMR peak lists are similar to classical $^1H$-NMR prints and contains therefore usually all peaks, which are listed at classical NMR-interpretation.

Additionally they can show like classical $^1H$-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1H$-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1H$-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | $[M + H]^+$ | 7.142 (2.94), 7.161 (4.44), 7.179 (2.33), 7.351 (7.88), 7.369 (5.89), 7.391 (2.42), 7.416 (5.69), 7.423 (5.81), 7.435 (5.30), 7.454 (2.26), 7.537 (3.95), 7.553 (3.04), 7.629 (3.41), 7.645 (5.92), 7.671 (3.87), 7.691 (4.59), 7.709 (2.20), 8.265 (4.40), 8.285 (4.07), 8.575 (9.62), 9.149 (3.43), 9.168 (3.26). |
| 320 | | LC-MS (Method L1): Rt = 1.27 min; MS (ESIpos): m/z = 590 $[M + H]^+$ | $^1H$-NMR (500 MHz, DMSO-d6) δ [ppm]: −0.006 (0.66), 0.006 (0.45), 0.992 (6.88), 1.006 (14.64), 1.020 (7.28), 1.175 (0.69), 1.914 (0.43), 1.921 (0.59), 1.928 (1.00), 1.935 (0.80), 1.941 (0.98), 1.949 (0.81), 1.963 (0.80), 1.975 (1.05), 1.988 (2.98), 1.999 (2.31), 2.015 (2.16), 2.027 (1.48), 2.044 (1.11), 2.050 (0.91), 2.056 (0.64), 2.169 (0.46), 2.176 (0.69), 2.186 (0.98), 2.196 (1.00), 2.204 (0.98), 2.214 (0.73), 2.221 (0.48), 2.363 (0.83), 2.379 (0.99), 2.392 (0.95), 2.407 (0.54), 2.519 (0.54), 3.335 (0.80), 3.347 (1.08), 3.351 (1.20), 3.361 (1.13), 3.375 (0.71), 3.865 (0.61), 3.878 (1.35), 3.895 (1.41), 3.903 (1.08), 3.911 (1.18), 3.917 (0.96), 3.925 (2.97), 3.936 (3.39), 3.939 (3.31), 3.950 (2.96), 3.957 (0.88), 3.964 (0.87), 3.972 (0.69), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 4.173 (0.74), 4.201 (0.52), 4206 (0.61), 4.223 (1.57), 4.229 (1.11), 4.240 (1.23), 4.246 (1.02), 4.259 (1.03), 4.266 (1.36), 4.272 (1.21), 4279 (1.31), 4.288 (0.64), 4.294 (0.66), 4.301 (0.49), 4.604 (1.49), 4.615 (1.69), 4.621 (1.65), 4.631 (1.40), 5.243 (0.66), 5.254 (1.44), 5.270 (1.42), 5.281 (0.66), 5.754 (0.82), 6.792 (2.76), 6.807 (2.92), 6.809 (2.90), 6.925 (1.36), 6.927 (1.41), 6.940 (2.72), 6.942 (2.70), 6.955 (1.55), 6.957 (1.49), 7.168 (1.42), 7.171 (1.43), 7.185 (2.32), 7.199 (1.13), 7.201 (1.08), 7.397 (2.28), 7.411 (2.13), 7.636 (4.40), 7.639 (7.81), 7.642 (16.00), 7.645 (6.46), 7.653 (2.33), 7.667 (2.83), 7.670 (2.89), 7.684 (2.31), 7.725 (0.57), 7.729 (0.54), 7.819 (2.92), 7.822 (3.03), 7.834 (2.48), 7.836 (2.40), 8.343 (2.59), 8.345 (2.59), 8.360 (2.42), 8.362 (2.31), 8.680 (9.87), 9.196 (2.58), 9.212 (2.50). |
| 321 | 3.37 | | $^1$H-NMR (399, 953 MHz, CDCl3) δ = 9.1126 (4.72). 9.0958 (4.88). 9.0618 (1.78). 9.0408 (2.05). 8.1159 (0.51). 8.1073 (0.56). 8.0994 (0.58). 8.0917 (0.65). 8.0616 (0.48). 8.0511 (0.51). 8.0462 (0.52). 8.0366 (0.54). 7.9006 (1.45). 7.881 (1.8). 7.8347 (1.41). 7.8147 (2.11). 7.7661 (4.49). 7.761 (4.21). 7.7476 (6.54). 7.7434 (5.71). 7.7362 (3.9). 7.7155 (2.95). 7.6982 (1.01). 7.5821 (4.98). 7.5623 (5.73). 7.52 (0.37). 7.5044 (1.22). 7.4823 (1.25). 7.3467 (2.17). 7.3277 (5.49). 7.3079 (3.8). 7.2837 (3.47). 7.2612 (26.99). 7.2424 (6.4). 7.2359 (6.6). 7.2239 (5.17). 7.2163 (7.07). 7.1926 (3.1). 7.1696 (0.93). 6.9454 (1.11). 6.9262 (1.9). 6.9079 (0.91). 6.8815 (1.42). 6.8676 (6.02). 6.847 (7.37). 6.8332 (1.46). 6.8255 (2.03). 6.7513 (0.44). 6.7294 (0.44). 6.6499 (0.51). 6.6309 (0.48). 5.463 (0.52). 5.4511 (1.1). 5.4396 (1.55). 5.4277 (2.06). 5.4166 (1.59). 5.4055 (1.17). 5.3934 (0.57). 5.3772 (0.45). 5.3618 (0.93). 5.3447 (0.94). 5.3304 (0.42). 5.2987 (1.1). 4.345 (1.6). 4.327 (2.15). 4.3161 (2.64). 4.2918 (0.9). 4.284 (0.68). 4.2127 (0.88). 4.189 (2.02). 4.1633 (2.43). 4.1436 (2.4). 4.1261 (3.47). 4.1083 (3.64). 4.0904 (1.16). 3.2611 (13.51). 3.0936 (5.9). 3.0503 (16). 3.0032 (13.51). 2.9661 (13.47). |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.9245 (13.29). 2.3901 (0.54). 2.38 (0.86). 2.3661 (1.02). 2.3536 (1.63). 2.3427 (1.92). 2.3298 (1.66). 2.316 (1.68). 2.3065 (1.38). 2.2921 (0.68). 2.28 (0.49). 22702 (0.36). 2.1215 (1.79). 2.1092 (1.54). 2.1028 (1.49). 2.0868 (2). 2.0744 (1.46). 2.0598 (0.73). 2.041 (13. 3). 1.5769 (18.97). 1.3654 (0.45). 1.3479 (0.92). 1.3301 (0.51). 1.2747 (3.51). 1.2568 (7.17). 1.239 (3.48). −0.0003 (15.15) |
| 322 | | LC-MS (Method L6): Rt = 2.26 min; MS (ESIpos): m/z = 550 [M + H]+ | $^1$H-NMR (400 MHz, DMSO-d6) δ [ppm]: −0.149 (1.57), −0.008 (16.00), 0.008 (12.28), 0.146 (1.64), 1.049 (0.50), 2.087 (0.63), 2.327 (3.21), 2.366 (2.46), 2.523 (10.58), 2.669 (3.09), 2.710 (2.46), 3.611 (1.20), 3.879 (3.72), 4.269 (1.01), 5.259 (0.69), 6.787 (1.26), 6.807 (1.51), 6.915 (0.76), 6.932 (1.39), 6.950 (0.76), 7.153 (0.76), 7.174 (1.13), 7.374 (1.20), 7.391 (1.89), 7.410 (1.26), 7.583 (1.70), 7.596 (2.08), 7.615 (1.70), 7.627 (1.95), 7.687 (0.94), 7.706 (1.26), 7.726 (1.32), 7.806 (1.45), 7.822 (1.32), 8.270 (1.39), 8.291 (1.20), 8.660 (4.66), 9.158 (1.20), 9.180 (1.13). |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 323 | | LC-MS (Method L3): Rt = 2.90 min; m/z = 543/545 [M + 1]+ | $^1$H-NMR (400 MHz, DMSO-d6) δ 9.10 (d, J = 8.2 Hz, 1H), 8.60 (s, 1H), 8.19 (dd, J = 8.5, 1.3 Hz, 1H), 7.73 (dd, J = 7.1, 1.3 Hz, 1H), 7.62 (dd, J = 8.4, 7.2 Hz, 1H), 7.36 (d, J = 7.0 Hz, 1H), 7.22-7.12 (m, 1H), 7.09-6.97 (m, 3H), 6.97-6.87 (m, 1H), 6. |
| 324 | | LC-MS (Method L2): Rt = 2.91 min; m/z = 501/503 [M + 1]+ | $^1$H-NMR (400 MHz, DMSO-d6) δ 9.08 (d, J = 8.2 Hz, 1H), 8.51 (s, 1H), 8.17 (dd, J = 8.2, 1.7 Hz, 1H), 7.67-7.50 (m, 2H), 7.34 (d, J = 7.1 Hz, 1H), 7.23-7.06 (m, 2H), 6.97-6.86 (m, 1H), 6.86-6.67 (m, 3H), 5.33-5.18 (m, 1H), 4.37-4.15 (m, 2H), 3.0 |
| 325 | | LC-MS (Method L2): Rt = 3.19 min; m/z = 519/521 [M + 1]+ | $^1$H-NMR (400 MHz, DMSO-d6) δ 9.10 (d, J = 8.2 Hz, 1H), 8.63 (s, 1H), 8.20 (dd, J = 8.5, 1.3 Hz, 1H), 7.77 (dd, J = 7.1, 1.3 Hz, 1H), 7.63 (dd, J = 8.4, 7.2 Hz, 1H), 7.56-7.48 (m, 1H), 7.43 (dd, J = 13.3, 2.0 Hz, 1H), 7.37 (d, J = 6.9 Hz, 1H), 7.23-7.13 (m, 1H), 6.98-6.89 (m, 1H), 6.80 (dd, J = 8.2, 0.9 Hz, 1H), 5.31-5.20 (m, 1H), 4.35-4.18 (m, 2H), 3.06 (s, 6H), 2.86 (d, J = 2.3 Hz, 6H), 2.28-2.13 (m, 1H), 2.13-1.99 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 326 | | LC-MS (Method L2): Rt = 2.86 min; m/z = 522 (Cl2 pattern) [M + H]+ | $^1$H-NMR (400 MHz, DMSO-d6) δ 9.01 (d, J = 7.1 Hz, 1H), 8.42 (d, J = 1.6 Hz, 1H), 8.27 (d, J = 9.4 Hz, 1H), 7.66-7.55 (m, 2H), 7.43-7.30 (m, 2H), 7.23-7.12 (m, 2H), 6.89 (t, J = 7.4 Hz, 1H), 6.78 (d, J = 8.1 Hz, 1H), 5.21 (q, J = 5.9 Hz, 1H), 4.30-4 |
| 327 | | LC-MS (Method L2): Rt = 2.96 min; m/z = 522 (Cl2 pattern) [M + H]+ | $^1$H-NMR (400 MHz, DMSO-d6) δ 9.01 (d, J = 8.2 Hz, 1H), 8.49 (s, 1H), 8.25 (d, J = 9.5 Hz, 1H), 7.62-7.54 (m, 2H), 7.34 (d, J = 7.0 Hz, 1H), 7.30 (d, J = 1.9 Hz, 2H), 7.19-7.12 (m, 1H), 6.95-6.87 (m, 1H), 6.79 (d, J = 8.1 Hz, 1H), 5.27-5.18 (m, 1H), |
| 328 | 3.3 | | $^1$H-NMR (399, 9532 MHz, DMSO): δ = 9.1516 (1.99); 9.189 (2.07); 8.6957 (7.8); 8.3158 (0.74); 8.1756 (2.08); 8.1554 (2.33); 7.8284 (2.07); 7.8125 (2.84); 7.6916 (1.99); 7.6725 (2.46); 7.6445 (16); 7.5625 (0.42); 7.5064 (0.53); 7.4855 (0.5); 7.489 (0.53); 7.3832 (2.2); 7.3653 (2.8); 7.1937 (1.06); 7.1767 (2.08); 7.1581 (1.32); 6.948 (1.5); 6.9294 (2.46); 6.9118 (1.23); 6.8712 (0.85); 6.8097 (2.74); 6.79 (2.61); 6.6398 (0.41); 6.5791 (0.42); 5.2663 (0.57); 5.253 (1.33); 5.238 (1.23); 5.2205 (0.6); 4.872 (0.46); 4.287 (1.27); 4.278 (2.25); 4.2461 (1.37); 4.2259 (0.44); 3.538 (1.43); 3.5183 (3.51); 3.503 (2.16); 3.374 (2.24); 3.3585 (3.93); 3.3413 (2.21); 3.32 (177.93); 3.1924 (2.23); 3.1748 (4.03); 3.1575 (2.8); 3.0637 (15.58); 2.6707 (3.2); 2.5016 (591.34); 2.3283 (3.8); 2.2181 (0.84); 2.2067 (0.96); 2.1977 (0.96); 2.1833 (1.83); 2.1627 (2.11); 2.1422 (4.09); 2.1222 (2.63); 2.0859 (5); 1.7864 (0.63); 1.7681 (1.98); 1.7497 (2.66); 1.787 (1.77); 1.3554 (7.89); 1.2706 (0.49); 1.2335 (0.8); 1.1856 (0.8); 1.1692 (2.96); 0.1462 (1.19); 0 (271.12); −0.1493 (1.3) |
| 329 | | LC-MS (Method L1): Rt = 0.80 min; MS (ESIpos): m/z = 548 | $^1$H-NMR (400 MHz, DMSO-d6) δ [ppm]: −0.008 (0.68), 0.008 (0.56), 1.686 (0.43), 1.705 (0.40), 1.908 (16.00), 1, 98 (0.70), 1.999 (0.46), 2.012 (0.70), 2.030 (0.70), 2.047 (0.66), 2.057 (0.44), 2.409 (0.49), 2.523 (0.51), 3.409 (0.50), 3.478 (0.83), 3.496 (0.94), 3.503 (0.93), 3.520 (0.72), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | 3.689 (0.90), 3.707 (1.31), 3.722 (1.18), 3.740 (0.74), 3.746 (0.64), 3.764 (0.47), 4.234 (0.64), 4.242 (0.95), 4.254 (1.33), 4.730 (0.48), 5.206 (0.55), 5.225 (0.8), 6.778 (1.01), 6.799 (1.13), 6.895 (0.51), 6.912 (1.07), 6.931 (0.64), 7.142 (0.52), 7.145 (0.8), 7.163 (0.88), 7.18 (0.43), 7.184 (0.43), 7.322 (0.91), 7.341 (0.85), 7.478 (0.75), 7.496 (0.99), 7.499 (0.92), 7.517 (0.89), 7.601 (0.47), 7.606 (1.15), 7.610 (1.62), 7.618 (4.75), 7.622 (2.49), 7.709 (1.15), 7.712 (1.18), 7.727 (1.01), 7.729 (0.98), 8.139 (0.93), 8.258 (0.90), 8261 (0.90), 8.280 (0.91), 8.440 (3.42), 9.025 (1.00), 9.046 (0.98). |
| 330 | | LC-MS (Method L6): Rt = 2.01 min; MS (ESIpos): m/z = 510 [M + H]+ | $^{1}$H-NMR (400 MHz, DMSO-d6) δ [ppm]: −0.008 (1.17), 0.008 (0.88), 2.021 (0.41), 2.08 (0.47), 2.08 (0.52), 2.073 (1.14), 2.169 (0.52), 2.181 (0.50), 2.191 (0.48), 2.523 (0.76), 3.082 (16.00), 4.220 (0.74), 4.226 (0.64), 4.240 (1.18), 4.249 (1.20), 4.265 (0.72), 5.213 (0.69), 5.229 (0.68), 5.754 (1.51), 6.772 (1.8), 6.792 (1.55), 6.878 (0.73), 6.896 (1.52), 6.915 (0.91), 7.134 (0.75), 7.18 (0.79), 7.155 (1.26), 7.173 (0.63), 7.176 (0.61), 7.322 (1.8), 7.337 (1.8), 7.82 (0.91), 7.356 (0.87), 7.83 (0.63), 7.366 (0.62), 7.382 (0.84), 7.386 (0.81), 7.446 (0.76), 7.459 (0.83), 7.466 (1.28), 7.479 (1.28), 7.485 (0.72), 7.499 (0.63), 7.592 (1.03), 7.615 (1.76), 7.68 (1.08), 7.726 (1.8), 7.78 (1.40), 7.746 (1.23), 7.750 (1.17), 8.310 (0.92), 8.325 (1.02), 8.333 (0.99), 8.349 (0.90), 8.523 (2.23), 8.527 (2.23), 9.057 (0.8), 9.061 (0.87), 9.077 (0.8). |
| 331 | 3.14 | | $^{1}$H-NMR (399, 9532 MHz, DMSO): δ = 9.1403 (1.94). 9.1288 (2). 9.1208 (2.32). 9.1103 (1.85). 8.6012 (10.54). 8.4715 (0.58). 8.3155 (1.57). 8.2143 (2.25). 8.1975 (2.56). 8.1729 (1.06). 7.7323 (2.07). 7.7127 (5.31). 7.6894 (10.46). 7.6737 (1.95). 7.4635 (1.67). 7.4521 (1.74). 7.4433 (2.94). 7.4332 (2.77). 7.4235 (2.08). 7.4143 (1.65). 7.3824 (1.86). 7.3618 (4.63). 7.3428 (4.44). 7.3225 (1.63). 7.1895 (1.81). 7.171 (3.64). 7.1535 (2.27). 6.9433 (2.6). 6.9255 (4.32). 6.9084 (2.02). 6.8059 (4.77). 6.7848 (4.45). 6.5782 (0.9). 5.2488 (1.97). 5.237 (2). 4.725 (1.91). 4.697 (7.04). 4.6722 (5.48). 4.6575 (5.6). |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 4.5955 (1.22). 4.5844 (1.61). 4.2921 (2.17). 4.2752 (3.94). 4.2675 (3.64). 4.2552 (2.23). 4.2471 (2.41). 4.2281 (0.89). 3.3183 (319.34). 3.2701 (0.87). 3.2496 (0.61). 3.1747 (0.71). 3.081 (16). 3.0759 (15.54). 2.9497 (1.08). 2.6703 (8.96). 2.5893 (0.63). 2.5051 (1239.6). 2.5012 (1583.24). 2.4971 (1204.24). 2.3276 (9.3). 2.2832 (0.88). 22475 (1.34). 2.2286 (1.72). 2.2205 (1.78). 2.1313 (0.96). 2.074 (5.92). 2.0168 (0.96). 1.2694 (0.87). 1.169 (4.47). 1.0034 (0.71). 0.9887 (0.75). 0.1463 (2.93). −0.0001 (642.47). −0.0792 (0.67). −0.1497 (3.13). −3.3083 (0.55) |
| 332 | | LC-MS (Method L1): Rt = 0.84 min; MS (ESIpos): m/z = 562 [M + H]+ | $^1$H-NMR (400 MHz, DMSO-d6) δ [ppm]: −0.149 (0.57), 0.146 (0.52), 2.063 (1.66), 2.099 (1.25), 2.118 (1.43), 2.130 (1.93), 2.149 (2.41), 2.167 (1.95), 2.220 (1.77), 2.233 (1.79), 2.251 (1.61), 2263 (1.00), 2.327 (1.50), 2.366 (0.82), 2.669 (1.50), 2.710 (0.73), 3.195 (1.82), 3.214 (2.75), 3.232 (2.11), 3.670 (1.75), 3.682 (1.88), 3.727 (1.27), 3.745 (3.54), 3.768 (4.92), 3.788 (5.88), 3.807 (3.11), 3.831 (1.00), 4.241 (3.47), 4.252 (4.68), 5.212 (2.04), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 5.232 (2.04), 6.779 (3.36), 6.799 (3.81), 6.894 (1.72), 6.912 (3.65), 6.931 (2.13), 7.147 (1.88), 7.164 (3.13), 7.182 (1.54), 7.329 (3.36), 7.347 (3.06), 7.522 (2.18), 7.542 (3.36), 7.562 (2.63), 7.623 (16.00), 7.742 (3.99), 7.759 (3.43), 8.257 (3.50), 8.277 (3.29), 8.501 (9.67), 9.095 (3.34), 9.115 (3.29), 12.559 (0.52). |
| 333 | | LC-MS (Method L6): Rt = 2.56 min; MS (ESIpos): m/z = 497 [M + H]+ | $^1$H-NMR (400 MHz, DMSO-d6) delta [ppm]: 2.092 (0.76), 3.286 (3.16), 4.171 (16.00), 4.267 (1.78), 5.273 (1.01), 6.793 (1.51), 6.817 (1.83), 6.912 (0.84), 6.931 (1.63), 6.949 (1.01), 7.160 (0.88), 7.182 (1.36), 7.359 (1.40), 7.378 (1.33), 7.703 (1.10), 7.723 (1.64), 7.741 (1.31), 7.843 (4.97), 7.859 (4.94), 7.903 (1.82), 7.917 (1.37), 8.294 (1.60), 8.297 (1.77), 8.315 (1.52), 8.816 (5.70), 9.194 (1.47), 9.213 (1.36). |
| 334 | | LC-MS (Method L7): Rt = 2.60 min; MS (ESIpos): m/z = 477 | $^1$H-NMR (500 MHz, DMSO-d6) delta [ppm]: −0.007 (4.15), 0.007 (3.67), 1.235 (1.26), 1.395 (7.56), 1.409 (16.00), 1.423 (7.72), 1.950 (1.18), 1.966 (1.28), 1.975 (1.34), 1.991 (1.30), 2.522 (1.98), 2.853 (1.24), 2.869 (1.51), 2.885 (1.92), 2.901 (0.85), 2.981 (1.03), 2.989 (1.09), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]+ | 2.999 (1.11), 3.006 (1.07), 3.013 (0.81), 3.286 (5.84), 4.352 (1.51), 4.354 (1.53), 4.366 (4.56), 4.368 (4.83), 4.380 (4.46), 4.383 (4.79), 4.394 (1.38), 4.396 (1.51), 5.533 (0.78), 5.549 (2.29), 5.564 (2.27), 5.580 (0.78), 5.754 (0.91), 7.227 (2.02), 7.231 (3.49), 7.238 (4.46), 7.245 (4.52), 7.249 (3.34), 7.260 (1.11), 7.278 (2.99), 7.290 (1.65), 7.294 (1.20), 7.400 (2.19), 7.406 (2.33), 7.417 (2.00), 7.654 (2.35), 7.658 (5.35), 7.661 (4.98), 7.674 (15.77), 7.678 (10.55), 7.714 (2.52), 7.729 (3.39), 7.731 (3.32), 7.745 (2.97), 7.889 (3.47), 7.891 (3.80), 7.903 (3.01), 7.906 (3.03), 8.304 (3.32), 8.307 (3.57), 8.321 (3.16), 8.324 (3.16), 8.842 (11.93), 8.998 (2.83), 9.015 (2.77). |
| 335 | | LC-MS (Method L1): Rt = 1.42 min; MS (ESIpos): m/z = 507 [M + H]+ | $^1$H-NMR (400 MHz, DMSO-d6) delta [ppm]: −0.008 (1.09), 0.008 (1.03), 1.300 (13.37), 1.315 (15.22), 1.320 (15.14), 1.335 (13.44), 2.077 (1.40), 2.086 (1.14), 2.175 (0.96), 2.188 (1.01), 2.198 (1.11), 2.211 (0.97), 3.287 (1.40), 4.251 (1.94), 4.260 (2.90), 4.271 (3.78), 4.279 (2.28), 4.285 (1.96), 4.831 (0.79), 4.847 (2.11), 4.862 (2.86), 4.877 (2.07), 4.892 (0.76), 5.271 (1.74), 5.291 (1.73), 5.754 (1.60), 6.792 (2.95), 6.795 (3.21), 6.812 (3.38), 6.815 (3.52), 6.905 (1.65), 6.908 (1.68), 6.923 (3.35), 6.926 (3.31), 6.942 (2.06), 6.945 (1.96), 7.159 (1.66), 7.163 (1.75), 7.180 (2.64), 7.197 (1.36), 7.202 (1.34), 7.352 (2.66), 7.356 (2.66), 7.371 (2.57), 7.375 (2.32), 7.648 (1.92), 7.653 (4.51), 7.658 (3.68), 7.680 (16.00), 7.685 (11.73), 7.701 (2.83), 7.719 (3.62), 7.722 (3.32), 7.740 (3.41), 7.880 (3.80), 7.884 (4.07), 7.898 (3.21), 7.902 (3.13), 8.304 (3.63), 8.308 (3.69), 8.325 (3.41), 8.329 (3.23), 8.844 (13.48), 9.131 (3.03), 9.152 (2.95). |
| 336 | | LC-MS (Method L1): Rt = 1.47 min; MS (ESIpos): m/z = 491 [M + H]+ | $^1$H-NMR (400 MHz, DMSO-d6) delta [ppm]: −0.008 (3.40), 0.008 (3.27), 1.234 (1.59), 1.255 (13.29), 1.270 (13.33), 1.324 (13.22), 1.339 (13.35), 1.958 (1.08), 1.976 (1.27), 1.988 (1.33), 2.008 (1.28), 2.517 (2.28), 2.849 (1.21), 2.869 (1.58), 2.889 (2.03), 2.908 (0.90), 2.981 (1.12), 2.992 (1.19), 3.003 (1.21), 3.013 (1.12), 3.288 (2.34), 4.795 (0.80), 4.810 (2.09), 4.825 (2.87), 4.841 (2.06), 4.856 (0.77), 5.539 (2.27), 5.558 (2.27), 7.221 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.05), 7.226 (3.83), 7.234 (4.60), 7.243 (5.51), 7.248 (3.90), 7.261 (1.41), 7.266 (1.19), 7.275 (3.08), 7.289 (1.56), 7.297 (1.00), 7.402 (2.18), 7.409 (2.34), 7.423 (1.93), 7.651 (2.03), 7.656 (4.64), 7.661 (3.85), 7.682 (16.00), 7.687 (11.77), 7.702 (2.80), 7.720 (3.59), 7.723 (3.36), 7.741 (3.39), 7.879 (3.80), 7.883 (4.13), 7.897 (3.21), 7.901 (3.15), 8.305 (3.55), 8.309 (3.70), 8.326 (3.40), 8.330 (3.18), 8.861 (12.80), 8.984 (2.98), 9.004 (2.89). |
| 337 | | LC-MS (Method L1): Rt = 1.54 min; MS (ESIpos): m/z = 517 [M + H]+ | $^1$H-NMR (400 MHz, DMSO-d6) delta [ppm]: −0.008 (3.13), 0.008 (3.33), 1.233 (0.81), 1.599 (1.35), 1.607 (1.77), 1.618 (2.67), 1.624 (2.67), 1.655 (1.41), 1.671 (1.41), 1.685 (1.17), 1.707 (0.97), 1.760 (1.28), 1.773 (2.47), 1.785 (3.62), 1.791 (3.70), 1.799 (3.24), 1.804 (3.14), 1.813 (3.40), 1.818 (3.25), 1.824 (2.52), 1.829 (2.47), 1.852 (1.86), 1.861 (1.79), 1.873 (1.75), 1.952 (1.31), 1.963 (0.89), 1.970 (1.48), 1.982 (1.57), 1.990 (0.88), 2.002 (1.52), 2.021 (0.70), 2.517 (2.37), 2.845 (1.39), 2.865 (1.83), 2.885 (2.35), 2.905 (1.05), 2.979 (1.28), 2.989 (1.38), 3.001 (1.41), 3.011 (1.32), 3.018 (0.95), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.029 (0.85), 3.040 (0.83), 3.288 (1.16), 5.212 (1.44), 5.218 (2.09), 5.224 (2.42), 5.229 (2.21), 5.236 (1.36), 5.518 (0.92), 5.537 (2.66), 5.556 (2.65), 5.575 (0.92), 5.754 (1.62), 7.218 (2.33), 7.223 (4.35), 7.231 (4.99), 7.240 (6.10), 7.245 (4.34), 7.258 (1.57), 7.263 (1.32), 7 272 (3.57), 7.287 (1.82), 7.294 (1.20), 7.412 (2.53), 7.419 (2.76), 7.433 (2.33), 7.647 (1.83), 7.652 (4.58), 7.657 (3.89), 7.676 (16.00), 7.680 (11.73), 7.694 (2.99), 7.712 (3.95), 7.715 (3.80), 7.733 (3.62), 7.868 (4.03), 7.871 (4.39), 7.885 (3.41), 7.889 (3.40), 8.250 (3.81), 8.254 (4.05), 8.271 (3.65), 8.274 (3.52), 8.818 (13.85), 9.049 (3.54), 9.069 (3.47). |
| 338 | | LC-MS (Method L6): Rt = 2.62 min; MS (ESIpos): m/z = 523 [M + H]+ | $^1$H-NMR (400 MHz, DMSO-d6) delta [ppm]: −0.008 (1.69), 0.008 (1.48), 3.284 (16.00), 3.722 (1.56), 3.734 (2.60), 3.744 (1.75), 4.270 (1.58), 4.419 (0.92), 4.428 (1.44), 4.431 (1.39), 4.437 (1.43), 4.439 (1.46), 4.448 (0.90), 6.794 (1.04), 6.797 (1.09), 6.814 (1.20), 6.817 (1.20), 6.921 (1.21), 6.924 (1.15), 6.940 (0.75), 7.181 (0.92), 7.352 (0.93), 7.372 (0.91), 7.658 (1.44), 7.662 (1.50), 7.676 (5.94), 7.681 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.69), 7.721 (0.99), 7.739 (1.31), 7.742 (1.17), 7.760 (1.24), 7.895 (1.40), 7.899 (1.44), 7.913 (1.18), 7.916 (1.10), 8.335 (1.30), 8.339 (1.31), 8.356 (1.25), 8.360 (1.14), 8.877 (4.74), 9.141 (1.07), 9.161 (1.04). |
| 339 | | LC-MS (Method L6): Rt = 2.54 min; MS (ESIpos): m/z = 549 [M + H]+ | $^{1}$H-NMR (400 MHz, DMSO-d6) δ [ppm]: −0.149 (0.97), −0.008 (8.24), 0.008 (7.67), 0.146 (1.01), 1.147 (0.93), 1.750 (1.59), 1.915 (1.63), 2.075 (1.10), 2.204 (0.97), 2.366 (1.45), 2.669 (0.79), 2.710 (1.37), 3.287 (6.79), 3.337 (2.25), 3.366 (1.90), 3.390 (0.97), 3.865 (2.47), 3.895 (2.20), 4.253 (1.45), 4.282 (2.64), 4.748 (1.06), 4.758 (1.45), 5.272 (1.45), 5.292 (1.54), 6.795 (2.69), 6.798 (2.87), 6.815 (2.91), 6.818 (3.13), 6.910 (1.41), 6.913 (1.37), 6.929 (2.78), 6.932 (2.82), 6.948 (1.72), 6.951 (1.72), 7.165 (1.41), 7.169 (1.54), 7.189 (2.12), 7.208 (1.15), 7.387 (2.29), 7.407 (1.98), 7.652 (2.12), 7.657 (4.94), 7.661 (4.58), 7.678 (16.00), 7.683 (10.31), 7.725 (2.20), 7.742 (3.00), 7.746 (2.82), 7.764 (2.78), 7.894 (3.26), 7.898 (3.44), 7.912 (2.69), 7.916 (2.60), 8.366 (3.00), 8.370 (3.09), 8.387 (2.78), 8.391 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.60), 8.852 (11.94), 9.170 (2.51), 9.191 (2.51). |
| 340 | | LC-MS (Method L6): Rt = 2.35 min; MS (ESIpos): m/z = 509 [M + H]+ | $^{1}$H-NMR (400 MHz, DMSO-d6) δ [ppm]: 1.233 (1.46), 2.060 (1.17), 2.072 (1.22), 2.096 (1.85), 2.106 (1.52), 2.180 (1.45), 2.200 (1.60), 2.216 (1.38), 2.232 (1.09), 2.710 (0.59), 3.289 (2.29), 3.770 (2.50), 3.782 (6.45), 3.794 (6.45), 3.807 (2.58), 4.251 (3.09), 4.260 (3.55), 4.268 (6.08), 4.280 (3.73), 4.310 (0.75), 4.322 (1.11), 4.337 (3.05), 4.348 (6.79), 4.359 (6.81), 4.370 (2.86), 4.385 (0.96), 5.066 (2.32), 5.079 (4.75), 5.093 (2.23), 5.263 (1.21), 5.277 (2.42), 5.296 (2.39), 5.311 (1.08), 5.753 (12.22), 6.792 (4.39), 6.812 (4.98), 6.902 (2.47), 6.920 (4.70), 6.939 (2.63), 7.160 (2.23), 7.179 (3.73), 7.198 (2.03), 7.349 (3.82), 7.366 (3.59), 7.603 (0.66), 7.608 (0.74), 7.648 (2.33), 7.653 (5.18), 7.658 (5.13), 7.674 (16.00), 7.679 (12.12), 7.703 (2.84), 7.723 (4.62), 7.742 (3.57), 7.885 (3.87), 7.888 (4.97), 7.903 (3.20), 7.906 (3.94), 8.442 (3.94), 8.445 (4.43), 8.463 (3.83), 8.466 (4.03), 8.845 (14.44), 9.174 (4.04), 9.194 (3.96). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 341 | | LC-MS (Method L6): Rt = 2.64 min; MS (ESIpos): m/z = 493 [M + H]+ | $^1$H-NMR (400 MHz, DMSO-d6) δ [ppm]: 1.356 (12.14), 1.405 (7.22), 1.423 (15.61), 1.441 (7.48), 2.073 (1.45), 2.082 (1.17), 2.091 (0.93), 2.183 (2.15), 2.192 (0.97), 2.203 (0.95), 3.568 (4.88), 4.247 (1.66), 4.256 (2.16), 4.268 (2.79), 4.274 (2.58), 4.283 (1.57), 4.359 (1.14), 4.366 (1.13), 4.377 (3.75), 4.383 (3.69), 4.394 (3.64), 4.401 (3.71), 4.412 (1.11), 4.418 (1.11), 5.274 (1.50), 5.294 (1.49), 6.793 (2.69), 6.796 (2.93), 6.814 (3.05), 6.817 (3.20), 6.871 (0.97), 6.908 (1.45), 6.911 (1.48), 6.927 (2.96), 6.930 (2.93), 6.946 (1.82), 6.949 (1.73), 7.160 (1.45), 7.165 (1.54), 7.182 (2.32), 7.199 (1.17), 7.203 (1.14), 7.352 (2.34), 7.372 (2.26), 7.376 (2.03), 7.650 (1.93), 7.655 (4.49), 7.659 (4.77), 7.672 (16.00), 7.677 (9.62), 7.709 (2.46), 7.727 (3.23), 7.730 (3.00), 7.748 (3.04), 7.888 (3.41), 7.891 (3.59), 7.905 (2.88), 7.909 (2.77), 8.301 (3.25), 8.305 (3.35), 8.322 (3.10), 8.326 (2.87), 8.833 (12.05), 9.137 (2.57), 9.158 (2.52). |
| 342 | | LC-MS (Method L6): Rt = 3.11 min; MS (ESIpos): m/z = 533 [M + H]+ | $^1$H-NMR (400 MHz, DMSO-d6) δ [ppm] 0.951 (16.00), 1.175 (0.68), 1.783 (0.75), 1.802 (1.29), 1.820 (0.77), 1.988 (1.34), 4.409 (0.73), 4.414 (0.72), 7.655 (0.81), 7.659 (0.83), 7.670 (2.53), 7.675 (1.64), 7.720 (0.69), 7.878 (0.71), 8.816 (2.01). |
| 343 | | LC-MS (Method L6): Rt = 2.84 min; MS (ESIpos): m/z = 557 [M + H]+ | $^1$H-NMR (400 MHz, DMSO-d6) δ [ppm]: −0.008 (2.37), 0.008 (1.76), 1.147 (1.15), 1.926 (1.02), 1.944 (1.15), 1.957 (1.15), 1.976 (1.22), 2.366 (1.63), 2.710 (1.69), 2.838 (0.95), 2.858 (1.29), 2.878 (1.69), 2.956 (0.88), 2.966 (1.02), 2.979 (1.02), 2.987 (1.02), 3.289 (3.66), 5.382 (7.73), 5.386 (8.00), 5.415 (0.75), 5.565 (2.03), 5.584 (1.97), 7.132 (0.88), 7.150 (2.37), 7.169 (1.69), 7.204 (1.97), 7.223 (4.00), 7.232 (2.03), 7.242 (1.97), 7.252 (1.29), 7.264 (3.53), 7.282 (1.69), 7.318 (2.24), 7.336 (4.81), 7.365 (1.76), 7.381 (2.98), 7.400 (2.92), 7.447 (1.15), 7.463 (1.76), 7.468 (1.97), 7.483 (2.10), 7.488 (1.29), 7.503 (1.08), 7.661 (1.56), 7.666 (3.80), 7.670 (4.95), 7.681 (16.00), 7.686 (9.15), 7.718 (2.51), 7.736 (3.19), 7.739 (3.12), 7.757 (3.05), 7.903 (3.39), 7.906 (3.80), 7.920 (2.92), 7.924 (2.98), 8.278 (3.12), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.281 (3.46), 8.299 (3.05), 8.303 (2.98), 8.913 (11.73), 9.095 (2.71), 9.115 (2.71). |
| 344 | | LC-MS (Method L6): Rt = 2.84 min; MS (ESIpos): m/z = 575 [M + H]+ | $^1$H-NMR (400 MHz, DMSO-d6) δ [ppm]: 1.235 (1.30), 1.935 (1.60), 1.954 (1.98), 1.965 (2.10), 1.986 (1.91), 2.005 (0.73), 2.672 (0.79), 2.711 (0.59), 2.843 (1.62), 2.863 (2.27), 2.884 (2.82), 2.904 (1.36), 2.969 (1.94), 2.982 (1.99), 5.450 (1.65), 5.478 (7.32), 5.493 (7.42), 5.522 (1.77), 5.546 (1.27), 5.563 (3.23), 5.583 (3.15), 5.601 (1.18), 7.146 (1.70), 7.164 (4.06), 7.182 (3.27), 7.207 (2.49), 7.224 (4.59), 7.242 (2.89), 7.264 (6.36), 7.282 (5.13), 7.311 (1.84), 7.392 (5.56), 7.410 (6.38), 7.434 (2.03), 7.473 (1.31), 7.495 (2.55), 7.518 (2.46), 7.540 (1.11), 7.665 (7.07), 7.680 (16.00), 7.706 (2.83), 7.724 (4.62 7.744 (2.99), 7.898 (4.83), 7.916 (4.01), 8.213 (4.51), 8.234 (4.18), 8.918 (9.86), 9.128 (3.96), 9.147 (3.86). |
| 345 | | LC-MS (Method L6): Rt = 2.83 min; MS (ESIpos): m/z = 569 [M + H]+ | $^1$H-NMR (400 MHz, DMSO-d6) δ [ppm]: 1.964 (0.76), 2.524 (1.70), 2.861 (0.81), 2.881 (1.06), 3.288 (1.25), 3.759 (16.00 5.351 (4.36), 5.356 (4.34), 5.573 (1.21), 5.593 (1.19), 6.939 (1.06), 6.946 (1.14), 6.963 (1.25), 7.038 (1.56), 7.056 (4.26), 7.160 (1.59), 7.179 (1.19), 7.208 (0.94), 7.226 (1.85), 7.243 (1.17), 7.266 (2.21), 7.285 (1.11), 7.316 (1.26), 7.337 (1.99), 7.355 (1.09), 7.392 (1.78), 7.410 (1.52), 7.657 (1.23), 7.662 (2.51), 7.666 (2.55), 7.679 (7.30), 7.683 (4.89), 7.708 (1.19), 7.726 (1.75), 7.747 (1.41), 7.892 (1.85), 7.895 (1.92), 7.910 (1.52), 7.913 (1.46), 8.273 (1.73), 8.277 (1.74), 8.294 (1.66), 8.298 (1.55), 8.899 (5.35), 9.092 (1.61), 9.113 (1.58). |
| 346 | | LC-MS (Method L6): Rt = 1.65 min; MS (ESIpos): m/z = 518 [M − HCl + H]+ | $^1$H-NMR (400 MHz, DMSO-d6) δ [ppm]: 2.897 (1.03), 3.371 (1.10), 3.386 (1.01), 5.457 (1.45), 5.543 (1.27), 5.562 (1.29), 7.232 (1.04), 7.237 (1.87), 7.245 (2.18), 7.254 (2.72), 7.258 (2.05), 7.284 (1.61), 7.298 (0.86), 7.431 (1.08), 7.438 (1.17), 7.452 (1.00), 7.670 (16.00), 7.720 (1.27), 7.738 (1.69), 7.741 (1.59), 7.759 (1.49), 7.918 (1.80), 7.921 (1.89), 7.936 (1.57), 7.939 (1.51), 8.494 (1.49), 8.515 (1.46), 8.867 (5.92), 9.235 (1.48), 9.255 (1.44). |
| 347 | | LC-MS (METHOD L5): Rt = 1.39 min; | $^1$H-NMR (500 MHz, DMSO-d6) δ [ppm]: 1.166 (16.00), 2.055 (1.38), 2.069 (2.83 2.084 (1.40), 2.873 (0.61), 2.889 (0.78), 3.108 (11.26), 4.418 (0.63), 4.433 (1.14), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | MS (ESIpos): m/z = 549 [M + H]+ | 4.447 (0.94), 4.460 (1.14), 4.474 (0.60), 5.544 (0.93), 5.560 (0.92), 7.215 (1.08), 7.226 (1.40), 7.230 (1.64), 7.243 (1.31), 7.257 (0.63), 7.273 (1.47), 7.287 (0.74), 7.417 (1.21), 7.432 (1.02), 7.647 (0.90), 7.651 (2.01), 7.654 (1.86), 7.670 (4.81), 7.674 (4.24), 7.701 (0.83), 7.717 (1.39), 7.732 (0.97), 7.875 (1.18), 7.877 (1.48), 7.889 (1.02), 7.891 (1.21), 8.314 (1.14), 8.316 (1.40), 8.331 (1.09), 8.333 (1.27), 8.809 (3.64), 9.077 (1.18), 9.093 (1.15). |
| 348 | | LC-MS (Method L6): Rt = 3.09 min; MS (ESIpos): m/z = 531 [M + H]+ | $^1$H-NMR (400 MHz, DMSO-d6) δ [ppm]: 1.235 (2.39), 1.331 (1.53), 1.554 (1.87), 1.570 (3.23), 1.583 (3.23), 1.587 (3.23), 1.810 (1.44), 1.948 (0.98), 1.967 (1.15), 1.978 (1.21), 1.998 (1.12), 2.327 (0.78), 2.366 (1.18), 2.391 (1.44), 2.410 (1.90), 2.429 (1.44), 2.523 (3.83), 2.670 (0.81), 2.710 (1.10), 2.849 (1.01), 2.868 (1.33), 2.889 (1.90), 2.976 (0.95), 2.987 (1.07), 2.999 (1.01), 3.008 (0.98), 3.563 (4.90), 4.171 (1.21), 4.188 (1.44), 4.194 (3.17), 4.212 (3.11), 4.218 (3.26), 4.236 (3.11), 4.241 (1.53), 4.260 (1.15), 5.535 (2.02), 5.554 (1.96), 7.214 (2.13), 7226 (2.80), 7.230 (3.14), 7.243 (2.57), 7.247 (2.80), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.261 (1.53), 7.265 (1.27), 7.275 (3.06), 7.292 (1.38), 7.408 (2.42), 7.425 (1.96), 7.652 (1.99), 7.657 (4.73), 7.662 (5.19), 7.673 (16.00), 7.678 (9.23), 7.714 (2.36), 7.732 (3.11), 7.735 (2.85), 7.753 (2.88), 7.882 (3.20), 7.885 (3.57), 7.900 (2.74), 7.903 (2.68), 8.304 (3.11), 8.308 (3.23), 8.325 (2.91), 8.329 (2.77), 8.812 (11.70), 9.046 (2.62), 9.066 (2.51). |
| 349 | | LC-MS (METHOD L5): Rt = 1.37 min; MS (ESIpos): m/z = 490 [M + H]+ | $^1$H-NMR (500 MHz, DMSO-d6) δ [ppm]: 0.997 (1.88), 1.009 (1.89), 1.256 (13.03), 1.268 (13.05), 1.324 (13.05), 1.337 (13.09), 1.963 (1.17), 1.978 (1.34), 1.987 (1.38), 2.004 (1.32), 2.514 (1.83), 2.523 (1.17), 2.852 (1.36), 2.868 (1.69), 2.884 (2.08), 2.900 (0.98), 2.986 (1.14), 2.995 (1.24), 3.004 (1.25), 3.012 (1.20), 3.018 (0.90), 3.027 (0.85), 4.801 (0.80), 4.813 (2.08), 4.825 (2.81), 4.837 (2.05), 4.850 (0.77), 5.526 (0.97), 5.541 (2.48), 5.557 (2.44), 5.571 (0.85), 7.222 (2.17), 7.227 (3.29), 7.233 (4.98), 7.241 (4.15), 7.245 (3.67), 7.256 (1.43), 7.260 (1.07), 7.274 (3.36), 7.287 (1.98), 7.291 (1.44), 7.404 (2.36), 7.408 (2.57), 7.420 (2.24), 7.649 (3.36), 7.652 (6.92), 7.656 (4.92), 7.681 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (16.00), 7.685 (13.01), 7.704 (2.74), 7.718 (3.50), 7.720 (3.56), 7.735 (3.17), 7.878 (3.68), 7.881 (4.09), 7.892 (3.13), 7.895 (3.25), 8.306 (3.47), 8.309 (3.76), 8.323 (3.28), 8.326 (3.32), 8.861 (12.86), 8.984 (3.14), 9.001 (3.06). |
| 350 | 5.06 | LC-MS (Method L1): Rt = 1.35 min; MS (ESIpos): m/z = 477 [M + H]+ | $^1$H-NMR (400 MHz, DMSO-d6) δ [ppm]: 1.303 (2.43), 1.322 (5.61), 1.341 (2.50), 3.252 (2.09), 3.271 (2.06), 4.250 (1.06), 4.259 (1.62), 4.268 (1.95), 4.275 (1.54), 4.284 (1.06), 5.305 (0.92), 5.325 (0.92), 6.783 (1.53), 6.785 (1.66), 6.803 (1.75), 6.806 (1.83), 6.911 (0.78), 6.914 (0.83), 6.930 (1.72), 6.932 (1.71), 6.948 (1.03), 6.951 (1.00), 7.149 (0.86), 7.153 (0.89), 7.170 (1.43), 7.350 (1.48), 7.370 (1.41), 7.652 (16.00), 7.752 (1.09), 7.770 (1.68), 7.791 (1.47), 7.871 (1.93), 7.874 (2.04), 7.889 (1.44), 7.892 (1.42), 8.319 (1.50), 8.322 (1.58), 8.340 (1.43), 8.343 (1.39), 8.839 (5.77), 9.102 (1.60), 9.123 (1.55). |
| 351 | 5.1 | LC-MS (Method L1): Rt = 1.36 min; MS | $^1$H-NMR (400 MHz, DMSO-d6) δ [ppm]: −9.10 (d, 1H), 8.81 (s, 1H), 8.30 (d, 1H), 8.28 (br d, 1H), 7.71-7.84 (m, 2H), 7.46 (t, 1H), 7.30-7.40 (m, 3H), 7.12-7.22 (m, 1H), 6.93 (td, 1H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 471 [M + H]+ | 6.79 (dd, 1H), 5.24-5.37 (m, 1H), 4.19-4.33 (m, 2H), 3.26 (q, 3H), 2.64-2.74 (m, 2H), 2.16-2.27 (m, 1H), 2.01-2.12 (m, 1H), 1.32 (t, 3H), 1.23 (t, 3H). |
| 352 | | LC-MS (Method L1): Rt = 1.26 min; MS (ESIpos): m/z = 443 [M + H]+ | $^1$H-NMR (400 MHz, DMSO-d6): δ [ppm] = 9.08 (d, 1H), 8.82 (s, 1H), 8.25 (dd, 1H), 7.73-7.83 (m, 2H), 7.44 (s, 1H), 7.30-7.38 (m, 3H), 7.17 (t, 1H), 6.93 (t, 1H), 6.80 (d, 1H), 5.75 (s, 1H), 528-5.34 (m, 1H), 4.22-4.32 (m, 2H), 2.79 (s, 3H), 2.39 (s, 3H), 2.17-2.26 (m, 1H), 2.03-2.12 (m, 1H). |
| 353 | | LC-MS (Method L1): Rt = 1.28 min; MS (ESIpos): m/z = 463 [M + H]+ | $^1$H-NMR (400 MHz, DMSO-d6) δ [ppm]: 0.008 (0.60), 2.086 (0.58), 2.094 (0.47), 2.203 (0.46), 2.214 (0.45), 2.225 (0.41), 2.794 (10.72), 4.248 (0.87), 4.271 (1.29), 4.276 (1.30), 4.286 (0.77), 5.299 (0.74), 5.318 (0.76), 5.754 (1.41), 6.787 (1.44), 6.808 (1.54), 6.911 (0.70), 6.928 (1.45), 6.946 (0.85), 7.150 (0.73), 7.154 (0.77), 7.171 (1.18), 7.189 (0.58), 7.353 (1.24), 7.372 (1.13), 7.656 (16.00), 7.754 (1.00), 7.772 (1.46), 7.793 (1.32), 7.884 (1.64), 7.886 (1.70), 7.901 (1.28), 7.904 (1.19), 8.285 (1.42), 8.288 (1.42), 8.306 (1.32), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.309 (1.24), 8.844 (4.54), 9.082 (1.27), 9.103 (1.21). |
| 354 | | LC-MS (Method L6): Rt = 2.46 min; MS (ESIneg): m/z = 558 [M − H]− | $^1$H-NMR (400 MHz, DMSO-d6) δ [ppm]: −0.008 (0.46), 0.008 (0.44), 1.175 (0.60), 1.187 (0.74), 1.193 (1.32), 1.205 (1.44), 1.211 (0.70), 1.223 (0.71), 2.073 (0.67), 2.523 (0.41), 3.168 (16.00), 4.201 (0.40), 4.218 (0.81), 4.227 (0.56), 4.236 (0.80), 4245 (0.62), 6.804 (0.95), 6.826 (0.84), 7.683 (3.23), 7.897 (0.42), 8.001 (0.60), 8.018 (0.44), 9.111 (0.89), 9.124 (0.80). |
| 355 | | LC-MS (Method L1): Rt = 1.25 min; MS (ESIpos): m/z = 488 [M + H]+ | $^1$H-NMR (400 MHz, DMSO-d6) δ [ppm]: −0.008 (3.59), 0.008 (2.29), 2.135 (0.68), 2.224 (0.56), 2.327 (1.51), 2.366 (1.57), 2.522 (5.91), 2.669 (1.22), 2.710 (0.80), 4.264 (1.54), 4.275 (1.87), 4.710 (5.79), 5.292 (0.89), 5.311 (0.86), 6.798 (1.54), 6.816 (1.69), 6.896 (0.83), 6.915 (1.63), 6.933 (0.95), 7.163 (0.83), 7.180 (1.34), 7.198 (0.65), 7.384 (1.40), 7.404 (1.25), 7.678 (16.00), 7.883 (1.10), 7.901 (1.66), 7.923 (1.51), 7.989 (2.02), 8.004 (1.40), 8.417 (1.57), 8.435 (1.45), 9.029 (5.19), 9.375 (1.45), 9.395 (1.34). |
| 356 | | LC-MS (Method L1): Rt = 1.41 min; MS (ESIpos): m/z = 491 [M + H]+ | $^1$H-NMR (400 MHz, DMSO-d6): δ [ppm] = 9.12 (d, 1H), 8.83 (s, 1H), 8.33 (d, 1H), 7.88 (d, 1H), 7.72-7.79 (m, 1H), 7.65 (s, 3H), 7.36 (d, 1H), 7.14-7.22 (m, 1H), 6.93 (t, 1H), 6.80 (d, 1H), 5.25-5.37 (m, 1H), 4.20-4.34 (m, 2H), 3.17-3.26 (m, 2H), 2.20 (td, 1H), 1.99-2.11 (m, 1H), 1.64-1.78 (m, 2H), 1.02 (t, 3H). |
| 357 | | LC-MS (Method L1): Rt = 1.39 min; MS (ESIpos): m/z = 489 [M + H]+ | $^1$H-NMR (400 MHz, DMSO-d6): δ [ppm] = 8.89-9.00 (m, 2H), 8.04 (d, 1H), 7.90 (d, 1H), 7.72-7.80 (m, 1H), 7.67 (s, 3H), 7.28-7.39 (m, 1H), 7.16 (t, 1H), 6.92 (t, 1H), 6.78 (d, 1H), 5.54 (s, 1H), 5.19-5.29 (m, 1H), 5.03 (br s, 1H), 4.17-4.33 (m, 2H), 2.11-2.28 (m, 4H), 2.02 (br s, 1H). |
| 358 | 4.9 | LC-MS (Method L1): Rt = 1.34 min; MS (ESIpos): m/z = 489 [M + H]+ | $^1$H-NMR (500 MHz, DMSO-d6) δ [ppm]: 0.640 (1.22), 0.650 (1.42), 0.658 (1.28), 0.668 (0.69), 0.681 (0.74), 0.691 (1.29), 0.698 (1.52), 0.709 (1.18), 1.173 (1.12), 1.186 (2.68), 1.200 (2.43), 1203 (2.55), 1.216 (0.95), 2.067 (0.40), 2.073 (0.54), 2.079 (0.80), 2.085 (0.85), 2.095 (0.95), 2.107 (1.22), 2.112 (1.05), 2.118 (0.74), 2.124 (0.52), 2.201 (0.53), 2.208 (0.81), 2.218 (1.13), 2.228 (1.10), 2.235 (1.08), 2.246 (0.78), 2.253 (0.54), 2.409 (0.51), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 2.420 (1.04), 2.426 (1.14), 2.437 (1.81), 2.449 (1.05), 2.455 (1.00), 2.466 (0.59), 4.230 (0.57), 4.235 (0.67), 4.252 (1.84), 4.258 (1.37), 4.269 (1.59), 4.275 (1.46), 4.280 (1.41), 4.287 (1.66), 4.293 (1.43), 4.300 (1.50), 4.310 (0.60), 4.315 (0.65), 4.322 (0.46), 5.280 (0.80), 5.291 (1.74), 5.307 (1.69), 5.318 (0.75), 6.783 (3.28), 6.799 (3.54), 6.905 (1.59), 6.920 (3.31), 6.934 (1.85), 7.148 (1.91), 7.165 (2.68), 7.179 (1.30), 7.367 (2.83), 7.382 (2.86), 7.648 (16.00), 7.770 (1.92), 7.784 (3.02), 7.801 (2.71), 7.869 (3.37), 7.871 (3.35), 7.884 (2.52), 8.601 (2.89), 8.618 (2.72), 8.787 (0.65), 8.816 (9.10), 9.011 (2.78), 9.027 (2.65). |
| 359 | | LC-MS (Method L1): Rt = 1.38 min; MS (ESIpos): m/z = 491 [M + H]+ | $^1$H-NMR (500 MHz, DMSO-d6) δ [ppm]: −0.007 (1.53), 0.006 (1.15), 1.527 (11.61), 1.542 (11.90), 1.554 (11.58), 1.568 (11.39), 2.024 (0.41), 2.037 (0.85), 2.044 (0.90), 2.052 (0.94), 2.057 (0.92), 2.065 (1.24), 2.071 (1.06), 2.078 (0.75), 2.084 (0.55), 2.177 (0.52), 2.184 (0.80), 2.194 (1.16), 2.204 (1.11), 2.211 (1.11), 2.221 (0.74), 2.518 (0.93), 2.522 (0.72), 3.841 (0.48), 3.855 (1.08), 3.869 (1.42), 3.883 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (1.05), 3.898 (0.42), 4218 (0.51), 4.224 (0.67), 4.240 (2.00), 4.247 (1.53), 4257 (2.08), 4.262 (2.36), 4.268 (1.99), 4.274 (1.55), 4.281 (1.68), 4.290 (0.52), 4.297 (0.62), 4.303 (0.43), 5.264 (0.80), 5.276 (1.75), 5.292 (1.70), 5.303 (0.77), 6.784 (3.41), 6.798 (3.68), 6.916 (1.72), 6.918 (1.66), 6.930 (3.46), 6.945 (2.02), 7.151 (1.65), 7.154 (1.69), 7.168 (2.77), 7.182 (1.36), 7.185 (1.32), 7.353 (2.85), 7.368 (2.66), 7.616 (12.83), 7.620 (16.00), 7.643 (4.67), 7.647 (6.31), 7.651 (2.84), 7.720 (2.36), 7.735 (3.26), 7.738 (2.76), 7.752 (2.91), 7.840 (3.95), 7.842 (3.96), 7.854 (3.15), 7.856 (2.93), 8.446 (3.04), 8.461 (2.92), 8.757 (12.10), 9.108 (3.03), 9.125 (2.93). |
| 360 | | LC-MS (Method L1): Rt = 1.12 min; MS (ESIpos): m/z = 506 [M + H]+ | $^1$H-NMR (600 MHz, DMSO-d6) δ [ppm]: 0.005 (1.55), 2.061 (0.52), 2.067 (0.77), 2.071 (0.86), 2.079 (0.95), 2.083 (0.89), 2.090 (1.10), 2.094 (0.95), 2.101 (0.63), 2.197 (0.52), 2.202 (0.70), 2.211 (1.08), 2.219 (1.07), 2.225 (1.08), 2.234 (0.81), 2.386 (0.48), 2.517 (1.21), 2.520 (1.17), 2.523 (0.96), 2.614 (0.48), 4.190 (1.43), 4.199 (0.87), 4.204 (1.08), 4215 (5.45), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 4.223 (1.99), 4.229 (4.83), 4.253 (1.43), 4.266 (1.08), 4.271 (1.32), 4.277 (1.21), 4.283 (1.51), 4.290 (0.72), 4.296 (0.76), 4.301 (0.61), 5278 (0.77), 5.288 (1.58), 5.301 (1.57), 5.310 (0.71), 6.785 (3.04), 6.798 (3.20), 6.888 (1.54), 6.890 (1.54), 6.901 (3.04), 6.913 (1.75), 6.915 (1.67), 7.152 (1.45), 7.154 (1.49), 7.166 (2.44), 7.177 (1.22), 7.180 (1.20), 7.355 (2.91), 7.366 (4.77), 7.659 (8.30), 7.661 (16.00), 7.667 (5.88), 7.670 (4.36), 7.673 (1.81), 7.773 (2.24), 7.785 (2.96), 7.787 (2.70), 7.799 (2.65), 7.898 (3.37), 7.899 (3.46), 7.909 (2.76), 7.911 (2.71), 8.004 (2.52), 8.349 (2.84), 8.350 (2.88), 8.363 (2.68), 8.365 (2.58), 8.951 (10.28), 9.490 (2.95), 9.504 (2.84). |
| 361 | | LC-MS (Method L1): Rt = 1.44 min; MS (ESIpos): m/z = 474 [M + H]+ | $^1$H-NMR (400 MHz, DMSO-d6) δ [ppm]: −0.008 (0.70), 0.008 (0.49), 1.398 (16.00), 1.988 (0.45), 2.519 (0.43), 6.790 (0.48), 6.849 (0.44), 6.851 (0.45), 6.870 (0.51), 6.872 (0.48), 6.966 (0.40), 7.673 (0.41), 7.696 (4.12), 7.933 (0.43), 7.951 (0.60), 7.953 (0.54), 7.972 (0.53), 8.054 (0.67), 8.057 (0.62), 8.071 (0.49), 8.075 (0.41), 9.279 (0.96), 9.311 (0.50). |
| 362 | | LC-MS (Method L1): Rt = 1.25 min; MS (ESIpos): m/z = 509 [M + H]+ | $^1$H-NMR (400 MHz, DMSO-d6) delta [ppm]: −0.008 (3.35), 0.008 (3.09), 1.942 (0.95), 1.962 (1.01), 1.973 (1.12), 1.994 (1.07), 2.877 (0.97), 2.897 (1.34), 3.072 (2.46), 3.089 (5.60), 3.105 (2.97), 3.287 (1.80), 3.448 (1.02), 3.452 (1.05), 3.463 (2.26), 3.469 (2.04), 3.479 (2.06), 3.483 (2.02), 3.500 (0.82), 4.961 (1.79), 4.975 (4.01), 4.989 (1.75), 5.573 (1.56), 5.593 (1.55), 5.754 (4.61), 7.226 (2.94), 7.234 (3.06), 7.240 (3.44), 7.248 (5.14), 7.258 (1.67), 7.266 (2.16), 7.276 (1.40), 7.279 (1.19), 7.511 (1.39), 7.523 (1.39), 7.533 (1.20), 7.657 (3.86), 7.659 (5.48), 7.663 (16.00), 7.667 (6.58), 7.670 (3.35), 7.673 (2.04), 7.676 (1.25), 7.683 (0.83), 7.839 (1.73), 7.857 (2.68), 7.860 (1.98), 7.879 (2.73), 7.927 (2.89), 7.931 (3.10), 7.945 (2.00), 7.949 (1.80), 8.630 (2.51), 8.634 (2.52), 8.651 (2.41), 8.655 (2.15), 8.879 (10.16), 9.027 (2.07), 9.048 (2.05). |
| 363 | | LC-MS (Method L1): Rt = 1.37 min; MS | $^1$H-NMR (400 MHz, DMSO-d6) delta [ppm]: −0.008 (2.58), 0.008 (2.57), 1.356 (1.00), 2.085 (16.00), 4.144 (1.13), 5.754 (1.90), 6.743 (1.76), 6.747 (2.04), 6.764 (1.98), 6.767 (2.24), 6.788 (1.04), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | (ESIpos): m/z = 558 [M + H]+ | 6.791 (1.01), 6.807 (2.03), 6.810 (1.93), 6.826 (1.26), 6.829 (1.15), 6.992 (1.32), 6.995 (2.52), 6.997 (1.59), 7.013 (1.50), 7.015 (2.62), 7.017 (1.66), 7.111 (0.95), 7.116 (1.01), 7.132 (1.62), 7.138 (1.65), 7.141 (1.44), 7.150 (2.04), 7.153 (2.12), 7.157 (1.66), 7.159 (1.41), 7.169 (1.40), 7.171 (1.37), 7.265 (1.54), 7.285 (1.54), 7.584 (1.21), 7.589 (1.25), 7.604 (1.61), 7.609 (1.64), 7.623 (1.04), 7.628 (1.04), 7.681 (0.99), 7.684 (1.64), 7.686 (2.60), 7.690 (5.09), 7.695 (12.74), 7.698 (4.45), 7.700 (3.56), 7.734 (1.72), 7.751 (2.14), 7.755 (2.02), 7.773 (2.10), 7.916 (2.37), 7.919 (2.53), 7.934 (2.01), 7.938 (1.93), 8.298 (1.27), 8.300 (1.54), 8.303 (1.59), 8.305 (1.45), 8.310 (1.37), 8.312 (1.59), 8.315 (1.49), 8.317 (1.32), 8.336 (2.29), 8.339 (2.36), 8.357 (2.07), 8.361 (1.99), 9.071 (8.31), 9.124 (1.92), 9.144 (1.88). |
| 364 | | LC-MS (Method L1): Rt = 1.28 min; MS (ESIpos): m/z = 525 [M + H]+ | $^1$H-NMR (400 MHz, DMSO-d6) δ [ppm]: −0.008 (2.66), 0.008 (2.57), 2.119 (1.04), 2.128 (0.86), 2.366 (0.82), 2.710 (0.82), 3.060 (2.72), 3.077 (6.64), 3.093 (3.50), 3.287 (2.70), 3.438 (1.04), 3.454 (2.48), 3.468 (3.16), 3.481 (2.10), 3.497 (0.89), 4.254 (1.46), 4.263 (1.26), 4.273 (2.24), 4.282 (2.43), 4.297 (1.35), 4.946 (2.06), 4.960 (4.56), 4.974 (1.99), 5.291 (1.28), 5.310 (1.31), 6.781 (2.41), 6.784 (2.61), 6.802 (2.74), 6.805 (2.88), 6.910 (1.33), 6.913 (1.46), 6.928 (2.63), 6.932 (2.57), 6.947 (1.59), 6.950 (1.53), 7.151 (1.31), 7.156 (1.35), 7.173 (2.21), 7.190 (1.24), 7.194 (1.13), 7.448 (2.17), 7.465 (2.06), 7.627 (1.00), 7.632 (1.04), 7.658 (5.73), 7.662 (16.00), 7.666 (6.68), 7.669 (3.41), 7.675 (1.22), 7.838 (1.93), 7.856 (2.97), 7.859 (2.35), 7.877 (2.92), 7.929 (3.21), 7.932 (3.50), 7.946 (2.21), 7.950 (2.06), 8.624 (2.97), 8.627 (2.97), 8.645 (2.70), 8.649 (2.50), 8.881 (10.45), 9.155 (2.48), 9.175 (2.37). |
| 365 | | LC-MS (Method L1): Rt = 1.32 min; MS (ESIpos): m/z = 507 [M + H]+ | $^1$H-NMR (400 MHz, DMSO-d6) δ [ppm]: −0.150 (1.77), −0.008 (16.00), 0.008 (14.17), 0.146 (1.65), 1.236 (0.71), 2.104 (1.48), 2.217 (1.18), 2.327 (3.48), 2.366 (2.13), 2.523 (12.52), 2.669 (3.84), 2.709 (2.18), 4.249 (2.01), 4.269 (2.72), 4.297 (1.83), 5.284 (1.83), 5.303 (1.89), 5.754 (4.66), 6.784 (3.66), 6.804 (4.13), 6.917 (1.89), 6.932 (3.60), 6.951 (2.36), 7.155 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.89), 7.173 (2.89), 7.193 (1.54), 7.357 (3.25), 7.362 (7.38), 7.366 (5.20), 7.394 (13.99), 7.398 (11.04), 7.430 (3.01), 7.447 (2.95), 7.814 (2.48), 7.832 (4.07), 7.853 (4.07), 7.892 (4.43), 7.896 (4.84), 7.910 (2.89), 8.550 (3.96), 8.554 (3.84), 8.571 (3.72), 8.575 (3.48), 8.841 (14.23), 9.114 (3.31), 9.135 (3.25). |
| 366 | 4.79 | | $^{1}$H-NMR (399, 9532 MHz, DMSO): δ = 9.129 (0.47); 9.1148 (0.47); 9.1094 (0.47); 8.7855 (1.25); 8.7775 (1.27); 8.6377 (0.78); 8.6169 (0.83); 7.8685 (0.52); 7.8505 (0.85); 7.8295 (0.79); 7.7781 (1.03); 7.7634 (0.65); 7.7608 (0.66); 7.7301 (0.69); 7.7265 (0.81); 7.7101 (0.84); 7.7068 (0.92); 7.4773 (0.34); 7.4638 (0.65); 7.4576 (0.71); 7.4446 (0.66); 7.4301 (0.75); 7.4129 (0.41); 7.3928 (0.56); 7.3822 (0.55); 7.3662 (0.35); 7.1798 (0.35); 7.1614 (0.7); 7.1419 (0.43); 6.9335 (0.47); 6.915 (0.8); 6.8966 (0.39); 6.7926 (0.94); 6.7722 (0.84); 5.2907 (0.43); 5.2723 (0.45); 4.2863 (0.4); 4.2718 (0.77); 4.263 (0.76); 4.2526 (0.49); 4.2448 (0.48); 3.3189 (19.02); 3.0568 (0.38); 3.0385 (1.18); 3.0201 (1.27); 3.0017 (0.5); 2.5053 (32.31); 2.501 (45.79); 2.4969 (38.72); 1.3977 (16); 1.1703 (1.73); 1.1519 (3.55); 1.1335 (1.74); 0.0074 (1.2); −0.0002 (26.74) |
| 367 | 5.48 | | $^{1}$H-NMR (399, 9532 MHz, DMSO): δ = 9.1306 (2.01); 9.1101 (2.05); 8.8861 (7.98); 8.6364 (2); 8.6333 (2.17); 8.6154 (2.23); 8.6122 (2.26); 7.9429 (1.75); 7.9397 (1.94); 7.925 (2.69); 7.9218 (2.64); 7.8638 (2.19); 7.8429 (2.42); 7.8248 (1.46); 7.6937 (0.7); 7.6622 (16); 7.458 (1.87); 7.4401 (1.96); 7.1926 (0.85); 7.1892 (0.9); 7.1715 (1.84); 7.1543 (1.13); 7.1505 (1.13); 6.948 (1.34); 6.9295 (2.26); 6.9106 (1.06); 6.8025 (2.51); 6.7834 (2.23); 6.5799 (0.36); 5.7548 (2.41); 5.3226 (0.52); 5.3079 (1.15); 5.2891 (1.14); 5.2746 (0.5); 4.3171 (0.37); 4.2984 (1.12); 4.2828 (2.04); 4.2742 (1.92); 4.2638 (1.11); 4.2555 (1.22); 4.2357 (0.36); 3.3221 (28.56); 3.0452 (1.38); 3.0269 (4.39); 3.0085 (4.61); 2.9901 (1.55); 2.9503 (2.63); 2.5062 (35.71); 2.5018 (49.01); 2.4975 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (37.88); 2.2455 (0.37); 2.2396 (0.4); 2.2253 (0.63); 2.2154 (0.69); 2.2039 (0.74); 2.1923 (0.58); 2.183 (0.34); 2.1277 (0.35); 2.1193 (0.52); 2.1122 (0.71); 2.1045 (0.86); 2.0944 (0.61); 2.0876 (0.59); 2.078 (0.53); 2.0688 (0.48); 1.397 (6.52); 1.2337 (0.54); 1.1701 (1.44); 1.1529 (5.39); 1.1345 (11.03); 1.1161 (5.17); 0.0078 (2.03); −0.0002 (46.62) |
| 368 | 3.76 | | $^1$H-NMR (399, 9532 MHz, DMSO): δ = 9.4079 (0.91); 9.3936 (0.81); 9.3876 (0.93); 9.348 (0.54); 9.3284 (1.17); 9.3084 (0.7); 9.2139 (0.51); 9.2004 (1.18); 9.1877 (1.26); 9.1743 (0.63); 9.1376 (0.37); 9.124 (0.46); 9.1127 (0.45); 9.0815 (0.48); 9.069 (0.72); 9.0563 (0.54); 8.9299 (4.95); 8.9181 (2.18); 8.3146 (0.48); 7.8564 (6.67); 7.8446 (5.81); 7.8246 (0.32); 7.7421 (2.74); 7.7383 (2.93); 7.7222 (3.38); 7.7184 (3.39); 7.4976 (0.59); 7.4918 (1.24); 7.4783 (1.38); 7.4723 (2.72); 7.4633 (1.1); 7.4588 (1.07); 7.4523 (1.75); 7.4438 (0.68); 7.429 (1.04); 7.4219 (1.82); 7.4179 (1.54); 7.4031 (1.84); 7.399 (1.97); 7.3891 (1.42); 7.3854 (1.42); 7.38 (0.92); 7.3699 (1.26); 7.3497 (0.86); 7.3415 (0.86); 7.1887 (1.08); 7.1706 (2.27); 7.1526 (1.33); 6.9372 (1.41); 6.9184 (2.37); 6.8998 (1.11); 6.8025 (2.56); 6.782 (2.28); 5.7548 (16); 5.244 (0.78); 5.2248 (1.32); 4.3011 (0.47); 4.2715 (1.25); 4.2597 (1.64); 4.2386 (1.15); 4.2313 (1.34); 4.2105 (1.16); 4.19 (0.42); 4.0556 (0.74); 4.0378 (2.3); 4.02 (2.33); 4.0022 (0.78); 3.6324 (0.57); 3.6282 (0.47); 3.6193 (0.65); 3.6135 (1.07); 3.6005 (1.04); 3.595 (0.97); 3.5876 (0.71); 3.5816 (1.03); 3.569 (0.62); 3.5629 (0.59); 3.4779 (0.67); 3.3947 (0.75); 3.3771 (0.89); 3.3607 (0.77); 3.3457 (1.02); 3.3189 (76.03); 3.3011 (0.56); 3.2956 (0.52); 3.2762 (0.74); 2.6748 (0.91); 2.6703 (1.21); 2.6656 (0.94); 2.5235 (3.02); 2.5099 (69.23); 2.5056 (147.9); 2.501 (208.96); 2.4966 (158.74); 2.4924 (78.18); 2.3323 (0.85); 2.328 (1.2); 2.3235 (0.9); 2.2195 (0.41); 2.2066 (0.59); 2.1969 (0.68); 2.1869 (0.78); 2.1765 (0.84); 2.1662 (0.77); 2.1545 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

Example No | logP (Method L0) [a] | LC-MS (Method L2-L5) | NMR or NMR Peaklist

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.61); 2.0945 (0.63); 2.085 (0.73); 2.0685 (0.72); 2.0511 (0.6); 1.9884 (9.96); 1.3946 (1.94); 1.3881 (1.89); 1.376 (4.14); 1.3695 (3.96); 1.3626 (3.1); 1.3577 (2.54); 1.3506 (2.19); 1.344 (5.38); 1.3253 (2.43); 1.1927 (2.64); 1.1749 (5.28); 1.1571 (2.56); 0.008 (1.98); −0.0001 (61.25); −0.0084 (2.3) |
| 369 | 3.94 | | $^1$H-NMR (399, 9532 MHz, DMSO): δ = 9.2003 (2.67); 9.1806 (3.23); 9.167 (2.01); 9.0322 (8.51); 9.019 (6.5); 8.9438 (4.48); 8.9221 (4.91); 8.3143 (2.06); 7.9838 (3.69); 7.9659 (6.23); 7.9442 (6.22); 7.9065 (7.21); 7.889 (4.28); 7.7531 (5.21); 7.7495 (5.57); 7.7332 (6.28); 7.7295 (6.44); 7.508 (2.22); 7.4958 (2.14); 7.4886 (4.93); 7.4766 (4.41); 7.4689 (3.41); 7.4566 (5.08); 7.432 (6.44); 7.4078 (3.86); 7.3882 (1.78); 7.1782 (1.86); 7.1588 (3.64); 7.1396 (2.31); 6.9267 (1.91); 6.9158 (2); 6.908 (3.3); 6.8978 (2.95); 6.8915 (1.75); 6.8809 (1.36); 6.789 (5.67); 6.7684 (5.12); 5.7544 (10.27); 5.214 (1.39); 5.2001 (2.98); 5.1805 (2.91); 5.1675 (1.28); 4.305 (1.02); 4.2955 (1.49); 4.2776 (2.26); 4.2627 (2.39); 4.2546 (1.65); 4.2028 (1.82); 4.1938 (1.6); 4.1816 (2.42); 4.1738 (2.22); 4.1539 (1.1), 4.0375 (0.53); 4.0197 (0.62); 3.9026 (0.65); 3.7185 (0.69); 3.7005 (2.39); 3.6828 (6.64); 3.6642 (7.29); 3.6477 (3.14); 3.631 (1.2); 3.6135 (0.55); 3.5953 (0.33); 3.3784 (0.72); 3.3184 (262.18); 2.675 (3.55); 2.6703 (4.96); 2.666 (3.64); 2.5236 (12.22); 2.5055 (584.02); 2.5011 (819.49); 2.4967 (626.86); 2.3325 (3.45); 2.3279 (4.64); 2.3235 (3.47); 2.1791 (1.23); 2.1677 (1.59); 2.1578 (1.93); 2.1464 (2.45); 2.133 (2.65); 2.1234 (2.57); 2.0956 (1.25); 2.0828 (0.81); 1.9882 (2.46); 1.3887 (0.5); 1.3197 (7.73); 1.3046 (14.27); 1.301 (16); 1.2858 (7.08); 1.2826 (7.64); 1.2589 (1.64); 1.2352 (4.77); 1.193 (1.14); 1.1751 (1.98); 1.1573 (1.17); 1.1406 (0.7); 1.1176 (0.38); 1.0977 (0.35); 0.8541 (0.85); 0.8372 (0.72); 0.768 (0.51); 0.7585 (0.6); 0.7287 (0.37); 0.1458 (0.91); 0.0079 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (6.73); −0.0002 (210.64); −0.0083 (8.7); −0.1499 (0.88) |
| 370 | 4.44 | | $^1$H-NMR (399, 9532 MHz, DMSO): δ = 9.3994 (1.2), 9.3782 (2.63), 9.3572 (1.64), 9.1706 (1.25), 9.1482 (2.41), 9.1234 (1.62), 9.0407 (6.79), 9.0256 (5.14), 8.0137 (2.95), 7.9958 (3.69), 7.8636 (2.22), 7.8447 (3.05), 7.824 (1.78), 7.6865 (2.25), 7.6816 (5.53), 7.6774 (5.78), 7.6659 (16), 7.6613 (10.26), 7.4424 (1.15), 7.4242 (1.23), 7.3796 (1.54), 7.3615 (1.65), 7.1997 (1.27), 7.1795 (2.54), 7.1609 (1.67), 6.9491 (1.99), 6.9307 (3.38), 6.9119 (1.61), 6.8111 (3.75), 6.7907 (3.34), 5.7549 (6.05), 5.2713 (0.45), 5.2578 (1.23), 5.239 (1.43), 5.2251 (1.09), 5.2116 (0.34), 4.3107 (0.44), 4.3029 (0.54), 4.2848 (1.37), 4.2718 (2.3), 4.2635 (1.9), 4.2523 (1.39), 4.2444 (1.58), 4.2328 (0.73), 4.2244 (1.04), 4.217 (0.53), 4.2041 (0.33), 3.6141 (0.78), 3.6102 (0.99), 3.5958 (1.19), 3.5918 (1.15), 3.5813 (1.08), 3.5775 (1.52), 3.5627 (1.01), 3.5591 (1.28), 3.5409 (0.4), 3.3918 (1.1), 3.3729 (1.38), 3.3592 (1.03), 3.353 (1.23), 3.3401 (1.19), 3.3338 (1.2), 3.3202 (28.4), 3.3014 (0.76), 2.675 (0.44), 2.6707 (0.61), 2.6662 (0.47), 2.5235 (1.63), 2.5058 (73.82), 2.5014 (103.74), 2.497 (80.59), 2.493 (41.24), 2.3326 (0.43), 2.3281 (0.59), 2.3239 (0.48), 2.2328 (0.49), 2.2203 (0.71), 2.2113 (0.74), 2.1984 (1.03), 2.1872 (0.95), 2.1772 (0.91), 2.165 (0.61), 2.155 (0.35), 2.1416 (0.36), 2.1271 (0.7), 2.1187 (0.84), 2.1036 (0.67), 2.0935 (0.67), 2.0842 (0.76), 2.0783 (0.75), 2.0684 (0.55), 2.0605 (0.45), 2.0507 (0.37), 2.0437 (0.32), 1.3819 (3.75), 1.3633 (8.24), 1.3575 (3.82), 1.3445 (4.22), 1.3387 (6.43), 1.3199 (2.77), 1.2332 (0.72), 1.1754 (0.4), −0.0002 (0.66) |
| 371 | 4.54 | | $^1$H-NMR (399, 9532 MHz, DMSO): δ = 9.1895 (3.04); 9.1694 (3.1); 9.1296 (0.37); 9.1153 (10.56); 8.9396 (3.14); 8.9368 (3.35); 8.9178 (3.51); 8.915 (3.51); 8.3143 (0.49); 8.0499 (2.68); 8.0473 (2.89); 8.0321 (4.35); 8.0293 (4.1); 7.9727 (3.41); 7 .9543 (2.73); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.951 (3.52); 7.9328 (2.34); 7.7006 (3.22); 7.6959 (6.75); 7.6912 (4.54); 7.655 (16); 7.6503 (13.06); 7.4831 (2.66); 7.4649 (2.85); 7.1902 (1.31); 7.1863 (1.38); 7.1687 (2.79); 7.1515 (1.77); 7.1478 (1.69); 6.9385 (2.04); 6.9201 (3.47); 6.9036 (1.63); 6.9012 (1.66); 6.7982 (3.87); 6.779 (3.55); 5.7544 (1.92); 5.2344 (0.76); 5.2216 (1.73); 5.2018 (1.72); 5.1876 (0.75); 4.3164 (0.62); 4.3031 (0.84); 4.2899 (1.38); 4.2793 (1.29); 4.2738 (1.51); 4.2653 (1.02); 4.2225 (0.99); 4.2147 (1.33); 4.2016 (1.16); 4.1939 (1.75); 4.1864 (0.87); 4.1743 (0.72); 4.1658 (0.65); 3.7057 (0.34); 3.6883 (1.22); 3.6828 (1.08); 3.6702 (3.31); 3.6645 (3.08); 3.6516 (3.37); 3.6461 (3.16); 3.6329 (1.16); 3.6285 (1.24); 3.3193 (68.59); 2.675 (0.88); 2.6705 (1.18); 2.6659 (0.87); 2.5236 (3.14); 2.5101 (69.48); 2.5058 (144.19); 2.5013 (199.43); 2.4969 (149.23); 2.4928 (72.67); 2.3326 (0.83); 2.3282 (1.16); 2.3238 (0.81); 2.2169 (0.37); 2.204 (0.5); 2.1912 (0.95); 2.1785 (1.25); 2.1702 (1.47); 2.1564 (1.69); 2.1486 (1.83); 2.14 (1.59); 2.126 (0.94); 2.1147 (0.54); 2.1053 (0.46); 1.3515 (0.39); 1.3055 (7.28); 1.2869 (15.83); 1.2685 (7.21); 1.2352 (4.31); 1.17 (0.64); 1.1521 (0.57); 0.8536 (0.58); 0.835 (0.32); −0.0002 (1.18) |
| 372 | 4.08 | | $^1$H-NMR (399, 9532 MHz, DMSO): δ = 12.3602 (1.81), 9.1502 (2.55), 9.1301 (2.52), 8.892 (9.63), 8.8835 (0.49), 8.6271 (2.4), 8.624 (2.53), 8.6058 (2.71), 8.6028 (2.68), 7.9529 (2.14), 7.9502 (2.26), 7.9352 (3.25), 7.9323 (3.12), 7.9076 (0.43), 7.8737 (2.65), 7.8528 (2.81), 7.8346 (1.74), 7.6694 (8.23), 7.6663 (16), 7.4556 (2.26), 7.4372 (2.36), 7.1902 (1.1), 7.1719 (2.32), 7.1546 (1.4), 7.151 (1.4), 6.9475 (1.65), 6.9287 (2.79), 6.91 (1.31), 6.8025 (3.17), 6.7815 (2.81), 5.3004 (0.68), 5.2866 (1.49), 5.2669 (1.46), 5.2527 (0.64), 4.3167 (0.34), 4.3082 (0.53), 4.2896 (1.41), 4.2737 (2.43), 4.2645 (2.36), 4.2534 (1.28), 4.245 (1.54), 4.2252 (0.51), 4.2177 (0.4), 4.0377 (0.33), 4.0198 (0.37), 3.3181 (128.86), 3.1629 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.73), 3.145 (6.07), 3.1272 (3.01), 2.89 (0.57), 2.7306 (0.51), 2.6743 (2.28), 2.6697 (3.09), 2.6658 (2.38), 2.615 (0.4), 2.597 (0.4), 2.5228 (8.93), 2.5052 (404.28), 2.5009 (529.51), 2.4965 (389.18), 2.477 (6.31), 2.332 (2.29), 2.3276 (3.04), 2.323 (2.27), 2.2559 (0.33), 2.2437 (0.53), 2.2366 (0.54), 2.2221 (0.88), 2.2127 (1.01), 2.2005 (0.98), 2.1892 (0.78), 2.1288 (0.69), 2.1204 (0.93), 2.1136 (1.11), 2.1049 (0.78), 2.0969 (0.76), 2.0877 (0.7), 2.0787 (0.66), 1.9883 (1.45), 1.2344 (0.51), 1.1925 (0.48), 1.1741 (0.82), 1.1569 (0.42), 1.1054 (0.4), 0.0077 (1.78), −0.0003 (53.99), −0.008 (2.53) |
| 373 | | LC-MS (Method L1): Rt = 1.39 min; MS (ESIpos): m/z = 479 [M + H]+ | $^1$H-NMR (400 MHz, DMSO-d6) δ [ppm]: 4.172 (16.00 4.245 (0.90), 4.254 (1.07), 4.269 (1.49), 4.273 (1.51), 4.283 (0.86), 5.274 (0.83), 5.293 (0.83), 5.754 (12.35), 6.793 (1.40), 6.796 (1.53), 6.814 (1.59), 6.816 (1.66), 6.909 (0.74), 6.912 (0.74), 6.928 (1.55), 6.930 (1.54), 6.946 (0.93), 6.949 (0.91), 7.159 (0.76), 7.163 (0.82), 7.180 (1.29), 7.363 (1.33), 7.380 (1.25), 7.650 (0.88), 7.655 (2.07), 7.659 (2.33), 7.670 (7.40), 7.675 (4.39), 7.702 (1.20), 7.720 (1.66), 7.723 (1.57), 7.741 (1.47), 7.886 (1.69), 7.890 (1.80), 7.904 (1.44), 7.908 (1.42), 8.296 (1.61), 8.299 (1.63), 8.317 (1.54), 8.320 (1.45), 8.811 (5.57), 9.192 (1.36), 9.212 (1.34). |
| | 1.66 | | 384: $^1$H-NMR (400.0 MHz, $d_6$-DMSO): δ = 8.9731 (0.6); 8.9623 (0.6); 8.9531 (0.6); 8.9419 (0.5); 8.4859 (0.4); 8.3740 (0.7); 8.3670 (0.7); 8.3565 (0.8); 8.3495 (0.8); 8.3209 (2.7); 7.7618 (0.4); 7.7477 (0.4); 7.7333 (0.5); 7.7203 (0.4); 7.6684 (1.2); 7.6517 (1.2); 7.6483 (1.4); 7.5524 (0.5); 7.5423 (3.3); 7.5361 (1.8); 7.5245 (1.4); 7.5070 (0.4); 7.4333 (0.4); 7.4228 (0.5); 7.4138 (0.9); 7.4033 (0.8); 7.3941 (0.6); 7.3837 (0.5); 7.3046 (1.3); 7.2862 (1.8); 7.2711 (0.5); 7.1678 (0.5); 7.1476 (1.1); 7.1280 (0.6); 6.9086 (0.8); 6.8899 (1.2); 6.8713 (0.6); 6.7857 (1.6); 6.7654 (1.3); 5.2479 (0.3); 5.2338 (0.7); 5.2140 (0.7); 4.2573 (1.1); 4.2441 (1.8); 4.2314 (1.1); 3.3217 (36.1); 3.0620 (2.2); 3.0560 (2.8); 3.0504 (2.7); 3.0439 (2.5); 3.0278 (0.6); 2.5049 (33.4); 2.5007 (44.2); 2.4965 (34.0); 2.1736 (0.3); 2.1521 (0.4); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 2.1380 (0.6); 2.1241 (0.5); 2.0312 (0.5); 2.0163 (0.6); 2.0038 (0.3); 1.9947 (0.4); 1.9884 (0.4); 1.3971 (16.0); −0.0002 (19.8) |
| 385 | 1.55 | | 385: $^1$H-NMR (400.0 MHz, $d_6$-DMSO): δ = 8.9954 (0.7); 8.9747 (0.7); 8.4127 (0.8); 8.3889 (3.2); 7.8025 (0.5); 7.7890 (0.5); 7.6892 (0.8); 7.6729 (1.1); 7.5759 (0.9); 7.5701 (0.4); 7.5551 (1.2); 7.5367 (0.7); 7.3163 (0.7); 7.2977 (0.8); 7.1731 (0.7); 7.1561 (1.1); 7.1385 (0.6); 6.9188 (0.5); 6.9014 (0.9); 6.8835 (0.4); 6.7948 (1.0); 6.7745 (1.0); 5.2426 (0.5); 5.2229 (0.5); 4.2655 (0.8); 4.2517 (1.4); 4.2391 (0.8); 3.3230 (12.3); 3.0662 (2.8); 3.0538 (2.8); 2.5055 (17.4); 2.5013 (22.6); 2.4970 (17.0); 2.1478 (0.4); 2.1343 (0.4); 2.0450 (0.3); 2.0307 (0.4); 1.9884 (0.9); 1.3974 (16.0); 1.1746 (0.4); 0.0078 (0.5); −0.0002 (12.0) |
| 395 | 1.93 | | 395: $^1$H-NMR (400.0 MHz, $d_6$-DMSO): δ = 8.9826 (3.1), 8.9620 (3.2), 8.4484 (2.1), 8.4334 (2.3), 8.4245 (2.4), 8.4103 (12.6), 8.3268 (0.6), 7.9292 (1.8), 7.9165 (1.8), 7.6580 (3.8), 7.6532 (7.4), 7.6484 (4.2), 7.5327 (2.4), 7.5095 (4.5), 7.4864 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (2.4), 7.4628 (11.2), 7.4594 (10.8), 7.3192 (0.3), 7.3065 (2.9), 7.2879 (3.1), 7.1773 (1.4), 7.1738 (1.4), 7.1563 (2.9), 7.1388 (1.9), 7.1353 (1.8), 6.9190 (2.0), 6.9164 (2.2), 6.9001 (3.6), 6.8979 (3.8), 6.8819 (1.8), 6.8792 (1.8), 6.7961 (4.0), 6.7940 (4.1), 6.7757 (3.7), 6.7735 (3.6), 5.7559 (16.0), 5.2477 (0.8), 5.2330 (1.9), 5.2134 (1.9), 5.1997 (0.9), 4.2618 (3.1), 4.2486 (5.4), 4.2356 (3.4), 4.0379 (0.4), 4.0202 (0.4), 3.3218 (86.0), 3.0661 (11.7), 3.0536 (11.8), 2.6749 (0.6), 26705 (0.8), 2.6660 (0.6), 2.5238 (2.8), 2.5103 (50.5), 2.5060 (102.1), 2.5015 (134.9), 2.4970 (97.8), 2.4927 (47.7), 2.3328 (0.6), 2.3282 (0.8), 2.3237 (0.6), 2.1916 (0.4), 2.1780 (0.9), 2.1627 (1.0), 2.1574 (0.9), 2.1424 (1.6), 2.1289 (1.5), 2.1149 (0.6), 2.0549 (0.5), 2.0425 (1.3), 2.0280 (1.5), 2.0205 (0.8), 2.0150 (0.9), 2.0069 (1.1), 1.9887 (2.2), 1.3973 (10.5), 1.3516 (0.5), 1.2587 (0.4), 1.2492 (0.3), 1.2333 (0.9), 1.1926 (0.5), 1.1748 (1.0), 1.1570 (0.5), 0.0080 (1.2), −0.0001 (34.0), −0.0084 (1.3) |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 427 | 3.81 | | 427: $^1$H-NMR (400.0 MHz, $d_6$-DMSO): δ = 8.8749 (4.5); 8.8543 (4.6); 8.6918 (16.0); 8.2529 (4.8); 8.2338 (5.1); 8.2316 (5.1); 7.8425 (4.2); 7.8272 (6.1); 7.7693 (4.8); 7.7486 (5.2); 7.7304 (3.1); 7.6505 (0.9); 7.6422 (1.0); 7.6350 (1.2); 7.6273 (1.9); 7.6235 (2.0); 7.6142 (1.9); 7.6064 (1.9); 7.6016 (1.9); 7.5948 (1.2); 7.5866 (1.0); 7.5788 (0.8); 7.4334 (4.3); 7.4147 (4.7); 7.2421 (2.4); 7.2322 (2.4); 7.2202 (2.3); 7.1731 (2.1); 7.1554 (4.4); 7.1378 (2.7); 6.9373 (3.2); 6.9188 (5.5); 6.9002 (2.6); 6.7863 (6.0); 6.7657 (5.5); 5.2365 (1.2); 5.2204 (2.8); 5.2018 (2.8); 5.1875 (1.3); 4.2935 (0.8); 4.2753 (2.7); 4.2587 (4.8); 4.2499 (4.6); 4.2384 (2.6); 4.2310 (2.9); 4.2102 (0.9); 4.0554 (0.4); 4.0378 (0.9); 4.0205 (0.9); 3.4979 (41.4); 3.4611 (0.3); 3.3196 (127.6); 3.2906 (37.1); 3.2593 (0.4); 3.2518 (0.4); 2.6711 (1.5); 2.6075 (0.4); 2.5052 (201.2); 2.5014 (249.4); 2.3279 (1.4); 2.1701 (1.6); 2.1600 (1.7); 2.1500 (1.9); 2.1376 (1.4); 2.1280 (0.8); 2.0556 (1.8); 2.0483 (2.1); 2.0386 (1.5); 2.0298 (1.5); 2.0223 (1.3); 2.0126 (1.2); 1.9885 (3.7); 1.3978 (3.7); 1.2364 (0.7); 1.1922 (0.9); 1.1746 (1.9); 1.1566 (1.0); −0.0002 (4.5) |
| 445 | 2.13 | | 445: $^1$H-NMR (400.0 MHz, $d_6$-DMSO): δ = 8.4154 (0.6); 8.4123 (0.6); 7.6823 (0.4); 7.6786 (0.4); 7.6571 (0.4); 7.6475 (0.4); 7.6400 (0.9); 6.7637 (0.4); 5.7524 (16.0); 4.0645 (0.6); 3.8724 (0.6); 3.3200 (2.8); 2.5052 (4.9); 2.5008 (6.3); 2.4963 (4.5); 2.3205 (0.4); 1.9880 (0.7); 1.1752 (0.4); −0.0002 (4.8) |
| 452 | 3.94 | | 452: $^1$H-NMR (400.0 MHz, $d_6$-DMSO): δ = 8.7209 (3.6); 8.7000 (4.0); 8.6897 (16.0); 8.2701 (3.6); 8.2667 (4.0); 8.2490 (4.3); 8.2456 (4.2); 7.8441 (3.0); 7.8409 (3.3); 7.8265 (5.0); 7.823 3 (4.6); 7.7697 (4.4); 7.7515 (3.6); 7.7486 (4.4); 7.7308 (2.8); 7.6522 (0.7); 7.6444 (0.8); 7.6369 (0.9); 7.6300 (1.4); 7.6246 (1.4); 7.6163 (1.4); 7.6081 (1.3); 7.6034 (1.4); 7.5958 (0.9); 7.5887 (0.8); 7.5810 (0.6); 7.4927 (0.3); 7.4814 (2.2); 7.4729 (2.9); 7.4605 (2.8); 7.2674 (1.3); 7.2549 (3.5); 7.2449 (6.3); 7.2328 (9.0); 7.2219 (8.0); 7.2162 (3.8); 7.2103 (4.7); 7.1981 (0.5); 5.7572 (10.3); 5.5284 (1.0); 5.5088 (2.9); 5.4887 (2.9); 5.4687 (1.0); 3.4923 (37.5); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 3.3247 (16.2); 3.3105 (0.7); 3.2922 (32.1); 2.9922 (0.7); 2.9841 (0.8); 2.9705 (0.9); 2.9620 (1.0); 2.9529 (1.6); 2.9448 (1.6); 2.9309 (1.6); 2.9228 (1.4); 2.8834 (1.1); 2.8630 (2.4); 2.8426 (1.8); 2.8234 (1.2); 2.8026 (0.7); 2.5231 (1.6); 2.5094 (15.9); 2.5051 (32.4); 2.5007 (41 5); 2.4962 (30.3); 2.4728 (1.7); 2.4643 (1.4); 2.4530 (0.8); 2.4449 (0.6); 1.9656 (0.7); 1.9440 (1.9); 1.9342 (0.8); 1.9232 (1.9); 1.9127 (1.8); 1.9014 (0.8) 1.8918 (1.7); 1.8700 (0.6) |
| 481 | 3.33 | | 481: $^1$H-NMR (400.0 MHz, $d_6$-DMSO): δ = 9.8434 (0.4); 9.1777 (1.2); 9.1644 (1.4); 9.1583 (1.5); 9.1461 (1.1); 8.9656 (0.6); 8.5679 (0.4); 8.5578 (0.4); 8.3141 (0.4); 8.2906 (0.3); 8.2685 (0.4); 8.2490 (2.2); 8.2440 (2.2); 8.2295 (2.4); 8.2244 (2.4); 8.0111 (0.7); 7.9895 (0.6); 7.9522 (1.0); 7.6897 (2.8); 7.6861 (2.8); 7.6697 (3.4); 7.6661 (3.2); 7.6383 (1.3); 7.6206 (3.6); 7.6005 (6.3); 7.5945 (4.4); 7.5819 (1.4); 7.5774 (0.8); 7.5191 (0.4); 7.5077 (0.4); 7.4986 (0.4); 7.4872 (0.4); 7. 4510 (1.0); 7.4428 (0.9); 7.4319 (1.9); 7.4236 (1.7); 7.4122 (1.2); 7.4041 (1.0); 7.3352 (2.6); 7.3166 (3.0); 7.3077 (2.3); 7.2883 (0.9); 7.1880 (1.2); 7.1703 (2.4); 7.1527 (1.5); 6.9365 (1.3); 6.9169 (2.1); 6.8982 (1.0); 6.8079 (3.2); 6.7875 (2.9); 5.7540 (7.8); 5.2734 (1.3); 4.3307 (0.6); 4.3220 (0. 9); 4.3038 (1.1); 4.2925 (1.5); 4.2828 (0.9); 4.2350 (1.1); 4.2103 (1.5); 4.1831 (0.6); 4.1709 (0.8); 4.0380 (0.6); 4.0202 (0.6); 3.8597 (5.5); 3.8494 (7.9); 3.8384 (5.6); 3.5677 (1.0); 3.3182 (55.23); 3.2947 (0.7); 3.2627 (6.5); 2.8904 (6.9); 2.7313 (6.1); 2.6743 (0.9); 2.6700 (1.2); 2.6657 (0.9); 2.62 38 (0.6); 2.5054 (151.3); 2.5010 (194.0); 2.4966 (144.4); 2.4305 (16.0); 2.3321 (0.9); 2.3276 (1.2); 2.3234 (0.8); 2.2815 (0.4); 2.2703 (0.6); 2.2584 (0.6); 2.2457 (1.0); 2.2346 (1.0); 2.2223 (0.8); 2.2102 (0.7); 2.0907 (1.1); 2.0764 (0.8); 2.0611 (0.8); 1.9881 (2.2); 1.9643 (2.5); 1.9078 (0.7); 1.2982 (0.8); 1.2586 (1.2); 1.2354 (1.8); 1.1925 (0.7); 1.1749 (1.3); 1.1570 (0.7); 1.0448 (0 8); 1 0296 (0.9); 0.8533 (0.5); 0.8367 (0.4); −0.0002 (20.1) |
| 482 | 4.36 | | 482: $^1$H-NMR (400.0 MHz, $d_6$-DMSO): δ = 9.2312 (1.6); 9.2113 (1.7); 8.8635 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.8); 8.8560 (0.7); 8.6870 (4.9); 8.6846 (4.8); 8.4211 (0.4); 8.4187 (0.4); 8.4001 (0.5); 8.3976 (0.5); 8.3288 (2.1); 8.3253 (2.2); 8.3085 (2.4); 8.3046 (2.3); 7.9518 (2.0); 7.9399 (0.4); 7.9219 (0.6); 7.9013 (0.5); 7.8692 (0.6); 7.8658 (0.7); 7.8512 (0.4); 7.8481 (0.4); 7.7575 (1.4); 7.7398 (3.3); 7.7265 (0.8); 7.7194 (3.5); 7.7134 (3.1); 7.7092 (5.0); 7.7044 (3.8); 7.6931 (3.6); 7.6900 (4.4); 7.4756 (0.6); 7.4676 (0.9); 7.4573 (1.2); 7.4481 (1.9); 7.4380 (1.7); 7.4285 (1.2); 7.4184 (1.1); 7.4106 (0.4); 7.4063 (0.5); 7.3859 (0.6); 7.3624 (3.5); 7.3434 (4.0); 7.3282 (1.0); 7.1883 (1.2); 7.1679 (2.6); 7.1496 (1.6); 6.9420 (0.4); 6.9215 (1.7); 6.9027 (2.5); 6.8841 (1.1); 6.8042 (3.6); 6.7838 (3.2); 6.4934 (0.6); 6.3542 (1.2); 6.2153 (0.6); 5.2813 (0.6); 5.2666 (1.4); 5.2495 (1.3); 5.2341 (0.6); 4.3072 (0.4); 4.2994 (0.6); 4.2811 (1.5); 4.2661 (2.6); 4.2573 (2.4); 4.2461 (1.4); 4.2383 (1.6); 4.2184 (0.5); 3.6443 (1.0); 3.6356 (1.1); 3.6076 (2.1); 3.5982 (2.1); 3.5702 (1.1); 3.5611 (1.1); 3.3361 (8.5); 3.1204 (16.0); 28898 (12.3); 2.7309 (11.2); 2.6697 (0.4); 2.5464 (0.5); 2.5320 (0.4); 2.5051 (52.8); 2.5008 (69.0); 2.4966 (53.0); 2.3273 (0.4); 2.2272 (0.8); 22132 (1.0); 2.2032 (1.0); 2.1911 (1.0); 2.1802 (0.8); 2.1700 (0.5); 2.0712 (0.8); 2.0635 (1.0); 2.0557 (1.1); 2.0404 (0.8); 2.0291 (0.7); 2.0202 (0.7); 2.0057 (0.3); −0.0003 (6.8) |
| 483 | 4.51 | | 483: $^1$H-NMR (400.0 MHz, $d_6$-DMSO): δ = 9.1530 (3.3); 9.1331 (3.3); 8.3144 (0.4); 8.2384 (3.3); 8.2175 (3.5); 7.8013 (3.3); 7.7859 (4.0); 7.7833 (4.0); 7.6663 (12.9); 7.6617 (16.0); 7.6435 (3.0); 7.6257 (7.6); 7.6217 (9.8); 7.6044 (2.4); 7.3530 (3.1); 7.3342 (3.3); 7.1978 (1.5); 7.1799 (3.2); 7.1626 (1.9); 7.1501 (1.9); 6.9502 (2.2); 6.9325 (3.8); 6.9143 (1.8); 6.8162 (4.2); 6.7962 (3.8); 5.7539 (0.9); 5.3110 (0.9); 5.2992 (1.9); 5.2910 (1.6); 5.2806 (1.9); 5.2681 (0.9); 4.3430 (0.8); 4.3318 (1.2); 4.3146 (1.5); 4.3034 (1.9); 4.2377 (1.5); 4.2126 (2.1); 4.1903 (1.0); 4.1861 (0.8); 3.8582 (7.3); 3.8486 (9.8); 3.8372 (7.6); 3.3198 (91.4); 3.2545 (9.6); 2.8907 (1.6); 2.7317 (1.5); 2.6703 (1.1); 2.5307 (28.2); 2.5057 (131.0); 2.5014 (169.2); 2.4972 (132.2); 2.4303 (0.4); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.3280 (1.0); 2.3238 (0.9); 2.2931 (0.5); 2.2833 (0.7); 2.2694 (0.8); 2.2569 (1.3); 2.2474 (1.3); 2.2359 (1.1); 2.2245 (1.0); 2.1036 (1.5); 20895 (1.1); 2.0744 (1.0); 2.0689 (1.0); 1.3522 (0.3); 1.2983 (0.4); 1.2583 (0.6); 1.2331 (1.0); 1.0454 (0.5); 1.0302 (0.5); −0.0002 (21.6) |
| 484 | 1.75 | | 484: $^1$H-NMR (400.0 MHz, $d_6$-DMSO): δ = 9.0532 (4.3); 9.0323 (4.2); 8.5051 (0.4); 8.4393 (4.2); 8.4350 (4.5); 8.4201 (4.4); 8.4155 (4.6); 8.3939 (8.8); 8.3868 (9.2); 8.3142 (1.4); 7.6897 (0.4); 7.6761 (6.0); 7.6726 (6.4); 7.6560 (7.9); 7.6525 (8.2); 7.6359 (2.7); 7.6087 (1.6); 7.5964 (2.8); 7.5831 (42); 7.5660 (16.0); 7.5467 (7.3); 7.5290 (2.7); 7.4346 (2.4); 7.4274 (2.4); 7.4149 (4.7); 7.4079 (4.6); 7.3953 (2.9); 7.3881 (2.7); 7.3083 (6.5); 7.3013 (7.6); 7.2893 (5.4); 7.1723 (2.8); 7.1545 (5.6); 7.1369 (3.3); 6.9047 (4.1); 6.8873 (6.8); 6.8693 (3.2); 6.7945 (7.5); 6.7740 (6.8); 5.2588 (1.6); 5.2429 (3.5); 5.2246 (3.4); 5.2103 (1.5); 4.7025 (4.2); 4.6839 (6.9); 4.6682 (6.4); 4.6465 (2.6); 4.6386 (2.2); 4.3431 (1.0); 4.3325 (1.0); 4.2970 (6.9); 4.2829 (10.8); 4.2688 (9.9); 4.2575 (8.7); 4.2461 (5.4); 4.2278 (0.8); 4.0556 (1.0); 4.0378 (3.1); 4.0200 (3.2); 4.0022 (1.1); 3.7921 (5.4); 3.7775 (8.0); 3.7605 (5.6); 3.4061 (0.4); 3.3209 (633.3); 3.2515 (0.4); 2.6703 (5.2); 2.5056 (663.0); 2.5013 (852.3); 2.4971 (645.4); 2.3840 (0.4); 2.3324 (3.9); 2.3280 (52); 2.3082 (0.4); 2.191.9 (0.8); 2.1797 (1.6); 2.1597 (1.9); 2.1448 (2.9); 2.1293 (2.4); 2.1159 (1.1); 2.0312 (2.3); 2.0180 (2.4); 1.9883 (14.6); 1.2981 (0.3); 1.2593 (0.4); 1.2345 (1.1); 1.1926 (3.6); 1.1748 (7.1); 1.1570 (3.5); 1.0448 (6.4); 1.0295 (6.3); 0.8540 (0.3); 0.0078 (1.1); −0.0002 (31.7) |
| 485 | 4.61 | | 485: $^1$H-NMR (400.0 MHz, $d_6$-DMSO): δ = 9.0447 (1.3); 9.0241 (1.4); 8.6831 (5.0); 8.3580 (0.9); 8.3422 (1.0); 8.3344 (1.0); 8.3188 (1.0); 7.6986 (1.6); 7.6939 (3.0); 7.6892 (1 8); 7.6815 (1.1); 7.6582 (1.9); 7.6350 (1.0); 7.5067 (4.9); 7.5025 (4.7); 7.4296 (0.9); 7.4176 (1.1); 7.4087 (1.0); 7.2865 (0.5); 7.2766 (0.9); 7.2645 (1.5); 7.2529 (0.7); 7.2405 (2.7); 7.2354 (1.7); 7.2291 (1.7); 7.2245 (1.3); 7.2186 (1.6); 5.5624 (0.4); 5.5433 (1.1); 5.5237 (1.1); 5.5041 (0.4); 3.8775 (2.7); 3.8671 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (4.2); 3.8565 (2.8); 3.5679 (2.1); 3.3194 (17.3); 3.2870 (3.4); 3.2784 (3.4); 3.0030 (0.3); 2.9938 (0.4); 2.9851 (0.5); 2.9765 (0.6); 2.9634 (0.6); 2.9552 (0.5); 2.9048 (0.4); 2.8845 (0.9); 2.8646 (0.7); 2.8450 (0.5); 2.6708 (0.5); 2.6662 (0.4); 2.5661 (0.3); 2.5564 (0.6); 2.5453 (0.8); 2.5356 (1.0); 2.5237 (2.6); 2.505S 1 (67.0); 2.5015 (85.5); 2.4972 (64.1); 2.3327 (0.4); 2.3285 (0.5); 2.3238 (0.4); 1.9882 (1.2); 1.9554 (0.6); 1.9449 (0.3); 1.9351 (0.6); 1.9237 (0.6); 1.9042 (0.6); 1.3978 (16.0); 1.1752 (0.6); −0.0002 (3.5) |
| 486 | 2.63 | | 486: $^1$H-NMR (400.0 MHz, $d_6$-DMSO): δ = 9.3542 (5.2); 9.3302 (5.6); 9.1745 (3.3); 9.1546 (3.4); 8.5530 (16.0); 8.4199 (3.0); 8.4043 (3.3); 8.3963 (3.5); 8.3808 (3.2); 8.1903 (5.9); 8.1702 (6.4); 7.7341 (3.5); 7.7112 (6.5); 7.6943 (2.1); 7.6878 (5.3); 7.6762 (3.0); 7.6661 (2.0); 7.6563 (1.7); 7.5069 (2.7); 7.4864 (3.7); 7.4659 (2.1); 7.345 (4.0); 7.3267 (4.4); 7.1685 (2.0); 7.1506 (4.3); 7.1329 (2.6); 7.1302 (2.5); 6.9072 (3.0); 6.8889 (5.2); 6.8703 (2.4); 6.7892 (5.9); 6.7690 (5.4); 5.2557 (1.2); 5.2415 (2.6); 5.2224 (2.7); 5.2081 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (15); 4.2961 (0.7); 4.2873 (1.0); 4.2804 (0.9); 4.2686 (2.4); 4.2592 (2.3); 4.2526 (2.8); 4.2429 (3.4); 4.2350 (2.7); 4.2211 (2.2); 4.2140 (2.8); 4.1933 (1.0); 4.1864 (0.8); 4.0381 (0.5); 4.0204 (0.5); 3.8901 (13.8); 3.8786 (8.0); 3.8613 (1.1); 3.3619 (1.0); 3.3512 (1.8); 3.3217 (51.2); 3.3073 (9.9); 3.2947 (4.6); 3.2752 (1.7); 3.2647 (1.0); 2.6702 (0.9); 2.6662 (0.7); 2.5404 (3.4); 2.5054 (114.7); 2.5012 (147.6); 2.4969 (111.5); 2.3277 (0.9); 2.2413 (0.6); 2.2284 (0.9); 2.2203 (1.2); 2.2072 (1.7); 2.1979 (1.7); 2.1856 (1.8); 2.1736 (1.3); 2.1643 (0.8); 2.0621 (1.2); 2.0540 (1.7); 2.0471 (1.9); 2.0314 (1.4); 2.0198 (1.3); 2.0125 (1.2); 2.0049 (0.8); 1.9975 (0.6); 1.9883 (2.2); 1.2586 (0.4); 1.2350 (0.4); 1.1927 (0.6); 1.1749 (1.1); 1.1589 (5.2); 1.0697 (4.9); 1.0455 (0.4); 1.0301 (0.4); 0.1459 (0.7); 0.0073 (6.8); −0.0002 (147.2); −0.1497 (0.8) |
| 490 | 2.96 | | 490: $^1$H-NMR (400.0 MHz, $d_6$-DMSO): δ = 9.1477 (4.1); 9.1276 (4.1); 8.5827 (12.2); 8.3171 (2.9); 8.3016 (3.0); 8.2939 (3.1); 8.2782 (2.8); 7.9206 (2.2); 7.6395 (3.1); 7.6171 (5.3); 7.5945 (2.9); 7.3628 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.2); 7.3551 (2.2); 7.3452 (2.4); 7.3386 (2.3); 7.2276 (2.8); 7.2178 (2.4); 7.2081 (3.6); 7.1982 (3.5); 7.1819 (2.0); 7.1787 (2.0); 7.1607 (4.1); 7.1434 (6.7); 7.1244 (2.7); 7.0096 (0.5); 6.9931 (0.7); 6.9503 (3.6); 6.9211 (5.0); 6.9062 (4.3); 6.8877 (2.0); 6.7966 (5.4); 6.7764 (4.8); 5.2635 (1.1); 5.2495 (2.4); 5.2301 (2.4); 5.2154 (1.1); 4.2964 (0.9); 4.2773 (2.1); 4.2608 (2.5); 4.2515 (2.8); 4.2266 (2.2); 4.1995 (0.8); 4.0557 (1.2); 4.0379 (3.4); 4.0201 (3.4); 4.0023 (1.1); 3.8713 (11.2); 3.3206 (387.1); 3.2966 (7.4); 3.2905 (7.5); 3.2825 (7.0); 3.2732 (5.1); 3.2568 (2.4); 3.2395 (1.2); 2.6747 (1.8); 2.6703 (2.4); 2.6661 (1.8); 2.5057 (315.1); 2.5013 (404.4); 2.4970 (301.6); 2.4284 (0.4); 2.3278 (5.0); 2.2944 (14.1); 2.2808 (14.3); 2.2321 (3.2); 2.2139 (1.4); 2.2024 (1.5); 2.1933 (1.5); 2.1807 (1.2); 2.0542 (1.7); 2.0257 (1.2); 2.0200 (1.1); 2.0040 (0.6); 1.9883 (14.3); 1.8912 (14.0); 1.8683 (13.8); 1.3979 (16.0); 1.2586 (0.3); 1.2359 (0.8); 1.1927 (3.8); 1.1749 (7.5); 1.1571 (3.7); 1.0448 (0.8); 1.0296 (0.8); −0.0002 (5.2) |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 515 | 3.00 | | 515: $^1$H-NMR (400.0 MHz, $d_6$-DMSO): δ = 9.1233 (0.6); 9.1025 (0.6); 8.5606 (1.9); 8.2915 (0.5); 8.2868 (0.5); 8.2717 (0.5); 8.2669 (0.5); 8.1363 (10.5); 7.7032 (0.6); 7.6996 (0.6); 7.6S3 2 (0.8); 7.6797 (0.7); 7.6686 (0.8); 7.6482 (1.2); 7.6420 (0.9); 7.4385 (0.4); 7.4299 (0.4); 7.3534 (0.6); 7.3361 (0.7); 7.1628 (0.5); 7.1460 (0.3); 7.1422 (0.3); 6.9168 (0.4); 6.8993 (0.6); 6.7981 (0.7); 6.7787 (0.6); 4.2597 (0.6); 4.2485 (0.5); 4.2391 (0.3); 3.8361 (0.4); 3.8217 (0.4); 3.8088 (0.5); 3.3351 (2.2); 3.3298 (2.2); 3.3070 (2.3); 3.1311 (0.5); 3.1135 (0.7); 3.0824 (4.2); 2.6708 (0.4); 2.5061 (48.0); 2.5017 (62.2); 2.4973 (46.5); 2.3283 (0.4); 2.0857 (16.0); 2.0411 (0.4); 2.0329 (0.4); 1.7082 (0.4); −0.0002 (7.0) |
| 516 | 3.90 | | 516: $^1$H-NMR (400.0 MHz, $d_6$-DMSO): δ = 8.8758 (2.0); 8.8723 (2.0); 8.8550 (2.1); 8.7191 (6.4); 8.7148 (6.2); 8.3524 (1.2); 8.3445 (1.3); 8.3368 (1.4); 8.3289 (2.5); 8.3210 (1.5); 8.3134 (1.4); 8.3055 (1.3); 7.7689 (2.3); 7.7459 (4.2); 7.7227 (2.4); 7.7125 (0.7); 7.7045 (0.7); 7.6975 (1.2); 7.6926 (1.2); 7.6839 (1.1); 1.6712 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.2); 7.6640 (0.7); 7.6561 (0.6); 7.6484 (0.5); 7.4239 (1.8); 7.4047 (1.9); 7.3115 (0.8); 7.2995 (1.1); 7.2892 (1.4); 7.2665 (0.7); 7.1748 (1.3); 7.1716 (1.4); 7.1539 (2.8); 7.1364 (1.7); 7.1330 (1.7); 6.9314 (2.0); 6.9130 (3.4); 6.8946 (1.6); 6.7840 (3.8); 6.7652 (3.4); 5.2246 (0.7); 5.2093 (1.6); 5.1923 (1.6); 5.1773 (0.6); 4.2981 (0.4); 4.2901 (0.6); 4.2828 (0.5); 4.2711 (1.6); 4.2620 (1.6); 4.2542 (2.4); 4.2456 (2.6); 4.2255 (1.6); 4.2200 (1.2); 4.2049 (0.4); 4.1983 (0.5); 4.0560 (0.4); 4.0382 (1.3); 4.0204 (1.3); 4.0027 (0.5); 3.5003 (16.0), 3.4938 (15.3); 3.4796 (0.6); 3.3204 (13.4); 3.2904 (24.9); 3.2554 (0.4); 2.6753 (0.4); 2.6707 (0.6); 2.6667 (0.4); 2.5061 (71.2); 2.5017 (92.2); 2.4972 (69.1); 2.3327 (0.4); 2.3285 (0.5); 2.3241 (0.4); 2.1784 (0.7); 2.1686 (0.8); 2.1561 (1.0); 2.1492 (1.0); 2.1437 (1.0); 2.1362 (0.8); 2.0592 (0.7); 2.0512 (0.9); 2.0433 (1.2); 2.0354 (1.1); 2.0257 (0.9); 2017 8 (0.8); 2.0087 (0.8); 20018 (0.7); 1.9887 (6.0); 1.3975 (4.4); 1.1929 (1.5); 1.1751 (3.0); 1.1573 (1.4); 0.0079 (0.5); −0.0002 (12.2); 0.0082 (0.5) |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 518 | 2.19 | | 518: $^1$H-NMR (400.0 MHz, $d_6$-DMSO): δ = 9.0894 (1.9); 9.0689 (1.9); 8.5253 (6.9); 8.4176 (1.8); 8.3983 (2.0); 7.9524 (2.4); 7.7616 (2.1); 7.7592 (2.1); 7.7438 (2.6); 7.7414 (2.4); 7.7153 (0.8); 7.7027 (1.6); 7.6900 (0.8); 7.6238 (6.7); 7.6194 (12.3); 7.6103 (4.6); 7.6061 (3.5); 7.6009 (1.5); 7.5766 (1.8); 7.5583 (2.0); 7.5555 (2.0); 7.5374 (1.5); 7.3313 (1.8); 7.3134 (1.9); 7.1897 (0.9); 7.1870 (0.8); 7.1692 (1.8); 7.1516 (1.2); 7.1480 (1.1); 6.9265 (1.3); 6.9239 (1.3); 6.9076 (2.2); 6.8894 (1.1); 6.8867 (1.0); 6.8100 (2.5); 6.7896 (2.3); 5.2760 (0.5); 5.2619 (1.1); 5.2426 (1.1); 5.2280 (0.5); 4.6943 (1.5); 4.6787 (2.2); 4.6755 (2.2); 4.6691 (1.7); 4.6600 (1.9); 4.6536 (2.3); 4.6505 (2.1); 4.6349 (1.6); 4.3095 (0.3); 4.2989 (1.9); 4.2902 (3.4); 4.2843 (4.8); 4.2753 (5.3); 4.2612 (3.2); 3.8016 (1.6); 3.7850 (2.6); 3.7698 (1.8); 3.3394 (0.5); 3.3204 (30.7); 3.3072 (1.3); 32882 (0.7); 3.2737 (0.4); 2.8904 (16.0); 2.7318 (13.8); 2.6 747 (0.4); 2.6701 (0.5); 2.6659 (0.4); 2.5058 (64.7); 2.5014 (82.8); 2.4969 (60.3); 2.4927 (29.6); 2.3281 (0.5); 2.1972 (0.4); 2.1851 (0.4); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.1757 (0.6); 2.1616 (0.9); 2.1460 (0.7); 2.1320 (0.3); 2.0740 (2.6); 2.0620 (0.8); 2.0505 (0.8); 2.0356 (0.6); 2.0263 (0.6); 2.0164 (0.5); 0.0079 (1.5); −0.0002 (38.6); −0.0085 (1.5) |
| 522 | 2.88 | | 522: $^1$H-NMR (601.6 MHz, $d_6$-DMSO): δ = 9.0428 (0.8); 9.0296 (0.8); 8.1535 (0.8); 8.1513 (0.8); 8.1394 (0.9); 8.1372 (0.9); 7.7631 (0.8); 7.7608 (0.8); 7.7512 (1.0); 7.7490 (0.9); 7.6672 (3.5); 7.6640 (3.9); 7.6101 (0.9); 7.6069 (1.5); 7.6038 (0.7); 7.5892 (0.8); 7.5772 (0.8); 7.5752 (0.8); 7.5632 (0.7); 7.3301 (0.6); 7.3172 (0.7); 7.1857 (0.4); 7.1831 (0.4); 7.1716 (0.7); 7.1600 (0.4); 7.1574 (0.4); 6.9397 (0.5); 6.9380 (0.5); 6.9257 (0.8); 6.9149 (0.4); 6.9132 (0.4); 6.8047 (0.9); 7924 (0.9); 5.7502 (1.4); 5.2771 (0.4); 5.2642 (0.4); 4.2903 (0.4); 4.2268 (0.3); 4.2106 (0.5); 3.3053 (4.6); 3.0336 (16.0); 2.5150 (7.7); 2.5060 (4.4); 2.5030 (9.2); 2.5000 (12.7); 2.4970 (9.2); 2.4940 (4.3); 1.3973 (0.8); −0.0002 (9.1) |
| 523 | 2.11 | | 523: $^1$H-NMR (601.6 MHz, $d_6$-DMSO): δ = 9.0676 (0.4); 9.0547 (0.6); 9.0421 (0.3); 8.1664 (0.9); 8.1630 (0.9); 8.1534 (1.1); 8.1499 (1.0); 7.6767 (1.1); 7.6741 (1.1); 7.6632 (1.3); 7.6607 (1.2); 7.5844 (0.6); 7.5726 (1.4); 7.5593 (2.3); 7.5550 (1.3); 7.5467 (0.4); 7.4260 (0.6); 7.4174 (0.4); 7.3207 (0.5); 7.3128 (0.9); 7.3014 (1.2); 7.1740 (0.4); 7.1635 (0.8); 7.1501 (0.4); 6.9255 (0.4); 6.9132 (0.5); 6.7968 (1.0); 6.7823 (0.9); 5.3055 (0.4); 5.2630 (0.4); 5.2568 (0.4); 4.2883 (0.4); 4.2826 (0.4); 4.2086 (0.4); 4.1667 (0.4); 3.3028 (42.7); 3.0387 (16.0); 3.0127 (0.7); 2.6147 (0.4); 2.6116 (0.5); 2.6084 (0.4); 2.6054 (0.5); 2.5208 (0.9); 2.5178 (1.1); 2.5147 (1.2); 2.5059 (28.6); 2.5029 (63.1); 2.4999 (88.1); 2.4968 (63.1); 2.4938 (29.0); 24136 (4.2); 2.3869 (0.4); 2.3840 (0.5); 2.3811 (0.4); 2.2183 (0.4); 2.2113 (0.4); 1.3983 (11.6); 0.0052 (1.4); −0.0002 (61.6); −0.0058 (2.3) |
| 524 | 2.34 | | 524: $^1$H-NMR (601.6 MHz, $d_6$-DMSO): δ = 9.0713 (0.8); 9.0578 (0.8); 8.1990 (0.9); 8.1846 (0.9); 7.7017 (0.8); 7.6914 (1.0); 7.6896 (1.0); 7.6095 (0.9); 7.5972 (1.0); 7.5837 (0.8); 7.5631 (0.4); 7.3217 (0.8); 7.3096 (0.8); 7.1789 (0.8); 7.1680 (1.0); 7.1566 (0.6); 6.9311 (0.6); 6.9192 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.0); 6.9080 (0.6); 6.8015 (1.0); 6.7876 (0.9); 5.2704 (0.6); 5.2579 (0.5); 4.3124 (0.4); 4.3049 (0.4); 4.2890 (0.4); 4.2232 (0.5); 4.2075 (0.5); 4.1930 (0.3); 4.1891 (0.4); 3.3025 (59.1); 3.2911 (0.4); 3.0396 (16.0); 3.0127 (0.9); 2.6120 (0.9); 2.6084 (0.7); 2.6057 (0.8); 2.5210 (1.5); 2.5180 (1.8); 2.5145 (1.8); 2.5058 (51.6); 2.5030 (107.0); 2.5000 (145.0); 2.4970 (104.8); 2.4942 (49.6); 2.4679 (7.8); 2.3842 (1.0); 2.2364 (0.4); 2.2282 (0.3); 2.2188 (0.4); 2.0703 (0.4); 1.3984 (0.7); 1.2362 (0.8); 0.0966 (0.4); 0.0052 (2.0); −0.0002 (82.2); −0.0057 (3.6); −0.1001 (0.5) |
| 525 | 2.62 | | 525: $^1$H-NMR (400.0 MHz, $d_6$-DMSO): δ = 9.1140 (1.1); 9.1057 (1.1); 9.0945 (1.2); 9.0855 (1.0); 8.5540 (6.4); 8.3143 (0.7); 8.2423 (1.9); 8.2373 (1.8); 8.2225 (2.0); 8.2176 (2.0); 7.7020 (2.3); 7.6983 (2.3); 7.6822 (3.5); 7.6783 (2.8); 7.6659 (3.1); 7.6457 (5.0); 7.6395 (3.2); 7.6264 (1.0); 7.4582 (0.8); 7.4470 (0.9); 7.4388 (1.7); 7.4279 (1.6); 7.4191 (1.1); 7.4078 (0.9); 7.3495 (2.8); 7.3293 (3.4); 7.3094 (0.8); 7.1767 (1.0); 7.1592 (2.0); 7.1411 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.3); 6.9254 (1.4); 6.9072 (2.4); 6.8882 (1.1); 6.7955 (2.8); 6.7753 (2.5); 5.2371 (1.1); 5.2227 (1.1); 4.2896 (0.5); 4.2708 (1.3); 4.2555 (2.3); 4.2473 (2.1); 4.2358 (1.2); 4.2282 (1.4); 4.2078 (0.4); 4.2005 (0.3); 3.5676 (0.3); 3.3679 (1.4); 3.3498 (4.3); 3.3208 (300.6); 3.0155 (14.3); 2.6749 (1.8); 2.6704 (2.3); 2.6663 (1.7); 2.5234 (7.5); 2.5058 (309.0); 2.5014 (394.8); 2.4970 (286.9); 2.3325 (1.8); 2.3280 (2.3); 2.3240 (1.7); 2.2142 (0.5); 2.2047 (0.5); 2.1922 (0.8); 2.1823 (0.8); 2.1699 (0.8); 2.1586 (0.6); 2.1484 (0.4); 2.0360 (0.8); 2.0218 (0.7); 2.0092 (0.6); 2.0012 (0.6); 1.9885 (0.8); 1.3979 (16.0); 1.2461 (3.0); 1.22 88 (6.1); 1.2111 (3.0); 1.1924 (0.3); 1.1750 (0.4); −0.0002 (1.8) |
| 526 | 3.29 | | 526: $^1$H-NMR (400.0 MHz, $d_6$-DMSO): δ = 9.1145 (1.7); 9.0942 (1.7); 8.5403 (7.4); 8.1746 (1.7); 8.1548 (1.8); 7.6988 (2.3); 7.6951 (2.4); 7.6788 (2.9); 7.6748 (3.6); 7.6559 (2.9); 7.6357 (3.6); 7.6280 (3.1); 7.6136 (1.0); 7.4537 (0.9); 7.4429 (0.9); 7.4343 (1.8); 7.4235 (1.7); 7.4147 (1.2); 7.4039 (1.0); 7.3536 (3.2); 7.3346 (3.1); 7.30831 (0.9); 7.3051 (0.8); 7.1757 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.0); 7.1569 (2.0); 7.1382 (1.2); 6.9241 (1.2); 6.9056 (2.1); 6.8868 (1.0); 6.7922 (2.8); 6.7720 (2.5); 5.7549 (1.2); 5.2457 (0.5); 5.2315 (12); 5.2132 (1.2); 5.1980 (0.5); 4.2829 (0.5); 4.2761 (0.4); 4.2640 (12); 4.2546 (1.2); 4.2470 (1.8); 4.2373 (1.9); 4.2238 (1.1); 4.2164 (1.3); 4.1962 (0.4); 4.1885 (0.4); 3.9291 (0.3); 3.9131 (0.8); 3.8976 (1.1); 3.8822 (0.8); 3.8664 (0.4); 3.5675 (0.5); 3.3231 (30.0); 2.9033 (1 6.0); 2.5054 (39.1); 2.5010 (51.0); 2.4966 (38.0); 2.2017 (0.4); 2.1928 (0.5); 2.1801 (0.8); 2.1703 (0.8); 2.1590 (0.8); 2.1480 (0.6); 2.1392 (0.4); 2.0400 (0 6); 2.0328 (0.8); 2.0253 (0.9); 2.0145 (0.7); 2.0089 (0.7); 1.9987 (0.6); 1.9884 (0 8); 1.3068 (3.5); 1.2921 (5.6); 1.2777 (3.4); 1.2512 (3.4); 1.2373 (5.5); 1.2230 (3.7) |
| 527 | 3.63 | | 527: $^1$H-NMR (400.0 MHz, $d_6$-DMSO): δ = 9.1286 (1.0); 9.1083 (1.1); 8.6686 (4.7); 8.4516 (3.2); 8.2373 (1.1); 8.2341 (1.1); 8.2161 (1.3); 8.2128 (1.2); 7.8200 (1.1); 7.8167 (1.2); 7.8022 (1.5); 7.7989 (1.4); 7.7348 (2.1); 7.7297 (2.4); 7.6837 (1.2); 7.6655 (12); 7.6626 (1.3); 7.6443 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.1); 7.6384 (11.9); 7.6320 (2.0); 7.3779 (1.0); 7.3 605 (1.1); 7.1943 (0.5); 7.1905 (0.5); 7.1728 (1.0); 7.1559 (0.7); 7.1521 (0.6); 6.9502 (0.7); 6.9476 (0.8); 6.9293 (1.3); 6.9130 (0.6); 6.9103 (0.6); 6.8094 (1.4); 6.8075 (1.4); 6.7889 (1.4); 5.2566 (0.7); 5.2372 (0.7); 4.2852 (0.6); 4.2699 (12); 4.2609 (1.1); 4.2491 (0.6); 4.2412 (0.7); 3.3594 (0.7); 3.3415 (2.2); 3.3200 (56.0); 3.0101 (9.2); 2.6752 (0.5); 2.6706 (0.7); 2.6662 (0.5); 2.5237 (2.3); 2.5103 (47.2); 2.5060 (93.7); 2.5015 (122.2); 2.4970 (89.4); 2.4929 (452); 2.3326 (0.6); 2.3283 (0.7); 2.3238 (0.6); 2.2063 (0.4); 2.1961 (0.4); 2.1845 (0.5); 2.1724 (0.3); 2.0710 (0.4); 2.0632 (0.5); 2.0484 (0.4); 2.0365 (0.3); 1 3978 (16.0); 1.2311 (2.6); 1.2134 (5.1); 1.1956 (2.2); −0.0002 (0.5) |
| 534 | 4.51 | | 534: $^1$H-NMR (400.0 MHz, $d_6$-DMSO): δ = 10.4184 (1.5); 9.1346 (1.4); 9.1144 (1.4); 8.6595 (5.5); 8.1798 (1.4); 8.1587 (1.5); 7.8117 (1.4); 7.7965 (1.8); 7.7941 (1.7); 7.7032 (0.5); 7.681 5 (1.4); 7.6605 (1.7); 7.6458 (10.6); 7.3875 (1.3); 7.3689 (1.4); 7.1966 (0.6); 7.1784 (1.4); 7.1608 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.9); 6.9817 (0.5); 6.9771 (0.9); 6.9724 (0.5); 6.9544 (1.0); 6.9360 (1.6); 6.9173 (0.8); 6.8121 (1.9); 6.8008 (2.0); 6.7960 (2.5); 5.2728 (0.4); 5.2584 (0.8); 5.2391 (0.9); 5.2247 (0.4); 4.2869 (0.8); 4.2708 (1.1); 4.2589 (1.1); 4.2454 (0.7); 4.2376 (0.9); 3.8866 (0.7); 3.8705 (1.0); 3.8538 (0.7); 3.3288 (47.9); 2.9128 (10.7); 2.6782 (0.6); 2.5136 (82.9); 2.5093 (107.6); 2.5050 (80.2); 23403 (0.5); 2.3361 (0.6); 2.3319 (0.5); 22178 (0.4); 2.2040 (0.5); 2.1942 (0.6); 2.1821 (0.6); 2.1704 (0.5); 2.0675 (0.5); 2.0600 (0.6); 2.0439 (0.5); 2.0335 (0.4); 2.0261 (0.4); 1.4053 (16.0); 1.2887 (5.0); 1.2725 (5.0); 1.2420 (5.3); 1.2258 (5.0) |
| 535 | 4.46 | | 535: $^1$H-NMR (400.0 MHz, $d_6$-DMSO): δ = 8.8722 (0.8); 8.8516 (0.8); 8.7041 (2.9); 8.2580 (1.2); 8.2352 (1.4); 7.8664 (1.4); 7.8435 (1.3); 7.6619 (3.4); 7.4145 (0.7); 7.3959 (0.8); 7.1707 (0.4); 7.1537 (0.7); 7.1329 (0.4); 6.9285 (0.5); 6.9101 (0.9); 6.8908 (0.4); 6.7836 (1.0); 6.7635 (0.9); 5.2026 (0.5); 5.1839 (0.5); 4.2665 (0.4); 4.25 83 (0.4); 4.2499 (0.6); 4.2428 (0.6); 4.2229 (0.4); 4.2156 (0.5); 3.4842 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (7.0); 3.3198 (29.6); 3.2787 (6.2); 2.6708 (0.3); 2.5056 (44.2); 2.5014 (56.4); 2.4974 (43.0); 2.3286 (0.3); 2.0317 (0.4); 1.9886 (0.5); 1.3980 (16.0); −0.0003 (15.4) |
| 540 | 3.72 | | 540: $^1$H-NMR (400.0 MHz, $d_6$-DMSO): δ = 9.1842 (4.4); 9.1640 (4.4); 8.6741 (16.0); 8.4617 (0.4); 8.3556 (3.0); 8.3401 (3.2); 8.3321 (3.3); 8.3164 (3.3); 7.6826 (3.4); 7.6594 (6.4); 7.636 2 (3.2); 7.4662 (4.8); 7.4486 (5.5); 7.4447 (5.5); 7.4269 (4.5); 7.3795 (4.1); 7.3605 (4.4); 7.1914 (2.0); 7.1887 (2.0); 7.1711 (4.2); 7.1530 (2.6); 7.1500); (2.5); 6.9408 (3.0); 6.9222 (5.1); 6.9035 (2.4); 6.8037 (5.7); 6.7840 (5.1); 5.2738 (1.2); 5.2596 (2.6); 5.2405 (2.6); 5.2262 (1.1); 4.3027 (1.0); 4.2958 (0.9); 4.2846 (2.4); 4.2751 (2.3); 4.2681 (2.8); 4.2591 (3.5); 4.2517 (2.7); 4.2384 (2.1); 4.2312 (2.7); 4.2103 (1.0); 4.2029 (0.8); 4.0555 (0.7); 4.0377 (1.9); 4.0199 (1.9); 4.0021 (0.7); 3.9008 (1.0); 3.8822 (8.3); 3.8717 (14.3); 3.8610 (8.7); 3.3197 (180.6); 3.2906 (5.5); 3.2801 (11.1); 3.2687 (10.7); 3.2580 (4.7); 3.2387 (1.4); 2.6745 (1.6); 2.6702 (2.1); 2.5055 (277.9); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.5013 (357.7); 2.4970 (267.8); 2.3321 (1.6); 2.3279 (2.2); 2.255 3 (0.6); 2.2451 (0.9); 2.2347 (12); 2.2216 (1.7); 2.2121 (1.8); 2.1999 (1.8); 2.1877 (1.3); 2.1789 (0.8); 2.0746 (1.6); 2.0676 (1.9); 2.0556 (1.4); 2.0399 (1.3); 2.0329 (1.2); 1.9863 (8.1); 1.3978 (1.0); 1.2592 (0.3); 1.2341 (0.8); 1.1926 (2.1); 1.1748 (4.1); 1.1569 (2.1); −0.0002 (42.6) |
| 541 | 1.78 | | 541: $^1$H-NMR. (400.0 MHz, $d_6$-DMSO): δ = 8.9748 (0.6); 8.9542 (0.6); 8.4871 (0.4); 8.4708 (2.2); 8.4638 (0.5); 8.4484 (0.4); 8.3359 (2.1); 7.9088 (0.3); 7.8960 (0.4); 7.7294 (0.7); 7.7258 (0.8); 7.7093 (0.9); 7.7057 (0.9); 7.5431 (0.5); 7.5208 (0.8); 7.4979 (0.5); 7.4693 (0.5); 7.4610 (0.4); 7.4497 (1.0); 7.4300 (0.6); 7.3462 (0.3); 7.3415 (0.5); 7.3365 (0.4); 7.3272 (1.1); 7.3228 (0.7); 7.3076 (0.8); 7.3033 (1.1); 7.2820 (0.7); 7.1749 (0.3); 7.1716 (0.3); 7.1539 (0.7); 7.1363 (0.4); 7.1330 (0.4); 6.9111 (0.5); 6.8923 (0.8); 6.8739 (0.4); 6.7934 (0.9); 6.7732 (0.8); 5.2315 (0.4); 5.2128 (0.4); 4.2613 (0.7); 4.2476 (1.2); 4.2347 (0.7); 3.3288 (21.4); 3.0736 (2.0); 3.0669 (1.4); 3.0611 (2.2); 2.5180 (17.5); 2.5140 (34.2); 2.5095 (44.3); 2.5051 (32.0); 2.1427 (0.3); 2.0180 (0.3); 1.9968 (0.9); 1.4060 (16.0); 1.2437 (0.4); 1.1831 (0.4) |
| 542 | 1.66 | | 542: $^1$H-NMR (400.0 MHz, $d_6$-DMSO): δ = 8.9915 (1.7); 8.9705 (1.8); 8.5165 (1.4); 8.5013 (1.5); 8.4929 (1.5); 8.4778 (1.3); 8.3922 (7.2); 7.9585 (0.8); 7.9451 (1.0); 7.9379 (1.0); 7.9251 (0.8); 7.6623 (0.4); 7.6538 (0.5); 7.6394 (0.9); 7.6341 (0.9); 7.6261 (0.9); 7.6139 (0.9); 7.5986 (0.5); 7.5902 (0.4); 7.5685 (1.5); 7.5457 (2.8); 7.5228 (1.5); 7.3069 (1.8); 7.2877 (2.0); 7.2267 (0.6); 7.2113 (0.8); 7.2049 (1.0); 7.1995 (1.0); 7.1755 (1.5); 7.1717 (1.5); 7.1544 (2.2); 7.1367 (1.4); 7.1332 (1.2); 6.9136 (1.5); 6.8949 (2.6); 6.8763 (1.2); 6.7934 (3.0); 6.7729 (2.8); 5.7556 (16.0); 5.2463 (0.6); 5.2312 (1.4); 5.2118 (1.4); 5.1972 (0.6); 4.2576 (2.0); 4.2458 (3.6); 4.2342 (2.0); 4.0382 (0.6); 4.0204 (0.6); 3.3231 (35.1); 3.0726 (4.9); 3.0657 (6.0); 3.0603 (5.8); 3.0534 (4.9); 2.6753 (0.3); 2.6706 (0.4); 2.5103 (28.6); 2.5062 (55.4); 2.5017 (70.8); 2.4972 (50.6); 2.3286 (0.4); 2.1779 (0.8); 2.1644 (0.8); |

TABLE 2-continued

| LC-MS and NMR data |
|---|
| NMR peak forms are stated as they appear in the spectra, possible higher order effects have not been considered. |
| NMR peak lists |
| $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. Further details of NMR-data description with peak lists you find in the publication "Citation of NMR Peaklist Data within Patent Applications" of the Research Disclosure Database Number 564025. |

LC-MS and NMR data
NMR peak forms are stated as they appear in the spectra, possible higher order effects have not been considered.
NMR peak lists
$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.
The peak list of an example has therefore the form:
$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.1576 (0.7); 2.1428 (1.0); 2.1289 (1.0); 2.1160 (0.4); 2.0254 (0.8); 2.0189 (0.8); 2.0043 (0.7); 1.9887 (3.0); 1.3974 (0.6); 1.3525 (0.5); 1.2988 (0.3); 1.2590 (0.5); 1.2344 (1.2); 1.1928 (0.7); 1.1750 (1.4); 1.1572 (0.7); 0.0079 (1.9); −0.0002 (47.9); −0.0085 (1.8) |
| 543 | 4.25 | | 543: $^1$H-NMR (400.0 MHz, $d_6$-DMSO): δ = 9.1849 (4.4); 9.1647 (4.3); 8.7031 (1.0); 8.6905 (16.0); 8.6712 (0.7); 8.3740 (3.5); 8.3584 (3.8); 8.3503 (3.9); 8.3348 (3.6); 8.3149 (0.5); 7.6836 (3.9); 7.6607 (7.1); 7.6380 (3.7); 7.6243 (0.4); 7.3846 (4.1); 7.3651 (4.7); 7.2348 (0.5); 7.2223 (4.0); 7.1898 (5.8); 7.1718 (5.0); 7.1540 (3.1); 7.1505 (2.8); 6.9435 (3.5); 6.9267 (5.9); 6.9083 (2.7); 6.8046 (6.4); 6.7845 (5.9); 6.7131 (0.4); 5.7551 (0.4); 5.2587 (2.7); 5.2416 (2.7); 5.2278 (1.2); 4.3052 (1.2); 4.2978 (1.1); 4.2860 (2.8); 4.2761 (2.8); 4.2697 (3.2); 4.2611 (3.9); 4.2528 (2.9); 4.2390 (2.5); 4.2324 (3.0); 4.2105 (1.1); 4.2039 (0.9); 4.0559 (0.6); 4.0377 (1.8); 4.0200 (1.8); 4.0019 (0.6); 3.8664 (15.1); 3.3202 (106.3); 3.2860 (10.0); 3.2751 (9.5); 2.6740 (1.4); 2.6705 (1.8); 2.6660 (1.4); 2.5055 (243.9); 2.5012 (311.2); 2.4968 (223.6); 2.3279 (1.8); 2.3233 (1.3); 2.2376 (1.3); 2.2238 (1.9); 2.2145 (2.0); 2.2028 (2.0); 2.1943 (1.4); 2.1895 (1.5); 2.0685 (1.8); 2.0522 (1.6); 1.9883 (7.3); 1.3976 (5.4); 1.3510 (0.4); 1.2985 (0.4); 1.2588 (0.4); 1.2354 (1.3); 1.1925 (1.9); 1.1747 (3.9); 1.1568 (1.8); 0.1464 (0.7); 0.0222 (0.4); 0.0079 (6.3); −0.0002 (153.6); −0.0085 (5.8); −0.1493 (0.7) |
| 544 | 2.80 | | 544: $^1$H-NMR (400.0 MHz, $d_6$-DMSO): δ = 9.1606 (3.0); 9.1401 (3.1); 8.6477 (12.1); 8.2912 (2.2); 8.2755 (2.4); 8.2676 (2.5); 8.2521 (2.3); 7.6215 (2.5); 7.5986 (4.5); 7.5757 (2.5); 7.3791 (2.8); 7.3620 (3.0); 7.1920 (1.4); 7.1885 (1.4); 7.1709 (2.9); 7.1534 (1.8); 7.1497 (1.7); 6.9443 (2.1); 6.9421 (2.1); 6.9256 (3.6); 6.9236 (3.5); 6.9073 (1.7); 6.9047 (1.7); 6.8055 (4.1); 6.7851 (3.8); 6.6355 (2.1); 5.7553 (12.7); 5.2771 (0.8); 5.2633 (1.8); 5.2443 (1.8); 5.2300 (0.8); 4.3146 (0.5); 4.3063 (0.7); 4.2990 (0.6); 4.2870 (1.6); 4.2781 (1.6); 4.2711 (2.0); 4.2624 (2.4); 4.2554 (1.9); 4.2420 (1.5); 4.2344 (1.9); 4.2136 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.7); 4.2060 (0.5); 3.8626 (9.5); 3.8532 (5.6); 3.8342 (0.7); 3.8221 (0.4); 3.3200 (38.5); 3.2903 (3.2); 3.2796 (6.3); 3.2671 (6.0); 3.2350 (1.0); 2.6787 (0.3); 2.6702 (0.8); 2.5231 (2.6); 2.5097 (54.0); 2.5055 (106.3); 2.5010 (136.5); 2.4965 (96.8); 2.4922 (46.2); 2.4203 (16.0); 2.3242 (1.1); 2.2576 (0.5); 2.2436 (0.7); 2.2357 (0.9); 2.2233 (1.1); 2.2137 (1.2); 2.2007 (1.2); 2.1894 (0.9); 2.1807 (0.6); 2.0829 (7.5); 2.0400 (1.0); 2.0318 (0.8); 2.0158 (0.4); 1.9882 (0.8); 1.5432 (0.7); 1.3973 (1.0); 1.3513 (0.4); 1.2587 (0.5); 1.2336 (0.9); 1.1746 (0.4); 0.1459 (0.4); 0.0079 (3.7); −0.0002 (97.6); −0.0085 (3.4); −0.1493 (0.4) |
| 545 | 1.90 | | 545: $^1$H-NMR (400.0 MHz, $d_6$-DMSO): δ = 9.0012 (2.2); 8.9809 (2.3); 8.5133 (1.7); 8.4986 (1.6); 8.4897 (1.6); 8.4749 (1.4); 8.4325 (7.9); 8.2292 (0.6); 8.0071 (1.3); 7.9948 (1.2); 7.6863 (14.1); 7.5760 (1.7); 7.5526 (3.2); 7.5293 (1.7); 7.3076 (2.2); 7.2888 (2.2); 7.1799 (1.0); 7.1765 (1.2); 7.1589 (2.2); 7.1414 (1.4); 7.1380 (1.3); 6.9211 (1.7); 6.9184 (1.6); 6.9022 (2.7); 6.8999 (2.7); 6.8839 (1.3); 6.8811 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (1.3); 6.8673 (3.0); 6.8082 (0.3); 6.7983 (3.0); 6.7961 (3.0); 6.7779 (2.8); 6.7756 (2.6); 5.7552 (16.0); 5.2468 (0.7); 5.2319 (1.5); 5.2124 (1.4); 5.1971 (0.6); 4.2623 (2.5); 4.2494 (4.1); 4.2359 (2.4); 4.0381 (0.9); 4.0202 (1.0); 3.3223 (44.4); 3.0701 (8.6); 3.0576 (8.5); 3.0357 (0.8); 2.6753 (0.4); 2.6709 (0.6); 2.6665 (0.4); 2.5106 (38.2); 2.5063 (75.6); 2.5018 (97.9); 2.4973 (70.3); 2.4929 (33.9); 2.3332 (0.4); 2.3285 (0.6); 2.3240 (0.4); 2.1939 (0.3); 2.1795 (0.8); 2.1646 (0.8); 2.1595 (0.7); 2.1436 (1.1); 2.1303 (1.0); 2.1160 (0.4); 2.0570 (0.5); 2.0446 (1.0); 2.0307 (1.2); 2.0172 (0.7); 2.0089 (0.8); 1.9887 (4.5); 1.2590 (0.4); 1.2335 (0.7); 1.1928 (1.2); 1.1750 (2.3); 1.1573 (1.2); −0.0002 (3.4) |
| 546 | 3.68 | | 546: $^1$H-NMR (400.0 MHz, $d_6$-DMSO): δ = 9.1871 (4.2); 9.1669 (4.3); 8.6805 (16.0); 8.3627 (2.8); 8.3473 (3.0); 8.3393 (3.2); 8.3236 (2.9); 7.6904 (3.2); 7.6672 (6.0); 7.6441 (3.1); 7.539 4 (2.8); 7.4347 (8.4); 7.4122 (8.4); 7.3793 (3.9); 7.3591 (9.8); 7.1913 (2.0); 7.1880 (2.1); 7.1785 (3.6); 7.1709 (4.1); 7.1531 (2.5); 7.1496 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.3); 6.9405 (2.8); 6.9219 (4.7); 6.9054 (2.3); 6.9030 (2.3); 6.8038 (5.3); 6.7850 (4.9); 5.7551 (10.2); 5.2756 (1.1); 5.2613 (2.4); 5.2412 (2.4); 5.2271 (1.1); 4.3122 (0.6); 4.3044 (1.0); 4.2852 (2.2); 4.2768 (2.1); 4.2686 (2.6); 4.2604 (3.2); 4.2535 (2.5); 4.2393 (2.0); 4.2322 (2.6); 4.2123 (1.0); 3.8842 (7.5); 3.8735 (13.0); 3.8634 (7.8); 3.3201 (103.8); 3.2938 (4.9); 3.2835 (10.0); 3.2721 (9.7); 3.2610 (4.3); 32399 (1.3); 2.6748 (1.0); 2.6701 (1.4); 2.6655 (1.0); 2.5055 (190.0); 2.5011 (244.6); 2.4967 (177.2); 2.4494 (0.6); 2.3276 (1.4); 2.3242 (1.1); 2.2561 (0.6); 2.2356 (1.1); 2.2230 (1.5); 2.2142 (1.6); 2.2015 (1.6); 2.1897 (1.2); 2.1810 (0.7); 2.0889 (0.9); 2.0734 (1.5); 2.0661 (1.7); 2.0509 (1.3); 2.0397 (1.2); 2.0325 (1.2); 1.9882 (0.6); 1.2982 (0 4); 1.2589 (0.5); 1.2354 (1.3); 0.1459 (0.4); 0.0078 (3.5); −0.0002 (86.5); −0.0082 (3.6); −0.1499 (0.4) |
| 547 | 1.81 | | 547: $^1$H-NMR (400.0 MHz, $d_6$-DMSO): δ = 8.9803 (2.7); 8.9596 (2.7); 8.4533 (1.8); 8.4383 (2.0); 8.4292 (2.0); 8.4129 (11.0); 7.9213 (1.6); 7.9079 (1.6); 7.5407 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.0); 7.5240 (2.5); 7.5175 (4.0), 7.4943 (2.0); 7.3844 (5.7); 7.3618 (5.8); 7.3439 (4, 5); 7.3054 (2.7); 7.2871 (2.9); 7.1782 (1.3); 7.1748 (1.4); 7.1612 (3.1); 7.1396 (1.7); 7.1361 (1.6); 6.9171 (2.0); 6.8987 (3.4); 6.8820 (1.6); 6.8798 (1.6); 6.7965 (3.8); 6.7760 (3.5), 5.7553 (11.4); 5.2518 (0.8); 5.2370 (1.7), 5.2169 (1.7); 5.2030 (0.8); 4.2627 (2.9); 4.2496 (5.0); 4.2364 (2.9); 4.0557 (1.2), 4.0379 (3.6); 4.0201 (3.7); 4.0023 (12); 3.3210 (22.0), 3.0647 (10.6); 3.0522 (10.4); 2.6745 (0.4); 2.6702 (0.5); 2.6655 (0.4); 25056 (68.9); 2.5012 (88.8); 2.4968 (63.5); 23277 (0.6),2 1932 (0.4); 2.1801 (0.9); 2.1656 (0.9); 2.1595 (0.8); 2.1448 (1.4); 2.1311 (1.3); 2.1176 (0.5); 2.0530 (0.5); 2.0414 (1.2); 2.0266 (1.4); 2.0130 (0.8); 2.0054 (1.0); 1.9884 (16.0); 1.3975 (2.5); 1.1926 (4.0); 1.1748 (8.0); 1.1570 (3.9); 0 0078 (1.4); −0.0002 (35.4); −0.0085 (1.2) |
| 548 | 3.33 | | 548: $^1$H-NMR (400.0 MHz, $d_6$-DMSO): δ = 9.1827 (2.9); 9.1746 (2.9); 9.1624 (3.2); 9.1541 (2.8); 8.6506 (10.0); 8.6441 (9.3); 8.3965 (3.4); 8.3810 (3.7); 8.3731 (3.8); 8.3574 (3.6); 8.3157 (0.3); 7.7100 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.6); 7.6872 (6.5); 7.6643 (3.3); 7.5745 (1.2); 7.5534 (2.7); 7.5321 (2.9); 7.5111 (1.3); 7.3747 (4.9); 7.3560 (6.6); 7.3355 (3.1); 7.3257 (2.3); 7.3156 (1.9); 7.3046 (1.1); 7.2896 (1.7); 7.2743 (2.2); 7.2492 (2.1); 7.2300 (1.0); 7.1862 (2.3); 7.1655 (4.9); 7.1478 (3.0); 6.9332 (3.2); 6.9148 (5.4); 6.8959 (2.6); 6.8004 (6.6); 6.7799 (6.0); 5.7565 (3.2); 5.2752 (0.8); 5.2508 (2.6); 5.2420 (2.6); 4.3002 (1.2); 4.2936 (1.0); 4.2819 (2.8); 4.2723 (2.7); 4.2654 (3.1); 4.2555 (3.7); 4.2280 (2.8); 4.2046 (1.0); 3.8768 (16.0); 3.3206 (24.3); 3.2960 (10.6); 3.2914 (10.6); 3.2511 (1.4); 2.6702 (1.3); 2.5058 (182.0); 2.5015 (222.3); 2.4972 (161.2); 2.3286 (1.3); 2.2435 (1.1); 2.2317 (1.3); 2.2215 (1.8); 2.2084 (1.8); 2.1980 (1.8); 2.0647 (2.1); 2.0577 (1.9); 2.0466 (1.7); 2.0297 (1.5); 1.9886 (0.8); 1.3976 (0.6); 1.2331 (0.4); 1.1748 (0.4); 0.1462 (0.3); −0.0002 (64.9) |
| 549 | 3.59 | | 549: $^1$H-NMR (400.0 MHz, $d_6$-DMSO): δ = 9.1861 (3.0); 9.1775 (3.0); 9.1663 (3.2); 9.1573 (2.8); 8.6558 (10.4); 8.6485 (9.7); 8.4036 (3.6); 8.3879 (4.0); 8.3801 |

TABLE 2-continued

| Example No | logP (Method L0) [a] | LC-MS (Method L2-L5) | NMR or NMR Peaklist |
|---|---|---|---|
| | | | (4.1); 8.3645 (3.7); 7.71581 (3.7); 7.6930 (6.8); 7.6701 (3.6); 7.4984 (0.6); 7.4765 (1.7); 7.4585 (2.0); 7.4508 (1.9); 7.4253 (0.8); 7.3779 (5.5); 7.3587 (6.9); 7.3388 (2.2); 7.3334 (2.2); 7.3157 (1.4); 7.2930 (0.5); 7.1848 (2.4); 7.1676 (5.0); 7.1497 (3.0); 6.9361 (3.1); 6.9174 (5.4); 6.8989 (2.5); 6.8016 (6.9); 6.7814 (6.3); 5.7559 (2.5); 5.2740 (0.8); 5.2602 (2.1); 5.2512 (2.6); 5.2405 (2.6); 5.2313 (2.0); 4.3086 (0.8); 4.3013 (1.2); 4.2948 (1.0); 4.2818 (2.8); 4.2730 (2.7); 4.2658 1 (3.2); 4.2565 (3.6); 4.2288 (2.8); 4.2034 (1.0); 3.8760 (16.0); 3.3215 (55.4); 3.2905 (11.0); 3.2507 (1.4); 2.6706 (0.9); 2.5058 (119.4); 2.5015 (151.2); 2.4972 (110.3); 2.3287 (0.9); 2.3246 (0.7); 2.2345 (1.2); 2.2183 (1.8); 2.2090 (1.8); 2.2017 (1.8); 2.0818 (1.2); 2.0746 (1.7); 2.0663 (2.0); 2.0592 (1.9); 2.0404 (1.5); 2.0321 (1.5); 2.0254 (1.2); 1.2343 (0.6); −0.0002 (41.6) |
| 550 | 3.94 | | 550: $^1$H-NMR (400.0 MHz, $d_6$-DMSO): δ = 9.2014 (2.6); 9.1811 (2.6); 8.7076 (8.9); 8.4095 (1.7); 8.3941 (1.9); 8.3860 (1.9); 8.3705 (1.8); 7.7354 (16.0); 7.7206 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.0); 7.6972 (3.6); 7.674 0 (1.8); 7.3844 (2.5); 7.3654 (2.7); 7.1898 (1.2); 7.1721 (2.6); 7.1543 (1.6); 6.9445 (1.7); 6.9254 (3.0); 6.9075 (1.5); 6.8061 (3.4); 6.7859 (3.1); 5.7556 (5.5); 5.2691 (0.7); 5.2558 (1.6); 5.2362 (1.6); 5.2219 (0.7); 4.3031 (0.6); 4.2966 (0.6); 4.2847 (1.4); 4.2684 (1.7); 4.2592 (2.1); 4.2512 (1.6); 4.2303 (1.6); 4.2087 (0.6); 4.2024 (0.5); 3.8768 (8.7); 3.3202 (36.4); 3.2865 (6.7); 3.2752 (6.4); 3.2441 (0.8); 2.6703 (0.7); 2.5053 (96.3); 2.5013 (1 18.5); 2.4974 (89.0); 2.3275 (0.6); 2.2343 (0.7); 2.2204 (1.0); 2.2115 (1.1); 2.1996 (1.1); 2.1886 (0.8); 2.0703 (1.2); 2.0576 (0.9); 2.0431 (0.8); 2.0347 (0.7); 1.3974 (0.4); 1.2345 (0.4); −0.0002 (27.3) |
| 553 | 4.18 | | 553: $^1$H-NMR (400.0 MHz, $d_6$-DMSO): δ = 9.1942 (4.5); 9.1740 (4.6); 8.6557 (16.0); 8.3213 (6.5); 8.2983 (7.3); 8.2397 (0.6); 7.8522 (0.4); 7.8288 (0.5); 7.8164 (7.8); 7.7936 (7.3); 7.6328 (14.6); 7.5168 (0.4); 7.3705 (4.3); 7.3519 (4.8); 7.1870 (2.2); 7.1668 (4.5); 7.1485 (2.8); 6.9330 (3.1); 6.9143 (5.5); 6.8959 (2.6); 6.8001 (6.2); 6.7796 (5.6); 5.2596 (1.3); |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 52452 (2.9); 5.2264 (2.8); 5.2114 (1.2); 4.2957 (1.1); 4.2877 (1.0); 4.2761 (2.5); 4.2673 (2.4); 4.2605 (2.8); 4.2489 (3.1); 4.2407 (2.7); 4.2265 (2.3); 4.2194 (2.9); 4.1983 (1.1); 4.0552 (0.9); 4.0376 (2.5); 4.0198 (2.5); 4.0023 (0.8); 3.8740 (14.9); 3.3214 (154.1); 3.2935 (5.8); 3.2822 (11.0); 3.2705 (10.5); 3.2585 (4.9); 3.2385 (1.7); 3.2278 (1.0); 2.6701 (1.4); 2.5048 (207.4); 2.5012 (254.2); 2.3283 (1.5); 2.2354 (1.0); 2.2257 (1.3); 2.2134 (1.8); 2.2038 (1.8); 21918 (1.9); 2.1798 (1.4); 2.0681 (1.3); 2.0602 (1.8); 2.0537 (2.0); 2.0381 (1.6); 2.0268 (1.4); 2.019 4 (1.3); 1.9883 (10.2); 1.3975 (3.1); 1.1926 (2.6); 1.1748 (5.2); 1.1569 (2.6); −0.0002 (37.7) |
| 556 | 3.76 | | 556: $^1$H-NMR (400.0 MHz, $d_6$-DMSO): δ = 9.1775 (4.0); 9.1574 (4.0); 8.6286 (16.0); 8.2793 (6.4); 8.2565 (7.2); 7.7842 (7.7); 7.7614 (7.2); 7.3674 (3.9); 7.3493 (4.2); 7.3373 (1.2); 7.331 (1.8); 7.3260 (1.1); 7.3134 (2.1); 7.3077 (3.5); 7.3022 (2.0); 7.2894 (12); 7.2839 (1.8); 7.2783 (1.0); 7.1848 (19); 7.1813 (1.9); 7.1639 (4.0); 7.1462 (2.5); 7.1426 (2.4); 7.0495 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.6); 7.0319 (3.7); 6.9289 (2.8); 6.9112 (4.9); 6.8933 (2.3); 6.7977 (5.5); 6.7777 (5.0); 5.2649 (1.1); 5.2506 (2.5); 5.2315 (2.4); 5.2174 (1.1); 4.3044 (0.7); 4.2959 (0.9); 4.2888 (0.8); 4.2769 (2.2); 4.2680 (2.1); 4.2605 (2.5); 4.2509 (3.0); 4.2426 (2.4); 4.2290 (2.0); 4.2219 (2.6); 4.2011 (0.9); 4.1935 (0.7); 4.0555 (0.5); 4.0377 (1.3); 4.0200 (13); 4.0024 (0.4); 3.9436 (0.5); 3.9000 (10); 3.8818 (7.6); 3.8708 (13.2); 3.8600 (7.7); 3.8413 (0.9); 3.3245 (50.8); 3.2916 (4.7); 3.2805 (9.6); 3.2687 (9.2); 3.2568 (4.1); 3.2378 (1.4); 3.2256 (0.8); 2.6700 (0.7); 2.5055 (102.0); 2.5013 (130.9); 2.4971 (94.4); 2.3278 (0.7); 2.3235 (0.6); 2.2484 (0.5); 2.2360 (0.8); 2.2276 (1.1); 2.2147 (1.6); 2.2056 (1.6); 2.1931 (1.6); 2.1805 (1.1); 2.1718 (0.7); 2.0755 (0.8); 2.0686 (1.1); 2.0602 (1.5); 2.0533 (1.7); 2.0417 (1.3); 2.0374 (1.3); 20257 (1.2); 20184 (1.1); 2.0112 (0.7); 2.0030 (0.5); 1.9883 (5.2); 1.3974 (2.9); 1.1927 (1.3); 1.1749 (2.7); 1.1570 (1.3); 0.0076 (2.5); −0.0002 (60.6); −0.0083 (2.4) |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 557 | 4.23 | | 557: $^1$H-NMR (400.0 MHz, $d_6$-DMSO): δ = 9.1770 (4.0); 9.1568 (4.0); 8.6318 (16.0); 8.2815 (6.3); 8.2586 (7.2); 7.7872 (7.7); 7.7643 (7.2); 7.5227 (2.3); 7.5178 (3.8); 7.5126 (2.4); 7.500 6 (2.4); 7.4956 (3.8); 7.4903 (2.2); 7.3684 (3.9); 7.3501 (4.2); 7.2192 (3.2); 7.1851 (3.5); 7.1820 (3.5); 7.1648 (4.7); 7.1470 (2.6); 6.9298 (2.8); 6.9121 (4.8); 6.8925 (2.2); 6.7984 (5.5); 6.7782 (5.0); 5.2636 (1.1); 5.2493 (2.5); 5.2297 (2.4); 5.2151 (1.1); 4.3038 (0.7); 4.2952 (0.9); 4.2888 (0.8); 4.2770 (2.2); 4.2672 (2.1); 4.2608 (2.5); 4.2508 (3.0); 4.2422 (2.3); 4.2287 (1.9); 4.2214 (2.5); 4.2007 (0.9); 4.1935 (0.7); 4.0556 (0.6); 4.0380 (1.7); 4.0202 (1.7); 4.0025 (0.6); 3.8712 (12.8); 3.8615 (7.6); 3.8422 (1.0); 3.3270 (205.6); 3.2914 (4.9); 3.2806 (9.1); 3.2689 (8.6); 3.2572 (4.0); 3.2371 (1.4); 3.2266 (0.9); 2.6709 (1.1); 2.5062 (163.1); 2.5020 (209.0); 2.4978 (151.9); 2.3325 (0.9); 2.3283 (1.2); 2.2365 (0.8); 2.2271 (1.2); 2.2144 (1.6); 2.2047 (1.6); 2.1929 (1.6); 2.1816 (1.1); 2.0760 (0.8); 2.0596 (1.5); 2.0530 (1.7); 2.0413 (1.3); 2.0256 (1.2); 2.0181 (1.1); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 1.9885 (7.1); 1.3976 (3.1); 1.1928 (1.8); 1.1750 (3.6); 1.1571 (1.8); −0.0001 (4.8) |
| 558 | 4.13 | | 558: $^1$H-NMR (400.0 MHz, $d_6$-DMSO): δ = 9.1706 (2.1); 9.1527 (2.1); 8.6027 (16.0); 8.3154 (0.4); 8.2902 (6.2); 8.2673 (7.0); 7.8025 (8.8); 7.7881 (4.9); 7.7796 (7.8); 7.7481 (1.9); 7.728 6 (3.3); 7.7088 (1.6); 7.6194 (3.7); 7.3615 (3.8); 7.3434 (4.1); 7.1811 (1.8); 7.1774 (1.8); 7.1595 (3.9); 7.1424 (2.4); 6.9232 (2.7); 6.9052 (4.6); 6.8870 (2.1); 6.7953 (5.5); 6.7750 (4.9); 5.7551 (2.1); 5.2581 (1.1); 5.2446 (2.4); 5.2255 (2.4); 5.2107 (1.0); 4.2995 (0.7); 4.2915 (0.9); 4.2856 (0.9); 4.2727 (2.2); 4.2642 (2.1); 4.2566 (2.4); 4.2466 (2.5); 4.2376 (2.0); 4.2163 (2.1); 4.1951 (0.8); 4.0377 (0.4); 4.0201 (0.4); 3.8775 (11.0); 3.3239 (26 3.3); 3.2894 (6.2); 2.6705 (1.7); 2.5236 (4.5); 2.5060 (239.6); 2.5017 (306.1); 2.4975 (218.6); 2 3284 (1.8); 2.2452 (0.5); 2.2233 (1.1); 2.2104 (1.6); 2.2010 (1.6); 2.1894 (1.6); 2.1774 (1.2); 2.0573 (1.4); 2.0498 (1.6); 2.0372 (1.3); 2.0225 (1.1); 1.9886 (1.7); 1.3974 (1.0); 1.1924 (0.4); 1.1748 (0.9); 1.1577 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.4); 0.1461 (0.6); 0.0077 (5.0); −0.0002 (134.8); −0.0084 (5.2); −0.1496 (0.6) |
| 564 | | | 564: $^1$H-NMR (400.0 MHz, $d_6$-DMSO): δ = 9.1810 (3.4); 9.1696 (3.5); 9.1614 (3.8); 9.1496 (3.2); 8.6214 (12.6); 8.6138 (11.8); 8.3155 (9.4); 8.2926 (10.6); 7.8206 (10.0); 7.7978 (9.3); 7.7086 (2.5); 7.6910 (5.4); 7.6854 (4.8); 7.6715 (3.4); 7.6673 (2.9); 7.3843 (1.6); 7.3653 (9.7); 7.3517 (10.5); 7.3473 (13.2); 7.3334 (5.8); 7.3249 (2.6); 7.3201 (3.2); 7.3053 (2.8); 7.2898 (1.2); 7.1810 (2.8); 7.1612 (6.0); 7.1427 (3.7); 6.9258 (3.4); 09073 (5.7); 6.8889 (2.7); 6.7951 (8.5); 0.7751 (7.6); 5.2617 (1.1); 5.2413 (3.1); 5.2284 (3.2); 4.3001 (1.0); 4.2943 (1.4); 4.2870 (1.2); 4.2748 (3.3); 4.2656 (3.1); 4.2585 (3.6); 4.2497 (3.8); 4.2408 (3.2); 4.2317 (2.4); 4.2203 (3.4); 4.2129 (2.7); 4.1923 (1.3); 3.8727 (16.0); 3.3218 (136.5); 3.3010 (10.8); 3.2915 (10.8); 3.2796 (9.0); 3.2589 (3.1); 3.2398 (1.7); 2.6700 (2.2); 2.5051 (310.4); 2 5010 (398.1); 2.4968 (287.4); 2.4242 (0.4); 2.3275 (2.3); 22091 (2.0); 2.2014 (2.2); 2.1944 (2.1); 2.1809 (1.7); 2.0525 (22); 2.0436 (2.2); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 2.0258 (1.9); 2.0176 (1.6); 1.2348 (0.8); −0.0003 (13.2) |
| 565 | 4.03 | | 565:$^1$H-NMR (400.0 MHz, $d_6$-DMSO): δ = 9.1794 (1.1); 9.1588 (1.1); 8.7822 (0.5); 8.6253 (3.8); 8.6202 (3.9); 8.3083 (2.6); 8.2853 (2.9); 7.8100 (3.2); 7.7871 (3.1); 7.5936 (0.8); 7.5864 (0.9); 7.5823 (0.9); 7.5752 (0.9); 7.5711 (1.0); 7.5643 (1.2); 7.5604 (1.0); 7.5534 (0.9); 7.4579 (0.8); 7.4511 (0.8); 7.4423 (0.8); 7.4357 (0.8); 7.4271 (1.0); 7.4220 (1.0); 7.4150 (1.0); 7.4053 (2.2); 7.4002 (1.1); 7.3875 (1.7); 7.3829 (0.9); 7.3655 (2.0); 7.3489 (1.5); 7.1836 (0.8); 7.1634 (1.6); 7.1453 (1.0); 6.9293 (1.1); 6.9265 (1.2); 6.9101 (1.8); 6.8921 (0.9); 6.8893 (0.9); 6.7963 (2.2); 6.7760 (1.8); 5.2433 (0.8); 5.2305 (0.7); 4.2945 (0.4); 4.2750 (0.9); 4.2602 (0.9); 4.2468 (0.9); 4.2383 (0.9); 4.2248 (0.8); 4.2184 (1.0); 4.1975 (0.4); 3.8814 (3.0); 3.8723 (5.0); 3.8602 (3.1); 3.8410 (0.5); 3.3215 (139 8); 3.2898 (3.6); 3.2785 (3.4); 2.6746 (1.3); 2.6702 (1.7); 2.6655 (1.2); 2.5235 (4.2); 2.5187 (6.8); 2.5100 (110.3); 2.5057 (227.6); 2.5012 (299.7); 2.4966 (210.2); 2.4922 (97.2); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 2.3368 (0.6); 2.3323 (1.2); 2.3278 (1.7); 2.3233 (1.2); 2.2084 (0.6); 2.1892 (0.6); 2.0604 (0.5); 2.0532 (0.7); 2.0449 (0.6); 2.0371 (0.5); 2.0276 (0.4); 2.0192 (0.5); 1.5301 (3.1); 1.4948 (3.2); 1.4885 (1.2); 1.4529 (0.9); 1.3976 (16.0); 1.2344 (0.4); −0.0002 (8.6) |
| 566 | 1.71 | | 566: $^1$H-NMR (400.0 MHz, $d_6$-DMSO): δ = 8.9879 (3.8); 8.9680 (3.8); 8.4481 (5.6); 8.4300 (12.0); 8.4220 (8.5); 7.9521 (0.3); 7.9237 (2.0); 7.8814 (15.0); 7.8752 (16.0); 7.8612 (2.1); 7.6249 (5.2); 7.6083 (8.1); 7.5614 (6.4); 7.5405 (6.8); 7.5226 (4.2); 7.4339 (4.4); 7.4279 (4.8); 7.4173 (4.7); 7.4114 (4.0); 7.3027 (4.2); 7.2830 (4.5); 7.1708 (2.8); 7.1673 (2.8); 7.1501 (5.7); 7.1322 (3.5); 7.1285 (3.3); 6.9055 (4.0); 6.9032 (42); 6.8847 (7.0); 6.8684 (3.2); 6.8659 (3.2); 6.7898 (7.8); 6.7694 (7.1); 5.7569 (11.9); 5.2623 (1.4); 5.2467 (3.2); 5.2284 (3.1); 5.2128 (1.3); 4.9059 (4.0); 4.8931 (8.8); 4.8804 (4.0); 4.2857 (0.9); 4.2659 (3.8); 42579 (5.8); 4.2484 (6.9); 4.2336 (4.0); 42151 (1.0); 4.0556 (0.4); 4.0378 (1.2); 4.0198 (1.1); 4.0021 (0.4); 3.6850 (2.4); 3.6707 (7.8); |

TABLE 2-continued

| LC-MS and NMR data |
|---|
| NMR peak forms are stated as they appear in the spectra, possible higher order effects have not been considered. |
| NMR peak lists |
| $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. Further details of NMR-data description with peak lists you find in the publication "Citation of NMR Peaklist Data within Patent Applications" of the Research Disclosure Database Number 564025. |

| Example No | logP (Method L0) [a] | LC-MS (Method L2-L5) | NMR or NMR Peaklist |
|---|---|---|---|
| | | | 3.6573 (10.0); 3.6444 (4.9); 3.5952 (5.7); 3.5840 (6.8); 3.5721 (4.3); 3.3213 (90.6); 2.6744 (1.3); 2.6702 (1.8); 2.6657 (1.3); 2.5234 (4.8); 2.5098 (122.4); 2.5055 (249.9); 2.5011 (329.4); 2.4966 (234.1); 2.4923 (111.1); 2.3323 (1.3); 2.3278 (1.9); 2.3234 (1.4); 2.1873 (0.7); 2.1740 (1.2); 2.1642 (1.4); 2.1534 (1.8); 2.1403 (2.5); 2.1243 (2.1); 2.1117 (1.0); 2.0664 (1.0); 2.0521 (2.3); 2.0411 (2.4); 2.0253 (1.7); 2.0167 (1.6); 2.0074 (1.3); 1.9886 (5.2); 1.2582 (0.4); 1.2344 (1.0); 1.1922 (1.2); 1.1743 (2.6); 1.1567 (1.2); 0.1459 (0.7); 0.0079 (5.6); −0.0002 (166.0); −0.0084 (5.9); −0.1494 (0.7) |
| 567 | 1.42 | | 567: $^1$H-NMR (400.0 MHz, $d_6$-DMSO): δ = 9.0073 (3.6); 8.9868 (3.7); 8.4799 (13.7); 8.4638 (3.9); 8.4434 (4.0); 7.9315 (1.6); 7.9195 (3.1); 7.9073 (1.7); 7.7132 (4.1); 7.6963 (5.2); 7.5965 (0.8); 7.5887 (1.0); 7.5790 (4.5); 7.5685 (2.0); 7.5606 (5.4); 7.5581 (5.4); 7.5477 (1.9); 7.5399 (3.8); 7.5256 (0.8); 7.3116 (3.6); 7.2930 (4.0); 7.1762 (3.3); 7.1726 (3.6); 7.1555 (5.2); 7.1378 (2.3); 7.1341 (2.2); 6.9102 (2.7); 6.8919 (4.6); 6.8733 (2.2); 6.7949 (5.1); 6.7747 (4.7); 5.7571 (3.2); 5.2731 (1.0); 5.2573 (2.3); 5.2384 (2.3); 5.2240 (1.0); 4.9044 (2.7); 4.8916 (6.1); 4.8787 (2.9); 4.3020 (0.4); 4.2928 (0.6); 4.2733 (2.5); 4.2651 (3.9); 4.2551 (4.4); 4.2492 (4.0); 4.2396 (2.5); 4.2218 (0.6); 3.6817 (1.5); 3.6675 (5.2); 3.6542 (6.9); 3.6416 (3.4); 3.6086 (3.1); 3.5963 (6.2); 3.5830 (4.7); 3.5689 (1.4); 3.3218 (25.0); 2.6745 (0.7); 2.6703 (1.0); 2.6662 (0.8); 2.5233 (2.6); 2.5055 (133.6); 2.5012 (174.2); 2.4970 (126.3); 2.3276 (1.0); 2.1948 (0.4); 2.1840 (0.8); 2.1720 (0.9); 2.1606 (1.2); 2.1486 (1.7); 2.1341 (1.4); 2.1194 (0.7); 2.0856 (16.0); 2.0641 (1.7); 2.0532 (1.6); 2.0376 (1.2); 2.0288 (1.1); 2.0193 (0.9); 2.0128 (0.7); 2.0046 (0.4); 1.9887 (0.9); 1.2351 (0.7); 1.1745 (0.4); −0.0001 (3.6) |
| 568 | 1.53 | | 568: $^1$H-NMR (400.0 MHz, $d_6$-DMSO): δ = 9.0342 (1.9); 9.0140 (2.0); 8.5727 (6.2); 8.4892 (2.2); 8.4672 (2.2); 8.4420 (0.6); 8.2975 (0.4); 8.2615 (1.1); 8.0721 (0.9); 8.0606 (1.6); 8.0483 (1.0); 7.9562 (0.5); 7.8662 (2.1); 7.8497 (2.5); 7.8153 (16.0); 7.7977 (0.8); 7.5936 (1.8); 7.5727 (2.1); 7.5543 (1.6); 7.3204 (1.8); 7.3024 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.2); 7.1821 (0.9); 7.1645 (2.0); 7.1470 (1.4); 7.1436 (1.4); 6.9222 (1.3); 6.9040 (2.4); 6.8850 (1.3); 6.8045 (2.6); 6.7848 (2.5); 5.7572 (7.2); 5.7396 (0.3); 5.2804 (0.6); 5.2654 (1.3); 5.2464 (1.4); 5.2318 (0.7); 4.9134 (1.6); 4.9007 (3.2); 4.8881 (1.6); 4.3032 (0.4); 4.2833 (1.4); 4.2743 (2.1); 4.2633 (2.5); 1.2580 (2.6); 4.2482 (1.7); 4.2305 (0.6); 4.0379 (0.8); 4.0201 (0.9); 4.0023 (0.3); 3.6661 (2.9); 3.6533 (3.7); 3.6407 (2.2); 3.6145 (2); 3.6024 (3.4); 3.5894 (2.6); 3.3241 (7.3); 3.3074 (0.5); 2 5060 (41.9); 2.5018 (53.4); 2.4975 (40.1); 2.1877 (0.4); 2.1793 (0.5); 2.1681 (0.8); 2.1557 (1.0); 2.1410 (0.9); 2.1258 (0.6); 2.0946 (0.5); 2.0799 (0.9); 2.0699 (1.0); 2.0542 (0.8); 2.0447 (0.7); 2.0357 (0.6); 2.0293 (0.5); 1.9890 (3.5); 1.2988 (0.4); 1 2585 (0.5); 1.2312 (0.7); 1.1925 (1.0); 1.1747 (1.8); 1.1569 (1.0); −0.0002 (1.2) |
| 576 | 3.90 | | 576: $^1$H-NMR (400.0 MHz, $d_6$-DMSO): δ = 20.0029 (0.9); 9.1889 (6.0); 9.1694 (6.2); 8.6464 (14.7); 8.6381 (15.0); 8.3318 (10.9); 8.3089 (11.9); 7.8301 (11.0); 7.8072 (10.0); 7.6892 (1.6); 7.6682 (2.6); 7.6486 (2.6); 7.4026 (1.1); 7.3714 (3.5); 7.3527 (4.2); 7.1816 (5.1); 7.1646 (7.5); 7.1472 (4.8); 6.9296 (4.4); 6.9103 (7.1); 6.8923 (3.8); 6.7973 (8.0); 6.7765 (7.6); 5.2293 (3.2); 4.2951 (1.7); 4.2767 (3.3); 4.2608 (3.3); 4.2507 (3.5); 4.2420 (3.3); 4.2203 (3.7); 4.1924 (1.5); 3.9161 (1.0); 3.9087 (1.1); 3.8728 (16.0); 3.7425 (1.0); 3.3196 (381.7); 3.2976 (12.2); 3.2873 (11.7); 3.2380 (1.9); 2.6744 (7.0); 2.6702 (9.7); 2.6655 (7.0); 2.6612 (3.6); 2.5233 (22.0); 2.5099 (648.2); 2.5055 (1360.8); 2.5010 (1822.1); 2.4965 (1299.0); 2.4920 (613.8); 2.4282 (2.0); 2.3323 (7.9); 2.3277 (10.7); 2.3234 (7.8); 2.2851 (1.0); 2.2044 (2.7); 2.0556 (2.4); 2.0356 (2.2); 1.2408 (1.1); −0.0002 (68.2) |
| 577 | 1.66 | | 577: $^1$H-NMR (400.0 MHz, $d_6$-DMSO): δ = 8.9783 (4.8); 8.9578 (4.8); 8.5458 (3.4); 8.5302 (3.7); 8.5222 (3.6); 8.5068 (3.4); 8.4827 (1.4); 8.4655 (0.4); 8.4574 (0.4); 8.4398 (0.4); 8.4133 (2.7); 8.4054 (16.0); 8.0443 (0.8); 8.0308 (0.5); 8.0114 (0.4); 7.9945 (1.9); 7.9831 (3.6); 7.9722 (1.9); 7.7219 (5.6); 7.7183 (5.8); 7.7019 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (6.8); 7.6982 (6.6); 7.5396 (0.4); 7.5281 (3.8); 7.5054 (6.4); 7.4834 (4.5); 7.4711 (5.3); 7.4516 (9.8); 7.4431 (1.6); 7.4319 (5.6); 7.4231 (0.9); 7.3921 (0.3); 7.3727 (0.6); 7.3473 (6.3); 7.3436 (6.5); 7.3281 (5.6); 7.3245 (4.7); 7.3118 (0.8); 7.2873 (4.7); 7.2693 (5.2); 7.1660 (2.4); 7.1634 (2.4); 7.1455 (5.1); 7.1282 (3.2); 7.1246 (3.0); 6.8960 (3.8); 6.8769 (6.2); 6.8606 (2.8); 6.7853 (6.9); 6.7650 (6.3); 6.6074 (0.5); 6.5916 (0.4); 5.7570 (8.6); 5.2502 (1.6); 5.2353 (3.1); 5.2157 (3.0); 5.2010 (1.4); 4.9112 (3.8); 4.8980 (8.6); 4.8853 (3.9); 4.2747 (0.8); 4.2402 (7.3); 4.2276 (4.6); 4.2100 (0.7); 4.1986 (0.4); 4.0553 (0.7); 4.0376 (2.0); 4.0197 (1.9); 4.0019 (0.8); 3.6838 (2.3); 3.6695 (7.4); 3.6560 (9.4); 3.6437 (4.5); 3.5967 (4.6); 3.5846 (8.3); 3.5711 (6.6); 3.5569 (2.0); 3.5289 (0.4); 3.4240 (0.3); 3.3211 (225.0); 2.6744 (2.4); 2.6700 (32); 2.6655 (2.3); 2.6025 (0.4); 2.5795 (0.3); 2.5234 (7.9); 2.5096 (213.1); 2.5055 (434.5); 2.5010 (573.6); 2.4966 (408.4); 2.4923 (193.6); 2.4434 (0.9); 2.4385 (0.9); 2.3322 (2.3); 2.3277 (3.3); 2.3232 (2.3); 2.1689 (1.4); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 2.1475 (1.8); 2.1338 (2.6); 2.1207 (2.2); 2.1056 (1.0); 2.0549 (1.1); 2.0409 (2.3); 2.0263 (2.3); 2.0117 (1.7); 2.0043 (1.6); 1.9886 (9.4); 1.9081 (0.3); 1.3974 (0.7); 1.3508 (0.3); 1.2979 (2.2); 1.2583 (3.0); 1.2351 (2.6); 1.1922 (2.3); 1.1743 (4.8); 1.1565 (2.2); 0.8663 (0.4); 0.8537 (0.6); 0.8378 (0.4); −0.0002 (22.2) |
| 578 | 1.84 | | 578: $^1$H-NMR (400.0 MHz, $d_6$-DMSO): δ = 8.9985 (2.2); 8.9780 (2.3); 8.5049 (8.6); 8.4947 (2.0); 8.4861 (1.8); 8.4710 (1.5); 8.1238 (1.0); 8.1117 (1.8); 8.1003 (1.0); 7.6592 (3.0); 7.6544 (5.7); 7.6497 (3.2); 7.5218 (1.8); 7.4987 (3.4); 7.4750 (10.7); 7.4705 (9.2); 7.2997 (2.3); 7.2817 (2.5); 7.1770 (1.1); 7.1734 (1.1); 7.1561 (2.4); 7.1 383 (1.5); 7.1350 (1.4); 6.9084 (1.7); 6.8916 (3.0); 6.8733 (1.4); 6.8711 (1.4); 6.7964 (3.3); 6.7761 (3.0); 5.7570 (13.6); 5.2638 (0.6); 5.2483 (1.5); 5.2298 (1.5); 5.2142 (0.7); 4.9160 (1.7); 4.9034 (4.0); 4.8907 (1.9); 4.2892 (0.4); 4.2697 (1.7); 4.2614 (2.4); 4.2520 (3.0); 4.2376 (1.8); 4.2191 (0.4); 4.0557 (0.6); 4.0379 (1.9); 4.0201 (1.9); 4.0023 (0.6); 3.6763 (1.0); 3.6615 (3.2); 3.6485 (4.3); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.6362 (2.3); 3.6094 (2.1); 3.5974 (3.8); 3.5842 (2.9); 3.5725 (0.9); 3.3230 (35.7); 2.6747 (0.4); 2.6706 (0.5); 2.6663 (0.4); 2.5238 (1.2); 2.5059 (68.9); 2.5015 (90.7); 2.4971 (65.0); 2.3284 (0.5); 2.3240 (0.4); 2.1790 (0.5); 2.1660 (0.6); 2.1552 (0.8); 2.1422 (1.1); 2.1265 (0.9); 2.1138 (0.4); 2.0744 (0.4); 2.0596 (1.1); 2.0484 (1.0); 2.0333 (0.7); 2.0239 (0.7); 2.0148 (0.6); 2.0076 (0.4); 1.9971 (0.3); 1.9888 (8.2); 1.3971 (16.0); 1.2586 (0.4); 1.1925 (2.1); 1.1747 (4.2); 1.1568 (2.0); −0.0002 (3.7) |
| 579 | 1.61 | | 579: $^1$H-NMR (400.0 MHz, $d_6$-DMSO): δ = 9.0615 (0.4); 9.0402 (0.5); 9.0006 (7.4); 8.9800 (7.6); 8.6025 (1.7); 8.5834 (5.4); 8.5682 (5.9); 8.5596 (5.8); 8.5445 (5.4); 8.5056 (1.2); 8.4832 (15.4); 8.4772 (16.0); 8.4524 (0.5); 8.4436 (0.4); 8.4293 (0.3); 8.1268 (3.0); 8.1146 (2.0); 8.0994 (2.0); 8.0864 (3.4); 7.6673 (1.6); 7.6596 (2.1); 7.6507 (2.3); 7.6445 (3.2); 7.6391 (3.2); 7.6309 (3.2); 7.6236 (3.1); 7.6180 (3.2); 7.6113 (2.0); 7.6033 (1.7); 7.5953 (1.4); 7.5580 (5.5); 7.5351 (10.2); 7.5124 (5.4); 7.4985 (1.0); 7.4754 (1.7); 7.3275 (0.5); 7.3007 (7.9); 7.2816 (8.6); 7.2356 (2.1); 7.2214 (3.4); 7.2145 (3.9); 7.1940 (2.2); 7.1750 (4.5); 7.1713 (4.3); 7.1539 (8.4); 7.1364 (5.3); 7.1328 (4.8); 6.9344 (0.4); 6.9060 (6.0); 6.8874 (10.0); 6.8689 (5.0); 6.8113 (0.6); 6.7940 (12.0); 6.7918 (11.6); 6.7736 (10.7); 6.7713 (9.7); 5.7574 (15.4); 5.2606 (2.2); 5.2456 (4.9); 5.2266 (4.8); 5.2116 (2.0); 4.9170 (4.8); 4.9062 (9.9); 4.9041 (10.1); 4.8926 (5.4); 4.8800 (0.5); 4.2823 (1.2); 4.2589 (7.8); 4.2481 (10.8); 4.2360 (6.9); 4.2174 (1.2); 4.2072 (0.5); 4.0559 (0.9); 4.0380 (2.7); 4.0203 (2.8); 4.0024 (0.9); 3.6805 (3.2); 3.6666 (11.4); 3.6537 (15.0); 3.6414 (8.3); 3.6174 (42); 3.6062 (8.8); 3.5961 (10.2); 3.5835 (7.1); 3.5594 (1.0); 3.5452 (0.4); 3.3229 (55.3); 2.6798 (0.6); 2.6752 (1.2); 2.6707 (1.6); 2.6660 (1.2); 2.5240 (4.0); 2.5191 (6.4); 2.5106 (102.4); 2.5061 (214.3); 2.5016 (285.4); 2.4971 (201.0); 2.4926 (93.2); 2.3326 (1.1); 2.3283 (1.6); 2.3239 (1.2); 2.1891 (1.0); 2.1779 (2.0); 2.1654 (2.1); 2.1559 (2.6); 2.1423 (4.1); 2.1277 (3.3); 2.1137 (1.4); 2.0676 (1.7); 2.0536 (3.7); 2.0411 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.4); 2.0261 (2.4); 2.0174 (2.4); 2.0082 (1.9); 1.9890 (12.6); 1.3971 (1.9); 1.2992 (2.0); 1.2588 (2.8); 1.2348 (1.5); 1.1924 (3.3); 1.1747 (6.6); 1.1569 (3.2); 0.8537 (0.4); 0.0081 (0.4); −0.0002 (12.9); −0.0081 (0.4) |
| 589 | 2.43 | | 589: $^1$H-NMR (400.0 MHz, $d_6$-DMSO): δ = 9.3204 (1.1); 9.3135 (1.1); 9.3003 (1.2); 9.2927 (1.0); 8.5653 (7.4); 8.3124 (1.6); 8.3036 (1.4); 8.2966 (1.7); 8.2873 (1.7); 8.2791 (0.4); 7.7025 (2.2); 7.6989 (2.4); 7.6825 (2.7); 7.6788 (2.7); 7.6719 (0.8); 7.6538 (3.4); 7.6470 (3.3); 7.6381 (6.8); 7.4567 (0.8); 7.4467 (0.8); 7.4374 (1.7); 7.4275 (1.6); 7.4178 (1.1); 7.4076 (1.0); 7.3623 (2.7); 7.3323 (3.6); 7.3134 (0.9); 7.1863 (0.9); 7.1659 (2.0); 7.1482 (1.2); 6.9252 (1.3); 6.9067 (2.2); 6.8881 (1.0); 6.8028 (2.7); 6.7823 (2.4); 5.7568 (16.0); 5.2942 (0.5); 5.2792 (1.2); 5.2607 (1.2); 5.2464 (0.6); 5.1484 (0.9); 5.1392 (1.6); 5.1338 (1.5); 5.1246 (0.8); 4.2956 (0.4); 4.2771 (1.2); 4.2614 (2.0); 4.2522 (2.0); 4.2406 (1.0); 4.2328 (1.2); 4.2129 (0.4); 4.2075 (0.3); 4.0374 (0.7); 4.0196 (0.6); 3.6661 (0.4); 3.6505 (1.0); 3.6383 (1.8); 3.6256 (1.9); 3.5831 (0.4); 3.5455 (2.6); 3.3210 (21.3); 3.3034 (0.4); 3.0572 (15.5); 2.6701 (0.6); 2.6654 (0.5); 2.5051 (83.3); 2.5007 (109.1); 2.4964 (79.4); 2.3273 (0.6); 2.3233 (0.5); 2.2266 (0.5); 2.2137 (0.8); 2.2033 (0.8); 2.1911 (0.8); 2.1798 (0.6); 2.0667 (0.8); 2.0593 (0.9); 2.0497 (0.7); 2.0377 (0.6); 2.0327 (0.6); 2.0238 (0.5); 1.9884 (2.9); 1.2347 (0.5); 1.1919 (0.8); 1.1742 (1.5); 1.1564 (0.7); −0.0002 (9.7) |
| 590 | 3.44 | | 590: $^1$H-NMR (400.0 MHz, $d_6$-DMSO): δ = 9.3230 (1.9); 9.3026 (1.9); 8.7282 (0.8); 8.6746 (0.3); 8.5838 (8.2); 8.3304 (1.7); 8.3262 (1.8); 8.3102 (1.8); 8.3060 (2.0); 7.9109 (4.6); 7.9048 (4.8); 7.6985 (1.1); 7.6845 (3.0); 7.6738 (3.3); 7.6536 (2.8); 7.6410 (0.9); 7.6360 (1.4); 7.4926 (1.6); 7.4863 (1.7); 7.4607 (1.5); 7.4549 (1.4); 7.3529 (1.9); 7.3362 (2.0); 7.1897 (1.2); 7.1866 (1.2); 7.1682 (2.1); 7.1514 (1.3); 7.1473 (1.2); 6.9385 (0.3); 6.9281 (1.4); 6.9100 (2.3); 6.8922 (1.1); 6.8203 (0.4); 6.8035 (2.9); 6.7849 (2.4); 5.7568 (4.1); 5.2936 (0.6); 5.2778 (1.2); 5.2600 (1.2); 5.2445 (0.6); 5.1331 (1.4); 4.3052 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.4); 4.2974 (0.6); 4.2901 (0.6); 4.2777 (1.3); 4.2616 (2.0); 4.2525 (2.0); 4.2406 (1.1); 4.2325 (1.2); 4.2122 (0.4); 3.6684 (0.4); 3.6540 (0.9); 3.6401 (1.6); 3.6268 (1.8); 3.5844 (0.4); 3.5555 (2.0); 3.5444 (2.6); 3.5068 (0.4); 3.4949 (0.4); 3.3197 (31.2); 3.0560 (16.0); 3.0377 (1.8); 2.6746 (0.8); 2.6700 (1.1); 2.6654 (0.8); 2.5231 (2.9); 2.5096 (69.2); 2.5054 (141.9); 2.5009 (188.1); 2.4965 (135.6); 2.4922 (65.6); 2.3321 (0.8); 2.3276 (1.1); 2.3232 (0.8); 2.2478 (0.4); 2.2268 (0.6); 2.2135 (0.9); 2.2041 (0.9); 2.1919 (0.9); 2.1835 (0.6); 2.0762 (0.6); 2.0685 (0.8); 2.0611 (1.0); 2.0519 (0.7); 2.0343 (0.7); 2.0262 (0.6); 1.9885 (0.4); 1.2580 (0.4); 1.2349 (1.4); 0.0079 (0.4); −0.0002 (12.9) |
| 591 | 3.25 | | 591: $^1$H-NMR (400.0 MHz, $d_6$-DMSO): δ = 9.3476 (1.8); 9.3272 (1.8); 8.7005 (7.3); 8.5245 (0.4); 8.3686 (2.0); 8.3493 (2.2); 8.2720 (1.2); 7.9656 (0.5); 7.9319 (2.0); 7.9142 (2.4); 7.8341 (16.0); 7.7034 (1.8); 7.6847 (2.0); 7.6642 (1.4); 7.3800 (1.9); 7.3618 (2.0); 7.2027 (0.9); 7.1993 (0.9); 7.1815 (2.0); 7.1641 (1.2); 7.1611 (1.2); 6.9518 (1.3); 6.9330 (2.3); 6.9146 (1.2); 6.8173 (2.8); 6.7968 (2.5); 5.7572 (12.0); 5.3147 (0.5); 5.3002 (1.2); 5.2813 (1.3); 5.2664 (0.6); 5.1438 (1.1); 5.1288 (2.4); 5.1136 (1.1); 4.3120 (0.4); 4.3050 (0.4); 4.2928 (1.2); 4.2757 (1.9); 4.2668 (1.9); 4.2535 (1.1); 4.2460 (1.3); 4.2258 (0.4); 4.2188 (0.4); 4.0382 (0.9); 4.0204 (0.9); 3.6465 (1.0); 3.6331 (2.4); 3.6200 (2.6); 3.6066 (1.4); 3.5492 (2.4); 3.5372 (2.9); 3.3260 (25.5); 3.3049 (0.4); 3.0624 (14.0); 2.5058 (36.3); 2.5017 (45.5); 2.4977 (33.2); 2.2521 (0.4); 2.2430 (0.5); 2.2305 (0.8); 2.2209 (0.8); 2.2089 (0.9); 2.1975 (0.7); 2.1887 (0.4); 2.1046 (0.6); 2.0965 (0.8); 2.0895 (0.9); 2.0738 (0.7); 2.0620 (0.6); 2.0537 (0.6); 1.9891 (3.8); 1.2320 (0.3); 1.1926 (1.0); 1.1748 (1.9); 1.1572 (1.0); −0.0001 (4.5) |
| 595 | 3.61 | | 595: $^1$H-NMR (400.0 MHz, $d_6$-DMSO): δ = 9.1408 (0.9); 9.1232 (1.7); 9.1128 (1.2); 9.1059 (1.3); 8.5911 (7.4); 8.3494 (1.9); 8.3335 (2.1); 8.3258 (2.1); 8.3102 (1.9); 8.1409 (0.4); 7.7554 (3.0); 7.7518 (3.1); 7.7353 (3.7); 7.7317 (3.6); 7.6777 (2.3); 7.6551 (3.9); 7.6324 (2.2); 7.5002 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (1.4); 7.4897 (1.3); 7.4808 (2.9); 7.4702 (2.7); 7.4610 (1.8); 7.4505 (1.6); 7.4116 (1.0); 7.4079 (1.1); 7.3993 (1.1); 7.3919 (1.8); 7.3883 (1.6); 7.3754 (1.7); 7.3681 (12); 7.3560 (2.0); 7.3479 (1.6); 7.3377 (1.5); 7.3327 (1.4); 7.1785 (1.3); 7.1608 (2.8); 7.1431 (1.7); 6.9110 (1.4); 6.8927 (2.5); 6.8746 (1.2); 6.7951 (3.5); 6.7747 (3.2); 5.7569 (16.0); 5.2309 (1.4); 5.2174 (1.3); 4.2882 (0.5); 4.2691 (1.6); 4.2537 (2.7); 4.2444 (2.3); 4.2322 (1.3); 4.2033 (0.4); 4.0557 (0.6); 4.0378 (1.6); 4.0201 (1.6); 4.0023 (0.6); 3.7509 (0.6); 3.7434 (0.5); 3.7279 (1.0); 3.7217 (1.2); 3.7117 (0.7); 3.7041 (1.5); 3.6822 (1.2); 3.6640 (0.7); 3.6542 (0.7); 3.6478 (1.1); 3.6339 (1.7); 3.6281 (1.2); 3.6209 (1.1); 3.6138 (1.3); 3.6008 (1.6); 3.5817 (2.2); 3.5630 (1.8); 3.5434 (0.5); 3.3865 (0.6); 3.3682 (1.5); 3.3552 (1.7); 3.3473 (2.1); 3.3228 (43.4); 3.2960 (0.8); 3.2790 (0.6); 3.2636 (1.0); 3.2544 (1.1); 3.2470 (1.0); 3.2390 (1.1); 3.2120 (1.6); 3.1913 (1.2); 3.1782 (1.4); 3.1674 (0.5); 3.1565 (0.9); 3.1462 (0.7); 3.1236 (0.4); 3.0852 (14.4); 3.0806 (13.3); 2.6985 (1.0); 2.6799 (1.2); 2.6746 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (1.3); 2.6704 (1.5); 2.5233 (2.1); 2.5057 (103.8); 2.5013 (135.2); 2.4969 (96.5); 2.3325 (0.6); 2.3281 (0.8); 2.2037 (0.7); 2.1932 (0.9); 2.1822 (1.1); 2.1701 (1.0); 2.1617 (0.8); 2.1490 (0.5); 2.0299 (1.2); 2.0158 (1.4); 1.9887 (8.2); 1.9661 (1.1); 1.9539 (0.6); 1.4852 (0.6); 1.4798 (0.6); 1.4688 (1.0); 1.4532 (1.1); 1.4363 (0.9); 1.4216 (0.6); 1.2352 (0.5); 1.1923 (1.8); 1.1745 (3.6); 1.1567 (1.8); 0.0075 (0.3); −0.0002 (9.6) |
| 596 | 2.30 | | 596: $^1$H-NMR (400.0 MHz, $d_6$-DMSO): δ = 9.0701 (3.4); 9.0498 (3.5); 8.5625 (0.6); 8.5278 (0.5); 8.4640 (2.2); 8.4489 (2.6); 8.4390 (11.6); 8.4253 (2.3); 8.1352 (0.7); 7.8085 (0.8); 7.795 5 (1.7); 7.7758 (1.8); 7.7613 (0.9); 7.7046 (6.4); 7.6992 (7.6); 7.6691 (0.7); 7.6622 (1.0); 7.6543 (0.9); 7.6470 (1.4); 7.6418 (1.4); 7.6338 (1.4); 7.6213 (1.4); 7.6135 (0.9); 7.5969 (2.8); 7.5738 (4.2); 7.5512 (2.2); 7.5380 (0.3); 7.4597 (6.8); 7.4558 (6.8); 7.4405 (0.4); 7.2706 (2.3); 7.2503 (2.8); 7.2145 (1.7); 7.1920 (0.9); 7.1737 (1.8); 7.1528 (3.5); 7.1353 (2.1); 6.8948 (1.7); 6.8760 (2.8); 6.8579 (1.3); 6.7898 (4.9); 6.7697 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (4.4); 6.2235 (4.2); 6.2186 (7.2); 6.2137 (42); 6.1947 (0.4); 5.7572 (15.7); 5.2260 (1.1); 5.2118 (2.2); 5.1921 (2.1); 5.1777 (0.9); 4.4811 (3.3); 4.4655 (7.5); 4.4500 (3.9); 4.4309 (0.4); 4.2266 (4.2); 4.2215 (4.5); 4.0560 (1.1); 4.0380 (3.4); 4.0202 (3.4); 4.0023 (1.2); 3.8362 (3.8); 3.8227 (3.4); 3.3218 (25.8); 2.8900 (0.6); 2.7311 (0.6); 2.6707 (1.0); 2.5236 (2.6); 2.5057 (130.4); 2.5014 (170.3); 2.4971 (122.6); 2.3282 (1.0); 2.1418 (0.9); 2.1256 (1.2); 2.1084 (1.4); 2.0941 (1.3); 2.0746 (0.7); 2.0126 (1.0); 1.9999 (1.6); 1.9888 (16.0); 1.9666 (1.0); 1.9535 (0.7); 1.2347 (0.6); 1.1924 (3.8); 1.1746 (7.5); 1.1568 (3.7); 0.0080 (0.4); −0.0001 (12.0) |
| 597 | 1.84 | | 597: $^1$H-NMR (400.0 MHz, $d_6$-DMSO): δ = 9.0160 (2.4); 8.9955 (2.4); 8.5800 (1.6); 8.5647 (1.7); 8.5564 (1.7); 8.5410 (1.7); 8.5257 (8.0); 8.2056 (1.8); 7.6979 (16.0); 7.5619 (1.8); 7.5385 (3.4); 7.5151 (1.7); 7.2990 (2.3); 7.2808 (2.6); 7.1797 (1.1); 7.1764 (1.2); 7.1586 (2.4); 7.1412 (1.5); 6.9103 (1.7); 6.8921 (2.9); 6.8735 (1.4); 6.7985 (3.3); 6.7784 (3.0); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 5.2605 (0.7); 5.2452 (1.5); 5.2258 (1.5); 5.2103 (0.6); 4.9247 (1.7); 4.9122 (3.9); 4.8996 (1.8); 4.2873 (0.3); 4.2603 (2.4); 4.2512 (3.2); 4.2197 (0.4); 3.6760 (0.9); 3.6623 (3.1); 3.6494 (4.2); 3.6376 (2.3); 3.6131 (22); 3.6014 (3.8); 3.5884 (2.8); 3.3245 (128.5); 2.6710 (0.9); 2.5058 (125.4); 2.5015 (161.2); 2.4973 (117.7); 2.3284 (0.9); 2 1769 (0.5); 2.1553 (0.8); 2.1416 (1.1); 2.1263 (1.0); 2.1128 (0.5); 2.0598 (1.1); 2.0478 (1.1); 2.0324 (0.8); 2.0239 (0.7); 2.0143 (0.6); −0.0001 (5.0) |
| 599 | 1.26 | | 599: $^1$H-NMR (400.0 MHz, $d_6$-DMSO): δ = 9.0562 (3.0); 9.0349 (3.1); 8.5743 (0.4); 8.4690 (1.5); 8.4526 (1.9); 8.4440 (1.9); 8.4303 (1.6); 8.3837 (8.0); 8.1530 (1.3); 7.9531 (0.3); 7.8091 (1.4); 7.7969 (1.3); 7.7809 (1.2); 7.7236 (3.8); 7.7207 (3.8); 7.7033 (4.5); 7.6086 (1.1); 7.5735 (2.2); 7.5518 (3.6); 7.5294 (2.0); 7.4708 (1.4); 7.4608 (1.8); 7.4511 (2.7); 7.4413 (3.2); 7.4317 (1.7); 7.4217 (1.9); 7.3433 (2.1); 7.3279 (3.6); 7.3127 (2.0); 7.2532 (3.2); 7.2358 (3.5); 7.2145 (0.4); 7.1976 (0.5); 7.1703 (2.3); 7.1507 (4.4); 7.1322 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.8); 6.9427 (0.3); 6.8980 (2.9); 6.8795 (4.7); 6.8617 (2.6); 6.8121 (0.5); 6.7871 (4.7); 6.7668 (4.2); 5.7564 (16.0); 5.2306 (1.0); 5.2157 (2.1); 5.1972 (2.0); 5.1830 (0.9); 4.3402 (3.3); 4.2258 (4.6); 3.7613 (3.1); 3.5706 (0.3); 3.5591 (0.4); 3.5486 (0.4); 3.4758 (0.7); 3.3304 (5.7); 3.1731 (0.6); 2.8900 (1.4); 2.7307 (1.4); 2.6707 (1.6); 2.5587 (0.4); 2.5016 (305.4); 2.4478 (0.8); 2.4148 (0.4); 2.40 82 (0.4); 2.3283 (1.8); 2.1700 (0.5); 2.1196 (1.4); 1.9881 (2.0); 1.9618 (1.2); 1.1742 (0.4); −0.0003 (14.4) |
| 606 | 2.63 | | 606: $^1$H-NMR (400.0 MHz, $d_6$-DMSO): δ = 20.0019 (0.4); 11.6374 (0.5); 9.3368 (2.0); 9.3164 (1.9); 8.6542 (0.4); 8.6320 (8.0); 8.3582 (2.0); 8.3369 (2.2); 8.1752 (0.6); 8.1559 (0.5); 7.7946 (2.0); 7.7787 (2.7); 7.7011 (2.2); 7.6792 (2.2); 7.6623 (1.5); 7.6399 (0.6); 7.6304 (0.7); 7.6154 (0.9); 7.6105 (0.9); 7.5953 (0.9); 7.5661 (0.6); 7.3732 (2.0); 7.3566 (2.2); 7.2327 (1.2); 7.2036 (1.6); 7.1824 (2.2); 7.1642 (1.3); 6.9450 (1.6); 6.9252 (2.4); 6.9067 (1.2); 6.8179 (2.7); 6.7965 (2.4); 5.3127 (0.7); 5.2980 (1.3); 5.2805 (1.4); 5.2646 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.6); 5.1508 (1.2); 5.1352 (2.6); 5.1201 (1.3); 4.3135 (0.6); 1.3101 (0.6); 4.2925 (1.2); 4.2749 (1.8); 4.2657 (1.9); 4.2452 (1.4); 4.2228 (0.6); 3.6428 (2.3); 3.6278 (2.6); 3.6139 (1.6); 3.5956 (0.5); 3.5628 (2.5); 3.5489 (3.0); 3.3286 (367.5); 3.0681 (16.0); 2.6830 (4.0); 2.6784 (5.4); 2.6738 (4.0); 2.6571 (0.4); 2.5916 (0.5); 2.5585 (1.2); 2.5138 (734.5); 2.5095 (960.4); 2.5050 (690.4); 2.4327 (0.8); 2.3888 (0.5); 2.3406 (4.0); 2.3362 (5.6); 2.3320 (4.1); 2.2638 (0.5); 2.2521 (0.8); 2.2294 (0.9); 2.2202 (0.8); 2.2097 (0.9); 2.1954 (0.9); 2.1014 (0.6); 2.0870 (1.1); 2.0807 (1.0); 2.0641 (0.9); 2.0539 (0.8); 1.7536 (0.4); 0.0082 (27); −2.4241 (0.4); −2.6703 (0.5) |
| 625 | 1.24 | | 625: $^1$H-NMR (400.0 MHz, $d_6$-DMSO): δ = 9.0900 (1.0); 9.0696 (1.1); 8.5142 (4.0); 8.3294 (1.0); 8.3092 (1.0); 7.7732 (0.5); 7.7612 (2.0); 7.7455 (1.8); 7.6202 (3.0); 7.6160 (7.0); 7.6102 (2.8); 7.6064 (1.8); 7.5945 (2.0); 7.5821 (1.0); 7.5610 (1.1); 7.5428 (0.8); 7.2876 (1.0); 7.2700 (1.0); 7.1885 (0.5); 7.1848 (0.5); 7.1681 (1.0); 7.1501 (0.6); 7.1463 (0.6); 7.1283 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.2); 6.9241 (0.7); 6.9055 (1.3); 6.8866 (0.7); 6.8599 (2.3); 6.8053 (1.4); 6.7852 (1.3); 5.7568 (16.0); 5.2445 (0.6); 5.2257 (0.6); 4.3461 (0.9); 4.3314 (2.0); 4.3165 (1.0); 4.2612 (1.0); 4.2481 (1.7); 4.2348 (1.1); 3.7783 (1.0); 3.7693 (0.9); 3.7633 (0.9); 3.3256 (11.9); 3.1318 (1.5); 2.5236 (0.7); 2.5101 (19.3); 2.5058 (40.5); 2.5013 (54.2); 2.4968 (38.5); 2.4925 (18.1); 2.1600 (0.3); 2.1388 (0.5); 2.1255 (0.5); 2.0744 (0.4); 2.0394 (0.4); 2.0254 (0.5); 2.0027 (0.3); 0.0079 (0.7); −0.0002 (21.3); −0.0084 (0.7) |
| 629 | 2.09 | | 629: $^1$H-NMR (400.0 MHz, $d_6$-DMSO): δ = 8.9739 (1.9); 8.9538 (1.9); 8.5544 (0.4); 8.3842 (2.7); 8.3611 (3.0); 8.3534 (6.7); 7.8907 (1.2); 7.8785 (1.2); 7.6553 (3.6); 7.6515 (2.8); 7.6466 (4.6); 7.6418 (2.6); 7.6325 (3.3); 7.3204 (1.6); 7.2981 (2.8); 7.2783 (1.9); 7.1724 (0.9); 7.1505 (1.7); 7.1331 (12); 7.1292 (1.1); 6.9069 (1.3); 6.8885 (2.2); 6.8727 (1.1); 6.7876 (2.5); 6.7691 (2.1); 5.2365 (0.6); 5.2227 (1.1); 5.2020 (1.0); 5.1865 (0.5); 4.2514 (1.9); 4.2395 (3.2); 4.2256 (1.8); 3.3205 (162.9); 3.0650 (1.7); 3.0510 (6.7); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.0385 (6.8); 2.6746 (1.3); 2.6702 (1.7); 2.6658 (1.3); 2.5456 (0.4); 2.5233 (4.5); 2.5098 (111.1); 2.5055 (228.2); 2.5011 (302.5); 2.4966 (215.4); 2.4923 (102.0); 2.3324 (1.2); 2.3278 (1.7); 2.3236 (1.2); 2.1786 (0.4); 2.1705 (0.6); 2.1564 (0.7); 2.1345 (0.8); 2.1206 (0.8); 2.1072 (0.3); 2.0227 (0.7); 2.0119 (0.9); 1.9896 (0.6); 1.9757 (0.6); 1.3975 (16.0); 1.2981 (0.4); 1.2580 (0.6); 1.2351 (3.6); 0.8536 (0.5); 0.0078 (1.2); −0.0002 (36.1); −0.0084 (1.4) |
| 630 | 5.59 | | 630: $^1$H-NMR (400.0 MHz, $d_6$-DMSO): δ = 9.0221 (2.2); 9.0014 (2.2); 8.6578 (9.6); 8.2917 (3.5); 8.2688 (4.0); 7.7935 (4.4); 7.7706 (4.1); 7.6936 (2.7); 7.6889 (5.3); 7.6841 (2.9); 7.3740 (3.2); 7.3575 (3.9); 7.2960 (0.5); 7.2779 (1.4); 7.2596 (5.4); 7.2490 (2.8); 7.2439 (2.0); 7.2315 (1.8); 7.2267 (1.4); 7.2158 (0.7); 7.2100 (0.7); 6.7934 (0.4); 6.7889 (0.4); 5.7565 (13.4); 5.6226 (0.6); 5.6026 (1.6); 5.5824 (1.6); 5.5623 (0.6); 3.9150 (0.5); 3.8839 (6.4); 3.8527 (0.5); 3.3624 (0.7); 3.3515 (1.3); 3.3314 (2.0); 3.3200 (16.7); 3.2889 (1.5); 3.2793 (2.4); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.2661 (1.7); 3.2475 (1.3); 3.2366 (0.7); 2.6747 (0.4); 2.6701 (0.6); 2.6658 (0.4); 2.5236 (1.4); 2.5100 (39.3); 2.5057 (82.0); 2.5012 (109.3); 2.4967 (78.5); 2.4924 (37.7); 2.4266 (1.5); 2.4077 (1.6); 2.3956 (1.7); 2.3767 (1.5); 2.3323 (0.5); 2.3280 (0.6); 2.3233 (0.5); 1.9885 (0.7); 1.8670 (1.4); 1.8451 (1.4); 1.8359 (1.4); 1.8144 (12); 1.3617 (16.0); 1.2982 (0.6); 1.2583 (0.8); 1.2329 (1.9); 1.2207 (14.1); 1.1928 (0.4); 1.1747 (0.5); 0.8528 (0.3); 0.0081 (0.4); −0.0002 (13.8); −0.0083 (0.5) |
| 635 | 4.08 | | 635: $^1$H-NMR (400.0 MHz, $d_6$-DMSO): δ = 16.1140 (0.5); 10.4114 (5.2); 9.2742 (4.1); 9.2545 (4.1); 8.6672 (16.0); 8.4984 (0.8); 8.3161 (0.7); 8.2805 (5.8); 8.2574 (6.8); 7.9468 (0.5); 7.8498 (0.5); 7.8211 (0.5); 7.8071 (1.9); 7.7922 (13.1); 7.7695 (10.8); 7.7494 (1.6); 7.7007 (4.7); 7.6894 (5.4); 7.6846 (12.3); 7.6801 (10.0); 7.6549 (0.5); 7.6293 (0.5); 7.5660 (2.6); 7.5463 (3.9); 7.5265 (1.9); 7.4103 (0.6); 7.3731 (7.7); 7.3420 (0.5); 7.2955 (0.6); 7.2790 (0.5); 7.2579 (0.6); 7.174 8 (0.6); 7.1587 (0.5); 6.9763 (2.6); 6.9717 (4.9); 6.9672 (2.8); 6.7934 (10.6); 6.7888 (10.5); 5.7571 (3.0); 5.7200 (1.4); 5.7123 (1.4); 5.7007 (2.3); 5.6927 (2.3); 5.6827 (1.4); 5.6722 (1.3); 4.2620 (0.6); 3.9041 (0.7); 3.8714 (10.6); 3.8595 (8.3); 3.3202 (437.6); 3.2547 (10.3); 3.2474 (9.8); 3.2274 (3.3); 3.2003 (3.5); 3.1809 (2.7); 3.0561 (0.6); 3.0434 (0.7); 3.0415 (0.8); 3.0359 (1.0); 3.0236 (1.1); 2.6887 (0.9); 2.6736 (7.4); 2.6705 (7.5); 2.6653 (7.5); 2.6262 (2.8); 2.6181 (3.1); 2.5684 (1.0); 2.5234 (15.1); 2.5055 (828.6); 2.5011 (1116.3); 2.4966 (810.8); 2.4925 (396.0); 2.3321 (4.3); 2.3276 (6.2); 2.3235 (4.8); 1.6275 (0.5); 1.5493 (0.6); 1.3738 (0.7); 1.3611 (0.6); 1.3526 (0.7); 1.3364 (0.7); 1.3137 (0.6); 1.2976 (3.0); 1.2584 (4.5); 1.2492 (1.9); 1.2336 (4.7); 1.1866 (0.7); 1.1670 (0.7); 1.1470 (0.5); 0.8837 (0.6); 0.8665 (1.0); 0.8532 (1.2); 0.8343 (0.9); 0.7968 (0.5); 0.0080 (3.9); −0.0001 (140.0); −0.0082 (6.0); −0.1495 (0.7) |
| 636 | 1.89 | | 636: $^1$H-NMR (400.0 MHz, $d_6$-DMSO): δ = 8.9971 (1.4); 8.9919 (1.4); 8.9766 (1.4); 8.9719 (1.4); 8.5599 (0.3); 8.5003 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.6); 8.4458 (2.8); 8.4226 (3.0); 8.3554 (7.4); 8.3047 (0.3); 8.0757 (1.1); 8.0706 (0.5); 8.0539 (12); 7.9316 (0.8); 7.9195 (1.1); 7.9128 (1.1); 7.9002 (0.8); 7.6950 (3.1); 7.6724 (3.0); 7.6539 (0.6); 7.6428 (0.5); 7.6285 (0.9); 7.6152 (0.9); 7.6017 (0.9); 7.5872 (0.4); 7.5792 (0.4); 7.4949 (0.8); 7.4737 (0.7); 7.3020 (1.7); 7.2826 (1.7); 7.1716 (1.2); 7.1510 (2.4); 7.1329 (1.9); 7.1156 (0.9); 7.0876 (0.6); 6.9221 (0.3); 6.9074 (1.5); 6.8887 (2.4); 6.8702 (1.2); 6.7886 (3.0); 6.7683 (2.6); 5.7565 (1.4); 5.2367 (0.7); 5.2226 (1.4); 5.2034 (1.3); 5.1877 (0.6); 4.2500 (2.2); 4.2386 (3.3); 4.2272 (2.0); 3.3214 (36.9); 3.0794 (2.4); 3.0597 (4.7); 3.0529 (5.6); 3.0474 (5.6); 3.0406 (4.9); 3.0261 (0.9); 2.6705 (0.8); 2.6665 (0.6); 2.5422 (0.5); 2.5379 (0.5); 2.5324 (0.4); 2.5238 (1.9); 2.5102 (57.4); 2.5061 (114.6); 2.5017 (149.9); 2.4973 (108.3); 2.3331 (0.6); 2.3287 (0.8); 2.3240 (0.7); 2.1869 (0.4); 2.1731 (0.8); 2.1589 (0.9); 2.1531 (0.7); 2.1394 (0.9); 2.1240 (0.9); 2.1119 (0.4); 2.0419 (0.4); 2.0252 (0.8); 2.0171 (0.9); 2.0075 (0.9); 1.9889 (0.9); 1.9713 (0.5); 1.3979 (16.0); 1.2984 (0.6); 1.2590 (0.9); 1.2353 (1.0); 1.1749 (0.4); 0.8534 (0.4); 0.1464 (0.6); 0.0362 (0.5); 0.0081 (6.1); 0.0000 (147.3); −0.0077 (6.7); −0.0332 (0.4); −0.1494 (0.7) |
| 637 | | | 637 (Atopisomer 1): $^1$H-NMR (400.0 MHz, $d_6$-DMSO): δ = 8.9812 (3.0); 8.9606 (3.1); 8.5585 (2.1); 8.5432 (2.2); 8.5347 (2.2); 8.5195 (2.0); 8.4472 (1.0); 8.3740 (10.8); 7.8585 (1.3); 7.8460 (2.4); 7.8330 (1.3); 7.7210 (3.3); 7.7173 (3.5); 7.7009 (4.0); 7.6972 (4.0); 7.5268 (2.4); 7.5043 (4.0); 7.4818 (2.7); 7.4707 (3.7); 7.4513 (6.4); 7.4315 (3.6); 7.3 428 (4.1); 7.3391 (4.3); 7.3237 (3.3); 7.3200 (3.0); 7.2841 (2.8); 7.2656 (3.1); 7.1683 (1.4); 7.1645 (1.4); 7.1474 (2.9); 7.1298 (1.8); 7.1259 (1.7); 6.9122 (0.3); 6.9043 (2.1); 6.9019 (2.2); 6.8834 (3.6); 6.8671 (1.7); 6.8646 (1.7); 6.7869 (4.0); 6.7664 (3.6); 6.5264 (1.2); 5.7564 (10.6); 5.2486 (1.0); 5.2332 (1.9); 5.2138 (1.8); 5.1993 (0.8); 4.2563 (3.3); 4.2421 (5.3); 4.2296 (3.1); 4.0381 (0.5); 4.0202 (0.5); 3.5676 (1.2); 3.5530 (1.0); 3.5354 (3.3); 3.5218 (3.7); 3.5179 (3.7); 3.5043 (3.3); 3.4865 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.0); 3.3244 (162.6); 2.6748 (0.7); 2.6705 (1.0); 2.6659 (0.7); 2.5238 (2.2); 2.5189 (3.5); 2.5103 (62.0); 2.5059 (130.8); 2.5015 (175.3); 2.4970 (125.4); 2.4927 (59.8); 2.3326 (0.7); 2.3281 (1.0); 2.3240 (0.7); 2.1843 (0.4); 2.1710 (0.9); 2.1540 (0.9); 2.1492 (1.0); 2.1351 (1.7); 2.1215 (1.5); 2.1070 (0.5); 2.0365 (0.6); 2.0236 (1.4); 2.0079 (1.5); 1.9886 (3.0); 1.9756 (0.8); 1.9606 (0.4); 1.3973 (1.0); 1.2982 (0.6); 1.2779 (7.4); 1.2600 (16.0); 1.2422 (7.8); 1.2362 (2.8); 1.1924 (0.7); 1.1745 (1.4); 1.1568 (0.7); 1.1179 (0.4); 0.1460 (0.7); 0.0079 (5.2); −0.0002 (164.7); −0.0085 (6.1); −0.1496 (0.8) |
| 637 | 2.00 | | 637 (Atopisomer 2): $^1$H-NMR (400.0 MHz, $d_6$-DMSO): δ = 8.9813 (3.2); 8.9607 (3.1); 8.5586 (2.0); 8.5432 (2.5); 8.5346 (2.2); 8.5195 (2.0); 8.4528 (0.5); 8.4472 (1.0); 8.3793 (4.0); 8.3740 (10.1); 7.8910 (0.4); 7.8462 (2.8); 7.8341 (1.5); 7.7210 (3.6); 7.7173 (3.4); 7.7009 (4.4); 7.6971 (3.8); 7.5269 (2.3); 7.5044 (4.0); 7.4817 (2.8); 7.4763 (1.8); 7.4707 (3.8); 7.4564 (2.4); 7.4512 (6.1); 7.4370 (1.4); 7.4315 (3.4); 7.3722 (0.4); 7.3429 (4.6); 7.3392 (4.1); 7.3238 (3.5); 7.3201 (2.9); 7.2866 (3.1); 7.2675 (3.4); 7.1684 (1.7); 7.1647 (1.5); 7.1491 (3.3); 7.1299 (2.1); 7.1260 (1.7); 6.9045 (2.3); 6.9017 (2.3); 6.8858 (3.8); 6.8672 (1.8); 6.8647 (1.6); 6.7871 (4.2); 6.7666 (3.8); 6.5259 (1.0); 5.7618 (3.4); 5.7564 (9.6); 5.2477 (1.1); 5.2335 (2.3); 5.2150 (2.0); 5.1991 (0.8); 4.2561 (4.1); 4.2423 (5.9); 4.2302 (3.3); 4.0378 (0.5); 4.0201 (0.5); 3.5734 (0.5); 3.5677 (1.2); 3.5530 (1.3); 3.5355 (3.7); 3.5222 (4.6); 3.5181 (4.1); 3.5044 (3.6); 3.4867 (1.0); 3.3292 (56.4); 3.3241 (147.2); 2.6749 (1.0); 2.6704 (1.0); 2.5100 (97.7); 2.5060 (162.3); 2.5014 (184.8); 2.4969 (125.4); 2.3326 (0.9); 2.32 82 (1.0); 2.1711 (1.0); 2.1543 (1.2); 2.1482 (1.2); 2.1349 (1.8); 2.1213 (1.6); 2.1069 (0.6); 2.0234 (1.7); 2.0079 (1.8); 1.9942 (1.9); 1.9885 (3.2); 1.9758 (1.0); 1.3973 (1.0); 1.2984 (0.7); 1.2778 (7.7); 1.2650 (7.0); 1.2599 (16.0); 1.2421 (8.2); 1.1924 (0.8); 1.1803 (0.7); 1.1746 (1.4); 1.1624 (0.5); 1.1566 (0.8); 1.1175 (0.4); 0.8531 (0.3); 0.1461 (0.7); 0.0054 (57.5); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | −0.0002 (161.4); −0.0084 (7.7); −0.1496 (0.7) |
| 638 | 2.23 | | 638: $^1$H-NMR (400.0 MHz, $d_6$-DMSO): δ = 9.0008 (3.2); 8.9802 (3.2); 8.5200 (2.1); 8.5049 (2.3); 8.4962 (2.3); 8.4812 (2.3); 8.4700 (11.1); 7.9621 (1.4); 7.9491 (2.6); 7.9360 (1.4); 7.656 9 (3.9); 7.6521 (7.7); 7.6473 (4.4); 7.5206 (2.6); 7.4975 (4.7); 7.4688 (12.2); 7.4645 (11.6); 7.2968 (3.0); 7.2782 (32); 7.1784 (1.5); 7.1750 (1.5); 7.1575 (3.0); 7.1400 (1.9); 7.1363 (1.8); 6.9153 (2.2); 6.8968 (3.8); 6.8803 (1.8); 6.8780 (1.8); 6.7978 (4.2); 6.7776 (3.9); 5.7568 (14.4); 5.2612 (0.8); 5.2462 (1.9); 5.2271 (1.9); 52124 (0.8); 4.2879 (0.4); 4.2684 (2.9); 4.2535 (5.0); 4.2416 (3.2); 4.2248 (0.4); 4.0559 (0.5); 4.0381 (1.4); 4.0204 (1.4); 4.0025 (0.5); 3.5657 (1.0); 3.5479 (3.4); 3.5341 (3.8); 3.5305 (3.9); 3.5167 (3.4); 3.4992 (1.0); 3.3244 (45.5); 2.6751 (0.3); 2.6708 (0.4); 2.6664 (0.3); 2.5240 (1.0); 2.5062 (58.1); 2.5018 (77.3); 2.4974 (55.4); 2.4933 (26.6); 2.3284 (0.4); 2.3242 (0.3); 2.1917 (0.4); 2.1800 (0.8); 2.1675 (0.8); 2.1582 (1.0); 2.1439 (1.7); 2.1299 (1.4); |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 2.1160 (0.6); 2.0571 (0.6); 2.0444 (1.4); 2.0300 (1.4); 2.0168 (0.9); 2.0079 (1.0); 1.9976 (0.8); 1.9889 (6.3); 1.3966 (2.5); 1.2716 (7.6); 1.2537 (16.0); 1.2359 (7.6); 1.1928 (1.6); 1.1750 (3.2); 1.1572 (1.6); 1.1006 (0.4); 0.1459 (0.4); 0.0078 (2.9); −0.0002 (85.1); −0.0085 (3.2); −0.1498 (0.4) |
| 639 | 2.03 | | 639: $^1$H-NMR (400.0 MHz, $d_6$-DMSO): δ = 9.0037 (3.5); 8.9833 (3.6); 8.5928 (2.3); 8.5776 (2.5); 8.5692 (2.5); 8.5540 (2.3); 8.4447 (8.2); 7.9683 (0.9); 7.9555 (1.6); 7.9411 (1.6); 7.9269 (1.7); 7.9141 (0.9); 7.6638 (0.8); 7.6566 (0.8); 7.6367 (1.6); 7.6280 (1.5); 7.6154 (1.5); 7.6000 (0.8); 7.5928 (0.6); 7.5575 (2.4); 7.5348 (4.5); 7.5123 (2.4); 7.2980 (3.6); 7.2784 (4.0); 7.2281 (1.0); 7.2073 (1.8); 7.1856 (1.1); 7.1760 (2.3); 7.1556 (3.8); 7.1373 (2.3); 6.9128 (2.6); 6.8941 (4.4); 6.8755 (2.1); 6.7945 (5.2); 6.7742 (4.7); 5.7562 (7.5); 5.2574 (1.0); 5.2421 (2.3); 5.2232 (2.3); 5.2089 (1.0); 4.2637 (3.6); 4.2504 (6.3); 4.2383 (3.7); 4.0560 (0.4); 4.0382 (12); 4.0202 (1.2); 4.0029 (0.4); 3.5615 (0.9); 3.5447 (2.8); 3.5317 (4.0); 3.5142 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.9); 3.3254 (108.5); 2.6706 (0.7); 2.5017 (124.2); 2.3283 (0.7); 2.1918 (0.5); 2.1788 (1.1); 2.1587 (1.2); 2.1432 (2.0); 2.1298 (1.7); 2.1157 (0.7); 2.0354 (1.5); 2.0224 (1.6); 2 0015 (1.1); 1.9 887 (6.0); 1.3972 (0.8); 1.2987 (0.3); 1.2755 (7.7); 1.2577 (16.0); 1.2399 (8.0); 1.1925 (1.4); 1.1748 (2.8); 1.1570 (1.4); 1.1112 (0.4); 0.1461 (0.5); −0.0003 (106.4); −0.1497 (0.5) |
| 640 | 2.48 | | 640: $^1$H-NMR (400.0 MHz, $d_6$-DMSO): δ = 9.0190 (2.7); 8.9986 (2.8); 8.5860 (1.9); 8.5708 (1.8); 8.5624 (1.9); 8.5471 (1.6); 8.4880 (8.4); 8.4794 (1.3); 8.4515 (0.7); 8.4433 (0.4); 8.2878 (0.5); 8.2279 (2.1); 8.0387 (1.2); 8.0254 (2.1); 8.0125 (1.1); 7.7914 (0.8); 7.6916 (16.0); 7.5748 (0.5); 7.5631 (1.8); 7.5519 (0.4); 7.5398 (3.4); 7.5166 (1.7); 7.2969 (2.4); 7.2786 (2.7); 7.1814 (1.1); 7.1778 (1.2); 7.1606 (2.5); 7.1428 (1.6); 6.9190 (1.7); 6.9002 (3.0); 6.8820 (1.5); 6.7996 (3.4); 6.7792 (3.1); 5.7563 (6.7); 5.2566 (0.7); 5.2422 (1.7); 5.2228 (1.7); 5.2079 (0.8); 4.2673 (2.5); 4.2530 (4.4); 4.2411 (2.9); 4.0382 (0.5); 4.0200 (0.5); 3.5675 (1.1); 3.5501 (2.9); 3.5331 (3.2); 3.5189 (2.7); 3.5015 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.8); 3.3250 (141.3); 2.6708 (0.8); 2.5059 (106.3); 2.5018 (136.0); 2.4976 (97.9); 2.3285 (0.7); 2.1793 (0.7); 2.1585 (0.9); 2.1438 (1.4); 2.1299 (12); 2.1166 (0.5); 2.0576 (0.5); 2.0442 (12); 2.0302 (1.3); 2.0171 (0.8); 2.0082 (0.9); 1.9888 (2.3); 1.3974 (1.0); 1.2982 (0.3); 12718 (5.9); 1.2620 (2.4); 1.2539 (12.0); 12362 (6.0); 1.1928 (0.6); 1.1750 (1.1); 1.1571 (0.6); −0.1461 (0.6); 0.0073 (4.4); −0.0001 (110.9); −0.0082 (4.5); −0.1496 (0.6) |
| 641 | 1.92 | | 641: $^1$H-NMR (400.0 MHz, $d_6$-DMSO): δ = 9.0727 (0.5); 9.0637 (0.6); 9.0525 (0.6); 8.4190 (0.8); 8.4096 (1.8); 8.4004 (2.2); 7.7346 (0.4); 7.6795 (1.2); 7.6757 (1.2); 7.6593 (1.2); 7.6558 (1.2); 7.5940 (0.5); 7.5815 (2.6); 7.5618 (1.4); 7.5440 (0.4); 7.4389 (0.5); 7.4315 (0.5); 7.4194 (0.9); 7.4111 (0.8); 7.4002 (0.5); 7.3915 (0.5); 7.3174 (0.7); 7.3021 (1.5); 7.2863 (1.2); 7.1704 (0.5); 7.1530 (1.0); 7.1323 (0.6); 6.9077 (0.7); 6.8882 (1.2); 6.8702 (0.6); 6.7922 (1.4); 6.7715 (1.2); 5.2376 (0.6); 5.2210 (0.6); 4.2559 (2.4); 4.2484 (2.3); 3.7210 (1.1); 3.7090 (0.9); 3.3195 (59.6); 2.6702 (1.5); 2.5231 (3.5); 2.5054 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (198.0); 2.5011 (259.6); 2.4968 (186.2); 2.3320 (1.1); 2.3277 (1.5); 2.1827 (0.3); 2.1601 (0.4); 2.1464 (0.6); 2.1325 (0.5); 2.0385 (0.4); 2.0240 (0.5); 1.9970 (11.1); 1.9022 (1.6); 1.3977 (16.0); 0.1461 (1.0); 0.0077 (7.6); −0.0002 (219.7); −0.0081 (8.5); −0.1498 (1.1) |
| 644 | 2.03 | | 644: $^1$H-NMR (400.0 MHz, $d_6$-DMSO): δ = 9.1762 (2.1); 9.1562 (2.2); 8.6798 (7.4); 7.9799 (1.3); 7.9643 (1.5); 7.9565 (1.5); 7.9407 (1.4); 7.6877 (2.4); 7.6832 (4.5); 7.6479 (3.0); 7.5660 (1.5); 7.5426 (2.8); 7.5196 (1.4); 7.4951 (8.0); 7.4914 (7.9); 7.3265 (2.0); 7.3076 (2.2); 7.1882 (1.1); 7.1662 (4.4); 7.1530 (1.6); 6.9288 (1.5); 6.9104 (2.5); 6.8919 (1.2); 6.8417 (3.1); 6.8047 (2.9); 6.7842 (2.6); 5.2372 (0.6); 5.2226 (1.3); 5.2037 (1.3); 5.1892 (0.6); 4.3111 (2.0); 4.2962 (4.0); 4.2811 (2.3); 4.2538 (1.2); 4.2359 (1.7); 4.2269 (1.8); 4.2119 (1.1); 4.2052 (1.3); 4.1841 (0.4); 4.0378 (0.5); 4.0200 (0.6); 3.5379 (2.0); 3.5229 (3.8); 3.5078 (1.9); 3.3232 (6.1); 3.0749 (16.0); 2.8662 (2.9); 2.6705 (0.7); 2.5480 (0.8); 2.5053 (97.3); 2.5014 (124.4); 2.3284 (0.7); 2.2069 (0.4); |
| | | | 2.1981 (0.6); 2.1838 (0.8); 2.1745 (0.8); 2.1629 (0.8); 2.1517 (0.6); 2.0745 (3.5); 2.0303 (0.9); 2.0162 (0.7); 2.0025 (0.6); 1.9887 (2.6); 1.2341 (0.9); 1.1924 (0.6); 1.1746 (1.2); 1.1568 (0.6); −0.0001 (61.3) |
| 647 | 3.90 | | 647: $^1$H-NMR (400.0 MHz, $d_6$-DMSO): δ = 9.2469 (1.6); 9.2267 (1.7); 8.7138 (6.9); 8.4548 (3.2); 8.3695 (1.3); 8.3539 (1.4); 8.3458 (1.4); 8.3303 (1.3); 7.7363 (2.2); 7.7312 (2.4); 7.6970 (2.2); 7.6921 (4.6); 7.6877 (3.4); 7.6656 (2.6); 7.6424 (1.4); 7.6381 (0.9); 7.6330 (1.2); 7.6280 (0.6); 7.5214 (6.3); 7.5172 (6.1); 7.3823 (1.5); 7.3649 (1.6); 7.1937 (0.8); 7.1902 (0.8); 7.1726 (1.6); 7.1552 (1.0); 7.1517 (1.0); 6.9391 (1.1); 6.9366 (1.2); 6.9180 (2.0); 6.9019 (1.0); 6.8993 (1.0); 6.8088 (2 2); 6.8068 (2.2); 6.7884 (2.0); 6.7863 (2.0); 5.7561 (12.1); 5.2495 (0.4); 5.2362 (1.0); 5.2167 (1.0); 5.2022 (0.5); 4.2875 (0.3); 4.2695 (0.9); 4.2546 (1.8); 4.2458 (1.6); 4.2339 (0.9); 4.2262 (1.0); 4.2061 (0.3); 4.0558 (0.6); 4.0380 (1.7); 4.0202 (1.7); 4 0024 (0.6); 3.7243 (0.9); 3.7057 (2.6); 3.6886 (2.0); 3.6540 (0.4); 3.6195 (1.1); 3.6034 (2.2); 3.5864 (1.6); 3.5681 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.8); 3.5517 (0.4); 3.3229 (30.8); 3.0469 (13.3); 3.0228 (0.8); 2.9728 (16.0); 2.9526 (0.6); 2.6705 (0.4); 2.5240 (0.9); 2.5104 (24.8); 2.5061 (52.1); 2.5016 (69.8); 2.4971 (49.8); 2.4928 (23.6); 2.3283 (0.4); 2.2263 (0.3); 2.2177 (0.4); 2.2054 (0.6); 2.1949 (0.6); 2.1835 (0.7); 2.1718 (0.5); 2.0912 (0.5); 2.0835 (0.6); 2.0764 (0.8); 2.0614 (0.5); 2.0499 (0.5); 2.0418 (0.5); 1.9888 (7.6); 1.1927 (2.0); 1.1749 (4.0); 1.1571 (1.9); 0.0079 (0.6); −0.0002 (19.9); −0.0085 (0.7) |
| 648 | 2.06 | | 648: $^1$H-NMR (400.0 MHz, $d_6$-DMSO): δ = 9.0572 (2.9); 9.0367 (2.9); 8.4493 (10.6); 8.1700 (2.0); 8.1550 (2.1); 8.1463 (2.1); 8.1314 (2.0); 7.7358 (0.7); 7.7309 (0.8); 7.6651 (3.6); 7.6604 (7.0); 7.6556 (4.0); 7.6378 (0.4); 7.6329 (0.5); 7.4698 (11.0); 7.4663 (10.8); 7.4519 (2.4); 7.4287 (4.1); 7.4056 (2.1); 7.3170 (2.8); 7.2990 (3.1); 7.1870 (1.4); 7.1840 (1.4); 7.1665 (2.9); 7.1487 (1.8); 7.1452 (1.7); 6.9224 (2.0); 6.9044 (3.5); 6.8874 (1.7); 6.8060 (4.0); 6.7857 (3.6); 5.7560 (16.0); 5.5709 (0.8); 5.5640 (1.0); 5.5582 (0.9); 5.4176 (1.0); 5.2110 (0.8); 5.1968 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.8); 5.1775 (1.8); 5.1628 (0.8); 4.7415 (0.4); 4.7258 (0.5); 4.7120 (0.9); 4.6976 (0.9); 4.6840 (0.9); 4.6565 (3.0); 4.6425 (1.9); 4.6234 (1.6); 4.6147 (1.7); 4.5979 (2.4); 4.5899 (2.1); 4.5582 (1.4); 4.5287 (0.6); 4.2661 (3.1); 4.2539 (5.1); 4.2399 (3.1); 4.0569 (0.6); 4.0380 (1.8); 4.0202 (1.8); 4.0026 (0.6); 3.3241 (88.4); 3.0496 (0.4); 2.6708 (0.7); 2.5060 (93.6); 2.5017 (121.8); 2.4974 (88.1); 2.3287 (0.7); 2.2024 (0.4); 2.1879 (1.0); 2.1736 (1.1); 2.1537 (1.3); 2.1387 (1.3); 2.1252 (0.5); 2.0539 (0.6); 2.0402 (1.2); 2.0284 (1.4); 2.0149 (0.9); 2.0067 (1.0); 1.9888 (8.4); 1.3973 (2.6); 1.1928 (2.1); 1.1750 (4.1); 1.1572 (2.0); 0.0080 (1.0); −0.0001 (30.3) |
| 649 | 3.76 | | 649: $^1$H-NMR (400.0 MHz, $d_6$-DMSO): δ = 9.3085 (1.9); 9.2880 (2.0); 8.6476 (8.2); 8.3888 (1.4); 8.3732 (1.6); 8.3651 (1.6); 8.3496 (1.5); 8.1547 (0.5); 7.6899 (2.7); 7.6851 (5.2); 7.6803 (2.9); 7.6387 (1.6); 7.6155 (3.1); 7.5923 (1.6); 7.5128 (7.7); 7.5088 (7.6); 7.3587 (2.0); 7.3408 (2.1); 7.1945 (0.9); 7.1910 (1.0); 7.1736 (2.0); 7.1559 (1.2); 7.1525 (1.2); 6.9340 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.5); 6.9157 (2.4); 6.8992 (1.2); 6.8968 (1.2); 6.8099 (2.7); 6.7897 (2.5); 5.2926 (0.5); 5.2790 (1.2); 5.2593 (1.2); 5.2449 (0 6); 5.1397 (1.0); 5.1247 (2.2); 5.1092 (1.0); 4.3009 (0.4); 4.2935 (0.4); 4.2812 (1.1); 4.2719 (1.1); 4.2537 (1.6); 4.2400 (1.0); 4.2326 (1.2); 4.2124 (0.4); 4.2051 (0.3); 4.0377 (0.8); 4.0200 (0.8); 3.6455 (0.8); 3.6328 (2.3); 3.6195 (2.5); 3.6063 (12); 3.5285 (2.3); 3.5160 (3.1); 3.5041 (1.4); 3.3211 (12.7); 3.0487 (16.0); 2.6747 (0.4); 2.6700 (0.6); 2.6660 (0.4); 2.5234 (1.3); 2.5097 (37.4); 2.5056 (78.3); 2.5011 (104.9); 2.4967 (76.0); 2.3324 (0.4); 2.3278 (0.6); 2.3234 (0.5); 2.2371 (0.4); 2.2287 (0.5); 22165 (0.8); 2.2074 (0.8); 2.1953 (0.8); 2.1839 (0.6); 2.1748 (0.4); 2.0742 (9.8); 2.0583 (0.7); 2.0518 (0.7); 20411 (0.6); 20328 (0.6); 1.9885 (3.7); 1.1924 (1.0); 1.1746 (1.9); 1.1568 (0, 9); 0.0079 (0.6); −0.0003 (20.1); −0.0085 (0.8) |
| 650 | 4.51 | | 650: $^1$H-NMR (400.0 MHz, $d_6$-DMSO): δ = 9.1837 (1.2); 9.1634 (1.3); 8.6809 (4.8); 8.2435 (0.9); 8.2277 (1.0); 8.2197 (1.0); 8.2043 (1.0); 7.6933 (1.4); 7.6887 (2.8); 7.6837 (2.0); 7.6575 (1.9); 7.6343 (0.9); 7.5177 (4.8); 7.5133 (4.7); 7.3620 (1.2); 7.3438 (1.3); 7.1910 (0.6); 7.1874 (0.6); 7.1697 (12); 7.1524 (0.8); 7.1492 (0.7); 6.9344 (0.9); 6.9161 (1.5); 6.8981 (0.7); 6.8052 (1.7); 6.7851 (1.5); 5.7556 (7.6); 5.2537 (0.3); 5.2391 (0.8); 5.2201 (0.8); 5.2061 (0.3); 4.2758 (0.7); 4.2596 (1.2); 4.2506 (1.2); 4.2386 (0.7); 4.2304 (0.8); 3.5520 (1.3); 3.5365 (16.0); 3.5178 (1.3); 3.3250 (452); 3.0097 (10.2); 2.7359 (1.0); 2.7216 (1.8); 2.7177 (1.9); 2.7048 (0.9); 2.7002 (0.9); 2.5236 (0.6); 2.5059 (34.1); 2.5017 (45.7); 2.4974 (33.7); 2.2010 (0.5); 2.1907 (0.5); 2.1792 (0.5); 2.1683 (0.4); 2.0735 (0.3); 2.0661 (0.4); 2.0583 (0.5); 2.0435 (0.4); 2.0318 (0.4); 2.0234 (0.4); 0.0074 (0.6); −0.0002 (16.6); −0.0080 (0.7) |
| 661 | 3.48 | | 661: $^1$H-NMR (400.0 MHz, $d_6$-DMSO): δ = 9.2660 (1.8); 9.2458 (1.8); 8.7364 (6.3); 8.4266 (1.2); 8.4110 (1.3); 8.4029 (1.3); 8.3875 (1.3); 7.7469 (11.3); 7.7294 (1.3); 7.7061 (2.5); 7.6829 (1.3); 7.3840 (1.6); 7.3651 (1.8); 7.1922 (0.8); 7.1746 (1.7); 7.1566 (1.0); 7.1535 (1.0); 6.9384 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.2); 6.9200 (2.1); 6.9014 (1.0); 6.8085 (2.4); 6.7883 (2.1); 5.2480 l (0.5); 5.2343 (1.0); 5.2148 (1.1); 5.2011 (0.5); 4.2879 (0.3); 4.2693 (0.9); 4.2543 (1.8); 4.2453 (1.7); 4.2331 (0.9); 4.2256 (1.1); 4 2045 (0.3); 3.7270 (1.0); 3.7089 (2.8); 3.6921 (2.1); 3.6562 (0.3); 3.6219 (1.1); 3.6061 (2.4); 3.5891 (1.7); 3.5707 (0.8); 3.3195 (31.5); 3.0513 (13.4); 2.9714 (16.0); 2.6701 (0.4); 2.5050 (45.4); 2.5008 (60.1); 2.4965 (44.9); 2.3276 (0.4); 2.2270 (0.4); 2.2193 (0.4); 2.2055 (0.6); 2.1953 (0.7); 2.1842 (0.7); 2.1722 (0.5); 2.0920 (0.5); 2.0848 (0.7); 2.0775 (0.8); 2.0634 (0.6); 2.0509 (0.5); 2.0426 (0.5); 0.0077 (2.0); −0.0002 (58.4); −0.0083 (3.0) |
| 666 | 4.19 | | 666: $^1$H-NMR (400.0 MHz, $d_6$-DMSO): δ = 9.1886 (0.4); 9.1756 (2.0); 9.1551 (2.1); 8.8415 (0.9); 8.6572 (7.6); 8.3810 (1.4); 8.3654 (1.5); 8.3574 (1.6); 8.3419 (1.4); 8.1800 (1.9); 7.7145 (0.7); 7.7106 (0.7); 7.7059 (0.4); 7.6898 (2.4); 7.6854 (4.3); 7.6809 (2.5); 7.6365 (1.6); 7.6133 (3.0); 7.5902 (1.5); 7.5413 (1.0); 7.5373 (0.9); 7.5138 (7.7); 7.5099 (7.4); 7.4093 (1.7); 7.3948 (1.9); 7.3893 (1.9); 7.2887 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.0); 7.2836 (1.3); 7.2686 (2.6); 7.2587 (1.1); 7.2540 (1.1); 7.2404 (2.9); 7.2351 (3.5); 7.2262 (3.2); 7.2177 (2.7); 7.1992 (0.5); 5.7554 (11.4); 5.5865 (0.6); 5.5671 (1.7); 5.5474 (1.8); 5.5277 (0.6); 5.1663 (0.3); 4.4586 (0.6); 4.4451 (0.3); 3.6266 (3.1); 3.6152 (2.4); 3.5424 (2.7); 3.5304 (3.5); 3.3506 (1.4); 3.2177 (0.4); 3.0483 (16.0); 3.0232 (0.8); 3.0095 (0.7); 2.9999 (0.8); 2.9917 (1.0); 2.9833 (1.0); 2.9700 (1.0); 2.9614 (0.9); 2.9068 (0.8); 2.8863 (1.6); 2.8662 (1.3); 2.8468 (0.9); 2.8263 (0.5); 2.6707 (0.3); 2.569 4 (0.4); 2.5600 (0.5); 2.5497 (0.8); 2.5390 (1.1); 2.5290 (1.2); 2.5059 (41.4); 2.5017 (53.0); 2.4974 (39.4); 2.3925 (2.1); 2.3288 (0.3); 1.9889 (1.1); 1.9703 (1.1); 1.9596 (0.6); 1.9500 (1.1); 1.9391 (1.1); 1.9293 (0.5); 1.9188 (0.9); 1.8974 (0.3); 1.2324 (0.6); 1.1749 (0.4); −0.0001 (16.4) |
| 667 | 2.20 | | 667: $^1$H-NMR (400.0 MHz, $d_6$-DMSO): δ = 9.1838 (0.9); 9.1637 (0.9); 8.6672 (3.8); 8.2561 (0.9); 8.2533 (1.0); 8.2348 (1.1); 8.2318 (1.0); 7.8167 (1.1); 7.8136 (1.0); 7.7994 (2.0); 7.7952 (1.8); 7.7744 (1.0); 7.7549 (0.4); 7.7051 (1.0); 7.6860 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.3); 7.6714 (1.0); 7.6531 (1.0); 7.6502 (1.1); 7.6352 (10.7); 7.5676 (0.6); 7.5485 (1.0); 7.5297 (0.4); 5.7451 (0.3); 5.7340 (0.6); 5.7256 (0.6); 5.7149 (0.3); 3.5677 (1.1); 3.3192 (50.0); 3.2454 (0.6); 3.2261 (0.7); 3.1987 (0.8); 3.1793 (0.7); 3.0654 (16.0); 2.6876 (0.8); 2.6787 (1.0); 2.6704 (0.7); 2.6658 (0.5); 2.6408 (0.7); 2.6321 (0.7); 2.5234 (1.7); 2.5056 (81.8); 2.5013 (106.7); 2.4968 (76.8); 2.3320 (0.5); 2.3280 (0.6); 2.3241 (0.4); 1.9883 (1.2); 1.3976 (5.9); 1.1925 (0.3); 1.1747 (0.7); 1.1568 (0.3); 0.1461 (0.4); 0.0078 (3.7); −0.0002 (99.3); −0.0084 (4.0); −0.1496 (0.5) |
| 668 | 3.94 | | 668: $^1$H-NMR (400.0 MHz, $d_6$-DMSO): δ = 9.1048 (0.6); 9.0845 (0.6); 8.5684 (2.2); 8.2951 (0.9); 8.2722 (1.1); 7.7677 (1.1); 7.7447 (1.0); 7.6197 (2.0); 7.3464 (0.6); 7.3272 (0.6); 7.1808 (0.3); 7.1623 (0.6); 7.1415 (0.4); 6.9222 (0.4); 6.9036 (0.8); 6.8863 (0.3); 6.7970 (0.8); 6.7766 (0.7); 5.2280 (0.4); 5.2096 (0.4); 4.2664 (0.4); 4.2398 (0.5); 4.2239 (0.3); 4.2180 (0.4); 3.3213 (197.3); 3.0723 (9.7); 3.0549 (1.1); 2.6700 (1.0); 2.5051 (126.7); 2.5011 (167.6); 2.4969 (130.1); 2.3278 (1.0); 1.3975 (16.0); 0.1457 (0.6); −0.0003 (133.9); −0.1501 (0.7) |
| 669 | 2.67 | | 669: $^1$H-NMR (400.0 MHz, $d_6$-DMSO): δ = 9.0888 (1.0); 9.0685 (1.0); 8.5482 (3.5); 8.2431 (1.6); 8.2203 (1.8); 7.7361 (1.8); 7.7132 (1.7); 7.3437 (1.0); 7.3234 (1.3); 7.2978 (0.9); 7.2924 (0.6); 7.2742 (0.4); 7.1768 (0.5); 7.1503 (1.0); 7.1385 (0.6); 7.0392 (1.0); 7.0204 (1.0); 6.9196 (0.7); 6.9008 (1.2); 6.8822 (0.6); 6.7944 (1.4); 6.7741 (1.2); 5.2331 (0.7); 5.2138 (0.6); 4.2661 (0.6); 4.2491 (0.9); 4.2400 (1.0); 4.2265 (0.6); 4.2192 (0.7); 3.3208 (107.7); 3.0636 (16.0); 2.6703 (0.9); 2.5052 (108.3); 2.5012 (145.2); 2.4972 (117.6); 2.3278 (0.9); 2.1920 (0.4); 2.1823 (0.4); 2.1690 (0.4); 2.0407 (0.4); 2.0341 (0.5); 20229 (0.4); 2.0072 (0.3); 1.3976 (2.0); 0.1458 (0.5); −0.0002 (112.9); −0.1499 (0.5) |
| 670 | 2.84 | | 670: $^1$H-NMR (400.0 MHz, $d_6$-DMSO): δ = 9.0781 (0.7); 9.0580 (0.8); 8.5100 (2.0); 8.1805 (1.6); 8.1576 (1.9); 7.6967 (2.0); 7.6738 (1.8); 7.3393 (0.8); 7.3205 (0.9); 7.2257 (1.6); 7.1779 (0.4); 7.1741 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.4); 7.1563 (0.8); 7.1392 (0.5); 7.1353 (0.5); 7.0548 (0.5); 7.0243 (0.5); 6.9152 (0.7); 6.8967 (1.1); 6.8779 (0.6); 6.8661 (0.5); 6.8407 (0.5); 6.7933 (1.2); 6.7749 (1.1); 5.7551 (0.4); 5.2322 (0.5); 5.2138 (0.5); 4.2667 (0.5); 4.2575 (0.5); 4.2498 (0.6); 4.2380 (0.7); 4.2252 (0.4); 4.2173 (0.6); 3.5677 (5.0); 3.3190 (47.9); 3.0537 (16.0); 2.6747 (0.4); 2.6701 (0.6); 2.6656 (0.4); 2.5235 (1.3); 2.5099 (32.8); 2.5056 (69.2); 2.5011 (93.6); 2.4966 (68.7); 2.4922 (34.2); 2.3633 (0.6); 2.3451 (2.6); 2.3280 (0.8); 2.323S (0.6); 2.1902 (0.4); 2.1802 (0.3); 2.1680 (0.3); 2.0341 (0.4); 1.3975 (0.9); 1.3203 (1.7); 1.2826 (8.0); 0.8894 (0.7); 0.1460 (0.4); 0.0079 (3.1); −0.0002 (94.5); −0.0084 (4.2); −0.1497 (0.4) |
| 671 | 3.00 | | 671: $^{1}$H-NMR (400.0 MHz, $d_6$-DMSO): δ = 9.0854 (0.5); 9.0650 (0.5); 8.6944 (0.6); 8.5236 (3.9); 8.2521 (1.7); 8.2292 (1.8); 7.7986 (0.6); 7.7790 (1.0); 7.7534 (1.9); 7.7395 (0.5); 7.7304 (2.0); 7.7225 (1.0); 7.7009 (0.6); 7.6084 (0.8); 7.3380 (0.8); 7.3199 (0.9); 7.1766 (0.5); 7.1728 (0.4); 7.1553 (0.9); 7.1381 (0.5); 7.1340 (0.5); 6.9150 (0.6); 6.8944 (1.0); 6.8759 (0.5); 6.7934 (1.3); 6.7728 (1.1); 5.7556 (0.5); 5.2278 (0.6); 5.2078 (0.6); 4.2631 (0.6); 4.2545 (0.6); 4.2459 (0.7); 4.2376 (0.8); 4.2136 (0.5); 3.3202 (122.1); 3.0699 (16.0); 3.0549 (2.9); 2.6746 (0.7); 2.6700 (0.9); 2.6656 (0.7); 2.5233 (2.3); 2.5098 (55.6); 2.5055 (115.1); 2.5011 (154.0); 2.4966 (112.5); 2.4923 (56.1); 2.3322 (0.6); 2.3278 (0.9); 2.3234 (0.7); 2.1869 (0.4); 2.1780 (0.4); 2.1659 (0.4); 2.0309 (0.4); 0.8892 (0.7); 0.1457 (0.7); 0.0077 (4.8); −0.0002 (143.2); −0 0084 (6.6); −0.1498 (0.7) |
| 672 | 2.20 | | 672: $^{1}$H-NMR (400.0 MHz, $d_6$-DMSO): δ = 9.0722 (0.4); 9.0608 (0.9); 9.0405 (0.9); 8.5074 (3.8); 8.1786 (1.6); 8.1557 (1.9); 7.6922 (1.9); 7.6693 (1.8); 7.3389 (0.8); 7.3198 (0.9); 7.1783 (0.4); 7.1747 (0.4); 7.1572 (0.8); 7.1400 (0.5); 7.1359 (0.5); 7.0250 (1.5); 6.9161 (0.6); 6.8975 (1.1); 6.8814 (0.5); 6.8787 (0.5); 6.8394 (1.0); 6.8085 (1.0); 6.7953 (1.3); 6.7748 (1.1); 6.3561 (0.3); 5.2342 (0.5); 5.2146 (0.5); 4.2667 (0.5); 4.2568 (0.5); 4.2498 (0.7); 4.2396 (0.8); 4.2261 (0.5); 4.2188 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.6); 3.3229 (33.8); 3.0542 (16.0); 2.5234 (0.5); 2.5097 (11.7); 2.5056 (24.2); 2.5011 (32.4); 2.4966 (23.8); 2.4923 (11.9); 2.3130 (4.7); 2.3061 (4.8); 2.1910 (0.3); 2.1813 (0.4); 2.1686 (0.4); 2.1573 (1.8); 2.0410 (0.3); 2.0334 (0.4); 1.2344 (0.4); 0.0079 (1.1); −0.0002 (31.5); −0.0084 (1.4) |
| 673 | 2.73 | | 673: $^1$H-NMR (400.0 MHz, $d_6$-DMSO): δ = 9.0829 (2.0); 9.0626 (2.0); 8.4835 (6.9); 8.4575 (1.2); 8.4426 (1.3); 8.4336 (1.3); 8.4188 (1.2); 7.8687 (0.8); 7.8560 (1.6); 7.8426 (0.8); 7.6931 (16.0); 7.5995 (1.6); 7.5762 (3.1); 7.5529 (2.2); 7.5258 (0.6); 7.5058 (0.5); 7.4980 (0.5); 7.4886 (0.4); 7.4803 (0.5); 7.4548 (3.8); 7.4504 (3.9); 7.2728 (1.8); 7.2546 (1.9); 7.1790 (0.9); 7.1752 (0.9); 7.1581 (1.8); 7.1405 (1.2); 7.1365 (1.1); 6.9004 (1.4); 6.8818 (2.3); 6.8654 (1.0); 6.8631 (1.1); 6.7942 (2.6); 6.7756 (2.3); 6.2176 (2.4); 6.2126 (4.3); 6.2077 (2.5); 5.7555 (10.1); 5.2284 (0.5); 5.2139 (1.2); 5.1949 (1.2); 5.1806 (0.5); 4.4965 (0.6); 4.4922 (0.6); 4.4773 (1.9); 4.4617 (4.2); 4.4463 (2.1); 4.2421 (1.9); 4.2296 (3.2); 4.2156 (2.5); 3.8610 (1.0); 3.8460 (2.6); 3.8316 (2.5); 3.8166 (0.9); 3.3249 (29.4); 2.6705 (0.3); 2.5239 (0.8); 2.5189 (1.2); 2.5103 (18.1); 2.5061 (37.6); 2.5017 (50.5); 2.4972 (37.0); 2.4929 (18.4); 2.1465 (0.6); 2.1327 (0.6); 2.1260 (0.6); 2.1119 (0.9); 2.0972 (0.9); 2.0828 (0.3); 2.0328 (0.4); 2.0199 (0.8); 2.0077 (0.9); 1.9943 (0.6); 1.9858 (0.6); 1.9715 (0.5); 1.3520 (0.8); 1.2586 (0.4); 1.2276 (0.9); 0.0072 (2.0); −0.0002 (60.0); −0.0084 (2.8) |
| 674 | 4.13 | | 674: $^1$H-NMR (400.0 MHz, $d_6$-DMSO): δ = 9.2997 (1.7); 9.2792 (1.7); 8.6010 (6.9); 8.3134 (2.8); 8.2904 (3.1); 7.7458 (3.3); 7.7229 (3.2); 7.6789 (2.2); 7.6743 (4.1); 7.6696 (2.4); 7.6590 (0.4); 7.6355 (0.7); 7.5524 (0.4); 7.3767 (1.8); 7.3464 (1.8); 7.3278 (1.8); 7.1892 (0.9); 7.1856 (0.9); 7.1683 (1.7); 7.1509 (1.1); 7.1473 (1.0); 6.9239 (1.2); 6.9054 (2.1); 6.8889 (1.0); 6.8866 (1.0); 6.8042 (2.4); 6.7835 (2.0); 5.7555 (1.3); 5.2834 (0.5); 5.2687 (1.0); 5.2494 (1.1); 5.2346 (0.6); 5.1224 (1.1); 5.1071 (2.5); 5.0920 (1.1); 4.2941 (0.5); 4.2867 (0.5); 4.2744 (1.1); 4.2654 (1.0); 4.2580 (1.2); 4.2502 (1.4); 4.2432 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

δ1 (intensity1); δ2 (intensity2); . . . ; δi (intensityi); . . . ; δn (intensityn) or δ1 (intensity1), δ2 (intensity2), . . . ; δi (intensityi), . . . . δn (intensityn)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D6 and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.2); 4.2303 (0.9); 4.2227 (1.1); 4.2024 (0.4); 4.1950 (0.3); 3.7342 (0.3); 3.7229 (0.4); 3.7106 (0.4); 3.6435 (0.8); 3.6309 (2.1); 3.6172 (2.4); 3.6039 (1.3); 3.5678 (16.0); 3.5277 (2.0); 3.5149 (2.7); 3.5038 (1.3); 3.3194 (58.5); 3.0752 (0.5); 3.0653 (1.3); 3.0459 (13.7); 2.6748 (0.7); 2.6702 (1.0); 2.6658 (0.7); 2.5097 (63.1); 2.5057 (123.7); 2.5013 (161.6); 2.4968 (118.2); 2.3325 (0.7); 2.3281 (0.9); 2.3237 (0.7); 2.2229 (0.5); 2.2097 (0.7); 2.2002 (0.7); 2.188 2 (0.8); 2.1771 (0.6); 2.1664 (0.4); 2.0605 (0.7); 2.0529 (0.8); 2.0428 (0.6); 2.0365 (0.6); 2.0267 (0.6); 2.0185 (0.6); 1.2586 (0.5); 1.2492 (0.6); 1.2355 (1.6); 0.1461 (0.6); 0.0077 (5.9); 0.0000 (131.3); −0.0081 (7.0); −0.1495 (0.6) |
| 377 | | LC-MS (Method L2): $R_t$ = 2.83 min; m/z = 473 $[M + H]^+$. | $^1$H-NMR (400 MHz, Chloroform-d) δ 8.97 (s, 1H), 8.22 (m, 1H), 8.09 (d, J = 1.1 Hz, 1H), 7.68 (d, J = 6.3 Hz, 1H), 7.60 (m, 1H), 7.29 (d, J = 7.4 Hz, 1H), 7.26-7.16 (m, 2H), 6.96-6.81 (m, 3H), 5.41-5.33 (m, 1H), 4.34 (m, 1H), 4.19 (m, 1H), 3.96 (s, 3H), 3.13 (s, 6H), 2.44-2.33 (m, 1H), 2.25-2.15 (m, 1H). |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 378 | | LC-MS (Method L2): $R_t$ = 2.82 min; m/z = 450 $[M + H]^+$. | $^1$H-NMR (400 MHz, Chloroform-d) δ 8.91 (s, 1H), 8.77 (d, J = 5.0 Hz, 1H), 8.25 (m, 1H), 8.03 (s, 1H), 7.79 (m, 1H), 7.72 (m, 1H), 7.67-7.59 (m, 1H), 7.31 (d, J = 7.3 Hz, 1H), 7.24-7.17 (m, 1H), 7.13 (d, J = 7.5 Hz, 1H), 6.98-6.90 (m, 1H), 6.87 (d, J = 8.2 Hz, 1H), 5.37 (q, J = 5.4 Hz, 1H), 4.35 (m, 1H), 4.21 (m, 1H), 3.15 (s, 6H), 2.46-2.34 (m, 1H), 2.22 (m, 1H). |
| 379 | | LC-MS (Method L2): $R_t$ = 2.08 min; m/z = 440 $[M + H]^+$. | $^1$H-NMR (400 MHz, Chloroform-d) δ 9.01 (s, 1H), 8.15 (t, J = 6.3 Hz, 2H), 7.68 (d, J = 6.3 Hz, 1H), 7.62-7.54 (m, 1H), 7.41 (d, J = 7.3 Hz, 1H), 7.30 (d, J = 7.5 Hz, 1H), 7.21 (t, J = 7.7 Hz, 1H), 6.90 (m, 3H), 6.76 (s, 1H), 5.38 (q, J = 5.4 Hz, 1H), 4.48 (s, 2H), 4.35 (m, 1H), 4.25-4.16 (m, 1H), 3.12 (s, 6H), 2.39 (m, 1H), 2.21 (m, 1H). |
| 380 | | LC-MS (Method L2): $R_t$ = 2.24 min; m/z = 439 | $^1$H-NMR (400 MHz, Chloroform-d) δ 9.00 (s, 1H), 8.58 (d, J = 5.1 Hz, 1H), 8.18 (m, 1H), 7.69 (m, 1H), 7.59 (m, 1H), 7.43-7.28 (m, 4H), 7.24-7.17 (m, 1H), 6.97-6.83 (m, 2H), 5.38 (q, J = 5.4 Hz, 1H), 4.35 (m, 1H), 4.20 (m, 1H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H]$^+$. | 3.13 (s, 6H), 2.63 (s, 3H), 2.45-2.34 (m, 1H), 2.22 (m, 1H). |
| 381 | | LC-MS (Method L2): $R_t$ = 2.26 min; m/z = 439 [M + H]$^+$. | $^1$H-NMR (400 MHz, Chloroform-d) δ 8.92 (s, 1H), 8.52-8.43 (m, 2H), 8.20 (m, 1H), 7.63-7.56 (m, 1H), 7.52 (m, 1H), 7.31 (m, 2H), 7.23-7.17 (m, 1H), 7.14 (d, J = 4.8 Hz, 1H), 6.96-6.82 (m, 2H), 5.37 (q, J = 5.4 Hz, 1H), 4.34 (m, 1H), 4.19 (m, 1H), 3.15 (s, 6H), 2.38 (m 1H), 2.26-2.15 (m, 1H), 2.01 (s, 3H). |
| 382 | | LC-MS (Method L2): $R_t$ = 2.63 min; m/z = 259 [M + H]$^+$. | $^1$H-NMR (400 MHz, Chloroform-d) δ 8.91 (s, 1H), 8.70 (s, 1H), 8.55 (d, J = 4.9 Hz, 1H), 8.28-8.20 (m, 1H), 7.65-7.57 (m, 2H), 7.35-7.27 (m, 2H), 7.24-7.14 (m, 2H), 6.92 (m, 1H), 6.86 (d, J = 8.2 Hz, 1H), 5.41-5.33 (m, 1H), 4.39-4.29 (m, 1H), 4.19 (m, 1H), 3.15 (s, 6H), 2.44-2.33 (m, 1H), 2.20 (m, 1H). |
| 383 | | LC-MS (Method L2): $R_t$ = 2.59 min; m/z = 443 [M + H]$^+$. | $^1$H-NMR (400 MHz, Chloroform-d) δ 8.94 (s, 1H), 8.55 (s, 1H), 8.49 (d, J = 4.8 Hz, 1H), 8.23 (m, 1H), 7.70 (d, J = 6.9 Hz, 1H), 7.61 (m, 1H), 7.45-7.38 (m, 1H), 7.29 (d, J = 7.6 Hz, 1H), 7.25 (d, J = 6.5 Hz, 1H), 7.23-7.16 (m, 1H), 6.92 (m, 1H), 6.86 (d, J = 8.2 Hz, 1H), 5.41-5.32 (m, 1H), 4.34 (m, 1H), 4.19 (m, 1H), 3.14 (s, 6H), 2.44-2.33 (m, 1H), 2.21 (m, 1H). |
| 387 | | LC-MS (Method M14): Rt = 1.40 min; m/z = 469 [M + H]+ | $^1$H-NMR (400 MHz, DMSO-d6): δ [ppm] = 2.05-2.10 (m, 1H), 2.19-2.24 (m, 1H), 2.44 (s, 3H), 3.09 (s, 6H), 4.23-4.30 (m, 2H), 5.26 (q, 1H), 6.81 (d, 1H), 6.94 (t, 1 H), 7.19 (t, 1H), 7.39 (d, 1H), 7.66 (t, 1H), 7.99 (s, 1H), 8.20 (d, 1H), 8.46 (d, 1H), 8.73 (s, 1H), 9.17 (d, 1H). |
| 388 | | LC-MS (Method M24): Rt = 1.27 min; m/z = 458 [M + H]+ | $^1$H-NMR (400 MHz, DMSO-d6): δ [ppm] = 2.04-2.08 (m, 1H), 2.16-2.23 (m, 4H), 2.41 (s, 3H), 3.05 (s, 6H), 4.22-4.30 (m, 2H), 5.26 (q, 1H), 6.72 (s, 1H), 6.80 (s, 1H), 6.94 (t, 1H), 7.17 (t, 1H), 7.36 (d, 1H), 7.58-7.62 (m, 2H), 7.13-7.17 (m, 1H), 8.56 (s, 1H), 9.09 (d, 1H). |
| 389 | | LC-MS (Method M23): Rt = 1.65 min; m/z = 455 [M + H]+ | $^1$H-NMR (400 MHz, DMSO-d6): δ [ppm] = 2.06-2.09 (m, 1H), 2.20-2.22 (m, 1H), 3.10 (s, 6H), 4.25-4.29 (m, 2H), 5.26 (q, 1H), 6.81 (d, 1H), 6.96 (t, 1H), 7.18 (t, 1H), 7.40 (d, 1H), 7.67 (t, 1H), 7.97 (d, 1H), 8.11 (d, 1H), 8.21 (d, 1H), 8.53 (d, 1H), 8.75 (s, 1H), 9.18 (d, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 390 | | LC-MS (Method M23): Rt = 1.67 min; m/z = 464 [M + H]+ | $^1$H-NMR (400 MHz, DMSO-d6): δ [ppm]: = 2.08-2.09 (m, 1H), 2.20-2.23 (m, 1H), 3.07 (s, 6H), 4.25-4.30 (m, 2H), 5.26 (q, 1H), 6.81 (d, 1H), 6.94 (t, 1H), 7.16-7.21 (m, 2H), 7.40 (d, 1H), 7.61 (t, 1H), 7.81 (d, 1H), 8.10 (d, 1H), 8.33 (d, 1H), 8.70 (s, 1H), 9.15 (d, 1H). |
| 391 | | LC-MS (Method M14): Rt = 1.01 min; m/z = 444 [M + H]+ | $^1$H-NMR (400 MHz, DMSO-d6): δ [ppm] = 2.05-2.10 (m, 1H), 2.18-2.24 (m, 1H), 2.49 (s, 3H), 3.05 (s, 6H), 4.25-4.30 (m, 2H), 5.27 (q, 1H), 6.80-6.85 (m, 2H), 6.95 (t, 1H), 7.19 (t, 1H), 7.39 (d, 1H), 7.57 (t, 1H), 7.66 (d, 1H), 8.05 (d, 1H), 8.15 (d, 1H), 8.67 (s, 1H), 9.14 (d, 1H). |
| 399 | | LC-MS (Method L2): $R_t$ = 2.31 min; m/z = 510 [M + H]$^+$. | $^1$H-NMR (400 MHz, Chloroform-d) δ 9.02 (s, 1H), 8.29 (d, J = 5.1 Hz, 1H), 8.16 (d, J = 8.4 Hz, 1H), 7.70 (d, J = 7.0 Hz, 1H), 7.63-7.54 (m, 1H), 7.33 (m, 2H), 7.21 (t, J = 7.7 Hz, 1H), 6.91 (m, 4H), 5.38 (q, J = 5.4 Hz, 1H), 4.40-4.31 (m, 1H), 4.26-4.16 (m, 1H), 3.88-3.79 (m, 4H), 3.59-3.51 (m, 4H), 3.13 (s, 6H), 2.40 (m, 1H), 2.27-2.17 (m, 1H). |
| 400 | | LC-MS (Method L2): $R_t$ = 2.86 min; m/z = 489 [M + H]$^+$. | $^1$H-NMR (400 MHz, Chloroform-d) δ 8.95 (s, 1H), 8.27-8.18 (m, 2H), 7.58 (q, J = 4.5 Hz, 2H), 7.29 (d, J = 7.6 Hz, 1H), 7.20 (t, J = 7.2 Hz, 2H), 6.92 (t, J = 7.5 Hz, 1H), 6.86 (d, J = 8.2 Hz, 1H), 6.78 (s, 1H), 5.37 (q, J = 5.4 Hz, 1H), 4.33 (m, 1H), 4.24-4.13 (m, 1H), 3.96 (s, 3H), 3.14 (s, 6H), 2.44-2.33 (m, 1H), 2.25-2.14 (m, 1H). |
| 401 | | LC-MS (Method L9): $R_t$ = 3.59 min; m/z = 510 [M + H]$^+$. | $^1$H-NMR (400 MHz, Chloroform-d) δ 8.96 (s, 1H), 8.41-8.25 (m, 2H), 8.18 (d, J = 8.2 Hz, 1H), 7.59 (m, 3H), 7.30 (d, J = 7.6 Hz, 1H), 7.21 (m, 2H), 6.97-6.83 (m, 2H), 5.37 (q, J = 5.4 Hz, 1H), 4.34 (m, 1H), 4.25-4.16 (m, 1H), 3.77 (s, 3H), 3.13 (s, 6H), 2.39 (m, 1H), 2.26-2.15 (m, 1H). |
| 402 | | LC-MS (Method L2): $R_t$ = 2.25 min; m/z = 455 [M + H]$^+$. | $^1$H-NMR (400 MHz, Chloroform-d) δ 8.96 (s, 1H), 8.63 (d, J = 5.0 Hz, 1H), 8.19 (d, J = 8.4 Hz, 1H), 7.71 (d, J = 7.0 Hz, 1H), 7.60 (t, J = 7.8 Hz, 1H), 7.50 (s, 1H), 7.47 (d, J = 5.0 Hz, 1H), 7.30 (d, J = 7.5 Hz, 2H), 7.21 (t, J = 7.7 Hz, 1H), 6.93 (t, J = 7.5 Hz, 1H), 6.86 (d, J = 8.2 Hz, 1H), 5.42-5.33 (m, 1H), 4.83 (s, 2H), 4.39-4.30 (m, 1H), 4.25-4.15 (m, 1H), 3.14 (s, 6H), 2.39 (m, 1H), 2.26-2.16 (m, 1H), 1.68 (s, 1H). |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 403 | | LC-MS (Method L2): $R_t$ = 2.89 min; m/z = 461 $[M + H]^+$. | $^{1}$H-NMR (400 MHz, Chloroform-d) δ 8.91 (s, 1H), 8.46 (s, 2H), 8.28 (d, J = 8.5 Hz, 1H), 7.71 (d, J = 6.9 Hz, 1H), 7.68-7.60 (m, 1H), 7.29 (d, J = 7.6 Hz, 1H), 7.24-7.12 (m, 2H), 6.92 (t, J = 7.5 Hz, 1H), 6.86 (d, J = 8.2 Hz, 1H), 5.37 (q, J = 5.4 Hz, 1H), 4.34 (m, 1H), 4.24-4.14 (m, 1H), 3.15 (s, 6H), 2.38 (m, 1H), 2.21 (m, 1H). |
| 413 | | LC-MS (Method L2): $R_t$ = 3.02 min; m/z = 461 $[M + H]^+$. | $^{1}$H-NMR (400 MHz, Chloroform-d) δ 8.94 (s, 1H), 8.24 (m, 1H), 7.72 (m, 1H), 7.65-7.57 (m, 1H), 7.30 (d, J = 7.6 Hz, 1H), 7.25-7.17 (m, 1H), 7.12 (s, 3H), 6.94 (t, J = 7.5 Hz, 1H), 6.87 (d, J = 8.2 Hz, 1H), 5.38 (q, J = 5.4 Hz, 1H), 4.35 (m, 1H), 4.21 (m, 1H), 3.15 (s, 6H), 2.46-2.34 (m, 1H), 2.22 (m, 1H). |
| 414 | | LC-MS (Method L2): $R_t$ = 2.97 min; m/z = 477 $[M + H]^+$. | $^{1}$H-NMR (400 MHz, Chloroform-d) δ 8.91 (s, 1H), 8.32-8.22 (m, 2H), 7.70 (d, J = 6.9 Hz, 1H), 7.66-7.58 (m, 1H), 7.36 (t, J = 4.8 Hz, 1H), 7.30 (d, J = 7.5 Hz, 1H), 7.25-7.17 (m, 1H), 7.12 (d, J = 7.4 Hz, 1H), 6.93 (t, J = 7.5 Hz, 1H), 6.87 (d, J = 8.2 Hz, 1H), 5.37 (q, J = 5.3 Hz, 1H), 4.35 (m, 1H), 4.20 (m, 1H), 3.15 (s, 6H), 2.39 (m, 1H), 2.21 (m, 1H). |
| 415 | | LC-MS (Method L2): $R_t$ = 3.02 min; m/z = 493 $[M + H]^+$. | $^{1}$H-NMR (400 MHz, Chloroform-d) δ 8.88 (s, 1H), 8.47 (s, 1H), 8.25 (m, 1H), 7.65-7.56 (m, 2H), 7.36 (s, 1H), 7.29 (d, J = 7.5 Hz, 1H), 7.24-7.17 (m, 1H), 7.09 (d, J = 7.5 Hz, 1H), 6.92 (t, J = 7.2 Hz, 1H), 6.86 (d, J = 8.2 Hz, 1H), 5.37 (q, J = 5.3 Hz, 1H), 4.34 (m, 1H), 4.19 (m, 1H), 3.16 (s, 6H), 2.39 (m, 1H), 2.20 (m, 1H). |
| 416 | | LC-MS (Method L2): $R_t$ = 3.14 min; m/z = 501 $[M + H]^+$. | $^{1}$H-NMR (400 MHz, Chloroform-d) δ 8.98 (s, 1H), 8.21 (m, 1H), 8.09-8.03 (m, 1H), 7.67 (d, J = 6.3 Hz, 1H), 7.63-7.55 (m, 1H), 7.30 (d, J = 7.6 Hz, 1H), 7.25-7.16 (m, 2H), 6.96-6.83 (m, 2H), 6.76 (d, J = 4.8 Hz, 1H), 5.37 (q, J = 5.4 Hz, 1H), 5.27 (m, 1H), 4.34 (m, 1H), 4.19 (m, 1H), 3.13 (s, 6H), 2.38 (m, 1H), 2.20 (m, 1H), 1.37 (d, J = 6.2 Hz, 6H). |
| 429 | | LC-MS (Method L2): $R_t$ = 3.017 min; | $^{1}$H-NMR (400 MHz, DMSO-d6) δ 10.23 (s, 1H), 9.07 (d, J = 8.2 Hz, 1H), 8.44 (s, 1H), 7.69-7.55 (m, 3H), 7.49 (d, J = 2.6 Hz, 1H), 7.36 (d, J = 7.5 Hz, 1H), 7.31 (d, J = 2.6 Hz, 1H), 7.17 (t, J = 7.3 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | m/z = 508/510/512 [M + H]$^+$. | Hz, 1H), 6.92 (t, J = 7.4 Hz, 1H), 6.79 (d, J = 8.2 Hz, 1H), 5.24 (q, J = 5.9 Hz, 1H), 4.29-4.15 (m, 2H), 2.99 (s, 6H), 2.29-2.12 (m, 1H), 2.10-1.96 (m, 1H). |
| 433 | | LC-MS (Method L2): $R_t$ = 3.189 min; m/z = 560 [M + H]$^+$. | $^1$H-NMR (400 MHz, DMSO-d6) δ 9.10 (d, J = 8.1 Hz, 1H), 8.50 (d, J = 0.8 Hz, 1H), 8.29-8.21 (m, 1H), 7.95-7.87 (m, 1H), 7.66-7.58 (m, 2H), 7.52-7.43 (m, 1H), 7.33 (d, J = 7.7 Hz, 1H), 7.27-7.19 (m, 1H), 7.15 (t, J = 7.1 Hz, 1H), 6.90 (t, J = 7.4 Hz, 1H), 6.78 (d, J = 8.0 Hz, 1H), 5.27-5.17 (m, 1H), 4.32-4.16 (m, 2H), 3.07 (s, 6H), 2.24-2.12 (m, 1H), 2.08-1.96 (m, 1H). |
| 434 | | LC-MS (Method L2): $R_t$ = 2.894 min; m/z = 510 [M + H]$^+$. | $^1$H-NMR (400 MHz, DMSO-d6) δ 9.10 (d, J = 8.1 Hz, 1H), 8.50 (d, J = 0.8 Hz, 1H), 8.29-8.21 (m, 1H), 7.95-7.87 (m, 1H), 7.66-7.58 (m, 2H), 7.52-7.43 (m, 1H), 7.33 (d, J = 7.7 Hz, 1H), 7.27-7.19 (m, 1H), 7.15 (t, J = 7.1 Hz, 1H), 6.90 (t, J = 7.4 Hz, 1H), 6.78 (d, J = 8.0 Hz, 1H), 5.27-5.17 (m, 1H), 4.32-4.16 (m, 2H), 3.07 (s, 6H), 2.24-2.12 (m, 1H), 2.08-1.96 (m, 1H). |
| 435 | | LC-MS (Method L2): $R_t$ = 2.808 min; m/z = 483/485 [M + H]$^+$. | $^1$H-NMR (400 MHz, DMSO-d6) δ 9.10 (d, J = 8.2 Hz, 1H), 8.53 (s, 1H), 8.32-8.23 (m, 1H), 7.96-7.84 (m, 2H), 7.80 (d, J = 8.3 Hz, 1H), 7.71-7.62 (m, 2H), 7.34 (d, J = 7.4 Hz, 1H), 7.16 (t, 1H), 6.91 (t, 1H), 6.79 (d, 1H), 5.29-5.17 (m, 1H), 4.33-4.17 (m, 2H), 3.08 (s, 6H), 2.25-2.13 (m, 1H), 2.10-1.95 (m, 1H). |
| 436 | | LC-MS (Method L2): $R_t$ = 2.711 min; m/z = 456 [M + H]$^+$. | $^1$H-NMR (400 MHz, DMSO-d6) δ 9.08 (d, J = 8.2 Hz, 1H), 8.53 (s, 1H), 8.22 (dd, J = 8.4, 1.4 Hz, 1H), 7.66-7.60 (m, 1H), 7.59-7.53 (m, 1H), 7.37-7.26 (m, 2H), 7.20-7.07 (m, 2H), 6.97 (d, J = 9.3 Hz, 1H), 6.91 (t, J = 7.5, 1.0 Hz, 1H), 6.79 (d, 1H), 5.28-5.19 (m, 1H), 4.32-4.18 (m, 2H), 3.07 (s, 6H), 2.25-2.13 (m, 1H), 2.1H.97 (m, 1H), 1.90 (s, 3H). |
| 437 | | LC-MS (Method L2): $R_t$ = 2.763 min; m/z = 456 [M + H]$^+$. | $^1$H-NMR (400 MHz, DMSO-d6) δ 9.08 (d, J = 8.2 Hz, 1H), 8.54 (s, 1H), 8.22 (dd, J = 8.0, 2.0 Hz, 1H), 7.69-7.59 (m, 2H), 7.35 (d, J = 7.5 Hz, 1H), 7.28-7.07 (m, 4H), 6.91 (t, J = 7.5, 1.1 Hz, 1H), 6.79 (d, J = 8.2, 0.9 Hz, 1H), 5.29-5.20 (m, 1H), 4.33-4.19 (m, 2H), 3.07 (s, 6H), 2.34 (s, 3H), 2.26-2.13 (m, 1H), 2.11-1.99 (m, 1H). |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 441 | | LC-MS (Method M22): Rt = 1.67 min; m/z = 540 [M + H]+ | $^{1}$H-NMR (400 MHz, DMSO-d6): δ [ppm] = 2.03-2.09 (m, 1H), 2.20-2.25 (m, 1H), 3.27-3.29 (m, 4H), 3.86-3.88 (m, 4H), 4.21-4.29 (m, 2H), 5.26 (q, 1H), 6.80 (d, 1H), 6.94 (t, 1H), 7.18 (t, 1H), 7.24 (s, 1H), 7.38 (d, 1H), 7.70 (t, 1H), 7.79 (d, 1H), 8.28 (d, 1H), 8.67 (s, 1H), 9.19 (d, 1H). |
| 442 | | LC-MS (Method M22): Rt = 1.46 min; m/z = 506 [M + H]+ | $^{1}$H-NMR (400 MHz, DMSO-d6): δ [ppm] = 2.07-2.08 (m, 1H), 2.21-2.23 (m, 1H), 3.29-3.31 (m, 4H), 3.87-3.88 (m, 4H), 4.22-4.31 (m, 2H), 5.27 (q, 1H), 6.80 (d, 1H), 6.93 (t, 1H), 7.17-7.20 (m, 2H), 7.39 (d, 1H), 7.71 (t, 1H), 7.81 (d, 1H), 7.92 (d, 1H), 8.30 (d, 1H), 8.67 (s, 1H), 9.21 (d, 1H). |
| 443 | | LC-MS (Method M22): Rt = 1.84 min; m/z = 506 [M + H]+ | $^{1}$H-NMR (400 MHz, DMSO-d6): δ [ppm]: = 2.07-2.12 (m, 1H), 2.21-2.26 (m, 1H), 3.28-3.30 (m, 4H), 3.87-3.90 (m, 4H), 4.23-4.31 (m, 2H), 5.28 (q, 1H), 6.81 (d, 1H), 6.96 (t, 1H), 7.17-7.21 (m, 2H), 7.42 (d, 1H), 7.67 (t, 1H), 7.83 (d, 1H), 8.14 (d, 1H), 8.37 (d, 1H), 8.77 (s, 1H), 9.24 (d, 1H). |
| 456 | | LC-MS (Method L2): Rt = 2.76 min; m/z = 445 [M + H]$^+$. | $^{1}$H-NMR (400 MHz, DMSO-d6) δ 9.14 (d, J = 8.2 Hz, 1H), 8.67 (s, 1H), 8.38 (s, 1H), 8.28 (d, J = 7.3 Hz, 1H), 8.13 (d, J = 8.4 Hz, 1H), 7.65-7.57 (m, 1H), 7.39 (d, J = 72 Hz, 1H), 7.22-7.15 (m, 1H), 6.95 (t, J = 7.4 Hz, 1H), 6.81 (d, J = 8.2 Hz, 1H), 5.30-5.22 (m, 1H), 4.34-4.21 (m, 2H), 3.07 (s, 6H), 2.68 (s, 3H), 2.27-2.16 (m, 1H), 2.12-2.01 (m, 1H). |
| 457 | | LC-MS (Method L2): $R_t$ = 3.33 min; m/z = 464 [M + H]$^+$ with Cl pattern. | $^{1}$H-NMR (400 MHz, Chloroform-d) δ 9.05 (s, 1H), 8.03 (m, 2H), 7.58 (d, J = 1.5 Hz, 1H), 7.53 (m, 1H), 7.39 (d, J = 7.4 Hz, 1H), 7.32 (d, J = 7.6 Hz, 1H), 7.26-7.17 (m, 2H), 6.95 (m, 1H), 6.88 (d, J = 8.2 Hz, 1H), 5.38 (q, J = 5.3 Hz, 1H), 4.41-4.31 (m, 1H), 4.22 (m, 1H), 3.11 (s, 6H), 2.45-2.34 (m, 1H), 2.23 (m, 1H). |
| 458 | | LC-MS (Method L2): $R_t$ = 3.82 min; m/z = 498 [M + H]$^+$. | $^{1}$H-NMR (400 MHz, Chloroform-d) δ 9.02 (s, 1H), 8.14-8.04 (m, 2H), 7.66-7.50 (m, 1H), 7.55 (m, 1H), 7.48-7.41 (m, 1H), 7.32 (d, δ = 7.7 Hz, 1H), 7.26-7.17 (m, 2H), 6.95 (m, 1H), 6.91-6.84 (m, 1H), 5.42-5.33 (m, 1H), 4.41-4.32 (m, 1H), 4.22 (m, 1H), 3.12 (s, 6H), 2.46-2.34 (m, 1H), 2.28-2.16 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (m, 1H), contains 2.696 (w/w) EtOAc and 0.296 (w/w) DIP. |
| 459 | | LC-MS (Method L2): $R_t$ = 3.26 min; m/z = 448 [M + H]$^+$. | $^1$H-NMR (400 MHz, Chloroform-d) δ 9.04 (s, 1H), 8.00 (m, 2H), 7.56-7.49 (m, 1H), 7.46 (d, J = 7.4 Hz, 1H), 7.36-7.29 (m, 2H), 7.25-7.17 (m, 1H), 6.95 (m, 1H), 6.88 (d, J = 8.2 Hz, 1H), 6.52 (m, 1H), 5.38 (q, J = 5.3 Hz, 1H), 4.41-4.31 (m, 1H), 4.22 (m, 1H), 3.10 (s, 6H), 2.45-2.34 (m, 1H), 2.28-2.17 (m, 1H). |
| 460 | | LC-MS (Method L2): $R_t$ = 2.96 min; m/z = 493 [M + H]$^+$ with 2*Cl pattern. | $^1$H-NMR (400 MHz, Chloroform-d) δ 8.86 (s, 1H), 8.65-8.59 (m, 2H), 8.27 (m, 1H), 7.64 (m, 1H), 7.55 (m, 1H), 7.28 (d, J = 7.8 Hz, 1H), 7.24-7.17 (m, 1H), 7.06 (d, J = 7.5 Hz, 1H), 6.92 (m, 1H), 6.86 (d, J = 8.3 Hz, 1H), 5.37 (q, J = 5.3 Hz, 1H), 4.38-4.30 (m, 1H), 4.19 (m, 1H), 3.17 (s, 6H), 2.44-2.33 (m, 1H), 2.20 (m, 1H). |
| 461 | | LC-MS (Method L2): $R_t$ = 3.774 min; m/z = 602 [M + H] $^+$. | $^1$H-NMR (400 MHz, DMSO-d6) δ 9.19 (t, 1H), 8.57 (d, J = 2.4 Hz, 1H), 8.35-8.28 (m, 1H), 8.15-8.08 (m, 1H), 8.06-8.00 (m, 1H), 7.74-7.65 (m, 3H), 7.35 (d, J = 7.7 Hz, 1H), 7.16 (t, J = 7.6 Hz, 1H), 6.90 (t, J = 7.4 Hz, 1H), 6.78 (d, J = 8.1 Hz, 1H), 5.27-5.19 (m, 1H), 4.31-4.17 (m, 2H), 3.94-3.85 (m, 4H), 3.37-3.22 (m, 4H, coinicdes with water signal), 2.26-2.15 (m, 1H), 2.09-1.97 (m, 1H). |
| 462 | | LC-MS (Method L2): $R_t$ = 3.556 min; m/z = 534/536/538 [M + H] $^+$. | $^1$H-NMR (400 MHz, DMSO-d6) δ 9.18 (d, J = 8.2 Hz, 1H), 8.60 (s, 1H), 8.33-8.25 (m, 1H), 7.73-7.66 (m, 2H), 7.62 7.56 (m, 1H), 7.52 (dd, J = 8.6, 2.5 Hz, 1H), 7.44 (bs, 1H), 7.37 (d, J = 7.3 Hz, 1H), 7.16 (t, 1H), 6.92 (t, J = 7.3 Hz, 1H), 6.79 (d, J = 8.1 Hz, 1H), 5.29-5.20 (m, 1H), 4.33-4.19 (m, 2H), 3.94-3.81 (m, 4H), 3.36-3.22 (m, 4H, coincides with water signal), 2.27-2.15 (m, 1H), 2.11-1.99 (m, 1H). |
| 463 | | LC-MS (Method L2): $R_t$ = 3.464 min; m/z = 552 [M + H] $^+$. | $^1$H-NMR (400 MHz, DMSO-d6) δ 9.19 (d, J = 8.2 Hz, 1H), 8.57 (d, J = 2.4 Hz, 1H), 8.29 (dd, J = 7.8.2.1 Hz, 1H), 7.92 (dt, J = 9.2.4.9 Hz, 1H), 7.71-7.62 (m, 2H), 7.49 (td, J = 8.5, 2.3 Hz, 1H), 7.35 (dd, J = 7.1, 2.8 Hz, 1H), 7.24 (ddd, J = 17.1, 9.3, 2.5 Hz, 1H), 7.18-7.11 (m, 1H), 6.91 (t, J = 7.4 Hz, 1H), 6.78 (d, J = 8.1 Hz, 1H), 5.28-5.20 (m, 1H), 4.32-4.18 (m, 2H), 3.94-3.82 (m, 4H), 3.37- |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.21 (m, 4H, coincides with water signal), 2.28-2.15 (m, 1H), 2.09-1.98 (m, 1H). |
| 464 | | LC-MS (Method L2): $R_t$ = 3.359 min; m/z = 525/527 [M + H] +. | $^1$H-NMR (400 MHz, DMSO-d6) δ 9.18 (d, J = 8.2 Hz, 1H), 8.59 (s, 1H), 8.35-8.28 (m, 1H), 7.93 (dd, J = 8.3, 2.0 Hz, 1H), 7.89 (s, 1H), 7.80 (d, J = 8.3 Hz, 1H), 7.72 (d, J = 5.1 Hz, 2H), 7.36 (d, J = 7.2 Hz, 1H), 7.16 (t, 1H), 6.91 (t, J = 7.3 Hz, 1H), 6.79 (d, J = 8.1 Hz, 1H), 5.25 (q, J = 5.8 Hz, 1H), 4.33-4.19 (m, 2H), 3.94-3.85 (m, 4H), 3.37-3.22 (m, 4H, coincides with water signal), 2.27-2.16 (m, 1H), 2.10-1.99 (m, 1H). |
| 465 | | LC-MS (Method L2): $R_t$ = 3.263 min; m/z = 514/516 [M + H] +. | $^1$H-NMR (400 MHz, DMSO-d6) δ 9.17 (d, J = 8.0 Hz, 1H), 8.58 (s, 1H), 8.26 (dd, J = 8.4, 1.3 Hz, 1H), 7.72-7.64 (m, 1H), 7.64-7.59 (m, 1H), 7.41 (d, J = 8.1 Hz, 1H), 7.36 (d, J = 7.3 Hz, 1H), 7.24 (dd, J = 8.3, 1.8 Hz, 1H), 7.21-7.11 (m, 2H), 6.91 (t, J = 7.3 Hz, 1H), 6.79 (d, J = 8.1 Hz, 1H), 5.30-5.21 (m, 1H), 4.33-4.19 (m, 2H), 3.93-3.80 (m, 4H), 3.36-3.21 (m, 4H, coincides with water signal), 2.33 (s, 3H), 2.27-2.15 (m, 1H), 2.10-1.99 (m, 1H). |
| 466 | | LC-MS (Method L2): $R_t$ = 3.112 min; m/z = 498 [M + H] +. | $^1$H-NMR (400 MHz, DMSO-d6) δ 9.16 (d, J = 8.2 Hz, 1H), 8.59 (s, 1H), 8.26 (dd, J = 8.4.1.3 Hz, 1H), 7.72-7.64 (m, 1H), 7.64-7.57 (m, 1H), 7.36 (d, J = 7.2 Hz, 1H), 7.31 (dd, J = 8.3, 6.2 Hz, 1H), 7.20-7.09 (m, 2H), 6.97 (d, J = 8.5 Hz, 1H), 6.91 (L 1H), 6.79 (d, J = 8.1 Hz, 1H), 5.29-5.21 (m, 1H), 4.33-4.19 (m, 2H), 3.93-3.82 (m, 4H), 3.36-3.22 (m, 4H, coincides with water peak), 2.27-2.16 (m, 1H), 2.10-2.00 (m, 1H), 1.89 (s, 3H). |
| 467 | | LC-MS (Method L2): $R_t$ = 3.239 min; m/z = 498 [M + H] +. | $^1$H-NMR (400 MHz, DMSO-d6) δ 9.17 (d, J = 8.2 Hz, 1H), 8.60 (s, 1H), 8.27 (dd, J = 7.4, 2.6 Hz, 1H), 7.74-7.65 (m, 2H), 7.37 (d, J = 7.1 Hz, 1H), 7.28-7.22 (m, 1H), 7.22-7.10 (m, 3H), 6.92 (t, J = 7.5, 1.0 Hz, 1H), 6.80 (d, 1H), 5.30-5.22 (m, 1H), 4.33-4.19 (m, 2H), 3.93-3.84 (m, 4H), 3.36-3.22 (m, 6H, coincides with water signal), 2.34 (s, 3H), 2.27-2.16 (m, 1H), 2.11-2.01 (m, 1H). |
| 468 | | LC-MS (Method L2): | $^1$H-NMR (400 MHz, DMSO-d6) δ 9.15 (d, J = 8.1 Hz, 1H), 8.56 (s, 1H), 8.23 (dd, J = 8.5, 1.2 Hz, 1H), 7.66 (dd, J = |

NMR peak forms are stated as they appear in the spectra, possible higher order effects have not been considered.
NMR peak lists
$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.
The peak list of an example has therefore the form:
$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)
Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.
For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.
The $^1$H-NMR peak lists are similar to classical $^1$H-NMR prints and contains therefore usually all peaks, which are listed at classical NMR-interpretation.
Additionally they can show like classical $^1$H-NMR prints signals of solvents, stereoisomers of the target compounds, which are also object of the invention, and/or peaks of impurities.
To show compound signals in the delta-range of solvents and/or water the usual peaks of solvents, for example peaks of DMSO in DMSO-$D_6$ and the peak of water are shown in our $^1$H-NMR peak lists and have usually on average a high intensity.
The peaks of stereoisomers of the target compounds and/or peaks of impurities have usually on average a lower intensity than the peaks of target compounds (for example with a purity >90%).
Such stereoisomers and/or impurities can be typical for the specific preparation process. Therefore their peaks can help to recognize the reproduction of our preparation process via "side-products-fingerprints".
An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.
Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | $R_t$ = 3.043 min; m/z = 494 [M + H] $^+$. | 8.3, 7.1 Hz, 1H), 7.56 (dd, J = 7.0, 1.2 Hz, 1H), 7.36 (d, J = 7.4 Hz, 1H), 7.21-7.12 (m, 2H), 7.12-7.05 (m, 1H), 6.98-6.87 (m, 2H), 6.79 (d, J = 8.1 Hz, 1H), 5.31-5.20 (m, 1H), 4.34-4.18 (m, 2H), 3.87 (s, 4H), 3.36-3.22 (m, 4H, coincides with water signal), 2.29 (s, 3H), 2.26-2.15 (m, 1H), 2.1H.99 (m, 1H), 1.87 (d, J = 6.7 Hz, 3H). |
| 469 | | LC-MS (Method L2): $R_t$ = 2.944 min; m/z = 492/494/496 [M + H] $^+$. | $^1$H-NMR (400 MHz, DMSO-d6) δ 9.09 (d, J = 8.2 Hz, 1H), 8.53 (s, 1H), 8.30-8.20 (m, 1H), 7.65 (d, J = 5.1 Hz, 2H), 7.59 (d, J = 8.6 Hz, 1H), 7.51 (dd, J = 8.6, 2.6 Hz, 1H), 7.43 (bs, 1H), 7.34 (d, J = 7.4 Hz, 1H), 7.17 (t, 1H), 6.91 (t, J = 7.3 Hz, 1H), 6.79 (d, J = 8.1 Hz, 1H), 5.27-5.19 (m, 1H), 4.32-4.18 (m, 2H), 3.07 (s, 6H), 2.26-2.13 (m, 1H), 2.10-1.96 (m, 1H). |
| 470 | | LC-MS (Method L9): $R_t$ = 2.815 min; m/z = 472/474 [M + H] $^+$. | $^1$H-NMR (400 MHz, DMSO-d6) δ 9.09 (d, J = 8.1 Hz, 1H), 8.51 (s, 1H), 8.22 (dd, J = 8.3, 1.4 Hz, 1H), 7.67-7.55 (m, 2H), 7.40 (d, J = 8.0 Hz, 1H), 7.34 (d, J = 7.5 Hz, 1H), 7.23 (d, J = 8.2, 1.8 Hz, 1H), 7.20-7.10 (m, 2H), 6.91 (t, J = 7.4 Hz, 1H), 6.79 (d, J = 8.1 Hz, 1H), 5.28-5.19 (m, 1H), 4.32-4.19 (m, 2H), 3.07 (s, 6H), 2.33 (s, 3H), 2.25-2.14 (m, 1H), 2.09-1.97 (m, 1H). |
| 471 | | LC-MS (Method L2): $R_t$ = 2.770 min; m/z = 452 [M + H] $^+$. | $^1$H-NMR (400 MHz, DMSO-d6) δ 9.07 (d, J = 8.2 Hz, 1H), 8.50 (s, 1H), 8.19 (d, 7.6 Hz, 1H), 7.61 (t, 1H), 7.52 (d, J = 6.1 Hz, 1H), 7.34 (d, J = 7.5 Hz, 1H), 7.21-7.12 (m, 2H), 7.09 (d, J = 7.9 Hz, 1H), 6.98-6.86 (m, 2H), 6.79 (d, J = 8.1 Hz, 1H), 5.29-5.18 (m, 1H), 4.32-4.17 (m, 2H), 3.06 (s, 6H), 2.29 (s, 3H), 2.25-2.13 (m, 1H), 2.09-1.97 (m, 1H), 1.88 (d, J = 7.0 Hz, 3H). |
| 472 | | LC-MS (Method L2): $R_t$ = 2.75 min; m/z = 485 [M + H] $^+$. | $^1$H-NMR (400 MHz, Chloroform-d) δ 9.03 (s, 1H), 8.15 (m, 1H), 7.68 (m, 1H), 7.57 (m, 1H), 7.38 (d, J = 7.5 Hz, 1H), 7.30 (d, J = 7.6 Hz, 1H), 7.24-7.17 (m, 1H), 6.93 (m, 1H), 6.87 (m, 1H), 6.55 (s, 2H), 5.38 (q, J = 5.4 Hz, 1H), 4.35 (m, 1H), 4.20 (m, 1H), 3.96 (s, 6H), 3.12 (s, 6H), 2.45-2.34 (m, 1H), 2.21 (m, 1H). |
| 473 | | LC-MS (Method L2): $R_t$ = 2.76 | $^1$H-NMR (400 MHz, Chloroform-d) δ 8.97 (s, 1H), 8.20 (m, 1H), 7.68 (m, 1H), 7.59 (m, 1H), 7.40 (s, 1H), 7.34 (s, 1H), 7.31 (d, J = 7.7 Hz, 1H), 7.24-7.16 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$δ_1$ (intensity$_1$); $δ_2$ (intensity$_2$); . . . ; $δ_i$ (intensity$_i$); . . . ; $δ_n$ (intensity$_n$) or $δ_1$ (intensity$_1$), $δ_2$ (intensity$_2$), . . . ; $δ_i$ (intensity$_i$), . . . . $δ_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | min; m/z = 473 [M + H]$^+$ with Cl pattern. | (m, 2H), 6.94 (m, 1H), 6.90-6.84 (m, 1H), 5.38 (q, J = 5.3 Hz, 1H), 4.40-4.31 (m, 1H), 4.21 (m, 1H), 3.14 (s, 6H), 2.61 (s, 3H), 2.46-2.34 (m, 1H), 2.22 (m, 1H). |
| 474 | | LC-MS (Method L2): $R_t$ = 2.54 min; m/z = 485 [M + H]$^+$. | $^1$H-NMR (400 MHz, Chloroform-d) δ 9.00 (s, 1H), 8.17 (m, 1H), 7.96 (d, J = 5.1 Hz, 1H), 7.65 (m, 1H), 7.58 (m, 1H), 7.42 (d, J = 7.5 Hz, 1H), 7.29 (d, J = 7.6 Hz, 1H), 7.24-7.16 (m, 1H), 6.92 (m, 1H), 6.89-6.83 (m, 2H), 5.37 (q, J = 5.4 Hz, 1H), 4.34 (m, 1H), 4.19 (m, 1H), 4.06 (s, 3H), 3.57 (s, 3H), 3.13 (s, 6H), 2.45-2.33 (m, 1H), 2.21 (m, 1H). |
| 475 | | LC-MS (Method L2): $R_t$ = 2.76 min; m/z = 489 [M + H]$^+$ with Cl pattern. | $^1$H-NMR (400 MHz, Chloroform-d) δ 8.94 (s, 1H), 8.25-8.18 (m, 1H), 8.13 (d, J = 5.1 Hz, 1H), 7.64-7.56 (m, 2H), 7.28 (d, J = 7.7 Hz, 1H), 7.26-7.15 (m, 2H), 6.95-6.89 (m, 2H), 6.86 (d, J = 8.2 Hz, 1H), 5.37 (q, J = 5.4 Hz, 1H), 4.34 (m, 1H), 4.19 (m, 1H), 4.08 (s, 3H), 3.14 (s, 6H), 2.44-2.32 (m, 1H), 2.20 (m, 1H). |
| 476 | | LC-MS (Method L2): | $^1$H-NMR (400 MHz, Chloroform-d) δ 8.88 (s, 1H), 8.36 (d, J = 4.8 Hz, 1H), 8.25 (m, 1H), 7.65-7.56 (m, 2H), 7.29 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$δ_1$ (intensity$_1$); $δ_2$ (intensity$_2$); . . . ; $δ_i$ (intensity$_i$); . . . ; $δ_n$ (intensity$_n$) or $δ_1$ (intensity$_1$), $δ_2$ (intensity$_2$), . . . ; $δ_i$ (intensity$_i$), . . . . $δ_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | $R_t$ = 2.91 min; m/z = 493 [M + H]$^+$ with 2*Cl pattern. | (d, J = 7.7 Hz, 1H), 7.25 (d, J = 4.8 Hz, 1H), 7.23-7.16 (m, 1H), 7.10 (d, J = 6.5 Hz, 1H), 6.92 (m, 1H), 6.89-6.83 (m, 1H), 5.37 (q, J = 5.3 Hz, 1H), 4.38-4.30 (m, 1H), 4.19 (m, 1H), 3.16 (s, 6H), 2.44-2.33 (m, 1H), 2.20 (m, 1H). |
| 480 | | LC-MS (Method M22): Rt = 1.26 min; m/z = 500 [M + H]+ | $^1$H-NMR (400 MHz, DMSO-d6): δ [ppm] = 2.05-2.06 (m, 1H), 2.16 (s, 3H), 2.19-2.21 (m, 1H), 2.42 (s, 3H), 3.26-3.30 (m, 4H), 3.85-3.88 (m, 4H), 4.24-4.28 (m, 2H), 5.25 (q, 1H), 6.72 (d, 1H), 6.80 (d, 1H), 6.94 (t, 1H), 7.18 (t, 1H), 7.38 (d, 1H), 7.62-7.65 (m, 2H), 8.20 (d, 1H), 8.63 (s, 1H), 9.16 (d, 1H). |
| 491 | | LC-MS (Method L2): $R_t$ = 3.75 min; m/z = 536 [M + H]$^+$. | $^1$H-NMR (400 MHz, Chloroform-d) δ 8.82 (d, J = 2.4 Hz, 1H), 8.29 (m, 1H), 7.56 (m, 1H), 7.44 (t, J = 8.8 Hz, 1H), 7.34 (m, 2H), 7.28 (s, 2H), 7.24 (m, 2H), 6.50 (d, J = 6.1 Hz, 1H), 5.72 (m, 1H), 3.94 (t, J = 3.9 Hz, 4H), 3.43 (m, 4H), 3.10-2.90 (m, 2H), 2.74 (m, 1H), 1.96 (m, 1H). |
| 492 | | LC-MS (Method L2): $R_t$ = 3.87 | $^1$H-NMR (400 MHz, Chloroform-d) δ 8.83 (d, J = 1.1 Hz, 1H), 8.29 (m, 1H), 7.56 (m, 1H), 7.44 (t, J = 8.8 Hz, 1H), 7.33 (m, 2H), 7.25-7.08 (m, 4H), 6.65- |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | min; m/z = 550 [M + H]$^+$. | 6.54 (m, 1H), 5.45-5.36 (m, 1H), 4.12 (q, J = 7.2 Hz, 0H), 3.92 (m, 4H), 3.43 (m, 4H), 2.89-2.74 (m, 2H), 2.24-2.11 (m, 1H), 2.09-1.98 (m, 1H), 1.97-1.77 (m, 2H). |
| 496 | | LC-MS (Method L2): Rt = 2.93 min; m/z = 564/566 [M + H]$^+$; Cl2 pattern. | $^1$H-NMR (400 MHz, Chloroform-d) δ 8.90 (d, J = 3.7 Hz, 1H), 7.55-7.47 (m, 2H), 7.36 (dd, J = 21.1, 7.6 Hz, 1H), 7.29 (d, J = 9.6 Hz, 2H), 7.24-7.18 (m, 2H), 6.99 (d, J = 8.1 Hz, 1H), 6.92 (t, J = 7.5 Hz, 1H), 6.87 (d, J = 8.3 Hz, 1H), 5.39 (q, J = 5.5 Hz, 1H), 4.39-4.30 (m, 1H), 4.24-4.16 (m, 1H), 4.06 (s, 3H), 3.76 (d, J = 4.1 Hz, 4H), 3.36 (d, J = 4.3 Hz, 4H), 2.49-2.32 (m, 1H), 2.28-2.16 (m, 1H). |
| 497 | | LC-MS (Method L2): Rt = 2.92 min; m/z = 548 [M + H]$^+$; Cl pattern. | $^1$H-NMR (400 MHz, Chloroform-d) δ 8.93 (s, 1H), 7.60 (d, J = 8.1 Hz, 1H), 7.42-7.35 (m, 2H), 7.35-7.28 (m, 2H), 7.21 (t, J = 7.1 Hz, 1H), 7.10 (t, J = 8.9 Hz, 1H), 6.99 (d, J = 8.2 Hz, 1H), 6.92 (t, J = 7.5 Hz, 1H), 6.87 (d, J = 8.2 Hz, 1H), 5.39 (q, J = 5.2 Hz, 1H), 4.39-4.31 (m, 1H), 4.25-4.15 (m, 1H), 4.06 (s, 3H), 3.76 (d, J = 11.3, 6.7, 5.6 Hz, 4H), 3.34 (t, J = 4.3 Hz, 4H), 2.47-2.34 (m, 1H), 2.27-2.15 (m, 1H). |
| 498 | | LC-MS (Method L2): $R_t$ = 3.98 min; m/z = 564/566 [M + H]$^+$. | $^1$H-NMR (400 MHz, DMSO-d6) δ 9.18 (d, J = 8.2 Hz, 1H), 8.56 (s, 1H), 7.65 (d, J = 2.3 Hz, 3H), 7.53 (dd, J = 13.3, 2.7 Hz, 2H), 7.38 (d, J = 7.4 Hz, 1H), 7.17 (t, J = 7.2 Hz, 1H), 6.93 (t, J = 7.5 Hz, 1H), 6.80 (d, J = 8.1 Hz, 1H), 5.26 (q, J = 5.9 Hz, 1H), 4.34-4.20 (m, 2H), 3.98 (s, 3H), 3.88 (t, J = 4.0 Hz, 4H), 3.31-3.20 (m, 4H), 2.28-2.16 (m, 1H), 2.12-2.01 (m, 1H). |
| 499 | | LC-MS (Method L2): $R_t$ = 3.61 min; m/z = 564/566 [M + H]$^+$. | $^1$H-NMR (400 MHz, DMSO-d6) δ 9.22-9.11 (m, 1H), 8.45 (d, J = 1.6 Hz, 1H), 7.73-7.67 (m, 1H), 7.53 (d, J = 2.7 Hz, 1H), 7.47-7.40 (m, 1H), 7.35 (d, J = 7.1 Hz, 3H), 7.16 (t, J = 7.6 Hz, 1H), 6.91 (t, J = 7.4 Hz, 1H), 6.78 (d, J = 8.2 Hz, 1H), 5.25 (d, J = 6.2 Hz, 1H), 4.25 (dt, J = 7.8, 4.6 Hz, 2H), 3.97 (s, 3H), 3.88 (s, 4H), 3.30-3.19 (m, 4H), 2.26-2.15 (m, 1H), 2.09-2.00 (m, 1H). |
| 500 | | LC-MS (Method L2): $R_t$ = 3.65 | $^1$H-NMR (400 MHz, DMSO-d6) δ 9.17 (d, J = 8.2 Hz, 1H), 8.49 (s, 1H), 7.58-7.49 (m, 3H), 7.45 (d, J = 2.7 Hz, 1H), 7.39-7.31 (m, 2H), 7.17 (t, J = 7.2 Hz, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | min; m/z = 548/550 [M + H]$^+$. | 1H), 6.92 (t, J = 7.2 Hz, 1H), 6.79 (d, J = 8.1 Hz, 1H), 5.26 (q, J = 5.9 Hz, 1H), 4.33-4.19 (m, 2H), 3.97 (s, 3H), 3.88 (t, J = 4.2 Hz, 4H), 3.31-3.21 (m, 4H), 2.29-2.15 (m, 1H), 2.11-2.00 (m, 1H). |
| 501 | | LC-MS (Method L2): $R_t$ = 3.42 min; m/z = 522/524 [M + H]$^+$. | $^1$H-NMR (400 MHz, DMSO-d6) δ 9.11 (d, J = 8.2 Hz, 1H), 8.51 (s, 1H), 7.64 (s, 3H), 7.52-7.46 (m, 2H), 7.37 (d, J = 7.5 Hz, 1H), 7.17 (t, J = 7.1 Hz, 1H), 6.93 (t, J = 7.4 Hz, 1H), 6.80 (d, J = 8.1 Hz, 1H), 5.25 (q, J = 5.8 Hz, 1H), 4.34-4.20 (m, 2H), 3.96 (s, 3H), 3.03 (s, 6H), 2.26-2.15 (m, 1H), 2.09-2.01 (m, 1H). |
| 502 | | LC-MS (Method L2): $R_t$ = 3.09 min; m/z = 522/524 [M + H]$^+$. | $^1$H-NMR (400 MHz, DMSO-d6) δ 9.09 (dd, J = 8.0, 5.0 Hz, 1H), 8.40 (s, 1H), 7.69 (dd, J = 8.0, 1.4 Hz, 1H), 7.50 (d, J = 2.8 Hz, 1H), 7.47-7.40 (m, 1H), 7.32 (dd, J = 11.9, 5.4 Hz, 3H), 7.16 (t, J = 7.2 Hz, 1H), 6.90 (t, J = 7.4 Hz, 1H), 6.78 (d, J = 8.0 Hz, 1H), 5.23 (d, J = 5.9 Hz, 1H), 4.31-4.19 (m, 2H), 3.96 (s, 3H), 3.04 (s, 6H), 2.25-2.13 (m, 1H), 2.06 (d, J = 15.1 Hz, 1H). |
| 503 | | LC-MS (Method L2): $R_t$ = 3.15 min; m/z = 506 [M + H]$^+$. | $^1$H-NMR (400 MHz, DMSO-d6) δ 9.10 (d, J = 8.2 Hz, 1H), 8.44 (s, 1H), 7.56-7.48 (m, 3H), 7.42 (d, J = 2.8 Hz, 1H), 7.34 (t, J = 8.9 Hz, 2H), 7.20-7.12 (m, 1H), 6.91 (t, J = 7.1 Hz, 1H), 6.79 (d, J = 8.0 Hz, 1H), 5.24 (q, J = 5.8 Hz, 1H), 4.31-4.19 (m, 2H), 3.96 (s, 3H), 3.04 (s, 6H), 2.25-2.14 (m, 1H), 2.09-1.98 (m, 1H). |
| 504 | | LC-MS (Method L9): $R_t$ = 4.28 min; m/z = 522/524 [M + H]$^+$. | $^1$H-NMR (400 MHz, Chloroform-d) δ 9.15 (s, 1H), 8.20 (d, J = 7.4 Hz, 1H), 7.59 (d, J = 8.1 Hz, 1H), 7.46 (d, J = 1.8 Hz, 2H), 7.37-7.29 (m, 2H), 7.21 (t, J = 7.2 Hz, 1H), 6.90 (dd, J = 26.6, 8.1 Hz, 3H), 5.40 (q, J = 5.3 Hz, 1H), 4.40-4.31 (m, 1H), 4.26-4.16 (m, 1H), 4.04 (s, 3H), 2.89 (s, 6H), 2.44-2.33 (m, 1H), 2.27-2.16 (m, 1H). |
| 505 | | LC-MS (Method L9): $R_t$ = 4.00 min; m/z = 522/524 (Cl2 pattern; [M + H]$^+$. | $^1$H-NMR (400 MHz, Chloroform-d) δ 9.14 (d, J = 5.6 Hz, 1H), 8.33 (dd, J = 21.9, 7.3 Hz, 1H), 7.55-7.47 (m, 2H), 7.34-7.27 (m, 2H), 7.21 (dd, J = 16.7, 8.0 Hz, 2H), 7.01-6.77 (m, 3H), 5.44-5.32 (m, 1H), 4.38-4.30 (m, 1H), 4.25-4.16 (m, 1H), 4.05 (s, 3H), 2.89 (s, 6H), 2.37 (td, J = 9.7.4.7 Hz, 1H), 2.27-2.15 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 506 | | LC-MS (Method L2): Rt = 2.74 min; m/z = 506/508 [M + H]$^+$. | $^1$H-NMR (400 MHz, Chloroform-d) δ 9.17 (s, 1H), 8.33 (d, J = 7.5 Hz, 1H), 7.60 (d, J = 8.1 Hz, 1H), 7.40 (dd, J = 6.2, 2.6 Hz, 1H), 7.32 (dd, J = 8.5, 4.4 Hz, 2H), 7.24-7.16 (m, 1H), 7.10 (t, J = 8.9 Hz, 1H), 7.01-6.84 (m, 3H), 5.39 (q, 3 = 5.3 Hz, 1H), 4.39-4.30 (m, 1H), 4.25-4.16 (m, 1H), 4.04 (s, 3H), 2.88 (s, 6H), 2.43-2.32 (m, 1H), 2.26-2.16 (m, 1H). |
| 507 | | LC-MS (Method L2): Rt = 3.29 min; m/z = 526/528. | $^1$H-NMR (400 MHz, Chloroform-d) δ 8.67 (s, 1H), 7.57-7.49 (m, 2H), 7.45 (d, J = 1.8 Hz, 2H), 7.38 (t, J = 1.9 Hz, 1H), 7.30 (dd, J = 7.7, 1.6 Hz, 1H), 7.21 (dd, J = 15.4, 1.7 Hz, 1H), 6.98-6.90 (m, 1H), 6.86 (dd, J = 8.3, 1.2 Hz, 1H), 6.24 (d, J = 7.7 Hz, 1H), 5.38 (q, J = 5.6 Hz, 1H), 4.40-4.31 (m, 1H), 4.25-4.15 (m, 1H), 3.06 (s, 6H), 2.46-2.34 (m, 1H), 2.27-2.16 (m, 1H). |
| 508 | | LC-MS (Method L2): Rt = 3.06 min; m/z = 526/528. | $^1$H-NMR (400 MHz, Chloroform-d) δ 8.64 (s, 1H), 7.57 (d, J = 7.7 Hz, 1H), 7.51 (dd, J = 8.0, 1.7 Hz, 1H), 7.44 (d, J = 7.8 Hz, 1H), 7.29 (d, J = 7.4 Hz, 2H), 7.24-7.16 (m, 2H), 6.91 (t, J = 7.5 Hz, 1H), 6.85 (dd, J = 8.3, 1.2 Hz, 1H), 6.31-6.15 (m, 1H), 5.41-5.30 (m, 1H), 4.39-4.26 (m, 1H), 4.18 (t, 3 = 9.3 Hz, 1H), 3.06 (s, 6H), 2.44-2.33 (m, 1H), 225-2.14 (m, 1H). |
| 509 | | LC-MS (Method L2): Rt = 3.07 min; m/z = 510/512 (Cl2 pattern, M + H)$^+$. | $^1$H-NMR (400 MHz, Chloroform-d) δ 8.66 (s, 1H), 7.59-7.49 (m, 2H), 7.41-7.31 (m, 2H), 7.29 (dd, J = 7.7, 1.7 Hz, 1H), 7.24-7.16 (m, 1H), 7.11 (t, J = 8.9 Hz, 1H), 6.96-6.89 (m, 1H), 6.85 (dd, J = 8.3, 1.2 Hz, 1H), 6.23 (d, J = 7.6 Hz, 1H), 5.37 (q, J = 5.7 Hz, 1H), 4.39-4.30 (m, 1H), 4.23-4.14 (m, 1H), 3.06 (s, 6H), 2.44-2.33 (m, 1H), 2.25-2.15 (m, 1H). |
| 510 | | LC-MS (Method L2): $R_t$ = 3.828 min; m/z = 560/562/564 [M + H] $^+$. | $^1$H-NMR (400 MHz, DMSO-d6) δ 9.23-9.11 (m, 1H), 8.65 (s, 1H), 8.54 (s, 1H), 7.93 (s, 1H), 7.73 (d, 1H), 7.50-7.43 (m, 1H), 7.43-7.31 (m, 2H), 7.16 (t, J = 7.7 Hz, 1H), 6.91 (t, J = 7.4 Hz, 1H), 6.79 (d, J = 8.1 Hz, 1H), 5.28-5.19 (m, 1H), 4.32-4.17 (m, 2H), 3.11 (s, 6H), 2.25-2.14 (m, 1H), 2.09-1.97 (m, 1H). |
| 511 | | LC-MS (Method L2): $R_t$ = | $^1$H-NMR (400 MHz, DMSO-d6) δ 9.18 (d, J = 8.1 Hz, 1H), 8.68 (s, 1H), 8.54 (s, 1H), 8.03 (s, 1H), 7.62-7.53 (m, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | 3.897 min; m/z = 544/546 [M + H] $^+$. | 2H), 7.41-7.32 (m, 2H), 7.17 (t, J = 7.5 Hz, 1H), 6.92 (t, J = 7.3 Hz, 1H), 6.79 (d, J = 8.2 Hz, 1H), 5.24 (q, J = 5.6 Hz, 1H), 4.33-4.17 (m, 2H), 3.11 (s, 6H), 2.26-2.14 (m, 1H), 2.11-1.98 (m, 1H). |
| 512 | | LC-MS (Method L2): $R_t$ = 4.340 min; m/z = 602/604/606 [M + H] $^+$. | $^1$H-NMR (400 MHz, DMSO-d6) δ 9.28 (d, J = 8.1 Hz, 1H), 8.85 (s, 1H), 8.53 (s, 1H), 8.11 (s, 1H), 7.70 (s, 3H), 7.40 (d, J = 7.3 Hz, 1H), 7.18 (t, J = 7.2 Hz, 1H), 6.94 (t, J = 7.4 Hz, 1H), 6.80 (d, J = 8.0 Hz, 1H), 5.26 (q, J = 5.6 Hz, 1H), 4.35-4.17 (m, 2H), 3.95-3.83 (m, 4H), 3.37-3.25 (m, 4H, coincides with water signal, 2.29-2.16 (m, 1H), 2.14-2.02 (m, 1H). |
| 513 | | LC-MS (Method L2): $R_t$ = 4.099 min; m/z = 602/604/606 [M + H] $^+$. | $_1$H-NMR (400 MHz, DMSO-d6) δ 9.31-9.22 (m, 1H), 8.75 (d, J = 3.2 Hz, 1H), 8.55 (s, 1H), 7.98 (s, 1H), 7.74 (dd, J = 8.0, 1.4 Hz, 1H), 7.52-7.44 (m, 1H), 7.44-7.33 (m, 2H), 7.17 (t, J = 7.6 Hz, 1H), 6.92 (t, J = 7.4 Hz, 1H), 6.79 (d, J = 8.1 Hz, 1H), 5.30-5.19 (m, 1H), 4.34-4.17 (m, 2H), 3.96-3.82 (m, 4H), 3.40-3.23 (m, 4H, coincides with water signal), 2.29-2.15 (m, 1H), 2.12-1.97 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 514 | | | $^1$H-NMR (400 MHz, DMSO-d6) δ 9.27 (d, J = 8.1 Hz, 1H), 8.78 (s, 1H), 8.55 (s, 1H), 8.08 (s, 1H), 7.65-7.54 (m, 2H), 7.44-7.33 (m, 2H), 7.17 (t, J = 7.2 Hz, 1H), 6.93 (t, J = 7.5 Hz, 1H), 6.80 (d, J = 8.0 Hz, 1H), 5.26 (q, J = 5.7 Hz, 1H), 4.34-4.16 (m, 2H), 3.95-3.82 (m, 4H), 3.39-3.23 (m, 4H, coincides with water signal), 2.29-2.16 (m, 1H), 2.13-2.00 (m, 1H). |
| 517 | | LC-MS (Method L2): $R_t$ = 3.108 min; m/z = 550/552/554 [M + H] $^+$. | $^1$H-NMR (400 MHz, DMSO-d6) δ 10.23 (s, 1H), 9.17-9.07 (m, 1H), 8.37 (d, J = 2.2 Hz, 1H), 7.69 (dd, J = 8.0, 1.5 Hz, 1H), 7.53 (d, J = 2.7 Hz, 1H), 7.47-7.38 (m, 1H), 7.38-7.26 (m, 2H), 7.22-7.11 (m, 2H), 6.91 (t, J = 7.5 Hz, 1H), 6.79 (d, J = 8.2 Hz, 1H), 5.24 (q, 1H), 4.34-4.18 (m, 2H), 3.92-3.77 (m, 4H), 3.30-3.16 (m, 4H), 2.28-2.12 (m, 1H), 2.1H.95 (m, 1H). |
| 528 | | LC-MS (Method L2): $R_t$ = 2.588 min; m/z = 491/493 | $^1$H-NMR (400 MHz, DMSO-d6) δ 8.91 (d, J = 8.3 Hz, 1H), 8.29 (s, 1H), 7.93 (d, J = 9.2 Hz, 1H), 7.50-7.41 (m, 1H), 7.35-7.29 (m, 2H), 7.29-7.19 (m, 1H), 7.19-7.08 (m, 2H), 6.89 (t, J = 7.5 Hz, 1H), 6.77 (d, J = 8.0 Hz, 1H), 5.47 (s, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$δ_1$ (intensity$_1$); $δ_2$ (intensity$_2$); . . . ; $δ_i$ (intensity$_i$); . . . ; $δ_n$ (intensity$_n$) or $δ_1$ (intensity$_1$), $δ_2$ (intensity$_2$), . . . ; $δ_i$ (intensity$_i$), . . . . $δ_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | [M + H] +. | 2H), 5.25-5.15 (m, 1H), 4.30-4.17 (m, 2H), 2.99 (s, 6H), 2.21-2.10 (m, 1H), 2.06-1.93 (m, 1H). |
| 529 | | LC-MS (Method L2): $R_t$ = 2.722 min; m/z = 507/509/511 [M + H] +. | $^1$H-NMR (400 MHz, DMSO-d6) δ 8.91 (d, J = 8.2 Hz, 1H), 8.31 (s, 1H), 7.91 (d, J = 9.2 Hz, 1H), 7.56 (t, J = 1.7 Hz, 1H), 7.31 (d, J = 7.5 Hz, 1H), 7.22 (d, J = 1.6 Hz, 2H), 7.19-7.07 (m, 2H), 6.90 (t, J = 7.3 Hz, 1H), 6.78 (d, J = 8.1 Hz, 1H), 5.48 (s, 2H), 5.20 (q, J = 6.0 Hz, 1H), 4.27-4.19 (m, 2H), 2.98 (s, 6H), 2.21-2.10 (m, 1H), 2.05-1.95 (m, 1H). |
| 530 | | LC-MS (Method L10): Rt = 1.91 min; m/z = 564 [M + H] +. | $^1$H-NMR (400 MHz, Chloroform-d) δ 8.93 (s, 1H), 7.59 (d, J = 8.2 Hz, 1H), 7.44 (d, J = 1.9 Hz, 2H), 7.39-7.28 (m, 4H), 7.26-7.16 (m, 2H), 7.01-6.82 (m, 3H), 5.51-5.20 (m, 1H), 4.48-4.28 (m, 1H), 4.28-4.12 (m, 1H), 4.05 (s, 3H), 3.76 (dt, J = 8.1.4.7 Hz, 6H), 3.34 (t, J = 4.5 Hz, 6H), 2.55-2.33 (m, 1H), 2.33-2.14 (m, 1H). |
| 531 | | LC-MS (Method L2): Rt = 3.76 min; m/z = 552/554 (Cl2 pattern, [M + H] +. | $^1$H-NMR (400 MHz, Chloroform-d) δ 8.63 (s, 1H), 7.62 (d, J = 7.8 Hz, 1H), 7.54 (d, J = 7.8 Hz, 1H), 7.36 (dd, J = 7.8, 4.8 Hz, 2H), 7.30 (dd, J = 7.8, 1.6 Hz, 1H), 7.23-7.17 (m, 1H), 7.15-7.07 (m, 1H), 6.93 (td, J = 7.5, 1.2 Hz, 1H), 6.86 (dd, J = 8.1, 1.2 Hz, 1H), 6.20 (d, J = 7.6 Hz, 1H), 5.38 (q, J = 5.6 Hz, 1H), 4.40-4.31 (m, 1H), 4.24-4.14 (m, 1H), 4.15-3.75 (m, 4H), 3.43 (s, 4H), 2.46-2.35 (m, 1H). |
| 532 | | LC-MS (Method L2): Rt = 3.74 min; m/z = 568/570 [M + H]+. | $^1$H-NMR (400 MHz, Chloroform-d) δ 8.61 (d, J = 3.9 Hz, 1H), 7.63 (d, J = 7.8 Hz, 1H), 7.52 (dd, J = 8.0, 1.6 Hz, 1H), 7.47 (d, J = 7.7 Hz, 1H), 7.33-7.27 (m, 2H), 7.20 (td, J = 7.6.1.7 Hz, 2H), 6.96-6.82 (m, 2H), 6.20 (t, J = 6.5 Hz, 1H), 5.42-5.33 (m, 1H), 4.39-4.31 (m, 1H), 4.23-4.13 (m, 1H), 3.99 (d, J = 50.2 Hz, 4H), 3.44 (s, 4H), 2.46-2.34 (m, 1H), 2.26-2.16 (m, 1H). |
| 533 | | LC-MS (Method L9): Rt = 4.38 min; m/z = 568/570 [M + H]+. | $^1$H-NMR (400 MHz, Chlofoform-d) δ 8.65 (s, 1H), 7.60 (d, J = 7.8 Hz, 1H), 7.53 (d, J = 7.8 Hz, 1H), 7.43 (d, J = 1.9 Hz, 2H), 7.39 (t, J = 1.9 Hz, 1H), 7.31 (dd, J = 7.6, 1.6 Hz, 1H), 7.21 (dd, J = 15.6, 1.7 Hz, 1H), 6.98-6.91 (m, 1H), 6.86 (dd, J = 8.3, 1.2 Hz, 1H), 6.20 (d, J = 7.6 Hz, 1H), 5.39 (q, J = 5.6 Hz, 1H), 4.41-4.33 (m, 1H), 4.25-4.16 (m, 1H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 3.95 (s, 4H), 3.43 (s, 4H), 2.47-2.36 (m, 1H), 2.29-2.19 (m, 1H). |
| 536 | | LC-MS (Method L2): $R_t$ = 2.60 min; m/z = 533/535 [M + H]$^+$. | $^1$H-NMR (400 MHz, DMSO-d6) δ 8.99 (d, J = 8.3 Hz, 1H), 8.33 (s, 1H), 7.98 (d, J = 9.2 Hz, 1H), 7.50-7.43 (m, 1H), 7.33 (dt, J = 7.8, 4.6 Hz, 2H), 7.28-7.22 (m, 1H), 7.15 (t, J = 7.9 Hz, 2H), 6.90 (t, J = 7.0 Hz, 1H), 6.78 (d, J = 8.1 Hz, 1H), 5.52 (s, 2H), 5.27-5.17 (m, 1H), 4.24 (dt, J = 8.6, 4.0 Hz, 2H), 3.83 (s, 4H), 3.28-3.15 (m, 4H), 2.24-2.12 (m, 1H), 2.06-1.95 (m, 1H). |
| 537 | | LC-MS (Method L2): $R_t$ = 2.67 min; m/z = 549/551 [M + H]$^+$. | $^1$H-NMR (400 MHz, DMSO-d6) δ 9.00 (dd, J = 8.3, 2.3 Hz, 1H), 8.31 (d, J = 2.0 Hz, 1H), 7.97 (d, J = 9.2 Hz, 1H), 7.64 (dd, J = 8.1, 1.4 Hz, 1H), 7.41 (td, J = 7.8, 5.9 Hz, 1H), 7.32 (d, J = 7.3 Hz, 1H), 7.21-7.11 (m, 3H), 6.89 (t, J = 7.4 Hz, 1H), 6.77 (d, J = 8.1 Hz, 1H), 5.37 (s, 2H), 5.21 (q, J = 6.0 Hz, 1H), 4.25 (t, J = 8.5 Hz, 2H), 3.82 (s, 4H), 3.28-3.16 (m, 4H), 2.23-2.12 (m, 1H), 2.06-1.95 (m, 1H). |
| 538 | | LC-MS (Method L2): $R_t$ = 2.72 min; m/z = 549/551 [M + H]$^+$. | $^1$H-NMR (400 MHz, DMSO-d6) δ 8.98 (d, J = 8.3 Hz, 1H), 8.36 (s, 1H), 7.96 (d, J = 9.2 Hz, 1H), 7.57 (t, J = 1.9 Hz, 1H), 7.33 (d, J = 7.3 Hz, 1H), 7.22 (d, J = 1.8 Hz, 2H), 7.18-7.11 (m, 2H), 6.95-6.87 (m, 1H), 6.78 (d, J = 8.1 Hz, 1H), 5.54 (s, 2H), 5.22 (q, J = 5.9 Hz, 1H), 4.31-4.18 (m, 2H), 3.82 (s, 4H), 3.28-3.14 (m, 4H), 2.19 (dq, J = 13.4, 4.8 Hz, 1H), 2.02 (dq, J = 10.4, 3.7, 3.3 Hz, 1H). |
| 551 | | LC-MS (Method L2): 2.66 min; m/z = 507/509 [M + H]$^+$. | $^1$H-NMR (400 MHz, DMSO-d6) δ 8.92 (dd, J = 8.4, 2.4 Hz, 1H), 8.27 (s, 1H), 7.93 (d, J = 9.3 Hz, 1H), 7.63 (dd, J = 8.1, 1.7 Hz, 1H), 7.47-7.37 (m, 1H), 7.30 (dd, J = 7.6, 1.6 Hz, 1H), 7.23-7.07 (m, 3H), 6.88 (t, J = 7.4 Hz, 1H), 6.77 (dd, J = 8 3, 1.2 Hz, 1 H), 5.31 (d, J = 2.5 Hz, 2H), 5.20 (q, J = 6.2 Hz, 1H), 4.24 (t, J = 5.9 Hz, 2H), 2.99 (s, 6H), 2.23-2.10 (m, 1H), 2.06-1.92 (m, 1H). |
| 559 | | LC-MS (Method L2): $R_t$ = 2.60 min; m/z = 492 [M + H]$^+$. | $^1$H-NMR (400 MHz, DMSO-d6) δ 10.37 (s, 1H), 8.98 (d, J = 8.3 Hz, 1H), 8.41 (s, 1H), 8.09 (d, J = 9.2 Hz, 1H), 7.48-7.40 (m, 1H), 7.35-7.24 (m, 4H), 7.18-7.12 (m, 1H), 6.90 (t, J = 7.3 Hz, 1H), 6.78 (d, J = 8.1 Hz, 1H), 5.21 (dd, J = 7.9, 5.1 Hz, 1H), 4.30-4.18 (m, 2H), 3.03 (s, 6H), 2.22-2.12 (m, 1H), 2.06-1.96 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 560 | | LC-MS (Method L2): $R_t$ = 2.66 min; m/z = 508/510 [M + H]$^+$. | $^1$H-NMR (400 MHz, DMSO-d6) δ 10.20 (s, 1H), 8.98 (dd, J = 8.3, 2.4 Hz, 1H), 8.37 (s, 1H), 8.08 (d, J = 9.2 Hz, 1H), 7.61 (dd, J = 8.0, 1.5 Hz, 1H), 7.41-7.27 (m, 3H), 7.23-7.11 (m, 2H), 6.89 (t, J = 7.4 Hz, 1H), 6.77 (d, J = 8.1 Hz, 1H), 5.21 (q, J = 6.4 Hz, 1H), 4.25 (td, J = 9.4, 8.0, 5.5 Hz, 2H), 3.03 (s, 6H), 2.22-2.11 (m, 1H), 2.06-1.94 (m, 1H). |
| 561 | | LC-MS (Method L2): $R_t$ = 2.74 min; m/z = 508/510 [M + H]$^+$. | $^1$H-NMR (400 MHz, DMSO-d6) δ 10.33 (s, 1H), 8.98 (d, J = 8.2 Hz, 1H), 8.44 (s, 1H), 8.07 (d, J = 9.3 Hz, 1H), 7.54 (t, J = 2.0 Hz, 1H), 7.37-7.28 (m, 4H), 7.19-7.13 (m, 1H), 6.91 (td, J = 7.5, 1.2 Hz, 1H), 6.78 (dd, J = 8.2, 1.1 Hz, 1H), 5.26-5.18 (m, 1H), 4.30-4.19 (m, 2H), 3.02 (s, 6H), 2.23-2.12 (m, 1H), 2.07-1.97 (m, 1H). |
| 580 | | LC-MS (Method M11): Rt = 1.52 min; m/z = 570 [M + H]+ | $^1$H-NMR (400 MHz, DMSO-d6): δ [ppm] = 2.04-2.09 (m, 1H), 2.17-2.30 (m, 1H), 3.07 (s, 6H), 4.22-4.32 (m 2H), 5.21-5.26 (m, 1H), 6.79 (d, 1H), 7.33 (dd, 1H), 7.53 (d, 1H), 7.64-7.68 (m, 4H), 7.81 (dd, 1H), 8.25 (dd, 1H), 8.66 (s, 1H), 9.13 (d, 1H). |
| 581 | | LC-MS (Method M11): Rt = 1.29 min; m/z = 4.92 [M + H]+ | $^1$H-NMR (300 MHz, DMSO-d6): δ [ppm] = 3.06 (s, 6H), 3.87 (dd, 1H), 4.05 (dd, 1H), 4.75 (d, 2H), 5.18-5.21 (m, 1H), 7.09-7.13 (m, 1H), 7.25-7.30 (m, 2H), 7.47-7.50 (m, 1H), 7.62-7.67 (m, 4H), 7.80 (dd, 1H), 8.23 (dd, 1H), 8.62 (s, 1H), 9.11 (d, 1H), |
| 584 | | LC-MS (Method L2): $R_t$ = 2.79 min; m/z = 534 [M + H]$^+$. | $^1$H-NMR (400 MHz, Chloroform-d) δ 8.90 (d, J = 2.5 Hz, 1H), 8.21 (d, J = 9.3 Hz, 1H), 7.47-7.40 (m, 1H), 7.40-7.34 (m, 1H), 7.34-7.27 (m, 2H), 7.25-7.17 (m, 3H), 6.92 (t, J = 7.4 Hz, 1H), 6.87 (d, J = 8.2 Hz, 1H), 5.46 (s, 1H), 5.36 (dd, J = 7.6, 4.4 Hz, 1H), 4.38-4.30 (m, 1H), 4.22-4.14 (m, 1H), 3.84 (q, J = 5.9 Hz, 4H), 3.40 (q, J = 4.4 Hz, 4H), 2.43-2.33 (m, 1H), 2.27-2.16 (m, 1H). |
| 609 | | LC-MS (Method L10): $R_t$ = 3.98 min; m/z = 602 [M + H]$^+$. | $^1$H-NMR (400 MHz, DMSO-d6) δ 9.19 (dd, J = 8.1, 2.7 Hz, 1H), 8.68 (d, J = 1.9 Hz, 1H), 8.44 (d, J = 9.5 Hz, 1H), 7.77 (dt, J = 9.3, 1.6 Hz, 1H), 7.62-7.56 (m, 1H), 7.49-7.34 (m, 3H), 7.20-7.14 (m, 1H), 6.92 (td, J = 7.5, 1.2 Hz, 1H), 6.79 (d, J = 8.2 Hz, 1H), 5.37-5.10 (m, 1H), 4.32-4.18 (m, 2H), 3.88 (t, J = 4.8 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | Hz, 4H), 3.32-3.25 (m, 4H), 2.27-2.17 (m, 1H), 2.09-2.00 (m, 1H). |
| 610 | | LC-MS (Method L10): $R_t$ = 4.00 min; m/z = 618/620 $[M + H]^+$. | $^1$H-NMR (400 MHz, DMSO-d6) δ 9.19 (dd, J = 8.1, 4.2 Hz, 1H), 8.65 (d, J = 3.7 Hz, 1H), 8.43 (d, J = 9.4 Hz, 1H), 7.76 (td, J = 8.8, 8.0, 1.6 Hz, 2H), 7.48 (td, J = 7.9, 5.1 Hz, 1H), 7.38-7.29 (m, 2H), 7.26-7.06 (m, 1H), 6.91 (tt, J = 7.5, 1.5 Hz, 1H), 6.79 (dd, J = 8.3, 1.2 Hz, 1H), 5.23 (d, J = 6.5 Hz, 1H), 4.31-4.19 (m, 2H), 3.98-3.77 (m, 4H), 3.32-3.23 (m, 4H), 2.26-2.16 (m, 1H), 2.08-1.99 (m, 1H). |
| 611 | | LC-MS (Method L10): $R_t$ = 4.20 min; m/z = 618/620 $[M + H]^+$. | $^1$H-NMR (400 MHz, DMSO-d6) δ 9.19 (d, J = 8.1 Hz, 1H), 8.71 (s, 1H), 8.41 (d, J = 9.5 Hz, 1H), 7.84-7.66 (m, 2H), 7.39 (dd, J = 19.0, 1.8 Hz, 3H), 7.22-7.13 (m, 1H), 6.96-6.88 (m, 1H), 6.79 (d, J = 8.1 Hz, 1H), 5.24 (q, J = 6.0 Hz, 1H), 4.32-4.19 (m, 2H), 3.98-3.71 (m, 4H), 3.32-3.22 (m, 4H), 2.27-2.17 (m, 1H), 2.10-2.01 (m, 1H). |
| 612 | | LC-MS (Method L10): $R_t$ = 3.67 min; m/z = 560 $[M + H]^+$. | $^1$H-NMR (400 MHz, DMSO-d6) δ 9.10 (dd, J = 8.2, 2.8 Hz, 1H), 8.60 (s, 1H), 8.41 (d, J = 9.5 Hz, 1H), 7.71 (dq, J = 9.3, 1.5 Hz, 1H), 7.61-7.55 (m, 1H), 7.47-7.33 (m, 3H), 7.16 (td, J = 7.8, 1.6 Hz, 1H), 6.91 (td, J = 7.5, 1.2 Hz, 1H), 6.79 (d, J = 8.1 Hz, 1H), 5.22 (dt, J = 8.4, 4.3 Hz, 1H), 4.31-4.18 (m, 2H), 3.09 (s, 6H), 2.25-2.14 (m, 1H), 2.09-1.91 (m, 1H). |
| 613 | | LC-MS (Method L10): $R_t$ = 3.60 min; m/z = 576/578 $[M + H]^+$. | $^1$H-NMR (400 MHz, DMSO-d6) δ 9.11 (dd, J = 8.2, 3.8 Hz, 1H), 8.56 (d, J = 2.3 Hz, 1H), 8.40 (d, J = 9.4 Hz, 1H), 7.76-7.68 (m, 2H), 7.47 (td, J = 7.9, 5.1 Hz, 1H), 7.36-7.28 (m, 2H), 7.19-7.12 (m, 1H), 6.90 (tt, J = 7.3, 1.5 Hz, 1H), 6.78 (dd, J = 8.2, 1.2 Hz, 1H), 5.22 (d, J = 6.7 Hz, 1H), 4.31-4.17 (m, 2H), 3.09 (s, 6H), 2.19 (td, J = 9.1, 8.7, 3.9 Hz, 1H), 2.08-1.96 (m, 1H). |
| 614 | | LC-MS (Method L10): $R_t$ = 3.82 min; m/z = 576/578 $[M + H]^+$. | $^1$H-NMR (400 MHz, DMSO-d6) δ 9.10 (d, J = 8.2 Hz, 1H), 8.62 (s, 1H), 8.38 (d, J = 9.4 Hz, 1H), 7.70 (td, J = 4.4, 2.2 Hz, 2H), 7.40 (d, J = 1.8 Hz, 2H), 7.35 (dd, J = 7.8, 1.6 Hz, 1H), 7.20-7.13 (m, 1H), 6.91 (t, J = 7.3 Hz, 1H), 6.79 (d, J = 8.2 Hz, 1H), 5.23 (q, J = 6.2 Hz, 1H), 4.31-4.19 (m, 2H), 3.08 (s, 6H), 2.24-2.14 (m, 1H), 2.08-1.99 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 615 | | LC-MS (Method L2): $R_t$ = 2.79 min; m/z = 550/552 [M + H]$^+$. | $^1$H-NMR (400 MHz, DMSO-d6) δ 10.24 (s, 1H), 9.06 (dd, J = 8.3, 2.9 Hz, 1H), 8.43 (d, J = 2.5 Hz, 1H), 8.13 (d, J = 9.3 Hz, 1H), 7.62 (dd, J = 7.9, 1.6 Hz, 1H), 7.45-7.30 (m, 3H), 7.24-7.11 (m, 211), 6.90 (t, J = 7.5 Hz, 1H), 6.78 (dd, J = 8.3, 1.2 Hz, 1H), 5.22 (q, J = 6.3 Hz, 1H), 4.30-4.19 (m, 2H), 3.85 (q, J = 4.8.3.8 Hz, 4H), 3.30-3.18 (m, 4H), 2.24-2.13 (m, 1H), 2.09-1.96 (m, 1H). |
| 616 | | LC-MS (Method L2): $R_t$ = 2.92 min; m/z = 550/552 [M + H]$^+$. | $^1$H-NMR (400 MHz, DMSO-d6) δ 10.36 (s, 1H), 9.06 (d, J = 8.2 Hz, 1H), 8.51 (s, 1H), 8.13 (d, J = 9.3 Hz, 1H), 7.55 (d, J = 2.1 Hz, 1H), 7.41-7.30 (m, 4H), 6.92 (t, J = 7.4 Hz, 1H), 6.79 (d, J = 8.1 Hz, 1H), 5.23 (q, J = 5.9 Hz, 1H), 4.32-4.19 (m, 2H), 4.04 (s, 1H), 3.90-3.79 (m, 4H), 3.24 (q, J = 5.3 Hz, 4H), 2.22-2.14 (m, 1H), 2.09-1.98 (m, 1H). |
| 617 | | LC-MS (Method L9): $R_t$ = 4.03 min; m/z = 517/519 [M + H]$^+$. | $^1$H-NMR (400 MHz, DMSO-d6) δ 9.16 (d, J = 8.1 Hz, 1H), 8.67 (s, 1H), 8.36 (d, J = 8.6 Hz, 1H), 7.97 (d, J = 8.7 Hz, 1H), 7.77 (t, J = 1.9 Hz, 1H), 7.58 (s, 2H), 7.35 (d, J = 7.6 Hz, 1H), 7.17 (t, J = 7.7 Hz, 1H), 6.91 (t, J = 7.5 Hz, 1H), 6.79 (d, J = 8.2 Hz, 1H), 5.23 (q, J = 6.2 Hz, 1H), 4.31-4.19 (m, 2H), 3.08 (s, 6H), 2.25-2.14 (m, 1H), 2.09-1.98 (m, 1H). |
| 618 | | LC-MS (Method L2): $R_t$ = 2.818 min; m/z = 492/494/496 [M + H] $^+$. | $^1$H-NMR (400 MHz, DMSO-d6) δ 10.18 (s, 1H), 9.06 (d, J = 8.2 Hz, 1H), 8.37 (s, 1H), 7.55-7.44 (m, 3H), 7.38-7.29 (m, 2H), 7.25 (d, J = 2.6 Hz, 1H), 7.16 (t, J = 7.7 Hz, 1H), 6.91 (t, J = 7.4 Hz, 1H), 6.79 (d, J = 8.0 Hz, 1H), 5.24 (q, J = 5.9 Hz, 1H), 4.31-4.17 (m, 2H), 3.00 (s, 6H), 2.26-2.13 (m, 1H), 2.09-1.95 (m, 1H). |
| 619 | | LC-MS (Method L2): $R_t$ = 2.836 min; m/z = 508/510/512 [M + H] $^+$. | $^1$H-NMR (400 MHz, DMSO-d6) δ 10.16 (s, 1H), 9.10-9.00 (m, 1H), 8.33 (s, 1H), 7.68 (d, 1H), 7.48 (d, J = 2.6 Hz, 1H), 7.47-7.36 (m, 1H), 7.36-7.27 (m, 2H), 7.20-7.10 (m, 2H), 6.90 (t, J = 7.4 Hz, 1H), 6.78 (d, J = 8.1 Hz, 1H), 5.29-5.16 (m, 1H), 4.31-4.15 (m, 2H), 3.00 (s, 6H), 2.17 (dd, J = 8.6, 4.2 Hz, 1H), 2.01 (d, J = 13.7 Hz, 1H). |
| 620 | | LC-MS (Method M24): Rt = 1.34 min; | $^1$H-NMR (400 MHz, $CD_3OD$-d4): δ [ppm] = 2.22-2.25 (m, 1H), 2.31-2.35 (m, 1H), 3.18 (s, 6H), 4.29-4.34 (m, 1H), 4.38-4.43 (m, 1H), 5.36 (t, 1H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | m/z = 510 [M + H]+ | 6.86-6.92 (m, 1H), 6.98-7.03 (m, 1H), 7.17 (d, 1H), 7.47 (t, 1H), 7.52 (d, 2H), 7.63 (dd, 1H), 7.71 (dd, 1H), 8.28 (dd, 1H), 8.55 (s, 1H). |
| 621 | | LC-MS (Method M47): Rt = 2.86 min; m/z = 560 [M + H]+ | $^1$H-NMR (400 MHz, $CD_3OD$-d4): δ [ppm]: = 2.20-2.26 (m, 1H), 2.29-2.35 (m, 1H), 3.19 (s, 6H), 4.33-4.39 (m, 1H), 4.43-4.48 (m, 1H), 5.35 (t, 1H), 7.33-7.36 (m, 2H), 7.47 (t, 1H), 7.52 (d, 2H), 7.63 (dd, 1H), 7.72 (dd, 1H), 8.29 (dd, 1H), 8.56 (s, 1H). |
| 622 | | LC-MS (Method M24): Rt = 1.43 min; m/z = 526 [M + H]+ | $^1$H-NMR (400 MHz, $CD_3OD$-d4): δ [ppm]: = 2.16-2.21 (m, 1H), 2.27-2.32 (m, 1H), 3.19 (s, 6H), 4.23-4.34 (m, 2H), 5.32 (t, 1H), 6.80 (d, 1H), 7.15 (dd, 1H), 7.37 (d, 1H), 7.47 (t, 1H), 7.52 (d, 2H), 7.63 (dd, 1H), 7.72 (dd, 1H), 8.29 (dd, 1H), 8.56 (1 H, s). |
| 623 | | LC-MS (Method M47): Rt = 2.86 min; m/z = 510 [M + H]+ | $^1$H-NMR (300 MHz, DMSO-d6) δ [ppm]: = 1.99-2.05 (1H, m), 2.18-2.21 (m, 1H), 3.06 (s, 6H), 4.19-4.27 (m, 2H), 5.19-5.24 (m, 1H), 6.84 (dd, 1H), 7.00-7.07 (m, 1H), 7.17-7.22 (dd, 1H), 7.64-7.68 (m, 4H), 7.81 (dd, 1H), 8.24 (dd, 1H), 8.68 (s, 1H), 9.13 (d, 1H). |
| 626 | | LC-MS (Method L2): $R_t$ = 3.240 min; m/z = 534/536/538 [M + H] $^+$. | $^1$H-NMR (400 MHz, DMSO-d6) δ 10.25 (s, 1H), 9.12 (d, J = 8.2 Hz, 1H), 8.40 (s, 1H), 7.58-7.49 (m, 2H), 7.47 (dd, J = 6.2, 2.7 Hz, 1H), 7.40-7.29 (m, 2H), 7.27 (d, J = 2.6 Hz, 1H), 7.16 (t, 1H), 6.92 (t, J = 7.5, 1.0 Hz, 1H), 6.79 (d, J = 8.2 Hz, 1H), 5.26 (q, 1H), 4.33-4.18 (m, 2H), 3.93-3.77 (m, 4H), 3.30-3.15 (m, 4H), 2.28-2.14 (m, 1H), 2.12-1.97 (m, 1H). |
| 627 | | LC-MS (Method L2): $R_t$ = 3.529 min; m/z = 550/552/554 [M + H] $^+$. | $^1$H-NMR (400 MHz, DMSO-d6) δ 10.41 (s, 1H), 9.12 (d, J = 8.2 Hz, 1H), 8.46 (s, 1H), 7.63 (t, J = 1.9 Hz, 1H), 7.60 (d, J = 1.9 Hz, 2H), 7.52 (d, J = 2.4 Hz, 1H), 7.37 (d, J = 7.2 Hz, 1H), 7.32 (d, J = 2.6 Hz, 1H), 7.17 (t, 1H), 6.93 (t, 1H), 6.79 (d, J = 8.1 Hz, 1H), 5.25 (q, 1H), 4.33-4.18 (m, 2H), 3.89-3.74 (m, 4H), 3.27-3.13 (m, 4H), 2.29-2.12 (m, 1H), 2.12-1.98 (m, 1H). |
| 632 | | LC-MS (Method M30): Rt = 1.65 min; m/z = 526 [M + H]+ | $^1$H-NMR (300 MHz, DMSO-d6) δ [ppm] = 2.07-2.11 (m, 1H), 2.23-2.27 (m, 1H), 3.06 (s, 6H), 4.31-4.45 (m, 2H), 5.28 (d, 1H), 6.94 (t, 1H), 7.35 (t 2H), 7.63-7.67 (m, 4H), 7.81 (d, 1H), 8.24 (d, 1H), 8.64 (s, 1H), 9.12 (d, 1H). |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 633 | | LC-MS (Method M14): Rt = 1.43 min; m/z = 570 [M + H]+ | $^{1}$H-NMR (400 MHz, DMSO-d6) δ [ppm] = 2.06-2.10 (m, 1H), 2.20-2.24 (m, 1H), 3.06 (s, 6H), 4.31-4.44 (m, 2H), 5.26-5.31 (m, 1H), 6.88 (t, 1H), 7.40 (d, 1H), 7.48 (d, 1H), 7.63-7.67 (m, 4H), 7.80 (d, 1H), 8.24 (d, 1H), 8.64 (s, 1H), 9.13 (d, 1H). |
| 634 | | LC-MS (Method M14): Rt = 1.43 min; m/z = 570 [M + H]+ | $^{1}$H-NMR (400 MHz, DMSO-d6): δ [ppm] = 2.06-2.10 (m, 1H), 2.20-2.24 (m, 1H), 3.06 (s, 6H), 4.31-4.44 (m, 2H), 5.26-5.31 (m, 1H), 6.88 (t, 1H), 7.40 (d, 1H), 7.48 (d, 1H), 7.63-7.67 (m, 4H), 7.80 (d, 1H), 8.24 (d, 1H), 8.64 (s, 1H), 9.13 (d, 1H). |
| 642 | | LC-MS (Method L9): $R_t$ = 3.75 min; m/z = 543/545 $[M + H]^+$. | $^{1}$H-NMR (400 MHz, DMSO-d6) δ 9.24 (dd, J = 8.1, 2.0 Hz, 1H), 8.74 (d, J = 2.7 Hz, 1H), 8.42 (d, J = 8.8 Hz, 1H), 8.04 (d, J = 8.8 Hz, 1H), 7.69-7.60 (m, 2H), 7.46 (td, J = 9.3, 7.0 Hz, 1H), 7.37 (dd, J = 7.6.1.6 Hz, 1H), 7.20-7.14 (m, 1H), 6.92 (td, J = 7.5, 1.2 Hz, 1H), 6.79 (d, J = 8.1 Hz, 1H), 5.24 (dq, J = 10.3, 5.4 Hz, 1H), 4.31-4.18 (m, 2H), 3.88 (t, J = 4.5 Hz, 4H), 3.29 (d, J = 4.8 Hz, 4H), 2.28-2.15 (m, 1H), 2.05 (s, 1H). |
| 651 | | LC-MS (Method L2): $R_t$ = 3.79 min; m/z = 534 $[M + H]^+$. | $^{1}$H-NMR (400 MHz, Chloroform-d) δ 8.80 (s, 1H), 8.11 (d, J = 7.4 Hz, 1H), 7.78 (d, J = 7.5 Hz, 1H), 7.45-7.37 (m, 2H), 7.31 (dd, J = 7.8, 1.7 Hz, 1H), 7.24-7.18 (m, 1H), 7.15 (t, J = 8.8 Hz, 1H), 6.97-6.91 (m, 1H), 6.87 (dd, J = 8.1, 1.2 Hz, 1H), 6.21 (d, J = 7.6 Hz, 1H), 5.45-5.38 (m, 1H), 4.49 (s, 2H), 4.41-4.33 (m, 1H), 4.24-4.15 (m, 1H), 3.86 (s, 2H), 3.68 (s, 2H), 3.17 (s, 2H), 2.51-2.37 (m, 1H), 2.30-2.22 (m, 1H). |
| 652 | | LC-MS (Method L): $R_t$ = 3.88 min; m/z = 559/661 $[M + H]^+$. | $^{1}$H-NMR (400 MHz, DMSO-d6) δ 9.24 (d, J = 8.1 Hz, 1H), 8.76 (s, 1H), 8.39 (d, J = 8.8 Hz, 1H), 8.01 (d, J = 8.8 Hz, 1H), 7.78 (t, J = 1.9 Hz, 1H), 7.59 (d, J = 1.9 Hz, 2H), 7.37 (dd, J = 7.8, 1.6 Hz, 1H), 7.20-7.14 (m, 1H), 6.92 (td, J = 7.5, 1.2 Hz, 1H), 6.79 (dd, J = 8.1, 1.2 Hz, 1H), 5.28-5.21 (m, 1H), 4.32-4.18 (m, 2H), 3.88 (t, J = 4.8 Hz, 4H), 3.31-3.24 (m, 4H), 2.26-2.18 (m, 1H), 2.09-2.01 (m, 1H). |
| 656 | | LC-MS (Method L2): $R_t$ = 2.697 min; | $^{1}$H-NMR (400 MHz, DMSO-d6) δ 13.31 (s, 1H), 9.19 (d, J = 8.2 Hz, 1H), 8.69 (s, 1H), 8.51 (dd, J = 7.4,1.4 Hz, 1H), 8.17 (dd, J = 8.5, 1.5 Hz, 1H), 7.65 (t, J = |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | m/z = 448/450 [M + H]$^+$. | 8.4, 7.4 Hz, 1H), 7.36 (dd, J = 7.9, 1.6 Hz, 1H), 7.32 (s, 1H), 7.19 (ddd, J = 8.7, 7.4, 1.7 Hz, 1H), 6.95 (t, J = 7.5, 1.2 Hz, 1H), 6.82 (dd, J = 8.2, 1.1 Hz, 1H), 5.28 (q, J = 5.8 Hz, 1H), 4.34-4.19 (m, 2H), 3.09 (s, 6H), 2.28-2.16 (m, 1H), 2.12-2.00 (m, 1H). |
| 657 | | LC-MS (Method L2): $R_t$ = 3.83 min; m/z = 559/561 [M + H]$^+$. | $^1$H-NMR (400 MHz, Chloroform-d) δ 8.77 (d, J = 4.0 Hz, 1H), 8.12 (d, J = 7.4 Hz, 1H), 7.70 (d, J = 7.3 Hz, 1H), 7.57 (dd, J = 8.1, 1.5 Hz, 1H), 7.36-727 (m, 2H), 7.24-7.17 (m, 2H), 6.93 (t, J = 7.3 Hz, 1H), 6.86 (dd, J = 8.3, 1.1 Hz, 1H), 6.21 (t, J = 6.6 Hz, 1H), 5.41 (t, J = 6.2 Hz, 1H), 4.50 (s, 2H), 4.40-4.32 (m, 1H), 4.24-4.14 (m, 1H), 3.87 (s, 2H), 3.69 (s, 2H), 3.31-3.03 (m, 2H), 2.42 (dd, J = 12.0, 6.7 Hz, 1H), 2.31-2.18 (m, 1H). |
| 658 | | LC-MS (Method L2): $R_t$ = 3.86 min; m/z = 501 [M + H]$^+$. | $^1$H-NMR (400 MHz, Chloroform-d) δ 8.83 (s, 1H), 8.10 (d, J = 7.4 Hz, 1H), 7.78 (d, J = 7.5 Hz, 1H), 7.47-7.39 (m, 2H), 7.31 (dd, J = 7.9, 1.6 Hz, 1H), 7.26-7.21 (m, 1H), 7.20-7.13 (m, 1H), 6.99-6.92 (m, 1H), 6.89 (dd, J = 8.3, 1.2 Hz, 1H), 6.23 (d, J = 7.7 Hz, 1H), 5.41 (q, J = 5.6 Hz, 1H), 4.38 (dq, J = 10.3, 3.3 Hz, 1H), 4.26-4.18 (m, 1H), 3.08 (s, 6H), 2.48-2.38 (m, 1H), 2.30-2.21 (m, 1H). |
| 659 | | LC-MS (Method L2): $R_t$ = 3.89 min; m/z = 517/519 [M + H]$^+$. | $^1$H-NMR (400 MHz, Chloroform-d) δ 8.78 (d, J = 1.3 Hz, 1H), 8.08 (d, J = 7.4 Hz, 1H), 7.67 (d, J = 7.4 Hz, 1H), 7.57 (dd, J = 8.1, 1.5 Hz, 1H), 7.36-7.29 (m, 1H), 7.28 (s, 1H), 7.24-7.17 (m, 2H), 6.96-6.89 (m, 1H), 6.86 (dd, J = 8.3, 1.1 Hz, 1H), 6.21 (t, J = 7.2 Hz, 1H), 5.38 (s, 1H), 4.39-4.31 (m, 1H), 4.23-4.14 (m, 1H), 3.07 (s, 6H), 2.47-2.35 (m, 1H), 2.26-2.16 (m, 1H). |
| 660 | | LC-MS (Method L2): $R_t$ = 3.65 min; m/z = 491 [M + H]$^+$. | $^1$H-NMR (400 MHz, DMSO-d6) δ 9.26 (d, J = 8.1 Hz, 1H), 8.87 (s, 1H), 7.91-7.87 (m, 1H), 7.84-7.73 (m, 2H), 7.70-7.57 (m, 1H), 7.35 (d, J = 7.8 Hz, 1H), 7.30-7.23 (m, 1H), 7.19 (t, J = 7.8 Hz, 1H), 6.93 (t, J = 7.5 Hz, 1H), 6.81 (d, J = 8.2 Hz, 1H), 5.31-5.11 (m, 4H), 4.84-4.70 (m, 2H), 4.34-4.21 (m, 2H), 2.25-2.15 (m, 1H), 2.08-2.01 (m, 1H). |
| 662 | | LC-MS (Method | $^1$H-NMR (400 MHz, DMSO-d6) δ 9.22 (d, J = 8.2 Hz, 1H), 8.66 (s, 1H), 8.29 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | L2): $R_t$ = 3.91 min; m/z = 561 [M + H]$^+$. | (dd, J = 8.3, 1.7 Hz, 1H), 7.96-7.87 (m, 2H), 7.68-7.60 (m, 1H), 7.48-7.43 (m, 1H), 7.31-7.25 (m, 1H), 7.21-7.14 (m, 1H), 6.92 (td, J = 7.5, 1.2 Hz, 1H), 6.79 (dd, J = 8.2, 1.1 Hz, 1H), 5.27 (q, J = 6.0 Hz, 1H), 4.34-4.19 (m, 2H), 2.23 (dp, J = 13.4, 4.3 Hz, 1H), 2.16-2.06 (m, 1H). |
| 663 | | LC-MS (Method L2): $R_t$ = 4.04 min; m/z = 559/561 [M + H]$^+$. | $^1$H-NMR (400 MHz, DMSO-d6) δ 9.35 (d, J = 8.0 Hz, 1H), 8.87 (s, 1H), 8.28 (d, J = 7.6 Hz, 1H), 7.99 (d, J = 7.5 Hz, 1H), 7.72 (t, J = 1.9 Hz, 1H), 7.67 (d, J = 1.9 Hz, 2H), 7.45-7.38 (m, 1H), 7.22-7.15 (m, 1H), 6.94 (t, J = 7.4 Hz, 1H), 6.84-6.78 (m, 1H), 5.28 (q, J = 6.1 Hz, 1H), 4.34-4.17 (m, 4H), 3.78 (d, J = 10.9 Hz, 2H), 3.52 (s, 2H), 3.09 (s, 2H), 2.29-2.20 (m, 1H), 2.14-2.05 (m, 1H). |
| 664 | | LC-MS (Method L2): $R_t$ = 4.11 min; m/z = 517/519 [M + H]$^+$. | $^1$H-NMR (400 MHz, DMSO-d6) δ 9.28 (d, J = 8.1 Hz, 1H), 8.86 (s, 1H), 8.26, (d, J = 7.6 Hz, 1H), 7.98 (d, J = 7.5 Hz, 1H), 7.72 (t, J = 2.0 Hz, 1H), 7.69 (d, J = 2.0 Hz, 2H), 7.39 (d, J = 7.3 Hz, 1H), 7.22-7.15 (m, 1H), 6.93 (t, J = 7.4 Hz, 1H), 6.81 (d, J = 8.1 Hz, 1H), 5.26 (q, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | J = 5.9 Hz, 1H), 4.31-4.22 (m, 2H), 2.91 (s, 6H), 2.27-2.15 (m, 1H), 2.14-2.01 (m, 1H). |
| 665 | | LC-MS (Method M29): Rt = 2.82 min; m/z = 510 [M + H]+ | $^1$H-NMR (300 MHz, DMSO-d6): δ [ppm] = 3.05 (s, 6H), 3.88 (dd, 1H), 4.04 (dd, 1H), 4.79 (d, 2H), 5.19-5.22 (m, 1H), 7.11-7.17 (m, 1H), 7.36 (dd, 2H), 17.62-7.67 (m, 4H), 7.80 (dd, 1H), 8.23 (dd, 1H), 8.63 (s, 1H), 9.14 (d, 1H). |
| 677 | | LC-MS (Method L2): $R_t$ = 2.83 min; m/z = 504 [M + H]$^+$. | $^1$H-NMR (400 MHz, DMSO-d6) δ 9.19 (dd, J = 8.3, 4.4 Hz, 1H), 8.80-8.67 (m, 2H), 7.83 (dd, J = 7.1, 1.2 Hz, 1H), 7.75 (dd, J = 8.6, 7.0 Hz, 1H), 7.61 (dtd, J = 11.0, 5.9, 3.0 Hz, 1H), 7.35 (dd, J = 7.7, 2.1 Hz, 1H), 7.22 (dp, J = 7.8, 2.4 Hz, 1H), 7.19-7.14 (m, 1H), 6.92 (dd, J = 8.0, 6.8 Hz, 1H), 6.79 (dd, J = 8.2. 1.2 Hz, 1H), 5.29 (q, J = 6.4 Hz, 1H), 4.26 (td, J = 7.4, 7.0, 3.3 Hz, 2H), 3.99 (t, J = 8.9 Hz, 1H), 3.31-3.22 (m, 4H), 3.02 (q, J = 8.3 Hz, 1H), 2.26-2.10 (m, 3H), 2.09-2.00 (m, 1H). |
| 678 | | LC-MS (Method L11): $R_t$ = 3.80 min | $^1$H-NMR (400 MHz, DMSO-d6) δ 9.29-9.14 (m, 1H), 8.75 (s, 1H), 8.53-8.19 (m, 1H), 7.97-7.71 (m, 2H), 7.61 (qd, J = 8.8, 3.3 Hz, 1H), 7.37 (d, J = 7.8 Hz, |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | and 3.84 min; m/z = 505 [M + H]$^+$. | 1H), 7.20 (dt, J = 27.0, 6.7 Hz, 2H), 6.93 (tt, J = 7.5, 1.4 Hz, 1H), 6.79 (dd, J = 8.2, 12 Hz, 1H), 5.30 (q, J = 6.2 Hz, 1H), 4.34 (p, J = 8.8, 8.2 Hz, 1H), 4.27-4.13 (m, 3H), 4.02 (dt, J = 29.8, 9.3 Hz, 1H), 3.87-3.56 (m, 1H), 3.25-3.15 (m, 1H), 2.44-2.36 (m, 1H), 2.32-2.18 (m, 2H), 2.10-2.01 (m, 1H). |
| 679 | | LC-MS (Method L2): $R_t$ = 2.83 min; m/z = 532 [M + H]$^+$. | $^1$H-NMR (400 MHz, DMSO-d6) δ 9.14 (d, J = 8.3 Hz, 1H), 8.72 (s, 1H), 8.53 (d, J = 8.5 Hz, 1H), 7.80 (dt, J = 15.6, 7.2 Hz, 2H), 7.61 (dq, J = 12.7, 8.0, 6.9 Hz, 1H), 7.40 (d, J = 7.6 Hz, 1H), 7.25-7.13 (m, 2H), 6.93 (t, J = 7.4 Hz, 1H), 6.79 (d, J = 8.3 Hz, 1H), 5.31 (q, J = 6.5 Hz, 1H), 4.31-4.19 (m, 2H), 2.94 (t, 7 = 11.7 Hz, 2H), 2.44 (d, J = 13.3 Hz, 3H), 2.25 (s, 4H), 2.00 (dt, J = 23.1, 11.4 Hz, 3H), 1.77 (dd, J = 22.3, 12.8 Hz, 2H). |
| 680 | | LC-MS (Method L9): $R_t$ = 3.973 min; m/z = 550/552 [M + H]$^+$. | $^1$H-NMR (400 MHz, DMSO-d6) δ 13.95 (d, J = 7.7 Hz, 1H), 9.35 (dd, J = 8.2, 2.8 Hz, 1H), 8.67 (d, J = 3.3 Hz, 1H), 7.66 (dd, J = 8.0, 1.5 Hz, 1H), 7.55 (d, J = 7.9 Hz, 1H), 7.44-7.34 (m, 2H), 7.30 (t, J = 7.4, 1.5 Hz, 1H), 7.17 (t, J = 7.8 Hz, 1H), 6.96 (d, J = 8.0 Hz, 1H), 6.92 (t, J = 7.7 Hz, 1H), 6.79 (dd, J = 8.2, 1.2 Hz, 1H), 5.25 (q, 1H), 4.35-4.15 (m, 2H), 3.85 (bs, 4H), 3.32 (bs, 4H, coincides with water signal), 2.30-2.15 (m, 1H), 2.13-1.99 (m, 1H). |
| 681 | | LC-MS (Method L2): $R_t$ = 4.067 min; m/z = 550/552 [M + H]$^+$. | $^1$H-NMR (400 MHz, DMSO-d6) δ 14.16 (s, 1H), 9.36 (d, J = 8.0 Hz, 1H), 8.79 (d, J = 1.6 Hz, 1H), 7.75 (dd, J = 8.1, 1.6 Hz, 1H), 7.61-7.54 (m, 3H), 7.41 (d, J = 7.8 Hz, 1H), 7.22-7.14 (m, 1H), 6.99-6.90 (m, 2H), 6.81 (dd, J = 8.2, 1.4 Hz, 1H), 5.28 (q, J = 6.3 Hz, 1H), 4.35-4.18 (m, 2H), 3.85 (bs, 4H), 3.32 (bs, 4H, coincides with water peak), 2.29-2.17 (m, 1H), 2.14-2.02 (m, 1H). |
| 682 | | LC-MS (Method L9): $R_t$ = 4.036 min; m/z = 508/510 [M + H]$^+$. | $^1$H-NMR (400 MHz, DMSO-d6) δ 14.15, (s, 1H), 9.30 (d, J = 8.0 Hz, 1H), 8.67, (d, J = 2.4 Hz, 1H), 7.65 (dd, J = 8.0, 1.6 Hz, 1H), 7.53 (d, J = 8.0 Hz, 1H), 7.44-7.33 (m, 2H), 7.33-7.26 (m, 1H), 7.17 (t, J = 7.6 Hz, 1H), 6.92 (dd, J = 7.9, 2.9 Hz, 2H), 6.79 (dd, J = 8.3, 1.2 Hz, 1H), 5.24 (q, J = 6.0 Hz, 1H), 4.31-4.20 (m, 2H), 2.99 (s, 6H), 2.23-2.15 (m, 1H), 2.09-1.99 (m, 1H). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 683 | | LC-MS (Method L2): $R_t$ = 3.335 min; m/z = 505/510 [M + H]$^+$. | $^1$H-NMR (400 MHz, DMSO-d6) δ 14.36 (s, 1H), 9.32 (d, J = 8.0 Hz, 1H), 8.79 (s, 1H), 7.74 (d, J = 8.1 Hz, 1H), 7.61-7.57 (m, 2H), 7.57-7.54 (m, 1H), 7.39 (dd, J = 7.8.1.6 Hz, 1H), 7.18 (td, J = 7.8, 7.3, 1.7 Hz, 1H), 6.97-6.90 (m, 2H), 6.81 (d, J = 8.2, 1.2 Hz, 1H), 5.26 (q, J = 5.9 Hz, 1H), 4.33-4.18 (m, 2H), 2.99 (s, 6H), 2.27-2.16 (m, 1H), 2.13-2.02 (m, 1H). |
| 689 | | LC-MS (Method M48): $R_t$ = 2.70 min; m/z = 556 [M + H]+ | $^1$H-NMR (400 MHz, DMSO-d6): δ [ppm] = 2.10-2.11 (m, 1H), 2.20-2.25 (m, 1H), 3.20-3.25 (m, 4H), 3.73-3.74 (m, 4H), 4.24-4.32 (m, 2H), 5.24 (q, 1H), 6.81 (dd, 1H), 6.95 (t, 1H), 7.19 (t, 1H), 7.39 (d, 1H), 7.54-7.55 (m, 1H), 7.77-7.83 (m, 2H), 8.68 (s, 1H), 924 (d, 1H). |
| 690 | | LC-MS (Method M29): Rt = 2.91 min; m/z = 514 [M + H]+ | $^1$H-NMR (400 MHz, DMSO-d6): δ [ppm] = 2.05-2.10 (m, 1H), 2.19-2.22 (m, 1H), 2.97 (s, 6H), 4.23-4.29 (m, 2H), 5.22-5.24 (m, 1H), 6.81 (d, 1H), 6.94 (t, 1H), 7.17-7.21 (m, 1H), 7.36 (d, 1H), 7.52 (s, 1H), 7.72-7.75 (m, 2H), 8.59 (s, 1H), 9.14 (d, 1H). |
| 691 | | LC-MS (Method M48): Rt = 2.41 min; m/z = 570 [M + H]+ | $^1$H-NMR (400 MHz, DMSO-d6): δ [ppm] = 2.06-2.10 (m, 1H), 2.20-2.24 (m, 1H), 3.27-3.32 (m, 4H), 3.72-3.73 (m, 4H), 4.24-4.29 (m, 2H), 5.24 (q, 1H), 6.81 (d, 1H), 6.95-6.97 (m, 1H), 7.17-7.19 (m, 1H), 7.38-7.40 (m, 1H), 7.70-7.78 (m, 4H), 8.65 (s, 1H), 9.24 (d, 1H). |
| 692 | | LC-MS (Method M7): Rt = 1.67 min; m/z = 528 [M + H]+ | $^1$H-NMR (400 MHz, $CD_3OD$-d4): δ [ppm]: = 2.18-2.23 (m, 1H), 2.26-2.33 (m, 1H), 3.09 (d, 6H), 4.24-4.32 (m, 2H), 5.30 (t, 1H), 6.80-6.83 (m, 1H), 6.91-6.96 (m, 1H), 7.15-7.20 (m, 1H), 7.33-7.36 (m, 1H), 7.50-7.58 (m, 4H), 8.50 (s, 1H). |
| 693 | | LC-MS (Method M7): Rt = 1.71 min; m/z = 570 [M + H]+ | $^1$H-NMR (400 MHz, DMSO-d6) δ [ppm] = 2.08-2.10 (m, 1H), 2.22-2.25 (m, l H), 3.20-3.32 (m, 4H), 3.70 (s, 4H), 4.23-4.30 (m, 2H), 5.24 (q, 1H), 6.81 (d, 1H), 6.94 (t, 1H), 7.19 (t, 1H), 7.39 (d, 1H), 7.57 (t, 1H), 7.63-7.65 (m, 1H), 7.78-7.85 (m, 2H), 8.68 (s, 1H), 9.22 (t, 1H). |
| 694 | | LC-MS (Method M7): Rt = | $^1$H-NMR (400 MHz, DMSO-d6): δ [ppm] = 2.05-2.07 (m, 1H), 2.18-2.21 (m, 1H), 2.97 (s, 6H), 4.23-4.29 (m, 2H), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | 1.61 min; m/z = 528 [M + H]+ | 5.21 (q, 1H), 6.81 (d, 1H), 6.94 (t, 1H), 7.19 (t, 1H), 7.36 (d, 1H), 7.53-7.57 (m, 1H), 7.63-7.64 (m, 1H), 7.72 (d, 1H), 7.81-7.84 (m, 1H), 8.58 (s, 1H), 9.12-9.14 (m, 1H). |
| 374 | | LC-MS (Method L1): Rt = 1.38 min; m/z = 602 [M + H]$^+$ | $^1$H-NMR (400 MHz, DMSO-d6) δ [ppm]: −0.149 (1.57), −0.008 (14.94), 0.008 (13.32), 0.146 (1.57), 2.038 (0.71), 2.103 (0.71), 2.179 (0.86), 2.214 (1.11), 2.327 (1.52), 2.366 (1.11), 2.523 (4.71), 2.670 (1.62), 2.694 (1.01), 2.709 (1.16), 3.363 (2.08), 3.379 (1.47), 3.405 (1.47), 3.436 (1.52), 3.462 (1.37), 3.490 (0.76), 4.120 (3.70), 4.204 (0.96), 4.258 (1.67), 4.278 (1.92), 4.287 (1.97), 4.645 (0.96), 5.243 (1.06), 5.285 (0.96), 6.798 (3.54), 6.818 (4.00), 6.861 (0.86), 6.879 (1.77), 6.899 (1.06), 6.924 (0.91), 6.945 (1.82), 6.961 (1.11), 7.160 (1.06), 7.178 (1.67), 7.188 (1.77), 7.285 (1.47), 7.304 (1.32), 7.418 (1.57), 7.435 (1.52), 7.646 (14.89), 7.648 (16.00), 7.681 (0.86), 7.717 (2.43), 7.735 (3.49), 7.756 (3.14), 7.868 (4.00), 7.886 (3.19), 8.329 (1.87), 8.346 (2.53), 8.363 (1.57), 8.773 (6.43), 8.786 (6.73), 8.962 (0.61), 9.262 (1.82), 9.282 (3.29), 9.303 (1.57). |
| 375 | | LC-MS (Method L1): Rt = 0.93 min; MS (ESIpos): m/z = 536 [M + H]$^+$ | $^1$H-NMR (400 MHz, DMSO-d6) δ [ppm]: 2.028 (0.47), 2.050 (0.77), 2.065 (0.73), 2.132 (0.72), 2.145 (0.85), 2.160 (0.51), 3.644 (16.00), 4.253 (1.62), 4.264 (2.51), 4.279 (1.47), 4.388 (1.53), 4.404 (1.52), 4.412 (1.50), 4.429 (1.52), 5.206 (0.44), 5.221 (0.97), 5.240 (0.94), 5.255 (0.45), 5.754 (0.63), 6.782 (1.85), 6.802 (2.07), 6.891 (0.88), 6.910 (1.89), 6.928 (1.09), 7.147 (0.94), 7.165 (1.54), 7.183 (0.71), 7.302 (1.62), 7.321 (1.48), 7.575 (1.18), 7.594 (1.75), 7.616 (3.91), 7.626 (8.51), 7.631 (4.90), 7.769 (2.16), 7.787 (1.79), 8.075 (0.67), 8.091 (1.40), 8.106 (0.67), 8.160 (0.82), 8.351 (1.65), 8.372 (1.58), 8.522 (5.37), 9.077 (1.61), 9.098 (1.57). |
| 376 | | LC-MS (Method L1): Rt = 1.21 min; MS (ESIpos): m/z = 449 [M + H]$^+$ | $^1$H-NMR (400 MHz, DMSO-d6) δ [ppm]: 2.074 (0.92), 2.081 (0.95), 2.090 (1.23), 2.099 (1.37), 2.107 (1.62), 2.115 (1.60), 2.167 (1.52), 2.189 (1.28), 2.328 (0.53), 2.671 (0.49), 4.258 (0.94), 4.276 (2.38), 4.286 (2.24), 4.307 (2.99), 4.317 (2.25), 4.325 (2.52), 4.345 (0.91), 5.311 (1.02), 5.327 (2.32), 5.344 (2.34), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 5.361 (1.07), 6.814 (4.66), 6.835 (5.19), 6.877 (2.09), 6.894 (4.48), 6.912 (2.65), 7.163 (2.38), 7.181 (3.70), 7.202 (1.79), 7.253 (3.98), 7.272 (3.65), 7.400 (3.14), 7.405 (3.55), 7.420 (6.02), 7.424 (5.83), 7.457 (5.34), 7.477 (7.81), 7.496 (3.47), 7.718 (5.20), 7.723 (5.42), 7.738 (4.66), 7.742 (4.46), 7.755 (1.40), 7.772 (6.63), 7.781 (7.42), 7.789 (16.00), 7.798 (1.88), 8.164 (3.15), 8.173 (2.91), 8.180 (2.79), 8.188 (2.77), 8.943 (7.32), 8.948 (7.68), 9.208 (4.01), 9.217 (9.88), 9.222 (9.87), 9.228 (4.19). |
| 386 | | LC-MS (Method L1): Rt = 1.36 min; MS (ESIpos): m/z = 526 [M + H]$^+$ | $^1$H-NMR (400 MHz, DMSO-d6) δ [ppm]: −0.149 (1.19), −0.008 (9.91), 0.146 (1.21), 1.523 (9.91), 1.529 (10.20), 1.541 (11.31), 1.552 (14.84), 1.572 (12.60), [2.009 (1.32), 2.018 (1.45), 2.028 (1.53), 2.045 (2.19), 2.052 (1.79), 2.072 (1.11), 2.178 (1.87), 2.190 (1.79), 2.200 (1.69), 2.327 (1.11), 2.366 (1.08), 2.669 (1.16), 2.709 (1.08), 3.848 (1.69), 4.207 (1.05), 4.226 (3.16), 4.234 (2.79), 4.245 (4.93), 4.254 (5.27), 4.270 (2.85), 4.289 (0.90), 5.243 (1.19), 5.258 (2.66), 5.276 (2.74), 5.292 (1.13), 5.753 (6.70), 6.771 (5.67), |
| | | | 6.791 (6.19), 6.895 (2.45), 6.914 (5.22), 6.933 (3.03), 7.141 (2.95), 7.159 (4.56), 7.176 (2.19), 7.327 (2.64), 7.334 (2.87), 7.353 (2.53), 7.465 (3.58), 7.471 (3.85), 7.489 (3.95), 7.495 (3.98), 7.736 (16.00), 7.745 (7.93), 7.752 (7.78), 7.769 (1.27), 7.911 (8.30), 7.918 (8.20), 8.473 (3.87), 8.483 (3.43), 8.489 (3.37), 8.498 (3.51), 8.669 (7.54), 8.679 (8.20), 9.119 (5.19), 9.139 (5.06). |
| 392 | | LC-MS (Method L1): Rt = 0.85 min; MS (ESIpos): m/z = 522 [M + H]$^+$ | $^1$H-NMR (400 MHz, DMSO-d6) δ [ppm]: −0.149 (0.44), −0.008 (3.87), 0.008 (3.75), 0.146 (0.44), 1.235 (0.52), 2.012 (0.57), 2.023 (0.75), 2.033 (0.65), 2.046 (1.16), 2.060 (1.08), 2.073 (1.84), 2.135 (0.41), 2.149 (1.12), 2.163 (1.23), 2.181 (0.72), 2.199 (0.67), 2.327 (0.42), 2.366 (0.41), 2.523 (1.29), 2.670 (0.43), 2.710 (0.44), 4.252 (2.47), 4.264 (4.03), 4.278 (2.39), 4.512 (0.46), 4.544 (1.08), 4.577 (2.07), 4.606 (1.41), 4.637 (1.95), 4.647 (2.10), 4.661 (0.77), 4.676 (0.74), 4.691 (0.69), 4.705 (0.72), 4.718 (0.44), 5.178 (0.62), 5.193 (1.42), 5.212 (1.43), 5.226 (0.63), 5.411 (0.80), 5.557 (0.79), 5.754 (4.87), 6.791 (2.68), 6.812 (2.97), 6.894 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (1.29), 6.897 (1.35), 6.915 (2.76), 6.931 (1.62), 6.934 (1.63), 7.150 (1.32), 7.154 (1.43), 7.171 (2.22), 7.189 (1.09), 7.192 (1.09), 7.314 (2.35), 7.331 (2.17), 7.472 (1.95), 7.490 (2.54), 7.493 (2.57), 7.511 (2.33), 7.614 (16.00), 7.737 (3.27), 7.753 (2.63), 7.755 (2.75), 8.065 (2.69), 8.084 (2.39), 8.181 (0.62), 8.488 (9.91), 9.045 (2.49), 9.065 (2.43). |
| 393 | | LC-MS (Method L1): Rt = 1.31 min; MS (ESIpos): m/z = 550 [M + H]$^+$ | $^1$H-NMR (400 MHz, DMSO-d6) δ [ppm]: −0.149 (0.46), 0.146 (0.50), 2.004 (1.48), 2.054 (1.02), 2.073 (1.42), 2.129 (0.86), 2.179 (1.60), 2.192 (1.83), 2.203 (1.71), 2.214 (1.57), 2.327 (0.49), 2.366 (0.54), 2.669 (0.51), 2.710 (0.49), 3.015 (0.72), 3.192 (1.52), 3.220 (1.63), 3.403 (0.84), 3.429 (1.56), 3.454 (1.45), 4.219 (0.48), 4.240 (1.51), 4.248 (1.25), 4.261 (2.24), 4.270 (2.16), 4.287 (1.32), 4.306 (0.49), 4.909 (0.62), 5.030 (0.63), 5.226 (0.65), 5.241 (1.44), 5.260 (1.43), 5.274 (0.66), 6.787 (2.64), 6.807 (2.91), 6.912 (1.29), 6.931 (2.76), 6.950 (1.60), 7.156 (1.39), 7.174 (2.28), 7.195 (1.06), 7.368 (2.41), 7.386 (2.21), 7.636 (16.00), 7.682 (1.66), 7.701 (2.56), 7.721 (2.23), 7.826 (3.11), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.844 (2.39), 8.205 (2.59), 8.225 (2.30), 8.680 (8.42), 9.126 (2.54), 9.147 (2.47). |
| 394 | | LC-MS (Method L1): Rt = 1.00 min; MS (ESIpos): m/z = 540 [M + H]$^+$ | $^1$H-NMR (400 MHz, DMSO-d6) δ [ppm]: −0.008 (3.00), 0.008 (2.42), 2.044 (0.47), 2.054 (0.42), 2.066 (0.71), 2.080 (0.65), 2.169 (0.68), 2.183 (0.74), 2.202 (0.45), 2.219 (0.41), 2.523 (0.83), 4.253 (1.55), 4.266 (2.43), 4.279 (1.48), 4.798 (2.52), 4.830 (5.19), 4.861 (2.27), 5.198 (0.90), 5.217 (0.92), 5.754 (0.78), 6.795 (1.66), 6.815 (1.81), 6.902 (0.81), 6.918 (1.67), 6.937 (0.99), 7.155 (0.84), 7.159 (0.87), 7.176 (1.38), 7.194 (0.66), 7.340 (1.43), 7.359 (1.33), 7.517 (1.16), 7.535 (1.55), 7.538 (1.50), 7.556 (1.38), 7.620 (16.00), 7.779 (1.90), 7.795 (1.64), 8.074 (1.60), 8.093 (1.48), 8.170 (0.52), 8.557 (5.90), 9.136 (1.49), 9.156 (1.43). |
| 396 | | LC-MS (Method L1): Rt = 1.18 min; MS (ESIpos): m/z = 526 [M + H]$^+$ | $^1$H-NMR (400 MHz, DMSO-d6) δ [ppm]: 0.008 (3.25), 1.618 (0.63), 1.631 (0.69), 1.648 (0.77), 1.909 (0.75), 1.922 (0.75), 1.930 (0.75), 1.943 (0.59), 2.327 (0.50), 2.366 (0.50), 2.669 (0.53), 2.710 (0.51), 3.929 (0.61), 3.951 (1.23), 3.972 (0.85), 4.084 (0.88), 4.094 (0.85), 4.102 (1.06), 4.122 (0.64), 4.979 (0.55), 4.994 (1.22), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 5.013 (1.22), 5.028 (0.55), 6.717 (2.55), 6.737 (2.73), 6.787 (5.10), 6.797 (4.07), 7.101 (0.99), 7.113 (1.39), 7.123 (1.52), 7.134 (1.07), 7.144 (0.75), 7.421 (1.35), 7.469 (1.36), 7.580 (1.91), 7.601 (2.47), 7.699 (16.00), 7.717 (2.39), 7.739 (1.49), 7.940 (2.48), 7.956 (2.12), 8.753 (1.33), 8.764 (1.43), 8.806 (1.46), 8.817 (1.31), 8.867 (1.92), 8.888 (1.86), 9.071 (6.62). |
| 397 | | LC-MS (Method L1): Rt = 1.05 min; MS (ESIpos): m/z = 541 [M + H]$^+$ | $^1$H-NMR (400 MHz, DMSO-d6) δ [ppm]: −0.008 (2.62), 0.844 (1.37), 0.859 (1.40), 1.235 (0.54), 1.800 (0.44), 2.047 (0.57), 2.523 (1.33), 2.670 (0.42), 4.167 (0.67), 5.116 (0.76), 6.516 (0.46), 6.737 (2.19), 6.757 (2.43), 6.847 (1.09), 6.865 (0.73), 7.118 (1.00), 7.136 (1.73), 7.154 (0.84), 7.465 (0.93), 7.679 (16.00), 7.726 (1.42), 7.747 (2.19), 7.765 (2.16), 7.869 (2.66), 7.890 (1.84), 7.917 (2.54), 7.920 (2.39), 7.934 (2.12), 8.852 (1.93), 8.873 (1.95), 8.981 (6.99). |
| 398 | | LC-MS (Method L1): Rt = 1.38 min; MS | $^1$H-NMR (400 MHz, DMSO-d6) δ [ppm]: −0.008 (2.48), 0.008 (2.72), 2.032 (0.71), 2.039 (0.77), 2.052 (0.85), 2.067 (1.16), 2.074 (0.99), 2.082 (0.73), 2.181 (0.77), 2.192 (1.10), 2.204 (1.13), 2.214 (1.15), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | (ESIpos): m/z = 568 [M + H]$^+$ | 2.251 (1.94), 2.289 (2.48), 2.322 (1.97), 2.366 (0.45), 3.331 (1.13), 3.348 (2.49), 3.364 (4.98), 3.378 (4.86), 3.393 (2.42), 3.410 (0.88), 4.210 (0.45), 4.217 (0.58), 4.238 (1.67), 4.245 (1.31), 4.259 (1.70), 4.266 (2.15), 4.275 (1.76), 4.281 (1.44), 4.290 (1.42), 4.303 (0.49), 4.309 (0.58), 5.228 (0.69), 5.243 (1.61), 5.262 (1.61), 5.276 (0.71), 6.789 (3.07), 6.810 (3.40), 6.911 (1.52), 6.929 (3.14), 6.948 (1.84), 7.156 (1.45), 7.159 (1.59), 7.176 (2.50), 7.194 (1.18), 7.198 (1.22), 7.367 (2.67), 7.384 (2.44), 7.636 (5.96), 7.639 (16.00), 7.692 (2.00), 7.713 (2.93), 7.731 (2.60), 7.847 (3.64), 7.864 (2.74), 8.262 (3.00), 8.283 (2.65), 8.719 (10.73), 9.173 (2.85), 9.193 (2.80). |
| 404 | | LC-MS (Method L1): Rt = 1.37 min; MS (ESIpos): m/z = 503 [M + H]$^+$ | $^1$H-NMR (400 MHz, DMSO-d6) δ [ppm]: −0.149 (0.92, −0.008 (7.44), 0.008 (8.20), 0.146 (0.97), 1.759 (0.46), 1.783 (1.32), 1.806 (1.48), 1.830 (0.56), 2.045 (1.32), 2.071 (2.55), 2.096 (1.99), 2.117 (0.82), 2.179 (1.12), 2.191 (1.17), 2.201 (1.07), 2.270 (0.97), 2.295 (1.43), 2.322 (2.50), 2.327 (2.39), 2.347 (1.43), 2.366 (1.99), 2.523 (4.48), 2.605 (1.22), 2.626 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.60), 2.650 (2.45), 2.669 (2.29), 2.710 (1.58), 4.221 (0.61), 4.241 (1.89), 4.249 (1.68), 4.260 (2.80), 4.269 (3.26), 4.283 (1.73), 4.301 (0.61), 4.343 (0.41), 4.366 (1.02), 4.387 (1.63), 4.407 (0.97), 5.218 (0.82), 5.233 (1.73), 5.252 (1.78), 5.266 (0.82), 6.781 (3.26), 6.801 (3.62), 6.902 (1.68), 6.921 (3.46), 6.940 (2.09), 7.145 (1.68), 7.149 (1.83), 7.166 (2.75), 7.187 (1.38), 7.342 (2.90), 7.359 (2.70), 7.630 (8.76), 7.635 (16.00 7.645 (4.54J 7.649 (3.52), 7.654 (1.58), 7.684 (2.39), 7.702 (3.26), 7.705 (3.11), 7.723 (3.11), 7.828 (3.87), 7.831 (4.23), 7.846 (3.16), 7.849 (3.26), 8.185 (3.31), 8.203 (2.96), 8.747 (11.87), 9.091 (3.11), 9.111 (3.01). |
| 406 | | LC-MS (Method L1): Rt = 1.27 min; MS (ESIpos): m/z = 457 [M + H]$^+$ | $^1$H-NMR (400 MHz, DMSO-d6) δ [ppm]: −0.008 (1.56), 0.008 (1.55), 1.529 (14.85), 1.546 (16.00), 1.555 (15.65), 1.573 (14.94), 2.014 (0.47), 2.030 (1.05), 2.038 (1.09), 2.048 (1.15), 2.056 (1.17), 2.065 (1.65), 2.072 (1.41), 2.080 (1.01), 2.089 (0.68), 2.171 (0.64), 2.181 (1.09), 2.193 (1.44), 2.204 (1.41), 2.214 (1.31), 2.228 (0.85), 2.236 (0.73), 2.248 (0.47), 3.830 (0.61), 3.848 (1.53), 3.866 (2.04), 3.884 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.51), 3.902 (0.60), 4.211 (0.53), 4.219 (0.74), 4.239 (2.42), 4.247 (2.13), 4 258 (3.89), 4.267 (4.11), 4.282 (2.22), 4.294 (0.55), 4.301 (0.71), 4.310 (0.46), 5.261 (1.00), 5.276 (2.23), 5.296 (2.26), 5.310 (1.00), 6.781 (4.24), 6.801 (4.69), 6.910 (2.06). |
| 407 | | LC-MS (Method L1): Rt = 1.31 min; MS (ESIpos): m/z = 507 [M + H]$^+$ | $^1$H-NMR (400 MHz, DMSO-d6) δ [ppm]: −0.149 (0.46), 0.008 (4.67), 0.146 (0.51), 1.530 (14.63), 1.548 (16.00), 1.557 (15.62), 1.575 (14.69), 2.030 (1.04), 2.039 (1.13), 2.056 (1.22), 2.065 (1.66), 2.073 (1.40), 2.081 (1.00), 2.172 (0.67), 2.181 (1.08), 2.193 (1.51), 2.205 (1.40), 2.214 (1.35), 2.229 (0.87), 2.248 (0.49), 2.327 (0.62), 2.366 (0.53), 2.670 (0.66), 2.710 (0.58), 3.830 (0.62), 3.849 (1.53), 3.866 (2.02), 3.885 (1.48), 3.903 (0.58), 4.217 (0.77), 4.237 (2.46), 4.245 (2.06), 4.257 (3.81), 4.266 (3.83), 4.283 (2.19), 4.302 (0.77), 5.262 (1.00), 5.276 (2.28), 5.296 (2.28), 5.310 (1.00), 6.781 (4.30), 6.802 (4.74), 6.912 (2.10), 6.928 (4.43), 6.947 (2.61), 7.147 (2.22), 7.150 (2.30), 7.167 (3.61), 7.185 (1.73), 7.189 (1.71), 7.344 (3.83), 7.362 (3.72), 7.399 (2.33), 7.415 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or
$\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.61), 7.478 (0.44), 7.498 (0.67), 7.561 (4.92), 7.579 (1.68), 7.598 (6.14), 7.608 (4.99), 7.615 (10.39 7.627 (1.57, 7.706 (0.73), 7.720 (3.01), 7.738 (4.46), 7.760 (4.03), 7.815 (5.50), 7.830 (3.57), 8.429 (3.90), 8.448 (3.68), 8.717 (14.67, 9.099 (3.86), 9.120 (3.81). |
| 408 | | LC-MS (Method L1): Rt = 1.26 min; MS (ESIpos): m/z = 509 [M + H]$^+$ | $^1$H-NMR (400 MHz, DMSO-d6) δ [ppm]: 1.533 (14.48), 1.551 (16.00), 1.559 (15.43), 1.577 (14.51), 2.019 (1.10), 2.027 (1.16), 2.037 (1.29), 2.043 (1.30), 2.053 (1.77), 2.061 (1.48), 2.069 (1.06), 2.170 (1.16), 2.182 (1.57), 2.193 (1.49), 2.204 (1.42), 2.216 (0.97), 2.669 (0.41), 3.835 (0.65), 3.852 (1.60), 3.870 (2.11), 3.888 (1.53), 3.906 (0.64), 4.206 (0.81), 4.227 (2.52), 4.234 (2.16), 4.247 (3.95), 4.256 (3.84), 4.273 (2.27), 4.292 (0.78), 5.247 (1.07), 5.261 (2.45), 5.280 (2.43), 5295 (1.05), 6.773 (4.46), 6.793 (5.02), 6.899 (2.19), 6.917 (4.73), 6.936 (2.74), 7.142 (2.33), 7.161 (3.88), 7.179 (1.81), 7.338 (4.13), 7.357 (3.80), 7.499 (2.10), 7.518 (4.65), 7.538 (2.73), 7.571 (0.56), 7.591 (1.20), 7.610 (0.68), 7.746 (2.26), 7.763 (5.20), 7.774 (3.98), 7.784 (4.83), 7.806 (5.93), 7.826 (3.63), 7.848 (3.46), 7.865 (1.75), 7.910 (0.66), 7.926 (0.75), 7.945 (0.64), 8.492 (3.95), 8.513 (3.73), 8.684 (13.95), 9.126 (4.03), 9.147 (3.92). |
| 409 | | LC-MS (Method L1): Rt = 1.24 min; MS (ESIpos): m/z = 475 [M + H]$^+$ | $^1$H-NMR (400 MHz, DMSO-d6) δ [ppm]: −0.149 (0.49), −0.008 (4.30), 0.008 (4.43), 0.146 (0.48), 1.531 (14.92), 1.549 (16.00), 1.558 (15.65), 1.576 (14.94), 2.016 (1.06), 2.025 (1.12), 2.034 (1.15), 2.041 (1.17), 2.051 (1.63), 2.059 (1.41), 2.067 (0.01), 2.163 (0.62), 2.172 (1.08), 2.184 (1.45), 2.196 (1.41), 2.205 (1.30), 2.219 (0.84), 2.226 (0.75), 2.239 (0.48), 2.327 (0.49), 2.366 (0.70), 2.669 (0.59), 2.709 (0.71), 3.828 (0.60), 3.845 (1.48), 3.863 (1.98), 3.881 (1.45), 3.899 (0.57), 4.202 (0.55), 4.210 (0.79), 4.230 (2.42), 4.238 (2.09), 4.249 13.86), 4.258 (3.99), 4.275 (2.18), 4.286 (0.59), 4.294 (0.75), 4.302 (0.48), 5.250 (0.99), 5.264 (2.18), 5.284 (2.22), 5.298 (0.99), 6.774 (4.12), 6.792 (4.36), 6.795 (4.54), 6.900 (2.03), 6.902 (2.11), 6.919 (4.30), 6.921 (4.32), 6.937 (2.60), 6.940 (2.56), 7.140 (2.12), 7.144 (2.29), 7.161 (3.50), 7.179 (1.70), 7.182 (1.70), 7.309 (2.18), 7.329 (5.82), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.339 (3.97), 7.348 (4.54), 7.357 (3.62), 7.384 (2.38), 7.388 (2.82), 7.399 (2.69), 7.403 (3.70), 7.418 (1.65), 7.423 (1.54), 7.628 (1.94), 7.633 (2.05), 7.648 (3.06), 7.666 (1.81), 7.670 (1.70), 7.730 (2.00), 7.748 (4.98), 7.768 (6.90), 7.771 (6.96), 7.776 (6.74), 7.788 (2.22), 7.793 (1.39), 8.470 (3.41), 8.475 (3.42), 8.491 (3.33), 8.495 (3.17), 8.692 (14.76), 9.114 (3.73), 9.135 (3.70). |
| 410 | | LC-MS (Method L1): Rt = 1.26 min; MS (ESIpos): m/z = 475 [M + H]$^+$ | $^1$H-NMR (400 MHz, DMSO-d6) δ [ppm]: −0.008 (3.13), 0.008 (3.29), 0.146 (0.40), 1.528 (14.85), 1.546 (16.00), 1.555 (15.61), 1.573 (15.00), 2.001 (0.49), 2.016 (1.06), 2.025 (1.11), 2.035 (1.18), 2.042 (1.17), 2.052 (1.64), 2.059 (1.39), 2.067 (1.00), 2.163 (0.65), 2.173 (1.07), 2.185 (1.47), 2.197 (1.40), 2.207 (1.31), 2.218 (0.85), 2.327 (0.48), 2.366 (0.42), 2.669 (0.53), 2.709 (0.46), 3.821 (0.64), 3.839 (1.49), 3.857 (1.95), 3.874 (1.44), 3.892 (0.60), 4.202 (0.56), 4.210 (0.78), 4 230 (2.43), 4.238 (2.08), 4.249 (3.91), 4.259 (3.92), 4.275 (2.22), 4.294 (0.76), 5.251 (1.01), 5.265 (2.22), 5.285 (2.26), 5.300 (0.99), 6.774 (4.47), 6.795 (4.89), 6.900 (2.08), 6.903 (2.17), 6.921 (4.49), 6.937 (2.63), 6.940 (2.65), 7.141 (2.17), 7.144 (2.30), 7.162 (3.63), 7.179 (1.71), 7.183 (1.71), 7.323 (3.21), 7.338 (4.16), 7.345 (6.69), 7.355 (3.75), 7.368 (3.97), 7.485 (2.85), 7.492 (4.04), 7.500 (2.96), 7.507 (4.05), 7.515 (2.58), 7.522 (2.10), 7.525 (2.92), 7.533 (1.86), 7.536 (2.35), 7.544 (1.88), 7.547 (2.22), 7.554 (1.51), 7.721 (2.43), 7.739 (4.57), 7.760 (4.71), 7.785 (5.80), 7.799 (2.83), 8.463 (3.64), 8.466 (3.77), 8.484 (3.54), 8.487 (3.37), 8.687 (15.55), 9.113 (3.86), 9.133 (3.75). |
| 411 | | LC-MS (Method L1): Rt = 1.31 min; MS (ESIpos): m/z = 491 [M + H]$^+$ | $^1$H-NMR (400 MHz, DMSO-d6) δ [ppm]: −0.149 (0.52), −0.008 (4.69), 0.008 (4.82), 0.146 (0.52), 1.534 (14.70), 1.552 (16.00), 1.560 (15.73), 1.578 (14.85), 2.031 (1.01), 2.039 (1.07), 2.056 (1.17), 2.066 (1.67), 2.074 (1.42), 2.170 (0.64), 2.191 (1.44), 2.203 (1.40), 2.213 (1.34), 2.225 (0.87), 2.328 (0.66), 2.366 (0.78), 2.670 (0.70), 2.710 (0.72), 3.840 (0.62), 3.856 (1.50), 3.874 (2.00), 3.892 (1.50), 3.909 (0.58), 4.216 (0.76), 4.236 (2.41), 4.245 (2.10), 4.256 (3.85), 4.265 (3.95), 4.282 (2.20), 4.300 (0.76), 5.259 (0.97), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 5.274 (2.22), 5.293 (2.27), 5.308 (1.01), 6.781 (4.32), 6.801 (4.72), 6.910 (2.06), 6.928 (4.39), 6.945 (2.59), 7.145 (2.20), 7.149 (2.33), 7.167 (3.62), 7.184 (1.71), 7.188 (1.69), 7.347 (3.77), 7.364 (3.48), 7.511 (0.54), 7.694 (1.57), 7.713 (4.35), 7.732 (6.71), 7.750 (4.76), 7.754 (5.35), 7.759 (5.37), 7.771 (4.57), 7.836 (5.46), 7.852 (3.71), 7.874 (3.95), 7.897 (7.35), 8.441 (3.99), 8.461 (3.67), 8.721 (15.16), 9.107 (3.85), 9.128 (3.77). |
| 412 | | LC-MS (Method L1): Rt = 1.12 min; MS (ESIpos): m/z = 542 [M + H]$^+$ | $^{1}$H-NMR (400 MHz, DMSO-d6) δ [ppm]: 0.146 (0.43), 1.233 (0.49), 1.756 (0.67), 1.768 (0.74), 1.784 (0.78), 2.002 (0.81), 2.015 (0.83), 2.023 (0.78), 2.037 (0.56), 2.327 (0.67), 2.366 (0.58), 2.669 (0.76), 2.709 (0.61), 3.946 (0.74), 3.967 (1.32), 3.988 (0.85), 4.134 (0.94), 4.152 (1.10), 4.171 (0.72), 5.059 (0.65), 5.074 (1.28), 5.093 (1.21), 5.107 (0.54), 6.729 (2.29), 6.749 (2.44), 6.854 (0.94), 6.874 (2.31), 6.892 (1.77), 6.932 (2.42), 6.949 (1.39), 7.094 (5.94), 7.108 (1.79), 7.130 (1.99), 7.147 (1.01), 7.685 (16.00), 7.719 (1.55), 7.738 (2.20), 7.758 (2.11), 7.861 (2.62), 7.880 (1.93), 7.921 (2.62), 7.938 (2.15), 8.272 (1.86), 8.864 (2.29), 8.884 (2.13), 8.993 (6.79). |
| 418 | | LC-MS (Method L1): Rt = 1.23 min; MS (ESIpos): m/z = 475 [M + H]$^+$ | $^{1}$H-NMR (400 MHz, DMSO-d6) δ [ppm]: −0.008 (1.65), 0.008 (1.55), 1.529 (9.91), 1.546 (10.68), 1.556 (11.45), 1.574 (10.97), 2.011 (0.79), 2.019 (0.83), 2.329 (0.86), 2.036 (0.88), 2.046 (1.25), 2.054 (1.05), 2.061 (0.78), 2.070 (0.55), 2.085 (16.00), 2.158 (0.47), 2.167 (0.82 2.180 (1.09), 2.191 (1.07), 2.201 (0.98), 2.212 (0.63), 2.523 (0.80), 3.816 (0.45), 3.833 (1.04), 3.851 (1.38), 3.869 (1.03), 3.887 (0.42), 4.208 (0.56), 4.228 (1.84), 4.236 (1.62), 4.247 (2.92), 4.255 (3.09), 4.271 (1.69), 4.283 (0.43), 4.290 (0.53), 5.247 (0.74), 5.261 (1.64), 5.281 4.65), 5.295 (0.75), 6.771 (3.27), 5.791 (3.58), 6.894 (1.53), 6.897 (1.53), 6.913 (3.26), 6.932 (1.99), 6.934 (1.87), 7.137 (1.66), 7.141 (1.75), 7.158 (2.68), 7.175 (1.32), 7.179 (1.28), 7.258 (1.26), 7.279 (1.22), 7.293 (1.89), 7.301 (1.38), 7.315 (2.98), 7.323 (2.78), 7.331 (2.81), 7.336 (2.95), 7.344 (2.35), 7.349 (2.44), 7.577 (1.76), 7.590 (1.90), 7.599 (1.75), 7.612 (1.58), 7.682 (1.73), 7.686 (2.13), 7.700 (4.61), 7.703 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (4.23), 7.717 (3.84), 7.738 (3.71), 7.756 (1.81), 8.452 (2.70), 8.456 (2.79), 8.473 (2.60), 8.477 (2.48), 8.660 (9.72), 9.115 (2.91), 9.136 (2.80). |
| 419 | | LC-MS (Method L1): Rt = 1.30 min; MS (ESIpos): m/z = 475 [M + H]$^+$ | $^1$H-NMR (400 MHz, DMSO-d6) δ [ppm]: −0.149 (0.50), −0.008 (4.19), 0.008 (4.14), 0.146 (0.48), 1.525 (14.78), 1.543 (16.00), 1.552 (15.64), 1.569 (14.85), 2.030 (1.00), 2.038 (1.03), 2.048 (1.12), 2.055 (1.12), 2.065 (1.63), 2.073 (1.39), 2.081 (1.00), 2.171 (0.65), 2.180 (1.08), 2.192 (1.46), 2.204 (1.39), 2.214 (1.24), 2.228 (0.84), 2.327 (0.79), 2.366 (0.62), 2.669 (0.84), 2.709 (0.67), 3.832 (0.62), 3.848 (1.48), 3.866 (2.03), 3.884 (1.48), 3.902 (0.60), 4.210 (0.55), 4.219 (0.79), 4.239 (2.42), 4.247 (2.06), 4.258 (3.87), 4.267 (3.99), 4.283 (2.18), 4.302 (0.72), 4.311 (0.50), 5.260 (0.96), 5.275 (2.20), 5.294 (2.22), 5.309 (0.98), 6.781 (4.28), 6.802 (4.71), 6.911 (2.01), 6.913 (2.08), 6.932 (4.35), 6.948 (2.63), 6.951 (2.58), 7.147 (2.13), 7.151 (2.32), 7.169 (3.54), 7.186 (1.70), 7.190 (1.75), 7.350 (3.71), 7.368 (3.44), 7.419 (3.16), 7.423 (2.92), 7.444 (3.09), 7.447 (3.04), 7.457 (2.15), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.462 (3.32), 7.467 (2.25), 7.479 (1.87), 7.484 (3.52), 7.489 (2.87), 7.496 (5.60), 7.500 (7.01), 7.624 (0.55), 7.717 (2.82), 7.735 (4.69), 7.756 (4.26), 7.838 (5.41), 7.854 (3.78), 7.856 (3.73), 8.442 (3.97), 8.461 (3.61), 8.753 (15.50 9.106 (3.90), 9.126 (3.80). |
| 420 | | LC-MS (Method L1): Rt = 1.27 min; MS (ESIpos): m/z = 525 [M + H]$^+$ | $^1$H-NMR (400 MHz, DMSO-d6) δ [ppm]: −0.008 (3.45), 0.008 (3.55), 0.146 (0.41), 1.529 (9.38), 1.539 (9.80), 1.547 (11.02), 1.559 (16.00), 1.578 (11.91), 1.581 (11.87), 2.011 (1.20), 2.030 (1.39), 2.039 (1.60), 2.046 (1.79), 2.054 (1.43), 2.085 (5.81), 2.174 (1.52), 2.186 (1.56), 2.196 (1.37), 2.327 (0.68), 2.366 (0.75), 2.669 (0.68), 2.710 (0.73), 3.848 (1.31), 3.865 (1.68), 3.878 (1.31), 4.199 (0.71), 4.219 (1.78), 4.227 (2.57), 4.241 (3.61), 4.250 (4.05), 4.267 (2.68), 4.285 (0.85), 5.257 (2.24), 5.271 (2.20), 5.754 (2.22), 6.767 (5.06), 6.788 (5.62), 6.888 (1.37), 6.892 (1.52), 6.906 (2.91), 6.911 (3.15), 6.925 (1.81), 6.929 (1.89), 7.135 (2.64), 7.155 (4.03), 7.174 (2.05), 7.319 (2.22), 7.337 (4.15), 7.354 (2.18), 7.424 (0.50), 7.440 (0.83), 7.444 (0.87), 7.458 (0.42), 7.475 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.42), 7.487 (0.77), 7.505 (0.62), 7.609 (0.89), 7.627 (2.80), 7.640 (3.51), 7.646 (3.20), 7.658 (5.83), 7.677 (3.53), 7.680 (3.53), 7.700 (1.81), 7.706 (2.86), 7.709 (3.38), 7.723 (7.68), 7.727 (7.16), 7.736 (5.71), 7.757 (5.40), 7.775 (2.37), 7.894 (0.44), 7.916 (4.48), 7.921 (4.48), 7.935 (3.88), 7.940 (3.80), 8.475 (4.00), 8.479 (4.25), 8.496 (3.88), 8.500 (3.84), 8.649 (8.55), 8.658 (9.36), 9.107 (2.39), 9.126 (3.82), 9.145 (2.35). |
| 421 | | LC-MS (Method L1): Rt = 1.22 min; MS (ESIpos): m/z = 475 $[M + H]^+$ | $^1$H-NMR (400 MHz, DMSO-d6) δ [ppm]: −0.008 (0.74), 0.008 (0.66), 1.398 (16.00), 1.531 (2.32), 1.549 (2.57), 1.558 (3.55), 1.576 (3.28), 2.044 (0.42), 3.853 (0.41), 4.226 (0.60), 4.235 (0.52), 4.245 (0.96), 4.254 (1.03), 4.270 (0.56), 5.259 (0.53), 5.278 (0.54), 6.770 (1.05), 6.790 (1.17), 6.894 (0.43), 6.913 (0.95), 6.931 (0.55), 7.136 (0.49), 7.139 (0.53), 7.157 (0.86), 7.175 (0.41), 7.178 (0.42), 7.223 (0.50), 7.329 (0.63), 7.348 (0.59), 7.451 (1.08), 7.460 (1.29), 7.472 (1.04), 7.479 (1.04), 7.685 (0.58), 7.688 (0.73), 7.702 (1.46), 7.706 (1.42), 7.723 (1.24), 7.744 (1.24), 7.762 (0.62), 8.461 (0.89), 8.464 (0.98), 8.482 (0.88), 8.485 (0.89), 8.653 (1.41), 9.113 (0.66), 9.133 (0.64). |
| 422 | | LC-MS (Method L1): Rt = 1.26 min; MS (ESIpos): m/z = 457 $[M + H]^+$ | $^1$H-NMR (400 MHz, DMSO-d6) δ [ppm]: −0.008 (2.40), 0.008 (2.26), 1.141 (0.70), 1.520 (7.81), 1.537 (8.37), 1.547 (8.11), 1.564 (7.78), 2.023 (0.54), 2.031 (0.58), 2.048 (0.63), 2.058 (0.85), 2.066 (0.74), 2.075 (0.59), 2.085 (6.90), 2.161 (16.00), 2.177 (0.76), 2.189 (0.78), 2.201 (0.76), 2.211 (0.70), 2.327 (0.45), 2.386 (0.52), 2.395 (0.44), 2.416 (12.94), 2.670 (0.45), 3.822 (0.75), 3.841 (1.02), 3.858 (0.72), 4.238 (1.26), 4.246 (1.09), 4.257 (2.03), 4.265 (2.14), 4.282 (1.14), 5.259 (0.50), 5.273 (1.16), 5.293 (1.14), 5.307 (0.53), 5.754 (0.60), 6.710 (3.80), 6.712 (3.83), 6.779 (2.31), 6.799 (2.52), 6.911 (1.13), 6.927 (2.33), 6.946 (1.40), 7.145 (1.16), 7.149 (1.23), 7.167 (1.85), 7.184 (0.91), 7.341 (1.95), 7.359 (1.78), 7.624 (1.06), 7.628 (1.41), 7.642 (3.30), 7.646 (3.02), 7.655 (2.78), 7.676 (2.61), 7.694 (1.18), 8.342 (1.79), 8.346 (1.89), 8.363 (1.74), 8.367 (1.66), 8.686 (8.47), 9.079 (1.98), 9.100 (1.92). |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 423 | | LC-MS (Method L1): Rt = 1.35 min; MS (ESIpos): m/z = 497 $[M + H]^+$ | $^{1}$H-NMR (400 MHz, DMSO-d6) δ [ppm]: 1.141 (0.76), 1.356 (1.34), 1.519 (14.63), 1.537 (16.00), 1.546 (15.53), 1.564 (14.65), 2.023 (1.05), 2.031 (1.09), 2.049 (1.27), 2.058 (1.67), 2.066 (1.49), 2.085 (11.52), 2.183 (1.31), 2.191 (1.53), 2.203 (1.48), 2.212 (1.37), 2.327 (0.60), 2.366 (0.65), 2.670 (0.66), 2.709 (0.66), 3.811 (0.65), 3.829 (1.53), 3.847 (2.05), 3.865 (1.54), 3.881 (0.61), 4.215 (0.80), 4.235 (2.49), 4.243 (2.19), 4.255 (3.96), 4.264 (3.93), 4.281 (2.31), 4.300 (0.76), 5.257 (1.04), 5.273 (2.31), 5.292 (2.38), 5.306 (1.02), 5.754 (1.15), 6.779 (4.42), 6.799 (4.85), 6.912 (2.14), 6.930 (4.56), 6.947 (2.64), 7.149 (2.39), 7.167 (3.78), 7.188 (1.87), 7.231 (13.75), 7.346 (3.92), 7.364 (3.67), 7.716 (2.56), 7.734 (4.37), 7.755 (4.14), 7.800 (5.63), 7.815 (3.43), 8.454 (3.95), 8.473 (3.67), 8.737 (14.24), 9.105 (3.82), 9.125 (3.71). |
| 424 | | LC-MS (Method L1): Rt = 0.83 min; MS (ESIpos): m/z = 492 $[M + H]^+$ | $^{1}$H-NMR (400 MHz, DMSO-d6) δ [ppm]: −0.149 (0.62), 0.146 (0.58), 2.082 (0.85), 2.092 (0.94), 2.118 (1.45), 2.126 (1.23), 2.220 (1.28), 2.232 (1.23), 2.242 (1.10), 2.328 (0.69), 2.366 (0.74), 2.670 (0.75), 2.710 (0.77), 3.046 (2.57), 3.168 (0.82), 3.426 (3.56), 3.443 (4.68), 4.227 (0.88), 4.247 (2.21), 4.256 (1.97), 4.267 (3.31), 4.275 (3.45), 4.292 (1.93), 4.310 (0.72), 5.298 (1.79), 5.314 (1.79), 6.790 (3.71), 6.811 (4.03), 6.913 (1.81), 6.931 (3.79), 6.949 (2.21), 7.158 (1.97), 7.176 (3.10), 7.196 (1.57), 7.376 (3.26), 7.394 (2.97), 7.646 (8.78), 7.650 (16.00), 7.658 (5.74), 7.662 (4.49), 7.772 (1.84), 7.790 (3.18), 7.811 (2.48), 7.898 (4.35), 7.915 (3.20), 8.337 (0.98), 8.400 (2.78), 8.421 (2.49), 8.895 (10.41), 9.594 (1.37). |
| 425 | | LC-MS (Method L1): Rt = 1.26 min; MS (ESIpos): m/z = 475 $[M + H]^+$ | $^{1}$H-NMR (400 MHz, DMSO-d6) δ [ppm]: −0.008 (1.52), 0.008 (1.58), 1.509 (12.78), 1.527 (13.71), 1.536 (13.42), 1.554 (12.80), 2.013 (0.92), 2.022 (1.01), 2.032 (1.08), 2.039 (1.12), 2.049 (1.52), 2.056 (1.44), 2.085 (7.75), 2.172 (0.94), 2.184 (1.30), 2.196 (1.24), 2.206 d-19), 2.219 (0.80), 2.240 (0.47), 2.327 (0.45), 2.366 (0.47), 2.423 (16.00), 2.669 (0.46), 2.710 (0.40), 3.804 (0.54), 3.823 (1.32), 3.840 (1.76), 3.859 (1.30), 3.876 (0.52), 4.201 (0.51), 4.208 (0.72), 4.228 (2.09), 4236 (1.71), 4.249 (2.84), 4.259 (2.77), 4.267 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (1.88), 4.277 (1.91), 4.288 (0.56), 4.295 (0.68), 4.304 (0.47), 5.246 (0.87), 5.260 (1.95), 5.280 (1.96), 5.294 (0.85), 5.754 (7.58), 6.631 (2.13), 6.777 (3.89), 6.797 (4.26), 6.902 (1.75), 6.904 (1.90), 6.923 (3.94), 6.939 (2.29), 6.942 (2.32), 7.143 (1.85), 7.147 (2.06), 7.164 (3.17), 7.182 (1.50), 7.185 (1.53), 7.334 (3.33), 7.352 (3.03), 7.618 (2.57), 7.641 (4.67), 7.664 (2.68), 8.442 (2.31), 8.457 (2.47), 8.465 (2.46), 8.481 (2.28), 8.709 (12.28), 9.081 (3.16), 9.102 (3.09). |
| 426 | | LC-MS (Method L1): Rt = 1.32 min; MS (ESIpos): m/z = 515 [M + H]$^+$ | $^{1}$H-NMR (400 MHz, DMSO-d6) δ [ppm]: −0.149 (0.83), −0.008 (6.50), 0.008 (7.02), 0.146 (0.83), 1.235 (0.67), 1.508 (14.93), 1.526 (15.98), 1.534 (16.00), 1.552 (15.19), 2.051 (1.31), 2.073 (1.29), 2.085 (2.88), 2.185 (1.50), 2.198 (1.48), 2.207 (1.40), 2.220 (0.98), 2.327 (0.90), 2.366 (0.95), 2.669 (0.93), 2.710 (0.93), 3.828 (1.33), 3.846 (1.74), 3.863 (1.31), 4.206 (0.79), 4.225 (2.29), 4.233 (1.88), 4.252 (2.95), 4.259 (2.71), 4.267 (2.05), 4.276 (2.19), 4.295 (0.83), 5.245 (0.93), 5.259 (2.12), 5.278 (2.17), 5.292 (0.98), 6.776 (4.48), 6.796 (4.88), 6.905 (2.21), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.924 (4.50), 6.940 (2.71), 7.144 (2.24), 7.147 (2.40), 7.165 (3.71), 7.186 (1.83), 7.205 (3.79), 7.230 (3.98), 7.333 (1.83), 7.346 (2.26), 7.362 (1.69), 7.687 (2.98), 7.710 (5.17), 7.732 (3.05), 8.553 (2.71), 8.568 (2.88), 8.577 (2.88), 8.593 (2.71), 8.764 (7.26), 9.111 (3.05), 9.132 (3.05). |
| 428 | | LC-MS (L2): Rt = 3.893 min; m/z = 517/5519 [M + H]+ | $^{1}$H-NMR (400 MHz, DMSO-d6) δ 9.16 (d, J = 8.1 Hz, 1H), 8.72 (s, 1H), 8.69 (d, J = 1.9 Hz, 1H), 8.14 (d, J = 1.8 Hz, 1H), 7.71-7.66 (m, 3H), 7.37 (d, J = 7.9, 1.7 Hz, 1H), 7.17 (t, J = 8.5, 7.4, 1.7 Hz, 1H), 6.92 (t, J = 7.4, 1.2 Hz, 1H), 6.80 (d, J = 8.3, 1.2 Hz, 1H), 5.23 (q, J = 5.8 Hz, 1H), 4.32-4.17 (m, 2H), 3.12 (s, 6H), 2.26-2.14 (m, 1H), 2.10-1.99 (m, 1H). |
| 430 | | LC-MS (Method L1): Rt =1.23 min; MS (ESIpos): m/z = 459 [M + H]$^+$ | $^{1}$H-NMR (400 MHz, DMSO-d6) δ [ppm]: 0.008 (1.38), 1.526 (14.80), 1.543 (16.00), 1.552 (15.65), 1.570 (14.87), 2.029 (1.04), 2.038 (1.12), 2.047 (1.19), 2.055 (1.21), 2.064 (1.68), 2.072 (1.42), 2.080 (1.02), 2.087 (0.71), 2.172 (0.65), 2.181 (1.10), 2.193 (1.48), 2.205 (1.42), 2.215 (1.36), 2.228 (0.86), 3.828 (0.64), 3.845 (1.58), 3.863 (2.07), 3.881 (1.54), 3.899 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (0.60), 4.211 (0.56), 4.219 (0.77), 4.239 (2.44), 4.247 (2.13), 4.258 (3.96), 4.267 (4.09), 4.283 (2.26), 4.302 (0.73), 5.262 (1.01), 5.277 (2.33), 5.296 (2.31), 5.311 (1.05), 6.781 (4.65), 6.801 (5.20), 6.912 (2.17), 6.930 (4.68), 6.949 (2.74), 7.150 (2.33), 7.168 (3.75), 7.189 (1.74), 7.252 (1.63), 7.258 (1.26), 7.276 (3.15), 7.282 (3.16), 7.301 (6.35), 7.318 (6.19), 7.334 (1.02), 7.348 (4.05), 7.366 (3.67), 7.716 (2.63), 7.734 (4.12), 7.755 (3.67), 7.834 (5.55), 7.851 (4.00), 8.438 (4.18), 8.459 (3.86), 8.750 (14.88), 9.106 (3.97), 9.126 3.90). |
| 431 | | LC-MS (Method L1): Rt = 1.37 min; MS (ESIpos): m/z = 525 $[M + H]^+$ | $^1$H-NMR (400 MHz, DMSO-d6) δ [ppm]: 0.008 (2.75), 1.530 (14.75), 1.548 (16.00), 1.556 (15.84), 1.574 (14.95), 2.034 (1.00), 2.043 (1.11), 2.053 (1.16), 2.059 (1.19), 2.069 (1.70), 2.077 (1.41), 2.085 (1.05), 2.191 (1.50), 2.203 (1.47), 2.213 (1.38), 2.226 (0.88), 2.328 (0.61), 2.366 (0.66), 2.670 (0.63), 2.710 (0.66), 3.843 (0.64), 3.860 (1.58), 3.878 (2.08), 3.896 (1.53), 3.914 (0.61), 4.209 (0.61), 4.217 (0.75), 4.237 (2.49), 4.245 (2.13), 4.257 (3.91), 4.266 (4.02), 4.282 (2.22), 4.301 (0.75), 5.258 (1.02), 5.273 (2.30), 5.292 (2.31), 5.307 (1.03), 6.782 (4.49), 6.802 (4.96), 6.913 (2.21), 6.931 (4.58), 6.950 (2.69), 7.151 (2.39), 7.168 (3.68), 7.190 (1.78), 7.351 (3.93), 7.370 (3.58), 7.740 (2.83), 7.758 (4.07), 7.761 (3.88), 7.779 (3.71), 7.891 (10.85), 7.902 (6.54), 7.909 (5.57), 7.968 (6.30), 8.471 (4.19), 8.492 (3.75), 8.752 (15.12), 9.117 (4.02), 9.138 (3.91). |
| 432 | | LC-MS (Method L1): Rt = 0.93 min; MS (ESIpos): m/z = 506 $[M + H]^+$ | $^1$H-NMR (500 MHz, DMSO-d6) δ [ppm]: 2.063 (0.44), 2.074 (1.74), 2.085 (0.57), 2.091 (0.49), 2.154 (16.00), 2.213 (0.54), 2.223 (0.51), 2.230 (0.52), 3.994 (3.21), 4.221 (0.41), 4.226 (0.88), 4.232 (0.59), 4.243 (0.65), 4249 (0.52), 4.271 (0.53), 4.278 (0.67), 4.284 (0.59), 4.291 (0.69), 5.297 (0.75), 5.313 (0.74), 6.792 (1.44), 6.793 (1.49), 6.808 (1.59), 6.810 (1.58), 6.918 (0.74), 6.920 (0.73), 6.933 (1.47), 6.935 (1.43), 6.948 (0.86), 6.950 (0.81), 7.160 (0.72), 7.163 (0.74), 7.177 (1.18), 7.191 (0.60), 7.194 (0.57), 7.404 (1.21), 7.418 (1.15), 7.646 (0.87), 7.655 (9.82), 7.725 (1.04), 7.739 (1.43), 7.741 (1.26), 7.756 (1.25), 7.863 (1.61), 7.866 (1.64), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.877 (1.33), 7.880 (1.26), 8.164 (1.66), 8.523 (1.33), 8.526 (1.33), 8.540 (1.27), 8.543 (1.20), 8.920 (5.25), 9.432 (1.31), 9.448 (1.27). |
| 438 | | LC-MS (Method L1): Rt = 1.37 min; MS (ESIpos): m/z = 509 $[M + H]^+$ | $^1$H-NMR (400 MHz, DMSO-d6) δ [ppm]: −0.149 (0.41), −0.008 (3.62), 0.008 (3.26), 1.356 (1.83), 1.523 (14.77), 1.541 (16.00), 1.550 (15.57), 1.568 (14.88), 2.032 (1.00), 2.041 (1.04), 2.051 (1.14), 2.058 (1.00), 2.067 (1.68), 2.073 (2.66), 2.084 (1.01), 2.170 (0.66), 2.183 (1.20), 2.192 (1.42), 2.203 (1.34), 2.213 (1.30), 2.225 (0.81), 2.323 (0.49), 2.327 (0.62), 2.366 (0.55), 2.523 (1.52), 2.670 (0.68), 2.709 (0.55), 3.833 (0.60), 3.851 (1.50), 3.869 (2.02), 3.887 (1.45), 3.905 (0.60), 4.211 (0.54), 4.219 (0.74), 4.239 (2.40), 4.247 (2.04), 4.258 (3.83), 4.267 (3.95), 4.283 (2.15), 4.301 (0.70), 5.260 (0.98), 5.274 (2.17), 5.294 (2.20), 5.308 (0.96), 5.754 (6.17), 6.780 (4.02), 6.782 (4.25), 6.800 (4.58), 6.803 (4.65), 6.912 (2.09), 6.915 (2.10), 6.931 (4.36), 6.933 (4.28), 6.949 (2.67), 6.952 (2.58), 7.148 (2.17), 7.152 (2.29), 7.169 (3.48), 7.187 (1.71), 7.190 (1.68), 7.351 (3.62), 7.370 (3.40), 7.717 (2.99), 7.735 (4.36), 7.738 (3.68), 7.756 (4.00), 7.786 (15.35), 7.802 (15.29), 7.853 (5.04), 7.855 (5.31), 7.870 (4.03), 7.873 (3.81), 7.907 (0.55), 7.923 0.54), (8.444 (3.89), 8.464 (3.67), 8.762 (15.95), 9.108 (3.86), 9.129 (3.76). |
| 439 | | LC-MS (Method L1): Rt = 1.10 min; MS (ESIpos): m/z = 560 $[M + H]^+$ | $^1$H-NMR (400 MHz, DMSO-d6) δ [ppm]: −0.008 (2.89), 0.008 (3.10), 1.826 (0.43), 2.073 (1.46), 2.086 (0.91), 2.327 (0.43), 2.366 (0.59), 2.670 (0.47), 2.710 (0.59), 4.178 (0.90), 5.127 (1.22), 5.141 (1.19), 6.747 (2.96), 6.767 (3.31), 6.836 (0.98), 6.920 (0.57), 7.045 (0.47), 7.124 (1.50), 7.145 (2.50), 7.162 (1.27), 7.258 (0.57), 7.333 (0.67), 7.467 (0.72), 7.672 (7.22), 7.676 (16.00), 7.682 (6.08), 7.685 (3.72), 7.732 (2.26), 7.750 (2.96), 7.753 (3.13), 7.771 (3.12), 7.911 (3.10), 7.929 (5.80), 7.932 (5.43), 7.946 (3.43), 8.870 (1.48), 8.885 (1.41), 9.005 (5.27), 12.563 (0.65). |
| 444 | | LC-MS (Method L1): Rt = 1.30 min; MS (ESIpos): | $^1$H-NMR (400 MHz, DMSO-d6) δ [ppm]: −0.008 (3.30), 0.008 (2.88), 1.528 (9.79), 1.546 (10.48), 1.555 (10.17), 1.573 (9.77), 2.017 (0.68), 2.025 (0.71), 2.035 (0.76), 2.043 (0.78), 2.052 (1.09), 2.060 (0.90), 2.068 (0.66), 2.162 (0.45), 2.171 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | m/z = 489 [M + H]$^+$ | (0.73), 2.184 (1.01), 2.196 (0.94), 2.205 (0.87), 2.219 (0.57), 2.327 (0.73), 2.346 (16.00), 2.366 (0.80), 2.523 (1.25), 2.665 (0.40), 2.669 (0.54), 2.710 (0.61), 3.841 (0.97), 3.859 (1.27), 3.877 (0.94), 4.211 (0.50), 4.231 (1.58), 4.239 (1.35), 4250 (2.53), 4.259 (2.64), 4.275 (1.46), 4.294 (0.47), 5.249 (0.64), 5.264 (1.44), 5.283 (1.46), 5.297 (0.61), 6.775 (2.69), 6.793 (2.86), 6.795 (2.95), 6.901 (1.37), 6.904 (1.39), 6.920 (2.83), 6.922 (2.83), 6.938 (1.75), 6.941 (1.70), 7.141 (1.39), 7.145 (1.49), 7.162 (2.34), 7.180 (2.86), 7.183 (2.93), 7.195 (1.84), 7.199 (1.79), 7.340 (2.41), 7.357 (2.27), 7.451 (1.63), 7.455 (1.58), 7.468 (1.65), 7.472 (1.56), 7.716 (1.16), 7.734 (3.42), 7.753 (6.32), 7.756 (5.45), 7.768 (1.30), 8.457 (2.15), 8.462 (2.08), 8.476 (2.08), 8.482 (1.96), 8.687 (9.91), 9.113 (2.57), 9.133 (2.50). |
| 446 | | LC-MS (Method L1): Rt = 1.28 min; MS (ESIpos): | $^{1}$H-NMR (500 MHz DMSO-d6) δ [ppm]: 0.006 (0.83), 1.528 (15.59), 1.542 (16.00), 1.554 (15.53), 1.569 (15.22), 2.022 (0.59), 2.029 (0.75), 2.035 (1.20), 2.042 (1.26), 2.049 (1.35), 2.055 (1.35), 2.063 (1.74), 2.069 (1.50), 2.076 (1.05), 2.082 |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | m/z = 475 [M + H]$^+$ | (0.74), 2.178 (0.75), 2.185 (1.16), 2.195 (1.62), 2.205 (1.56), 2.212 (1.50), 2.222 (1.07), 2.229 (0.80), 2.239 (0.53), 3.836 (0.65), 3.851 (1.49), 3.865 (1.95), 3.879 (1.44), 3.893 (0.59), 4.218 (0.74), 4.224 (0.93), 4.240 (2.73), 4.246 (2.13), 4256 (2.85), 4.261 (3.43), 4.268 (2.78), 4.274 (2.18), 4.281 (2.36), 4.290 (0.72), 4.296 (0.86), 4.303 (0.60), 5.266 (1.16), 5.278 (2.45), 5.293 (2.39), 5.305 (1.07), 5.753 (2.04), 6.783 (4.78), 6.799 (5.11), 6.916 (2.31), 6.931 (4.75), 6.945 (2.64), 7.151 (2.25), 7.154 (2.34), 7.168 (3.85), 7.182 (1.85), 7.184 (1.80), 7.350 (4.06), 7.364 (3.73), 7.492 (2.91), 7.509 (5.77), 7.528 (4.33), 7.571 (2.42), 7.575 (2.60), 7.581 (2.67), 7.585 (2.75), 7.593 (1.86), 7.598 (1.61), 7.602 (1.61), 7.712 (2.90), 7.726 (4.39), 7.743 (3.94), 7.772 (3.91), 7.776 (3.80), 7.786 (3.97), 7.790 (3.76), 7.806 (5.60), 7.819 (3.92), 8.418 (4.24), 8.434 (3.91), 8.736 (14.80, 9.100 (4.07), 9.116 (3.94). |
| 447 | | LC-MS (Method L1): | $^{1}$H-NMR (400 MHz, DMSO-d6) δ [ppm]: 0.008 (1.67), 0.008 (1.74), 1.531 (11.51), 1.549 (12.60), 1.558 (16.00), 1.576 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | Rt = 1.27 min; MS (ESIpos): m/z = 451 [M + H]$^+$ | (15.03), 1.860 (10.28), 1.875 (10.05), [2.011 (1.17), 2.019 (1.28), 2.028 (1.43), 2.035 (1.35), 2.045 (1.78), 2.053 (1.52), 2.061 (1.12), 2.069 (0.78), 2.085 (3.05), 2.168 (3.67), 2.179 (1.64), 2.191 (1.75), 2.201 (1.41), 2.214 (1.00), 2.234 (0.57), 2.285 (42.65), 2.292 (14.54), 2.327 (0.48), 2.669 (0.41), 3.818 (0.64), 3.835 (1.53), 3.853 (2.04), 3.871 (1.49), 3.888 (0.61), 4.199 (0.69), 4.207 (0.86), 4.227 (2.74), 4.235 (2.35), 4.247 (4.38), 4.256 (4.48), 4.272 (2.50), 4.284 (0.69), 4.290 (0.91), 4.299 (0.59), 5.246 (1.09), 5.260 (2.43), 5.280 (2.46), 5.294 (1.09), 5.754 (9.81), 6.772 (4.79), 6.792 (5.26), 6.894 (1.96), 6.912 (4.26), 6.932 (4.96), 6.950 (2.92), 7.005 (0.53), 7.090 (2.60), 7.109 (4.90), 7.141 (3.48), 7.155 (5.80), 7.175 (3.08), 7.303 (0.65), 7.324 (3.77), 7.343 (2.96), 7.412 (0.62), 7.431 (0.77), 7.562 (4.28), 7.565 (4.58), 7.580 (5.85), 7.582 (5.76), 7.673 (4.25), 7.691 (3.82), 7.694 (4.77), 7.712 (3.30), 8.378 (4.53), 8.397 (4.13), 8.616 (12.23), 9.077 (4.12), 9.098 (4.04). |
| 448 | | LC-MS (Method L1): Rt = 1.27 min; MS (ESIpos): m/z = 455 [M + H]$^+$ | $^1$H-NMR (400 MHz, DMSO-d6) δ [ppm]: ] −0.008 (2.15), 0.008 (2.01), 1.526 (8.21), 1.543 (8.87), 1.552 (8.65), 1.570 (8.25), 2.028 (0.57), 2.037 (0.60), 2.047 (0.61), 2.053 (0.63), 2.063 (0.89), 2.071 (0.76), 2.079 (0.53), 2.179 (0.59), 2.192 (0.77), 2.203 (0.76), 2.213 (0.69), 2.227 (0.52), 2.366 (0.49), 2.388 (16.00), 3.842 (0.82), 3.860 (1.10), 3.878 (0.79), 4.239 (1.31), 4.248 (1.14), 4 258 (2.05), 4.267 (2.19), 4.282 (1.16), 5.261 (0.56), 5.276 (1.18), 5.295 (1.18), 5.310 (0.53), 6.778 (220), 6.781 (2.35), 6.799 (2.50), 6.801 (2.55), 6.909 (1.16), 6.912 (1.18), 6.928 (2.39), 6.930 (2.36), 6.946 (1.47), 6.949 (1.40), 7.052 (1.36), 7.076 (1.37), 7.146 (1.22), 7.150 (1.28), 7.167 (3.29), 7.190 (2.18), 7.204 (3.78), 7.346 (1.99), 7.365 (1.85), 7.691 (1.43), 7.709 (2.47), 7.731 (2.48), 7.763 (2.94), 7.766 (3.19), 7.781 (1.79), 7.784 (1.62), 8.393 (2.00), 8.396 (2.06), 8.415 (1.96), 8.418 (1.84), 8.721 (8.75), 9.097 (2.09), 9.117 (2.02). |
| 449 | | LC-MS (Method L1): | $^1$H-NMR (400 MHz, DMSO-d6) δ [ppm]: −0.149 (0.44), −0.008 (3.46), 0.008 (3.37), 0.146 (0.41), 1.522 (14.76), 1.540 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | Rt = 1.27 min; MS (ESIpos): m/z = 477 [M + H]$^+$ | (16.00), 1.548 (15.61), 1.566 (14.88), 2.014 (0.46), 2.030 (1.02), 2.038 (1.07), 2.048 (1.14), 2.055 (1.14), 2.064 (1.61), 2.072 (1.35), 2.080 (0.98), 2.088 (0.68), 2.171 (0.62), 2.181 (1.07), 2.193 (1.41), 2.205 (1.37), 2.214 (1.27), 2.229 (0.85), 2.235 (0.72), 2.248 (0.46), 2.327 (0.52), 2.366 (0.54), 2.669 (0.59), 2.710 (0.55), 3.826 (0.62), 3.843 (1.51), 3.861 (2.02), 3.879 (1.48), 3.896 (0.57), 4.210 (0.55), 4.218 (0.76), 4.238 (2.44), 4.246 (2.05), 4.258 (3.89), 4.267 (3.93), 4.283 (2.16), 4.295 (0.59), 4.302 (0.73), 5.261 (0.98), 5.276 (2.18), 5.296 (2.20), 5.310 (0.99), 6.782 (4.05), 6.802 (4.47), 6.911 (2.03), 6.914 (2.08), 6.930 (4.31), 6.932 (4.24), 6.948 (2.63), 6.951 (2.50), 7.148 (2.11), 7.152 (2.23), 7.169 (3.50), 7.187 (1.71), 7.190 (1.69), 7.348 (3.67), 7.366 (3.41), 7.538 (4.10), 7.546 (1.25), 7.555 (4.44), 7.561 (4.49), 7.578 (4.34), 7.587 (0.80), 7.594 (0.47), 7.716 (2.81), 7.734 (4.18), 7.737 (3.56), 7.756 (3.90), 7.834 (4.93), 7.836 (5.20), 7.851 (3.82), 8.441 (3.93), 8.460 (3.67), 8.754 (14.49), 9.107 (3.76), 9.128 (3.64). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 450 | | LC-MS (Method L1): 1.22 Rt = min; MS (ESIpos): m/z = 477 [M + H]$^+$ | $^1$H-NMR (400 MHz DMSO-d6) δ [ppm]: −0.008 (3.44), 0.008 (2.25), 1.528 (14.93), 1.546 (16.00), 1.555 (15.22), 1.573 (14.27), 2.003 (0.56), 2.018 (1.14), 2.027 (1.17), 2.036 (1.20), 2.044 (1.21), 2.053 (1.64), 2.061 (1.36), 2.069 (0.97), 2.077 (0.66), 2.165 (0.73), 2.174 (1.14), 2.187 (1.49), 2.198 (1.42), 2.208 (1.32), 2.219 (0.87), 2.229 (0.70), 2.241 (0.45), 2.524 (1.57), 3.824 (0.68), 3.841 (1.51), 3.859 (1.93), 3.877 (1.40), 3.895 (0.55), 4.203 (0.69), 4.210 (0.92), 4.230 (2.57), 4.238 (2.17), 4.250 (3.83), 4.260 (3.63), 4.267 (2.17), 4.276 (2.10), 4.288 (0.60), 4.295 (0.73), 4.304 (0.47), 5.251 (1.07), 5.266 (2.23), 5.285 (2.13), 5.300 (0.94), 6.774 (3.85), 6.776 (3.91), 6.794 (4.27), 6.796 (4.17), 6.902 (2.14), 6.905 (2.10), 6.921 (4.27), 6.923 (4.08), 6.939 (2.56), 6.942 (2.34), 7.142 (2.24), 7.146 (2.30), 7.163 (3.45), 7.181 (1.81), 7.185 (1.77), 7.207 (1.78), 7.215 (1.67), 7.229 (1.65), 7.241 (0.79), 7.340 (3.62), 7.359 (3.30), 7.567 (0.70), 7.575 (0.84), 7.582 (0.97), 7.590 (1.44), 7.595 (1.32), 7.603 (1.42), 7.610 (1.33), 7.616 (1.34), 7.623 (0.84), 7.631 |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.75), 7.639 (0.66), 7.743 (2.63), 7.761 (4.44), 7.782 (4.33), 7.815 (5.04), 7.818 (5.19), 7.832 (3.04), 8.495 ( 3.72), 8.498 (3.67), 8.516 (3.54), 8.519 (3.18), 8.716 9.146 (3.50). |
| 451 | | LC-MS (Method L1): Rt = 1.32 min; MS (ESIpos): m/z = 505 [M + H]$^+$ | $^1$H-NMR (400 MHz, DMSO-d6) δ [ppm]: −0.008 (2.87), 0.008 (2.99), 1.535 (13.93), 1.553 (15.28), 1.562 (16.00), 1.580 (15.01), 2.015 (11.45), 2.043 (1.86), 2.073 (0.70), 2.086 (1.48), 2.156 (0.80), 2.165 (1.28), 2.178 (1.76), 2.190 (1.65), 2.199 (1.57), 2.211 (1.06), 2.220 (0.84), 2.233 (0.55), 2.301 (1.08), 2.327 (0.40), 3.833 (0.67), 3.851 (1.64), 3.868 (2.17), 3.886 (1.60), 3.904 (0.65), 4.194 (0.64), 4.202 (0.82), 4.222 (2.46), 4.230 (2.05), 4.244 (3.50), 4.254 (3.47), 4.261 (2.45), 4.271 (2.47), 4.282 (0.76), 4.289 (0.90), 4.298 (0.61), 5.241 (1.14), 5.256 (2.55), 5.275 (2.57), 5.290 (1.14), 5.754 (11.28), 6.769 (4.42), 6.771 (4.75), 6.789 (5.07), 6.792 (5.21), 6.890 (2.32), 6.892 (2.35), 6.909 (4.87), 6.911 14.82), 6.927 (2.95), 6.930 (2.82), 7.136 (2.44), 7.140 (2.63), 7.157 (4.04), 7.175 (2.01), 7.178 (1.96), 7.323 (4.16), 7.341 (3.86), 7.398 (0.50), 7.402 (0.46), 7.439 (2.71), 7.483 (0.53), 7.535 (2.86), 7.555 (3.81), 7.665 (5.56), 7.668 (4.53), 7.683 (8.94), 7.719 (5.14), 7.737 (3.59), 7.741 (5.33), 7.758 (3.09), 8.445 (4.24), 8.448 (4.48), 8.467 (4.12), 8.469 (3.99), 8.640 (15.04), 9.087 (2.78), 9.107 (2.71). |
| 453 | | LC-MS (Method L1): Rt = 1.29 min; MS (ESIpos): m/z = 491 [M + H]$^+$ | $^1$H-NMR (400 MHz, DMSO-d6) δ [ppm]: −0.008 (2.92), 0.008 (2.81), 1.528 (13.71), 1.546 (14.79), 1.555 (16.00), 1.573 (15.23), 1.995 (0.48), 2.011 (1.10), 2.019 (1.19), 2.029 (1.25), 2.037 (1.25), 2.046 (1.76), 2.054 (1.47), 2.062 (1.08), 2.158 (0.66), 2.167 (1.14), 2.179 (1.56), 2.191 (1.52), 2.201 (1.38), 2.215 (0.95), 2.224 (0.79), 2.234 (0.51), 2.327 (0.53), 2.366 (0.64), 2.522 (1.30), 2.669 (0.57), 2.710 (0.64), 3.818 (0.59), 3.836 (1.47), 3.854 (1.91), 3.871 (1.43), 3.889 (0.57), 4.199 (0.57), 4.207 (0.81), 4.227 (2.55), 4.235 (2.24), 4.246 (4.18), 4.255 (4.37), 4.271 (2.40), 4.283 (0.66), 4.290 (0.79), 4.299 (0.51), 5.245 (1.03), 5.259 (2.33), 5.279 (2.42), 5.294 (1.12), 6.771 (4.44), 6.792 (4.88), 6.895 (2.11), 6.897 (2.18), 6.913 (4.53), 6.916 (4.55), 6.932 (2.84), 6.934 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (2.70), 7.137 (2.24), 7.141 (2.42), 7.158 (3.78), 7.176 (1.82), 7.179 (1.82), 7.331 (3.49), 7.349 (3.32), 7.446 (2.55), 7.457 (3.58), 7.470 (1.80), 7.478 (1.08), 7.484 (1.54), 7.489 (1.34), 7.495 (1.12), 7.505 (4.07), 7.511 (3.08), 7.526 (6.37), 7.533 (5.60), 7.585 (4.48), 7.599 (1.47), 7.607 (2.68), 7.622 (0.88), 7.693 (1.47), 7.698 (2.37), 7.711 (6.81), 7.716 (6.90), 7.719 (7.23), 7.739 (5.49), 7.757 (2.24), 8.456 (3.58), 8.460 (3.76), 8.476 (3.45), 8.480 (3.43), 8.661 (11.47), 8.729 (0.46), 9.113 (4.07), 9.134 (4.00). |
| 454 | | LC-MS (Method L1): Rt = 1.13 min; MS (ESIpos): m/z = 515 [M + H]$^+$ | $^1$H-NMR (500 MHz, DMSO-d6): δ [ppm] = 13.33 (br s, 1H), 8.92 (s, 1H), 8.75 (d, 1H), 8.12-7.96 (m, 2H), 7.90 (dd, 1H), 7.73-7.66 (m, 5H), 7.12 (t, 1H), 6.92 (d, 1H), 6.83 (t, 1H), 6.73 (dd, 1H), 5.12-5.06 (m, 1H), 4.18-4.07 (m, 1H), 3.99 (ddd, 1H), 2.56-2.52 (m, 1H), 2.09-1.96 (m, 1H), 1.78 (td, 1H) |
| 455 | | LC-MS (Method L1): Rt = 1.36 min; MS (ESIpos): m/z = 509 [M + H]$^+$ | $^1$H-NMR (400 MHz, DMSO-d6) δ [ppm]: −0.008 (3.81), 0.008 (2.57), 0.853 (0.46), 1.235 (2.17), 1.300 (0.52), 1.316 (0.51), 1.398 (1.60), 1.513 (14.80), 1.531 (16.00), 1.540 (15.55), 1.558 (14.28), 2.016 (1.21), 2.023 (1.32), 2.033 (1.33), 2.040 (1.33), 2.050 (1.72), 2.057 (1.47), 2.181 (1.67), 2.194 (1.60), 2.203 (1.49), 2.216 (1.01), 2.327 (0.52), 2.669 (0.63), 2.710 (0.49), 3.829 (0.77), 3.847 (1.66), 3.865 (2.13), 3.882 (1.55), 3.900 (0.64), 4.205 (1.06), 4.225 (2.72), 4.233 (2.29), 4.246 (3.46), 4.265 (2.32), 4.274 (2.31), 4.293 (0.84), 5.242 (1.17), 5.256 (2.44), 5.276 (2.34), 5.290 (1.06), 5.754 (5.78), 6.776 (4.38), 6.795 (4.71), 6.900 (2.25), 6.919 (4.51), 6.937 (2.66), 7.146 (2.46), 7.164 (3.72), 7.181 (1.83), 7.335 (3.97), 7.353 (3.56), 7.505 (11.79), 7.509 (11.98), 7.682 (3.19), 7.692 (4.34), 7.697 (7.04), 7.702 (5.43), 7.705 (5.86), 7.728 (2.85), 8.525 (2.64), 8.540 (2.80), 8.549 (2.69), 8.564 (2.43), 8.745 (13.37), 9.099 (3.97), 9.120 (3.77). |
| 477 | | LC-MS (Method L1): Rt = 1.26 min; MS (ESIpos): m/z = 509 | $^1$H-NMR (400 MHz, DMSO-d6) δ [ppm]: 0.837 (0.43), 0.854 (0.54), 0.891 (0.49), 1.141 (0.54), 1.235 (1.16), 1.317 (0.60), 1.343 (0.89), 1.359 (1.03), 1.519 (11.49), 1.522 (11.46), 1.536 (12.92), 1.541 (13.45), 1.548 (16.00), 1.566 (14.61), 2.000 (1.38), 2.008 (1.47), 2.024 (1.68), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | [M + H]+ | 2.035 (2.05), 2.174 (1.95), 2.186 (1.92), 2.196 (1.86), 2.210 (1.48), 2.328 (0.62), 2.366 (0.58), 2.669 (0.65), 2.710 (0.54), 3.849 (1.72), 3.858 (1.72), 4.196 (1.05), 4.216 (3.08), 4.224 (2.77), 4.240 (4.11), 4.265 (2.93), 4.284 (1.16), 5.232 (1.14), 5.247 (2.57), 5.264 (2.59), 6.767 (4.85), 6.787 (5.50), 6.888 (2.50), 6.906 (5.25), 6.924 (3.19), 7.137 (2.79), 7.155 (4.52), 7.172 (2.28), 7.316 (2.70), 7.326 (2.95), 7.333 (2.84), 7.343 (2.62), 7.358 (2.21), 7.361 (2.23), 7.380 (4.65), 7.399 (3.04), 7.403 (2.97), 7.457 (2.43), 7.469 (2.86), 7.477 (4.20), 7.489 (4.31), 7.496 (2.32), 7.508 (2.35), 7.694 (3.04), 7.717 (5.27), 7.739 (7.60), 7.758 (4.31), 7.762 (4.11), 8.555 (2.91), 8.570 (3.22), 8.579 (3.15), 8.594 (2.82), 8.675 (6.93), 8.686 (7.13), 9.115 (4.16), 9.135 (3.98). |
| 478 | | LC-MS (Method L1): Rt = 1.31 min; MS (ESIpos): m/z = 475 | $^1$H-NMR (400 MHz, DMSO-d6) δ [ppm]: −0.008 (1.30), 0.008 (1.39), 1.157 (0.78), 1.175 (1.56), 1.192 (0.80), 1.398 (0.65), 1.988 (3.13), 2.002 (0.44), 2.012 (0.46), 2.019 (0.47), 2.029 (0.65), 2.036 (0.56), 2.044 (0.40), 2.086 (1.10), 2.135 (0.42), 2.148 (0.61), 2.160 (0.56), 2.169 (0.53), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | [M + H]+ | 4.021 (0.69), 4.038 (0.69), 4.216 (0.98), 4.223 (0.77), 4.236 (1.07), 4.243 (1.18), 4.250 (1.04), 4.257 (0.80), 4.266 (0.84), 5.227 (0.88), 5.247 (0.89), 5.677 (1.55), 5.681 (1.65), 5.722 (1.60), 5.725 (1.76), 5.754 (2.74), 5.810 (1.65), 5.813 (1.59), 5.839 (1.68), 5.842 (1.68), 6.775 (1.68), 6.796 (1.85), 6.899 (0.83), 6.917 (1.72), 6.934 (1.01), 7.142 (0.82), 7.146 (0.88), 7.163 (1.40), 7.180 (0.67), 7.184 (0.68), 7.305 (1.47), 7.324 (1.41), 7.331 (1.46), 7.360 (1.32), 7.376 (1.31), 7.405 (1.17), 7.664 (16.00), 7.741 (1.18), 7.759 (1.71), 7.780 (1.56), 7.895 (1.87), 7.898 (2.02), 7.913 (1.52), 7.916 (1.50), 8.242 (1.70), 8.245 (1.76), 8.262 (1.59), 8.266 (1.54), 8.909 (5.42), 9.001 (1.53), 9.021 (1.48). |
| 479 | | LC-MS (Method L1): Rt = 1.29 min; MS (ESIpos): m/z = 525 [M + H]+ | $^1$H-NMR (400 MHz, DMSO-d6) δ [ppm]: 1.519 (14.64), 1.536 (16.00), 1.545 (15.88), 1.563 (14.91), 2.013 (1.08), 2.021 (1.17), 2.031 (1.28), 2.038 (1.29), 2.048 (1.72), 2.055 (1.49), 2.063 (1.07), 2.071 (0.76), 2.161 (0.68), 2.170 (1.10), 2.182 (1.58), 2.194 (1.51), 2.203 (1.44), 2.216 (1.01), 2.237 (0.51), 3.827 (0.66), 3.845 (1.63), 3.863 (2.19), 3.881 (1.61), 3.898 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (0.66), 4.196 (0.63), 4.203 (0.84), 4.223 (2.53), 4.230 (2.07), 4.249 (3.21), 4.256 (2.97), 4.264 (2.19), 4.273 (2.28), 4.284 (0.71), 4.292 (0.84), 4.300 (0.57), 5.244 (1.06), 5.258 (2.41), 5.277 (2.44), 5.292 (1.07), 6.774 (4.57), 6.795 (5.08), 6.898 (2.22), 6.916 (4.75), 6.935 (2.76), 7.143 (2.39), 7.162 (3.87), 7.182 (1.81), 7.329 (4.15), 7.348 (3.78), 7.421 (5.41), 7.454 (3.25), 7.466 (3.77), 7.486 (4.52), 7.607 (4.06), 7.627 (6.11), 7.646 (2.60), 7.677 (2.67), 7.700 (5.22), 7.723 (2.75), 8.510 (2.55), 8.525 (2.75), 8.534 (2.70), 8.549 (2.46), 8.707 (13.60), 9.091 (4.09), 9.111 (3.99). |
| 487 | | LC-MS (Method L12): Rt = 1.56 min; MS (ESIpos): m/z = 495 [M + H]$^+$ | $^1$H-NMR (400 MHz, DMSO-d6) δ [ppm]: −0.150 (0.50), 0.146 (0.45), 0.852 (0.69), 1.234 (3.42), 1.299 (0.54), 1.518 (13.51), 1.536 (14.79), 1.544 (16.00), 1.562 (14.83), 2.006 (1.08), 2.014 (1.24), 2.023 (1.45), 2.031 (1.35), 2.040 (1.61), 2.049 (1.65), 2.056 (1.35), 2.182 (1.69), 2.194 (1.63), 2.203 (1.56), 2.217 (1.13), 2.327 (0.52), 2.669 (0.48), 3.839 (1.13), 3.857 (1.54), 3.866 (1.54), 3.884 (1.08), 4.197 (0.78), 4.223 (2.32), 4.246 (3.38), 4.255 (2.97), 4.263 (2.34), 4.272 (2.41), 4.291 (0.93), 5.256 (2.25), 5.270 (2.26), 6.773 (4.60), 6.793 (5.14), 6.897 (2.13), 6.916 (4.58), 6.934 (2.71), 7.144 (2.47), 7.162 (4.06), 7.180 (1.89), 7.279 (1.78), 7.323 (2.19), 7.342 (4.10), 7.360 (2.08), 7.638 (0.65), 7.646 (0.80), 7.661 (1.58), 7.674 (1.60), 7.687 (1.61), 7.702 (0.89), 7.710 (0.84), 7.724 (2.62), 7.747 (4.86), 7.770 (2.69), 8.596 (2.77), 8.611 (2.95), 8.620 (2.95), 8.635 (2.69), 8.736 (6.87), 8.747 (7.18), 9.121 (4.19), 9.142 (4.12). |
| 488 | | LC-MS (Method L12): Rt = 1.60 min; MS (ESIpos): m/z = 509 [M + H]$^+$ | $^1$H-NMR (400 MHz, DMSO-d6) δ [ppm]: −0.149 (0.83), −0.008 (6.41), 0.008 (6.73), 0.146 (0.80), 1.141 (0.40), 1.157 (0.99), 1.175 (1.92), 1.193 (0.96), 1.235 (0.88), 1.398 (2.11), 1.522 (14.80), 1.540 (16.00), 1.548 (15.71), 1.566 (14.90), 1.988 (3.66), 2.013 (1.04), 2.022 (1.15), 2.031 (1.20), 2.048 (1.63), 2.056 (1.39), 2.180 (1.52), 2.192 (1.44), 2.202 (1.39), 2.215 (0.91), 2.327 (0.75), 2.670 (0.83), 3.836 (0.59), 3.853 (1.50), 3.871 (2.03), 3.889 (1.44), 3.907 (0.59), 4.021 (0.83), 4.038 (0.83), 4.202 (0.85), 4.222 (2.51), 4.230 (1.98), 4.248 (2.86), 4.255 (2.80), |

TABLE 2-continued

| LC-MS and NMR data |
|---|
| NMR peak forms are stated as they appear in the spectra, possible higher order effects have not been considered. |
| NMR peak lists |
| $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via “side-products-fingerprints”. An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. Further details of NMR-data description with peak lists you find in the publication “Citation of NMR Peaklist Data within Patent Applications” of the Research Disclosure Database Number 564025. |

| Example No | logP (Method L0) [a] | LC-MS (Method L2-L5) | NMR or NMR Peaklist |
|---|---|---|---|
| | | | 4.263 (2.06), 4.272 (2.16), 4.291 (0.88), 5.240 (0.99), 5.255 (2.16), 5.275 (2.22), 5.290 (1.04), 6.774 (4.51), 6.795 (4.99), 6.895 (2.11), 6.897 12.19), 6.916 (4.43), 6.932 (2.70), 6.935 (2.62), 7.140 (2.22), 7.143 (2.32), 7.161 (3.58), 7.178 (1.82), 7.182 (1.84), 7.330 (3.69), 7.348 (3.42), 7.691 (2.96), 7.714 (6.17), 7.737 (5.96), 7.752 (11.25), 7.767 (7.93), 7.802 (3.53), 7.817 (2.03), 8.524 (2.59), 8.538 (2.78), 8.547 (2.83), 8.563 (2.59), 8.710 (15.17), 9.096 (3.79), 9.117 (3.69). |
| 489 | | LC-MS (Method L1): Rt = 1.38 min; MS (ESIpos): m/z = 531 [M + H]$^+$ | $^1$H-NMR (600 MHz, DMSO-d6) δ [ppm]: 1.670 (0.68), 1.681 (1.19), 1.688 (1.28), 1.692 (1.29), 1.700 (1.35), 1.704 (1.28), 1.710 (0.81), 1.938 (0.60), 1.946 (0.88), 1.952 (1.34), 1.960 (1.43), 1.966 (1.42), 1.975 (1.17), 1.980 (0.77), 1.983 (0.76), 1.988 (0.57), 3.957 (1.00), 3.961 (1.18), 3.975 (2.40), 3.989 (1.44), 3.993 (1.28), 4.105 (1.24), 4.110 (1.53), 4.116 (1.46), 4.122 (2.04), 4.128 (1.21), 4.135 (1.18), 4.139 (1.00), 5.034 (0.99), 5.044 (2.14), 5.057 (2.17), 5.067 (0.99), 5.747 (5.67), 6.713 (4.06), 6.726 (4.34), 6.811 (1.78), 6.823 (4.08), 6.835 (2.55), 6.899 (3.76), |

TABLE 2-continued

| LC-MS and NMR data |
|---|
| NMR peak forms are stated as they appear in the spectra, possible higher order effects have not been considered. |
| NMR peak lists |
| $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via “side-products-fingerprints”. An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. Further details of NMR-data description with peak lists you find in the publication “Citation of NMR Peaklist Data within Patent Applications” of the Research Disclosure Database Number 564025. |

| Example No | logP (Method L0) [a] | LC-MS (Method L2-L5) | NMR or NMR Peaklist |
|---|---|---|---|
| | | | 6.912 (2.80), 7.101 (1.95), 7.113 (3.41), 7.126 (1.67), 7.259 (4.11), 7.267 (4.21), 7.669 (9.16), 7.672 (9.94), 7.681 (16.00), 7.684 (12.40), 7.691 (2.86), 7.705 (4.02), 7.717 (3.37), 7.795 (5.01), 7.798 (4.25), 7.803 (4.06), 7.806 (6.59), 7.892 (4.03), 7.894 (4.31), 7.904 (3.65), 7.906 (3.78), 8.700 (3.70), 8.714 (3.63), 8.975 (11.32). |
| 493 | | LC-MS (Method L1): Rt = 1.07 min; MS (ESIpos): m/z = 494 [M + H]$^+$ | $^1$H-NMR (400 MHz, DMSO-d6) δ [ppm] −0.008 (1.23), 0.008 (1.23), 1.235 (0.64), 2.073 (0.59), 3.063 (16.00), 3.283 (0.84), 3.332 (1.24), 3.707 (0.83), 3.726 (0.96), 3.735 (0.87), 3.754 (0.75), 5.790 (0.75), 5.810 (0.75), 7.121 (0.41), 7.124 (0.46), 7.140 (0.96), 7.143 (1.04), 7.158 (0.66), 7.161 (0.71), 7.229 (0.45), 7.248 (1.01), 7.266 (0.67), 7.288 (1.37), 7.306 (0.61), 7.389 (1.07), 7.408 (0.94), 7.640 (7.94), 7.651 (2.13), 7.655 (2.38), 7.673 (1.13), 7.798 (1.17), 7.801 (1.35), 7.816 (1.24), 7.819 (1.23), 8.233 (0.99), 8.236 (1.09), 8.254 (0.96), 8.258 (0.98), 8.581 (0.48), 8.683 (3.65), 9.242 (0.98), 9.263 (0.98). |
| 494 | | LC-MS (Method L1): | $^1$H-NMR (400 MHz, DMSO-d6) δ [ppm]: −0.008 (2.50), 1.234 (1.19), 1.797 (2.72), 1.813 (2.16), 1.831 (1.22), 2.017 (3.78), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | Rt = 1.44 min; MS (ESIpos): m/z = 517 [M + H]$^+$ | 2.027 (5.23), 2.042 (4.61), 2.052 (4.11), 2.118 (2.71), 2.141 (2.97), 2.166 (2.48), 2.174 (2.13), 2.187 (2.12), 2.198 (1.81), 2.209 (1.47), 2.242 (0.49), 3.802 (1.35), 3.825 (1.96), 3.849 (1.31), 4.211 (0.45), 4.219 (0.64), 4.238 (2.26), 4.247 (2.23), 4.257 (3.32), 4.265 (3.75), 4.279 (2.16), 4.297 (0.65), 4.306 (0.41), 5.268 (0.94), 5.283 (2.12), 5.303 (2.15), 5.317 (0.95), 5.754 (0.50), 6.780 (3.97), 6.800 (4.42), 6.906 (1.93), 6.924 (4.12), 6.943 (2.41), 7.146 (1.92), 7.150 (2.10), 7.167 (3.36), 7.185 (1.57), 7.188 (1.61), 7.334 (3.58), 7.352 (3.29), 7.615 (11.95),7.620 (16.00), 7.643 (3.83), 7.648 (5.15), 7.652 (2.49), 7.709 (2.30), 7.728 (3.62), 7.749 (3.21), 7.835 (4.99), 7.853 (3.64), 8.277 (3.63), 8.297 (3.29), 8.751 (13.22), 9.097 (3.72), 9.117 (3.65). |
| 519 | | LC-MS (Method L1): Rt = 0.91 min; MS (ESIpos): m/z = 518 [M + H]$^+$ | $^1$H-NMR (400 MHz, DMSO-d6) δ [ppm] 1.157 (2.50), 1.175 (5.02), 1.193 (2.67), 1.234 (1.23), 1.540 (3.03), 1.988 (9.10), 2.063 (2.50), 2.079 (2.80), 2.198 (2.93), 2.221 (2.26), 2.328 (0.95), 2.366 (0.77), 2.670 (0.84), 2.694 (0.44), 2.710 (0.45), 2.961 (1.24), 2.983 (1.72), 3.003 (1.27), 3.192 (2.79), 3.209 (2.69), 3.510 (0.78), 3.568 (1.00), 3.687 (1.02), 3.944 (1.29), 3.964 1.72), 3.984 (1.23), 4.003 (1.27), 4.020 (2.57), 4.038 (2.55), 4.056 (1.22), 4.264 (6.12), 5.271 (1.44), 5.287 (3.19), 5.305 (3.16), 5.320 (1.42), 6.779 (5.67), 6.799 (6.10), 6.907 (2.67), 6.926 (5.43), 6.944 (3.19), 7.147 (3.24), 7.166 (5.08), 7.185 (2.43), 7.345 (4.52), 7.364 (4.26), 7.621 (16.00), 7.641 (6.46), 7.646 (7.29), 7.666 (3.01), 7.691 (2.20), 7.711 (3.99), 7.731 (3.09), 7.832 (6.29), 7.849 (4.99), 7.890 (0.71), 7.908 (0.56), 8.417 (0.70), 8.654 (2.62), 8.675 (2.44), 8.759 (14.38), 8.912 (1.06), 9.129 (2.46), 9.139 (2.89), 9.149 (2.97), 9.159 (2.67). |
| 520 | | LC-MS (Method L1): Rt = 1.26 min; MS (ESIpos): m/z = 565 [M + H]$^+$ | $^1$H-NMR (400 MHz, DMSO-d6) δ [ppm]: 1.735 (0.54), 1.741 (0.60), 1.753 (0.64), 1.769 (0.75), 1.775 (0.68), 1.785 (0.45), 1.982 (0.46), 1.994 (0.70), 2.008 (0.73), 2.016 (0.72), 2.029 (0.56), 3.944 (0.51), 3.950 (0.61), 3.972 (1.56), 3.993 (0.80), 3.999 (0.65), 4.118 (0.63), 4.125 (0.83), 4.134 (0.77), 4.142 (0.98), 4.153 (0.60), 4.162 (0.60), 4.169 (0.47), 5.070 (0.51), 5.084 (1.14), 5.104 (1.15), 5.118 (0.50), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 5.754 (1.74), 6.728 (2.15), 6.748 (2.40), 6.803 (0.98), 6.822 (2.24), 6.840 (1.42), 6.951 (2.12), 6.969 (1.59), 7.106 (1.04), 7.127 (1.79), 7.145 (0.87), 7.684 (16.00), 7.737 (1.24), 7.757 (2.35), 7.776 (1.77), 7.862 (1.30), 7.929 (2.60), 7.940 (3.02), 7.943 (2.91), 7.961 (2.06), 8.010 (7.93), 8.156 (1.16), 8.519 (6.04), 8.866 (2.07), 8.886 (2.02), 8.999 (6.20). |
| 539 | | LC-MS (Method L1): Rt = 1.28 min; MS (ESIpos): m/z = 533 [M + H]$^+$ | $^1$H-NMR (400 MHz DMSO-d6) δ [ppm]: 0.008 (2.51), 1.235 (0.43), 1.676 (1.54), 1.713 (2.60), 1.751 (1.67), 2.057 (0.97), 2.072 (1.11), 2.085 (1.87), 2.218 (1.33), 2.231 (1.31), 2.240 (1.26), 2.252 (0.92), 2.327 (0.56), 2.366 (0.60), 2.429 (2.14), 2.460 (2.25), 2.670 (0.69), 2.710 (0.67), 3.464 (1.07), 3.493 (1.97), 3.520 (2.14), 3.546 (2.15), 3.575 (1.18), 3.738 (1.26), 4.010 (3.17), 4.023 (2.81), 4.038 (2.85), 4.219 (0.82), 4.240 (2.21), 4.247 (1.78), 4.260 (2.15), 4.268 (2.70), 4.279 (2.21), 4.295 (1.97), 5.293 (0.94), 5.307 (2.08), 5.327 (2.08), 5.342 (0.90), 5.754 (5.00), 6.785 (3.97), 6.804 (4.38), 6.918 (1.97), 6.937 (4.07), 6.956 (2.40), 7.158 (2.10), 7.176 (3.37), 7.193 (1.61), 7.405 (3.52), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.423 (3.20), 7.613 (13.15), 7.617 (16.00), 7.648 (4.20), 7.653 (5.68), 7.748 (2.29), 7.766 (3.65), 7.787 (3.20), 7.856 (4.95), 7.874 (3.52), 8.510 (3.43), 8.531 (3.17), 8.777 (12.63), 9.140 (3.54), 9.161 (3.54). |
| 552 | | LC-MS (Method L1): Rt = 1.16 min; MS (ESIpos): m/z = 463 [M + H]$^+$ | $^1$H-NMR (500 MHz, DMSO-d6) δ [ppm] 0.006 (2.45), 2.035 (0.75), 2.042 (0.79), 2.050 (0.83), 2.056 (0.84), 2.063 (1.08), 2.070 (0.92), 2.076 (0.65), 2.084 (0.55), 2.177 (0.48), 2.184 (0.73), 2.194 (0.96), 2.204 (0.93), 2.212 (0.89), 2.222 (0.61), 2.361 (0.44), 2.635 (0.42), 2.784 (16.00), 4.218 (0.41), 4.240 (1.35), 4.253 (2.26), 4.260 (2.33), 4.273 (1.44), 4.289 (0.47), 5.276 (0.62), 5.288 (1.38), 5.303 (1.35), 5.315 (0.58), 5.753 (1.80), 6.779 (2.82), 6.795 (3.02), 6.899 (1.36), 6.913 (2.78), 6.928 (1.56), 7.147 (1.37), 7.161 (2.32), 7.175 (1.13), 7.336 (2.58), 7.342 (1.47), 7.351 (3.50), 7.367 (1.58), 7.434 (1.15), 7.440 (1.23), 7.450 (1.98), 7.456 (2.00), 7.465 (1.00), 7.471 (0.96), 7.698 (2.97), 7.701 (2.98), 7.714 (4.43), 7.727 (3.55), 7.729 (3.39), 7.757 (2.79), 7.773 (3.09), 7.788 (1.77), 8.296 (2.65), 8.299 (2.73), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.313 (2.51), 8.315 (2.43), 8.725 (3.78), 8.730 (3.80), 9.066 (1.31), 9.073 (1.41), 9.083 (1.35), 9.089 (1.27). |
| 554 | | LC-MS (Method L1): Rt = 1.11 min; MS (ESIpos): m/z = 449 [M + H]$^+$ | $^1$H-NMR (400 MHz, DMSO-d6) δ [ppm]: 2.040 (0.54), 2.049 (0.56), 2.058 (0.59), 2.066 (0.62), 2.075 (0.86), 2.084 (0.82), 2.199 (0.74), 2.211 (0.72), 2.221 (0.67), 2.791 (16.00), 4.239 (1.25), 4.248 (1.18), 4.258 (1.91), 4.266 (2.10), 4.281 (1.17), 5.278 (0.52), 5.292 (1.15), 5.311 (1.17), 5.326 (0.53), 5.754 (2.08), 6.782 (2.11), 6.802 (2.36), 6.902 (1.03), 6.921 (2.23), 6.939 (1.30), 7.149 (1.12), 7.167 (1.84), 7.184 (0.89), 7.228 (0.92), 7.240 (0.93), 7.250 (0.92), 7.346 (1.97), 7.365 (1.80), 7.584 (0.41), 7.599 (0.74), 7.612 (0.76), 7.624 (0.74), 7.639 (0.41), 7.779 (1.17), 7.798 (2.28), 7.818 (2.13), 7.853 (2.63), 7.868 (1.51), 8.336 (2.03), 8.339 (2.04), 8.357 (1.93), 8.795 (6.37), 9.088 (1.87), 9.109 (1.81). |
| 555 | | LC-MS (Method L1): Rt = 1.11 min; MS | $^1$H-NMR (400 MHz, DMSO-d6) δ [ppm]: −0.008 (0.81), 0.008 (0.91), 1.235 (0.83), 1.583 (5.80), 1.773 (0.41), 1.790 (0.55), 1.800 (0.64), 2.756 (0.59), 2.782 (0.54), 2.812 (0.68), 2.820 (0.83), 2.977 (16.00), |
| | | (ESIpos): m/z = 504 [M + H]$^+$ | 7.042 (0.46), 7.061 (1.18), 7.070 (0.71), 7.072 (0.72), 7.087 (0.98), 7.090 (1.00), 7.106 (0.45), 7.109 (0.43), 7.131 (0.52), 7.150 (0.77), 7.502 (1.01), 7.520 (0.90), 7.610 (0.79), 7.628 (1.21), 7.632 (1.38), 7.638 (10.75), 7.649 (1.14), 7.771 (1.14), 7.774 (1.26), 7.789 (0.96), 7.792 (0.96), 8.202 (1.03), 8.205 (1.09), 8.223 (0.99), 8.227 (0.96), 8.645 (3.75), 8.744 (1.76). |
| 562 | | LC-MS (Method L1): Rt = 0.74 min; MS (ESIpos): m/z = 533 [M + H]$^+$ | $^1$H-NMR (400 MHz, DMSO-d6) δ [ppm]: −0.149 (0.58), −0.008 (5.47), 0.008 (4.38), 0.146 (0.61), 1.235 (1.34), 2.036 (1.59), 2.073 (0.95), 2.159 (1.17), 2.172 (1.51), 2.183 (1.48), 2.193 (1.40), 2.327 (1.17), 2.366 (0.64), 2.523 (2.77), 2.670 (1.31), 2.710 (0.67), 3.996 (0.51), 4.032 (9.72), 4.078 (0.42), 4.203 (0.70), 4.243 (3.57), 4.252 (4.02), 4.267 (2.26), 4.285 (0.76), 4.941 (4.22), 4.966 (2.98), 5.213 (0.97), 5.228 (2.18), 5.247 (2.17), 5.261 (0.90), 5.754 (8.48), 6.780 (4.08), 6.800 (4.58), 6.885 (1.79), 6.903 (3.77), 6.922 (2.20), 7.146 (2.20), 7.164 (3.60), 7.182 (1.68), 7.304 (3.88), 7.322 (3.85), 7.353 (2.26), 7.415 (1.60), 7.427 (2.01), 7.435 (2.80), 7.447 (3.08), 7.454 (1.54), 7.466 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | (1.53), 7.649 (1.29), 7.666 (5.30), 7.676 (5.97), 7.684 (13.71), 7.689 (6.43), 7.705 (4.35), 7.709 (4.08), 8.136 (4.77), 8.308 (0.72), 8.317 (3.74), 8.325 (3.26), 8.334 (3.46), 8.342 (3.29), 8.630 (16.00), 8.707 (5.45), 9.196 (1.74), 9.214 (2.90), 9.233 (1.90). |
| 563 | | LC-MS (Method L1): Rt = 0.85 min; MS (ESIpos): m/z = 567 [M + H]$^+$ | $^1$H-NMR (400 MHz, DMSO-d6) δ [ppm]: −0.149 (1.20), −0.008 (9.34), 0.008 (9.02), 0.146 (1.08), 0.854 (0.58), 1.148 (0.41), 1.235 (3.04), 2.039 (1.61), 2.085 (3.50), 2.183 (1.52), 2.194 (1.37), 2.327 (1.81), 2.366 (0.93), 2.669 (2.04), 2.709 (1.02), 3.508 (0.47), 4.039 (9.81), 4.253 (3.88), 4.268 (2.28), 4.948 (4.73), 4.972 (2.77), 5.225 (2.25), 5.243 (2.22), 5.754 (7.04), 6.782 (4.76), 6.803 (5.23), 6.888 (2.10), 6.907 (4.29), 6.925 (2.45), 7.149 (2.36), 7.167 (3.91), 7.184 (1.96), 7.305 (3.50), 7.325 (3.18), 7.454 (2.39), 7.477 (2.69), 7.483 (2.60), 7.652 (2.51), 7.670 (4.47), 7.691 (4.44), 7.721 (5.26), 7.737 (2.92), 7.910 (8.35), 7.916 (8.23), 8.163 (2.04), 8.338 (4.35), 8.341 (4.50), 8.359 (4.20), 8.362 (3.94), 8.642 (16.00), 8.717 (5.69), 9.213 (2.63), 9.233 (2.51). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| 569 | | LC-MS (Method L1): Rt = 0.78 min; MS (ESIpos): m/z = 549 [M + H]$^+$ | $^1$H-NMR (400 MHz, DMSO-d6) δ [ppm]: −0.008 (2.40), 0.008 (2.06), 2.061 (1.27), 2.185 (1.12), 2.327 (0.94), 2.669 (0.87), 4.025 (5.86), 4.065 (0.57), 4.238 (1.84), 4.258 (2.64), 4.266 (2.99), 4.913 (1.72), 4.926 (3.39), 4.946 (3.52), 4.959 (1.75), 5.246 (1.74), 5.266 (1.56), 6.792 (3.51), 6.813 (3.85), 6.904 (1.66), 6.922 (3.36), 6.939 (2.06), 7.158 (1.80), 7.175 (2.74), 7.197 (1.28), 7.321 (2.74), 7.338 (2.56), 7.392 (1.86), 7.411 (2.11), 7.578 (2.92), 7.588 (4.18), 7.597 (5.85), 7.616 (4.05), 7.627 (5.32), 7.647 (1.93), 7.652 (2.84), 7.670 (3.21), 7.691 (2.98), 7.814 (3.61), 7.817 (3.83), 7.832 (3.05), 8.291 (3.30), 8.310 (3.02), 8.706 (16.00), 9.217 (2.96), 9.237 (2.95). |
| 570 | | LC-MS (Method L1): Rt = 1.27 min; MS (ESIpos): m/z = 493 [M + H]$^+$ | $^1$H-NMR (400 MHz, DMSO-d6) δ [ppm]: −0.008 (0.87), 0.008 (0.82), 1.308 (6.89), 1.327 (16.00), 1.345 (7.07), 2.024 (0.53), 2.039 (1.21), 2.049 (1.28), 2.058 (1.29), 2.066 (1.35), 2.075 (1.94), 2.083 (1.61), 2.090 (1.19), 2.099 (0.77), 2.180 (0.74), 2.190 (1.30), 2.203 (1.54), 2.213 (1.54), 2.225 (1.35), 2.243 (0.95), 2.256 (0.53), 3.233 (1.89), 3.252 (5.94), 3.271 (5.86), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 3.289 (1.97), 4.220 (0.46), 4.229 (0.69), 4.249 (2.90), 4.258 (4.37), 4.268 (5.05), 4.275 (4.55), 4.284 (2.85), 4.302 (0.68), 5.294 (1.14), 5.309 (2.53), 5.329 (2.56), 5.344 (1.15), 6.785 (4.65), 6.805 (5.16), 6.910 (2.22), 6.913 (2.38), 6.931 (4.95), 6.948 (2.88), 6.950 (2.91), 7.148 (2.35), 7.152 (2.57), 7.169 (4.01), 7.187 (1.89), 7.190 (1.93), 7.348 (4.27), 7.366 (3.97), 7.402 (2.57), 7.421 (3.07), 7.587 (3.08), 7.606 (10.61), 7.626 (5.62), 7.636 (4.50), 7.639 (7.18), 7.658 (2.73), 7.756 (2.88), 7.774 (4.86), 7.795 (4.63), 7.845 (5.60), 7.847 (6.27), 7.862 (3.86), 7.865 (3.83), 8.305 (4.57), 8.324 (4.08), 8.326 (4.06), 8.800 (15.69), 9.096 (4.36), 9.117 (4.28). |
| 571 | | LC-MS (Method L1): Rt = 1.21 min; MS (ESIpos): m/z = 479 [M + H]$^+$ | $^1$H-NMR (400 MHz, DMSO-d6) δ [ppm]: 2.051 (0.52), 2.060 (0.52), 2.087 (0.83), 2.095 (0.71), 2.206 (0.69), 2.217 (0.69), 2.227 (0.59), 2.793 (16.00), 4.247 (1.21), 4266 (1.74), 4.272 (1.87), 4.287 (1.09), 5.288 (0.50), 5.303 (1.10), 5.323 (1.10), 5.338 (0.49), 6.788 (2.15), 6.808 (2.34), 6.911 (1.04), 6.927 (2.14), 6.946 (1.29), 7.154 (1.12), 7.171 (1.74), 7.189 (0.83), 7.350 (1.84), 7.369 (1.70), 7.405 (1.21), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | | 7.425 (1.42), 7.591 (1.39), 7.610 (5.39), 7.629 (2.38), 7.646 (3.07), 7.665 (125), 7.758 (1.35), 7.776 (2.19), 7.797 (2.04), 7.857 (2.46), 7.860 (2.60), 7.875 (1.77), 7.878 (1.68), 8.268 (2.07), 8.271 (2.11), 8.289 (1.94), 8.292 (1.85), 8.810 (6.83), 9.075 (1.81), 9.095 (1.79). |
| 572 | | LC-MS (Method L1): Rt = min; MS (ESIpos): m/z = [M + H]$^+$ | $^1$H-NMR (400 MHz, DMSO-d6) δ [ppm]: 2.032 (0.65), 2.041 (0.71), 2.050 (0.76), 2.058 (0.79), 2.067 (1.04), 2.075 (0.91), 2.172 (0.41), 2.181 (0.73), 2.193 (0.92), 2.204 (0.91), 2.215 (0.83), 2.787 (16.00), 4.216 (0.41), 4.236 (1.41), 4.254 (2.29), 4.261 (2.58), 4.276 (1.47), 4.294 (0.44), 5.271 (0.58), 5.286 (1.35), 5.304 (1.38), 5.320 (0.61), 6.778 (2.39), 6.799 (2.67), 6.897 (1.24), 6.915 (2.63), 6.934 (1.54), 7.145 (1.36), 7.163 (2.20), 7.184 (1.05), 7.337 (2.34), 7.355 (2.19), 7.495 (2.29), 7.502 (1.52), 7.657 (0.42), 7.771 (6.93), 7.779 (3.68), 7.787 (3.32), 7.805 (0.67), 7.922 (2.71), 7.928 (2.67), 8.315 (1.92), 8.324 (1.81), 8.332 (1.66), 8.340 (1.74), 8.751 (4.10), 9.078 (2.11), 9.099 (2.06). |
| 573 | | LC-MS (Method | $^1$H-NMR (400 MHz, DMSO-d6) δ [ppm]: −0.008 (2.08), 0.008 (1.69), 1.311 (7.04), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | L1): Rt = 1.32 min; MS (ESIpos): m/z = 511 [M + H]$^+$ | 1.329 (16.00), 1.348 (7.23), 2.018 (1.23), 2.028 (1.39), 2.037 (1.33), 2.053 (2.00), 2.062 (1.64), 2.188 (1.63), 2.198 (1.61), 2.210 (1.49), 2.229 (1.04), 2.241 (0.61), 2.327 (0.71), 2.670 (0.76), 3.241 (3.86), 3.260 (3.83), 4.217 (0.70), 4.236 (2.98), 4.246 (4.20), 4.256 (5.08), 4.263 (4.65), 4.272 (2.85), 4.290 (0.68), 5.274 (1.17), 5.289 (2.57), 5.308 (2.57), 5.323 (1.14), 6.776 (5.42), 6.796 (5.89), 6.897 (2.61), 6.899 (2.58), 6.915 (5.46), 6.934 (3.26), 7.140 (2.67), 7.144 (2.76), 7.161 (4.38), 7.179 (2.11), 7.332 (4.46), 7.351 (4.10), 7.492 (4.02), 7.498 (7.24), 7.504 (4.01), 7.755 (2.30), 7.767 (14.83), 7.772 (8.12), 7.785 (6.89), 7.803 (1.92), 7.919 (10.30), 7.925 (9.81), 8.348 (4.00), 8.355 (3.95), 8.367 (3.57), 8.373 (3.60), 8.742 (7.68), 8.747 (7.69), 9.108 (3.20), 9.127 (3.19). |
| 574 | | LC-MS (Method L1): Rt = 0.91 min; MS (ESIpos): m/z = 480 | $^1$H-NMR (400 MHz DMSO-d6) δ [ppm]: 1.196 (5.36), 1.216 (11.90), 1.234 (5.37), 2.071 (0.42), 2.613 (1.31), 2.632 (3.68), 2.651 (3.53), 2.669 (1.23), 3.055 (16.00), 4.243 (0.61), 4.251 (0.57), 4.262 (0.88), 4.270 (0.97), 4.284 (0.51), 5.245 (0.56), 5.264 (0.54), 6.788 (1.10), 6.806 (1.17), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | [M + H]$^+$ | 6.902 (0.54), 6.905 (0.53), 6.921 (1.09), 6.939 (0.67), 6.942 (0.61), 7.064 (1.62), 7.148 (0.57), 7.152 (0.61), 7.169 (0.97), 7.191 (3.92), 7.351 (0.92), 7.368 (0.83), 7.588 (0.68), 7.606 (1.18), 7.626 (1.17), 7.657 (1.35), 7.661 (1.40), 7.675 (0.81), 7.679 (0.68), 8.153 (1.09), 8.156 (1.06), 8.173 (0.99), 8.177 (0.92), 8.573 (4.21), 9.076 (0.96), 9.096 (0.92). |
| 575 | | LC-MS (Method L1): Rt = 1.22 min; MS (ESIpos): m/z = 477 [M + H]$^+$ | $^1$H-NMR (400 MHz DMSO-d6) δ [ppm]: 1.315 (7.37), 1.334 (16.00), 1.352 (7.13), 2.016 (1.34), 2.026 (1.38), 2.034 (1.42), 2.051 (2.04), 2.060 (1.67), 2.188 (1.64), 2.210 (1.45), 2.224 (1.01), 2.327 (0.50), 2.669 (0.61), 3.238 (3.99), 3.257 (4.06), 4.245 (4.33), 4.256 (5.35), 4.271 (2.97), 5.276 (1.22), 5.290 (2.56), 5.309 (2.47), 5.324 (1.11), 6.773 (5.14), 6.792 (5.52), 6.895 (2.45), 6.913 (5.11), 6.932 (2.89), 7.141 (2.70), 7.159 (4.13), 7.176 (1.99), 7.330 (4.58), 7.349 (6.16), 7.359 (3.61), 7.363 (4.57), 7.425 (2.86), 7.431 (3.07), 7.444 (4.36), 7.451 (4.11), 7.464 (2.31), 7.470 (2.10), 7.693 (6.38), 7.697 (6.72), 7.702 (4.33), 7.705 (4.53), 7.713 (6.16), 7.717 (7.18), 7.719 (7.98), 7.723 (6.68), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.752 (5.37), 7.772 (5.59), 7.790 (3.08), 8.326 (4.48), 8.329 (4.58), 8.347 (4.17), 8.718 (7.77), 8.724 (7.76), 9.099 (4.38), 9.120 (4.17). |
| 582 | | LC-MS (Method L1): Rt = 0.99 min; MS (ESIpos): m/z = 514 [M + H]$^+$ | $^1$H-NMR (400 MHz, DMSO-d6) δ [ppm]: 1.161 (1.21), 1.180 (2.69), 1.196 (3.31), 1.216 (3.24), 1.230 (2.47), 1.235 (1.47), 1.249 (1.09), 1.356 (0.40), 2.044 (0.41), 2.184 (0.41), 2.595 (0.99), 2.609 (1.17), 2.628 (1.01), 2.728 (0.96), 2.745 (1.23), 2.763 (0.79), 3.065 (16.00), 4.229 (0.62), 4.237 (0.58), 4.248 (0.91), 4.256 (1.04), 4.270 (0.58), 5.227 (0.48), 5.241 (0.48), 6.774 (1.04), 6.794 (1.15), 6.883 (0.48), 6.902 (1.01), 6.920 (0.59), 6.967 (0.72), 6.972 (0.72), 6.996 (0.74), 7.001 (0.75), 7.138 (0.56), 7.156 (0.90), 7.174 (0.45), 7.218 (1.64), 7.223 (1.57), 7.331 (0.76), 7.350 (0.71), 7.550 (0.70), 7.567 (1.32), 7.595 (1.22), 7.616 (1.30), 7.633 (0.71), 8.199 (1.07), 8.203 (1.13), 8.220 (1.01), 8.224 (1.00), 8.506 (2.86), 9.055 (0.47), 9.073 (0.74), 9.092 (0.49). |
| 583 | | LC-MS (Method L1): Rt = 1.20 min; MS (ESIpos): m/z = 556 [M + H]$^+$ | $^1$H-NMR (400 MHz, DMSO-d6) δ [ppm]: 0.008 (1.62), 1.142 (0.89), 1.161 (6.60), 1.180 (13.02), 1.195 (16.00), 1.216 (15.26), 1.229 (11.19), 1.234 (6.42), 1.248 (5.03), 1.356 (2.57), 2.034 (1.17), 2.061 (1.72), 2.182 (1.53), 2.194 (1.58), 2.207 (1.56), 2.217 (1.57), 2.327 (0.56), 2.366 (0.40), 2.578 (1.59), 2.596 (4.14), 2.610 (4.95), 2.629 (4.33), 2.648 (1.32), 2.709 (1.71), 2.728 (3.88), 2.745 (4.90), 2.763 (3.19), 3.875 (11.89), 4.211 (0.84), 4.232 (2.57), 4.252 (3.80), 4.262 (3.67), 4.279 (2.36), 5.242 (2.14), 5.256 (2.13), 6.776 (4.90), 6.796 (5.51), 6.892 (1.72), 6.910 (3.66), 6.929 (2.06), 6.969 (3.24), 6.974 (3.27), 7.000 (3.63), 7.005 (3.58), 7.141 (2.39), 7.161 (3.89), 7.180 (2.02), 7.225 (7.39), 7.230 (6.95), 7.352 (4.16), 7.370 (3.84), 7.591 (3.42), 7.607 (5.69), 7.646 (5.21), 7.667 (5.45), 7.685 (3.27), 8.243 (4.62), 8.246 (4.72), 8.263 (4.30), 8.267 (4.07), 8.566 (8.87), 8.571 (9.34), 9.136 (2.13), 9.154 (3.49), 9.173 (2.18). |
| 585 | | LC-MS (Method L4): Rt = 3.93 min; MS (ESIpos): | $^1$H-NMR (400 MHz, DMSO-d6) δ [ppm] −0.008 (0.77), 0.008 (0.70), 2.009 (0.45), 2.124 (0.42), 2.137 (0.56), 2.159 (0.67), 2.173 (0.54), 2.729 (16.00), 3.132 (8.33), 3.140 (9.59), 4.242 (1.09), 4.256 (1.79), 4.268 (1.30), 4.285 (0.74), 4.304 (0.47), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

| Example No | logP (Method L0) [a] | LC-MS (Method L2-L5) | NMR or NMR Peaklist |
|---|---|---|---|
| | | m/z = 520 [M + H]$^+$ | 4.313 (0.51), 5.228 (0.59), 5.244 (0.74), 5.261 (0.70), 5.277 (0.49), 5.754 (5.28), 6.788 (0.97), 6.800 (1.15), 6.807 (1.12), 6.818 (1.26), 6.861 (0.47), 6.879 (1.00), 6.898 (0.64), 6.905 (0.63), 6.923 (1.16), 6.942 (0.70), 7.145 (0.53), 7.163 (1.32), 7.184 (1.31), 7.201 (1.14), 7.217 (0.79), 7.322 (0.99), 7.341 (0.88), 7.673 (1.37), 7.677 (3.00), 7.682 (2.18), 7.707 (7.29), 7.712 (5.77), 7.789 (0.70), 7.809 (2.12), 7.827 (3.94), 7.832 (2.99), 7.849 (0.62), 7.852 (0.68), 7.975 (1.92), 7.980 (1.72), 7.991 (1.71), 7.996 (1.45), 9.158 (4.20), 9.183 (4.34), 9.199 (1.01). |
| 586 | | LC-MS (Method L1): Rt = 0.98 min; MS (ESIpos): m/z = 494 [M + H]$^+$ | $^1$H-NMR (400 MHz, DMSO-d6) δ [ppm]: 1.313 (16.00), 2.359 (3.34), 3.056 (5.98), 4.262 (0.45), 4.271 (0.52), 6.788 (0.52), 6.809 (0.57), 6.924 (0.54), 7.173 (1.16), 7.218 (0.69), 7.346 (0.96), 7.367 (0.45), 7.611 (0.52), 7.631 (0.52), 7.659 (0.59), 8.157 (0.42), 8.564 (1.24), 9.083 (0.42), 9.103 (0.42). |
| 587 | | LC-MS (Method L1): Rt = 1.18 min; MS (ESIpos): m/z = 536 [M + H]$^+$ | $^1$H-NMR (400 MHz, DMSO-d6) δ [ppm]: 1.295 (2.20), 1.313 (16.00), 2.360 (4.01), 3.276 (1.42), 3.287 (1.54), 3.875 (2.03), 4.268 (0.54), 6.789 (0.67), 6.810 (0.75), 6.932 (0.71), 6.950 (0.41), 7.156 (0.40), 7.175 (1.57), 7.225 (0.98), 7.349 (1.06), 7.373 (0.71), 7.392 (0.66), 7.659 (0.78), 7.679 (0.75), 7.698 (0.86), 7.712 (0.44), 8.213 (0.58), 8.230 (0.53), 8.623 (1.85), 9.157 (0.60), 9.178 (0.59). |
| 588 | | LC-MS (Method L1): Rt = 1.14 min; MS (ESIpos): m/z = 522 [M + H]$^+$ | $^1$H-NMR (400 MHz, DMSO-d6) δ [ppm]: −0.008 (1.01), 0.008 (0.99), 1.197 (7.08), 1.216 (16.00), 1.234 (7.43), 2.089 (0.55), 2.096 (0.46), 2.208 (0.52), 2.220 (0.48), 2.230 (0.47), 2.327 (0.44), 2.522 (1.17), 2.615 (1.76), 2.634 (5.17), 2.653 (5.02), 2.671 (1.92), 3.243 (0.45), 3.262 (1.26), 3.275 (2.62), 3.287 (2.82), 3.874 (4.06), 4.245 (0.80), 4.253 (0.63), 4.267 (1.07), 4.277 (1.01), 4.293 (0.68), 5.259 (0.75), 5.278 (0.75), 5.754 (1.39), 6.789 (1.42), 6.810 (1.58), 6.913 (0.73), 6.932 (1.50), 6.948 (0.89), 6.951 (0.88), 7.073 (2.20), 7.152 (0.74), 7.156 (0.80), 7.173 (1.25), 7.194 (5.31), 7.373 (1.25), 7.391 (1.18), 7.638 (0.84), 7.656 (1.64), 7.676 (1.69), 7.695 (1.79), 7.699 (2.07), 7.713 (0.99), 7.717 (0.85), 8.208 (1.34), 8.212 (1.38), 8.229 (126), 8.233 (1.22), 8.629 (5.50), 9.153 (1.39), 9.173 (1.34). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via “side-products-fingerprints”.

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication “Citation of NMR Peaklist Data within Patent Applications” of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 592 | | LC-MS (Method L1): Rt = 1.14 min; MS (ESIpos): m/z = 479 [M + H]$^+$ | $^1$H-NMR (500 MHz, DMSO-d6) δ [ppm]: 1.234 (0.47), 2.106 (0.61), 2.117 (0.70), 2.129 (0.79), 2.134 (0.71), 2.262 (0.49), 2.273 (0.68), 2.283 (0.72), 2.290 (0.70), 2.301 (0.52), 4.035 (0.41), 4.195 (0.49), 4.200 (0.56), 4.218 (1.25), 4.235 (0.87), 4.240 (0.70), 4.289 (0.70), 4.295 (0.92), 4.301 (0.85), 4.308 (0.93), 4.318 (0.57), 4.323 (0.56), 4.330 (0.43), 4.742 (1.91), 5.390 (0.52), 5.400 (1.12), 5.416 (1.11), 5.427 (0.51), 5.554 (0.98), 6.793 (2.09), 6.808 (2.27), 6.937 (1.02), 6.952 (2.13), 6.966 (1.23), 7.163 (1.03), 7.166 (1.07), 7.180 (1.76), 7.194 (0.87), 7.197 (0.82), 7.410 (1.80), 7.424 (1.69), 7.665 (16.00), 7.737 (1.30), 7.752 (2.11), 7.768 (1.83), 7.845 (2.28), 7.848 (2.39), 7.860 (1.82), 7.862 (1.73), 7.967 (1.51), 7.984 (1.29), 8.488 (0.66), 9.045 (5.88), 9.260 (1.85), 9.277 (1.82). |
| 593 | | 1.18 min; MS (ESIpos): m/z = 493 [M + H]$^+$ | $^1$H-NMR (500 MHz, DMSO-d6) δ [ppm]: 1.190 (0.46), 2.062 (0.53), 2.068 (0.53), 2.076 (0.53), 2.090 (0.66), 2.096 (0.59), 2.213 (0.59), 2.223 (0.59), 2.230 (0.53), 2.362 (0.53), 2.519 (0.72), 2.522 (0.53), 2.636 (0.53), 3.460 (0.99), 3.473 (2.24), 3.487 (1.32), 3.780 (1.05), 3.790 (1.51), 3.799 (0.99), 4.230 (0.46), 4.246 (1.12), 4.253 (0.79), 4.263 (1.05), 4.268 (1.32), 4.275 (0.99), 4.281 (0.79), 4.288 (0.86), 5.091 (0.86), 5.101 (1.78), 5.111 (0.79), 5.286 (0.40), 5.297 (0.86), 5.314 (0.86), 6.786 (1.91), 6.789 (1.91), 6.803 (2.17), 6.805 (2.11), 6.906 (1.05), 6.908 (1.12), 6.921 (1.91), 6.923 (1.84), 6.935 (1.19), 6.938 (1.12), 7.153 (0.99), 7.156 (0.99), 7.170 (1.51), 7.184 (0.79), 7.352 (1.12), 7.359 (1.58), 7.374 (1.38), 7.537 (0.40), 7.648 (4.54), 7.651 (16.00), 7.654 (3.23), 7.659 (0.72), 7.693 (0.66), 7.754 (1.45), 7.769 (1.91), 7.771 (1.65), 7.786 (1.78), 7.877 (2.17), 7.880 (2.24), 7.891 (1.78), 7.894 (1.65), 8.359 (1.58), 8.362 (1.65), 8.377 (1.58), 8.869 (7.57), 9.225 (1.65), 9.242 (1.58). |
| 594 | | LC-MS (Method L1): Rt = 1.04 min; MS (ESIpos): m/z = 505 | $^1$H-NMR (400 MHz, DMSO-d6) δ [ppm]: 2.050 (0.60), 2.058 (0.65), 2.069 (0.70), 2.085 (0.97), 2.092 (0.83), 2.100 (0.60), 2.197 (0.65), 2.209 (0.88), 2.221 (0.86), 2.230 (0.81), 2.243 (0.56), 2.252 (0.44), 2.327 (0.42), 2.429 (16.00), 2.670 (0.44), 3.252 (0.90), 3.272 (2.69), 3.283 (5.98), |

TABLE 2-continued

| LC-MS and NMR data |
|---|
| NMR peak forms are stated as they appear in the spectra, possible higher order effects have not been considered. |
| NMR peak lists |
| $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters. |
| The peak list of an example has therefore the form: |
| $\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$) |
| Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. |
| For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. |
| The $^1$H-NMR peak lists are similar to classical $^1$H-NMR prints and contains therefore usually all peaks, which are listed at classical NMR-interpretation. |
| Additionally they can show like classical $^1$H-NMR prints signals of solvents, stereoisomers of the target compounds, which are also object of the invention, and/or peaks of impurities. |
| To show compound signals in the delta-range of solvents and/or water the usual peaks of solvents, for example peaks of DMSO in DMSO-$D_6$ and the peak of water are shown in our $^1$H-NMR peak lists and have usually on average a high intensity. |
| The peaks of stereoisomers of the target compounds and/or peaks of impurities have usually on average a lower intensity than the peaks of target compounds (for example with a purity >90%). |
| Such stereoisomers and/or impurities can be typical for the specific preparation process. Therefore their peaks can help to recognize the reproduction of our preparation process via "side-products-fingerprints". |
| An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation. |
| Further details of NMR-data description with peak lists you find in the publication "Citation of NMR Peaklist Data within Patent Applications" of the Research Disclosure Database Number 564025. |

| Example No | logP (Method L0) [a] | LC-MS (Method L2-L5) | NMR or NMR Peaklist |
|---|---|---|---|
| | | [M + H]$^+$ | 3.295 (7.10), 3.867 (4.41), 3.878 (7.26), 3.889 (4.17), 4.224 (0.46), 4.245 (1.41), 4.252 (1.14), 4.266 (1.97), 4.275 (1.86), 4.292 (1.23), 4.311 (0.44), 5.243 (0.60), 5.257 (1.32), 5.276 (1.32), 5290 (0.58), 6.788 (2.37), 6.809 (2.62), 6.914 (1.18), 6.916 (1.21), 6.933 (2.50), 6.951 (1.48), 7.153 (1.23), 7.156 (1.30), 7.174 (2.09), 7.192 (1.02), 7.195 (1.00), 7.376 (2.23), 7.394 (2.09), 7.685 (3.87), 7.702 (2.60), 7.723 (2.30), 7.741 (3.73), 7.802 (2.78), 7.805 (2.92), 7.820 (2.32), 7.823 (2.62), 7.831 (3.66), 8.267 (2.32), 8.270 (2.39), 8.288 (2.20), 8.291 (2.13), 8.679 (8.26), 9.161 (2.34), 9.182 (2.30). |
| 598 | | LC-MS (Method L1): Rt = 0.84 min; MS (ESIpos): m/z = 463 [M + H]$^+$ | $^1$H-NMR (400 MHz, DMSO-d6) δ [ppm]: −0.008 (0.75), 0.008 (0.48), 2.068 (0.58), 2.076 (0.47), 2.175 (0.42), 2.188 (0.51), 2.199 (0.49), 2.209 (0.45), 2.427 (9.40), 2.523 (1.01), 3.070 (16.00), 4.242 (0.87), 4.250 (0.80), 4.261 (1.24), 4.269 (1.37), 4.284 (0.72), 5.241 (0.79), 5.261 (0.75), 6.785 (1.39), 6.787 (1.45), 6.805 (1.56), 6.808 (1.54), 6.905 (0.76), 6.908 (0.76), 6.924 (1.51), 6.926 (1.43), 6.942 (0.91), 6.945 (0.84), 7.149 (0.77), 7.153 (0.79), 7.170 (1.19), 7.187 (0.59), 7.191 (0.55), 7.354 (1.25), 7.372 (1.15), 7.632 (1.11), 7.650 (1.59), 7.654 (1.36), 7.672 (1.79), 7.680 (1.98), 7.737 (2.19), 7.739 (2.19), 7.762 (1.69), 7.766 (1.74), 7.780 (1.33), 7.783 (1.21), 7.828 (2.17), 8.220 (1.41), 8.223 (1.38), 8.241 (1.29), 8.244 (1.19), 8.613 (3.96), 9.082 (1.26), 9.103 (1.19). |
| 600 | | LC-MS (Method L1): Rt = 1.13 min; MS (ESIpos): m/z = 447 [M + H]$^+$ | $^1$H-NMR (400 MHz, DMSO-d6) δ [ppm]: 2.033 (0.49), 2.041 (0.52), 2.068 (0.76), 2.076 (0.68), 2.195 (0.64), 2.205 (0.65), 2.216 (0.57), 2.783 (16.00), 4.236 (1.14), 4.255 (1.65), 4.262 (1.79), 4.276 (1.08), 5.274 (0.47), 5.288 (1.06), 5.308 (1.05), 5.323 (0.49), 6.778 (2.06), 6.799 (2.26), 6.898 (1.00), 6.914 (2.08), 6.933 (1.25), 7.141 (1.01), 7.145 (1.08), 7.163 (1.66), 7.180 (0.81), 7.266 (1.14), 7.274 (1.67), 7.289 (1.20), 7.296 (1.69), 7.303 (1.14), 7.311 (0.77), 7.324 (1.88), 7.333 (2.15), 7.345 (1.33), 7.354 (2.23), 7.584 (1.59), 7.597 (1.64), 7.606 (1.48), 7.619 (1.41), 7.717 (1.13), 7.720 (1.36), 7.734 (2.93), 7.738 (2.68), 7.753 (2.46), 7.773 (2.49), 7.791 (1.20), 8.293 (1.91), 8.297 (2.02), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.314 (1.85), 8.318 (1.75), 8.738 (6.49), 9.072 (1.70), 9.093 (1.64). |
| 601 | | LC-MS (Method L1): Rt = 1.01 min; MS (ESIpos): m/z = 528 [M + H]$^+$ | $^1$H-NMR (400 MHz, DMSO-d6) δ [ppm]: −0.008 (0.79), 0.008 (0.75), 1.270 (12.17), 1.284 (12.89), 2.388 (3.41), 2.401 (3.26), 2.523 (0.94), 3.065 (16.00), 4.232 (0.55), 4.245 (0.88), 4.255 (1.03), 4.270 (0.61), 5.224 (0.60), 5.243 (0.60), 5.754 (1.14), 6.774 (1.15), 6.795 (1.28), 6.885 (0.58), 6.903 (1.22), 6.922 (0.69), 7.096 (0.63), 7.102 (0.70), 7.123 (0.72), 7.128 (0.75), 7.135 (0.65), 7.139 (0.65), 7.156 (0.97), 7.178 (0.46), 7.331 (0.94), 7.350 (0.87), 7.411 (1.63), 7.416 (1.58), 7.550 (0.92), 7.565 (1.38), 7.601 (1.33), 7.621 (1.46), 7.639 (0.85), 8.203 (1.13), 8.206 (1.22), 8.224 (1.07), 8.228 (1.06), 8.503 (1.65), 8.508 (1.79), 9.069 (1.03), 9.089 (1.02). |
| 602 | | LC-MS (Method L1): Rt = 0.72 min; MS (ESIpos): m/z = 517 | $^1$H-NMR (400 MHz, DMSO-d6) δ [ppm]: −0.008 (2.43), 0.008 (2.43), 2.005 (1.56), 2.014 (1.65), 2.040 (2.57), 2.048 (2.04), 2.174 (2.09), 2.186 (2.16), 2.196 (2.02), 2.327 (0.80), 2.366 (0.85), 2.669 (0.73), 2.710 (0.83), 4.032 (11.82), 4.207 (1.19), 4.227 (3.60), 4.235 (3.19), 4.246 (5.44), |
| | | [M + H]$^+$ | 4.254 (6.06), 4.270 (3.19), 4.287 (1.12), 4.938 (5.67), 4.956 (5.44), 5.217 (1.58), 5.231 (3.35), 5.251 (3.28), 5.265 (1.40), 6.782 (6.82), 6.803 (7.51), 6.889 (3.33), 6.907 (6.61), 6.924 (4.02), 7.145 (3.35), 7.149 (3.63), 7.166 (5.42), 7.187 (2.64), 7.252 (2.89), 7.274 (2.87), 7.293 (2.71), 7.307 (6.36), 7.314 (5.28), 7.323 (7.92), 7.335 (2.94), 7.343 (2.32), 7.576 (3.70), 7.589 (4.11), 7.598 (3.56), 7.611 (3.28), 7.650 (2.62), 7.667 (7.67), 7.686 (13.61), 7.701 (2.46), 8.132 (3.35), 8.319 (5.26), 8.325 (4.96), 8.338 (4.77), 8.344 (4.55), 8.642 (16.00), 8.708 (6.38 9.213 (4.73), 9.234 (4.61). |
| 603 | | LC-MS (Method L1): Rt = 1.20 min; MS (ESIpos): m/z = 461 [M + H]$^+$ | $^1$H-NMR (400 MHz, DMSO-d6) δ [ppm]: 1.312 (7.07), 1.330 (16.00), 1.349 (7.30), 2.004 (0.55), 2.019 (1.26), 2.030 (1.33), 2.038 (1.35), 2. (347 (1.47), 2.055 (2.00), 2.063 (1.72), 2.071 (1.26), 2.079 (0.81), 2.167 (0.77), 2.178 (1.39), 2.190 (1.60), 2.200 (1.63), 2.212 (1.45), 2.226 (1.03), 2.243 (0.57), 3.220 (1.71), 3.238 (4.68), 3.256 (4.64), 3.274 (1.72), 4.218 (0.71), 4.237 (3.03), 4.246 (4.63), 4.256 (5.41), 4.263 (4.80), 4.272 (3.05), 4.291 (0.73), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 5.278 (1.19), 5.293 (2.62), 5.312 (2.65), 5.328 (1.20), 6.775 (4.64), 6.795 (5.15), 6.897 (2.35), 6.900 (2.37), 6.916 (5.03), 6.934 (3.02), 7.139 (2.49), 7.143 (2.59), 7.160 (4.16), 7.178 (2.02), 7.181 (1.96), 7.269 (2.88), 7.276 (4.09), 7.292 (3.57), 7.299 (6.76), 7.307 (2.30), 7.321 (4.84), 7.330 (5.77), 7.342 (3.34), 7.350 (5.55), 7.436 (0.55), 7.444 (0.73), 7.460 (2.03), 7.470 (1.50), 7.483 (0.63), 7.488 (0.63), 7.582 (3.46), 7.595 (3.67), 7.604 (3.36), 7.617 (3.13), 7.635 (0.42), 7.708 (2.96), 7.712 (3.38), 7.726 (6.55), 7.729 (6.17), 7.751 (5.10), 7.772 (5.47), 7.790 (2.85), 8.326 (4.37), 8.329 (4.51), 8.347 (4.16), 8.350 (4.04), 8.731 (14.58), 9.104 (4.09), 9.124 (3.99). |
| 604 | | LC-MS (Method L1): Rt = 0.76 min; MS (ESIpos): m/z = 517 [M + H]$^+$ | $^1$H-NMR (400 MHz, DMSO-d6) δ [ppm]: −0.008 (3.57), 0.008 (3.20), 2.011 (1.02), 2.020 (1.09), 2.046 (1.71), 2.054 (1.42), 2.167 (1.15), 2.178 (1.46), 2.189 (1.42), 2.200 (1.38), 2.327 (1.33), 2.366 (0.84), 2.523 (2.88), 2.669 (1.31), 2.710 (0.80), 3.998 (0.69), 4.038 (7.81), 4.078 (0.67), 4.210 (0.82), 4.230 (2.51), 4.238 (2.22), 4.249 (3.71), 4.258 (4.19), 4.272 (2.17), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 4.927 (2.42), 4.940 (4.59), 4.963 (4.55), 4.975 (2.31), 5.221 (1.04), 5.234 (2.24), 5.255 (2.20), 5.268 (0.95), 6.785 (4.62), 6.806 (4.88), 6.892 (2.31), 6.911 (4.53), 6.929 (2.71), 6.954 (0.51), 6.961 (0.47), 6.974 (0.51), 6.980 (0.47), 7.149 (2.60), 7.170 (3.77), 7.187 (1.84), 7.191 (1.80), 7.200 (0.51), 7.313 (4.11), 7.320 (3.57), 7.330 (3.82), 7.342 (6.10), 7.365 (3.68), 7.486 (3.11), 7.493 (4.44), 7.502 (3.13), 7.508 (4.84), 7.522 (3.02), 7.529 (1.75), 7.533 (2.37), 7.540 (1.93), 7.544 (2.24), 7.551 (1.58), 7.650 (3.11), 7.667 (4.50), 7.671 (3.77), 7.688 (4.24), 7.776 (4.79), 7.791 (3.62), 8.133 (0.44), 8.323 (4.42), 8.326 (4.28), 8.344 (4.04), 8.347 (3.75), 8.661 (16.00), 8.710 (5.68 9.208 (3.97), 9.228 (3.79), 10.355 (1.09). |
| 605 | | LC-MS (Method L1): Rt = 1.16 min; MS (ESIpos): m/z = 447 [M + H]$^+$ | $^1$H-NMR (400 MHz, DMSO-d6) δ [ppm]: 2.038 (0.55), 2.048 (0.59), 2.057 (0.62), 2.064 (0.65), 2.074 (0.89), 2.082 (0.75), 2.089 (0.55), 2.185 (0.61), 2.197 (0.74), 2.209 (0.73), 2.219 (0.68), 2.787 (16.00), 4.239 (1.30), 4.248 (1.30), 4.258 (1.93), 4.265 (2.14), 4.279 (1.20), 5.277 (0.53), 5.292 (1.20), 5.311 (1.21), 5.326 (0.54), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 6.780 (2.05), 6.800 (2.32), 6.901 (1.05), 6.920 (2.28), 6.938 (1.33), 7.148 (1.14), 7.166 (1.88), 7.183 (0.88), 7.333 (1.49), 7.343 (2.14), 7.356 (3.17), 7.378 (1.66), 7.505 (1.11), 7.511 (1.81), 7.526 (2.33), 7.534 (1.46), 7.545 (1.03), 7.556 (1.03), 7.562 (0.70), 7.757 (1.11), 7.776 (2.36), 7.796 (2.24), 7.821 (2.68), 7.836 (1.38), 8.304 (2.03), 8.325 (1.92), 8.769 (6.05), 9.077 (1.92), 9.097 (1.89). |
| 607 | | LC-MS (Method L1): Rt = 1.26 min; MS (ESIpos): m/z = 570 [M + H]$^+$ | $^1$H-NMR (400 MHz, DMSO-d6) δ [ppm]: −0.149 (0.48), −0.008 (3.63), 0.008 (3.53), 0.146 (0.46), 1.175 (0.42), 1.269 (14.91), 1.283 (16.00), 1.398 (0.57), 1.988 (0.79), 2.065 (0.44), 2.195 (0.48), 2.327 (0.69), 2.366 (0.79), 2.388 (4.14), 2.401 (3.93), 2.669 (0.75), 2.709 (0.77), 3.283 (1.88), 3.876 (3.43), 4.231 (0.63), 4.252 (1.03), 4.279 (0.69), 5.238 (0.73), 5.258 (0.77), 5.754 (0.79), 6.776 (1.43), 6.797 (1.53), 6.891 (0.65), 6.910 (1.35), 6.928 (0.81), 7.102 (0.85), 7.131 (0.91), 7.143 (0.77), 7.161 (1.15), 7.180 (0.54), 7.353 (1.27), 7.370 (1.19), 7.418 (2.00), 7.424 (1.98), 7.590 (1.03), 7.607 (1.61), 7.652 (1.47), 7.673 (1.61), 7.690 (1.01), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 8.250 (1.37), 8.267 (1.23), 8.564 (1.86), 8.572 (2.04), 9.148 (1.21), 9.168 (1.17). |
| 608 | | LC-MS (Method L1): Rt = 1.12 min; MS (ESIpos): m/z = 559 [M + H]$^+$ | $^1$H-NMR (400 MHz, DMSO-d6) δ [ppm]: −0.008 (2.94), 0.008 (2.84), 2.026 (1.36), 2.034 (1.46), 2.045 (1.57), 2.061 (2.14), 2.068 (1.86), 2.076 (1.39), 2.183 (1.38), 2.196 (1.99), 2.207 (1.94), 2.217 (1.90), 2.230 (1.30), 2.252 (0.65), 2.327 (0.62), 2.366 (0.58), 2.669 (0.72), 2.710 (0.61), 3.254 (1.39), 3.294 (9.84), 3.879 (15.30), 4.202 (0.81), 4.209 (1.06), 4.230 (3.23), 4.238 (2.57), 4.251 (4.00), 4.263 (3.86), 4.279 (2.90), 4.298 (1.09), 4.306 (0.75), 5.239 (2.49), 5.253 (2.51), 5.754 (2.12), 6.778 (5.59), 6.798 (6.16), 6.895 (2.42), 6.913 (5.26), 6.932 (3.13), 7.142 (2.78), 7.146 (3.03), 7.164 (4.72), 7.181 (2.33), 7.185 (2.30), 7.354 (5.00), 7.372 (4.65), 7.706 (2.07), 7.724 (7.43), 7.737 (7.97), 7.742 (16.00), 7.754 (2.22), 7.885 (2.90), 7.892 (3.07), 7.917 (3.30), 7.921 (3.26), 8.052 (0.43), 8.297 (0.70), 8.310 (4.84), 8.316 (4.51), 8.328 (4.39), 8.334 (4.48), 8.342 (7.65), 8.347 (7.65), 8.604 (10.28), 8.706 (0.70), 9.165 (3.36), 9.184 (3.22). |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| 624 | | LC-MS (Method L1): Rt = 0.97 min; MS (ESIpos): m/z = 517 [M + H]$^+$ | $^1$H-NMR (400 MHz, DMSO-d6) δ [ppm]: −0.008 (1.20), 0.008 (1.22), 2.044 (0.43), 2.185 (0.41), 2.195 (0.40), 3.080 (16.00), 4.227 (0.67), 4.246 (1.04), 4.254 (1.15), 4.269 (0.62), 5.235 (0.51), 5.754 (3.68), 6.776 (1.33), 6.796 (1.47), 6.887 (0.57), 6.905 (1.24), 6.924 (0.75), 7.142 (0.65), 7.159 (1.03), 7.180 (0.52), 7.331 (0.80), 7.350 (0.73), 7.652 (0.64), 7.670 (1.58), 7.690 (2.46), 7.697 (1.81), 7.710 (0.61), 7.882 (0.81), 7.908 (0.84), 8.278 (1.17), 8.283 (1.16), 8.298 (1.11), 8.303 (1.04), 8.333 (2.42), 8.337 (2.34), 8.531 (4.40), 9.078 (0.75), 9.098 (0.70). |
| 628 | | LC-MS (Method L1): Rt = 1.22 min; MS (ESIpos): m/z = 461 [M + H]$^+$ | $^1$H-NMR (400 MHz, DMSO-d6) δ [ppm]: 1.308 (7.60), 1.326 (16.00), 1.345 (7.79), 2.061 (2.32), 2.203 (2.13), 2.327 (0.52), 2.670 (0.63), 3.243 (6.84), 3.262 (6.74), 3.280 (2.77), 4.260 (6.66), 5.298 (3.26), 5.314 (3.18), 6.777 (5.35), 6.797 (5.91), 6.903 (2.66), 6.921 (5.56), 6.940 (3.25), 7.145 (3.07), 7.163 (4.94), 7.182 (2.42), 7.339 (6.05), 7.354 (9.10), 7.375 (3.63), 7.511 (5.22), 7.526 (7.31), 7.550 (2.82), 7.756 (2.29), 7.774 (5.35), 7.794 (5.18), 7.810 (7.32), 7.827 (3.38), 8.338 (4.91), 8.358 (4.55), 8.763 (13.33), 9.106 (4.65), 9.126 (4.63). |
| 631 | | LC-MS (Method L1): Rt = 3.90 min; MS (ESIpos): m/z = 534 [M + H]$^+$ | $^1$H-NMR (400 MHz, DMSO-d6) δ [ppm] 1.091 (0.41), 1.235 (1.08), 1.259 (0.68), 1.299 (0.43), 2.066 (16.00), 2.100 (0.88), 2.214 (0.78), 2.226 (0.77), 2.235 (0.72), 2.268 (1.76), 2.328 (0.58), 2.669 (0.60), 2.750 (15.89), 4.208 (0.55), 4.228 (1.45), 4.249 (1.16), 4.258 (1.27), 4.269 (1.15), 4.286 (1.02), 5.143 (5.73), 5.250 (0.77), 5.282 (1.13), 5.301 (1.12), 6.790 (2.18), 6.810 (2.37), 6.917 (1.17), 6.935 (2.21), 6.953 (1.25), 7.157 (1.18), 7.177 (1.96), 7.195 (0.95), 7.381 (1.90), 7.400 (1.94), 7.654 (11.00), 7.658 (5.85), 7.723 (1.28), 7.741 (1.94), 7.762 (1.68), 7.882 (2.40), 7.898 (1.87), 8.251 (2.03), 8.270 (1.81), 8.917 (0.60), 8.948 (6.71), 9.278 (1.90), 9.298 (1.82). |
| 643 | | LC-MS (Method L1): Rt = 0.91 min; MS (ESIpos): m/z = 520 | $^1$H-NMR (400 MHz, DMSO-d6) δ [ppm]: 0.008 (0.88), 2.089 (0.52), 2.238 (16.00), 2.669 (1.25), 3.317 (2.60), 3.422 (1.31), 3.438 (1.42), 3.460 (1.08), 4.250 (0.72), 4.269 (1.14), 4.278 (1.25), 4.293 (0.65), 5.290 (0.69), 5.310 (0.69), 5.754 (0.94), 6.792 (1.36), 6.812 (1.48), 6.900 (0.70), |

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^{1}$H-NMR data of selected examples are written in form of $^{1}$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}$H spectra, we use tetramethylsilane and/or the chemical shift of the solvent used, especially in the case of spectra measured in DMSO. Therefore in NMR peak lists, tetramethylsilane peak can occur but not necessarily.

The $^{1}$H-NMR peak lists are similar to classical $^{1}$H-NMR prints and contains therefore usually all peaks, which are listed at classical NMR-interpretation.

Additionally they can show like classical $^{1}$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | $[M + H]^+$ | 6.919 (1.32), 6.937 (0.81), 7.158 (0.66), 7.175 (1.10), 7.193 (0.52), 7.366 (1.17), 7.383 (1.06), 7.654 (11.60), 7.771 (0.81), 7.789 (1.28), 7.810 (1.17), 7.885 (1.61), 7.900 (1.17), 8.145 (3.08), 8.283 (1.19), 8.302 (1.09), 8.871 (4.70), 9.325 (1.18), 9.345 (1.13). |
| 645 | | LC-MS (Method L1): Rt = 1.18 min; MS (ESIpos): m/z = 443 $[M + H]^+$ | $^{1}$H-NMR (500 MHz, DMSO-d6) δ [ppm]: 2.039 (0.59), 2.046 (0.63), 2.054 (0.65), 2.059 (0.66), 2.067 (0.88), 2.072 (1.06), 2.080 (0.51), 2.186 (0.59), 2.196 (0.76), 2.205 (0.79), 2.212 (0.72), 2.224 (0.47), 2.229 (0.41), 2.335 (10.23), 2.779 (16.00), 4.223 (0.40), 4.239 (1.31), 4.246 (1.16), 4.254 (2.05), 4.261 (2.12), 4.274 (1.15), 5.280 (0.52), 5.292 (1.13), 5.307 (1.10), 5.319 (0.50), 6.780 (2.18), 6.795 (2.35), 6.900 (1.09), 6.901 (1.08), 6.915 (2.22), 6.929 (1.29), 6.931 (1.20), 7.145 (1.11), 7.147 (1.14), 7.161 (1.96), 7.176 (3.03), 7.178 (3.05), 7.239 (1.53), 7.242 (1.36), 7.255 (1.82), 7.258 (1.60), 7.338 (1.91), 7.353 (1.78), 7.411 (2.22), 7.427 (1.81), 7.663 (1.80), 7.666 (1.84), 7.677 (2.62), 7.680 (2.49), 7.731 (2.08), 7.746 (1.86), 7.748 (2.32), 7.762 (1.51), 8.260 (2.18), 8.262 (2.20), 8.277 (2.05), 8.279 (1.93), 8.716 (5.69), 9.065 (1.86), 9.082 (1.80). |
| 646 | | LC-MS (Method L1): Rt = 1.24 min; MS (ESIpos): m/z = 457 $[M + H]^+$ | $^{1}$H-NMR (500 MHz, DMSO-d6): δ [ppm] = 9.10 (br d, 1H), 8.71 (s, 1H), 8.30 (d, 1H), 7.75 (t, 1H), 7.66 (d, 1H), 7.42 (d, 1H), 7.34 (d, 1H), 7.25 (dd, 1H), 7.19-7.14 (m, 2H), 6.92 (t, 1H), 6.78 (d, 1H), 5.33-5.28 (m, 1H), 4.29-4.22 (m, 2H), 3.36 (br s, 1H), 3.28-3.20 (m, 2H), 2.33 (s, 3H), 2.27-2.16 (m, 1H), 2.05 (ddd, 1H), 1.33 (t, 3H) |
| 653 | | LC-MS (Method L1): Rt = 1.20 min; MS (ESIpos): m/z = 531 $[M + H]^+$ | $^{1}$H-NMR (500 MHz, DMSO-d6) δ [ppm]: 1.160 (0.41), 1.175 (1.01), 1.189 (0.61), 1.235 (0.61), 1.397 (2.84), 1.988 (3.65), 2.004 (2.63), 2.085 (7.09), 2.155 (2.63), 2.165 (2.63), 2.172 (2.43), 2.362 (1.01), 2.432 (3.04), 2.636 (0.81), 3.375 (0.61), 3.904 (2.23), 4.023 (0.61), 4.037 (0.61), 4.219 (4.46), 4.242 (6.08), 4.249 (6.08), 4.256 (5.47), 4.263 (5.87), 4.278 (3.24), 5.233 (3.44), 5.247 (3.44), 5.752 (2.23), 5.856 (5.06), 6.764 (9.32), 6.766 (9.72), 6.780 (10.33), 6.782 (10.33), 6.888 (2.84), 6.902 (5.87), 6.918 (3.24), 7.138 (4.25), 7.141 (4.46), 7.155 (7.29), 7.169 |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters.

This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | (3.65), 7.334 (6.08), 7.349 (6.48), 7.375 (4.46), 7.441 (3.85), 7.447 (4.46), 7.457 (6.48), 7.463 (6.89), 7.472 (3.24), 7.478 (3.44), 7.708 (11.75), 7.711 (11.75), 7.724 (15.39), 7.728 (16.00), 7.738 (14.38), 7.742 (12.96), 7.751 (12.76), 7.767 (12.35), 7.781 (5.67), 8.059 (9.11), 8.062 (9.11), 8.075 (7.90), 8.078 (7.49), 8.819 (13.57), 8.827 (13.57), 8.933 (5.27), 8.949 (4.25). |
| 654 | | LC-MS (Method L1): Rt = 1.17 min; MS (ESIpos): m/z = 587 [M + H]$^+$ | $^1$H-NMR (500 MHz, CHLOROFORM-d) δ [ppm]: 0.006 (1.86), 1.222 (0.43), 1.255 (1.78), 1.549 (4.29), 2.005 (0.63), 2.009 (0.62), 2.025 (0.45), 2.034 (0.78), 2.038 (0.71), 2.170 (2.80), 2.175 (0.46), 2.270 (0.45), 2.281 (0.47), 2.285 (0.45), 2.292 (0.67), 2.302 (0.60), 3.056 (15.99), 3.423 (4.44), 3.459 (16.00, 3.534 (4.30), 4.074 (0.85), 4.079 (0.78), 4.097 (1.34), 4.101 (1.18), 4.119 (0.75), 4.124 (0.61), 4.294 (0.63), 4.302 (1.10), 4.311 (0.65), 4.317 (0.54), 4.325 (0.84), 4.333 (0.42), 5.348 (0.49), 5.358 (0.84), 5.367 (0.90), 5.375 (0.81), 5.385 (0.43), 6.731 (0.89), 6.733 (0.88), 6.746 (1.75), 6.760 (1.01), 6.762 (0.97), 6.823 (2.09), 6.840 (2.28), 6.922 (0.50), 7.080 (1.31), 7.092 (1.92), 7.099 (1.43), 7.105 (1.69), 7.178 (1.13), 7.181 (0.97), 7.195 (1.67), 7.209 (1.14), 7.212 (1.11), 7.220 (5.56), 7.282 (0.46), 7.376 (1.54), 7.423 (2.79), 7.427 (3.79), 7.430 (1.97), 7.526 (2.61), 7.532 (7.59), 7.536 (6.59), 7.590 (1.03), 7.604 (1.42), 7.607 (1.87), 7.621 (2.19), 7.645 (2.30), 7.648 (2.42), 7.656 (0.71), 7.662 (1.26), 7.665 (1.03), 7.736 (2.01), 7.739 (1.84), 7.749 (2.20), 7.752 (1.94), 7.764 (0.48), 7.766 (0.43), 7.818 (0.54), 7.821 (0.50), 7.835 (0.46), 9.108 (1.57), 9.133 (5.65). |
| 655 | | LC-MS (Method L1): Rt = 1.18 min; MS (ESIpos): m/z = 463 [M + H]$^+$ | $^1$H-NMR (500 MHz, DMSO-d6) δ [ppm]: 1.311 (7.80), 1.327 (16.00), 1.341 (7.58), 2.033 (1.52), 2.041 (1.61), 2.047 (1.74), 2.054 (1.78), 2.061 (2.13), 2.067 (1.87), 2.198 (1.93), 2.207 (1.91), 2.215 (1.83), 3.235 (2.53), 3.250 (6.81), 3.265 (6.83), 3.279 (3.01), 4.227 (1.01), 4.244 (3.29), 4.258 (5.03), 4.264 (5.39), 4.276 (3.07), 4.290 (0.97), 5.288 (1.40), 5.300 (2.99), 5.315 (2.94), 5.327 (1.35), 6.781 (5.15), 6.797 (5.61), 6.909 (2.60), 6.924 (5.33), 6.939 (3.03), 7.151 (2.73), 7.165 (4.53), 7.180 (2.23), 7.228 (2.53), 7.236 (2.62), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 7.345 (4.77), 7.360 (4.45), 7.601 (2.02), 7.607 (2.10), 7.614 (2.02), 7.782 (2.66), 7.797 (5.11), 7.813 (4.47), 7.845 (6.38), 7.857 (3.89), 8.374 (4.77), 8.389 (4.49), 8.789 (13.74), 9.121 (4.49, 9.137 (4.40). |
| 676 | | LC-MS (Method L1): Rt = 1.27 min; MS (ESIpos): m/z = 437 $[M + H]^+$ | $^1$H-NMR (500 MHz, DMSO-d6) δ [ppm]: 1.319 (6.59), 1.334 (14.59), 1.349 (6.59), 1.869 (13.65), 2.031 (1.41), 2.052 (1.88), 2.059 (1.41), 2.200 (1.41), 2.292 (16.00), 2.362 (1.41), 2.636 (1.88), 3.236 (3.29), 3.251 (3.76), 3.375 (0.94), 3.418 (0.94), 4.238 (2.35), 4.253 (3.29), 4.259 (3.76), 4.271 (2.35), 5.282 (0.94), 5.295 (1.88), 5.310 (1.88), 6.778 (4.24), 6.793 (4.71), 6.901 (1.88), 6.916 (4.24), 6.931 (2.35), 6.962 (5.18), 7.099 (2.35), 7.114 (4.24), 7.147 (2.35), 7.157 (5.18), 7.171 (3.29), 7.330 (3.29), 7.345 (2.82), 7.590 (4.24), 7.592 (4.24), 7.604 (5.18), 7.606 (4.71), 7.712 (4.24), 7.726 (3.76), 7.729 (4.24), 7.743 (3.29), 8.252 (3.76), 8.254 (4.24), 8.269 (3.76), 8.689 (13.65), 9.070 (2.35), 9.088 (1.88). |
| 684 | | LC-MS (Method L1): Rt = 1.28 min; MS (ESIpos): m/z = 469 $[M + H]^+$ | $^1$H-NMR (500 MHz, DMSO-d6) δ [ppm]: −0.120 (0.78), −0.007 (5.46), 0.007 (3.90), 0.117 (0.39), 1.520 (12.10), 1.523 (11.71), 1.534 (12.49), 1.538 (11.71), 1.548 (14.05), 1.563 (13.66), 1.866 (16.00), 1.884 (16.00), 2.036 (1.56), 2.176 (1.56), 2.281 (16.00), 2.294 (16.00), 2.362 (1.95), 2.636 (1.56), 3.363 (1.17), 3.853 (1.95), 4.219 (2.34), 4.245 (2.34), 4.252 (2.73), 4.259 (2.34), 4.266 (2.34), 5.248 (2.73), 5.264 (2.34), 6.771 (5.46), 6.786 (5.85), 6.892 (2.73), 6.906 (5.46), 6.924 (5.46), 6.948 (3.51), 7.131 (3.51), 7.138 (3.12), 7.142 (3.90), 7.147 (5.07), 7.169 (2.34), 7.206 (3.90), 7.215 (3.90), 7.221 (2.73), 7.230 (2.73), 7.318 (3.90), 7.333 (3.51), 7.642 (3.51), 7.660 (5.46), 7.678 (3.51), 8.473 (3.12), 8.484 (3.51), 8.492 (3.51), 8.504 (3.12), 8.640 (11.32), 8.643 (10.54), 9.075 (2.73), 9.082 (2.73), 9.092 (2.73), 9.098 (2.73). |
| 685 | | LC-MS (Method L1): Rt = 1.18 min; MS (ESIpos): m/z = 423 $[M + H]^+$ | $^1$H-NMR (500 MHz, DMSO-d6) δ [ppm]: −0.007 (1.56), 0.006 (1.12), 1.861 (5.14), 2.038 (0.49), 2.044 (0.51), 2.052 (0.51), 2.058 (0.54), 2.066 (0.72), 2.072 (0.58), 2.079 (0.42), 2.185 (0.47), 2.195 (0.63), 2.205 (0.63), 2.212 (0.58), 2.297 (7.94), 2.778 (16.00), 4.237 (0.98), 4.243 (0.79), 4.254 (1.52), 4.261 (1.45), 4.268 (0.93), |

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 2-continued

LC-MS and NMR data

NMR peak forms are stated as they appear in the spectra, possible higher order effects have not been considered.

NMR peak lists $^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 4.275 (0.98), 5.278 (0.42), 5.290 (0.91), 5.306 (0.89), 5.317 (0.40), 6.779 (1.89), 6.781 (1.96), 6.796 (2.10), 6.798 (2.06), 6.899 (0.84), 6.915 (1.68), 6.929 (0.96), 6.965 (2.03), 7.101 (1.03), 7.116 (1.78), 7.145 (1.00), 7.148 (1.10), 7.157 (2.34), 7.172 (1.31), 7.179 (0.84), 7.335 (1.31), 7.350 (1.19), 7.599 (1.92), 7.602 (1.92), 7.613 (2.38), 7.616 (2.27), 7.714 (1.96), 7.728 (1.78), 7.731 (2.15), 7.745 (1.64), 8.219 (2.08), 8.222 (2.13), 8.236 (1.96), 8.239 (1.82), 8.701 (6.47), 9.043 (1.66), 9.060 (1.66). |
| 686 | | LC-MS (Method L1): Rt = 1.14 min; MS (ESIpos): m/z = 479 [M + H]$^+$ | $^1$H-NMR (600 MHz, DMSO-d6) δ [ppm]: 0.005 (1.04), 2.043 (0.47), 2.048 (0.60), 2.053 (0.96), 2.058 (1.04), 2.065 (1.12), 2.069 (1.07), 2.077 (1.37), 2.081 (1.20), 2.087 (2.11), 2.092 (0.63), 2.193 (0.58), 2.199 (0.86), 2202 (0.81), 2.207 (1.32), 2.213 (0.97), 2.216 (1.31), 2.221 (1.32), 2.230 (0.99), 2.236 (0.64), 2.239 (0.62), 2.244 (0.46), 2.793 (0.55), 3.345 (8.00), 4.220 (0.71), 4.225 (0.87), 4.234 (0.90), 4.239 (2.32), 4.244 (1.61), 4.253 (1.77), 4.258 (1.47), 4.268 (1.42), 4273 (1.80), 4.279 (1.58), 4.285 (1.91), 4.292 (0.78), 4.298 (0.84), 4.303 (0.65), 5.037 (16.00), 5.287 (0.91), 5.297 (1.95), 5.310 (1.96), 5.320 (0.92), 6.790 (3.66), 6.791 (3.76), 6.803 (4.00), 6.804 (3.99), 6.917 (1.85), 6.918 (1.84), 6.929 (3.75), 6.931 (3.68), 6.942 (2.14), 6.943 (2.05), 7.159 (1.78), 7.161 (1.80), 7.173 (3.01), 7.184 (1.56), 7.187 (1.49), 7.259 (1.51), 7.267 (1.49), 7.274 (1.49), 7.376 (3.08), 7.388 (2.95), 7.609 (0.49), 7.614 (0.63), 7.619 (0.75), 7.624 (1.18), 7.628 (1.14), 7.633 (1.23), 7.638 (1.18), 7.642 (1.18), 7.646 (0.74), 7.651 (0.65), 7.657 (0.56), 7.800 (2.66), 7.812 (3.85), 7.814 (3.18), 7.826 (3.61), 7.873 (4.17), 7.875 (4.29), 7.885 (3.06), 7.887 (2.94), 8.416 (3.61), 8.418 (3.65), 8.430 (3.48), 8.432 (3.27), 8.890 (12.74), 9.184 (3.52), 9.197 (3.43). |
| 687 | | LC-MS (Method L1): Rt = 1.24 min; MS (ESIpos): m/z = 445 [M + H]$^+$ | $^1$H-NMR (500 MHz, DMSO-d6) δ [ppm]: 1.306 (6.83), 1.321 (15.00), 1.336 (6.50), 2.030 (0.50), 2.043 (1.17), 2.050 (1.17), 2.058 (1.17), 2.064 (1.33), 2.072 (6.00), 2.078 (1.33), 2.084 (1.00), 2.091 (0.67), 2.187 (0.67), 2.194 (1.17), 2.205 (1.33), 2.214 (1.33), 2.222 (1.17), 2.234 (0.83), 2.248 (0.50), 2.363 (0.50), 2.637 (0.50), |

TABLE 2-continued

LC-MS and NMR data

NMR peak forms are stated as they appear in the spectra, possible higher order effects have not been considered.

NMR peak lists

$^1$H-NMR data of selected examples are written in form of $^1$H-NMR peak lists. To each signal peak are listed the δ-value in ppm and the signal intensity in round brackets. Between the δ-value - signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . . $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

| Example No | logP (Method L0) [a] | LC-MS (Method L2-L5) | NMR or NMR Peaklist |
|---|---|---|---|
| | | | 3.235 (1.83), 3.250 (5.50), 3.265 (5.67), 3.280 (2.50), 3.352 (3.17), 3.358 (2.17), 3.365 (1.17), 3.376 (0.83), 3.429 (0.50), 4.236 (0.83), 4.251 (2.67), 4.261 (2.83), 4.266 (3.50), 4.270 (3.67), 4.274 (3.67), 4.282 (2.33), 4.297 (0.67), 5.298 (1.00), 5.310 (2.17), 5.326 (2.17), 5.337 (1.00), 6.786 (4.17), 6.788 (4.33), 6.802 (4.67), 6.804 (4.50), 6.916 (2.17), 6.918 (2.17), 6.931 (4.33), 6.933 (4.17), 6.945 (2.67), 6.948 (2.50), 7.153 (2.17), 7.156 (2.17), 7.170 (3.50), 7.184 (1.83), 7.187 (1.67), 7.257 (0.83), 7.261 (1.67), 7.266 (1.33), 7.276 (1.67), 7.280 (3.50), 7.285 (2.33), 7.294 (1.00), 7.299 (1.67), 7.304 (1.17), 7.333 (4.67), 7.337 (5.17), 7.350 (8.83), 7.364 (3.83), 7.757 (3.17), 7.771 (4.50), 7.774 (3.83), 7.788 (4.17), 7.868 (5.17), 7.871 (5.17), 7.882 (4.00), 7.885 (3.67), 8.316 (4.00), 8.318 (4.00), 8.333 (3.83), 8.335 (3.50), 8.828 (16.00), 9.103 (3.67), 9.120 (3.67). |
| 688 | | LC-MS (Method L1): Rt = 1.21 min; MS (ESIpos): m/z = 463 [M + H]+ | $^1$H-NMR (600 MHz, DMSO-d6): d [ppm] = 9.15 (d, 1H), 8.78 (s, 1H), 8.37 (dd, 1H), 7.83 (d, 1H), 7.80 (d, 1H), 7.47-7.40 (m, 1H), 7.37-7.31 (m, 2H), 7.17 (t, 1H), 6.93 (t, 1H), 6.79 (d, 1H), 5.33-5.29 (m, 1H), 4.30-4.22 (m, 2H), 3.33-3.20 (m, 2H), 2.24-2.17 (m, 1H), 2.09-2.01 (m, 1H), 1.33 (t, 3H) |
| 695 | | LC-MS (Method L1): Rt = 1.17 min; MS (ESIpos): m/z = 431 [M + H]+ | $^1$H-NMR (600 MHz, DMSO-d6) δ [ppm]: 2.063 (0.84), 2.069 (0.94), 2.074 (0.95), 2.081 (1.08), 2.086 (1.02), 2.209 (1.01), 2.217 (1.02), 2.223 (0.98), 2.231 (0.76), 2.790 (16.00), 4.237 (0.59) 4.250 (1.61), 4.255 (1.39), 4.269 (2.17), 4.275 (1.71), 4.280 (1.46), 4.286 (1.51), 4.299 (0.61), 5.297 (0.70), 5.307 (1.52), 5.319 (1.53), 5.329 (0.70), 5.762 (2.23), 6.793 (2.52), 6.807 (2.70), 6.919 (1.29), 6.932 (2.60), 6.944 (1.48), 7.162 (1.32), 7.174 (2.26), 7.187 (1.14), 7.280 (0.92), 7.295 (1.78), 7.311 (0.98), 7.349 (3.64), 7.358 (5.29), 7.369 (3.11), 7.762 (1.45), 7.774 (2.50), 7.788 (1.76), 7.885 (2.83), 7.897 (2.35), 8.285 (2.53), 8.299 (2.38), 8.841 (5.87), 9.107 (2.25), 9.120 (2.21). |

Table 3a-3e: Intermediates

TABLE 3a

1Q-OEt

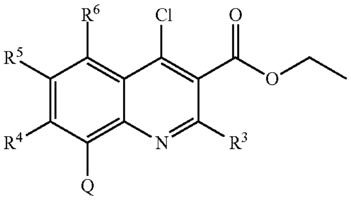

| Number | R3 | R4 | R5 | R6 | Q |
|---|---|---|---|---|---|
| 1Q-1 | H | H | H | H | 3,5-dichlorophenyl |
| 1Q-2 | H | H | H | H | 2,3,5-trichlorophenyl |
| 1Q-3 | H | H | H | H | 2,3-dichlorophenyl |
| 1Q-4 | H | H | H | H | 3,5-difluorophenyl |
| 1Q-5 | H | H | H | H | 2,3,5-trifluorophenyl |
| 1Q-6 | H | H | H | H | 2,3-difluorophenyl |
| 1Q-7 | H | F | H | H | 3,5-dichlorophenyl |
| 1Q-8 | H | F | H | H | 2,3,5-trichlorophenyl |
| 1Q-9 | H | F | H | H | 2,3-dichlorophenyl |
| 1Q-10 | H | F | H | H | 3,5-difluorophenyl |
| 1Q-11 | H | F | H | H | 2,3,5-trifluorophenyl |
| 1Q-12 | H | F | H | H | 2,3-difluorophenyl |
| 1Q-13 | H | H | H | H | 3,5-dimethylphenyl |

TABLE 3b

1U-OEt

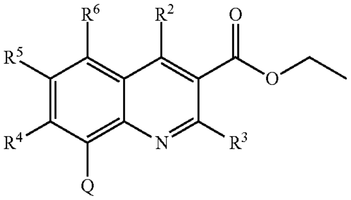

| Number | R2 | R3 | R4 | R5 | R6 | Q |
|---|---|---|---|---|---|---|
| 1U-1 | dimethylamino | H | H | H | H | 3,5-dichlorophenyl |
| 1U-2 | dimethylamino | H | H | H | H | 2,3,5-trichlorophenyl |
| 1U-3 | dimethylamino | H | H | H | H | 2,3-dichlorophenyl |
| 1U-4 | dimethylamino | H | H | H | H | 3,5-difluorophenyl |
| 1U-5 | dimethylamino | H | H | H | H | 2,3,5-trifluorophenyl |
| 1U-6 | dimethylamino | H | H | H | H | 2,3-difluorophenyl |
| 1U-7 | dimethylamino | H | F | H | H | 3,5-dichlorophenyl |
| 1U-8 | dimethylamino | H | F | H | H | 2,3,5-trichlorophenyl |
| 1U-9 | dimethylamino | H | F | H | H | 2,3-dichlorophenyl |
| 1U-10 | dimethylamino | H | F | H | H | 3,5-difluorophenyl |
| 1U-11 | dimethylamino | H | F | H | H | 2,3,5-trifluorophenyl |
| 1U-12 | dimethylamino | H | F | H | H | 2,3-difluorophenyl |
| 1U-13 | morpholin-4-yl | H | H | H | H | 3,5-dichlorophenyl |
| 1U-14 | morpholin-4-yl | H | H | H | H | 2,3,5-trichlorophenyl |
| 1U-15 | morpholin-4-yl | H | H | H | H | 2,3-dichlorophenyl |
| 1U-16 | morpholin-4-yl | H | H | H | H | 3,5-difluorophenyl |
| 1U-17 | morpholin-4-yl | H | H | H | H | 2,3,5-trifluorophenyl |
| 1U-18 | morpholin-4-yl | H | H | H | H | 2,3-difluorophenyl |
| 1U-19 | morpholin-4-yl | H | F | H | H | 3,5-dichlorophenyl |
| 1U-20 | morpholin-4-yl | H | F | H | H | 2,3,5-trichlorophenyl |
| 1U-21 | morpholin-4-yl | H | F | H | H | 2,3-dichlorophenyl |
| 1U-22 | morpholin-4-yl | H | F | H | H | 3,5-difluorophenyl |
| 1U-23 | morpholin-4-yl | H | F | H | H | 2,3,5-trifluorophenyl |
| 1U-24 | morpholin-4-yl | H | F | H | H | 2,3-difluorophenyl |

TABLE 3c

1R

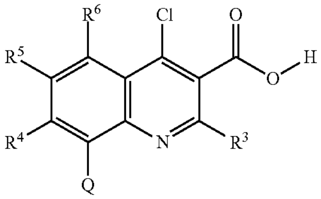

| Number | R3 | R4 | R5 | R6 | Q |
|---|---|---|---|---|---|
| 1R-1 | H | H | H | H | 3,5-dichlorophenyl |
| 1R-2 | H | H | H | H | 2,3,5-trichlorophenyl |
| 1R-3 | H | H | H | H | 2,3-dichlorophenyl |
| 1R-4 | H | H | H | H | 3,5-difluorophenyl |
| 1R-5 | H | H | H | H | 2,3,5-trifluorophenyl |
| 1R-6 | H | H | H | H | 2,3-difluorophenyl |
| 1R-7 | H | F | H | H | 3,5-dichlorophenyl |
| 1R-8 | H | F | H | H | 2,3,5-trichlorophenyl |
| 1R-9 | H | F | H | H | 2,3-dichlorophenyl |
| 1R-10 | H | F | H | H | 3,5-difluorophenyl |
| 1R-11 | H | F | H | H | 2,3,5-trifluorophenyl |
| 1R-12 | H | F | H | H | 2,3-difluorophenyl |
| 1R-13 | H | H | H | H | 3,5-dimethylphenyl |

TABLE 3d

1W

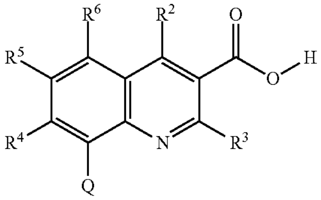

| Number | R2 | R3 | R4 | R5 | R6 | Q |
|---|---|---|---|---|---|---|
| 1W-1 | dimethylamino | H | H | H | H | 3,5-dichlorophenyl |
| 1W-2 | dimethylamino | H | H | H | H | 2,3,5-trichlorophenyl |
| 1W-3 | dimethylamino | H | H | H | H | 2,3-dichlorophenyl |
| 1W-4 | dimethylamino | H | H | H | H | 3,5-difluorophenyl |
| 1W-5 | dimethylamino | H | H | H | H | 2,3,5-trifluorophenyl |
| 1W-6 | dimethylamino | H | H | H | H | 2,3-difluorophenyl |
| 1W-7 | dimethylamino | H | F | H | H | 3,5-dichlorophenyl |
| 1W-8 | dimethylamino | H | F | H | H | 2,3,5-trichlorophenyl |
| 1W-9 | dimethylamino | H | F | H | H | 2,3-dichlorophenyl |
| 1W-10 | dimethylamino | H | F | H | H | 3,5-difluorophenyl |
| 1W-11 | dimethylamino | H | F | H | H | 2,3,5-trifluorophenyl |
| 1W-12 | dimethylamino | H | F | H | H | 2,3-difluorophenyl |
| 1W-13 | morpholin-4-yl | H | H | H | H | 3,5-dichlorophenyl |
| 1W-14 | morpholin-4-yl | H | H | H | H | 2,3,5-trichlorophenyl |
| 1W-15 | morpholin-4-yl | H | H | H | H | 2,3-dichlorophenyl |
| 1W-16 | morpholin-4-yl | H | H | H | H | 3,5-difluorophenyl |
| 1W-17 | morpholin-4-yl | H | H | H | H | 2,3,5-trifluorophenyl |
| 1W-18 | morpholin-4-yl | H | H | H | H | 2,3-difluorophenyl |
| 1W-19 | morpholin-4-yl | H | F | H | H | 3,5-dichlorophenyl |
| 1W-20 | morpholin-4-yl | H | F | H | H | 2,3,5-trichlorophenyl |
| 1W-21 | morpholin-4-yl | H | F | H | H | 2,3-dichlorophenyl |
| 1W-22 | morpholin-4-yl | H | F | H | H | 3,5-difluorophenyl |
| 1W-23 | morpholin-4-yl | H | F | H | H | 2,3,5-trifluorophenyl |
| 1W-24 | morpholin-4-yl | H | F | H | H | 2,3-difluorophenyl |

TABLE 3e

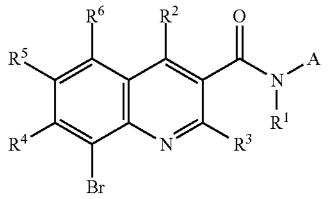

1T-Br

| Number | R1 | R2 | R3 | R4 | R5 | R6 | A |
|---|---|---|---|---|---|---|---|
| 1T-1 | H | dimethylamino | H | H | H | H | (4S)-3,4-dihydro-2H-chromen-4-yl |
| 1T-2 | H | dimethylamino | H | H | H | H | (1S)-2,3-dihydro-1H-inden-1-yl |
| 1T-3 | H | dimethylamino | H | F | H | H | (4S)-3,4-dihydro-2H-chromen-4-yl |
| 1T-4 | H | dimethylamino | H | F | H | H | (1S)-2,3-dihydro-1H-inden-1-yl |
| 1T-5 | H | morpholin-4-yl | H | H | H | H | (4S)-3,4-dihydro-2H-chromen-4-yl |
| 1T-6 | H | morpholin-4-yl | H | H | H | H | (1S)-2,3-dihydro-1H-inden-1-yl |
| 1T-7 | H | morpholin-4-yl | H | F | H | H | (4S)-3,4-dihydro-2H-chromen-4-yl |
| 1T-8 | H | morpholin-4-yl | H | F | H | H | (1S)-2,3-dihydro-1H-inden-1-yl |

TABLE 4

LC-MS and NMR or NMR Peaklist of Intermediates

| Example No | logP (Method L0) [a] | LC-MS (Method L2-L5) | NMR or NMR Peaklist |
|---|---|---|---|
| 1-Q3 | 5.19 | | $^1$H-NM R (400.0 MHz, $d_6$-DMSO): δ = 9.100 (11.2); 8.521 (2.9); 8.516 (3.1); 8.501 (3.1); 8.496 (3.3); 7.983 (1.5); 7.965 (4.5); 7.945 (9.0); 7.941 (6.3); 7.928 (1.8); 7.756 (2.9); 7.752 (3.4); 7.736 (3.6); 7.732 (3.8); 7.504 (2.2); 7.485 (5.2); 7.465 (3.5); 7.434 (4.1); 7.431 (4.7); 7.415 (2.5); 7.412 (2.4); 4.454 (2.4); 4.436 (7.3); 4.418 (7.3); 4.400 (2.5); 3.321 (80.5); 2.891 (0.5); 2.731 (0.5); 2.672 (1.1); 2.502 (195.0); 2.329 (1.1); 2.075 (1.2); 1.387 (7.9); 1.369 (16.0); 1.351 (7.7); 0.146 (0.4); 0.000 (90.1); −0.150 (0.5) |
| 1Q-13 | | LC-MS (Method L1): Rt = 1.43 min; MS (ESIpos): m/z = 340 [M +H]$^+$ | 1H-NMR (400MHz, DMSO-d6): δ [ppm] = 9.13 (s, 1H), 8.42 (dd, 1H), 7.87-7.96 (m, 2H), 7.20 (s, 2H), 7.07 (s, 1H), 4.44 (q, 2H), 2.35 (s, 6H), 1.38 (t, 3H). |
| 1U-5 | 2.40 | | 1H-NMR (400MHz, DMSO-d6): δ [ppm] = 8.73 (s, 1H), 8.35 (d, 1H), 7.83 (d, 1H), 7.72-7.69 (t, 1H), 7.61-7.58 (m, 1H), 7.24-7.22 (m, 1H), 4.41-4.35 (q, 2H), 3.09 (s, 6H), 1.36 (t, 3H). |
| 1U-8 | 4.57 | | $^1$H-NMR (400.0 MHz, $d_6$-DMSO): δ = 8.857 (1.9); 8.703 (3.6); 8.425 (0.7); 8.409 (0.8); 8.401 (0.8); 8.386 (0.7); 8.305 (0.4); 8.290 (0.5); 8.281 (0.5); 8.266 (0.5); 7.967 (2.0); 7.961 (2.1); 7.687 (0.8); 7.664 (1.2); 7.647 (0.5); 7.641 (0.8); 7.626 (0.5); 7.623 (0.5); 7.603 (0.4); 7.586 (2.0); 7.580 (2.0); 5.758 (5.2); 4.420 (0.4); 4.403 (1.3); 4.391 (0.8); 4.385 (1.4); 4.374 (2.3); 4.367 (0.6); 4.356 (2.3); 4.338 (0.7); 3.326 (10.9); 3.094 (16.0); 3.071 (9.4); 2.514 (7.9); 2.509 (15.9); 2.505 (21.1); 2.500 (15.4); 2.496 (7.6); 1.382 (1.4); 1.364 (3.0); 1.357 (2.6); 1.346 (1.6); 1.339 (5.3); 1.321 (2.4); 1.299 (0.5); 1.269 (0.5); 0.008 (0.8); 0.000 (20.5); −0.008 (0.9) |
| 1U-11 | 2.40 | | $^1$H-NMR (400.0 MHz, $d_6$-DMSO): δ = 8.730 (3.6); 8.348 (1.0); 8.345 (0.9); 8.327 (1.1); 7.828 (0.9); 7.813 (1.3); 7.725 (1.0); 7.707 (1.0); 7.704 (1.0); 7.686 (0.7); 7.607 (0.4); 7.601 (0.4); 7.594 (0.4); 7.586 (0.4); 7.581 (0.4); 7.243 (0.5); 7.233 (0.4); 7.221 (0.5); 4.407 (0.8); 4.390 (2.4); 4.372 (2.4); 4.354 (0.8); 3.327 (5.3); 3.089 (16.0); 2.509 (10.6); 2.505 (13.3); 2.501 (9.7); 1.397 (10.3); 1.372 (2.5); 1.355 (5.2); 1.337 (2.4); 0.008 (0.5); 0.000 (10.8); −0.009 (0.5) |
| 1U-13 | 5.19 | LC-MS (Method 1): Rt = 2.36 min; m/z = 431/433 (M + H)$^+$ | $^1$H-NMR (400.0 MHz, $d_6$-DMSO): δ = 8.829 (5.1); 8.335 (1.1); 8.332 (1.2); 8.314 (1.2); 8.311 (1.2); 7.900 (1.1); 7.897 (1.2); 7.882 (1.5); 7.879 (1.4); 7.759 (1.2); 7.740 (1.3); 7.737 (1.4); 7.719 (0.9); 7.646 (16.0); 4.441 (0.9); 4.423 (3.1); 4.405 (3.1); 4.388 (1.0); 3.896 (2.6); 3.885 (3.5); 3.874 (2.7); 3.320 (6.3); 3.273 (2.7); 3.262 (3.4); 3.251 (2.4); 2.525 (0.6); 2.511 (14.8); 2.507 (30.3); 2.503 (39.9); 2.498 (28.5); 2.494 (13.8); 1.397 (6.5); 1.376 (7.1); 1.359 (3.3); 0.000 (3.3) |
| 1U-15 | 3.90 | LC-MS (Method 1): $R_t$ = 2.17 min; m/z = 431/433 (M + H)$^+$ | $^1$H-NMR (400.0 MHz, $d_6$-DMSO): δ = 8.726 (8.4); 8.345 (1.6); 8.337 (1.6); 8.327 (1.7); 8.320 (1.8); 7.768 (0.8); 7.751 (3.0); 7.740 (3.4); 7.733 (6.7); 7.723 (1.0); 7.713 (2.2); 7.709 (2.3); 7.693 (2.5); 7.689 (2.5); 7.468 (1.8); 7.448 (3.6); 7.429 (2.2); 7.369 (2.7); 7.366 (2.8); 7.350 (1.9); 7.347 (1.7); 4.427 (1.5); 4.409 (4.8); 4.391 (4.9); 4.373 (1.6); 3.899 (4.4); 3.887 (8.0); 3.876 (4.6); 3.321 (37.8); 3.293 (2.5); 3.282 (5.5); 3.270 (5.3); 3.259 (2.2); 3.239 (0.6); 2.671 (0.4); 2.506 (61.9); 2.502 (81.2); 2.498 (60.0); 2.329 (0.5); 1.397 (16.0); 1.380 (5.5); 1.362 (11.1); 1.344 (5.2); 0.008 (2.2); 0.000 (45.4) |
| 1R-1 | | LC-MS (Method L1): $R_t$ = 1.16 min; MS (ESIpos): m/z = 352 [M + H]$^+$ | 1H-NMR (400 MHz, DMSO-d6) δ [ppm]: −0.008 (1.29), 0.008 (1.20), 1.760 (0.44), 2.329 (0.64), 2.367 (0.44), 2.524 (2.38), 2.671 (0.63), 2.711 (0.43), 3.601 (0.50), 7.654 (1.72), 7.660 (4.30), 7.664 (6.77), 7.669 (16.00), 7.673 (7.64), 7.804 (1.91), 7.823 (3.49), 7.843 (3.22), 7.887 (3.53), 7.890 (3.71), 7.904 (2.79), 8.354 (3.04), 8.357 (3.11), 8.375 (2.85), 8.378 (2.73), 8.907 (6.32). |
| 1R-3 | | LC-MS (Method L1): $R_t$ = 1.05 min; MS (ESIpos): m/z = 352 [M + H]$^+$ | 1H-NMR (400 MHz, DMSO-d6) δ [ppm]: 1.175 (0.47), 1.356 (0.45), 1.989 (0.90), 2.074 (8.95), 2.329 (0.81), 2.369 (0.60), 2.671 (0.95), 2.711 (0.65), 2.865 (0.47), 3.092 (0.78), 7.362 (0.70), 7.381 (1.05), 7.409 (6.34), 7.427 (11.32), 7.462 (7.73), 7.481 (11.58), 7.500 (5.55), 7.530 (1.06), 7.550 (0.60), 7.585 (0.87), 7.693 (1.21), 7.728 (9.06), 7.747 (7.85), 7.895 (5.45), 7.911 (13.10), 7.923 (10.39), 7.943 (10.33), 7.961 (4.26), 7.992 (0.98), 8.009 (0.69), 8.448 (0.92), 8.485 (8.46), 8.505 (8.03), 9.072 (16.00), 9.141 (1.24), 14.022 (0.91). |

TABLE 4-continued

| LC-MS and NMR or NMR Peaklist of Intermediates | | | |
|---|---|---|---|
| Example No | logP (Method L0) [a] | LC-MS (Method L2-L5) | NMR or NMR Peaklist |
| 1R-13 | | LC-MS (Method L1): $R_t$ = 1.15 min; MS (ESIpos): m/z = 312 $[M + H]^+$ | 1H-NMR (400 MHz, DMSO-d6) δ [ppm]: 2.346 (16.00), 7.062 (1.52), 7.189 (3.52), 7.884 (1.52), 7.895 (1.68), 7.902 (3.49), 8.396 (0.99), 8.403 (0.92), 8.414 (0.88), 8.421 (0.87), 9.116 (2.83). |
| 1W-8 | 2.17 | | $^1$H-NMR (400.0 MHz, $d_6$-DMSO): δ = 8.717 (3.1); 8.422 (0.7); 8.406 (0.8); 8.399 (0.9); 8.383 (0.8); 7.965 (2.0); 7.960 (2.1); 7.823 (0.5); 7.815 (0.5); 7.809 (0.5); 7.796 (0.6); 7.783 (0.6); 7.675 (0.9); 7.652 (1.4); 7.630 (0.9); 7.586 (2.0); 7.580 (2.0); 7.502 (0.4); 7.478 (0.7); 7.466 (1.1); 7.385 (0.6); 7.344 (0.6); 6.579 (0.3); 3.328 (75.7); 3.106 (16.0); 3.077 (0.5); 2.671 (0.7); 2.549 (1.8); 2.503 (106.1); 2.339 (0.8); 2.329 (0.8); 2.324 (0.7); 1.271 (0.7); 1.170 (2.7); 0.146 (0.4); 0.000 (76.2); −0.150 (0.4) |
| 1W-15 | 1.86 | LC-MS (Method 1): Rt = 1.78 min; m/z = 403/405 $(M + H)^+$ [mass of free base] | $^1$H-NMR (400.0 MHz, $d_6$-DMSO): δ = 8.449 (15.5); 8.278 (3.9); 8.275 (4.0); 8.257 (4.4); 8.254 (4.3); 7.688 (4.2); 7.684 (4.3); 7.668 (5.2); 7.664 (5.0); 7.603 (3.0); 7.586 (4.8); 7.565 (4.2); 7.502 (5.2); 7.499 (5.4); 7.484 (3.9); 7.481 (3.6); 7.447 (3.6); 7.428 (7.2); 7.408 (4.5); 7.343 (5.4); 7.339 (5.5); 7.324 (4.0); 7.320 (3.6); 3.823 (9.2); 3.812 (16.0); 3.801 (9.9); 3.601 (0.4); 3.353 (665.1); 3.325 (9.0); 3.314 (7.9); 2.672 (0.7); 2.508 (106.3); 2.503 (137.7); 2.499 (101.0); 2.330 (0.8); 1.759 (0.5); 0.000 (19.5) |
| 1-T1 | | LC-MS (Method L1): $R_t$ = 0.73 min; MS (ESIpos): m/z = 426 $[M + H]^+$ | 1H-NMR (400 MHz, DMSO-d6) δ [ppm]: 3.050 (16.00), 4.241 (0.59), 4.249 (0.48), 4.262 (0.64), 4.268 (0.76), 4.276 (0.62), 4.283 (0.49), 4.292 (0.50), 5.245 (0.56), 5.264 (0.55), 6.794 (0.98), 6.814 (1.10), 6.919 (0.49), 6.938 (1.05), 6.956 (0.61), 7.163 (0.52), 7.181 (0.86), 7.198 (0.40), 7.362 (0.91), 7.381 (0.84), 7.441 (0.75), 7.461 (1.18), 7.481 (0.82), 8.082 (1.07), 8.099 (1.02), 8.159 (1.09), 8.180 (1.03), 8.680 (3.34), 9.095 (0.82), 9.115 (0.80). |
| 1-T5 | | LC-MS (Method L1): $R_t$ = 0.92 min; MS (ESIneg): m/z = 466 $[M - H]^-$ | 1H-NMR (400 MHz, DMSO-d6) δ [ppm]: −0.149 (0.41), −0.008 (4.42), 0.008 (3.18), 2.041 (0.54), 2.048 (0.76), 2.056 (1.13), 2.063 (1.19), 2.076 (1.30), 2.091 (1.80), 2.098 (1.57), 2.106 (1.11), 2.197 (0.74), 2.206 (1.17), 2.218 (1.70), 2.231 (1.59), 2.240 (1.58), 2.253 (1.13), 2.262 (0.74), 2.274 (0.52), 2.327 (0.60), 2.366 (0.49), 2.523 (2.30), 2.669 (0.66), 2.710 (0.48), 3.217 (0.69), 3.228 (1.18), 3.248 (4.71), 3.258 (11.00), 3.269 (11.28), 3.279 (5.00), 3.842 (8.92), 3.853 (14.13), 3.864 (8.07), 4.214 (0.80), 4.221 (1.01), 4.242 (2.68), 4.249 (2.03), 4.263 (2.41), 4.271 (2.08), 4.276 (2.00), 4.286 (2.44), 4.293 (2.07), 4.302 (2.18), 4.314 (0.86), 4.321 (0.96), 4.329 (0.65), 5.245 (1.10), 5.259 (2.45), 5.279 (2.44), 5.292 (1.06), 6.797 (4.29), 6.815 (4.84), 6.927 (2.26), 6.929 (2.16), 6.946 (4.75), 6.964 (2.87), 7.164 (2.33), 7.167 (2.40), 7.185 (3.85), 7.202 (1.91), 7.206 (1.79), 7.385 (4.05), 7.403 (3.77), 7.499 (3.74), 7.518 (5.40), 7.538 (4.06), 8.123 (4.80), 8.125 (5.04), 8.142 (4.71), 8.144 (4.51), 8.197 (4.92), 8.199 (4.64), 8.218 (4.71), 8.753 (16.00), 9.177 (3.99), 9.197 (3.89). |
| 1-T7 | 2.69 | | $^1$H-NMR (400.0 MHz, $d_6$-DMSO): δ = 9.220 (2.1); 9.200 (2.1); 8.789 (9.2); 8.283 (1.8); 8.268 (1.9); 8.260 (2.0); 8.244 (1.9); 7.671 (2.0); 7.650 (2.6); 7.627 (1.8); 7.402 (2.0); 7.385 (2.2); 7.203 (1.1); 7.186 (2.2); 7.169 (1.3); 7.165 (1.3); 6.964 (1.6); 6.945 (2.6); 6.929 (1.3); 6.926 (1.2); 6.819 (2.9); 6.798 (2.7); 5.286 (0.6); 5.272 (1.3); 5.252 (1.3); 5.238 (0.6); 4.329 (0.4); 4.320 (0.5); 4.312 (0.5); 4.301 (1.1); 4.292 (1.1); 4.284 (1.3); 4.276 (1.0); 4.267 (1.1); 4.260 (1.3); 4.246 (1.1); 4.238 (1.4); 4.218 (0.5); 4.211 (0.5); 3.865 (4.4); 3.854 (7.4); 3.843 (4.7); 3.726 (3.9); 3.715 (4.8); 3.703 (4.1); 3.568 (16.0); 3.487 (0.4); 3.332 (12.7); 3.280 (4.6); 3.270 (7.3); 3.259 (6.7); 3.229 (1.2); 3.023 (3.6); 3.011 (4.6); 2.999 (3.4); 2.675 (0.7); 2.671 (0.9); 2.666 (0.7); 2.510 (61.4); 2.506 (124.6); 2.502 (165.2); 2.497 (119.8); 2.329 (1.0); 2.272 (0.4); 2.261 (0.5); 2.250 (0.6); 2.237 (0.9); 2.228 (0.9); 2.215 (1.0); 2.202 (0.7); 2.193 (0.4); 2.103 (0.6); 2.095 (0.8); 2.088 (1.0); 2.071 (0.8); 2.060 (0.7); 2.053 (0.6); 1.470 (0.4); 0.936 (0.4); 0.008 (1.0); 0.000 (24.6); −0.008 (1.1) |

EXPERIMENTAL SECTION—BIOLOGICAL ASSAYS

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1*: C. elegans* Slo-1a—Action at a Recombinant *C. elegans* Cell Line Generation of a Stable *C. elegans* CHO Cell Line A CHO cell line was obtained from ATCC, code ATCC CRL-9096. For transfection with plasmid DNA to express *C. elegans* Slo-1a (accession number AAL28102) CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *C. elegans* Slo 1a gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *C. elegans* Slo-1a.

Cell Culture Conditions

Cells were cultured at 37° C. and 5% $CO_2$ in MEMalpha with Gutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>5.3-6.5 has been found for: 27, 28, 85, 87, 88, 109, 131, 182, 183, 243, 345, 361, 363, 402, 424, 440, 510, 511, 521, 534, 547, 555, 580, 592, 599, 656.

For the following examples, $pE_{50}$>6.5-7.5 has been found for: 1, 62, 68, 69, 71, 95, 114, 120, 122, 125, 129, 136, 148, 185, 216, 230, 241, 242, 246, 264, 276, 289, 299, 324, 346, 354, 372, 379, 389, 390, 399, 401, 424, 432, 439, 456, 459, 474, 512, 513, 514, 519, 546, 560, 568, 578, 581, 584, 625, 632, 634, 654, 665.

For the following examples, $pE_{50}$>7.5-8.5 has been found for: 2, 3, 4, 5, 6, 23, 55, 58, 63, 64, 65, 66, 73, 74, 90, 93, 98, 102, 110, 117, 119, 124, 127, 128, 144, 145, 147, 150, 152, 154, 158, 159, 163, 173, 180, 188, 195, 196, 203, 204, 212, 213, 218, 219, 224, 229, 231, 232, 236, 245, 252, 253, 255, 257, 258, 259, 263, 266, 268, 269, 270, 273, 280, 284, 287, 288, 291, 295, 297, 301, 304, 308, 311, 312, 317, 319, 320, 321, 323, 325, 342, 343, 344, 348, 360, 370, 375, 378, 380, 381, 383, 384, 385, 386, 391, 392, 393, 394, 397, 403, 405, 412, 429, 433, 434, 443, 447, 454, 457, 458, 460, 461, 463, 464, 466, 471, 472, 473, 475, 476, 480, 481, 482, 483, 484, 486, 493, 494, 495, 499, 500, 501, 502, 503, 507, 508, 509, 515, 517, 518, 522, 523, 524, 525, 526, 527, 528, 529, 530, 531, 532, 533, 535, 536, 537, 538, 541, 545, 550, 551, 559, 561, 562, 563, 566, 567, 569, 570, 571, 572, 573, 574, 575, 577, 579, 585, 590, 593, 595, 597, 602, 615, 619, 620, 621, 622, 623, 626, 630, 633, 635, 640, 643, 661.

For the following examples, $pE_{50}$>8.5 has been found for: 7, 8, 9, 10, 11, 12, 13, 14, 15, 16, 17, 18, 19, 20, 21, 22, 24, 25, 26, 29, 30, 31, 32, 33, 34, 35, 36, 37, 39, 40, 41, 42, 43, 44, 45, 46, 47, 48, 49, 50, 51, 52, 53, 54, 56, 57, 60, 61, 70, 72, 75, 76, 77, 80, 81, 82, 83, 89, 100, 101, 108, 112, 115, 121, 130, 132, 133, 134, 135, 137, 138, 139, 140, 141, 142, 143, 146, 151, 153, 155, 156, 157, 160, 161, 162, 164, 165, 166, 167, 168, 169, 170, 171, 172, 174, 175, 176, 177, 178, 179, 181, 184, 186, 187, 189, 190, 191, 192, 193, 194, 197, 200, 201, 205, 206, 207, 208, 209, 210, 211, 214, 215, 217, 220, 221, 222, 223, 225, 226, 227, 228, 233, 234, 235, 237, 238, 239, 240, 244, 247, 248, 249, 250, 251, 254, 256, 260, 261, 262, 265, 267, 271, 272, 274, 275, 277, 278, 279, 281, 282, 283, 290, 292, 293, 294, 296, 298, 300, 302, 305, 307, 309, 310, 313, 314, 315, 316, 318, 322, 326, 327, 328, 329, 330, 331, 332, 333, 334, 335, 338, 339, 340, 341, 349, 350, 351, 352, 353, 355, 356, 357, 358, 359, 362, 364, 365, 366, 367, 368, 369, 371, 373, 374, 376, 377, 382, 387, 388, 395, 396, 398, 400, 404, 406, 407, 408, 409, 410, 411, 413, 414, 415, 416, 417, 418, 419, 420, 421, 422, 423, 425, 426, 427, 428, 429, 430, 431, 435, 436, 437, 438, 441, 442, 444, 445, 446, 448, 449, 450, 451, 452, 453, 455, 462, 465, 467, 468, 469, 470, 477, 478, 479, 485, 487, 488, 489, 490, 491, 492, 496, 497, 498, 504, 505, 506, 516, 517, 520, 539, 540, 542, 543, 544, 548, 549, 552, 553, 554, 556, 557, 558, 564, 565, 576, 582, 583, 586, 587, 588, 589, 591, 594, 596, 598, 600, 601, 603, 604, 605, 606, 607, 608, 609, 610, 611, 612, 613, 614, 616, 617, 618, 624, 627, 628, 629, 631, 636, 637, 638, 639, 641, 642, 644, 645, 646, 647, 648, 649, 650, 651, 652, 653, 655, 657, 658, 659, 660, 662, 663, 664, 666.

In vitro assay 2: *Nippostrongylus brasiliensis* (NIPOBR)

Adult *Nippostrongylus brasiliensis* were washed with saline buffer containing 100 U/ml penicillin, 0.1 mg/ml streptomycin and 2.5 μg/ml amphotericin B. Test compounds were dissolved in DMSO and worms were incubated in medium in a final concentration of 10 μg/ml (10 ppm) respectively 1 μg/ml (1 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was higher than 80% at 10 μg/ml: 8, 9, 11, 12, 13, 15, 16, 17, 18, 19, 20, 21, 22, 23, 24, 25, 26, 29, 31, 32, 33, 34, 35, 36, 37, 39, 40, 41, 42, 43, 44, 45, 46, 47, 48, 49, 50, 51, 52, 53, 54, 57, 58, 59, 60, 61, 62, 64, 65, 66, 67, 69, 70, 71, 72, 73, 74, 75, 76, 77, 78, 81, 82, 83, 87, 89, 95, 100, 101, 104, 108, 112, 115, 116, 119, 122, 123, 127, 128, 130, 132, 133, 134, 135, 136, 137, 138, 139, 141, 142, 143, 144, 146, 147, 148, 333, 334, 336, 338, 339, 340, 341, 349, 362, 363, 364, 373, 609, 610, 611, 612, 613, 614, 615, 617, 618, 619, 620, 623, 630.

For the following examples, activity (reduction of AChE compared to negative control) was higher than 80% at 1 μg/ml: 8, 9, 12, 13, 15, 16, 17, 18, 19, 20, 21, 22, 23, 24, 25, 26, 29, 31, 32, 33, 34, 35, 36, 37, 39, 40, 41, 42, 43, 44, 45, 46, 47, 48, 49, 50, 51, 52, 53, 54, 57, 58, 60, 61, 65, 67, 69, 70, 73, 74, 75, 76, 77, 80, 81, 82, 83, 84, 89, 92, 93, 95, 100, 101, 108, 112, 114, 115, 116, 117, 118, 119, 122, 124, 125, 126, 127, 128, 129, 130, 132, 133, 134, 135, 136, 137, 138, 139, 142, 143, 144, 146, 149, 150, 151, 152, 153, 154, 155, 156, 157, 158, 160, 161, 162, 163, 165, 166, 167, 168, 169, 170, 171, 172, 176, 178, 181, 182, 185, 186, 187, 189, 190, 191, 192, 193, 194, 195, 197, 198, 200, 201, 203, 204, 205, 206, 207, 208, 209, 210, 211, 212, 214, 215, 217, 218, 220, 221, 222, 223, 224, 225, 226, 227, 228, 229, 231, 232, 233, 234, 235, 236, 237, 238, 239, 240, 247, 249, 250, 251, 254, 256, 257, 260, 261, 262, 263, 265, 266, 268, 271, 272, 273, 274, 275, 276, 277, 279, 280, 281, 282, 283, 284, 285, 287, 288, 289, 290, 291, 292, 293, 294, 301, 302, 307, 308, 309, 310, 311, 313, 314, 315, 318, 319, 321, 322, 326, 327, 328, 329, 330, 331, 332, 333, 334, 336, 338, 339, 340, 341, 342, 347, 349, 350, 352, 353, 355, 356, 357, 358, 359, 360, 362, 364, 365, 367, 369, 370, 373, 374, 375, 377, 382, 384, 385, 386, 388, 392, 394, 395, 396, 397, 400, 403, 404, 406, 407, 408, 409, 410, 411, 413, 414, 415, 417, 418, 419, 420, 421, 422, 424, 425, 426, 427, 428, 429, 430, 431, 432, 433, 434, 435, 436, 437, 441, 443, 444, 445, 446, 447, 448, 449, 450, 451, 452, 453, 454, 455, 458, 460, 461, 462, 463, 464, 465, 466, 467, 468, 469, 470, 471, 472, 473, 476, 477, 478, 479, 482, 485, 486, 487, 488, 490, 491, 492, 495, 496, 497, 498, 499, 500, 501, 504, 505, 506, 507, 508, 509, 516, 517, 520, 527, 528, 529, 530, 531, 532, 533, 535, 536, 537, 538, 540, 541, 542, 543, 544, 545, 548, 549, 550, 551, 552, 553, 554, 556, 557, 558, 561, 562, 563, 564, 565, 566, 569, 570, 571, 572, 573, 574, 575, 576, 577, 578, 579, 581, 582, 583, 585, 586, 587, 588, 590, 594, 596, 597, 598, 601, 602, 603, 604, 605, 606, 607, 608, 609, 610, 611, 612, 613, 614, 615, 617, 618, 619, 620, 623, 624, 626, 627, 628, 629, 631, 632, 633, 634, 635, 636, 637, 638, 639, 640, 641, 642, 645, 646, 647, 648, 649, 650, 651, 652, 653, 655, 657, 658, 660.

In Vitro Assay 3: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: 1, 4, 5, 6, 7, 8, 9, 10, 12, 13, 15, 16, 17, 22, 23, 24, 25, 26, 29, 30, 31, 32, 33, 34, 35, 36, 37, 39, 40, 41, 42, 43, 44, 45, 46, 47, 48, 50, 51, 52, 53, 54, 56, 57, 58, 60, 61, 64, 65, 69, 73, 74, 76, 77, 80, 81, 82, 83, 84, 89, 101, 103, 108, 111, 112, 115, 117, 119, 124, 125, 127, 128, 129, 130, 132, 133, 134, 138, 139, 140, 141, 142, 143, 144, 145, 146, 147, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 185, 186, 187, 188, 189, 190, 191, 192, 194, 196, 197, 200, 201, 203, 204, 205, 206, 207, 208, 209, 210, 211, 212, 214, 215, 217, 218, 219, 220, 221, 222, 223, 224, 225, 226, 227, 228, 229, 231, 232, 233, 234, 235, 236, 237, 238, 239, 240, 244, 247, 248, 249, 250, 251, 253, 255, 256, 257, 258, 259, 260, 261, 262, 265, 266, 267, 268, 269, 270, 271, 272, 273, 274, 275, 276, 277, 278, 279, 280, 281, 283, 290, 292, 293, 296, 300, 303, 304, 305, 306, 307, 308, 309, 310, 311, 312, 313, 314, 315, 317, 319, 322, 326, 327, 329, 330, 331, 332, 333, 334, 338, 339, 340, 340, 341, 342, 344, 350, 351, 352, 353, 355, 356, 357, 358, 359, 360, 362, 364, 365, 366, 367, 368, 369, 373, 374, 375, 376, 377, 381, 382, 383, 384, 385, 386, 388, 390, 391, 392, 394, 395, 396, 400, 403, 404, 405, 406, 407, 408, 409, 410, 411, 413, 414, 415, 417, 418, 419, 420, 421, 422, 423, 425, 426, 427, 428, 429, 430, 431, 433, 434, 435, 436, 437, 438, 441, 442, 443, 444, 445, 446, 447, 448, 449, 450, 451, 452, 453, 454, 455, 457, 458, 459, 460, 461, 462, 463, 464, 465, 466, 467, 468, 469, 470, 471, 472, 473, 474, 475, 476, 477, 478, 479, 480, 482, 483, 485, 486, 487, 488, 490, 491, 492, 493, 495, 497, 498, 499, 500, 501, 503, 504, 505, 506, 507, 508, 509, 516, 517, 521, 522, 523, 524, 525, 527, 528, 529, 530, 531, 532, 533, 536, 537, 538, 539, 540, 541, 542, 543, 544, 545, 546, 547, 548, 549, 550, 551, 552, 553, 554, 556, 557, 558, 559, 560, 561, 562, 563, 564, 565, 566, 567, 568, 569, 570, 571, 572, 573, 574, 575, 576, 577, 578, 579, 581, 582, 583, 584, 586, 587, 588, 589, 590, 591, 594, 596, 597, 598, 600, 601, 602, 603, 604, 605, 606, 607, 608, 609, 610, 611, 612, 613, 614, 615, 616, 617, 618, 619, 620, 622, 623, 624, 626, 627, 628, 629, 632, 633, 634, 635, 636, 638, 639, 641, 642, 645, 646, 647, 648, 649, 650, 651, 652, 653, 655, 657, 658, 660.

For the following examples, the $EC_{50}$ was <1 ppm: 3, 11, 19, 49, 55, 62, 63, 66, 67, 70, 71, 72, 75, 86, 90, 93, 94, 95, 99-1, 100, 102, 104, 105, 116, 135, 136, 137, 148, 182, 183, 184, 193, 195, 199, 213, 216, 230, 241, 242, 243, 245, 246, 252, 254, 263, 282, 288, 289, 291, 292, 294, 295, 299, 316, 320, 321, 323, 325, 343, 345, 348, 354, 361, 370, 371, 372, 373, 378, 379, 380, 401, 416, 424, 440, 456, 580, 585, 621, 630, 654.

For the following examples, the $EC_{50}$ was <10 ppm: 2, 9, 13, 14, 18, 20, 21, 27, 28, 59, 67, 68, 78, 87, 88, 91, 92, 96, 99-2, 106, 113, 114, 118, 120, 122, 123, 126, 131, 149, 198, 202, 264, 284, 285, 286, 287, 288, 301, 302, 318, 324, 328, 335, 336, 337, 346347, 349, 363, 387, 389, 393, 397, 398, 399, 402, 412, 432, 439, 481, 484, 485, 489, 491, 492, 494, 510, 511, 512, 513, 514, 515, 518, 519, 520, 526, 534, 535, 555, 595, 599, 625, 631, 637, 640, 643, 644, 656, 659.

In Vitro Assay 4: *Dirofilaria immitis* (DIROIM L4)

10 *Dirofilaria immitis* third-stage larvae, which were freshly isolated from their vector (intermediate host), were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: 7, 8, 9, 10, 11, 12, 13, 15, 16, 17, 18, 19, 21, 22, 23, 24, 25, 26, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, 64, 65, 66, 69, 73, 74, 75, 76, 77, 81, 82, 83, 89, 101, 108, 112, 117, 119, 124, 125, 127, 130, 132, 133, 134, 138, 139, 140, 141, 142, 143, 144, 146, 151, 152, 153, 154, 155, 156, 157, 158, 159, 160, 161, 162, 163, 164, 165, 166, 167, 168, 169, 170, 171, 172, 174, 175, 176, 177, 178, 179, 181, 186, 190, 191, 192, 194, 196, 197, 200, 203, 204, 205, 206, 207, 208, 209, 210, 211, 212, 214, 215, 217, 218, 220, 221, 222, 223, 224, 225, 226, 227, 228, 229, 231, 232, 233, 234, 235, 236, 237, 238, 239, 240, 247, 248, 249, 250, 251, 253, 256, 257, 258, 259, 260, 261, 262, 265, 267, 268, 271, 272, 275, 277, 278, 279, 280, 281, 283, 290, 300, 304, 309, 310, 313, 314, 315, 319, 322, 326, 327, 330, 331, 332, 333, 334, 336, 338, 339, 340, 341, 350, 351, 352, 353, 355, 356, 357, 358, 359, 360, 362, 365, 366, 367, 374, 376, 377, 382, 384, 385, 386, 388, 390, 392, 394, 395, 396, 400, 403, 404, 405, 406, 407, 408, 409, 410, 411, 413, 414, 415, 417, 418, 419, 420, 421, 422, 423, 425, 426, 427, 429, 430, 431, 433, 434, 436, 437, 438, 441, 442, 443, 444, 446, 447, 448, 449, 450, 451, 452, 453, 454, 455, 457, 462, 463, 465, 466, 467, 468, 469, 470, 476, 477, 478, 479, 480, 482, 485, 486, 487, 488, 490, 491, 492, 493, 495, 496, 497, 498, 499, 504, 505, 506, 507, 516, 517, 523, 525, 527, 528, 529, 530, 531, 532, 533, 536, 537, 538, 539, 540, 541, 542, 543, 544, 545, 548, 549, 550, 551, 552, 553, 554, 556, 557, 558, 559, 561, 562, 563, 564, 565, 566, 567, 568, 570, 571, 572, 573, 575, 576, 577, 578, 579, 582, 583, 584, 587, 589, 590, 591, 596, 597, 600, 602, 603, 604, 605, 606, 607, 608, 609, 610, 611, 612, 613, 614, 615, 617, 618, 619, 628, 629, 635, 638, 660.

For the following examples, the $EC_{50}$ was <1 ppm: 1, 2, 3, 14, 20, 54, 80, 115, 150, 201, 244, 266, 364, 373.

For the following examples, the $EC_{50}$ was <10 ppm: 133, 187

In Vitro Assay 5*: Litomosoides sigmodontis* (LTMOSI L3)

10 *Litomosoides sigmodontis* third-stage larvae, which were freshly isolated from the pleural cavity of an infected rodent, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: 8, 9, 10, 12, 13, 16, 17, 18, 19, 20, 21, 22, 23, 24, 25, 29, 32, 33, 34, 35, 36, 37, 45, 46, 48, 52, 53, 54, 74, 76, 77, 112, 133, 134, 141, 143, 339, 341, 350, 376, 382, 384, 385, 386, 394, 395, 396.

For the following examples, the $EC_{50}$ was <1 ppm: 3, 15, 44, 73, 373.

In Vitro Assay 6: *Cooperia curticei* (COOPCU L3)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded. 100% efficacy means all larvae are killed; 0% efficacy means no larvae are killed.

In this test for example, the following compounds from the preparation examples showed good activity of 100% at an application rate of 20 ppm: 8, 9, 10, 13, 17, 22, 23, 24, 29, 32, 33, 34, 36, 37, 45, 46, 52, 53, 57, 76, 77, 81, 83, 132, 133, 134, 139, 143, 150, 153, 155, 156, 157, 166, 167, 169, 170, 172, 191, 192, 193, 194, 195, 196, 197, 200, 204, 205, 206, 207, 208, 209, 210, 214, 215, 217, 218, 221, 222, 224, 226, 235, 236, 237, 247, 265, 266, 274, 280, 300, 309, 326, 327, 329, 332, 341, 350, 353, 356, 357, 359, 373, 377, 384, 385, 386, 395, 396, 407, 408, 410, 411, 415, 419, 420, 421, 426, 431, 438, 445, 449, 450, 451, 453, 454, 455, 464, 477, 479, 486, 487, 488, 496, 497, 504, 505, 506, 507, 516, 528, 529, 530, 531, 532, 533, 536, 537, 538, 539, 541, 542, 545, 551, 554, 557, 558, 562, 563, 564, 565, 569, 572, 573, 575, 576, 596, 600, 603, 604, 605, 607, 608, 624, 628, 631, 637, 638, 639, 642, 647, 651, 652, 655, 657, 658, 659, 660.

In this test for example, the following compounds from the preparation examples showed good activity of 90% at an application rate of 20 ppm: 16, 31, 40, 48, 50, 54, 60, 80, 108, 125, 142, 152, 176, 178, 179, 191, 201, 203, 220, 223, 229, 240, 251, 257, 259, 260, 271, 275, 276, 281, 292, 314, 330, 331, 333, 338, 339, 358, 382, 400, 406, 435, 444, 446, 462, 465, 467, 469, 473, 476, 491, 500, 509, 540, 543, 548, 552, 553, 601, 602, 615, 640, 648.

In this test for example, the following compounds from the preparation examples showed good activity of 80% at an application rate of 20 ppm: 15, 21, 30, 41, 42, 44, 47, 49, 51, 58, 65, 70, 75, 89, 135, 146, 154, 162, 163, 181, 211, 212, 228, 238, 239, 250, 272, 294, 298, 307, 310, 315, 318, 322, 328, 367, 394, 404, 409, 418, 424, 432, 460, 471, 482, 485, 490, 492, 495, 508, 556, 583, 587, 614, 650.

In this test for example, the following compounds from the preparation examples showed good activity of 100% at an application rate of 4 ppm: 8, 13, 17, 22, 23, 24, 32, 33, 34, 36, 37, 45, 46, 52, 53, 57, 76, 77, 81, 83, 132, 133, 134, 143, 151, 153, 155, 167, 169, 170, 172, 192, 194, 195, 197, 200, 205, 207, 209, 210, 214, 215, 217, 222, 226, 237, 265, 266, 273, 274, 300, 309, 327, 329, 332, 350, 353, 359, 373, 384, 385, 386, 395, 395, 396, 407, 408, 410, 411, 415, 420, 421, 426, 431, 438, 445, 449, 450, 451, 453, 455, 477, 479, 487, 488, 496, 497, 499, 504, 505, 529, 530, 531, 532, 533, 536, 539, 541, 542, 545, 554, 557, 558, 562, 563, 564, 565, 569, 572, 573, 575, 576, 596, 600, 604, 607, 608, 628, 631, 637, 638, 639, 642, 647, 651, 652, 655, 657, 658, 659, 660.

In this test for example, the following compounds from the preparation examples showed good activity of 90% at an application rate of 4 ppm: 9, 29, 31, 40, 54, 60, 125, 139, 142, 152, 156, 157, 166, 191, 193, 196, 208, 218, 221, 223, 229, 235, 236, 247, 271, 275, 292, 326, 330, 338, 341, 356, 357, 358, 419, 435, 446, 462, 464, 469, 476, 500, 506, 507, 540, 551, 552, 601, 603, 605, 648.

In this test for example, the following compounds from the preparation examples showed good activity of 80% at an application rate of 4 ppm: 10, 16, 39, 42, 44, 47, 48, 50, 51, 58, 80, 108, 146, 163, 171, 178, 201, 203, 206, 211, 212, 224, 240, 258, 260, 280, 281, 286, 318, 333, 339, 400, 406, 409, 430, 437, 444, 465, 467, 486, 491, 508, 509, 516, 528, 537, 548, 583, 602, 614, 624, 640.

In this test for example, the following compounds from the preparation examples showed good activity of 80% at an application rate of 0.8 ppm: 190, 549.

In Vitro Assay 7: *Haemonchus contortus* (HAEMCO L3)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days the percentage of larval mortality is recorded. 100% efficacy means all larvae are killed, 0% efficacy means no larvae are killed.

In this test for example, the following compounds from the preparation examples showed good activity of 100% at an application rate of 20 ppm: 8, 13, 15, 17, 22, 23, 24, 29, 32, 33, 34, 36, 37, 46, 47, 48, 50, 52, 53, 57, 60, 76, 77, 81, 83, 132, 133, 134, 135, 139, 142, 143, 153, 155, 166, 167, 169, 170, 172, 192, 194, 197, 200, 205, 206, 207, 214, 215, 218, 221, 222, 224, 226, 235, 237, 247, 265, 266, 274, 275, 280, 300, 309, 312, 326, 329, 330, 331, 332, 350, 353, 359, 373, 377, 384, 385, 386, 395, 396, 407, 410, 411, 415, 450, 455, 477, 486, 487, 488, 496, 497, 504, 505, 506, 509, 528, 529, 530, 531, 533, 537, 538, 539, 541, 542, 545, 551, 552, 554, 558, 562, 563, 564, 565, 569, 572, 573, 575, 576, 596, 604, 605, 608, 628, 631, 637, 638, 647, 651, 652, 655, 658, 659, 660.

In this test for example, the following compounds from the preparation examples showed good activity of 90% at an application rate of 20 ppm: 10, 31, 44, 45, 51, 74, 75, 136, 146, 150, 156, 179, 191, 203, 204, 209, 210, 217, 220, 223, 229, 236, 249, 250, 251, 258, 260, 271, 272, 327, 356, 357, 358, 400, 408, 421, 435, 438, 444, 445, 449, 451, 453, 460, 469, 476, 508, 532, 540, 548, 553, 557, 600, 602, 603, 615, 640, 642, 648, 657.

In this test for example, the following compounds from the preparation examples showed good activity of 80% at an application rate of 20 ppm: 12, 16, 39, 40, 42, 70, 125, 137, 138, 152, 157, 176, 178, 180, 208, 257, 259, 273, 276, 281, 292, 307, 310, 333, 341, 388, 392, 394, 419, 420, 432, 434, 446, 464, 473, 479, 491, 499, 500, 507, 516, 535, 543, 619, 624, 645, 646, 650.

In this test for example, the following compounds from the preparation examples showed good activity of 100% at an application rate of 4 ppm: 8, 9, 13, 17, 22, 23, 24, 29, 32, 34, 36, 37, 40, 46, 52, 57, 60, 76, 77, 81, 132, 133, 134, 139, 142, 143, 153, 155, 170, 192, 197, 200, 205, 214, 222, 237, 247, 265, 266, 274, 309, 330, 332, 339, 350, 359, 373, 384, 385, 386, 395, 410, 411, 455, 477, 488, 496, 497, 504, 509, 530, 531, 539, 541, 542, 545, 554, 558, 562, 563, 564, 565, 569, 572, 573, 575, 576, 596, 605, 608, 628, 631, 637, 639, 647, 651, 652, 655, 658, 659, 660.

In this test for example, the following compounds from the preparation examples showed good activity of 90% at an application rate of 4 ppm: 10, 15, 31, 33, 45, 47, 50, 83, 135, 146, 151, 166, 167, 169, 191, 194, 207, 209, 221, 226, 229, 235, 236, 271, 272, 275, 300, 326, 329, 353, 357, 358, 396, 400, 407, 408, 415, 421, 435, 436, 438, 445, 450, 451, 476, 487, 505, 508, 528, 529, 533, 536, 537, 540, 552, 600, 603, 604, 638, 640, 648.

In this test for example, the following compounds from the preparation examples showed good activity of 80% at an application rate of 4 ppm: 42, 44, 48, 51, 53, 74, 75, 150, 156, 172, 195, 206, 210, 215, 217, 218, 223, 232, 260, 281, 307, 327, 341, 356, 377, 392, 394, 403, 419, 42, 426, 444, 449, 453, 469, 470, 471, 479, 486, 500, 506, 507, 551, 557, 642, 645, 650, 657.

FORMULATION EXAMPLE

Exemplary formulations consisted of the active substance in 10% Transcutol, 10% Cremophor EL and 80% isotonic saline solution. First the active substance was dissolved in Transcutol. After solution in Transcutol, Cremophor and isotonic saline solution were added. These formulations were used as service formulations in the following in vivo assay.

An example for a formulation according to the present invention is the following formulation Example F1. Therein, the active substance was dissolved in Transcutol to form a stock solution A. Then 0.100 mL of this stock solution A were taken and 0.100 mL Cremophor EL and 0.800 mL isotonic saline solution were added. The resulting liquid formulation (formulation example F1) had a volume of 1 mL.

Stock Solution A:

| | |
|---|---|
| 4.0 mg | compound of example 8, |
| 0.100 mL | Transcutol. |

Formulation Example F1

| | |
|---|---|
| 0.100 mL | stock solution A, |
| 0.100 mL | Cremophor EL, and |
| 0.800 mL | isotonic saline solution. |

In Vivo Assay

*Haemonchus contortus/Trichostrongylus colubriformis*/Gerbil

Gerbils, experimentally infected with *Haemonchus* and/or *Trichostrongylus*, were treated once during late prepatency. Test compounds were formulated as solutions or suspensions and applied orally or intraperitoneally. For both applications the same service formulation was used. The volume of the application amounted to normally 20 ml/kg at a maximum. By way of example, a gerbil with 40 g body weight was treated with 0.200 mL of the formulation of formulation example F1. This corresponded to a treatment with 20 mg/kg body weight.

Efficacy was determined per group as reduction of worm count in stomach and small intestine, respectively, after necropsy compared to worm count in an infected and placebo-treated control group.

The following examples were tested and had an activity of >70% or higher at the given treatment:

| Treatment | *Haemonchus contortus* | *Trichostrongylus colubriformis* |
|---|---|---|
| ≤2.5 mg/kg intraperitoneally | Expl No 8, 9, 13, 15, 17, 18, 21, 22, 23, 24, 25, 33, 34, 36, 37, 44, 46, 52, 54, 130, 153, 156, 166, 167, 168, 181, 192, 200, 201, 203, 205, 206, 209, 214, 220, 221, 222, 232, 233, 234, 235, 237, 238, 239, 250, 251, 300, 301, 309, 310, 322, 326, 327, 330, 331, 355, 357, 358, 359, 360, 374, 385, 386, 392, 395, 409, 410, 411, 413, 415, 419, 427, 430, 431, 438, 444, 450, 455 462, 465, 467, 468, 477, 485, 487, 491, 492, 496, 516, 530, 533, 538, 540, 543, 548, 553, 557, 558, 564, 565, 660 | Expl No 8, 13, 17, 22, 37, 51, 52, 132, 133, 134, 142, 143, 168, 169, 170, 200 206, 222, 235, 251, 359, 395, 660 |

The invention claimed is:

1. A compound of formula (I):

(I)

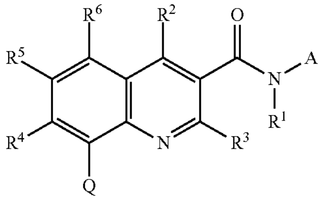

wherein:

A is A2,

A2

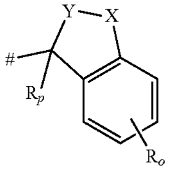

is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl, —S(O)-$C_1$-$C_4$-halogenoalkyl and —$SO_2$—$C_1$-$C_4$-halogenoalkyl having 1 to 5 halogen atoms, $R_p$ is selected from the group consisting of hydrogen and $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH-$C_1$-$C_4$-alkyl, —N($C_1$-$C_4$-alkyl)$_2$, $NH_2$-$C_1$-$C_4$-alkyl-, $C_1$-$C_4$-alkyl-NH-$C_1$-$C_4$-alkyl-, ($C_1$-$C_4$-alkyl)$_2$N-$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, —$SO_2$—$C_1$-$C_4$-halogenoalkyl having 1 to 5 halogen atoms, phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$-$C_1$-$C_4$-halogenoalkyl having 1 to 5 halogen atoms, and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$,

—$NR^{12}R^{13}$,

—$OR^{14}$,

—$SR^{15}$, —$S(O)R^{15}$, —$SO_2R^{15}$, $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, wherein each of the $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, and phenyl-$C_1$-$C_4$-alkyl is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)-, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl, $R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl, $R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (=O), or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl, $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—, $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, and phenyl-$C_1$-$C_4$-alkyl is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—

$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl, benzo-$C_5$-$C_6$-cycloalkyl, wherein each of the phenyl and benzo-$C_5$-$C_6$-cycloalkyl is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$-alkyl), —N($C_1$-$C_4$-alkyl)$_2$, $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, and phenyl-$C_1$-$C_4$-alkyl is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$-$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of hydrogen, $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, and phenyl-$C_1$-$C_4$-alkyl is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH ($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$,—NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms, wherein when Y is O, S or N—$R^9$, none of $R^7$ and $R^8$ is —OH, and wherein when X is O, S or N—$R^9$, none of $R^7$ and $R^8$ is —OH, or a stereoisomer, a tautomer, an N-oxide, a hydrate, a solvate, or a salt thereof, or a mixture of any of the foregoing.

2. The compound according to claim 1, wherein:

A is A2,

A2

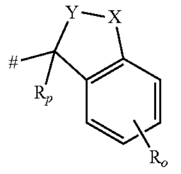

is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen and $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH-$C_1$-$C_4$-alkyl, —N($C_1$-$C_4$-alkyl)$_2$, $NH_2$-$C_1$-$C_4$-alkyl-, $C_1$-$C_4$-alkyl-NH-$C_1$-$C_4$-alkyl-, ($C_1$-$C_4$-alkyl)$_2$N-$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, —$SO_2$—$C_1$-$C_4$-halogenoalkyl having 1 to 5 halogen atoms, phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$,

—$NR^{12}R^{13}$,

—$OR^{14}$,

—$SR^{15}$, —S(O)$R^{15}$, —$SO_2R^{15}$, $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl phenyl-$C_1$-$C_4$-alkyl, wherein each of the $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl and phenyl-$C_1$-$C_4$-alkyl is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, "—NH($C_1$-$C_4$-alkyl), —N($C_1$-$C_4$-alkyl)$_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and 4- to 10-membered heterocycloalkyl, $R^3$ is hydrogen, or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl)$_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl)$_2$, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (═O), $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{12}$ and $R^{13}$ are independently selected from the group consisting of
hydrogen, —OH, —$NH_2$, —NH($C_1$-$C_4$-alkyl), —N($C_1$-$C_4$-alkyl)$_2$, —NH(—C(O)—$C_1$-$C_4$-alkyl), $C_1$-$C_4$-alkoxy,
$C_1$-$C_4$-alkyl, $C_3$-$C_6$-cycloalkyl, phenyl-$C_1$-$C_4$-alkyl, wherein each of the $C_1$-$C_4$-alkyl,
$C_3$-$C_6$-cycloalkyl, and phenyl-$C_1$-$C_4$-alkyl is optionally substituted by 1, 2 or 3 substituents independently selected from the group consisting of halogen, —OH, cyano, —COOH,
$C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)+C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl),
—N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and
($C_1$-$C_4$-alkoxy)$_2$P(═O)—,
heterocyclyl-$C_1$-$C_4$-alkyl, wherein the heterocyclyl substituent is selected from the group consisting of 4- to 10-membered heterocycloalkyl, 5-membered heteroaryl and
6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl),
—C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms,
$C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms,
phenyl, benzo-$C_5$-$C_6$-cycloalkyl, wherein each of the phenyl and benzo-$C_5$-$C_6$-cycloalkyl is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms,
$C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and
a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—,
—C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl,
$C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of
—$NH_2$, —NH($C_1$-$C_4$-alkyl), —N($C_1$-$C_4$-alkyl)$_2$,
$C_1$-$C_4$-alkyl, $C_3$-$C_6$-cycloalkyl, phenyl-$C_1$-$C_4$-alkyl, wherein each of the $C_1$-$C_4$-alkyl,
$C_3$-$C_6$-cycloalkyl, and phenyl-$C_1$-$C_4$-alkyl which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl),
—C(O)—N($C_1$-$C_4$-alkyl)$_2$, $C_1$-$C_4$-alkyl, $C_1$-$C_4$-halogenoalkyl having 1 to 5 halogen atoms,
$C_1$-$C_4$-alkoxy, $C_1$-$C_4$-halogenoalkoxy having 1 to 5 halogen atoms, $C_3$-$C_6$-cycloalkyl,
—$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms,
heterocyclyl-$C_1$-$C_4$-alkyl, wherein the heterocyclyl substituent is selected from the group consisting of 4- to 10-membered heterocycloalkyl, 5-membered heteroaryl and
6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl),
—C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of hydrogen, $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, and phenyl-$C_1$-$C_4$-alkyl which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is a substituted phenyl ring of formula (Q1)

(Q1)

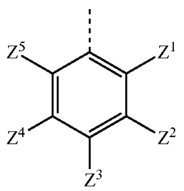

wherein:

$Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO ($C_3$-$C_6$-cycloalkyl), and —NHCO($C_1$-$C_4$-halogenoalkyl) having 1 to 5 halogen atoms, or $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)-($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)-($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms, or Q is a pyridine ring of formula (Q2)

(Q2)

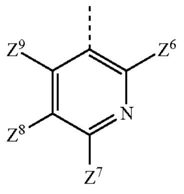

wherein:

$Z^6$, $Z^7$, $Z^8$ and $Z^9$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a pyrimidine ring of formula (Q3)

(Q3)

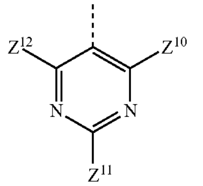

wherein:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a pyridine ring of formula (Q4)

(Q4)

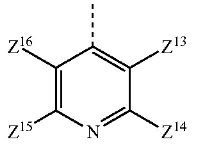

wherein:

$Z^{13}$, $Z^{14}$, $Z^{15}$ and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO-$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, and —$SO_2$—($C_1$-$C_4$-halogenoalkyl) having 1 to 5 halogen atoms, or Q is a pyridine ring of formula (Q5)

(Q5)

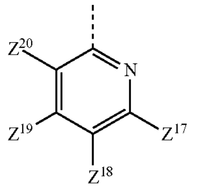

wherein:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a 5-membered aromatic heterocycle of formula (Q6)

(Q6)

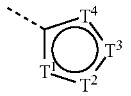

wherein:

$T^1$-$T^4$are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, and $C_1$-$C_4$-alkoxy-$C_1$-$C_4$-alkyl, or Q is a 5-membered aromatic heterocycle of formula (Q7)

(Q7)

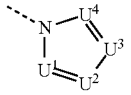

wherein:

$U^1$-$U^4$ are independently selected from the group consisting of N and C-$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, wherein when Y is O, S or N—$R^9$, none of $R^7$ and $R^8$ is —OH, and wherein when X is O, S or N—$R^9$, none of $R^7$ and $R^8$ is —OH, or a stereoisomer, a tautomer, an N-oxide, a hydrate, a solvate, or a salt thereof, or a mixture of any of the foregoing.

3. The compound according to claim 1, wherein:

A is A2,

A2

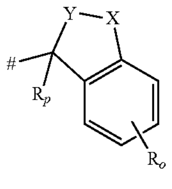

o is 0, 1 or 2,

R is selected from the group consisting of halogen, $C_1$-$C_4$-alkyl, $C_1$-$C_4$-alkoxy, cyano, and $C_1$-$C_4$-halogenoalkyl having 1 to 5 halogen atoms, $R_p$ is selected from the group consisting of hydrogen and $C_1$-$C_4$-alkyl, X, Y are independently selected from the group consisting of $CR^7R^8$, O, S, and N—$R^9$, wherein at least one of X and Y is $CR^7R^8$, $R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, and cyano-$C_1$-$C_4$-alkyl, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$,

—$NR^{12}R^{13}$,

—$OR^{14}$,

—$SR^{15}$, —S(O)$R^{15}$, —$SO_2R^{15}$, $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, wherein each of the $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl$)_2$, —NH(C(O)—$C_1$-$C_4$-alkyl), —N($C_1$-$C_4$-alkyl)(C(O)—$C_1$-$C_4$-alkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl$)_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl$)_2$, $R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl$)_2$, $R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), and —N($C_1$-$C_4$-alkyl$)_2$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{12}$ and $R^{13}$ are independently selected from the group consisting of hydrogen, —NH(—C(O)—$C_1$-$C_4$-alkyl), $C_1$-$C_4$-alkoxy, $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, phenyl-$C_1$-$C_4$-alkyl is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$, —NH—C(O)—$C_1$-$C_4$-alkyl, —N($C_1$-$C_4$-alkyl)+C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl$)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy$)_2$P(═O)—, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, phenyl, benzo-$C_5$-$C_6$-cycloalkyl, wherein each of the phenyl and benzo-$C_5$-$C_6$-cycloalkyl is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, and phenyl-$C_1$-$C_4$-alkyl is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and $C_3$-$C_6$-cycloalkyl, and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{15}$ is selected from the group consisting of hydrogen, $C_1$-$C_4$-alkyl, phenyl-$C_1$-$C_4$-alkyl, wherein each of the $C_1$-$C_4$-alkyl and phenyl-$C_1$-$C_4$-alkyl is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, Q is a substituted phenyl ring of formula (Q1)

(Q1)

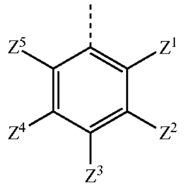

wherein:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), and —$SO_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, and $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, or Q is a pyridine ring of formula (Q2)

(Q2)

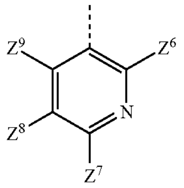

wherein:

$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a pyrimidine ring of formula (Q3)

(Q3)

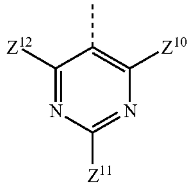

wherein:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a pyridine ring of formula (Q4)

(Q4)

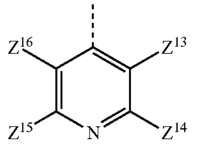

wherein:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO-$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, and —$SO_2$—($C_1$-$C_4$-halogenoalkyl) having 1 to 5 halogen atoms, or Q is a pyridine ring of formula (Q5)

(Q5)

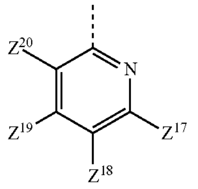

wherein:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), and —N($C_1$-$C_4$-alkyl)$_2$, or Q is a 5-membered aromatic heterocycle of formula (Q6)

(Q6)

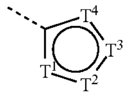

wherein:

$T^1$-$T^4$are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, and $C_1$-$C_4$-alkoxy-$C_1$-$C_4$-alkyl, or Q is a 5-membered aromatic heterocycle of formula (Q7)

(Q7)

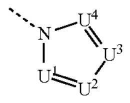

wherein:

$U^1$-$U^4$ are independently selected from the group consisting of N and C-$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy, wherein when Y is O, S or N—$R^9$ is not —OH, or a stereoisomer, a tautomer, an N-oxide, a hydrate, a solvate, or a salt thereof, or a mixture of any of the foregoing.

4. The compound according to claim 1, wherein:

A is A2,

A2

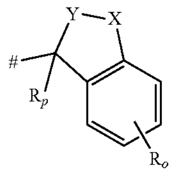

is 0, 1 or 2,

R is selected from the group consisting of halogen, $C_1$-$C_4$-alkyl and $C_1$-$C_4$-alkoxy, $R_p$ is selected from the group consisting of hydrogen and $C_1$-$C_4$-alkyl, X is selected from the group consisting of $CR^7R^8$, O, S, and N—$R^9$, Y is $CR^7R^8$ or O, $R^1$ is hydrogen or $C_1$-$C_4$-alkyl, $R^2$ is selected from the group consisting of hydrogen, halogen, —C(O)—N($C_1$-$C_4$-alkyl)$_2$,

—$NR^{12}R^{13}$,

—$OR^{14}$,

—$SR^{15}$, —S(O)$R^{15}$, —$SO_2R^{15}$, $C_1$-$C_4$-alkyl, $C_3$-$C_6$-cycloalkyl, $C_2$-$C_4$-alkenyl, $C_3$-$C_6$-cycloalkenyl, wherein each of the $C_1$-$C_4$-alkyl, $C_3$-$C_6$-cycloalkyl, $C_2$-$C_4$-alkenyl, and $C_3$-$C_6$-cycloalkenyl is optionally substituted by 1, 2, 3, 4 or 5 substituents independently selected from the group consisting of halogen, —OH, cyano, $C_1$-$C_4$-alkoxy-C(O)— and —C(O)—$NH_2C_1$-$C_4$-alkoxy, —$NH_2$, —N($C_1$-$C_4$-alkyl)$_2$, and —N($C_1$-$C_4$-alkyl)(C(O)—$C_1$-$C_4$-alkyl), and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^5$ is selected from the group consisting of hydrogen, halogen, —OH, cyano, $C_1$-$C_4$-alkyl, $C_1$-$C_4$-halogenoalkyl having 1 to 5 halogen atoms, and $C_1$-$C_4$-alkoxy, $R^6$ is selected from the group consisting of hydrogen, halogen, —OH, cyano, $C_1$-$C_4$-alkyl, $C_1$-$C_4$-halogenoalkyl having 1 to 5 halogen atoms, and $C_1$-$C_4$-alkoxy, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{12}$ and $R^{13}$ are independently selected from the group consisting of hydrogen, —NH(—C(O)—$C_1$-$C_4$-alkyl), $C_1$-$C_4$-alkoxy, $C_1$-$C_4$-alkyl, $C_3$-$C_6$-cycloalkyl, phenyl-$C_1$-$C_4$-alkyl, wherein each of the $C_1$-$C_4$-alkyl, $C_3$-$C_6$-cycloalkyl, phenyl-$C_1$-$C_4$-alkyl is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, and ($C_1$-$C_4$-alkoxy)$_2$P(═O)—, heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy, phenyl, benzo-$C_5$-$C_6$-cycloalkyl, wherein each of the phenyl and benzo-$C_5$-$C_6$-cycloalkyl is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl, and 4- to 10-membered heterocycloalkyl, $R^{15}$ is selected from the group consisting of hydrogen, $C_1$-$C_4$-alkyl, which is optionally substituted by 1, 2 or 3 substituents independently selected from the group consisting of —OH and —COOH, and a 6-membered heteroaryl, Q is a substituted phenyl ring of formula (Q1)

(Q1)

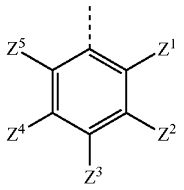

wherein:

$Z^1$ and $Z^5$ are independently selected from the group consisting of hydrogen, halogen, $C_1$-$C_4$-alkyl, $C_1$-$C_4$-alkoxy, and $C_1$-$C_4$-halogenoalkoxy having 1 to 5 halogen atoms, $Z^2$ and $Z^4$ are independently selected from the group consisting of hydrogen, halogen, cyano, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, $C_1$-$C_4$-halogenoalkoxy having 1 to 5 halogen atoms, and —N($C_1$-$C_4$-alkyl)$_2$, or $Z^1$ and $Z^2$ form, together with the carbon atoms that they are connected to, a 5-membered heterocycloalkyl or a 5-membered heteroaryl, each of which may be optionally substituted with one or two substituents selected from the group consisting of methyl, fluorine and oxo, $Z^3$ and $Z^5$ are hydrogen, and $Z^4$ is selected from the group consisting of hydrogen and $C_1$-$C_4$-alkoxy-C(O)—, or Q is a pyridine ring of formula (Q4)

(Q4)

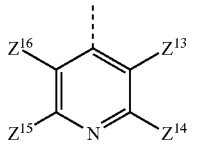

wherein:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, $NH_2$, —NH($C_1$-$C_4$-alkyl), —N($C_1$-$C_4$-alkyl)$_2$, —NH—CO-$C_1$-$C_4$-alkyl, and monocyclic heterocycle selected from the group of 4- to 7-membered heterocycloalkyl and 5-membered heteroaryl having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, and —$SO_2$—($C_1$-$C_4$-halogenoalkyl) having 1 to 5 halogen atoms, or Q is a pyridine ring of formula (Q5)

(Q5)

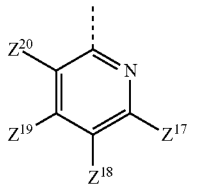

wherein:

$Z^{17}$, $Z^{18}$, and $Z^{19}$ are hydrogen, and $Z^{20}$ is halogen, or

Q is a 5-membered aromatic heterocycle of formula (Q6)

(Q6)

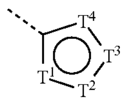

wherein:

$T^1$-$T^4$are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, and $C_1$-$C_4$-alkoxy-$C_1$-$C_4$-alkyl, or Q is a 5-membered aromatic heterocycle of formula (Q7)

(Q7)

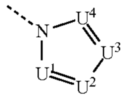

wherein:

$U^1$-$U^4$ are independently selected from the group consisting of N and C-$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy, or a stereoisomer, a tautomer, an N-oxide, a hydrate, a solvate, or a salt thereof, or a mixture of any of the foregoing.

5. The compound according to claim 1, wherein:

A is selected from the group consisting of

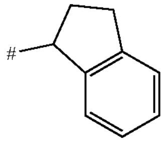 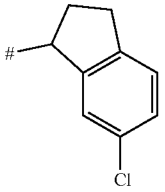

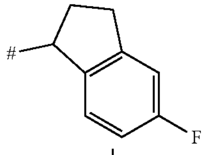 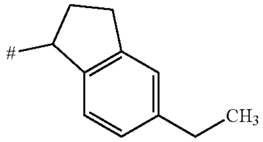

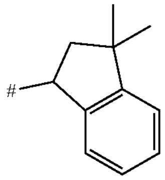 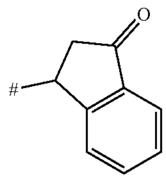

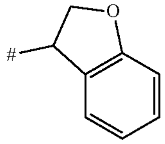 and 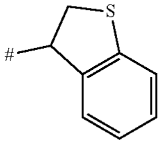 , $R^1$ is hydrogen or methyl, $R^2$ is selected from the group consisting of hydrogen, chlorine, iodine, —C(O)—N($CH_3$)$_2$,

—$NR^{12}R^{13}$,

—$OR^{14}$,

—$SR^{15}$, —S(O)$R^{15}$, —$SO_2R^{15}$, methyl, ethyl, propyl, isopropyl, cyclopropyl, cyclobutyl, cyclopentyl, cyclohexyl, ethenyl, propenyl, cyclopentenyl, cyclohexenyl, each of which is optionally substituted by 1 or 2 substituents independently selected from the group consisting of —OH, cyano, ethoxy-C(O)—, —C(O)—$NH_2$, methoxy, $NH_2$, $N(CH_3)_2$, and $N(CH_3)(C(O)CH_3)$, and a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, thiophene, imidazole, pyrazole, 1,2,4-triazole, 1,2,3-triazole, 1,2,3,4-tetrazole, pyridine, dihydropyridine, pyrimidine, tetrahydropyrimidine, and 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—$NH_2$, methyl, methyl-C(O)—, difluoromethyl, trifluoromethyl, hydroxymethyl-, methoxymethyl-, —$NH_2$, —$NMe_2$, and pyrrolidine, $R^3$ is hydrogen or methyl, $R^4$ is selected from the group consisting of hydrogen, fluorine, chlorine, —OH, cyano, methyl, methoxy, trifluoromethyl, trifluoromethoxy and $NH_2$, $R^5$ is selected from the group consisting of hydrogen, fluorine, chlorine, —OH, cyano, methyl, methoxy and trifluoromethyl, $R^6$ is selected from the group consisting of hydrogen, fluorine, chlorine, —OH, cyano, methyl and methoxy, $R^{12}$ and $R^{13}$ are independently selected from the group consisting of hydrogen, —NH(—C(O)-methyl), methoxy, methyl, ethyl, propyl, isopropyl, butyl, isobutyl, cyclopropyl, cyclobutyl, benzyl, 1-phenylethyl, wherein each of the methyl, ethyl, propyl, isopropyl, butyl, isobutyl, cyclopropyl, cyclobutyl, benzyl, and 1-phenylethyl is optionally substituted by 1, 2 or 3 substituents independently selected from the group consisting of fluorine, —OH, —COOH, methoxy-C(O)—, ethoxy-C(O)—, tert-butoxy-C(O)—, —C(O)—$NH_2$, —C(O)—$NMe_2$, —NH—C(O)-methyl, methyl, methoxy, cyclopropyl, —$NH_2$, $NMe_2$, S-methyl, S(O)-methyl, $SO_2$-methyl, and $(EtO)_2P(=O)$—, heterocyclyl-methyl, heterocyclyl-ethyl, wherein the heterocyclyl substituent is selected from the group consisting of oxetane, tetrahydrofurane, tetrahydropyrane, pyrrolidine, morpholine, pyrazole, imidazole, 1,2,4-oxadiazole, pyridine, each of which is optionally substituted by 1 substituent independently selected from the group consisting of fluorine, chlorine, —OH, oxo and methyl, phenyl, 2,3-dihydro-1H-indene, and a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, and methyl, $R^{14}$ is selected from the group consisting of methyl, ethyl, isopropyl, butyl, cyclopentyl, and benzyl, wherein each of the methyl, ethyl, isopropyl, butyl, cyclopentyl, and benzyl is optionally substituted by 1 or 2 substituents independently selected from the group consisting of fluorine, —OH, methyl, methoxy and cyclopentyl, and a monocyclic or a bicyclic heterocycle selected from the group consisting of pyrrolidine and tetrahydropyrane, $R^{15}$ is selected from the group consisting of methyl, ethyl, wherein each of the methyl and ethyl is optionally substituted by 1 substituent independently selected from the group consisting of —OH and —COOH, and pyridine, Q is a substituted phenyl ring of formula (Q1)

(Q1)

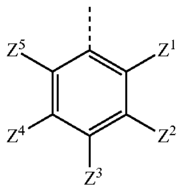

wherein:

$Z^1$ and $Z^5$ are independently selected from the group consisting of hydrogen, fluorine, chlorine, methyl, trifluoromethyl and methoxy, $Z^2$ and $Z^4$ are independently selected from the group consisting of hydrogen, fluorine, chlorine, —OH, cyano, methyl, ethyl, tert-butyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy, difluoromethoxy and —$NMe_2$, or Q is a pyridine ring of formula (Q4)

(Q4)

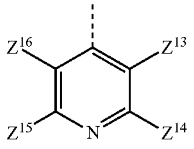

wherein:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, $NH_2$, —NHMe —$NMe_2$, —NH—C(O)-Me, and morpholinyl, or Q is a pyridine ring of formula (Q5)
(Q5)
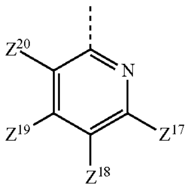
wherein:
$Z^{17}$, $Z^{18}$, and $Z^{19}$ are hydrogen, and
$Z^{20}$ is fluorine or chlorine, or
Q is selected from the group consisting of
(Q6-1)
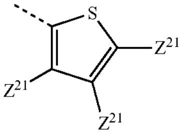
(Q6-2)
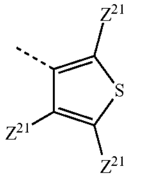
(Q6-3)
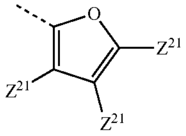
(Q6-4)
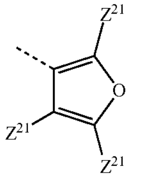
(Q6-5)
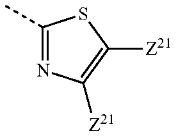
(Q6-6)
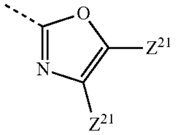
(Q6-7)
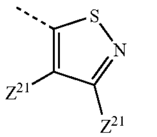
-continued
(Q6-8)
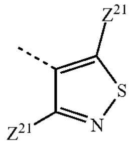
(Q6-9)
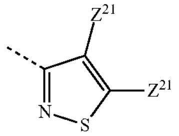
(Q6-10)
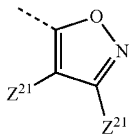
(Q6-11)
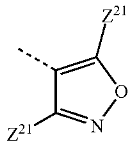
(Q6-12)
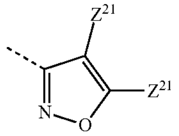
(Q6-13)
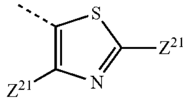
(Q6-14)
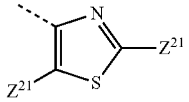
(Q6-15)
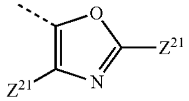
(Q6-16)
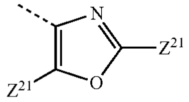
(Q6-17)
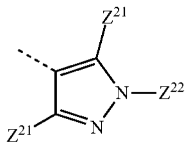
(Q6-18)
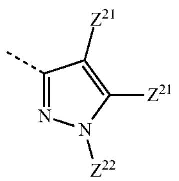

-continued
(Q6-19)
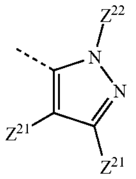
(Q6-20)
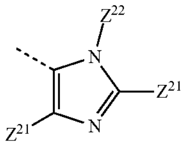
(Q6-21)
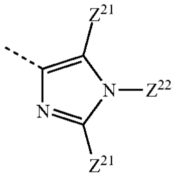
(Q6-22)
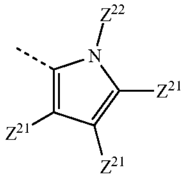
(Q6-23)
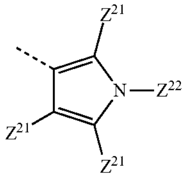
(Q6-24)
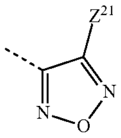
(Q6-25)
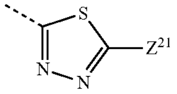
(Q6-26)
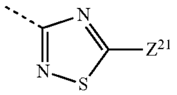
(Q6-27)
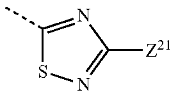
(Q6-28)
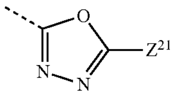
(Q6-29)
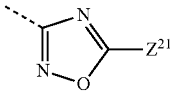
-continued
(Q6-30)
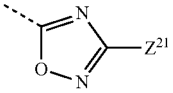
(Q6-31)
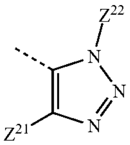
(Q6-32)
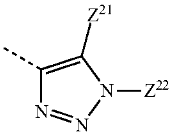
(Q6-33)
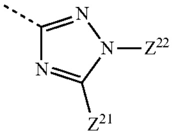
(Q6-34)
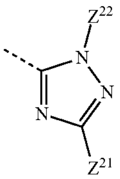
(Q6-35)
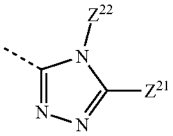
(Q6-36)
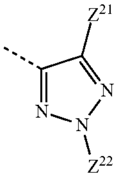
(Q6-37)
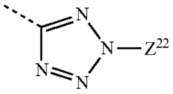
(Q6-38)
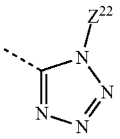
and
(Q6-39)
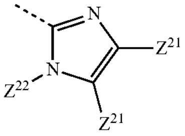
wherein:
each $Z^{21}$ is independently selected from the group consisting of hydrogen, fluorine, chlorine, cyano, methyl, trifluoromethyl, and methoxy and
$Z^{22}$ is hydrogen or methyl, or Q is selected from the group consisting of (Q7-1)

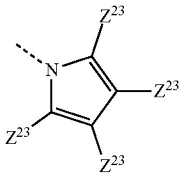

(Q7-2)

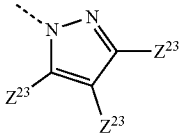

(Q7-3)

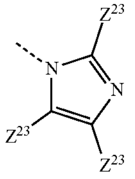

(Q7-4)

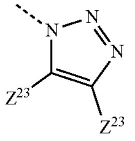

(Q7-5)

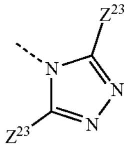

(Q7-6)

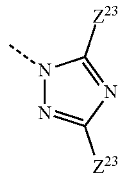

(Q7-7)

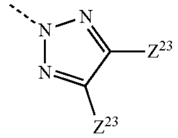

(Q7-8)

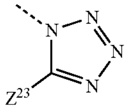

and (Q7-9)

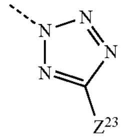

wherein:

each $Z^{23}$ is independently selected from the group consisting of hydrogen, fluorine, chlorine, cyano, methyl, trifluoromethyl, and methoxy, or Q is selected from the group consisting of

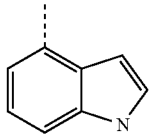
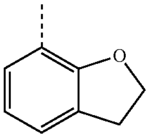
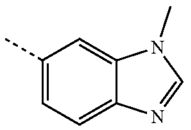
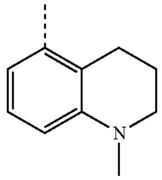
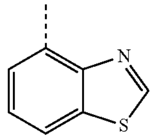
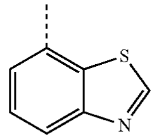
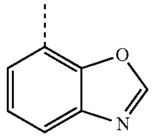
and
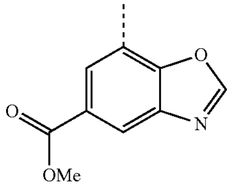
, or a stereoisomer, a tautomer, an N-oxide, a hydrate, a solvate, or a salt thereof, or a mixture of any of the foregoing.

6. The compound according to claim 1, wherein:

A is selected from the group consisting of

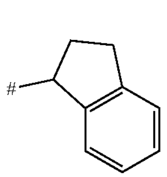
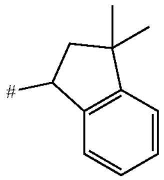
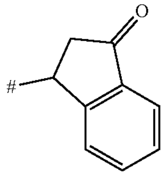
and
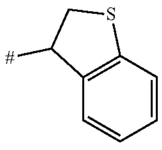

$R^1$ is hydrogen or methyl, $R^2$ is selected from the group consisting of
- chlorine, iodine, —C(O)—N($CH_3$)$_2$,
- —$NR^{12}R^{13}$,
- —$OR^{14}$,
- —$SR^{15}$, —S(O)$R^{15}$, —$SO_2R^{15}$,
- methyl, ethyl, propyl, isopropyl, cyclopropyl, cyclobutyl, cyclopentyl, ethenyl, propenyl, wherein each of the methyl, ethyl, propyl, isopropyl, cyclopropyl, cyclobutyl, cyclopentyl, ethenyl, and propenyl is optionally substituted by 1 or 2 substituents independently selected from the group consisting of —OH, cyano, ethoxy-C(O)—,
- —C(O)—$NH_2$, methoxy, $NH_2$, N($CH_3$)$_2$, and N($CH_3$)(C(O)$CH_3$), and
- a monocyclic or a bicyclic heterocycle selected from the group consisting of azetidine, oxetane, pyrrolidine, tetrahydrofurane, pyrazolidine, imidazolidine, 1,2,4-triazolidine, piperidine, piperazine, tetrahydropyrane, dihydro-2H-pyrane, 1,2-oxazolidine, morpholine, thiomorpholine, 3,4-dihydroisoquinoline, 2,3-dihydro-indole, 1,3-dihydro-isoindole, 3,9-dioxa-7-azabicyclo [3.3.1] nonane, 6-oxa-3-azabicyclo [3.1.1]heptane, 8-oxa-3-azabicyclo [3.2.1]octane, thiophene, imidazole, pyrazole, 1,2,3-triazole, 1,2,3,4-tetrazole, pyridine, dihydropyridine, pyrimidine, and tetrahydropyrimidine, each of which is optionally substituted by 1, 2, 3 or 4 substituents independently selected from the group consisting of fluorine, —OH, oxo, —COOH, methoxy-C(O)—, ethoxy-C(O)—, tert-butoxy-C (O)—, —C(O)—$NH_2$, methyl, methyl-C(O)—, difluoromethyl, trifluoromethyl, hydroxymethyl-, methoxymethyl-, —$NH_2$, —$NMe_2$, and pyrrolidine, $R^3$ is hydrogen or methyl, $R^4$ is selected from the group consisting of hydrogen, chlorine, fluorine, methyl, methoxy and trifluoromethyl, $R^5$ is selected from the group consisting of hydrogen, chlorine, fluorine, —OH, cyano, methyl, trifluoromethoxy and $NH_2$, $R^6$ is selected from the group consisting of hydrogen, fluorine, chlorine, —OH, cyano, methyl and methoxy, $R^{12}$ and $R^{13}$ are independently selected from the group consisting of hydrogen, —NH(—C(O)-methyl), methoxy, methyl, ethyl, propyl, isopropyl, butyl, isobutyl, cyclopropyl, cyclobutyl, benzyl, 1-phenylethyl, wherein each of the methyl, ethyl, propyl, isopropyl, butyl, isobutyl, cyclopropyl, cyclobutyl, benzyl, 1-phenylethyl is optionally substituted by 1, 2 or 3 substituents independently selected from the group consisting of fluorine, —OH, —COOH, methoxy-C(O)—, ethoxy-C(O)—, tert-butoxy-C(O)—, —C(O)—$NH_2$, —C(O)—$NMe_2$, —NH—C(O)-methyl, methyl, methoxy, cyclopropyl, —$NH_2$, —$NMe_2SO_2$-methyl and $(EtO)_2P(=O)$—, heterocyclyl-methyl, heterocyclyl-ethyl, wherein the heterocycyl substituent is selected from the group consisting of oxetane, tetrahydrofurane, tetrahydropyrane, pyrrolidine, pyrazole, imidazole 1, 2, 4-oxadiazole, morpholine, and pyridine, each of which is optionally substituted by 1 substituent independently selected from the group consisting of oxo and methyl, phenyl, 2,3-dihydro-1H-indene, and a monocyclic or a bicyclic heterocycle selected from the group of oxetane, morpholine, tetrahydropyrane, pyridine and pyrazole, $R^{14}$ is selected from the group consisting of methyl, ethyl, isopropyl, butyl, cyclopentyl, benzyl, wherein each of the methyl, ethyl, isopropyl, butyl, cyclopentyl, benzyl which is optionally substituted by 1 or 2 substituents independently selected from the group consisting of fluorine, —OH, methyl, methoxy and cyclopentyl, and a monocyclic or a bicyclic heterocycle selected from the group consisting of pyrrolidine and tetrahydropyrane, $R^{15}$ is selected from the group consisting of methyl, ethyl, wherein each of the methyl and ethyl is optionally substituted by 1 substituent independently selected from the group consisting of —OH and —COOH, and pyridine, Q is a substituted phenyl ring of formula (Q1)

(Q1)

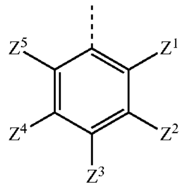

wherein:

$Z^1$ and $Z^5$ are independently selected from the group consisting of hydrogen, fluorine, chlorine, methyl, methoxy and trifluoromethyl, $Z^2$ and $Z^4$ are independently selected from the group consisting of hydrogen, fluorine, chlorine, —OH, cyano, methyl, ethyl, tert-butyl, —NHMe, —$NMe_2$, trifluoromethyl, methoxy, trifluoromethoxy, —SMe and morpholinyl, and $Z^3$ is independently selected from the group consisting of hydrogen, fluorine, chlorine, methyl, methoxy, difluoromethoxy and —$NMe_2$, or Q is a pyridine ring of formula (Q4)

(Q4)

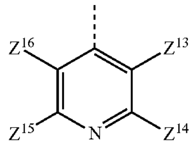

wherein:

$Z^{14}$ and $Z^{15}$ are independently selected from the group consisting of hydrogen, fluorine, chlorine, cyano, methyl, methoxy, ethoxy, isopropoxy, hydroxymethyl, $NH_2$, and morpholinyl and $Z^{13}$ and $Z^{16}$ are independently selected from the group consisting of hydrogen, fluorine, chlorine, methyl, and methoxy, or Q is a pyridine ring of formula (Q5)

(Q5)

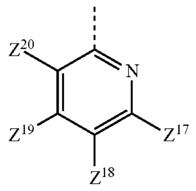

wherein:

$Z^{17}$, $Z^{18}$, and $Z^{19}$ are hydrogen, and $Z^{20}$ is fluorine, or

Q is selected from the group consisting of

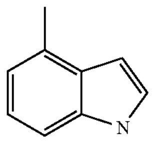

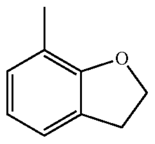

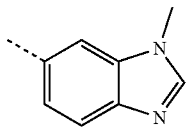

-continued

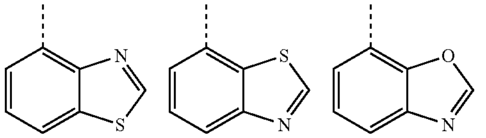

and

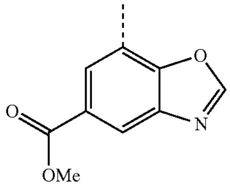

, or a stereoisomer, a tautomer, an N-oxide, a hydrate, a solvate, or a salt thereof, or a mixture of any of the foregoing.

7. A method of preparing a compound of formula (I) according to claim 1, said method comprising reacting an intermediate compound of formula 1N:

1N

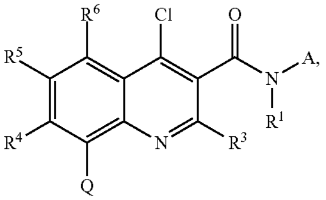

wherein A, $R^1$, $R^3$, $R^4$, $R^5$, $R^6$, and Q are as defined for the compound of formula (I) according to claim 1, with a compound of formula 1F:

$R^2H$ 1F, wherein $R^2$ is $NR^{12}R^{13}$, $OR^{14}$, or $SR^{15}$, each as defined for the compound of formula (I) according to claim 1, to give the compound of formula (I):

(I)

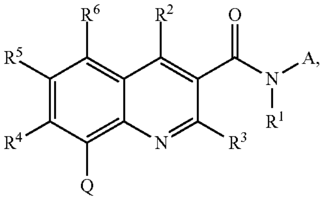

wherein A, $R^1$, $R^2$, $R^3$, $R^4$, $R^5$, $R^6$, and Q are as defined for the compound of formula (I) according to claim 1, or reacting an intermediate compound of formula 1T:

1T

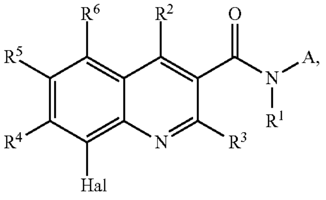

wherein A, $R^1$, $R^2$, $R^3$, $R^4$, $R^5$ and $R^6$ are as defined for the compound of formula (I) according to claim 1, and wherein Hal is halogen, with a compound of formula 1H:

$Q\text{-}B(OR)_2$ 1H, wherein Q is as defined for the compound of formula (I) according to claim 1, and each R may be individually H or Me or both R are pinacolate, to give the compound of formula (I):

(I)

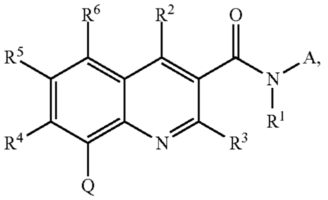

wherein A, $R^1$, $R^2$, $R^3$, $R^4$, $R^5$, $R^6$, and Q are as defined for the compound of formula (I) according to claim 1, or reacting an intermediate compound of formula 1W:

1W

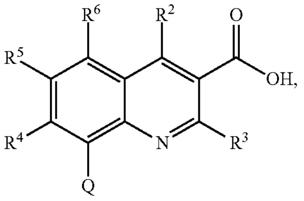

wherein Q, $R^2$, $R^3$, $R^4$, $R^5$ and $R^6$ are as defined for the compound of formula (I) according to claim 1, with a compound of formula 1M:

1M

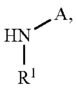

wherein $R^1$ and A are as defined for the compound of formula (I) according to claim 1, to give the compound of formula (I):

(I)

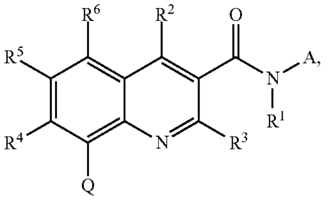

wherein A, $R^1$, $R^2$, $R^3$, $R^4$, $R^5$, $R^6$, and Q are as defined for the compound of formula (I) according to claim 1, or reacting an intermediate compound of formula 1X:

1X

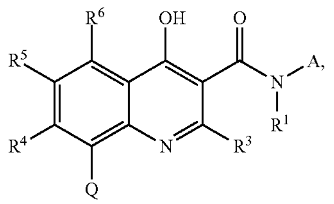

wherein Q, A, $R^1$, $R^3$, $R^4$, $R^5$ and $R^6$ are as defined for the compound of formula (I) according to claim 1, with a compound of formula 1Y:

$R^2H$ 1Y, wherein $R^2$ is $OR^{14}$ as defined for the compound of formula (I) according to claim 1, to give the compound of formula (I):

(I)

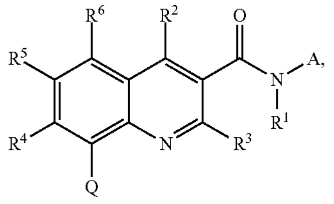

wherein A, $R^1$, $R^3$, $R^4$, $R^5$, $R^6$, and Q are as defined for the compound of formula (I) according to claim 1 and $R^2$ is $C^1$-$C^4$-alkoxy which is optionally substituted as defined for the compound of formula (I) according to claim 1, or reacting an intermediate compound of formula 1N:

1N

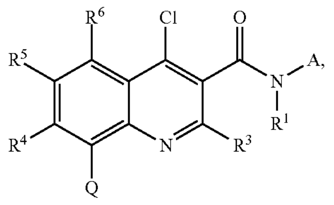

wherein Q, A, $R^1$, $R^3$, $R^4$, $R^5$ and $R^6$ are as defined for the compound of formula (I) according to claim 1, with a compound of formula 2A:

$R^2$Met-X 2A, wherein $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of formula (I) according to claim 1, Met is magnesium or zinc, and X is chlorine, bromine or iodine, to give the compound of formula (I):

(I)

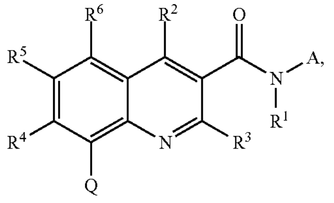

wherein A, $R^1$, $R^3$, $R^4$, $R^5$, $R^6$, and Q are as defined for the compound of formula (I) according to claim 1 and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of formula (I) according to claim 1.

8. A compound of formula (II):

(II)

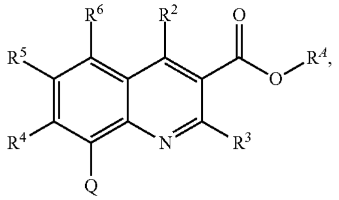

wherein:

$R^2$ is —OH or as defined for the compound of formula (I) according to claim 1, $R^3$, $R^4$, $R^5$, $R^6$, and Q are as defined for the compound of formula (I) according to claim 1, and $R^A$ is H or $C_1$-$C_4$-alkyl, or a stereoisomer, a tautomer, an N-oxide, a hydrate, a solvate, or a salt thereof, or a mixture of any of the foregoing.

9. A compound of formula (III):

(III)

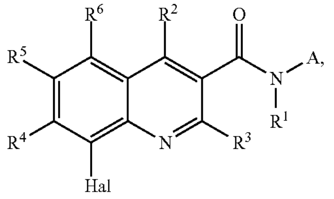

wherein:

$R^2$ is —OH or as defined for the compound of formula (I) according to claim 1, A, $R^1$, $R^3$, $R^4$, $R^5$, and $R^6$ are as defined for the compound of formula (I) according to claim 1, and Hal is halogen, or a stereoisomer, a tautomer, an N-oxide, a hydrate, a solvate, or a salt thereof, or a mixture of any of the foregoing.

10. A pharmaceutical composition comprising a compound of formula (I) according to claim 1, or a stereoisomer, a tautomer, an N-oxide, a hydrate, a solvate, or a salt thereof, or a mixture of any of the foregoing, and one or more pharmaceutically acceptable excipients.

11. A method for controlling helminth infections in humans and/or animals by administering an anthelminthically effective amount of at least one compound of formula (I) according to claim 1, or a stereoisomer, a tautomer, an N-oxide, a hydrate, a solvate, or a salt thereof, or a mixture of any of the foregoing, to a human or an animal in need thereof.

* * * * *

UNITED STATES PATENT AND TRADEMARK OFFICE

CERTIFICATE OF CORRECTION

PATENT NO. : 11,505,545 B2
APPLICATION NO. : 17/085880
DATED : November 22, 2022
INVENTOR(S) : Walter Hübsch et al.

It is certified that error appears in the above-identified patent and that said Letters Patent is hereby corrected as shown below:

In the Claims

Claim 1, Line 6 should read as -- o is 0, 1, 2, 3 or 4, --

Claim 2, Line 4 should read as -- o is 0, 1, 2, 3 or 4, --

Claim 4, Line 4 should read as -- o is 0, 1 or 2, --

Signed and Sealed this
Seventeenth Day of December, 2024

Derrick Brent
*Acting Director of the United States Patent and Trademark Office*